(12) United States Patent
Tavazoie et al.

(10) Patent No.: US 10,543,183 B2
(45) Date of Patent: *Jan. 28, 2020

(54) TREATMENT AND DIAGNOSIS OF MELANOMA

(71) Applicant: The Rockefeller University, New York, NY (US)

(72) Inventors: Sohail F. Tavazoie, New York, NY (US); Nora Pencheva, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/881,231

(22) Filed: Jan. 26, 2018

(65) Prior Publication Data

US 2018/0153833 A1 Jun. 7, 2018

Related U.S. Application Data

(63) Continuation of application No. 15/650,480, filed on Jul. 14, 2017, now Pat. No. 9,962,348, which is a continuation of application No. 15/228,643, filed on Aug. 4, 2016, now Pat. No. 9,707,195, which is a continuation of application No. 14/486,477, filed on Sep. 15, 2014, now Pat. No. 9,526,710, which is a continuation of application No. PCT/US2013/054690, filed on Aug. 13, 2013.

(60) Provisional application No. 61/784,057, filed on Mar. 14, 2013, provisional application No. 61/682,339, filed on Aug. 13, 2012.

(51) Int. Cl.

| | |
|---|---|
| A61K 31/195 | (2006.01) |
| C07F 9/6506 | (2006.01) |
| A61K 38/17 | (2006.01) |
| A61K 45/06 | (2006.01) |
| A61K 31/18 | (2006.01) |
| A61K 31/265 | (2006.01) |
| A61K 31/415 | (2006.01) |
| A61K 31/4164 | (2006.01) |
| A61K 31/47 | (2006.01) |
| A61K 31/5377 | (2006.01) |
| G01N 33/574 | (2006.01) |
| A61K 31/4174 | (2006.01) |
| A61K 31/675 | (2006.01) |
| C07C 217/54 | (2006.01) |
| C07D 233/64 | (2006.01) |
| A61K 31/136 | (2006.01) |
| A61K 31/4155 | (2006.01) |
| A61K 31/416 | (2006.01) |
| C12Q 1/6886 | (2018.01) |

(52) U.S. Cl.
CPC .......... *A61K 31/195* (2013.01); *A61K 31/136* (2013.01); *A61K 31/18* (2013.01); *A61K 31/265* (2013.01); *A61K 31/415* (2013.01); *A61K 31/416* (2013.01); *A61K 31/4155* (2013.01); *A61K 31/4164* (2013.01); *A61K 31/4174* (2013.01); *A61K 31/47* (2013.01); *A61K 31/5377* (2013.01); *A61K 31/675* (2013.01); *A61K 38/177* (2013.01); *A61K 38/1709* (2013.01); *A61K 45/06* (2013.01); *C07C 217/54* (2013.01); *C07D 233/64* (2013.01); *C07F 9/6506* (2013.01); *C12Q 1/6886* (2013.01); *G01N 33/5743* (2013.01); *C12Q 2600/118* (2013.01); *C12Q 2600/136* (2013.01); *C12Q 2600/158* (2013.01); *C12Q 2600/178* (2013.01); *G01N 2500/10* (2013.01)

(58) Field of Classification Search
CPC .................................................. A61K 31/195
See application file for complete search history.

(56) References Cited

U.S. PATENT DOCUMENTS

| | | | |
|---|---|---|---|
| 5,324,731 A | 6/1994 | Kaddurah-Daouk et al. | |
| 5,676,978 A | 10/1997 | Teicher et al. | |
| 6,316,503 B1 | 11/2001 | Li et al. | |
| 7,247,748 B2 | 7/2007 | Thompson et al. | |
| 7,365,085 B2 | 4/2008 | Bhat et al. | |
| 7,560,586 B2 | 7/2009 | Thompson et al. | |
| 7,576,215 B2 | 8/2009 | Collini et al. | |
| 7,998,995 B2 | 8/2011 | Boren et al. | |
| 9,399,028 B2 * | 7/2016 | Tavazoie | A61K 38/1709 |
| 9,526,710 B2 * | 12/2016 | Tavazoie | A61K 38/1709 |
| 9,707,195 B2 * | 7/2017 | Tavazoie | A61K 38/1709 |
| 9,962,348 B2 * | 5/2018 | Tavazoie | A61K 38/1709 |
| 2004/0072868 A1 | 4/2004 | Collins et al. | |
| 2005/0107444 A1 | 5/2005 | Thompsom et al. | |
| 2005/0113580 A1 | 5/2005 | Thompson et al. | |

(Continued)

FOREIGN PATENT DOCUMENTS

| | | |
|---|---|---|
| JP | H11507371 A | 6/1999 |
| JP | 2011525616 A | 9/2011 |

(Continued)

OTHER PUBLICATIONS

Bergenfelz et al, "Systemic Monocytic-MDSCs Are Generated from Monocytes and Correlate with Disease Progression in Breast Cancer Patients," PLoS One (2015); 10(5):e0127028 (pp. 1-15).

(Continued)

*Primary Examiner* — Rei Tsang Shiao
(74) *Attorney, Agent, or Firm* — Fox Rothschild LLP

(57) ABSTRACT

The present invention discloses novel agents and methods for diagnosis and treatment of melanoma. Also disclosed are related arrays, kits, and screening methods.

53 Claims, 59 Drawing Sheets

Specification includes a Sequence Listing.

(56) References Cited

U.S. PATENT DOCUMENTS

| | | |
|---|---|---|
| 2005/0131014 A1 | 6/2005 | Collini et al. |
| 2005/0282908 A1 | 12/2005 | Collins et al. |
| 2009/0286780 A1 | 11/2009 | Okuda et al. |
| 2010/0048944 A1 | 2/2010 | Parhami |
| 2010/0069367 A1 | 3/2010 | Boren et al. |
| 2011/0028384 A1 | 2/2011 | Blacklow et al. |
| 2011/0166079 A1 | 7/2011 | Vitek et al. |
| 2013/0071403 A1 | 3/2013 | Rolland et al. |

FOREIGN PATENT DOCUMENTS

| | | |
|---|---|---|
| WO | 03082802 A1 | 10/2003 |
| WO | 2007/002563 A1 | 1/2007 |
| WO | 2008011071 A2 | 1/2008 |
| WO | 2010138598 A2 | 12/2010 |
| WO | 2011130426 A2 | 10/2011 |
| WO | 2011158667 A1 | 12/2011 |
| WO | 2012095505 A1 | 7/2012 |
| WO | 2012135082 A1 | 10/2012 |

OTHER PUBLICATIONS

Chuu et al., "Modulation of Liver X Receptor Signaling as Novel Therapy for Prostate Cancer," Journal of Biomedical Science (Mar. 20, 2007): 14:543-553.

Gielen et al., "Increase in Both CD14-Positive and CD15-Positive Myeloid-Derived Suppressor Cell Subpopulations in the Blood of Patients with Glioma but Predominance of CD15-Positive Myeloid-Derived Suppressor Cells in Glioma Tissue," J NeuropatholExp Neurol (May 2015); 74(5):390-400.

Gros et al., "Myeloid Cells Obtained form the Blood but Not from the Tumor Can Suppress T-cell Proliferation in Patients with Melanoma," Clin Cancer Res. (Oct. 1, 2012); 18(19):5212-5223.

Haas, M.J., "Melanoma: three ways around BRAF inhibition," SciBX 3(47); doi:10.1038/scibx.2010.1400 published online Dec. 9, 2010.

Haas MJ. Melanoma:three ways around BRAF inhibition. SciBX 2010; 3(47).

Li et al., "miR-495 and miR-551a inhibit the migration and invasion of human gastric cancer cells by directly interacting with PRL-3," Cancer Lett (Mar. 30, 2012); 323(1):41-47.

Obermajer et al., "PGE2-Induced CXCL12 Production and CXCR4 Expression Controls the Accumulation of Human MDSCs in Ovarian Cancer Environment," Cancer Res. (2011); 71(24):7463-7470.

Pencheva et al., "Control of metastatic progression by microRNA regulatory networks," Nature Cell Biology (Jun. 3, 2013); 15(6):546-554.

Pencheva et al., "Broad-Spectrum Therapeutic Suppression of Metastatic melanoma thorugh Nuclear Hormone Receptor Activation," Cell (Feb. 27, 2014); 156(5):986-1001.

Rudolph et al., "Increased frequencies of CD11b+CD33+CD14+ HLA-DRlow myeloid-derived suppressor cells are an early eent in melanoma patients," Experimental Dermatology (2014); 23:199-218.

Scoles et al., "LiverX receptor agonist inhibits proliferation of ovarian carcinoma cells stimulated by oxidized low density lipoprotein," Gynecology Oncology (2010): 116:109-116.

Scoles et al., "Liver X receptor agonist inhibits proliferation of ovarian carcinoma cells stimulated by oxidized low tensity lipoprotein," GynecologicOncology 116 (2010) 109-116.

Talmadge et al., "History of myeloid derived suppressor cells (MDSCs) in the macro-and micro-environment of tumour-bearing hosts," Nat Rev Cancer (2013); 13(10):739-752.

Weber et al., "Phase I/II Study of Metastatic Melanoma Patients Treated with Nivolumab Who Had Progressed after Ipilimumab," Cancer Immunol Res (Apr. 2016); 4(4):345-353.

Zhang et al., "Liver X receptor activation induces apoptosis of melanoma cell through caspase pathway," Cancer Cell International (Feb. 25, 2014); 14(1):16 (1-6).

Zhang et al., A novel subset of B7-H3+CD14+HLA-DR-/low myeloid-derived suppressor cells are associated with progression of human NSCLC, OncoImmunology (Feb. 2015): 4(2): e977164-1-e977164-12.

Zigler et al., "Tumor Immuotheray in Melanoma—Strategies for Overcoming Mechanisms of Resistance and Escape," Am J Clin Dermatol (2008):9(50):307-311.

Zigler M, Villares GJ, Lev DC, Melnikova VO, Bar-Eli M. Tumor immunotherapy in melanoma: strategies for overcoming mechanisms of resistance and escape. Am J Clin Dermatol. 2008;9(5):307-11.

Zigler et al., "Tumor Immunotherapy in Melanoma—Strategies for Overcoming Mechanisms of Resistance and Escape," AM J Clin Dermatol (2008); 9(50):307-311.

\* cited by examiner

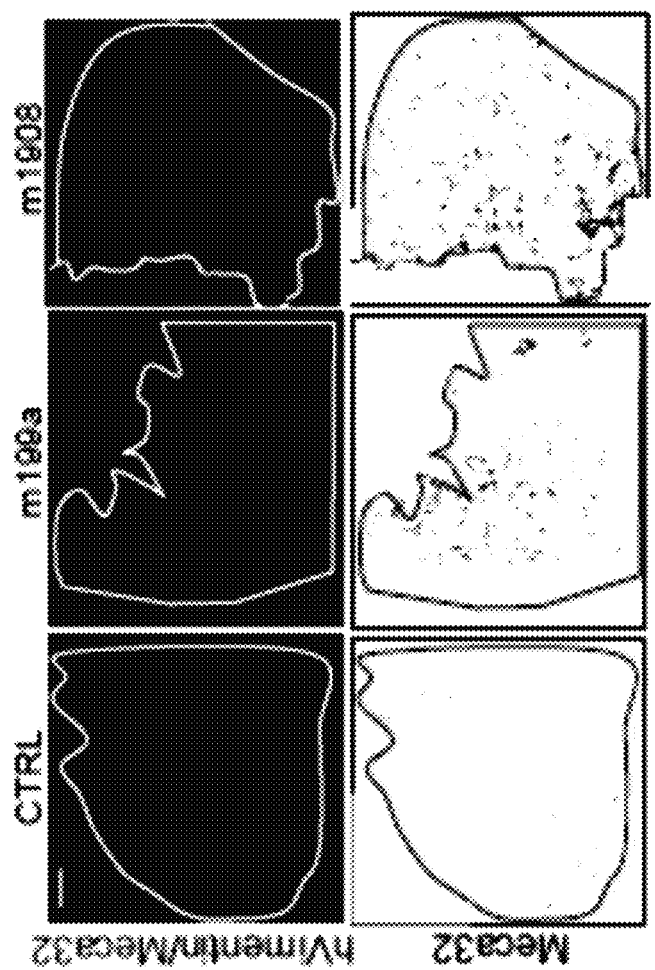
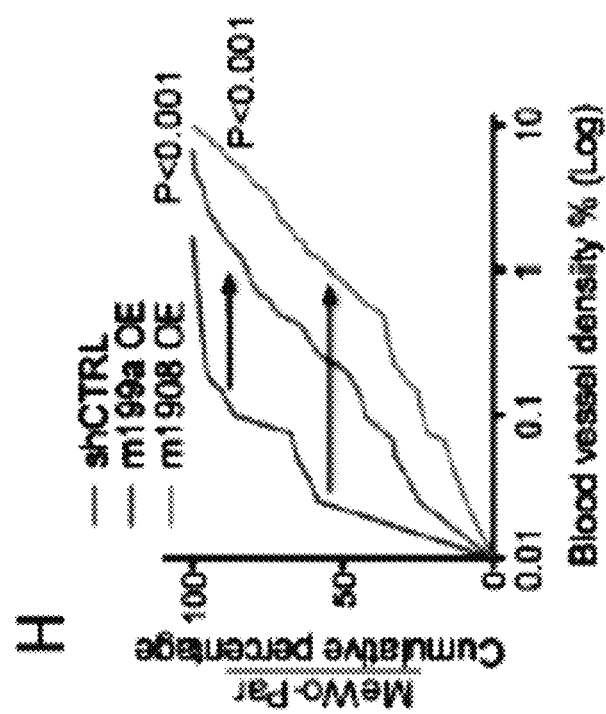
FIG. 13H

Table S1 List of the 50 most upregulated genes in MeWo human melanoma cells in response to GW3965 treatment

| Gene ID | Fold-change* | q-value | Rank | Gene ID | Fold-change* | q-value | Rank |
|---|---|---|---|---|---|---|---|
| ABCA1 | 19.34 | 1.98E-11 | 1 | CEACAM1 | 1.83 | 5.58E-06 | 26 |
| SREBF1 | 8.08 | 9.12E-15 | 2 | LDLR | 1.79 | 1.29E-05 | 27 |
| FABP7 | 7.43 | 1.85E-11 | 3 | IL1RAPL1 | 1.78 | 1.58E-09 | 28 |
| LOC645313 | 4.34 | 2.25E-10 | 4 | PPP1R3C | 1.78 | 1.64E-07 | 29 |
| APOE | 4.11 | 1.04E-07 | 5 | ABCD1 | 1.76 | 4.24E-07 | 30 |
| KRT34 | 4.09 | 5.99E-18 | 6 | C10ORF75 | 1.67 | 2.91E-06 | 31 |
| FASN | 3.72 | 2.48E-07 | 7 | LSS | 1.66 | 1.86E-05 | 32 |
| IGFBP5 | 2.91 | 1.15E-13 | 8 | DHCR7 | 1.64 | 2.58E-06 | 33 |
| TF | 2.88 | 2.37E-12 | 9 | CAPS | 1.63 | 8.35E-06 | 34 |
| INSIG1 | 2.62 | 3.15E-16 | 10 | PCYT2 | 1.63 | 3.08E-06 | 35 |
| MYLIP | 2.56 | 9.21E-07 | 11 | C5ORF28 | 1.62 | 3.71E-02 | 36 |
| LPCAT3 | 2.54 | 2.80E-15 | 12 | TMEM119 | 1.60 | 1.15E-04 | 37 |
| ACACA | 2.43 | 1.56E-12 | 13 | LPXN | 1.60 | 1.15E-07 | 38 |
| SCD | 2.42 | 3.56E-08 | 14 | SMPDL3A | 1.59 | 2.39E-04 | 39 |
| FCRLA | 2.19 | 9.13E-09 | 15 | SPOCD1 | 1.58 | 7.18E-07 | 40 |
| FADS1 | 2.12 | 2.01E-09 | 16 | ACLY | 1.58 | 6.56E-11 | 41 |
| ACSS2 | 2.02 | 1.88E-08 | 17 | VGLL3 | 1.57 | 1.32E-04 | 42 |
| SLC2A6 | 2.02 | 5.99E-18 | 18 | MVD | 1.57 | 1.13E-03 | 43 |
| ACSL3 | 1.94 | 5.35E-10 | 19 | NAV3 | 1.55 | 2.32E-04 | 44 |
| TMEM135 | 1.91 | 9.06E-07 | 20 | HS.538962 | 1.55 | 1.40E-07 | 45 |
| ADM | 1.88 | 3.78E-05 | 21 | TUBB2B | 1.53 | 3.46E-08 | 46 |
| LPIN1 | 1.88 | 5.94E-08 | 22 | LOC728285 | 1.53 | 2.19E-06 | 47 |
| MID1IP1 | 1.85 | 7.48E-09 | 23 | PHLDA2 | 1.52 | 2.77E-07 | 48 |
| FDPS | 1.84 | 5.49E-05 | 24 | APOLD1 | 1.51 | 9.50E-05 | 49 |
| CCL2 | 1.83 | 1.00E-08 | 25 | BEX1 | 1.51 | 1.08E-09 | 50 |

* Fold-upregulation in array-based gene expression for GW3965 treatment (1 µM, 48 hrs) versus DMSO control treatment

FIG. 26

SEQUENCE LISTING

```
<160> NUMBER OF SEQ ID NOS: 141

<210> SEQ ID NO 1
<211> LENGTH: 1223
<212> TYPE: DNA
<213> ORGANISM: Homo sapiens

<400> SEQUENCE: 1
gggatccttg agtcctactc agccccagcg gaggtgaagg acgtccttcc ccaggagccg      60
actggccaat cacaggcagg aagatgaagg ttctgtgggc tgcgttgctg gtcacattcc     120
tggcaggatg ccaggccaag gtggagcaag cggtggagac agagccggag cccgagctgc     180
gccagcagac cgagtggcag agcggccagc gctgggaact ggcactgggt cgcttttggg     240
```

```
attacctgcg ctgggtgcag acactgtctg agcaggtgca ggaggagctg ctcagctccc    300
aggtcaccca ggaactgagg gcgctgatgg acgagaccat gaaggagttg aaggcctaca    360
aatcggaact ggaggaacaa ctgaccccgg tggcggagga gacgcgggca cggctgtcca    420
aggagctgca ggcggcgcag gcccggctgg gcgcggacat ggaggacgtg tgcggccgcc    480
tggtgcagta ccgcggcgag gtgcaggcca tgctcggcca gagcaccgag gagctgcggg    540
tgcgcctcgc ctcccacctg cgcaagctgc gtaagcggct cctccgcgat gccgatgacc    600
tgcagaagcg cctggcagtg taccaggccg gggcccgcga gggcgccgag cgcggcctca    660
gcgccatccg cgagcgcctg ggcccctgg tggaacaggg ccgcgtgcgg gccgccactg     720
tgggctccct ggccggccag ccgctacagg agcgggccca ggcctggggc gagcggctgc    780
gcgcgcggat ggaggagatg ggcagccgga cccgcgaccg cctggacgag gtgaaggagc    840
aggtggcgga ggtgcgcgcc aagctggagg agcaggccca gcagatacgc ctgcaggccg    900
aggccttcca ggcccgcctc aagagctggt tcgagcccct ggtggaagac atgcagcgcc    960
agtgggccgg gctggtggag aaggtgcagg ctgccgtggg caccagcgcc gcccctgtgc   1020
ccagcgacaa tcactgaacg ccgaagcctg cagccatgcg accccacgcc acccccgtgcc  1080
tcctgcctcc gcgcagcctg cagcgggaga ccctgtcccc gccccagccg tcctcctggg   1140
gtggacccta gtttaataaa gattcaccaa gtttcacgca aaaaaaaaa aaaaaaaaa     1200
aaaaaaaaaa aaaaaaaaaa aaa                                          1223
```

<210> SEQ ID NO 2
<211> LENGTH: 317
<212> TYPE: PRT
<213> ORGANISM: Homo sapiens

<400> SEQUENCE: 2

```
Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
```

```
                195                 200                 205
Arg Ala Ala Thr Val Gly Ser Leu Ala Gly Gln Pro Leu Gln Glu Arg
        210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                    245                 250                 255

Val Arg Ala Lys Leu Glu Glu Gln Ala Gln Gln Ile Arg Leu Gln Ala
                260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
        290                 295                 300

Val Gly Thr Ser Ala Ala Pro Val Pro Ser Asp Asn His
305                 310                 315

<210> SEQ ID NO 3
<211> LENGTH: 3203
<212> TYPE: RNA
<213> ORGANISM: Homo sapiens

<400> SEQUENCE: 3
agucccaccc uucggcgcag ggcuccggcc aacacagccc uccaggccgc cuacucucca        60
gccagccggc uccacggacc cacggaaggg caaggggggcg gccucgggc ggcgggacag       120
uugucggagg gcgcccucca ggcccaagcc gccuucccg gccccgcca uggcccgggg         180
cggcagucag agcuggagcu ccggggaauc agacgggcag ccaaaggagc agacgcccga       240
gaagcccaga cacaagaugg ugaaggagac ccaguacuau gacauccugg gcgugaagcc       300
cagcgcguccc ccggaggaga ucaagaaggc cuaucggaag cuggcgcuca aguaccaccc      360
ggacaagaac ccggaugagg cgagaaguu uaaacucaua ucccaggcau augaagugcu       420
uucagaucca agaaaaggg auguuuauga ccaaggcgga gagcaggcaa uuaaagaagg       480
aggcucaggc agccccagcu ucucuucacc cauggacauc uuugacaugu ucuuugguug       540
ugguggacgg auggcuagag agagaagagg caagaauguu guacaccagu uaucucuaac      600
ucuugaagau cuauauaaug gagucacgaa gaaauuggcc cuccagaaaa auguaauuug       660
ugagaaaugu gaaggguguug gugggaagaa gggaucgguug gagaagugcc cgcugugcaa   720
ggggcgggggg augcagaucc acauccagca gaucgggccg ggcaugguac agcagaucca    780
gaccgugugc aucgagugca agggccaggg ugagcgcauc aacccaaggg accgcugcga      840
gagcugcagc ggggccaagg ugauccguga aagaagauu aucgagguac auguugaaaa       900
agguaugaaa gauggggcaaa gauacuauu ucauggagaa ggagaucagg agccugagcu      960
ggagccuggu gaugucauaa uugugcuuga ucagaaggau cauagugucu uucagagacg     1020
aggccaugac uugaucauga aaaugaaaau ucagcuuucu gaagcucuuu gggcuucaa      1080
gaagacgaua aaaacauugg acaaucgaau ucuuguuauu acauccaaag caggugaggu     1140
gauaaagcac ggggaccuga gaugcgugcg cgaugaagga augcccaucu acaaagcacc     1200
ccuggaaaaa gggauucgua ucauacaguu uuuaguaauc uuuccugaaa acacuggcu      1260
uucucuggaa aagcuuccuc agcuggaagc uuuacccccu ccucgacaga agugaggau      1320
uacagaugac auggaucagg uggagcugaa ggaguuuugu cccaaugagc agaacuggcg     1380
ucagcacagg gaggccuacg aggaggacga agacgggccc caggcuggag ugcagugcca     1440
```

```
gacggcauga cguggugcgg ggcagcgugg ccccaccgga cuagcacaug augaauguaa    1500
aguuggcaca augaaaauga caucgcuuua auggccuugu guuugggaug uccuguguau    1560
guguucagca uucuuaauug cugagugucu uuuuggcuuu ucuuuugguu guaacuuaag    1620
uuauagcuua auuuauauuu aaauguuuua aguauaaauc accucuaguc ugcauaugga    1680 aucguucau uucauuuuc aggauauacu uuugagaugu cagugauugc accaauacuu    1740
ugugcuucua guggcuuugc cauaauucag ugucaccaau aaggcacagc ccaguuagca    1800
gcuuagcccc ccuagcaaac cccaaggcac aaagugggca uccugacuca ucucuagguc    1860 uguggguuucu cccucuucc cuggcagag uuauugaggg caugaucuca gggcugcuaa    1920
gauaacauuu cugaggauuc uagaugaucc ucuuaaagaa uaaaagcaca uccgggauc    1980 ggacauggcu gcaugugccu gcuuaacagg gccaacuuag uuccacugu ucugugcccu    2040 ucaguggaug gaacgugagu gucugaucau cucucuugga aguuuucuga accuuccaag    2100
cucuguggug aggacaaacc aguguuugaa ucauaugcug auaacuguuu gccugugacc    2160
cucacaccuu guucuucagg guuuuaauga uuuucuguug acaacuuuug caaugcuuuc    2220
ccaccaaagu gcuuacuugu aaagaaaacu aaauccuucu gugucccggg cagcccagu    2280 gcagcaacag aagccaaggg agaaugcugc ugguuuggcc cauggcacag ccagcuucuc    2340
ugaccaguaa uccggggguga cuugagggguc ugcaaaggca uagaacuccc caguguuuuc    2400
caccucauuc ucccagauug agcucccuuc caaaggaucg uuccucucau ugcacagcca    2460
uauuacaaag gguuuccugc ucaagugaug uuuuggguaag aacuucgcug aguuccacug    2520
uggauuacag uuuguaugga cuacuacugu aaauuauagc uuguuuggag ggauauuagu    2580
cauuauuuua uucaugacag guagacuaca auucgaacuu agggguuaccu cagucuuuag    2640 ccauuacugc uuauuucuuu uccccaaguc acaaaaaacu uguaagcugc ugggguuaaag    2700 cagaggccac cugucagauc uacccuaccc uuauuugguu acauggcacc ugagaguuuc    2760
acucagacca gggaucuucc uuaggagggu caaagugcag aucagaccau gcagguaagg    2820
ugaaccagcu gcacggacca gguucccgca aaacauugcc agcagugag gcauaauuug    2880 cucaaaguau agaaacagcc caccugugcc cacuuugacc auuggugagg auagauauaa    2940
aaucacuucu uccaacgaag ccuaggugaa aaucuauuua uaaauggacc acaacucugg    3000
ggugucguuu uugugcugug acuuccuaau uauugcuaaa gaacuacugu uuaguuggua    3060
augguguaaa auuacauuca gcuccuucuu gucauauaaa aggaauuugg agggugucgc    3120
uuaaaauuuu auuccaccug uacauuuguc acuuuaaaau uaaaauugag cugguauagag    3180 agauaaaaaa aaaaaaaaaa aaa                                             3203
```

<210> SEQ ID NO 4
<211> LENGTH: 426
<212> TYPE: PRT
<213> ORGANISM: Homo sapiens

<400> SEQUENCE: 4

```
Met Ala Arg Gly Gly Ser Gln Ser Trp Ser Gly Glu Ser Asp Gly
1               5                   10                  15

Gln Pro Lys Glu Gln Thr Pro Glu Lys Pro Arg His Lys Met Val Lys
            20                  25                  30

Glu Thr Gln Tyr Tyr Asp Ile Leu Gly Val Lys Pro Ser Ala Ser Pro
        35                  40                  45

Glu Glu Ile Lys Lys Ala Tyr Arg Lys Leu Ala Leu Lys Tyr His Pro
    50                  55                  60
```

```
Asp Lys Asn Pro Asp Glu Gly Glu Lys Phe Lys Leu Ile Ser Gln Ala
 65                  70                  75                  80

Tyr Glu Val Leu Ser Asp Pro Lys Lys Arg Asp Val Tyr Asp Gln Gly
                 85                  90                  95

Gly Glu Gln Ala Ile Lys Glu Gly Gly Ser Ser Pro Ser Phe Ser
            100                 105                 110

Ser Pro Met Asp Ile Phe Asp Met Phe Phe Gly Gly Gly Gly Arg Met
            115                 120                 125

Ala Arg Glu Arg Arg Gly Lys Asn Val Val His Gln Leu Ser Val Thr
            130                 135                 140

Leu Glu Asp Leu Tyr Asn Gly Val Thr Lys Lys Leu Ala Leu Gln Lys
145                 150                 155                 160

Asn Val Ile Cys Glu Lys Cys Glu Gly Val Gly Gly Lys Lys Gly Ser
                165                 170                 175

Val Glu Lys Cys Pro Leu Cys Lys Gly Arg Gly Met Gln Ile His Ile
            180                 185                 190

Gln Gln Ile Gly Pro Gly Met Val Gln Gln Ile Gln Thr Val Cys Ile
            195                 200                 205

Glu Cys Lys Gly Gln Gly Glu Arg Ile Asn Pro Lys Asp Arg Cys Glu
            210                 215                 220

Ser Cys Ser Gly Ala Lys Val Ile Arg Glu Lys Lys Ile Ile Glu Val
225                 230                 235                 240

His Val Glu Lys Gly Met Lys Asp Gly Gln Lys Ile Leu Phe His Gly
                245                 250                 255

Glu Gly Asp Gln Glu Pro Glu Leu Glu Pro Gly Asp Val Ile Ile Val
            260                 265                 270

Leu Asp Gln Lys Asp His Ser Val Phe Gln Arg Arg Gly His Asp Leu
            275                 280                 285

Ile Met Lys Met Lys Ile Gln Leu Ser Glu Ala Leu Cys Gly Phe Lys
            290                 295                 300

Lys Thr Ile Lys Thr Leu Asp Asn Arg Ile Leu Val Ile Thr Ser Lys
305                 310                 315                 320

Ala Gly Glu Val Ile Lys His Gly Asp Leu Arg Cys Val Arg Asp Glu
                325                 330                 335

Gly Met Pro Ile Tyr Lys Ala Pro Leu Glu Lys Gly Ile Leu Ile Ile
            340                 345                 350

Gln Phe Leu Val Ile Phe Pro Glu Lys His Trp Leu Ser Leu Glu Lys
            355                 360                 365

Leu Pro Gln Leu Glu Ala Leu Leu Pro Pro Arg Gln Lys Val Arg Ile
            370                 375                 380

Thr Asp Asp Met Asp Gln Val Glu Leu Lys Glu Phe Cys Pro Asn Glu
385                 390                 395                 400

Gln Asn Trp Arg Gln His Arg Glu Ala Tyr Glu Glu Asp Glu Asp Gly
                405                 410                 415

Pro Gln Ala Gly Val Gln Cys Gln Thr Ala
            420                 425

<210> SEQ ID NO 5
<211> LENGTH: 3064
<212> TYPE: RNA
<213> ORGANISM: Homo sapiens

<400> SEQUENCE: 5
gugaccguga cgcgcgagcg ggcggcgggg gcgcgggcca ggggcgcggg ccagggugcc    60
```

-continued

```
ggcagggggcg uccggggcgc ucugaccggc cucgcccgcc ccccccgcag acacaagaug      120
gugaaggaga cccaguacua ugacauccug ggcgugaagc ccagcgcguc cccggaggag      180
aucaagaagg ccuaucggaa gcuggcgcuc aaguaccacc cggacaagaa cccggaugag      240
ggcgagaagu uuaaacucau auccccaggca uaugaagugc uuucagaucc aaagaaaagg    300
gauguuuaug accaaggcgg agagcaggca auuaagaag gaggcucagg cagccccagc      360
uucucuucac ccauggacau cuuugacaug uucuuuggug guguggacg gauggcuaga      420 gagagaagag gcaagaaugu uguacaccag uuaucuguaa ucuugaagaa ucuauauaau     480
ggagucacga agaaauuggc ccuccagaaa aauguaauuu ugagaaaug ugaaggguguu      540 gguggggaaga agggaucggu ggagaagugc ccgcugugca agggcgggg gaugcagauc      600 cacauccagc agaucgggcc gggcaugguaa cagcagaucc agaccgugug caucgagugc     660
aagggccagg gugagcgcau caaccccaag gaccgcugcg agagcugcag cggggccaag    720
gugauccgug agaagaagau uaucgagua caugugaaa aagguaugaa agaugggcaa     780
aagauacuau uucauggaga aggagaucag gagccugagc uggagccugg ugaugucaua     840
auugugcuug aucagaagga ucauagaguc uuucagagac gaggccauga cuugaucaug     900 aaaaaugaaaa uucagcuuuc ugaagcucuu uguggcuuca agaaagacgau aaaaacauug     960 gacaaucgaa uucuuguuau uaucuccaaaa gcaggggagg ugauaaagcaa cggggacccug    1020 agaugcgugc gcgaugaagg aaaaugcccauc uacaaagcac cccuggaaaa agggauucug    1080
aucauacagu uuuuaguaau cuuuccgaa aaacacugc uuucucuggaa aaaagcuuccu     1140 cagccuggaag cuuuacuccc uccucgacag aaagugagga uuacagauga caauggaucag    1200 guggagcuga aggaguuugg ucccaaugag cagaacuggc gucagcacag ggaggccuac     1260
gaggaggacg aagacggggcc ccaggcugga ggugcagugcc agacggcaug acguggugcg     1320
gggcagcgug gccccaccgg acuagcacau gaugaaugua aaguuggcac aaugaaaaug     1380
acaucgcuuu aauggccuug uguuuggau gucccugugua uguguucagc auucuuaaauu     1440 gcugagugcu uuuugggcuu uucuuugu ugguuaacuuaa guuauagcuu aauuuauauu     1500
uaaauguuuu aaguauaaau caccucuagu cugcauaugg aaucguucuca uuucuauuuu     1560 caggauauac uuuugagaug ucagugauug caccaauacu uugugcuucu aguggcuuug     1620
ccauaauuca gugucaccaa uaaggcacag cccaguuaga agcuuagccc ccuagcaaa      1680 ccccaaggca caaaguggggc auccugacuc aucucuaggu cuguggguuc ucccccucuuc    1740 ccuuggcaga guuauugagg gcaugaucuc agggcugcua agauaacauu ucugaggauu    1800
cuagaugauc ucucuaagaa auaaaagcac auccguggau cggacauggc ugcaugugcc    1860 ugcuuaaacag ggccaacuua guccuacug uucugugccc uucagugggau ggaacgugag    1920 ugucugauca ucucucuugg aaguuucug aaccuuccaa gcucuguggu gaggacaaac      1980 caguguuga aucauaugcu gauaacuguu ugccugugac ccucacaccu uguucuucag      2040
gguuuuaaug auuucugucu gacaacuuuu gcaaugcuuu cccaccaaag gcuuacuug      2100 uaaagaaaac uaaauccuuc ugugucccccg gcagccucag ugcagcaaca gaagccaagg    2160
gagaaugcug cugguuggcc ccaguggcaca gccagcuucu cugaccagua auccggggu    2220 acuugagggu cugcaaaggc auagaacccc ccaguguuuu ccaccucauu cucccagauu    2280
gagcucccuu ccaaagggauc guccucuca uugcacagcc auauuacaaa gggguuuccug    2340 cucaagugau guuuggguaa gaacuucgcu gaguccacu guggauuaca guuguauggg    2400
```

-continued

```
acuacuacug uaauuauag cuuguuugga gggauauuag ucauuauuuu auucaugaca    2460
gguagacuac aauucgaacu uagggunacc ucagucuuua gccauuacug cuuauuucuu    2520
uuccccaagu cacaaaaaac uuguaagcug cugggunaaa gcagaggcca ccugucagau    2580
cuacccuacc cuuauuuggu uacauggcac cugagaguuu cacucagacc agggaucuuc    2640
cuuaggaggg ucaaagugca gaucagacca ugcagguaag gugaaccagc ugcacggacc    2700
agguucccgc aaacauugc cagcuaguga ggcauaauuu gcucaaagua uagaaacagc    2760
ccaccugugc ccacuuugac cauuggugag gauagauaua aaaucacuuc uuccaacgaa    2820
gccuagguga aaaucuauuu auaaauggac cacaacucug ggugucguu uuugugcugu     2880 gacuuccuaa uuauugcuaa agaacuacug uuuaguuggu aaugguguaa aauuacauuc    2940
agcuccuucu ugucauauaa aaggaauuug gaggguugcg cuuaaaauuu uauuccaccu    3000
guacauuugu cacuuuaaaa uuaaaauuga gcugguauga gagauaaaaa aaaaaaaaaa    3060
aaaa                                                                 3064
```

<210> SEQ ID NO 6
<211> LENGTH: 397
<212> TYPE: PRT
<213> ORGANISM: Homo sapiens

<400> SEQUENCE: 6

```
Met Val Lys Glu Thr Gln Tyr Tyr Asp Ile Leu Gly Val Lys Pro Ser
1               5                   10                  15

Ala Ser Pro Glu Glu Ile Lys Lys Ala Tyr Arg Lys Leu Ala Leu Lys
                20                  25                  30

Tyr His Pro Asp Lys Asn Pro Asp Glu Gly Glu Lys Phe Lys Leu Ile
            35                  40                  45

Ser Gln Ala Tyr Glu Val Leu Ser Asp Pro Lys Lys Arg Asp Val Tyr
        50                  55                  60

Asp Gln Gly Gly Glu Gln Ala Ile Lys Glu Gly Ser Gly Ser Pro
65                  70                  75                  80

Ser Phe Ser Ser Pro Met Asp Ile Phe Asp Met Phe Gly Gly Gly
                85                  90                  95

Gly Arg Met Ala Arg Glu Arg Arg Gly Lys Asn Val Val His Gln Leu
            100                 105                 110

Ser Val Thr Leu Glu Asp Leu Tyr Asn Gly Val Thr Lys Lys Leu Ala
        115                 120                 125

Leu Gln Lys Asn Val Ile Cys Glu Lys Cys Glu Gly Val Gly Gly Lys
    130                 135                 140

Lys Gly Ser Val Glu Lys Cys Pro Leu Cys Lys Gly Arg Gly Met Gln
145                 150                 155                 160

Ile His Ile Gln Gln Ile Gly Pro Gly Met Val Gln Gln Ile Gln Thr
                165                 170                 175

Val Cys Ile Glu Cys Lys Gly Gln Gly Glu Arg Ile Asn Pro Lys Asp
            180                 185                 190

Arg Cys Glu Ser Cys Ser Gly Ala Lys Val Ile Arg Glu Lys Lys Ile
        195                 200                 205

Ile Glu Val His Val Glu Lys Gly Met Lys Asp Gly Gln Lys Ile Leu
    210                 215                 220

Phe His Gly Glu Gly Asp Gln Glu Pro Glu Leu Glu Pro Gly Asp Val
225                 230                 235                 240

Ile Ile Val Leu Asp Gln Lys Asp His Ser Val Phe Gln Arg Arg Gly
                245                 250                 255
```

-continued

```
His Asp Leu Ile Met Lys Met Lys Ile Gln Leu Ser Glu Ala Leu Cys
            260                 265                 270

Gly Phe Lys Lys Thr Ile Lys Thr Leu Asp Asn Arg Ile Leu Val Ile
        275                 280                 285

Thr Ser Lys Ala Gly Glu Val Ile Lys His Gly Asp Leu Arg Cys Val
    290                 295                 300

Arg Asp Glu Gly Met Pro Ile Tyr Lys Ala Pro Leu Glu Lys Gly Ile
305                 310                 315                 320

Leu Ile Ile Gln Phe Leu Val Ile Phe Pro Glu Lys His Trp Leu Ser
                325                 330                 335

Leu Glu Lys Leu Pro Gln Leu Glu Ala Leu Leu Pro Pro Arg Gln Lys
            340                 345                 350

Val Arg Ile Thr Asp Asp Met Asp Gln Val Glu Leu Lys Glu Phe Cys
        355                 360                 365

Pro Asn Glu Gln Asn Trp Arg Gln His Arg Gly Ala Tyr Glu Glu Asp
    370                 375                 380

Glu Asp Gly Pro Gln Ala Gly Val Gln Cys Gln Thr Ala
385                 390                 395
```

<210> SEQ ID NO 7
<211> LENGTH: 2891
<212> TYPE: RNA
<213> ORGANISM: Homo sapiens

<400> SEQUENCE: 7

```
acauuucagc aagcuggcua agacaugug ggaaagccug acccuggauu cagguccaaau      60
cucagcacuc acaagauuua aacucauauc ccaggcauau gaagugcuuu cagauccaaa    120
gaaaagggau guuuaugacc aaggcggaga gcaggcaauu aaagaaggag cucaggcag     180
ccccagcuuc ucuucaccca uggacaucuu ugacauguuc uuuggugguguggacggau      240
ggcuagagag agaagaggca agaauguugu acaccaguua ucuguaacuc uugaagaucu    300
auauaaugga gucacgaaga aauuggcccu ccagaaaaau guaauuugug agaaauguga    360
aggguuuggu gggaagaagg gaucggugga gaagugcccg cugugcaagg ggcggggau     420
gcagauccac auccagcaga ucgggccggg cauggucag cagauccaga ccgugugcau     480
cgagugcaag ggccaggug agcgcaucaa ccccaaggac cgcugcgaga gcugcagcgg    540
ggccaaggug auccgugaga agaagauuau cgagguacau guugaaaag guaugaaaga    600
ugggcaaaag auacuauuuc auggagaagg agaucaggag ccugagcugg agccuggug    660
ugucauaauu gugcuugauc agaaggauca uagugucuuu cagagacgag gccaugacuu    720
gaucaugaaa augaaaauc agcuuucuga agcucuuugu ggcuucaaga gacgauaaa    780
aacauuggac aaucgaauuc uuguuauuac auccaaagca ggugaggguga uaaagcacgg    840
ggaccugaga ugcgugcgcg augaaggaau gcccaucuac aaagcacccc uggaaaagg     900
gauucugauc auacaguuuu uaguaaucuu uccugaaaaa cacuggcuuu cucuggaaaa    960
gcuuccucag cuggaagcuu acucccucc ucgacagaaa gugaggauua cagaugacau    1020
ggaucaggug gagcugaagg aguuuugucc caaugagcag aacuggcguc agcacaggga    1080
ggccuacgag gaggacgaag acgggcccca ggcuggagug cagugccaga cggcauuuacg    1140
uggugcgggg cagcguggcc ccaccggacu agcacaugau gaauguaaag uuggcacaau    1200
gaaaaugaca ucgcuuuaau ggccuugugu uuggaugu cuguauugu guucagcauu    1260
cuuaauugcu gagugucuuu uuggcuuuuc uuuugguugu aacuuaaguu auagcuuaau    1320
```

-continued

```
uuauauuuaa auguuuuaag uauaaaucac cucuagucug cauauggaau cuguucauuu   1380
cuauuuucag gauauacuuu ugagauguca gugauugcac caauacuuug ugcuucuagu   1440
ggcuuugcca uaauucagug ucaccaauaa ggcacagccc aguuagcagc uuagccccc    1500 uagcaaaccc caaggcacaa aguggggcauc cugacucauc ucuaggucug ugguuucucc  1560
ccucuucccu uggcagaguu auugagggca ugaucucagg gcugcuaaga uaacauuucu   1620
gaggauucua gaugauccuc uuaaagaaua aaagcacauc cguggaucgg acauggcugc   1680
augugccugc uuaacagggc caacuuaguu ccuacuguuc uguccccuuc aguggaugga   1740
acgugagugu cugaucaucu cucuuggaag uuuucgaac cuuccaagcu cuguggugag    1800
gacaaaccag uguuugaauc auaugcugau aacuguuugc cugugacccu cacaccuugu   1860
ucuucagggu uuuaaugauu uucuguugac aacuuuugca augcuuuccc accaaagugc   1920
uuacuuguaa agaaaacuaa auccuucugu gucccggca gccucagugc agcaacagaa    1980
gccaagggag aaugcugcug guuuggccca uggcacagcc agcuucucug accaguaauc   2040
cggggugacu ugagggucug caaaggcaua gaacucccca guguuuucca ccucauucuc   2100
ccagauugag cucccuucca aaggaucguu ccucucauug cacagccaua uuacaaaggg   2160 uuccugcuc aagugauguu uugguaagaa cuucgcugag uuccacugug gauuacaguu   2220
uguauggacu acuacuguaa auuauagcuu guuuggaggg auauuaguca uuauuuauu    2280 caugacaggu agacuacaau ucgaacuuag gguuaccuca gucuuuagcc auuacugcuu   2340
auuucuuuuc cccaagucac aaaaaacuug uaagcugcug gguuaaagca gaggccaccu   2400
gucagaucua cccuaccuu auuugguuac auggcaccug agaguuucac ucagaccagg    2460
gaucuuccuu aggaggguca aagugcagau cagaccaugc agguaaggug aaccagcugc   2520
acggaccagg uucccgcaaa acauugccag cuagugaggc auaauuugcu caaaguauag   2580
aaacagccca ccugugccca cuuugaccau uggugaggau agauauaaaa ucacuucuuc   2640
caacgaagcc uaggugaaaa ucuauuuaua aauggaccac aacucggggg ugucguuuuu   2700
gugcugugac uuccuaauua uugcuaaaga acuacuguuu aguugguaau gguguaaaau   2760
uacauucagc uccuucuugu cauauaaaag gaauuuggag ggugucgcuu aaaauuuuau   2820
uccaccugua cauuugucac uuuuaaauua aaauugagcu gguaugagag auaaaaaaaa   2880
aaaaaaaaaa a                                                       2891
```

<210> SEQ ID NO 8
<211> LENGTH: 370
<212> TYPE: PRT
<213> ORGANISM: Homo sapiens

<400> SEQUENCE: 8

```
Met Trp Glu Ser Leu Thr Leu Asp Ser Gly Gln Ile Ser Ala Leu Thr
 1               5                  10                  15

Arg Phe Lys Leu Ile Ser Gln Ala Tyr Glu Val Leu Ser Asp Pro Lys
                20                  25                  30

Lys Arg Asp Val Tyr Asp Gln Gly Gly Glu Gln Ala Ile Lys Glu Gly
            35                  40                  45

Gly Ser Gly Ser Pro Ser Phe Ser Ser Pro Met Asp Ile Phe Asp Met
        50                  55                  60

Phe Phe Gly Gly Gly Gly Arg Met Ala Arg Glu Arg Arg Gly Lys Asn
 65                  70                  75                  80

Val Val His Gln Leu Ser Val Thr Leu Glu Asp Leu Tyr Asn Gly Val
```

```
                      85                  90                  95
Thr Lys Lys Leu Ala Leu Gln Lys Asn Val Ile Cys Glu Lys Cys Glu
                100                 105                 110

Gly Val Gly Gly Lys Gly Ser Val Glu Lys Cys Pro Leu Cys Lys
            115                 120                 125

Gly Arg Gly Met Gln Ile His Ile Gln Gln Ile Gly Pro Gly Met Val
            130                 135                 140

Gln Gln Ile Gln Thr Val Cys Ile Glu Cys Lys Gly Gln Gly Glu Arg
145                 150                 155                 160

Ile Asn Pro Lys Asp Arg Cys Glu Ser Cys Ser Gly Ala Lys Val Ile
                165                 170                 175

Arg Glu Lys Lys Ile Ile Glu Val His Val Glu Lys Gly Met Lys Asp
                180                 185                 190

Gly Gln Lys Ile Leu Phe His Gly Glu Gly Asp Gln Glu Pro Glu Leu
            195                 200                 205

Glu Pro Gly Asp Val Ile Ile Val Leu Asp Gln Lys Asp His Ser Val
210                 215                 220

Phe Gln Arg Arg Gly His Asp Leu Ile Met Lys Met Lys Ile Gln Leu
225                 230                 235                 240

Ser Glu Ala Leu Cys Gly Phe Lys Lys Thr Ile Lys Thr Leu Asp Asn
                245                 250                 255

Arg Ile Leu Val Ile Thr Ser Lys Ala Gly Glu Val Ile Lys His Gly
                260                 265                 270

Asp Leu Arg Cys Val Arg Asp Glu Gly Met Pro Ile Tyr Lys Ala Pro
            275                 280                 285

Leu Glu Lys Gly Ile Leu Ile Ile Gln Phe Leu Val Ile Phe Pro Glu
290                 295                 300

Lys His Trp Leu Ser Leu Glu Lys Leu Pro Gln Leu Glu Ala Leu Leu
305                 310                 315                 320

Pro Pro Arg Gln Lys Val Arg Ile Thr Asp Asp Met Asp Gln Val Glu
                325                 330                 335

Leu Lys Glu Phe Cys Pro Asn Glu Gln Asn Trp Arg Gln His Arg Glu
            340                 345                 350

Ala Tyr Glu Glu Asp Glu Asp Gly Pro Gln Ala Gly Val Gln Cys Gln
            355                 360                 365

Thr Ala
    370

<210> SEQ ID NO 9
<211> LENGTH: 14905
<212> TYPE: RNA
<213> ORGANISM: Homo sapiens

<400> SEQUENCE: 9
cagcggugcg agcuccaggc ccaugcacug aggaggcgga aacaagggga gcccccagag      60
cuccaucaag ccccccuccaa aggcucccccu acccggucca cgccccccac ccccccuccc    120
cgccuccucc caauugugca uuuuugcagc cggaggcggc uccgagaugg ggcugugagc     180
uucgcccggg gaggggggaaa gagcagcgag gagugaagcg ggggggugggg gugaagggguu   240 uggauuucgg ggcagggggc gcaccccccgu cagcaggccc ucccccaaggg gcucggaacu    300 cuaccucuuc acccacgccc cuggugcgcu uugccgaagg aaagaauaag aacagagaag     360
gaggaggggg aaaggaggaa aagggggacc ccccaacugg ggggggugaa ggagagaagu      420
agcaggacca gaggggaagg ggcugcugcu ugcaucagcc cacaccaugc ugaccccgcc     480
```

-continued

```
guugcuccug cugcugcccc ugcucucagc ucuggucgcg gcggcuaucg acgcccuaa    540 gacuugcagc cccaagcagu uugccugcag agaucaaaua accuguaucu caaagggcug   600
gcggugcgac ggugagaggg acugcccaga cggaucugac gaggcccug agauuugucc    660 acagaguaag gcccagcgau gccagccaaa cgagcauaac ugccugggua cugagcugug   720
uguucccaug ucccgccucu gcaaugggu ccaggacugc auggacggcu cagaugaggg    780
gccccacugc cgagagcucc aaggcaacug cucucgccug gcugccagc accaugugu     840 ccccacacuc gaugggccca ccugcuacug caacagcagc uuucagcuuc aggcagaugg   900
caagaccugc aaagauuuug augagugcuc aguacggc accugcagcc agcuaugcac     960
caacacagac ggcuccuuca uauguggcug uguugaagga uaccuccugc agccggauaa  1020
ccgcuccugc aaggccaaga cgagccagu agaccggccc cugugcugu ugauagccaa    1080 cucccagaac aucuuggcca cguaccugag ugggcccag gugucuacca ucacaccuac   1140
gagcacgcgg cagaccacag ccauggacuu cagcuaugcc aacgagaccg uaugcugggu  1200
gcauguuggg gacagugcug cucagacgca gcucaagugu gcccgcaugc cuggccuaaa  1260
gggcuucgug gaugagcaca ccaucaacau cccccucagu cugcaccacg uggaacagau  1320
ggccaucgac uggcugacag gcaacuucua cuuuguggau gacaucgaug auaggaucuu  1380
ugucugcaac agaaaugggg acacaugugu cacauugcua gaccuggaac ucuacaaccc  1440
caagggcauu gcccuggacc cugccauggg aaggguguuu ucacugacu augggcagau   1500 cccaaaggug gaacgcugug acauggaugg gcagaaccgc accaagcucg ucgacagcaa  1560
gauuguguuu ccucauggca ucacgcugga ccuggucagc cgccuugucu acgggcaga   1620 ugccuaucug gacauauaug aaguggugga cuaugagggc aagggccgcc agaccaucau  1680
ccagggcauc cugauugagc accuguacgg ccugacugug uuugagaauu aucucuaugc  1740
caccaacucg gacaaugcca augcccagca gaagacgagu gugauccgug uaaccgcuu   1800 uaacagcacc gaguaccagg uugucacccg gguggacaag ggugugcccc uccacaucua  1860 ccaccgagg cgucagcccc gagugaggag ccaugccugu gaaaacgacc aguaugggaa   1920 gccgggugc ugcucugaca ucugccugcu ggccaacagc cacaaggcgc ggaccugccg   1980
cugccguucc ggcuucagcc ugggcaguga cgggaaguca ugcaagaagc cggagcauga  2040
gcuguuccuc guguauggca agggccgcc aggcaucauc cggggcaugg auauggggc    2100 caagguccccg gaugagcaca ugauccccau ugaaaacccuc augaaccccc gagcccugga  2160
cuuccacgcu gagaccggcu ucaucuacuu ugccgacacc accagcuacc ucauuggccg  2220
ccagaagauu gauggcacug agcgggagac cauccugaag gacggcaucc acaaugugga  2280 gggugugcc guggacugga ugggagacaa ucuguacugg acggacgaug ggccaaaaaa  2340
gacaaucagc guggccaggc uggagaaagc ugcucagacc cgcaagacuu aaucgaggg   2400 caaaaugaca caccccaggg cuauuguggu ggaccacucc aaugggugga uguacuggac  2460
agacugggag gaggacccca aggacagucg gcgugggcgg cuggagaggg cguggaugga  2520
uggcucacac cgagacaucu uugucacccu caagacagug cuuugcccca augggcuaag  2580
ccuggacauc ccggcugggc gccucuacug ggugaugcc uucuacgacc gcaucgagac  2640
gauacugcuc aauggcacag accggaagau uguguaugaa ggccugagc ugaaccacgc   2700 cuuuggccug ugucaccaug gcaacuaccu cuucuggacu gaguaucgga guggcagugu  2760
cuaccgcuug gaacggggug uaggaggcgc accccccacu gugacccuuc ugcgcaguga  2820
```

```
gcggcccccc aucuuugaga uccgaaugua ugaugcccag cagcagcaag uuggcaccaa    2880
caaaugccgg gugaacaaug gcggcugcag cagccugugc uuggccaccc cugggagccg    2940
ccagugcgcc ugugcugagg accaggucuu ggacgcagac ggcgucacuu gcuuggcgaa    3000
cccauccuac gugccuccac cccagugcca gccaggcgag uuugccugug ccaacagccg    3060
cugcauccag gagcgcugga agugugacgg agacaacgau ugccuggaca acagugauga    3120
ggccccagcc cucugccauc agcacaccug ccccucggac cgauucaagu gcagaacaa    3180
ccggugcauc cccaaccgcu ggcucugcga cggggacaau gacuguggga acagugaaga    3240
ugaguccaau gccacuuguu cagcccgcac cugccccccc aaccaguucu ccugugccag    3300
uggccgcugc auccccaucu ccuggacgug ugaucuggaa gacgacugug ggaccgcuc    3360
ugaugagucu gcuucgugug ccuaucccac cugcuucccc cugacucagu uuaccugcaa    3420
caauggcaga uguaucaaca ucaacuggag augcgacaau gacaaugacu gugggacaa    3480
cagugacgaa gccggcugca gccacuccug uucuagcacc caguucaagu gcaacagcgg    3540
gcguugcauc cccgagcacu ggaccugcga uggggacaau gacugcggag acuacaguga    3600
ugagacacac gccaacugca ccaaccaggc cacgaggccc ccugguggcu gccacacuga    3660
ugaguuccag ugccggcugg auggacuaug caucccccug cgguggcgcu gcgauggga    3720
cacugacugc auggacucca gcgaugagaa gagcugugag ggagugaccc acgucugcga    3780
ucccagugc aaguuuggcu gcaaggacuc agcucgugc aucagcaaag cgugggugug    3840
ugauggcgac aaugacugug aggauaacuc ggacgaggag aacugcgagu cccuggccug    3900
caggccaccc ucgcaccccuu gugccaacaa caccucaguc ugccugcccc ugacaagcu    3960
gugugauggc aacgacgacu guggcgacgg ucagaugag ggcgagcucu gcgaccagug    4020
cucucugaau aacggugggcu gcagccacaa cugcucagug gcaccuggcg aaggcauugu    4080
guguuccugc ccucugggca uggagcuggg gcccgacaac cacaccugcc agaccagag    4140
cuacugugcc aagcaucuca aaugcagcca aaagugcgac cagaacaagu ucagcgugaa    4200
gugcuccugc uacgagggcu ggucccugga accgacggc gagagcugcc gcagccugga    4260
ccccuucaag ccguucauca uuucuccaa ccgccaugaa auccggcgca ucgaucuuca    4320
caaaggagac uacagcgucc uggugcccgg ccugcgcaac accaucgccc uggacuucca    4380
ccucagccag agcgccccucu acuggaccga cguggugag gacaagaucu accgcgggaa    4440
gcugcuggac aacggagccc ugacuaguu cgagguggug auucaguaug ccuggccac    4500
acccgagggc cuggcuguag acuggauugc aggcaacauc uacugggggg agaguaaccu    4560
ggaucagauc gagguggcca gcuggaugg gaccuccgg accacccugc uggccgguga    4620
cauugagcac ccaagggcaa ucgcacugga ucccgggau gggauccgu uuggacaga    4680
cugggaugcc agccugcccc gcauugaggc agccuccaug aguggggcug gcgccgcac    4740
cgugcaccgg gagaccggcu cugggggcug gcccaacggg cucaccgugg acuaccgga    4800
gaagcgcauc cuuggauug acgccaagguc agaugccauu acucagccc guuacgacgg    4860
cucuggccac auggaggugc uucgggggaca cgaguccugu ucgcacccgu uugcagugac    4920
gcuuacggg gggagcucu acuggacuga cuggcgaaca aacacacugg cuaaggccaa    4980
caagguggacc ggccacaaug ucaccgugguu acagaggacc aacacccagc ccuuugaccu    5040
gcaggugacu caccccuccc gccagcccau ggcucccaau cccugugagg ccaauggggg    5100
ccagggcccc ugcucccacc ugugucucau caacucacaac cggaccgugu ccugcgccug    5160
cccccaccuc augaagcucc acaaggacaa caccaccugc uaugaguuua gaaguuccu    5220
```

| | |
|---|---|
| gcuguacgca cgucagaugg agauccgagg uguggaccug gaugcucccu acuacaacua | 5280 |
| caucucucc uucacggugc ccgacaucga caacgucaca gugcuagacu acgaugcccg | 5340 |
| cgagcagcgu guguacuggu cugacgugcg gacacaggcc aucaagcggg ccuucaucaa | 5400 |
| cggcacaggc guggagacag ucgucucugc agacuugcca aaugcccacg ggcuggcugu | 5460 |
| ggacuggguc ucccgaaacc uguucuggac aagcuaugac accaauaaga agcagaucaa | 5520 |
| uguggcccgg cuggauggcu ccuucaagaa cgcaguggug cagggccugg agcagcccca | 5580 |
| uggccuuguc guccacccuc ugcgugggaa gcucuacugg accgauggug acaacaucag | 5640 |
| cauggccaac auggauggca gcaaucgcac ccugcucuuc aguggccaga agggccccgu | 5700 |
| gggccuggcu auugacuucc ugaaagcaa acucuacugg aucagcuccg ggaaccauac | 5760 |
| caucaaccgc ugcaaccugg augggagugg gcuggagguc aucgaugcca ugcggagcca | 5820 |
| gcugggcaag gccaccgccc uggccaucau ggggacaag cuggugggg cugaucaggu | 5880 |
| gucggaaaag augggcacau gcagcaaggc ugacggcucg ggcuccgugg ccuucggaa | 5940 |
| cagcaccacc cuggugaugc acaugaaggu cuaugacgag agcauccagc uggaccauaa | 6000 |
| gggcaccaac cccugcagug ucaacaacg ugacugcucc cagcucugcc ugcccacguc | 6060 |
| agagacgacc cgcuccugca ugugcacagc cggcuauagc cuccggagug ccagcaggc | 6120 |
| cugcgagggc guagguuccu uucuccugua cucugugcau gagggaauca ggggaauucc | 6180 |
| ccuggauccc aaugacaagu cagaugcccu ggucccagug uccgggaccu cgcuggcugu | 6240 |
| cggcaucgac uuccacgcug aaaaugacac caucuacugg guggacaugg gccugagcac | 6300 |
| gaucagccgg gccaagcggg accagacgug gcgugaagac guggugacca auggcauugg | 6360 |
| ccgugggag ggcauugcag uggacuggau cgcaggcaac aucuacugga cagaccaggg | 6420 |
| cuuugauguc aucgaggucg cccggcucaa uggcccuuc cgcuacgugg ugaucccca | 6480 |
| gggcucuagac aagccccggg ccaucaccgu ccacccggag aaagggguacu guucuggac | 6540 |
| ugagugggu caguauccgc guauugagcg gucucggcua gauggcacgg agcguguggu | 6600 |
| gcuggucaac gucagcauca gcuggcccaa cggcaucuca guggacuacc aggaugggaa | 6660 |
| gcuguacugg ugcgaugcac ggacagacaa gauugaacgg aucgaccugg agacagguga | 6720 |
| gaaccgcgag gugguucugu ccagcaacaa cauggacaug uuucagugu cuguuuuga | 6780 |
| ggauuucauc uacuggagug acaggacuca ugccaacgc ucuaucaagc gcgggagcaa | 6840 |
| agacaaugcc acagacuccg ugccccugcg aaccggcauc ggcguccagc uuaaagacau | 6900 |
| caaagucuuc aaccgggacc ggcagaaagg caccaacgug ugcgcggugg ccaauggcgg | 6960 |
| gugccagcag cugugccugu accggggccg ugggcagcgg gccugcgccu gugcccacgg | 7020 |
| gaugcuggcu aagacggag caucgugccg cgaguaugcc ggcuaccgc ucuacucaga | 7080 |
| gcgcaccauu ucaagaagua uccaccuguc ggaugagcgc aaccucaaug cgcccgugca | 7140 |
| gcccuucgag gacccugagc acaugaagaa cgucaucgcc cuggccuuug acuaccgggc | 7200 |
| aggcaccucu ccgggcaccc caaucgcau cuucuucagc gacauccacu uugggaacau | 7260 |
| ccaacagauc aacgacgaug gcuccaggag gaucaccauu guggaaaacg ugggcuccgu | 7320 |
| ggaaggccug gccuaucacc guggcuggga cacucucuau uggacaagcu acgacaucc | 7380 |
| caccaucacg cgccacacag uggaccagac ccgcccaggg gccuucgagc gugagaccgu | 7440 |
| caucacuaug ucuggagaug accccacgc ggcuucguu uuggacgagu gccagaaccu | 7500 |
| cauguucugg accaacugga augagcagca ucccagcauc augcgggcgg cgcucucggg | 7560 |

```
agccaauguc cugacccuua ucgagaagga cauccguacc cccaauggcc uggccaucga    7620
ccaccgugcc gagaagcucu acuucucuga cgccacccug gacaagaucg agcggugcga    7680
guaugacggc ucccaccgcu augugauccu aaagucagag ccugucacc ccuucgggcu     7740
ggccguguau ggggagcaca uuuucuggac ugacugggug cggcgggcag ugcagcgggc    7800
caacaagcac gugggcagca acaugaagcu gcugcgcgug gacaucccc agcagcccau     7860
gggcaucauc gccguggcca acgacaccaa cagcugugaa cucuccau gccgaaucaa      7920
caacggugcc ugcaggacc uguducugcu cacucaccag ggccauguca acugcucaug    7980
ccgaggggcgaa cgaauccucc aggaugaccu caccugccga gcggugaauu ccucuugccg  8040
agcacaagau gaguuugagu gugccaaugg cgagugcauc aacuucagcc ugaccugcga    8100
cggcguccc cacugcaagg acaaguccga ugagaagcca uccuacugca acucccgccg     8160
cugcaagaag acuuccggc agugcagcaa ugggcgcugu guguccaaca ugcugugug      8220
caacggggcc gacgacugug gggauggcuc ugacgagauc ccuugcaaca agacagccug    8280
uggugugggc gaguuccgcu gccgggacgg gaccugcauc gggaacucca gccgcugcaa    8340
ccaguuugug gauugugagg acgccucaga ugaugaaac ugcagugcca ccgacugcag     8400
cagcuacuuc cgccugggcg ugaagggcgu gcucuuccag cccugcgagc ggaccucacu    8460
cugcuacgca cccagcuggg ugugaugg cgccaaugac ugugggggacu acagugauga    8520
gcgcgacugc ccaggguguga aacgcccag augcccucug aauuacuucg ccugcccuag   8580
ugggcgcugc auccccauga gcuggacgug ugacaaagag gaugacugug aacauggcga    8640
ggacgagacc cacugcaaca guucugcuc agaggcccag uuugagugcc agaaccaucg    8700
cugcaucucc aagcaguggc ugugugacgg cagcgaugac ugggggaug gcucagacga    8760
ggcugcucac ugugaaggca agacgugcgg ccccuccucc uucuccugcc cuggcacccca   8820
cgugugcguc cccgagcgcu ggcucuguga cggugacaaa gacugugcug auggugcaga    8880
cgagagcauc gcagcuggu gcuugcacaa cagcacuugu gacgaccgug aguucaugug     8940
ccagaaccgc cagugcaucc ccaagcacuu cgugugugac cacgaccgug acugugcaga    9000
uggcucugau gagucccccg agugugagua cccgaccugc ggcccaguag auuccgcug     9060
ugccaauggg cgcugucuga gcucccgcca gugggagugu gauggcgaga augacugcca    9120
cgaccagagu gacgaggcuc caagaaccc acacugcacc agccaagagc acaagugcaa     9180
ugccucguca caguuccugu gcagcagugg gcgcugugug gcugaggcac ugcucugcaa    9240
cggccaggau gacugugggcg acagcucgga gagcgugggc ugccacauca augagugucu    9300
cagccgcaag cucagugggcu gcagccagga cugugaggac cucaagaucg gcuucaagug   9360
ccgcugucgc ccuggcuucc ggcugaagga cgacggccg acgugugcug auggggacga    9420
gugcagcacc accuucccu gcagccagcg cugcaucaac acucauggca gcauaagug      9480
ucugugugug gagggcuaug cacccccgcgg cggcgaccc cacagcugca aggcugugac   9540
ugacgaggaa ccguuucuga cuucgccaa ccgguacuac cugcgcaagc ucaaccugga    9600
cggguccaac uacacguuac uuaagcaggg ccugaacaac gccguugccu uggauuuga     9660
cuaccgagag cagaugaucu acuggacaga ugugccacc caggcagca ugauccgaag    9720
gaugcaccuu aacggagca augugcagu ccuacaccgu acaggccuca gcaaccccga    9780
ugggcuggcu guggacuggg ugguggcaa ccuacacgg ugcgacaaag gccgggacac    9840
caucgagug uccaagcuca auggggcua ucggacgguc cugucagcu cuggcuucg     9900
ugagcccagg gcucugguggg uggaugugca gaauggguac cuguacugga cagacugggg   9960
```

```
ugaccauuca cugaucggcc gcaucggcau ggaugggucc agccgcagcg ucaucgugga    10020
caccaagauc acauggccca auggccugac gcuggacuau gucacugagc gcaucuacug    10080
ggccgacgcc cgcgaggacu acauugaauu ugccagccug gauggcucca aucgccacgu    10140
ugugcugagc caggacaucc cgcacaucuu ugcacugacc cuguuugagg acuacgucua    10200
cuggaccgac ugggaaacaa aguccauuaa ccgagcccac aagaccacgg caccaacaa     10260 aacgcuccuc aucagcacgc ugcaccggcc cauggaccug caugucuucc augcccugcg    10320
ccagccagac gugcccaauc accccugcaa ggucaacaau gguggcugca gcaaccugug    10380
ccugcugucc cccgggggag ggcacaaaug ugccugcccc accaacuucu accugggcag    10440
cgaugggcgc accugugugu ccaacugcac ggcuagccag uuuguaugca agaacgacaa    10500
gugcaucccc uucggugga agugugacac cgaggacgac ugcggggacc acucagacga    10560
gcccccggac ugcccugagu caagugccg gcccggacag uuccagugcu ccacagguau    10620
cugcacaaac ccugccuuca ucugcgaugg cgacaaugac ugccaggaca cagugacga    10680 ggccaacugu gacauccacg ucugcuugcc cagucaguuc aaaugcacca acaccaaccg    10740
cuguauuccc ggcaucuucc gcugcaaugg gcaggacaac ugcggagaug ggaggauga    10800 gagggacugc cccgagguga ccugcgcccc caaccaguuc cagugcucca uuaccaaacg    10860
gugcaucccc cgggucuggg ucugcgaccg ggacaaugac ugugggaug gcagugauga    10920 gcccgccaac ugcacccaga ugaccugugg uguggacgag uuccgcugca aggauucggg    10980
ccgcugcauc ccagcgcguu ggaagugugac cggagaggau gacuggggg auggcucgga    11040 ugagcccaag gaagagugug augaacgcac cgugagcca uaccaguucc gcugcaagaa    11100
caaccgcugc gugccggcc gcuggcagug cgacuacgac aacgauugcg gugacaacuc    11160
cgaugaagag agcugcaccc cucggcccug ccccgagagu gaguucuccu gugccaacgg    11220
ccgcugcauc gcggggcgcu ggaaaugcga uggagaccac gacugcgcgg acggcucgga    11280
cgagaaagac ugcaccccc gcugugacau ggaccaguuc cagugcaaga gcggccacug    11340 cauccccug cgcuggcgcu gugacgcaga gccgacugc auggacggca gcgacgagga    11400
ggccugcggc acuggcgugc ggaccugccc ccuggacagu uccagugca acaacaccuu    11460 gugcaagccg cuggccugga agugcgaugg cgaggaugac ugugggggca acucagauga    11520
gaaccccgag gagugugccc gguucgugug cccucccaac cggccccuuc guugcaagaa    11580
ugaccgcguc ugucugugga ucgggcgcca augcgauggc acggacaacu gggggaugg    11640 gacugaugaa gaggacugug agccccccac agcccacacc acccacugca agacaagaa     11700 ggaguuucug ugccggaacc agcgcugccu ccuccuccuc cugcgcugca acauguucga    11760
ugacugcggg gacggcucug acgaggagga cugcagcauc gaccccaagc ugaccagcug    11820
cgccaccaau gccagcaucu gugggacga ggcacgcugc gugcgcaccg agaaagcggc    11880
cuacugugcc ugccgcucgg gcuuccacac cgugcccggc cagcccggau gccaagacau    11940
caacgagugc cugcgcuucg gcaccugcuc ccagcucugc aacaacacca agggcggcca    12000
ccucugcagc ugcgcucgga acuucaugaa gacgcacaac accugcaagg ccgaaggcuc    12060
ugaguaccag guccuguaca ucgcugauga caaugagauc gcagccgau ccccggcca     12120 ccccauucg gcuuacgagc aggcauucca gggugacgag aguccgca uugaugcuau       12180 ggauguccau gucaaggcug gccguguucua uuggaccaac uggcacacgg gcaccaucuc    12240
cuaccgcagc cugccaccug cugcgccucc uaccacuucc aaccgccacc ggcgacagau    12300
```

-continued

```
ugaccggggu gucacccacc ucaacauuuc agggcugaag augcccagag gcaucgccau   12360
cgacuggcug gccggaaacg uguacuggac cgacucgggc cgagauguga uugaggugge   12420 gcagaugaag ggcgagaacc gcaagacgcu caucucgggc augauugacg agccccacgc   12480
cauuguggug gacccacuga gggggaccau guacugguca gacuggggca accaccccaa   12540
gauugagacg gcagcgaugg augggacgcu ucgggagaca cuggugcagg acaacauuca   12600
guggcccaca ggccuggccg uggauuauca caaugagcgg cuguacuggg cagacgccaa   12660
gcuuucaguc aucggcagca uccggcucaa uggcacggac cccauguggg cugcugacag   12720
caaacgaggc cuaagucacc ccuucagcau cgacgucuuu gaggauuaca ucuauggugu   12780
caccuacauc aauaaucgug ucuucaagau ccauaaguuu ggccacagcc ccuuggucaa   12840
ccugacaggg ggccugagcc acgccucuga cgugguccuu uaccaucagc acaagcagcc   12900
cgaagugacc aacccaugug accgcaagaa augcgagugg cucugccugc ugagcccag   12960 uggccuguc ugcaccuguc ccaaugggaa gcggcuggac aacggcacau gcgugccugu   13020
gcccucucca acgccccccc cagaugcucc ccggccugga accuguaacc ugcagugcuu   13080 caacggugge agcuguuucc ucaaugcacg gaggcagccc aagugccgcu gccaaccccg   13140
cuacacgggu gacaaguguy aacuggacca gugcugggag cacugucgca auggggcac   13200 cugugcugcc uccccccucug gcaugcccac gugccggugc cccacgggcu cacgggccc   13260 caaaugcacc cagcagggugu gugcgggcua cugugccaac aacagcaccu gcacugucaa   13320
ccagggcaac cagccccagu gccgaugccu acccggcuuc cugggcgacc gcugccagua   13380
ccggcagugc ucuggcuacu gugagaacuu uggcacaugc cagauggcug cugauggcuc   13440
ccgacaaugc cgcugcacug ccuacuuuga gggaucgagg ugugaggua acaagugcag   13500 ccgcugucuc gaagggggccu guguggucaa caagcagagu ggggaugca ccugcaacug   13560 cacggauggc cgguggccc ccagcugucu gaccugcguc ggccacugca gcaauggcgg   13620
cuccuguacc augaacagca aaaugaugcc ugagugccag ugcccacccc acaugacagg   13680 gccccgguguu gaggagcacg ucuucagcca gcagcagcca ggacauauag ccuccauccu   13740
aaucccucug cuguugcugc ugcugcuggu ucuggugcc ggagugguau ucuggauaa   13800 gcggcgaguc caaggggcua agggcuucca gcaccaacgg augaccaacg gggccaugaa   13860
cguggagauu ggaaacccca ccuacaagau guacgaaggc ggagagccug augaugggg   13920 aggccuacug gacgcugacu uugcccugga cccugacaag cccaccaacu ucaccaaccc   13980
cguguaugcc acacucuaca uggggggcca ugggcagucgc cacucccugg ccagcacggga   14040 cgagaagcga gaaacccugg gccggggccc ugaggacgag auaggggacc ccuuggcaua   14100
gggcccugcc ccgucggacu gccccagaa agccuccugc cccugccgg ugaaguccuu   14160 cagugagccc cuccccagcc agcccuuccc uggcccgcc ggauguauaa auguaaaaau   14220
gaaggaauua cauuuuauau gugagcgagc aagccggcaa gcgagcacag uauuauuucu   14280 ccaucccccuc ccugccugcu ccuuggcacc cccaugcugcc cuucagggag acaggcaggg   14340 aggcuuggg gcugcaccuc cuacccucccc accagaacgc accccacugg gagagcuggu   14400 gugcagccu uccccucccu guauaagaca cuuugccaag gcucucccccu cucgcccau   14460 cccugcuugc ccgcucccac agcuuccuga gggcuaauuc ugggaaggga gaguucuuug   14520
cugccccugu cuggaagacg uggcucuggg ugaggugacgc gggaaaggau ggaguguuu   14580 aguucugggg ggaggccacc ccaaaccccca gccccaacuc caggggcacc uaugagaugg   14640
ccaugcucaa cccccccuccc agacaggccc uccccugucu cagggccccc accgagguuc   14700
```

```
ccagggcugg agacuuccuc ugguaaacau uccuccagcc ucccucccc ugggacgcc    14760 aaggaggugg gccacaccca ggaagggaaa gcgggcagcc ccguuuuggg gacgugaacg   14820
uuuuaauaau uuuugcugaa uuccuuuaca acuaaauaac acagauauug uuauaaauaa   14880
aauuguaaaa aaaaaaaaaa aaaaa                                         14905
```

<210> SEQ ID NO 10
<211> LENGTH: 4544
<212> TYPE: PRT
<213> ORGANISM: Homo sapiens

<400> SEQUENCE: 10

```
Met Leu Thr Pro Pro Leu Leu Leu Pro Leu Leu Ser Ala Leu
1               5                   10                  15

Val Ala Ala Ala Ile Asp Ala Pro Lys Thr Cys Ser Pro Lys Gln Phe
            20                  25                  30

Ala Cys Arg Asp Gln Ile Thr Cys Ile Ser Lys Gly Trp Arg Cys Asp
        35                  40                  45

Gly Glu Arg Asp Cys Pro Asp Gly Ser Asp Glu Ala Pro Glu Ile Cys
    50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
            100                 105                 110

Gly Asn Cys Ser Arg Leu Gly Cys Gln His His Cys Val Pro Thr Leu
        115                 120                 125

Asp Gly Pro Thr Cys Tyr Cys Asn Ser Ser Phe Gln Leu Gln Ala Asp
    130                 135                 140

Gly Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
        195                 200                 205

Ile Leu Ala Thr Tyr Leu Ser Gly Ala Gln Val Ser Thr Ile Thr Pro
    210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
        275                 280                 285

Trp Leu Thr Gly Asn Phe Tyr Phe Val Asp Ile Asp Asp Arg Ile
    290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
                325                 330                 335
```

-continued

```
Val Phe Phe Thr Asp Tyr Gly Gln Ile Pro Lys Val Glu Arg Cys Asp
                340                 345                 350

Met Asp Gly Gln Asn Arg Thr Lys Leu Val Asp Ser Lys Ile Val Phe
            355                 360                 365

Pro His Gly Ile Thr Leu Asp Leu Val Ser Arg Leu Val Tyr Trp Ala
        370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
                405                 410                 415

Thr Val Phe Glu Asn Tyr Leu Tyr Ala Thr Asn Ser Asp Asn Ala Asn
            420                 425                 430

Ala Gln Gln Lys Thr Ser Val Ile Arg Val Asn Arg Phe Asn Ser Thr
        435                 440                 445

Glu Tyr Gln Val Val Thr Arg Val Asp Lys Gly Gly Ala Leu His Ile
    450                 455                 460

Tyr His Gln Arg Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
                485                 490                 495

Asn Ser His Lys Ala Arg Thr Cys Arg Cys Arg Ser Gly Phe Ser Leu
            500                 505                 510

Gly Ser Asp Gly Lys Ser Cys Lys Lys Pro Glu His Glu Leu Phe Leu
        515                 520                 525

Val Tyr Gly Lys Gly Arg Pro Gly Ile Ile Arg Gly Met Asp Met Gly
    530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
                565                 570                 575

Asp Thr Thr Ser Tyr Leu Ile Gly Arg Gln Lys Ile Asp Gly Thr Glu
            580                 585                 590

Arg Glu Thr Ile Leu Lys Asp Gly Ile His Asn Val Glu Gly Val Ala
        595                 600                 605

Val Asp Trp Met Gly Asp Asn Leu Tyr Trp Thr Asp Asp Gly Pro Lys
    610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
                645                 650                 655

Pro Leu Asn Gly Trp Met Tyr Trp Thr Asp Trp Glu Glu Asp Pro Lys
            660                 665                 670

Asp Ser Arg Arg Gly Arg Leu Glu Arg Ala Trp Met Asp Gly Ser His
        675                 680                 685

Arg Asp Ile Phe Val Thr Ser Lys Thr Val Leu Trp Pro Asn Gly Leu
    690                 695                 700

Ser Leu Asp Ile Pro Ala Gly Arg Leu Tyr Trp Val Asp Ala Phe Tyr
705                 710                 715                 720

Asp Arg Ile Glu Thr Ile Leu Leu Asn Gly Thr Asp Arg Lys Ile Val
                725                 730                 735

Tyr Glu Gly Pro Glu Leu Asn His Ala Phe Gly Leu Cys His His Gly
            740                 745                 750
```

```
Asn Tyr Leu Phe Trp Thr Glu Tyr Arg Ser Gly Ser Val Tyr Arg Leu
            755                 760                 765

Glu Arg Gly Val Gly Gly Ala Pro Pro Thr Val Thr Leu Leu Arg Ser
770                 775                 780

Glu Arg Pro Pro Ile Phe Glu Ile Arg Met Tyr Asp Ala Gln Gln Gln
785                 790                 795                 800

Gln Val Gly Thr Asn Lys Cys Arg Val Asn Asn Gly Gly Cys Ser Ser
                805                 810                 815

Leu Cys Leu Ala Thr Pro Gly Ser Arg Gln Cys Ala Cys Ala Glu Asp
                820                 825                 830

Gln Val Leu Asp Ala Asp Gly Val Thr Cys Leu Ala Asn Pro Ser Tyr
                835                 840                 845

Val Pro Pro Pro Gln Cys Gln Pro Gly Glu Phe Ala Cys Ala Asn Ser
850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
                885                 890                 895

Ser Asp Arg Phe Lys Cys Glu Asn Asn Arg Cys Ile Pro Asn Arg Trp
                900                 905                 910

Leu Cys Asp Gly Asp Asn Asp Cys Gly Asn Ser Glu Asp Glu Ser Asn
                915                 920                 925

Ala Thr Cys Ser Ala Arg Thr Cys Pro Pro Asn Gln Phe Ser Cys Ala
                930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
                965                 970                 975

Phe Pro Leu Thr Gln Phe Thr Cys Asn Asn Gly Arg Cys Ile Asn Ile
                980                 985                 990

Asn Trp Arg Cys Asp Asn Asp Asn Asp Cys Gly Asp Asn Ser Asp Glu
                995                 1000                1005

Ala Gly Cys Ser His Ser Cys Ser Ser Thr Gln Phe Lys Cys Asn
    1010                1015                1020

Ser Gly Arg Cys Ile Pro Glu His Trp Thr Cys Asp Gly Asp Asn
    1025                1030                1035

Asp Cys Gly Asp Tyr Ser Asp Glu Thr His Ala Asn Cys Thr Asn
    1040                1045                1050

Gln Ala Thr Arg Pro Pro Gly Gly Cys His Thr Asp Glu Phe Gln
    1055                1060                1065

Cys Arg Leu Asp Gly Leu Cys Ile Pro Leu Arg Trp Arg Cys Asp
    1070                1075                1080

Gly Asp Thr Asp Cys Met Asp Ser Ser Asp Glu Lys Ser Cys Glu
    1085                1090                1095

Gly Val Thr His Val Cys Asp Pro Ser Val Lys Phe Gly Cys Lys
    1100                1105                1110

Asp Ser Ala Arg Cys Ile Ser Lys Ala Trp Val Cys Asp Gly Asp
    1115                1120                1125

Asn Asp Cys Glu Asp Asn Ser Asp Glu Glu Asn Cys Glu Ser Leu
    1130                1135                1140

Ala Cys Arg Pro Pro Ser His Pro Cys Ala Asn Asn Thr Ser Val
    1145                1150                1155

Cys Leu Pro Pro Asp Lys Leu Cys Asp Gly Asn Asp Asp Cys Gly
```

-continued

```
           1160                1165                1170
Asp Gly Ser Asp Glu Gly Glu Leu Cys Asp Gln Cys Ser Leu Asn
           1175                1180                1185
Asn Gly Gly Cys Ser His Asn Cys Ser Val Ala Pro Gly Glu Gly
           1190                1195                1200
Ile Val Cys Ser Cys Pro Leu Gly Met Glu Leu Gly Pro Asp Asn
           1205                1210                1215
His Thr Cys Gln Ile Gln Ser Tyr Cys Ala Lys His Leu Lys Cys
           1220                1225                1230
Ser Gln Lys Cys Asp Gln Asn Lys Phe Ser Val Lys Cys Ser Cys
           1235                1240                1245
Tyr Glu Gly Trp Val Leu Glu Pro Asp Gly Glu Ser Cys Arg Ser
           1250                1255                1260
Leu Asp Pro Phe Lys Pro Phe Ile Ile Phe Ser Asn Arg His Glu
           1265                1270                1275
Ile Arg Arg Ile Asp Leu His Lys Gly Asp Tyr Ser Val Leu Val
           1280                1285                1290
Pro Gly Leu Arg Asn Thr Ile Ala Leu Asp Phe His Leu Ser Gln
           1295                1300                1305
Ser Ala Leu Tyr Trp Thr Asp Val Val Glu Asp Lys Ile Tyr Arg
           1310                1315                1320
Gly Lys Leu Leu Asp Asn Gly Ala Leu Thr Ser Phe Glu Val Val
           1325                1330                1335
Ile Gln Tyr Gly Leu Ala Thr Pro Glu Gly Leu Ala Val Asp Trp
           1340                1345                1350
Ile Ala Gly Asn Ile Tyr Trp Val Glu Ser Asn Leu Asp Gln Ile
           1355                1360                1365
Glu Val Ala Lys Leu Asp Gly Thr Leu Arg Thr Thr Leu Leu Ala
           1370                1375                1380
Gly Asp Ile Glu His Pro Arg Ala Ile Ala Leu Asp Pro Arg Asp
           1385                1390                1395
Gly Ile Leu Phe Trp Thr Asp Trp Asp Ala Ser Leu Pro Arg Ile
           1400                1405                1410
Glu Ala Ala Ser Met Ser Gly Ala Gly Arg Arg Thr Val His Arg
           1415                1420                1425
Glu Thr Gly Ser Gly Gly Trp Pro Asn Gly Leu Thr Val Asp Tyr
           1430                1435                1440
Leu Glu Lys Arg Ile Leu Trp Ile Asp Ala Arg Ser Asp Ala Ile
           1445                1450                1455
Tyr Ser Ala Arg Tyr Asp Gly Ser Gly His Met Glu Val Leu Arg
           1460                1465                1470
Gly His Glu Phe Leu Ser His Pro Phe Ala Val Thr Leu Tyr Gly
           1475                1480                1485
Gly Glu Val Tyr Trp Thr Asp Trp Arg Thr Asn Thr Leu Ala Lys
           1490                1495                1500
Ala Asn Lys Trp Thr Gly His Asn Val Thr Val Val Gln Arg Thr
           1505                1510                1515
Asn Thr Gln Pro Phe Asp Leu Gln Val Tyr His Pro Ser Arg Gln
           1520                1525                1530
Pro Met Ala Pro Asn Pro Cys Glu Ala Asn Gly Gly Gln Gly Pro
           1535                1540                1545
Cys Ser His Leu Cys Leu Ile Asn Tyr Asn Arg Thr Val Ser Cys
           1550                1555                1560
```

```
Ala Cys Pro His Leu Met Lys Leu His Lys Asp Asn Thr Thr Cys
1565                1570            1575

Tyr Glu Phe Lys Lys Phe Leu Leu Tyr Ala Arg Gln Met Glu Ile
1580                1585            1590

Arg Gly Val Asp Leu Asp Ala Pro Tyr Tyr Asn Tyr Ile Ile Ser
1595                1600            1605

Phe Thr Val Pro Asp Ile Asp Asn Val Thr Val Leu Asp Tyr Asp
1610                1615            1620

Ala Arg Glu Gln Arg Val Tyr Trp Ser Asp Val Arg Thr Gln Ala
1625                1630            1635

Ile Lys Arg Ala Phe Ile Asn Gly Thr Gly Val Glu Thr Val Val
1640                1645            1650

Ser Ala Asp Leu Pro Asn Ala His Gly Leu Ala Val Asp Trp Val
1655                1660            1665

Ser Arg Asn Leu Phe Trp Thr Ser Tyr Asp Thr Asn Lys Lys Gln
1670                1675            1680

Ile Asn Val Ala Arg Leu Asp Gly Ser Phe Lys Asn Ala Val Val
1685                1690            1695

Gln Gly Leu Glu Gln Pro His Gly Leu Val Val His Pro Leu Arg
1700                1705            1710

Gly Lys Leu Tyr Trp Thr Asp Gly Asp Asn Ile Ser Met Ala Asn
1715                1720            1725

Met Asp Gly Ser Asn Arg Thr Leu Leu Phe Ser Gly Gln Lys Gly
1730                1735            1740

Pro Val Gly Leu Ala Ile Asp Phe Pro Glu Ser Lys Leu Tyr Trp
1745                1750            1755

Ile Ser Ser Gly Asn His Thr Ile Asn Arg Cys Asn Leu Asp Gly
1760                1765            1770

Ser Gly Leu Glu Val Ile Asp Ala Met Arg Ser Gln Leu Gly Lys
1775                1780            1785

Ala Thr Ala Leu Ala Ile Met Gly Asp Lys Leu Trp Trp Ala Asp
1790                1795            1800

Gln Val Ser Glu Lys Met Gly Thr Cys Ser Lys Ala Asp Gly Ser
1805                1810            1815

Gly Ser Val Val Leu Arg Asn Ser Thr Thr Leu Val Met His Met
1820                1825            1830

Lys Val Tyr Asp Glu Ser Ile Gln Leu Asp His Lys Gly Thr Asn
1835                1840            1845

Pro Cys Ser Val Asn Asn Gly Asp Cys Ser Gln Leu Cys Leu Pro
1850                1855            1860

Thr Ser Glu Thr Thr Arg Ser Cys Met Cys Thr Ala Gly Tyr Ser
1865                1870            1875

Leu Arg Ser Gly Gln Gln Ala Cys Glu Gly Val Gly Ser Phe Leu
1880                1885            1890

Leu Tyr Ser Val His Glu Gly Ile Arg Gly Ile Pro Leu Asp Pro
1895                1900            1905

Asn Asp Lys Ser Asp Ala Leu Val Pro Val Ser Gly Thr Ser Leu
1910                1915            1920

Ala Val Gly Ile Asp Phe His Ala Glu Asn Asp Thr Ile Tyr Trp
1925                1930            1935

Val Asp Met Gly Leu Ser Thr Ile Ser Arg Ala Lys Arg Asp Gln
1940                1945            1950
```

-continued

Thr Trp Arg Glu Asp Val Val Thr Asn Gly Ile Gly Arg Val Glu
    1955                1960                1965

Gly Ile Ala Val Asp Trp Ile Ala Gly Asn Ile Tyr Trp Thr Asp
    1970                1975                1980

Gln Gly Phe Asp Val Ile Glu Val Ala Arg Leu Asn Gly Ser Phe
    1985                1990                1995

Arg Tyr Val Val Ile Ser Gln Gly Leu Asp Lys Pro Arg Ala Ile
    2000                2005                2010

Thr Val His Pro Glu Lys Gly Tyr Leu Phe Trp Thr Glu Trp Gly
    2015                2020                2025

Gln Tyr Pro Arg Ile Glu Arg Ser Arg Leu Asp Gly Thr Glu Arg
    2030                2035                2040

Val Val Leu Val Asn Val Ser Ile Ser Trp Pro Asn Gly Ile Ser
    2045                2050                2055

Val Asp Tyr Gln Asp Gly Lys Leu Tyr Trp Cys Asp Ala Arg Thr
    2060                2065                2070

Asp Lys Ile Glu Arg Ile Asp Leu Glu Thr Gly Glu Asn Arg Glu
    2075                2080                2085

Val Val Leu Ser Ser Asn Asn Met Asp Met Phe Ser Val Ser Val
    2090                2095                2100

Phe Glu Asp Phe Ile Tyr Trp Ser Asp Arg Thr His Ala Asn Gly
    2105                2110                2115

Ser Ile Lys Arg Gly Ser Lys Asp Asn Ala Thr Asp Ser Val Pro
    2120                2125                2130

Leu Arg Thr Gly Ile Gly Val Gln Leu Lys Asp Ile Lys Val Phe
    2135                2140                2145

Asn Arg Asp Arg Gln Lys Gly Thr Asn Val Cys Ala Val Ala Asn
    2150                2155                2160

Gly Gly Cys Gln Gln Leu Cys Leu Tyr Arg Gly Arg Gly Gln Arg
    2165                2170                2175

Ala Cys Ala Cys Ala His Gly Met Leu Ala Glu Asp Gly Ala Ser
    2180                2185                2190

Cys Arg Glu Tyr Ala Gly Tyr Leu Leu Tyr Ser Glu Arg Thr Ile
    2195                2200                2205

Leu Lys Ser Ile His Leu Ser Asp Glu Arg Asn Leu Asn Ala Pro
    2210                2215                2220

Val Gln Pro Phe Glu Asp Pro Glu His Met Lys Asn Val Ile Ala
    2225                2230                2235

Leu Ala Phe Asp Tyr Arg Ala Gly Thr Ser Pro Gly Thr Pro Asn
    2240                2245                2250

Arg Ile Phe Phe Ser Asp Ile His Phe Gly Asn Ile Gln Gln Ile
    2255                2260                2265

Asn Asp Asp Gly Ser Arg Arg Ile Thr Ile Val Glu Asn Val Gly
    2270                2275                2280

Ser Val Glu Gly Leu Ala Tyr His Arg Gly Trp Asp Thr Leu Tyr
    2285                2290                2295

Trp Thr Ser Tyr Thr Thr Ser Thr Ile Thr Arg His Thr Val Asp
    2300                2305                2310

Gln Thr Arg Pro Gly Ala Phe Glu Arg Glu Thr Val Ile Thr Met
    2315                2320                2325

Ser Gly Asp Asp His Pro Arg Ala Phe Val Leu Asp Glu Cys Gln
    2330                2335                2340

Asn Leu Met Phe Trp Thr Asn Trp Asn Glu Gln His Pro Ser Ile

-continued

```
            2345                2350                2355
Met Arg Ala Ala Leu Ser Gly Ala Asn Val Leu Thr Leu Ile Glu
            2360                2365                2370
Lys Asp Ile Arg Thr Pro Asn Gly Leu Ala Ile Asp His Arg Ala
            2375                2380                2385
Glu Lys Leu Tyr Phe Ser Asp Ala Thr Leu Asp Lys Ile Glu Arg
            2390                2395                2400
Cys Glu Tyr Asp Gly Ser His Arg Tyr Val Ile Leu Lys Ser Glu
            2405                2410                2415
Pro Val His Pro Phe Gly Leu Ala Val Tyr Gly Glu His Ile Phe
            2420                2425                2430
Trp Thr Asp Trp Val Arg Arg Ala Val Gln Arg Ala Asn Lys His
            2435                2440                2445
Val Gly Ser Asn Met Lys Leu Leu Arg Val Asp Ile Pro Gln Gln
            2450                2455                2460
Pro Met Gly Ile Ile Ala Val Ala Asn Asp Thr Asn Ser Cys Glu
            2465                2470                2475
Leu Ser Pro Cys Arg Ile Asn Asn Gly Gly Cys Gln Asp Leu Cys
            2480                2485                2490
Leu Leu Thr His Gln Gly His Val Asn Cys Ser Cys Arg Gly Gly
            2495                2500                2505
Arg Ile Leu Gln Asp Asp Leu Thr Cys Arg Ala Val Asn Ser Ser
            2510                2515                2520
Cys Arg Ala Gln Asp Glu Phe Glu Cys Ala Asn Gly Glu Cys Ile
            2525                2530                2535
Asn Phe Ser Leu Thr Cys Asp Gly Val Pro His Cys Lys Asp Lys
            2540                2545                2550
Ser Asp Glu Lys Pro Ser Tyr Cys Asn Ser Arg Arg Cys Lys Lys
            2555                2560                2565
Thr Phe Arg Gln Cys Ser Asn Gly Arg Cys Val Ser Asn Met Leu
            2570                2575                2580
Trp Cys Asn Gly Ala Asp Asp Cys Gly Asp Gly Ser Asp Glu Ile
            2585                2590                2595
Pro Cys Asn Lys Thr Ala Cys Gly Val Gly Glu Phe Arg Cys Arg
            2600                2605                2610
Asp Gly Thr Cys Ile Gly Asn Ser Ser Arg Cys Asn Gln Phe Val
            2615                2620                2625
Asp Cys Glu Asp Ala Ser Asp Glu Met Asn Cys Ser Ala Thr Asp
            2630                2635                2640
Cys Ser Ser Tyr Phe Arg Leu Gly Val Lys Gly Val Leu Phe Gln
            2645                2650                2655
Pro Cys Glu Arg Thr Ser Leu Cys Tyr Ala Pro Ser Trp Val Cys
            2660                2665                2670
Asp Gly Ala Asn Asp Cys Gly Asp Tyr Ser Asp Glu Arg Asp Cys
            2675                2680                2685
Pro Gly Val Lys Arg Pro Arg Cys Pro Leu Asn Tyr Phe Ala Cys
            2690                2695                2700
Pro Ser Gly Arg Cys Ile Pro Met Ser Trp Thr Cys Asp Lys Glu
            2705                2710                2715
Asp Asp Cys Glu His Gly Glu Asp Glu Thr His Cys Asn Lys Phe
            2720                2725                2730
Cys Ser Glu Ala Gln Phe Glu Cys Gln Asn His Arg Cys Ile Ser
            2735                2740                2745
```

```
Lys Gln Trp Leu Cys Asp Gly Ser Asp Cys Gly Asp Gly Ser
    2750                2755                2760

Asp Glu Ala Ala His Cys Glu Gly Lys Thr Cys Gly Pro Ser Ser
    2765                2770                2775

Phe Ser Cys Pro Gly Thr His Val Cys Val Pro Glu Arg Trp Leu
    2780                2785                2790

Cys Asp Gly Asp Lys Asp Cys Ala Asp Gly Ala Asp Glu Ser Ile
    2795                2800                2805

Ala Ala Gly Cys Leu Tyr Asn Ser Thr Cys Asp Asp Arg Glu Phe
    2810                2815                2820

Met Cys Gln Asn Arg Gln Cys Ile Pro Lys His Phe Val Cys Asp
    2825                2830                2835

His Asp Arg Asp Cys Ala Asp Gly Ser Asp Glu Ser Pro Glu Cys
    2840                2845                2850

Glu Tyr Pro Thr Cys Gly Pro Ser Glu Phe Arg Cys Ala Asn Gly
    2855                2860                2865

Arg Cys Leu Ser Ser Arg Gln Trp Glu Cys Asp Gly Glu Asn Asp
    2870                2875                2880

Cys His Asp Gln Ser Asp Glu Ala Pro Lys Asn Pro His Cys Thr
    2885                2890                2895

Ser Gln Glu His Lys Cys Asn Ala Ser Ser Gln Phe Leu Cys Ser
    2900                2905                2910

Ser Gly Arg Cys Val Ala Glu Ala Leu Leu Cys Asn Gly Gln Asp
    2915                2920                2925

Asp Cys Gly Asp Ser Ser Asp Glu Arg Gly Cys His Ile Asn Glu
    2930                2935                2940

Cys Leu Ser Arg Lys Leu Ser Gly Cys Ser Gln Asp Cys Glu Asp
    2945                2950                2955

Leu Lys Ile Gly Phe Lys Cys Arg Cys Arg Pro Gly Phe Arg Leu
    2960                2965                2970

Lys Asp Asp Gly Arg Thr Cys Ala Asp Val Asp Glu Cys Ser Thr
    2975                2980                2985

Thr Phe Pro Cys Ser Gln Arg Cys Ile Asn Thr His Gly Ser Tyr
    2990                2995                3000

Lys Cys Leu Cys Val Glu Gly Tyr Ala Pro Arg Gly Gly Asp Pro
    3005                3010                3015

His Ser Cys Lys Ala Val Thr Asp Glu Glu Pro Phe Leu Ile Phe
    3020                3025                3030

Ala Asn Arg Tyr Tyr Leu Arg Lys Leu Asn Leu Asp Gly Ser Asn
    3035                3040                3045

Tyr Thr Leu Leu Lys Gln Gly Leu Asn Asn Ala Val Ala Leu Asp
    3050                3055                3060

Phe Asp Tyr Arg Glu Gln Met Ile Tyr Trp Thr Asp Val Thr Thr
    3065                3070                3075

Gln Gly Ser Met Ile Arg Arg Met His Leu Asn Gly Ser Asn Val
    3080                3085                3090

Gln Val Leu His Arg Thr Gly Leu Ser Asn Pro Asp Gly Leu Ala
    3095                3100                3105

Val Asp Trp Val Gly Gly Asn Leu Tyr Trp Cys Asp Lys Gly Arg
    3110                3115                3120

Asp Thr Ile Glu Val Ser Lys Leu Asn Gly Ala Tyr Arg Thr Val
    3125                3130                3135
```

-continued

Leu Val Ser Ser Gly Leu Arg Glu Pro Arg Ala Leu Val Val Asp
3140                3145                3150

Val Gln Asn Gly Tyr Leu Tyr Trp Thr Asp Trp Gly Asp His Ser
3155                3160                3165

Leu Ile Gly Arg Ile Gly Met Asp Gly Ser Ser Arg Ser Val Ile
3170                3175                3180

Val Asp Thr Lys Ile Thr Trp Pro Asn Gly Leu Thr Leu Asp Tyr
3185                3190                3195

Val Thr Glu Arg Ile Tyr Trp Ala Asp Ala Arg Glu Asp Tyr Ile
3200                3205                3210

Glu Phe Ala Ser Leu Asp Gly Ser Asn Arg His Val Val Leu Ser
3215                3220                3225

Gln Asp Ile Pro His Ile Phe Ala Leu Thr Leu Phe Glu Asp Tyr
3230                3235                3240

Val Tyr Trp Thr Asp Trp Glu Thr Lys Ser Ile Asn Arg Ala His
3245                3250                3255

Lys Thr Thr Gly Thr Asn Lys Thr Leu Leu Ile Ser Thr Leu His
3260                3265                3270

Arg Pro Met Asp Leu His Val Phe His Ala Leu Arg Gln Pro Asp
3275                3280                3285

Val Pro Asn His Pro Cys Lys Val Asn Asn Gly Gly Cys Ser Asn
3290                3295                3300

Leu Cys Leu Leu Ser Pro Gly Gly Gly His Lys Cys Ala Cys Pro
3305                3310                3315

Thr Asn Phe Tyr Leu Gly Ser Asp Gly Arg Thr Cys Val Ser Asn
3320                3325                3330

Cys Thr Ala Ser Gln Phe Val Cys Lys Asn Asp Lys Cys Ile Pro
3335                3340                3345

Phe Trp Trp Lys Cys Asp Thr Glu Asp Asp Cys Gly Asp His Ser
3350                3355                3360

Asp Glu Pro Pro Asp Cys Pro Glu Phe Lys Cys Arg Pro Gly Gln
3365                3370                3375

Phe Gln Cys Ser Thr Gly Ile Cys Thr Asn Pro Ala Phe Ile Cys
3380                3385                3390

Asp Gly Asp Asn Asp Cys Gln Asp Asn Ser Asp Glu Ala Asn Cys
3395                3400                3405

Asp Ile His Val Cys Leu Pro Ser Gln Phe Lys Cys Thr Asn Thr
3410                3415                3420

Asn Arg Cys Ile Pro Gly Ile Phe Arg Cys Asn Gly Gln Asp Asn
3425                3430                3435

Cys Gly Asp Gly Glu Asp Glu Arg Asp Cys Pro Glu Val Thr Cys
3440                3445                3450

Ala Pro Asn Gln Phe Gln Cys Ser Ile Thr Lys Arg Cys Ile Pro
3455                3460                3465

Arg Val Trp Val Cys Asp Arg Asp Asn Asp Cys Val Asp Gly Ser
3470                3475                3480

Asp Glu Pro Ala Asn Cys Thr Gln Met Thr Cys Gly Val Asp Glu
3485                3490                3495

Phe Arg Cys Lys Asp Ser Gly Arg Cys Ile Pro Ala Arg Trp Lys
3500                3505                3510

Cys Asp Gly Glu Asp Cys Gly Asp Gly Ser Asp Glu Pro Lys
3515                3520                3525

Glu Glu Cys Asp Glu Arg Thr Cys Glu Pro Tyr Gln Phe Arg Cys

-continued

```
            3530                3535                3540

Lys Asn Asn Arg Cys Val Pro Gly Arg Trp Gln Cys Asp Tyr Asp
    3545                3550                3555

Asn Asp Cys Gly Asp Asn Ser Asp Glu Glu Ser Cys Thr Pro Arg
    3560                3565                3570

Pro Cys Ser Glu Ser Glu Phe Ser Cys Ala Asn Gly Arg Cys Ile
    3575                3580                3585

Ala Gly Arg Trp Lys Cys Asp Gly Asp His Asp Cys Ala Asp Gly
    3590                3595                3600

Ser Asp Glu Lys Asp Cys Thr Pro Arg Cys Asp Met Asp Gln Phe
    3605                3610                3615

Gln Cys Lys Ser Gly His Cys Ile Pro Leu Arg Trp Arg Cys Asp
    3620                3625                3630

Ala Asp Ala Asp Cys Met Asp Gly Ser Asp Glu Glu Ala Cys Gly
    3635                3640                3645

Thr Gly Val Arg Thr Cys Pro Leu Asp Glu Phe Gln Cys Asn Asn
    3650                3655                3660

Thr Leu Cys Lys Pro Leu Ala Trp Lys Cys Asp Gly Glu Asp Asp
    3665                3670                3675

Cys Gly Asp Asn Ser Asp Glu Asn Pro Glu Glu Cys Ala Arg Phe
    3680                3685                3690

Val Cys Pro Pro Asn Arg Pro Phe Arg Cys Lys Asn Asp Arg Val
    3695                3700                3705

Cys Leu Trp Ile Gly Arg Gln Cys Asp Gly Thr Asp Asn Cys Gly
    3710                3715                3720

Asp Gly Thr Asp Glu Glu Asp Cys Glu Pro Pro Thr Ala His Thr
    3725                3730                3735

Thr His Cys Lys Asp Lys Lys Glu Phe Leu Cys Arg Asn Gln Arg
    3740                3745                3750

Cys Leu Ser Ser Ser Leu Arg Cys Asn Met Phe Asp Asp Cys Gly
    3755                3760                3765

Asp Gly Ser Asp Glu Glu Asp Cys Ser Ile Asp Pro Lys Leu Thr
    3770                3775                3780

Ser Cys Ala Thr Asn Ala Ser Ile Cys Gly Asp Glu Ala Arg Cys
    3785                3790                3795

Val Arg Thr Glu Lys Ala Ala Tyr Cys Ala Cys Arg Ser Gly Phe
    3800                3805                3810

His Thr Val Pro Gly Gln Pro Gly Cys Gln Asp Ile Asn Glu Cys
    3815                3820                3825

Leu Arg Phe Gly Thr Cys Ser Gln Leu Cys Asn Asn Thr Lys Gly
    3830                3835                3840

Gly His Leu Cys Ser Cys Ala Arg Asn Phe Met Lys Thr His Asn
    3845                3850                3855

Thr Cys Lys Ala Glu Gly Ser Glu Tyr Gln Val Leu Tyr Ile Ala
    3860                3865                3870

Asp Asp Asn Glu Ile Arg Ser Leu Phe Pro Gly His Pro His Ser
    3875                3880                3885

Ala Tyr Glu Gln Ala Phe Gln Gly Asp Glu Ser Val Arg Ile Asp
    3890                3895                3900

Ala Met Asp Val His Val Lys Ala Gly Arg Val Tyr Trp Thr Asn
    3905                3910                3915

Trp His Thr Gly Thr Ile Ser Tyr Arg Ser Leu Pro Pro Ala Ala
    3920                3925                3930
```

```
Pro Pro Thr Thr Ser Asn Arg His Arg Gln Ile Asp Arg Gly
    3935            3940            3945

Val Thr His Leu Asn Ile Ser Gly Leu Lys Met Pro Arg Gly Ile
    3950            3955            3960

Ala Ile Asp Trp Val Ala Gly Asn Val Tyr Trp Thr Asp Ser Gly
    3965            3970            3975

Arg Asp Val Ile Glu Val Ala Gln Met Lys Gly Glu Asn Arg Lys
    3980            3985            3990

Thr Leu Ile Ser Gly Met Ile Asp Glu Pro His Ala Ile Val Val
    3995            4000            4005

Asp Pro Leu Arg Gly Thr Met Tyr Trp Ser Asp Trp Gly Asn His
    4010            4015            4020

Pro Lys Ile Glu Thr Ala Ala Met Asp Gly Thr Leu Arg Glu Thr
    4025            4030            4035

Leu Val Gln Asp Asn Ile Gln Trp Pro Thr Gly Leu Ala Val Asp
    4040            4045            4050

Tyr His Asn Glu Arg Leu Tyr Trp Ala Asp Ala Lys Leu Ser Val
    4055            4060            4065

Ile Gly Ser Ile Arg Leu Asn Gly Thr Asp Pro Ile Val Ala Ala
    4070            4075            4080

Asp Ser Lys Arg Gly Leu Ser His Pro Phe Ser Ile Asp Val Phe
    4085            4090            4095

Glu Asp Tyr Ile Tyr Gly Val Thr Tyr Ile Asn Asn Arg Val Phe
    4100            4105            4110

Lys Ile His Lys Phe Gly His Ser Pro Leu Val Asn Leu Thr Gly
    4115            4120            4125

Gly Leu Ser His Ala Ser Asp Val Val Leu Tyr His Gln His Lys
    4130            4135            4140

Gln Pro Glu Val Thr Asn Pro Cys Asp Arg Lys Lys Cys Glu Trp
    4145            4150            4155

Leu Cys Leu Leu Ser Pro Ser Gly Pro Val Cys Thr Cys Pro Asn
    4160            4165            4170

Gly Lys Arg Leu Asp Asn Gly Thr Cys Val Pro Val Pro Ser Pro
    4175            4180            4185

Thr Pro Pro Pro Asp Ala Pro Arg Pro Gly Thr Cys Asn Leu Gln
    4190            4195            4200

Cys Phe Asn Gly Gly Ser Cys Phe Leu Asn Ala Arg Arg Gln Pro
    4205            4210            4215

Lys Cys Arg Cys Gln Pro Arg Tyr Thr Gly Asp Lys Cys Glu Leu
    4220            4225            4230

Asp Gln Cys Trp Glu His Cys Arg Asn Gly Gly Thr Cys Ala Ala
    4235            4240            4245

Ser Pro Ser Gly Met Pro Thr Cys Arg Cys Pro Thr Gly Phe Thr
    4250            4255            4260

Gly Pro Lys Cys Thr Gln Gln Val Cys Ala Gly Tyr Cys Ala Asn
    4265            4270            4275

Asn Ser Thr Cys Thr Val Asn Gln Gly Asn Gln Pro Gln Cys Arg
    4280            4285            4290

Cys Leu Pro Gly Phe Leu Gly Asp Arg Cys Gln Tyr Arg Gln Cys
    4295            4300            4305

Ser Gly Tyr Cys Glu Asn Phe Gly Thr Cys Gln Met Ala Ala Asp
    4310            4315            4320
```

| | | | | | | | | | | |
|---|---|---|---|---|---|---|---|---|---|---|
| Gly | Ser | Arg | Gln | Cys | Arg | Cys | Thr | Ala | Tyr | Phe | Glu | Gly | Ser | Arg |
| | 4325 | | | | 4330 | | | | | 4335 | | | | |

Gly Ser Arg Gln Cys Arg Cys Thr Ala Tyr Phe Glu Gly Ser Arg
    4325                4330                4335

Cys Glu Val Asn Lys Cys Ser Arg Cys Leu Glu Gly Ala Cys Val
    4340                4345                4350

Val Asn Lys Gln Ser Gly Asp Val Thr Cys Asn Cys Thr Asp Gly
    4355                4360                4365

Arg Val Ala Pro Ser Cys Leu Thr Cys Val Gly His Cys Ser Asn
    4370                4375                4380

Gly Gly Ser Cys Thr Met Asn Ser Lys Met Met Pro Glu Cys Gln
    4385                4390                4395

Cys Pro Pro His Met Thr Gly Pro Arg Cys Glu Glu His Val Phe
    4400                4405                4410

Ser Gln Gln Gln Pro Gly His Ile Ala Ser Ile Leu Ile Pro Leu
    4415                4420                4425

Leu Leu Leu Leu Leu Leu Val Leu Val Ala Gly Val Val Phe Trp
    4430                4435                4440

Tyr Lys Arg Arg Val Gln Gly Ala Lys Gly Phe Gln His Gln Arg
    4445                4450                4455

Met Thr Asn Gly Ala Met Asn Val Glu Ile Gly Asn Pro Thr Tyr
    4460                4465                4470

Lys Met Tyr Glu Gly Gly Glu Pro Asp Asp Val Gly Gly Leu Leu
    4475                4480                4485

Asp Ala Asp Phe Ala Leu Asp Pro Asp Lys Pro Thr Asn Phe Thr
    4490                4495                4500

Asn Pro Val Tyr Ala Thr Leu Tyr Met Gly Gly His Gly Ser Arg
    4505                4510                4515

His Ser Leu Ala Ser Thr Asp Glu Lys Arg Glu Leu Leu Gly Arg
    4520                4525                4530

Gly Pro Glu Asp Glu Ile Gly Asp Pro Leu Ala
    4535                4540

```
<210> SEQ ID NO 11
<211> LENGTH: 7783
<212> TYPE: RNA
<213> ORGANISM: Homo sapiens

<400> SEQUENCE: 11
```

| | | | | |
|---|---|---|---|---|
| gcuggcggcg | ccgcccagg | gccggggccg | cgcgcccagc | cugagcccgc | cccgccgccg | 60 |
| agcgucaccg | aaccugcuug | aaaugcagcc | gaggagccgg | ggcgggcggc | agcggcggcg | 120 |
| gcggcggcg | cggggggcagc | ggcaaccccg | gcgccgcggc | aaggacucgg | agggcugaga | 180 |
| cgcggcggcg | gcggcgcggg | gagcgcgggg | cgcggcggcc | ggagcccgg | gcccgccaug | 240 |
| ggccuccccg | agccgggccc | ucuccggcuu | cuggcgcugc | ugcugcugcu | gcugcugcug | 300 |
| cugcugcugc | agcuccagca | ucuugcggcg | gcagcggcug | auccgcugcu | cggcggccaa | 360 |
| gggccggcca | aggauugcga | aaaggaccaa | uuccagugcc | ggaacgagcg | cugcauccc | 420 |
| ucugugugga | gaugcgacga | ggacgaugac | ugcuuagacc | acagcgacga | ggacgacugc | 480 |
| cccaagaaga | ccugugcaga | cagugacuuc | accugugaca | acggccacug | cauccacgaa | 540 |
| cgguggaagu | gugacggcga | ggaggagugu | ccugauggcu | ccgaugaguc | cgaggccacu | 600 |
| ugcaccaagc | aggugugucc | ugcagagaag | cugagcugug | acccaccag | ccacaagugu | 660 |
| guaccugccu | cgguggcgcug | cgacggggag | aaggacugcg | agguggagc | ggaugaggcc | 720 |
| ggcugugcua | ccuugugcgc | cccgcacgag | uuccagugcg | gcaaccgcuc | ugccuggcc | 780 |

```
gccguguucg ugugcgacgg cgacgacgac uguggugacg cagcgauga gcgcggcugu    840 gcagacccgg ccugcgggcc ccgcgaguuc cgcugcggcg gcgauggcgg cggcgccugc    900
aucccggagc gcugggucug cgaccgccag uuugacugcg aggaccgcuc ggacgaggca    960
gccgagcucu gcggccgucc gggccccggg gccacguccg cgcccgccgc cugcgccacc   1020
gccucccagu ucgccugccg cagcggcgag ugcgugcacc ugggcuggcg cugcgacggc   1080
gaccgcgacu gcaaagacaa aucggacgag gccgacugcc cacugggcac cugccguggg   1140
gacgaguucc agugugggga ugggacaugu guccuugcaa ucaagcacug caaccaggag   1200
caggacuguc cagaugggag ugaugaagcu ggcugccuac aggggcugaa cgaguqucug   1260 cacaacaaug gcggcugcuc acacaucugc acugaccuca agauuggcuu ugaaugcacg   1320
ugcccagcag gcuuccagcu ccuggaccag aagaccugug cgacauuga ugagugcaag   1380 gacccagaug ccugcagcca gaucuguguc aauuacaagg gcuauuuuaa gugugagugc   1440
uacccuggcu acgagaugga ccacugacc aagaacugca aggcugcgc uggcaagagc   1500 ccaucccuaa ucuucaccaa ccggcacgag gugcggagga cgaccuggu gaagcggaac   1560 uauucacgcc ucaucccau gcucaagaau gucguggcac uagaugugga aguugccacc   1620
aaucgcaucu acuggugug ccucuccuac cguaagaucu auagcgccua cauggacaag   1680
gccagugacc cgaaagagca ggagguccuc auugacgagc aguugcacuc uccagagggc   1740
cuggcagugg acugggucca caagcacauc uacuggacug acucgggcaa uaagaccauc   1800
ucagugccca caguugaugg uggccgccga cgcacucucu ucagccguaa ccucagugaa   1860 cccccgggcca ucgcuguuga ccccugcga ggguucaugu auuggucuga cugggggggac   1920 caggccaaga uugagaaauc ugggcucaac ggugugggacc ggcaaacacu ggugucagac   1980
aauauugaau ggcccaacgg aaucacccug gaucugcuga ccagcgcuu guacugggua   2040 gacuccaagc uacaccaacu guccagcauu gacuucagug gaggcaacag aaagacgcug   2100
aucuccucca cugacuuccu gagccacccu uuugggauag cuguguuuga ggacaaggug   2160
uucuggacag accuggagaa cgaggccauu ucagugcaa ucggcucaa uggccuggaa   2220 aucuccaucc uggcugagaa ccucaacaac ccacaugaca uugucaucuu ccaugagcug   2280
aagcagccaa gagcuccaga ugccugugag cugagugucc agccuaaugg aggcugugaa   2340
uaccugugcc uuccugcucc ucagaucucc agcacucuc caaguacac augugccugu   2400 ccugacacaa uguggcuggg uccagacaug aagaggugcu accgagcacc ucaaucuacc   2460
ucaacuacga cguuagcuuc uaccaugacg aggacaguac cugccaccac aagagccccc   2520
gggaccaccg uccacagauc caccuaccag aaccacagca cagagacacc aagccugaca   2580
gcugcagucc caagcucagu uaguguccca agggcucccca gcaucagccc gucuacccua   2640
agcccugcaa ccagcaacca cucccagcac uaugcaaaug aagacaguaa gaugggcuca   2700
acagucacug ccgcuguuau cgggaucauc gugcccauag uggugauagc ccuccugugc   2760
augaguggau accugaucug gagaaacugg aagcggaaga acaccaaaag caugaauuuu   2820
gacaacccag ucuacaggaa aacaacagaa gaagaagacg aagaugagcu ccauauaggg   2880
agaacugcuc agauuggcca ugucuauccu gcagcaauca gcagcuuuga ucgcccacug   2940
ugggcagagc ccugucuugg ggagaccaga gaaccggaag acccagcccc ugcccucaag   3000
gagcuuuuug ucuugccggg ggaaccaagg ucacagcugc accaacuccc gaagaacccu   3060
cuuuccgagc ugccugucgu caaauccaag cgagugqcau uaagccuuga agaugaugga   3120
cuacccugag gaugggauca ccccuuucgu gccucaugga auucagqccc augcacuaca   3180
```

```
cucuggaugg uguaugacug gaugaauggg uuucuauaua ugggucugug ugaguguaug    3240
ugugugugug auuuuuuuu uaaauuuaug ugcggaaag guaaccacaa aguuaugaug     3300
aacugcaaac auccaaagga ugugagaguu uuucuaugua uaauguuuua uacacuuuuu    3360
aacugguugc acuacccaug aggaauucgu ggaauggcua cugcgacuua acaugaugca    3420
cauaaccaaa uggggggccaa uggcacagua ccuuacucau cauuuaaaaa cuauauuuac   3480
agaagauguu ugguugcugg gggggcuuuu uuagguuuug gggcauuugu uuuuguaaa    3540 uaagaugauu augcuuugug gcuauccauc aacauaagua aaaaaaaaaa aaaaacacuu   3600
caacucccuc ccccauuuag auuauuuauu aacauauuuu aaaaaucaga ugaguucuau   3660
aaauaauuua gagaagugag aguauuuauu uuggcaugu uuggcccacc acacagacuc    3720
ugugugugua uguguguguu uauaugugua ugugugugac agaaaaaucu guagagaaga   3780
ggcacaucua uggcuacugu ucaaauacau aaagauaaau uuauuuucac acaguccaca   3840 aggggguauau cuuguaguuu ucagaaaagc cuuggaaau cuggaucaga aaauagauac   3900 cauguuugu gcauuaugu aguaaaaaag gcaaaucuuu ucaccucugg cuauuccuga    3960
gaccccagga agucaggaaa agccuuucag cucacccaug gcugcuguga cuccuaccag   4020
ggcuuucuug gcuuuggcga aggucagugu acagacauuc cauggguacca gagugcucag  4080 aaacucaaga uaggauaugc cucacccuca gcuacuccuu guuuaaagu ucagcucuuu   4140 gaguaacuuc uucaauuucu uucaggacac uggguugaa uucaguaagu uccucugaa    4200 gcacccugaa ggguugccauc cuuacagagc uaaguggaga cguuuccaga ucagcccaag  4260
uuuacuauag agacuggccc aggcacugaa ugucuaggac augcugugga ugaagauaaa   4320 gauggugaa uagguuuuau cacaucucuu auuucucuuu uccccuuacu cucuaccauu   4380
uccuuuaugu ggggaaacau uuuaaggua uaaauagguu acuuaccauc auauguucau    4440
auagaugaaa cuauuuuug gcuuaaguca gaacaacugg ccaaaauuga agucauauuu   4500 gagggggaa auggcauacg caauauuaua uuauauugga uauuuaguu cacacaggaa    4560 uuuguuuac ugcuuuguaa auaaaagaa aaacuccggg uauaguaua gauguucuuc     4620 auuauagaca ucuucuuugc uuuucuuggc cuuggggag gaaggagaa gugcucuuuu    4680 cuacuugugg ggucucccau uggaaacaua auccuauagu cccagaagga uucaguccc    4740 aguggcuuuc ccauccaaag agaaagaguu ugaguuucuu aacucugcug uucugccacu   4800
uacucccacu agacaaccag ggacaaggug caacauggaa uguuugacu uaaguaggag    4860 cagaggagcu gcaucuaauc ucaucauacc uggaacuuga cacacuuaag caaaugccuu   4920
cccaucccua ccugccagau gcccccaacu caaugaaguu ggaugcuca ccagcuugau   4980 acccuuugaa uuucagucuca gacauucugg aguucuagca uccuguaccu aggaccuucc  5040
ucugugucac ucuuggccuc cuaaacucua agaaauaac uauauucugg agcuugggca   5100 guguguuug cauaauccag caaucucccuc augacaugca uguuugauua guccugaaac  5160
auucauugag agggguaaaug caguugaccu agaaugacca auaccaaaca gaauuuuaag  5220 aacaggugc caacuccuau ggagcuuacu cacauauuac uauucuuuua agaacggaaa   5280 guaaauuau uuugacuga agaaaaauga ugacagugaa aaacauggaa auguaccaa     5340 aacaagugac uuuucugua accuuccaaa gaaacugaau uuccaagga auuaaaugau   5400 aacaguggcu aaggcauagu ucuaaacuu ucaguaagau ccuggcauuc acagaaaaaa   5460
augaugaaug gggucuggac auacagccug agaucucaaa augacaauga aauucacaac  5520
```

-continued

```
uuuuucucag agacauucau guuuccugca uaugcuacaa cugcaguuug aaagaggcag  5580
caaugggagc aacccuuuac aagaaacaaa uugugauaua ucaugguguu ggacggcagu  5640
aaauaagaug aaaccugagg agucagaucc accuuccccc auucauagag gcuuuucagc  5700
cucauuuuga gguacaguua cauaucuuuu gccuuuugcc cccgugcaua gcaucuaca   5760
gccaaucaca gaucacagag ucacuggacu auagagcugg aaggaagcuc agagacaaug  5820
ccaaggggc agaaaauuua ucagaagcca gucccagugc guuucccca uuccuucug    5880
caggaagacu auuuugggcu gccugaacau uguaucaaac cugcuaccua acuauggus  5940
uaccuuccu ccaguggaau acaaaggca cuaacugaaa ugccuucuag aaacagagaa   6000
aacgaaacug uacuuauuua cucuugauac acagauuauu uauaaaacag auugaaguaa  6060
ccuguuaacu ggcaaaaaga gaaugagauc ggauuuaaau guauggcagu aaguccuauu  6120
gaucccucca guuaucucag uaugacugca guauauucau ucacuaaaac cacucacuag  6180
auaccaacua cacaccuggc acugcagaug uaaaggucag ucacacaugu ucugacuuua  6240
cagaguucac aguagcagug gaggaugaua uauguggaaa caaaaaggc auugauucua   6300
uucagagcac uguuagggcu caaaggagag aggggucuuu ccaccuaaga aaugaggaau  6360
aggucauca uagaagugac cuuaagucuu aaaaauuaag aaggggauuc caagcugcuu   6420
cagacagaga cacaucgagc uaaaacacag agguaugaaa gagcacaggg acuuuaggaa  6480
uugcacaguu cauucuaaca ggaacaaaag gcucaagggg ggcaagaaau gaggcuguau   6540
ggaaagagau ucaauguaag cacuuuauaa aauagauuaa uuucugauuc aaugaagcau   6600
uucuugauca uuguguacaa ggcacuacau gcaucaugga aaauucauua ggaugcauug   6660
ccagcacuuu gcagaacuga uauuuauucag ccucaagcuu uccagugcc aaagggaaau   6720
gcugacugcu uuucauauau uugagucaaa gauuuuuuau augucaaug aagacuaaua    6780
uaagggcagu gggauuuuca cagaugcaug ccauguuguc gagagccucu uagauuuucu   6840
caacugugag aaagaaaaac gaaaauguug aagacguuga gucuggagag gggauacuaa   6900
ucacugucca guugggcacu ggugggaaug gggaaauggc acaggaaugc aagccucucc   6960
acccuaccc ccgaacucca gccauacacu caucguuuca caaaauauaa augaguuagc    7020
auuaaauguu ucagaguaaa uaauuccuuu ucccgaaaug caugaagaua gaguaacaga   7080
cuucucacac uguauuuuua ggguauggag aauuuagaag guuaaagaau uacugcuuca   7140
auuuuucagu uaaaaaaaaa ucaggaagcu cuguucauuc aggcuaugca ccaugugcac   7200
agucaagaau uagcagaaac ccucugcauu uacaaacacu uugugcuaua aaaaguaau    7260
uuuuaaaaag ccacgugugu gugugguau auauauauau auauauauau uuaaagccaa    7320
gguuugaua cuuuuuuaca aaacuacaa gagaaaacaa auauaccugu ccaaaccaua    7380
uacuuuuaaa agagcauuuu uuuuuccaua caagcuguug uuaauuuggg gguaaagugc   7440
ugauuugcaa acuucaucaa auuguccca aguggauucu ccuuguuugu ucccccuac    7500
caaccccaaa guuaccauau uugaugaag aaucaggcau guuagaaugu ugugucacac    7560
uaacugauuc ugcucuuuuu gucuugucau ucaaguuccg uuagcuucug uacgcggugc    7620
ccuuugcagu cuggugucuc uuccagaggc gaggggcug aggaugggu gcugcaucuc    7680
acuagcuaua cuggcaucau cuugguaaac ugaaaaccaa auggacau uuguaaaauc    7740
agugcacugu uucuagagag agauuaaauu cauuuaaaaa aaa                    7783
```

<210> SEQ ID NO 12
<211> LENGTH: 963

<212> TYPE: PRT
<213> ORGANISM: Homo sapiens

<400> SEQUENCE: 12

Met Gly Leu Pro Glu Pro Gly Pro Leu Arg Leu Leu Ala Leu Leu Leu
1               5                   10                  15

Leu Leu Leu Leu Leu Leu Leu Gln Leu Gln His Leu Ala Ala Ala
            20                  25                  30

Ala Ala Asp Pro Leu Leu Gly Gly Gln Gly Pro Ala Lys Asp Cys Glu
        35                  40                  45

Lys Asp Gln Phe Gln Cys Arg Asn Glu Arg Cys Ile Pro Ser Val Trp
    50                  55                  60

Arg Cys Asp Glu Asp Asp Asp Cys Leu Asp His Ser Asp Glu Asp Asp
65                  70                  75                  80

Cys Pro Lys Lys Thr Cys Ala Asp Ser Asp Phe Thr Cys Asp Asn Gly
                85                  90                  95

His Cys Ile His Glu Arg Trp Lys Cys Asp Gly Glu Glu Cys Pro
            100                 105                 110

Asp Gly Ser Asp Glu Ser Glu Ala Thr Cys Thr Lys Gln Val Cys Pro
        115                 120                 125

Ala Glu Lys Leu Ser Cys Gly Pro Thr Ser His Lys Cys Val Pro Ala
    130                 135                 140

Ser Trp Arg Cys Asp Gly Glu Lys Asp Cys Glu Gly Gly Ala Asp Glu
145                 150                 155                 160

Ala Gly Cys Ala Thr Leu Cys Ala Pro His Glu Phe Gln Cys Gly Asn
                165                 170                 175

Arg Ser Cys Leu Ala Ala Val Phe Val Cys Asp Gly Asp Asp Asp Cys
            180                 185                 190

Gly Asp Gly Ser Asp Glu Arg Gly Cys Ala Asp Pro Ala Cys Gly Pro
        195                 200                 205

Arg Glu Phe Arg Cys Gly Gly Asp Gly Gly Ala Cys Ile Pro Glu
    210                 215                 220

Arg Trp Val Cys Asp Arg Gln Phe Asp Cys Glu Asp Arg Ser Asp Glu
225                 230                 235                 240

Ala Ala Glu Leu Cys Gly Arg Pro Gly Pro Gly Ala Thr Ser Ala Pro
                245                 250                 255

Ala Ala Cys Ala Thr Ala Ser Gln Phe Ala Cys Arg Ser Gly Glu Cys
            260                 265                 270

Val His Leu Gly Trp Arg Cys Asp Gly Asp Arg Asp Cys Lys Asp Lys
        275                 280                 285

Ser Asp Glu Ala Asp Cys Pro Leu Gly Thr Cys Arg Gly Asp Glu Phe
    290                 295                 300

Gln Cys Gly Asp Gly Thr Cys Val Leu Ala Ile Lys His Cys Asn Gln
305                 310                 315                 320

Glu Gln Asp Cys Pro Asp Gly Ser Asp Glu Ala Gly Cys Leu Gln Gly
                325                 330                 335

Leu Asn Glu Cys Leu His Asn Gly Gly Cys Ser His Ile Cys Thr
            340                 345                 350

Asp Leu Lys Ile Gly Phe Glu Cys Thr Cys Pro Ala Gly Phe Gln Leu
        355                 360                 365

Leu Asp Gln Lys Thr Cys Gly Asp Ile Asp Glu Cys Lys Asp Pro Asp
    370                 375                 380

Ala Cys Ser Gln Ile Cys Val Asn Tyr Lys Gly Tyr Phe Lys Cys Glu
385                 390                 395                 400

```
Cys Tyr Pro Gly Tyr Glu Met Asp Leu Leu Thr Lys Asn Cys Lys Ala
                405                 410                 415

Ala Ala Gly Lys Ser Pro Ser Leu Ile Phe Thr Asn Arg His Glu Val
            420                 425                 430

Arg Arg Ile Asp Leu Val Lys Arg Asn Tyr Ser Arg Leu Ile Pro Met
        435                 440                 445

Leu Lys Asn Val Val Ala Leu Asp Val Glu Val Ala Thr Asn Arg Ile
    450                 455                 460

Tyr Trp Cys Asp Leu Ser Tyr Arg Lys Ile Tyr Ser Ala Tyr Met Asp
465                 470                 475                 480

Lys Ala Ser Asp Pro Lys Glu Gln Glu Val Leu Ile Asp Glu Gln Leu
                485                 490                 495

His Ser Pro Glu Gly Leu Ala Val Asp Trp Val His Lys His Ile Tyr
            500                 505                 510

Trp Thr Asp Ser Gly Asn Lys Thr Ile Ser Val Ala Thr Val Asp Gly
        515                 520                 525

Gly Arg Arg Thr Leu Phe Ser Arg Asn Leu Ser Glu Pro Arg Ala
    530                 535                 540

Ile Ala Val Asp Pro Leu Arg Gly Phe Met Tyr Trp Ser Asp Trp Gly
545                 550                 555                 560

Asp Gln Ala Lys Ile Glu Lys Ser Gly Leu Asn Gly Val Asp Arg Gln
                565                 570                 575

Thr Leu Val Ser Asp Asn Ile Glu Trp Pro Asn Gly Ile Thr Leu Asp
            580                 585                 590

Leu Leu Ser Gln Arg Leu Tyr Trp Val Asp Ser Lys Leu His Gln Leu
        595                 600                 605

Ser Ser Ile Asp Phe Ser Gly Gly Asn Arg Lys Thr Leu Ile Ser Ser
    610                 615                 620

Thr Asp Phe Leu Ser His Pro Phe Gly Ile Ala Val Phe Glu Asp Lys
625                 630                 635                 640

Val Phe Trp Thr Asp Leu Glu Asn Glu Ala Ile Phe Ser Ala Asn Arg
                645                 650                 655

Leu Asn Gly Leu Glu Ile Ser Ile Leu Ala Glu Asn Leu Asn Asn Pro
            660                 665                 670

His Asp Ile Val Ile Phe His Glu Leu Lys Gln Pro Arg Ala Pro Asp
        675                 680                 685

Ala Cys Glu Leu Ser Val Gln Pro Asn Gly Gly Cys Glu Tyr Leu Cys
    690                 695                 700

Leu Pro Ala Pro Gln Ile Ser Ser His Ser Pro Lys Tyr Thr Cys Ala
705                 710                 715                 720

Cys Pro Asp Thr Met Trp Leu Gly Pro Asp Met Lys Arg Cys Tyr Arg
                725                 730                 735

Ala Pro Gln Ser Thr Ser Thr Thr Leu Ala Ser Thr Met Thr Arg
            740                 745                 750

Thr Val Pro Ala Thr Thr Arg Ala Pro Gly Thr Thr Val His Arg Ser
        755                 760                 765

Thr Tyr Gln Asn His Ser Thr Glu Thr Pro Ser Leu Thr Ala Ala Val
    770                 775                 780

Pro Ser Ser Val Ser Val Pro Arg Ala Pro Ser Ile Ser Pro Ser Thr
785                 790                 795                 800

Leu Ser Pro Ala Thr Ser Asn His Ser Gln His Tyr Ala Asn Glu Asp
                805                 810                 815
```

Ser Lys Met Gly Ser Thr Val Thr Ala Ala Val Ile Gly Ile Ile Val
            820                 825                 830

Pro Ile Val Val Ile Ala Leu Leu Cys Met Ser Gly Tyr Leu Ile Trp
        835                 840                 845

Arg Asn Trp Lys Arg Lys Asn Thr Lys Ser Met Asn Phe Asp Asn Pro
    850                 855                 860

Val Tyr Arg Lys Thr Thr Glu Glu Asp Glu Asp Glu Leu His Ile
865                 870                 875                 880

Gly Arg Thr Ala Gln Ile Gly His Val Tyr Pro Ala Ala Ile Ser Ser
                885                 890                 895

Phe Asp Arg Pro Leu Trp Ala Glu Pro Cys Leu Gly Glu Thr Arg Glu
            900                 905                 910

Pro Glu Asp Pro Ala Pro Ala Leu Lys Glu Leu Phe Val Leu Pro Gly
            915                 920                 925

Glu Pro Arg Ser Gln Leu His Gln Leu Pro Lys Asn Pro Leu Ser Glu
        930                 935                 940

Leu Pro Val Val Lys Ser Lys Arg Val Ala Leu Ser Leu Glu Asp Asp
945                 950                 955                 960

Gly Leu Pro

<210> SEQ ID NO 13
<211> LENGTH: 7273
<212> TYPE: RNA
<213> ORGANISM: Homo sapiens

<400> SEQUENCE: 13

```
gcuggcggcg gccgcccagg gccggggccg cgcgcccagc cugagcccgc ccgccgccg      60 agcgucaccg aaccugcuug aaaugcagcc gaggagccgg ggcggcggc agcggcggcg    120 gcggcggcgg cggggcagc ggcaaccccg cgccgcggc aaggacucgg agggcugaga     180
cgcggcggcg gcggcgcggg gagcgcgggg cgcggcggcc ggagcccgg gcccgccaug    240 ggccucccg agccgggccc ucuccggcuu cuggcgcugc ugcugcugcu gcugcugcug    300
cugcugcugc agcuccagca ucuucgcggcg gcagcggcug auccgcugcu cggcggccaa   360
gggccggcca aggauugcga aaaggaccaa uuccagugcc ggaacgagcg cugcauccc    420 ucugugugga gaugcgacga ggacgaugac ugcuuagacc acagcgacga ggacgacugc    480
cccaagaaga ccugugcaga cagugacuuc accugugaca cggcacugu cauccacgaa    540 cgguggaagu gugacggcga ggaggaggugu ccugauggcu ccgaugaguc cgaggccacu    600
ugcaccaagc aggugugucc ugcagagaag cugagcugug acccaccag ccacaagugu    660 guaccugccu cguggcgcug cgacggggag aaggacugcg agguggagc ggaugaggcc    720 ggcugugcua ccuggcugaa cgagugucug cacaacaaug cggcugcuc acacaucugc    780 acugaccuca agauuggcuu ugaaugcacg ugcccagcag gcuuccagcu ccuggaccag    840
aagaccugug gcgacauuga ugagugcaag gaccagaug ccugcagcca gaucuguguc    900
aauuacaagg gcuauuuuaa gugugagugc uacccuggcu acgagaugga ccuacugacc    960
aagaacugca agcugcugc uggcaagagc ccauccuuaa ucuucaccaa ccggcacgag   1020
gugcggagga ucgaccuggu gaagcggaac uauucacgcc ucauccccau gcucaagaau   1080
gucguggcac uagaugugga aguugccacc aaucgcauc acuggugug ccucuccuac   1140 cguaagaucu auagcgccua caugacaag gccagugacc gaaagagca ggaguccuc   1200 auugacgagc aguugcacuc uccagagggc cuggcagugg acugggucca caagcacauc   1260
```

-continued

```
uacuggacug acucgggcaa uaagaccauc ucaguggcca caguugaugg uggccgccga   1320
cgcacucucu ucagccguaa ccucagugaa ccccgggcca ucgcuguuga ccccugcga    1380 ggguucaugu auuggucuga cuggggggac caggccaaga uugagaaauc ugggcucaac   1440 ggugguggacc ggcaaacacu ggugucagac aauauugaau ggcccaacgg aaucacccug  1500
gaucugcuga gccagcgcuu guacugggua gacuccaagc uaccaaacu guccagcauu    1560 gacuucagug gaggcaacag aaagacgcug aucuccucca cugacuuccu gagccacccu   1620
uuugggauag cuguguuuga ggacaaggug uucuggacag accuggagaa cgaggccauu   1680 uucagcaaa aucggcucaa uggccuggaa aucuccaucc uggcugagaa ccucaacaac    1740
ccacaugaca uugucaucuu ccaugagcug aagcagccaa gagcuccaga ugccugugag   1800
cugagugucc agccuaaugg aggcugugaa uaccugugcc uuccugcucc ucagaucucc   1860
agccacucuc ccaaguacac auguaccugu ccgacacaa uguggcuggg uccagacaug    1920
aagaggugcu accgagcacc ucaaucuacc ucaacuacga cguuagcuuc uaccaugacg   1980
aggacaguac cugccaccac aagagccccc gggaccaccg uccacagauc caccuaccag   2040
aaccacagca cagagacacc aagccugaca gcugcagucc caagcucagu uagugucccc   2100
agggcuccca gcaucagccc gucuacccua agcccugcaa ccagcaacca cucccagcac   2160
uaugcaaaug aagacaguaa gaugggcuca acagucacug ccgcuguuau cgggaucauc   2220
gugcccauag ugguggaaugc ccuccugugc augagugggau accugaucug gagaaacugg  2280
aagcggaaga acaccaaag caugaauuu gacaacccag cucacaggaa aacaacagaa     2340
gaagaagacg aagaugagcu ccauauaggg agaacgcuc agauuggcca ugucuauccu    2400
gcagcaauca gcagcuuuga ucgcccacug ugggcagagc ccugucuugg ggagaccaga   2460
gaaccggaag acccagccccc ugccucaag gagcuuuuug ucuugccggg ggaaccaagg   2520
ucacagcugc accaacuccc gaagaacccu cuuuccgagc ugccugucgu caaauccaag   2580 cgagugggcau uaagccuuga agaugaugga cuacccugag gaugggauca cccccuucgu   2640 gcccucaugga auucaguccc augcacuaca cucuggaugg uguaugacug gaugaauggg   2700
uuucuauaua uggggucugug ugaguguaug ugugugugug auuuuuuuuu uaaauuauag   2760
uugcggaaag guaaccacaa aguuaugaug aacugcaaac auccaaagga ugugagaguu   2820
uuucuaugua uaaugguuuua uacacuuuuu aacggcuugc acuacccaug aggaauucgu   2880
ggaauggcua cugcugacua acaugaugca cauaaccaaa uggggccaa uggcacagua    2940 ccuuacucau cauuuaaaaa cuauauuuac agaagauguu uggugcugg ggggcuuuu     3000 uuaggucuug gggcauuugu uuuuuguaaa uaagaugauu augcuuugug gcuauccauc   3060
aacauaagua aaaaaaaaa aaaacacuu caacucccuc ccccauuuag auuauuuauu     3120
aacauauuuu aaaaucaga ugaguucau aaauaauuua gagaagugag aguauuuau      3180 uuugcaugu uggcccacc acacagacuc ugugugugua ugugugugu uauaugugua      3240 uguguguag agaaaaaucu guagagaaga ggcacaucua uggcuacugu ucaaauacau    3300
aaagauaaau uuauuuucac acaguccaca aggggauaua uuguaguuu ucagaaaagc    3360 cuuuggaaau cuggaucaga aauaagauac caugguuugu gcaauuagu aguaaaaag     3420 gcaaaucuuu ucaccucugg cuauuccuga gaccccagga agucaggaaa agccuuucag   3480
cucacccaug gcucugugua cuccuaccag ggcuuucuug gcuuuggcga aggucagugu   3540
acagacauuc cauggugacca gagugcucag aaacucaaga uaggauaugc cucaccucca   3600
gcuacuccuu guuuuaaagu ucagcucuuu gaguaacuuc uucaauuucu uucaggacac   3660
```

```
uugggunuugaa  uucaguaagu  uuccucugaa  gcacccugaa  ggguugccauc  cuuacagagc    3720 uaaguggaga  cguuuccaga  ucagcccaag  uuuacuauag  agacuggccc  aggcacugaa      3780
ugucuaggac  augcuugugga  ugaagauaaa  gauggugggaa  uagguuuuau  cacaucucuu     3840
auuucucuuu  uccccuuacu  cucuaccauu  uccuuuaugu  ggggaaacau  uuuaagguaa     3900 uaaauaagguu  acuuaccauc  auauguucau  auagaugaaa  cuaauuuuug  gcuuaaguca   3960
gaacaacugg  ccaaaauuga  agucauauuu  gagggggggaa  auggcauacg  caauauuaua   4020
uuauauugga  uauuuauguu  cacacaggaa  uugguuuac  ugcuuuguaa  auaaaaggaa    4080
aaacuccggg  uauauguaua  gauguucuuc  auuauagaca  ucuucuuugc  uuuucuuggc   4140 cuuggggggag  gaagggagaa  gugcucuuuu  cuacuugugg  ggucucccau  uggaaacaua  4200
auccuauagu  cccagaagga  uucagucccc  aguggcuuuc  ccauccaaag  agaaagaguu   4260
ugaguuucuu  aacucugcug  uucugccacu  uacucccacu  agacaaccag  ggacaaggug    4320
caacauggaa  guguuugacu  uaaguaggag  cagaggagcu  gcaucuaauc  ucaucauacc    4380
uggaacuuga  cacacuuaag  caaaugccuu  cccauccccua  ccugccagau  gcccccaacu    4440
caaugaaguu  ggaugucuca  ccagcuugau  acccuuugaa  uuucagucaa  gacauucugg   4500
aguucuagca  uccuguaccu  aggaccuucc  ucugugucac  ucuggccuc  cuaaacucua    4560 agaaaauaac  uauauucugg  agcuugggca  guguguuuug  cauaauccag  caaucuccuc   4620
augacaugca  uguguugaua  guccugaaac  auucauugag  aggguaaaug  caguugaccu    4680
agaaugacca  auaccaaaca  gaauuuuaag  aacaguggc  caacuccuau  ggagcuuacu     4740
cacauauuac  uauucuuuua  agaacggaaa  guaaauuau  uuugacuga  agaaaaauga     4800 ugacagugaa  aaacauggaa  auguacucaa  aacaagugac  uuuuucugua  accuccaaa     4860 gaaacugaau  uuccaagga  auuaaaugau  aacaguggcu  aaggcauagu  uucuaaacuu     4920
ucaguaagau  ccuggcauuc  acagaaaaaa  augaugaaug  gggucuggac  auacagccug    4980
agaucucaaa  augacaauga  aauucacaac  uuuuucucag  agacauucau  guuuccugca    5040
uaugcuacaa  cugcaguuug  aaagaggcag  caauggagc  aacccuuuac  aagaaacaaa    5100
uugugauaua  uucaugguguu  ggacggcagu  aaauaagaug  aaaccugagg  agucagaucc   5160
accuuccccc  auucauagag  gcuuuucagc  cucauuuuga  ggugacaguua  cauaucuuuu   5220 gccuuuugcc  cccgugcaua  gcuaucuaca  gccaaucaca  gaucagagag  ucacuggacu   5280
auagagcugg  aaggaagcuc  agagacaaug  ccaaggggggc  agaaaauuua  ucagaagcca   5340
gucccagugc  guuuccuucca  uuuccuucug  caggaagacu  auuuugggcu  gccugaacau   5400
uguaucaaac  cugcuaccua  uacuaugguc  uaccuuuccu  ccagugggaau  uacaaaggca    5460 cuaacugaaa  ugccuucuag  aaacagagaa  aacgaaacug  uacuuauuua  ucuuugauac     5520
acagauuauu  uauaaaacag  auugaaguaa  ccuguuaacu  ggcaaaaaga  gaaugagauc     5580
ggauuuaaau  guauggcagu  aaguccuauu  gaucccucca  guuaucucag  uaugacugca     5640
guauauucau  ucacuaaaac  cacucacuag  auaccaacua  cacaccuggc  acugcagaug   5700
uaaaggucag  ucacacaugu  ucugacuuua  cagaguucac  aguagcagug  gaggaugaua    5760
uauguggaaa  caaaaaggc  auugauucua  ucagagcac  uguuagggcu  caaaggagag    5820
aggggucuuu  ccaccuaaga  aauggaggaau  agggucauca  uagaagugac  cuuaagucuu    5880
aaaaauuaag  aaggggauuc  caagcugcuu  cagacagaga  cacaucgagc  uaaaacacag    5940
agguaugaaa  gagcacaggg  acuuuaggaa  uugcacaguu  cauucuaaca  ggaacaaaag    6000
```

-continued

```
gcucaagggg ggcaagaaau gaggcuguau ggaaagagau caauguaag cacuuuauaa    6060 aauagauuaa uuucugauuc aaugaagcau uucuugauca uuguguacaa ggcacuacau    6120
gcaucaugga aaauucauua ggaugcauug ccagcacuuu gcagaacuga uauuauucag    6180
ccucaagcuu uccaguggcc aaagggaaau gcugacugcu uuucauauau uugagucaaa    6240
gauuuuuuau auggucaaug aagacuaaua uaagggcagu gggauuuuca cagaugcaug    6300
ccauguuguc gagagccucu uagauuuucu caacugugag aaagaaaaac gaaaauguug    6360
aagacguuga gucuggagag gggauacuaa ucacugucca guugggcacu ggugggaaug    6420
gggaaauggc acaggaaugc aagccucucc acccuacccc ccgaaccuca gccauacacu    6480
caucguuuca caaauauaa augaguuagc auuaaauguu ucagaguaaa uaauuccuuu    6540
ucccgaaaug caugaagaua gaguaacaga cuucucacac uguauuuuua ggguauggag    6600
aauuuagaag guuaagaau uacugcuuca auuuucagu uaaaaaaaa ucaggaagcu    6660 cuguucauuc aggcuaugca ccaugugcac agucaagaau uagcagaaac ccucugcauu    6720
uacaaacacu uugugcuaua aaaaaguaau uuuuaaaaag ccacgugugu gugugugua    6780 auauauauau auauauauau uuaaagccaa gguuugaua cuuuuuuaca aaaacuacaa    6840
gagaaaacaa auauaccugu ccaaaccaua uacuuuaaa agagcauuuu uuuuuccaua    6900
caagcuguug uuaauuuggg gguaaagugc ugauugcaa acuucaucaa auuguuccca    6960
aguggauucu ccuuguuugu cuccccac caaccccaaa guuaccauau uugauguaag    7020
aaucaggcau guuagaaugu uguucacac uaacugauuc ugcucuuuuu gucuugucau    7080
ucaaguuccg uuagcuucug uacgcggugc ccuuugcagu cuggugucuc uuccagaggc    7140
gagggggcug aggauggggu gcugcaucuc acuagcuaua cuggcaucau cuugguaaac    7200
ugaaaaccaa auguggacau uuguaaaauc agugcacugu uucuagagag agauuaaauu    7260
cauuuaaaaa aaa                                                      7273
```

<210> SEQ ID NO 14
<211> LENGTH: 793
<212> TYPE: PRT
<213> ORGANISM: Homo sapiens

<400> SEQUENCE: 14

```
Met Gly Leu Pro Glu Pro Gly Pro Leu Arg Leu Leu Ala Leu Leu Leu
 1               5                  10                  15

Leu Leu Leu Leu Leu Leu Leu Leu Gln Leu Gln His Leu Ala Ala Ala
             20                  25                  30

Ala Ala Asp Pro Leu Leu Gly Gly Gln Gly Pro Ala Lys Asp Cys Glu
         35                  40                  45

Lys Asp Gln Phe Gln Cys Arg Asn Glu Arg Cys Ile Pro Ser Val Trp
     50                  55                  60

Arg Cys Asp Glu Asp Asp Asp Cys Leu Asp His Ser Asp Glu Asp Asp
 65                  70                  75                  80

Cys Pro Lys Lys Thr Cys Ala Asp Ser Asp Phe Thr Cys Asp Asn Gly
                 85                  90                  95

His Cys Ile His Glu Arg Trp Lys Cys Asp Gly Glu Glu Cys Pro
            100                 105                 110

Asp Gly Ser Asp Glu Ser Glu Ala Thr Cys Thr Lys Gln Val Cys Pro
        115                 120                 125

Ala Glu Lys Leu Ser Cys Gly Pro Thr Ser His Lys Cys Val Pro Ala
    130                 135                 140
```

```
Ser Trp Arg Cys Asp Gly Glu Lys Asp Cys Glu Gly Gly Ala Asp Glu
145                 150                 155                 160

Ala Gly Cys Ala Thr Trp Leu Asn Glu Cys Leu His Asn Asn Gly Gly
                165                 170                 175

Cys Ser His Ile Cys Thr Asp Leu Lys Ile Gly Phe Glu Cys Thr Cys
            180                 185                 190

Pro Ala Gly Phe Gln Leu Leu Asp Gln Lys Thr Cys Gly Asp Ile Asp
        195                 200                 205

Glu Cys Lys Asp Pro Asp Ala Cys Ser Gln Ile Cys Val Asn Tyr Lys
    210                 215                 220

Gly Tyr Phe Lys Cys Glu Cys Tyr Pro Gly Tyr Glu Met Asp Leu Leu
225                 230                 235                 240

Thr Lys Asn Cys Lys Ala Ala Gly Lys Ser Pro Ser Leu Ile Phe
                245                 250                 255

Thr Asn Arg His Glu Val Arg Arg Ile Asp Leu Val Lys Arg Asn Tyr
            260                 265                 270

Ser Arg Leu Ile Pro Met Leu Lys Asn Val Val Ala Leu Asp Val Glu
        275                 280                 285

Val Ala Thr Asn Arg Ile Tyr Trp Cys Asp Leu Ser Tyr Arg Lys Ile
290                 295                 300

Tyr Ser Ala Tyr Met Asp Lys Ala Ser Asp Pro Lys Glu Gln Glu Val
305                 310                 315                 320

Leu Ile Asp Glu Gln Leu His Ser Pro Glu Gly Leu Ala Val Asp Trp
                325                 330                 335

Val His Lys His Ile Tyr Trp Thr Asp Ser Gly Asn Lys Thr Ile Ser
            340                 345                 350

Val Ala Thr Val Asp Gly Gly Arg Arg Thr Leu Phe Ser Arg Asn
        355                 360                 365

Leu Ser Glu Pro Arg Ala Ile Ala Val Asp Pro Leu Arg Gly Phe Met
    370                 375                 380

Tyr Trp Ser Asp Trp Gly Asp Gln Ala Lys Ile Glu Lys Ser Gly Leu
385                 390                 395                 400

Asn Gly Val Asp Arg Gln Thr Leu Val Ser Asp Asn Ile Glu Trp Pro
                405                 410                 415

Asn Gly Ile Thr Leu Asp Leu Leu Ser Gln Arg Leu Tyr Trp Val Asp
            420                 425                 430

Ser Lys Leu His Gln Leu Ser Ser Ile Asp Phe Ser Gly Gly Asn Arg
        435                 440                 445

Lys Thr Leu Ile Ser Ser Thr Asp Phe Leu Ser His Pro Phe Gly Ile
    450                 455                 460

Ala Val Phe Glu Asp Lys Val Phe Trp Thr Asp Leu Glu Asn Glu Ala
465                 470                 475                 480

Ile Phe Ser Ala Asn Arg Leu Asn Gly Leu Glu Ile Ser Ile Leu Ala
                485                 490                 495

Glu Asn Leu Asn Asn Pro His Asp Ile Val Ile Phe His Glu Leu Lys
            500                 505                 510

Gln Pro Arg Ala Pro Asp Ala Cys Glu Leu Ser Val Gln Pro Asn Gly
        515                 520                 525

Gly Cys Glu Tyr Leu Cys Leu Pro Ala Pro Gln Ile Ser Ser His Ser
    530                 535                 540

Pro Lys Tyr Thr Cys Ala Cys Pro Asp Thr Met Trp Leu Gly Pro Asp
545                 550                 555                 560

Met Lys Arg Cys Tyr Arg Ala Pro Gln Ser Thr Ser Thr Thr Thr Leu
```

```
                  565                 570                 575
Ala Ser Thr Met Thr Arg Thr Val Pro Ala Thr Thr Arg Ala Pro Gly
                580                 585                 590

Thr Thr Val His Arg Ser Thr Tyr Gln Asn His Ser Thr Glu Thr Pro
            595                 600                 605

Ser Leu Thr Ala Ala Val Pro Ser Ser Val Ser Val Pro Arg Ala Pro
        610                 615                 620

Ser Ile Ser Pro Ser Thr Leu Ser Pro Ala Thr Ser Asn His Ser Gln
625                 630                 635                 640

His Tyr Ala Asn Glu Asp Ser Lys Met Gly Ser Thr Val Thr Ala Ala
                645                 650                 655

Val Ile Gly Ile Ile Val Pro Ile Val Val Ile Ala Leu Leu Cys Met
                660                 665                 670

Ser Gly Tyr Leu Ile Trp Arg Asn Trp Lys Arg Lys Asn Thr Lys Ser
            675                 680                 685

Met Asn Phe Asp Asn Pro Val Tyr Arg Lys Thr Thr Glu Glu Glu Asp
        690                 695                 700

Glu Asp Glu Leu His Ile Gly Arg Thr Ala Gln Ile Gly His Val Tyr
705                 710                 715                 720

Pro Ala Ala Ile Ser Ser Phe Asp Arg Pro Leu Trp Ala Glu Pro Cys
                725                 730                 735

Leu Gly Glu Thr Arg Glu Pro Glu Asp Pro Ala Pro Ala Leu Lys Glu
                740                 745                 750

Leu Phe Val Leu Pro Gly Glu Pro Arg Ser Gln Leu His Gln Leu Pro
            755                 760                 765

Lys Asn Pro Leu Ser Glu Leu Pro Val Val Lys Ser Lys Arg Val Ala
        770                 775                 780

Leu Ser Leu Glu Asp Asp Gly Leu Pro
785                 790

<210> SEQ ID NO 15
<211> LENGTH: 6994
<212> TYPE: RNA
<213> ORGANISM: Homo sapiens

<400> SEQUENCE: 15
gcuggcggcg gccgcccagg gccggggccg cgcgcccagc cugagcccgc cccgccgccg      60
agcgucaccg aaccugcuug aaaugcagcc gaggagccgg ggcggcggc agcggcggcg     120 gcggcggcgg cggggcagc ggcaacccg cgcgccgcggc aaggacucgg agggcugaga     180
cgcggcggcg gcggcgcggg gagcgcgggg cgcggcggcc ggagcccgg gcccgccaug     240 ggccucccg agccgggccc ucuccggcuu cuggcgcugc ugcugcugcu gcugcugcug     300
cugcugcugc agcuccagca ucuugcggcg gcagcggcug auccgcugcu cggcggccaa     360
gggccggcca aggauugcga aaaggaccaa uuccagugcc ggaacgagcg cugcauccc     420 ucugugugga gaugcgacga ggacgaugac ugcuuagacc acagcgacga ggacgacugc     480
cccaagaaga ccugugcaga cagugacuuc accugugaca cggccacugc cauccacgaa     540
cgguggaagu gugacggcga ggaggagugu ccugauggcu ccgaugaguc cgaggccacu     600
ugcaccaagc aggugugucc ugcagagaag cugagcugug accccaccag ccacaagugu     660
guaccugccu cguggcgcug cgacggggag aaggacugcg aggugggagc ggaugaggcc     720
ggcugugcua cccucugggg caccgccgu ggggacgagu ccagugugg ggaugggaca     780 ugguuccug caaucaagca cugcaaccag gagcaggacu guccagaugg gagugaugaa     840
```

```
gcuggcugcc uacaggggcu gaacgagugu cugcacaaca auggcggcug cucacacauc    900
ugcacugacc ucaagauugg cuuugaaugc acgugcccag caggcuucca gcuccuggac    960
cagaagaccu guggcgacau ugaugagugc aaggacccag augccugcag ccagaucugu    1020
gucaauuaca agggcuauuu aagugugag ugcuacccug cuacgagau ggaccuacug    1080
accaagaacu gcaaggcugc ugcuggcaag agcccauccc uaaucuucac caaccggcac    1140
gaggugcgga ggaucgaccu ggugaagcgg aacuauucac gccucauccc caugcucaag    1200
aaugucgugg cacuagaugu ggaaguugcc accaaucgca ucuacggug ugaccucucc    1260
uaccguaaga ucuauagcgc cuacauggac aaggccagug acccgaaaga gcaggagguc    1320
cucauugacg agcaguugca cucuccagag ggccuggcag uggacugggu ccacaagcac    1380
aucuacugga cugacucggg caauaagacc aucucagugg ccacaguuga ugguggccgc    1440
cgacgcacuc ucuucagccg uaaccucagu gaaccccggg ccaucgcugu ugaccccug    1500
cgaggguuca uguauugguc ugacgggggg gaccaggcca agauugagaa aucgggcuc    1560
aacggugugg accggcaaac acuggguca gacaauauug aauggcccaa cggaaucacc    1620
cuggaucugc ugagccagcg cuuguacugg guagacucca agcuacacca acuguccagc    1680
auugacuuca guggaggcaa cagaaagacg cugaucuccu ccacugacuu ccugagccac    1740
ccuuuuggga uagcugucuuu ugaggacaag guguucugga cagaccugga gaacgaggcc    1800
auuuucagug caaaucggcu caauggccug gaaaaucuca uccuggcuga gaaccucaac    1860
aacccacaug acauugucau cuuccaugag cugaagcagc caagagcucc agaugccugu    1920
gagcugagug uccagccuaa uggaggcugu gaauaccugu gccuuccugc uccucagauc    1980
uccagccacu cucccaagua cacaugugcc uguccugaca caaugugggcu ggguccagac    2040
augaagaggu gcuaccgaga ugcaaaugaa gacaguaaga ugggcucaac agucacugcc    2100
gcuguuaucg ggaucaucgu gcccauagug gugauagccc uccugugcau gagugggauac    2160
cugaucugga gaaacuggaa gcggaagaac accaaagca ugaauuugua aacccaguc    2220
uacaggaaaa caacagaaga agaagacgaa gaugagcucc auauagggag aacugcucag    2280
auuggccaug ucuauccugc acgagugca uuaagccuug aagaugaugg acuacccuga    2340
ggaugggauc accccccuucg ugccucaugg aauucaguccc caugcacuac acucuggaug    2400
guguaugacu ggaugaaugg guuucuauau augggucugu gugaguguau gugugugugu    2460
gauuuuuuuu uuaaauuuau guugcggaaa gguaaccaca aaguuaugau gaacugcaaa    2520
cauccaaagg augugagagu uuuucuaugu auaauguuuu auacacuuuu uaacugguug    2580
cacuacccau gaggaauucg uggaauggcu acugcugacu aacaugaugc acauaaccaa    2640
augggggcca auggcacagu accuuacuca ucauuuaaaa acuauauuua cagaagaugu    2700
uugguugcug ggggggcuuu uuuagguuuu ggggcauuug uuuuuuguaa auaagaugau    2760
uaugcuuugu ggcuaccccau caacauaagu aaaaaaaaaa aaaaaacacu ucaacucccu    2820
cccccauuua gauuauuuau uaacauauuu uaaaaaucag augaguucua uaauauuuu    2880
agagaaguga gaguauuuau uuuuggcaug uuuggcccac cacacagacu cuguguguu    2940
auguguguu uuauaugugu auguguguga cagaaaauc uguagagaag aggcacaucu    3000
auggcuacug uucaaauaca uaaagauaaa uuuauuuuca cacaguccac aaggggauaa    3060
ucuuguaguu uucagaaaag ccuuuggaaa ucuggaucaa aaauuagaua ccauggauuu    3120
ugcaauuaug uaguaaaaaa ggcaaaaucuu uucaccucug gcuauuccug agacccccagg    3180
```

```
aagucaggaa aagccuuuca gcucacccau ggcugcugug acuccuacca gggcuuucuu   3240
ggcuuuggcg aaggucagug uacagacauu ccaugguacc agagugcuca gaaacucaag   3300
auaggauaug ccucacccuc agcuacuccu uguuuuaaag uucagcucuu ugaguaacuu   3360
cuucaauuuc uuucaggaca cuuggguuga auucaguaag uuccucuga agcacccuga    3420
agggugccau ccuuacagag cuaaguggag acguuccag aucagcccaa guuuacuaua    3480
gagacuggcc caggcacuga augucuagga caugcugugg augaagauaa agauggugga   3540
auagguuuua ucacaucucu auuucucuu uuccccuuac ucucuaccau uccuuuaug     3600
uggggaaaca uuuuaaggua auaaauaggu uacuuaccau cauauguuca uauagaugaa   3660
acuaauuuuu ggcuuaaguc agaacaacug gccaaaauug aagucauauu ugagggggga   3720
aauggcauac gcaauauuau auuauauugg auauuuaugu ucacacagga auuugguuua   3780
cugcuuugua aauaaaagga aaaacuccgg guauaugauu agauguucuu cauuauagac   3840
aucuucuuug cuuucuuugg ccuugggga ggaagggaga agugcucuuu ucuacuugug    3900
gggucucca uuggaaacau aauccuauag ucccagaagg uucaguccc cagugggcuuu    3960
cccauccaaa gagaaagagu uugaguuucu uaacucugcu guucugccac uuacucccac   4020
uagacaacca gggacaaggu gcaacaugga agug uuugac uuaaguagga gcagaggagc  4080
ugcaucuaau cucaucauac cuggaacuug acacacuuaa gcaaaugccu ucccaucccu   4140
accugccaga ugcccccaac ucaaugaagu uggaugcuc accagcuuga uacccuuuga   4200
auuucaguc agacauucug gaguucuagc auccuguacc uaggaccuuc cucugugca    4260
cucuuggccu ccuaaacucu aagaaaauaa cuauauucug gagcuugggc agugugauuu   4320
gcauaaucca gcaaucuccu caugacaugc augugauugu agccugaaa cauucauuga   4380
gagguaaau gcaguugacc uagaaugacc aauaccaaac agaauuaaa gaacaggugg    4440
ccaacuccua uggagcuuac ucacauauua cuauucuuuu aagaacggaa aguaaaauua   4500
uuuuugacug aagaaaaaug augacaguga aaaacaugga aaugacuca aaacaaguga   4560
cuuuuucugu aaccuuccaa agaaacugaa uuuuccaagg aauuaaauga uaacagugcc  4620
uaaggcauag uuucuaaacu uucaguaaga uccggcauu cacagaaaaa aaugaugaau   4680
gggucugga cauacagccu gagaucucaa aaugacaaug aaauucacaa cuuuuucuca   4740
gagacauuca uguuuccugc auaugcuaca acugcaguuu gaaagaggca gcaaugggag  4800
caacccuuua caagaaacaa auugugauau auucaugugu uggacggcag uaaauaagau   4860
gaaaccugag gagucagauc caccuucccc cauucauaga ggcuuuucag ccucauuuug   4920
agguacaguu acauaucuuu ugccuuuugc ccccgugcau agcuaucuac agccaaucac   4980
agaucacaga gucacuggac uauagagcug gaaggaagcu cagagacaau gccaagggg    5040
cagaaaauuu aucagaagcc aguccccagug cguuccucc auuccuucu gcaggaagac   5100
uauuugggc ugccugaaca uuguaucaaa ccugcuaccu auacuauggu cuaccuuucc    5160
uccaguggaa uuacaaaggc acuaacgaa augccuucua gaaacagaga aaacgaaacu    5220
guacuuauuu acucuugaua cacagauuau uuauaaaaca gauugaagua accguuaac    5280
uggcaaaaag agaaugagau cggauuuaaa uguauggcag uaagucuau ugauccaucc    5340
aguuaucuca guaugacugc aguauauuca uucacuaaaa ccacucacua gauaccaacu   5400
acacaccugg cacugcagau guaaaggca gucacacaug uucugacuuu acagaguuca   5460
caguagcagu ggaggaugau auauguggaa acaaaaaagg cauugauucu auucagcaua   5520
cuguuagggc ucaaaggaga gaggggucuu uccaccuaag aaaugaggaa uagggucauc   5580
```

```
auagaaguga ccuuaagucu uaaaaauuaa gaaggggauu ccaagcugcu ucagacagag    5640
acacaucgag cuaaaacaca gagguaugaa agagcacagg gacuuuagga auugcacagu    5700
ucauucuaac aggaacaaaa ggcucaaggg gggcaagaaa ugaggcugua uggaaagaga    5760
uucaauguaa gcacuuuaua aaauagauua auuucugauu caaugaagca uuucuugauc    5820
auugugudca aggcacuaca ugcaucaugg aaaauucauu aggaugcauu gccagcacuu    5880
ugcagaacug auauuauuca gccucaagcu uccaguggc caaagggaaa ugcugacugc    5940
uuuucauaua uuugagucaa agauuuuuua uauggucaau gaagacuaau auaagggcag    6000
ugggauuuuc acagaugcau gccaugugu cgagagccuc uuagauuuuc ucaacuguga    6060
gaaagaaaaa cgaaaauguu gaagacguug agucuggaga ggggauacua aucacugucc    6120
aguugggcac ugguggggaau ggggaaaugg cacaggaaug caagccucuc cacccuaccc    6180
cccgaacucc agccauacac ucaucguuuc acaaaauaua aaugaguuag cauuaaaugu    6240
uucagaguaa auaauuccuu ucccgaaaau gcaugaagau agaguaacag acuucucaca    6300
cuguauuuuu agguaugga gaauuuagaa gguuaaagaa uuacugcuuc aauuuuucag    6360
uuaaaaaaaa aucaggaagc ucuguucauu caggcuaugc accaugugca cagucaagaa    6420
uuagcagaaa cccucugcau uuacaaacac uuugugcuau aaaaaaguaa uuuuuaaaaa    6480
gccacgugug ugugugugua uauauauaua uauauauaua uuuaaagcca agguuuugau    6540
acuuuuuuac aaaaacuaca agagaaaaca aauauaccug uccaaaccau auacuuuuaa    6600
aagagcauuu uuuuuuccau acaagcuguu guuaauuugg gggguaaagug cugauuugca    6660 aacuucauca aauuguuccc aaguggauuc uccuuguuug ucuccccua ccaaccccaa    6720 aguuaccaua uuugauguaa gaaucaggca uguuagaaug uugugucaca cuaacugauu    6780
cugcucuuuu ugucuuguca uucaaguucc guuagcuucu guacgcggug cccuuugcag    6840
ucuggugucu cuuccagagg cgagggggcu gaggaugggg ugcugcaucu cacuagcuau    6900
acuggcauca ucuugguaaa cugaaaacca aauguggaca uuuguaaaau cagugcacug    6960
uuucuagaga gagauuaaau ucauuuaaaa aaaa                                6994
```

<210> SEQ ID NO 16
<211> LENGTH: 700
<212> TYPE: PRT
<213> ORGANISM: Homo sapiens

<400> SEQUENCE: 16

```
Met Gly Leu Pro Glu Pro Gly Pro Leu Arg Leu Leu Ala Leu Leu Leu
1               5                   10                  15

Leu Leu Leu Leu Leu Leu Leu Leu Gln Leu Gln His Leu Ala Ala Ala
            20                  25                  30

Ala Ala Asp Pro Leu Leu Gly Gly Gln Gly Pro Ala Lys Asp Cys Glu
        35                  40                  45

Lys Asp Gln Phe Gln Cys Arg Asn Glu Arg Cys Ile Pro Ser Val Trp
    50                  55                  60

Arg Cys Asp Glu Asp Asp Asp Cys Leu Asp His Ser Asp Glu Asp Asp
65                  70                  75                  80

Cys Pro Lys Lys Thr Cys Ala Asp Ser Asp Phe Thr Cys Asp Asn Gly
                85                  90                  95

His Cys Ile His Glu Arg Trp Lys Cys Asp Gly Glu Glu Cys Pro
                100                 105                 110

Asp Gly Ser Asp Glu Ser Glu Ala Thr Cys Thr Lys Gln Val Cys Pro
```

```
            115                 120                 125
Ala Glu Lys Leu Ser Cys Gly Pro Thr Ser His Lys Cys Val Pro Ala
            130                 135                 140
Ser Trp Arg Cys Asp Gly Glu Lys Asp Cys Glu Gly Gly Ala Asp Glu
145                 150                 155                 160
Ala Gly Cys Ala Thr Ser Leu Gly Thr Cys Arg Gly Asp Glu Phe Gln
                165                 170                 175
Cys Gly Asp Gly Thr Cys Val Leu Ala Ile Lys His Cys Asn Gln Glu
            180                 185                 190
Gln Asp Cys Pro Asp Gly Ser Asp Glu Ala Gly Cys Leu Gln Gly Leu
        195                 200                 205
Asn Glu Cys Leu His Asn Asn Gly Gly Cys Ser His Ile Cys Thr Asp
    210                 215                 220
Leu Lys Ile Gly Phe Glu Cys Thr Cys Pro Ala Gly Phe Gln Leu Leu
225                 230                 235                 240
Asp Gln Lys Thr Cys Gly Asp Ile Asp Glu Cys Lys Asp Pro Asp Ala
                245                 250                 255
Cys Ser Gln Ile Cys Val Asn Tyr Lys Gly Tyr Phe Lys Cys Glu Cys
            260                 265                 270
Tyr Pro Gly Tyr Glu Met Asp Leu Leu Thr Lys Asn Cys Lys Ala Ala
        275                 280                 285
Ala Gly Lys Ser Pro Ser Leu Ile Phe Thr Asn Arg His Glu Val Arg
    290                 295                 300
Arg Ile Asp Leu Val Lys Arg Asn Tyr Ser Arg Leu Ile Pro Met Leu
305                 310                 315                 320
Lys Asn Val Val Ala Leu Asp Val Glu Val Ala Thr Asn Arg Ile Tyr
                325                 330                 335
Trp Cys Asp Leu Ser Tyr Arg Lys Ile Tyr Ser Ala Tyr Met Asp Lys
            340                 345                 350
Ala Ser Asp Pro Lys Glu Gln Glu Val Leu Ile Asp Glu Gln Leu His
        355                 360                 365
Ser Pro Glu Gly Leu Ala Val Asp Trp Val His Lys His Ile Tyr Trp
    370                 375                 380
Thr Asp Ser Gly Asn Lys Thr Ile Ser Val Ala Thr Val Asp Gly Gly
385                 390                 395                 400
Arg Arg Arg Thr Leu Phe Ser Arg Asn Leu Ser Glu Pro Arg Ala Ile
                405                 410                 415
Ala Val Asp Pro Leu Arg Gly Phe Met Tyr Trp Ser Asp Trp Gly Asp
            420                 425                 430
Gln Ala Lys Ile Glu Lys Ser Gly Leu Asn Gly Val Asp Arg Gln Thr
        435                 440                 445
Leu Val Ser Asp Asn Ile Glu Trp Pro Asn Gly Ile Thr Leu Asp Leu
    450                 455                 460
Leu Ser Gln Arg Leu Tyr Trp Val Asp Ser Lys Leu His Gln Leu Ser
465                 470                 475                 480
Ser Ile Asp Phe Ser Gly Gly Asn Arg Lys Thr Leu Ile Ser Ser Thr
                485                 490                 495
Asp Phe Leu Ser His Pro Phe Gly Ile Ala Val Phe Glu Asp Lys Val
            500                 505                 510
Phe Trp Thr Asp Leu Glu Asn Glu Ala Ile Phe Ser Ala Asn Arg Leu
        515                 520                 525
Asn Gly Leu Glu Ile Ser Ile Leu Ala Glu Asn Leu Asn Asn Pro His
    530                 535                 540
```

```
Asp Ile Val Ile Phe His Glu Leu Lys Gln Pro Arg Ala Pro Asp Ala
545                 550                 555                 560

Cys Glu Leu Ser Val Gln Pro Asn Gly Gly Cys Glu Tyr Leu Cys Leu
                565                 570                 575

Pro Ala Pro Gln Ile Ser Ser His Ser Pro Lys Tyr Thr Cys Ala Cys
            580                 585                 590

Pro Asp Thr Met Trp Leu Gly Pro Asp Met Lys Arg Cys Tyr Arg Asp
        595                 600                 605

Ala Asn Glu Asp Ser Lys Met Gly Ser Thr Val Thr Ala Ala Val Ile
    610                 615                 620

Gly Ile Ile Val Pro Ile Val Ile Ala Leu Leu Cys Met Ser Gly
625                 630                 635                 640

Tyr Leu Ile Trp Arg Asn Trp Lys Arg Lys Asn Thr Lys Ser Met Asn
                645                 650                 655

Phe Asp Asn Pro Val Tyr Arg Lys Thr Thr Glu Glu Asp Glu Asp
                660                 665                 670

Glu Leu His Ile Gly Arg Thr Ala Gln Ile Gly His Val Tyr Pro Ala
    675                 680                 685

Arg Val Ala Leu Ser Leu Glu Asp Asp Gly Leu Pro
    690                 695                 700

<210> SEQ ID NO 17
<211> LENGTH: 7606
<212> TYPE: RNA
<213> ORGANISM: Homo sapiens

<400> SEQUENCE: 17
gcuggcggcg gccgcccagg gccggggccg cgcgcccagc cugagcccgc cccgccgccg      60
agcgucaccg aaccugcuug aaaugcagcc gaggagccgg ggcgggcggc agcggcggcg     120
gcggcggcgg cggggggcagc ggcaaccccg cgccgcggc aaggacucgg agggcugaga    180
cgcggcggcg gcggcgcggg gagcgcgggg cgcggcggcc ggagcccgg gcccgccaug     240 ggccucccg agccgggccc ucuccggcuu cuggcgcugc ugcugcugcu gcugcugcu     300 cugcugcugc agcuccagca ucuugcgcg gcagcggcug auccgcugcu cggcggccaa     360
gggccggcca aggauugcga aaaggaccaa uuccagugcc ggaacgagcg cugcauccc     420 ucugugugga gaugcgacga ggacgaugac ugcuuagacc acagcgacga ggacgacugc     480
cccaagaaga ccugugcaga cagugacuuc accugugaca cggccacug cauccacgaa     540 cgguggaagu gugacggcga ggaggagugu ccugauggcu ccgaugaguc cgaggccacu     600
ugcaccaagc aggugugucc ugcagagaag cugagcugug acccaccag ccacaagugu     660 guaccugccu cguggcgcug cgacggggag aaggacugcg aggguggagc ggaugaggcc     720
ggcugugcua ccuugugcgc cccgcacgag uuccagugcg gcaaccgcuc gugccuggcc     780
gccguguucg ugugcgacgg cgacgacgac ugugguggacg cagcgauga gcgcggcugu     840 gcagacccgg ccugcgggcc ccgcgaguuc cgcugcggcg gcgauggcgg cggcgccugc     900 auccggagc gcugggucug cgaccgccag uuugacugcg aggaccgcuc ggacgaggca     960
gccgagcucu gcggccgucc ggggccccggg gccacguccg cgcccgccgc cugcgccacc    1020
gccucccagu ucgccugccg cagcggcgag ugcgugcacc ugggcuggcg cugcgacggc    1080
gaccgcgacu gcaaagacaa aucggacgag gccgacugcc acuggggcac cugccgggug    1140
gacgaguucc agugugggga uggacaugug guccuugcaa ucaagcacug caaccaggag    1200
```

```
caggacuguc cagaugggag ugaugaagcu ggcugccuac aggggcugaa cgagugucug    1260
cacaacaaug gcggcugcuc acacaucugc acugacccuca agauuggcuu ugaaugcacg    1320
ugcccagcag gcuuccagcu ccuggaccag aagaccugug gcgacauuga ugagugcaag    1380
gacccagaug ccugcagcca gaucugaguc aauuacaagg gcuauuuuaa gugugagugc    1440
uacccuggcu acgagaugga ccacugaccc aagaacugca aggcugcugc uggcaagagc    1500
ccaucccuaa ucuucaccaa ccggcacgag gugcggagga ucgaccuggu gaagcggaac    1560
uauucacgcc ucaucccau gcucaagaau gucguggcac uagaugugga aguugccacc    1620
aaucgcaucu acuggugugu ccucuccuac cguaagaucu auagcgccua cauggacaag    1680
gccagugacc cgaaagagca ggagguccuc auugacgagc aguugcacuc uccagagggc    1740
cuggcagugg acugggucca caagcacauc uacuggacug acucgggcaa uaagaccauc    1800
ucaguggcca caguugaugg uggccgccga cgcacucucu ucagccguaa ccucagugaa    1860
ccccgggcca ucgcuguuga ccccugcga gggucaugu auuggucuga cuggggggac    1920
caggccaaga uugagaaauc ugggcucaac ggugggacc ggcaaacacu ggugucagac    1980
aauauugaau ggcccaacgg aaucacccug gaucugcuga ccagcgcuu guacuggua    2040
gacuccaagc uacaccaacu guccagcauu gacuucagug gaggcaacag aaagacgcgc    2100
aucuccucca cugacuuccu gagccacccu uugggauag cuguguuga ggacaaggug    2160
uucuggacag accuggagaa cgaggccauu ucagcaga ucggcucaa uggccuggaa    2220
aucuccaucc uggcugagaa ccaacaac ccacaugaca uugucaucuu ccaugagcug    2280
aagcagccaa gagcuccaga ugccugcag cugagugucc agccuaaugg aggcugugaa    2340
uaccugugcc uuccugcucc ucagaucucc agccacucuc caaguacac augugccugu    2400
ccugacacaa guggcuggg uccagacaug aagaggugcu accgagcacc ucaaucuacc    2460
ucaacuacga cguuagcuuc uaccaugacg aggacaguac cugccaccac aagagccccc    2520
gggaccaccg uccacagauc caccuaccag aaccacagca cagagacacc aagccugaca    2580
gcugcagucc caagcucagu uagugucccc agggcuccca gcaucagccc gucuacccua    2640
agcccugcaa ccagcaacca cucccagcac uaugcaaaug aagacaguaa gaugggcuca    2700
acagucacug ccgcuguuau cgggaucauc gugcccauag uggugauagc ccuccugugc    2760
augaguggau accugaucug gagaaacugg aagcggaaga acaccaaaag caugaauuuu    2820
gacaacccag ucuacaggaa aacaacagaa gaagaagacg aagaugagcu ccauauaggg    2880
agaacugcuc agauuggcca ugucuauccu gcacgagugg cauuaagcc ugaagaugau    2940
ggacuacccu gaggauggga ucacccccuu cgugccucau ggaauucagu cccaugcacu    3000
acacucugga ugguguauga cuggaugaau ggggucuau auaugggucu gugugagugu    3060
augugugugu ugauuuuu uuuuaaauuu auguugcgga aagguaacca caaaguuaug    3120
augaacugca aacauccaaa ggaugugaga guuuucuau guauaauguu uuauacacuu    3180
uuuaacuggu ugcacuaccc augaggaauu cguggaaugg cuacgcuga cuaacaugau    3240
gcacauaacc aaauggggc caauggcaca guaccuuacu caucauuaa aaacuauauu    3300
uacagaagau guuggguugc ugggggggcu uuuuaggguu uggggcauu uguuuuugu    3360
aaauaagaug auuaugcuuu guggcuaucc aucaacauaa guaaaaaaa aaaaaaaaca    3420
cuucaacucc cucccccauu uagauuauuu auuaacauau uuuaaaaauc agaugaguuc    3480
uauaaauaau uuagagaagu gagaguauuu auuuuggca uguuuggccc accacacaga    3540
cucugugugu guaugugugu guuuauaugu guaugugugu gacagaaaaa ucguagaga    3600
```

| | |
|---|---|
| agaggcacau cuauggcuac uguucaaaua cauaaagaua aauuuauuuu cacacagucc | 3660 |
| acaaggggua uaucuuguag uuuucagaaa agccuuugga aaucuggauc agaaaauaga | 3720 |
| uaccaugguu ugugcaauua uguaguaaaa aaggcaaauc uuuucaccuc uggcuauucc | 3780 |
| ugagacccca ggaagucagg aaaagccuuu cagcucaccc auggcugcug ugacccuac | 3840 |
| cagggcuuuc uuggcuuugg cgaaggucag uguacagaca uuccaugguua ccagagugcu | 3900 |
| cagaaacuca agauaggaua ugccucaccc ucagcuacuc cuuguuuuaa aguucagcuc | 3960 |
| uuugaguaac uucuucaauu ucuuucagga acuuggguu gaauucagua aguuccucu | 4020 |
| gaagcacccu gaagggugcc auccuuacag agcuaagugg agacguuucc agaucagccc | 4080 |
| aaguuuacua uagagacugg cccaggcacu gaaugucuag gacaugcugu ggaugaagau | 4140 |
| aaagauggug gaauaggguu uaucacaucu cuuauuucuc uuuucccuu acucucuacc | 4200 |
| auuuccuuua ugugggaaaa cauuuuaagg uaauaaauag guuacuuacc aucauauguu | 4260 |
| cauauagaug aaacuaauuu uuggcuuaag ucagaacaac uggccaaaau ugaagucaua | 4320 |
| uuugaggggg gaaauggcau acgcaauauu auauuauauu ggauauuuau guucacacag | 4380 |
| gaauuugguu uacugcuuug uaaauaaaag gaaaaacucc ggguauaugu auagauguuc | 4440 |
| uucauuauag acaucuucuu ugcuuuucuu ggccuugggg gaggaaggga gaagugcucu | 4500 |
| uuucuacuug uggggucucc cauuggaaac auaauccuau agucccagaa ggauucaguc | 4560 |
| cccaguggcu uucccauccca aagagaaaga guuugaguuu cuuaacucug cuguucugcc | 4620 |
| acuuacuccc acuagacaac cagggacaag gugcaacaug gaaguguuug acuuaaguag | 4680 |
| gagcagagga gcugcaucua aucucaucau accuggaacu ugacacacuu aagcaaaugc | 4740 |
| cuucccaucc cuaccugcca gaugccccca acucaaugaa guuggaugucu caccagcuu | 4800 |
| gauacccuuu gaauuuucag ucagacauuc uggaguucua gcauccugua ccuaggaccu | 4860 |
| uccucugugu cacucuuggc cuccaaaacu cuaagaaaau aacuauauuc uggagcuugg | 4920 |
| gcagugguu uugcauaauc cagcaaucuc cucaugacau gcaugguug auaguccuga | 4980 |
| aacauucauu gagagggua augcaguuga ccuagaauga ccaauaccaa acagaauuuu | 5040 |
| aagaacaggu ggccaacucc uauggagcuu acucacauau uacuauucuu uuaagaacgg | 5100 |
| aaaguaaaau uauuuuugac ugaagaaaaa ugaugacagu gaaaaacaug gaaauguacu | 5160 |
| caaaacaagu gacuuuuucu guaaccuucc aagaaacug aauuuccaa ggaauuaaau | 5220 |
| gauaacagug gcuaaggcau aguuucaaaa cuuucaguaa gauccuggca uucacagaaa | 5280 |
| aaaaugauga auggggucug gacauacagc cugagaucuc aaaaugacaa ugaaauucac | 5340 |
| aacuuuuucu cagagacauu caugauuuccu gcauaugcua caacugcagu uugaagagg | 5400 |
| cagcaauggg agcaacccuu uacaagaaac aaauugugau auauucaugu guuggacggc | 5460 |
| aguaaauaag augaaaccug aggagucaga uccaccuucc cccauucaua gaggcuuuuc | 5520 |
| agccucauuu ugagguacag uuacauaucu uuugccuuuu gcccccgugc auagcuaucu | 5580 |
| acagccaauc acagaucaca gagucacugg acuauagagc uggaaggaag cucagagaca | 5640 |
| augccaaggg ggcagaaaau uuaucagaag ccagucccag ugcguuuccu ccauuuccuu | 5700 |
| cugcaggaag acuauuuugg gcugccugaa cauugauca aaccgcuac cuauacuaug | 5760 |
| gucuaccuuu ccuccagugg aauuacaaag gcacuaacug aaaugccuuc uagaaacaga | 5820 |
| gaaaacgaaa cuguacuuau uuacucuuga uacacagauu auuuauaaaa cagauugaag | 5880 |
| uaaccuguua acuggcaaaa agagaaugag aucggauuua aauguauggc aguaaguccu | 5940 |

```
auugaucccu ccaguuaucu caguaugacu gcaguauauu cauucacuaa aaccacucac    6000
uagauaccaa cuacacaccu ggcacugcag auguaaaggu cagucacaca uguucugacu    6060
uuacagaguu cacaguagca guggaggaug auauaugugg aaacaaaaaa ggcauugauu    6120
cuauucagag cacuguuagg gcucaaagga gagaggggguc uuuccaccua agaaaugagg   6180 aauagggguca ucauagaagu gaccuuaagu cuuaaaaauu aagaagggga uuccaagcug   6240
cuucagacag agacacaucg agcuaaaaca cagagguaug aaagagcaca gggacuuuag    6300
gaauugcaca guucauucua acaggaacaa aaggcucaag gggggcaaga aaugaggcug    6360
uauggaaaga gauucaaugu aagcacuuua uaaaauagau uaauuucuga uucaaugaag    6420 cauucuuga ucauugugua caaggcacua caugcaucau ggaaaauuca uuaggaugca    6480
uugccagcac uuugcagaac ugauauuauu cagccucaag cuuuccagug gccaaaggga    6540
aaugcugacu gcuuucaua uauuugaguc aaagauuuuu uauaugguca augaagacua    6600
auauaagggc aguggguauuu ucacagaugc augccauguu gucgagagcc ucuuagauuu   6660
ucucaacugu gagaaagaaa aacgaaaaug uugaagacgu ugagucugga gaggggauac    6720
uaaucacugu ccaguagggc acuggugga auggggaaau ggcacaggaa ugcaagccuc    6780
uccacccuac cccccgaacu ccagccauac acucaucguu ucacaaaaua uaaaugaguu    6840
agcauuaaau guuucagagu aaauaauucc uuuucccgaa augcaugaag auagaguaac    6900
agacuucuca cacuguauuu uuaggguaug gagaaauuuag aagguaaag aauuacugcu    6960 ucaauuuuc aguuaaaaaa aaaucaggaa gcucuguuca uucaggcuau gcaccaugug    7020
cacagucaag aauuagcaga aacccucugc auuuacaaac acuuugugcu auaaaaaagu    7080
aauuuuuaaa aagccacgug uguguguguug uauauauaua uauauauaua uauuuaaagc    7140
caagguuuug uacuuuuuuuu acaaaaacua caagagaaaa caaauauacc uguccaaacc    7200
auauacuuuu aaaagagcau uuuuuuuucc auacaagcug uuguuaauuu ggggguaaag    7260
ugcugauuug caaacuucau caaauuguuc ccaaguggau ucuccuuguu ugucuccccc    7320
uaccaccccc aaaguuacca uauuugaugu aagaaucagg cauguagaa uguuguguca    7380 cacuaacuga uucugcucuu uuugucugu cauucaaguu ccguuagcuu cuguacgcgg    7440
ugcccuuugc agucuggugu ucuuccaga ggcgagggggg cugaggaugg ggugcugcau    7500
cucacuagcu auacuggcau caucuugguua aacugaaaac caaaugugga cauuuguaaa    7560
aucagugcac uguuucuaga gagagauuaa auucauuuaa aaaaaa              7606
```

<210> SEQ ID NO 18
<211> LENGTH: 904
<212> TYPE: PRT
<213> ORGANISM: Homo sapiens

<400> SEQUENCE: 18

```
Met Gly Leu Pro Glu Pro Gly Pro Leu Arg Leu Leu Ala Leu Leu Leu
1               5                   10                  15

Leu Leu Leu Leu Leu Leu Leu Leu Gln Leu Gln His Leu Ala Ala Ala
            20                  25                  30

Ala Ala Asp Pro Leu Leu Gly Gly Gln Gly Pro Ala Lys Asp Cys Glu
        35                  40                  45

Lys Asp Gln Phe Gln Cys Arg Asn Glu Arg Cys Ile Pro Ser Val Trp
    50                  55                  60

Arg Cys Asp Glu Asp Asp Asp Cys Leu Asp His Ser Asp Glu Asp Asp
65                  70                  75                  80
```

```
Cys Pro Lys Lys Thr Cys Ala Asp Ser Asp Phe Thr Cys Asp Asn Gly
             85                  90                  95

His Cys Ile His Glu Arg Trp Lys Cys Asp Gly Glu Glu Glu Cys Pro
            100                 105                 110

Asp Gly Ser Asp Glu Ser Glu Ala Thr Cys Thr Lys Gln Val Cys Pro
            115                 120                 125

Ala Glu Lys Leu Ser Cys Gly Pro Thr Ser His Lys Cys Val Pro Ala
            130                 135                 140

Ser Trp Arg Cys Asp Gly Lys Asp Cys Glu Gly Ala Asp Glu
145                 150                 155                 160

Ala Gly Cys Ala Thr Leu Cys Ala Pro His Glu Phe Gln Cys Gly Asn
                165                 170                 175

Arg Ser Cys Leu Ala Ala Val Phe Val Cys Asp Gly Asp Asp Asp Cys
            180                 185                 190

Gly Asp Gly Ser Asp Glu Arg Gly Cys Ala Asp Pro Ala Cys Gly Pro
            195                 200                 205

Arg Glu Phe Arg Cys Gly Gly Asp Gly Gly Ala Cys Ile Pro Glu
            210                 215                 220

Arg Trp Val Cys Asp Arg Gln Phe Asp Cys Glu Asp Arg Ser Asp Glu
225                 230                 235                 240

Ala Ala Glu Leu Cys Gly Arg Pro Gly Pro Gly Ala Thr Ser Ala Pro
                245                 250                 255

Ala Ala Cys Ala Thr Ala Ser Gln Phe Ala Cys Arg Ser Gly Glu Cys
                260                 265                 270

Val His Leu Gly Trp Arg Cys Asp Gly Asp Arg Asp Cys Lys Asp Lys
            275                 280                 285

Ser Asp Glu Ala Asp Cys Pro Leu Gly Thr Cys Arg Gly Asp Glu Phe
            290                 295                 300

Gln Cys Gly Asp Gly Thr Cys Val Leu Ala Ile Lys His Cys Asn Gln
305                 310                 315                 320

Glu Gln Asp Cys Pro Asp Gly Ser Asp Glu Ala Gly Cys Leu Gln Gly
                325                 330                 335

Leu Asn Glu Cys Leu His Asn Asn Gly Gly Cys Ser His Ile Cys Thr
            340                 345                 350

Asp Leu Lys Ile Gly Phe Glu Cys Thr Cys Pro Ala Gly Phe Gln Leu
            355                 360                 365

Leu Asp Gln Lys Thr Cys Gly Asp Ile Asp Glu Cys Lys Asp Pro Asp
            370                 375                 380

Ala Cys Ser Gln Ile Cys Val Asn Tyr Lys Gly Tyr Phe Lys Cys Glu
385                 390                 395                 400

Cys Tyr Pro Gly Tyr Glu Met Asp Leu Leu Thr Lys Asn Cys Lys Ala
                405                 410                 415

Ala Ala Gly Lys Ser Pro Ser Leu Ile Phe Thr Asn Arg His Glu Val
            420                 425                 430

Arg Arg Ile Asp Leu Val Lys Arg Asn Tyr Ser Arg Leu Ile Pro Met
            435                 440                 445

Leu Lys Asn Val Val Ala Leu Asp Val Glu Val Ala Thr Asn Arg Ile
450                 455                 460

Tyr Trp Cys Asp Leu Ser Tyr Arg Lys Ile Tyr Ser Ala Tyr Met Asp
465                 470                 475                 480

Lys Ala Ser Asp Pro Lys Glu Gln Glu Val Leu Ile Asp Glu Gln Leu
                485                 490                 495

His Ser Pro Glu Gly Leu Ala Val Asp Trp Val His Lys His Ile Tyr
```

```
                500                 505                 510
Trp Thr Asp Ser Gly Asn Lys Thr Ile Ser Val Ala Thr Val Asp Gly
            515                 520                 525

Gly Arg Arg Thr Leu Phe Ser Arg Asn Leu Ser Glu Pro Arg Ala
530                 535                 540

Ile Ala Val Asp Pro Leu Arg Gly Phe Met Tyr Trp Ser Asp Trp Gly
545                 550                 555                 560

Asp Gln Ala Lys Ile Glu Lys Ser Gly Leu Asn Gly Val Asp Arg Gln
                565                 570                 575

Thr Leu Val Ser Asp Asn Ile Glu Trp Pro Asn Gly Ile Thr Leu Asp
            580                 585                 590

Leu Leu Ser Gln Arg Leu Tyr Trp Val Asp Ser Lys Leu His Gln Leu
            595                 600                 605

Ser Ser Ile Asp Phe Ser Gly Gly Asn Arg Lys Thr Leu Ile Ser Ser
            610                 615                 620

Thr Asp Phe Leu Ser His Pro Phe Gly Ile Ala Val Phe Glu Asp Lys
625                 630                 635                 640

Val Phe Trp Thr Asp Leu Glu Asn Glu Ala Ile Phe Ser Ala Asn Arg
                645                 650                 655

Leu Asn Gly Leu Glu Ile Ser Ile Leu Ala Glu Asn Leu Asn Asn Pro
            660                 665                 670

His Asp Ile Val Ile Phe His Glu Leu Lys Gln Pro Arg Ala Pro Asp
            675                 680                 685

Ala Cys Glu Leu Ser Val Gln Pro Asn Gly Gly Cys Glu Tyr Leu Cys
            690                 695                 700

Leu Pro Ala Pro Gln Ile Ser Ser His Ser Pro Lys Tyr Thr Cys Ala
705                 710                 715                 720

Cys Pro Asp Thr Met Trp Leu Gly Pro Asp Met Lys Arg Cys Tyr Arg
                725                 730                 735

Ala Pro Gln Ser Thr Ser Thr Thr Thr Leu Ala Ser Thr Met Thr Arg
            740                 745                 750

Thr Val Pro Ala Thr Thr Arg Ala Pro Gly Thr Thr Val His Arg Ser
            755                 760                 765

Thr Tyr Gln Asn His Ser Thr Glu Thr Pro Ser Leu Thr Ala Ala Val
770                 775                 780

Pro Ser Ser Val Ser Val Pro Arg Ala Pro Ser Ile Ser Pro Ser Thr
785                 790                 795                 800

Leu Ser Pro Ala Thr Ser Asn His Ser Gln His Tyr Ala Asn Glu Asp
                805                 810                 815

Ser Lys Met Gly Ser Thr Val Thr Ala Ala Val Ile Gly Ile Ile Val
            820                 825                 830

Pro Ile Val Val Ile Ala Leu Leu Cys Met Ser Gly Tyr Leu Ile Trp
            835                 840                 845

Arg Asn Trp Lys Arg Lys Asn Thr Lys Ser Met Asn Phe Asp Asn Pro
850                 855                 860

Val Tyr Arg Lys Thr Thr Glu Glu Glu Asp Glu Asp Glu Leu His Ile
865                 870                 875                 880

Gly Arg Thr Ala Gln Ile Gly His Val Tyr Pro Ala Arg Val Ala Leu
                885                 890                 895

Ser Leu Glu Asp Asp Gly Leu Pro
            900

<210> SEQ ID NO 19
```

<211> LENGTH: 2358
<212> TYPE: RNA
<213> ORGANISM: Homo sapiens

<400> SEQUENCE: 19

```
aaacucacac aacaacucuu ccccgcugag aggagacagc cagugcgacu ccacccucca      60
gcucgacggc agccgcccg gccgacagcc ccgagacgac agcccggcgc gucccgguc      120
ccaccuccga ccaccgccag cgcuccaggc cccgccgcuc cccgcucgcc gccaccgcgc     180
ccuccgcucc gcccgcagug ccaaccauga ccgccgccag uaugggcccc guccgcgucg     240
ccuucgugu ccuccucgcc cucucagcc ggccggccgu cggccagaac ugcagcgggc      300
cgugccggug cccggacgag ccggcgccgc gcugcccggc gggcgugagc cucgugcugg     360
acggcugcgg cugcugccgc gucugcgcca agcagcuggg cgagcugugc accgagcgcg     420
accccugcga cccgcacaag ggccucuucu gugacuucgg cucccggcc aaccgcaaga     480
ucggcgugug caccgccaaa gaugugcuc ccugcaucuu cggugguacg guguaccgca     540
gcggagaguc cuuccagagc agcugcaagu accagugcac gugccuggac ggggcgguugg    600
gcugcaugcc ccugugcagc augggacguuc gucugcccag cccgacugc cccuucccga    660
ggagggucaa gcugcccggg aaaugcugcg aggagugggu gugugacgag cccaaggacc    720
aaaccguggu ugggccugcc cucgcggcuu accgacugga agacacguuu ggcccagacc    780
caacuaugau uagagccaac ugccuggucc agaccacaga guggagcgcc uguccaaga     840
ccugugggau gggcaucucc acccgggua ccaaugacaa cgccuccugc aggcuagaga     900
agcagagccg ccugugcaug gucaggccuu gcgaagcuga ccuggaagag aacauuaaga    960
aggggcaaaaa gugcauccgu acucccaaaa ucuccaagcc uaucaaguuu gagcuuucug   1020
gcugcaccag caugaagaca uaccgagcua auucuguggg aguaguagcc gacggccgau   1080
gcugcacccc ccacagaacc accacccugc cgguggaguu caagugcccu gacggcgagg   1140
ucaugaagaa gaacaugaug uucaucaaga ccugugccug ccauuacaac ugucccggag   1200
acaaugacau cuuugaaucg cuguacuaca ggaagaugua cggagacaug gcaugaagcc   1260
agagagugag agacauuaac ucauuagacu ggaacuugaa cugauucaca ucucauuuuu   1320
ccguaaaaau gauuucagua gcacaaguua uuuaaaucug uuuuucuaac uggggggaaaa   1380
gauucccacc caauucaaaa cauugugcca ugucaaacaa auagcuauc aaccccagac    1440
acugguuuga agaauguuaa gacuugacag uggaacuaca uuaguacaca gcaccagaau   1500
guauauuaag guguggcuuu aggagcagug ggagggucc agcagaaagg uuaguaucau    1560
cagauagcau cuuauacgag uaauaugccu gcuauugaa guguaauuga gaaggaaaau    1620
uuuagcgugc ucacugaccu gccuguagcc ccagugacag cuaggaugug cauucuccag   1680
ccaucaagag acugagucaa guuguuccuu aagucagaac agcagacuca gcucugacau   1740
ucugauucga augacacugu ucaggaaucg gaauccuguc gauuagacug gacagcuugu   1800
ggcaagugaa uuugccugua acaagccaga uuuuuaaaa uuuauauugu aaauauugug    1860
ugugugugug uguguauaua uauauauaua uguacaguua ucuaaguuaa uuuaaaguug    1920
uuugugccuu uuuauuuuug uuuuuaaugc uuugauauuu caauguuagc cucaauuucu   1980
gaacaccaua gguagaaugu aaagcuuguc ugaucguuca aagcaugaaa uggauacuua   2040
uauggaaauu cugcucagau agaaugacag uccgucaaaa cagauuguuu gcaaggggga   2100
ggcaucagug uccuuggcag gcugauuucu agguaggaaa uguggagcc ucacuuuuaa    2160
ugaacaaaug gccuuuauua aaaacugagu gacucuauau agcugaucag uuuuuucacc   2220
```

```
uggaagcauu uguuucuacu uugauaugac uguuuucgg acaguuuauu uguugagagu    2280
gugaccaaaa guuacauguu ugcaccuuuc uaguugaaaa uaaaguguau auuuuuucua    2340
uaaaaaaaaa aaaaaaaa                                                 2358
```

<210> SEQ ID NO 20
<211> LENGTH: 349
<212> TYPE: PRT
<213> ORGANISM: Homo sapiens

<400> SEQUENCE: 20

```
Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
```

<210> SEQ ID NO 21
<211> LENGTH: 1939
<212> TYPE: RNA
<213> ORGANISM: Homo sapiens

<400> SEQUENCE: 21

| | | | | | |
|---|---|---|---|---|---|
| aggaaggagg | gguggccuga | ccccucggca | gucccucccc | ucagccuuuc | cccaaauugc | 60 |
| uacuucucug | gggcuccagg | uccugcuugu | gcucagcucc | agcucacugg | cuggccaccg | 120 |
| agacuucugg | acaggaaacu | gcaccauccu | cuucucccag | caaggggggcu | ccagagacug | 180 |
| cccacccagg | aagucuggug | gccugggggau | uggacagug | ccuugguaau | gaccagggcu | 240 |
| ccaggaagag | auguccuugu | ggcugggggc | cccugugccu | gacauuccuc | cugacucugc | 300 |
| gguggagcug | uggaagccag | gcgcacagga | ugcaagcagc | caggcccagg | gaggcagcag | 360 |
| cugcauccuc | agagaggaag | ccaggaugcc | ccacucugcu | gggguacug | caggggu ggg | 420 |
| gcuggaggcu | gcagagccca | cagcccugcu | caccagggca | gagcccccuu | cagaacccac | 480 |
| agagauccgu | ccacaaaagc | ggaaaaaggg | gccagccccc | aaaaugcugg | ggaacgagcu | 540 |
| augcagcgug | ugugggggaca | aggccucggg | cuuccacuac | aauguucuga | gcugcgaggg | 600 |
| cugcaaggga | uucuuccgcc | gcagcgucau | caagggagcg | cacuacaucu | gccacagugg | 660 |
| cggccacugc | cccauggaca | ccuacaugcg | ucgcaagugc | caggaguguc | ggcuucgcaa | 720 |
| augccgucag | gcuggcaugc | gggaggagug | uguccuguca | gaagaacaga | uccgccugaa | 780 |
| gaaacugaag | cggcaagagg | aggaacaggc | ucaugcccaca | uccuugcccc | cagggcuuc | 840 |
| cucacccccc | caaauccugc | cccagcucag | cccggaacaa | cugggcauga | ucgagaagcu | 900 |
| cgucgcugcc | cagcaacagu | guaaccggcg | cuccuuuucu | gaccggcuuc | gagucacgcc | 960 |
| uuggcccaug | gcaccagauc | cccauagccg | ggaggcccgu | cagcagcgcu | ugcccacuu | 1020 |
| cacugagcug | gccaucgucu | cugugcagga | gauaguugac | uuugcuaaac | agcuaccgg | 1080 |
| cuuccugcag | cucagccggg | aggaccagau | ugccugcug | aagaccucug | cgaucgaggu | 1140 |
| gaugcuucug | gagacaucuc | ggagguacaa | cccugggagu | gagaguauca | ccuuccucaa | 1200 |
| ggauuucagu | uauaaccggg | aagacuuugc | caaagcaggg | cugcaagugg | aauucaucaa | 1260 |
| ccccaucuuc | gaguucucca | gggccaugaa | ugagcugcaa | ucaaugaug | ccgaguuugc | 1320 |
| cuugcucauu | gcuaucagca | ucuucucugc | agaccggccc | aacgugcagg | accagcucca | 1380 |
| gguagagagg | cugcagcaca | cauaugugga | agcccgcau | gccuacgucu | ccauccacca | 1440 |
| uccccaugac | cgacugaugu | ucccacggau | gcuaaugaaa | cuggugagcc | uccggacccu | 1500 |
| gagcagcguc | cacucagagc | aaguguuugc | acugcgucug | caggacaaaa | agcucccacc | 1560 |
| gcugcucucu | gagaucuggg | augugcacga | augacuguuc | ugucccaua | uuuucuguuu | 1620 |
| ucuuggccgg | auggcugagg | ccugguggcu | gccuccuaga | aguggaacag | acugagaagg | 1680 |
| gcaaacauuc | cugggagcug | ggcaaggaga | uccucccgug | gcauuaaaag | agagucaaag | 1740 |
| gguugcgagu | uuguggcua | cugagcagug | gagcccucgc | uaacacugug | cugugucuga | 1800 |
| agaucaugcu | gaccccacaa | acggauggggc | cugggggcca | cuuugcacag | gguucuccag | 1860 |
| agcccugccc | auccugccuc | caccacuucc | uguuuuuccc | acagggcccc | aagaaaaauu | 1920 |
| cuccacuguc | aaaaaaaaa | | | | | 1939 |

<210> SEQ ID NO 22
<211> LENGTH: 447

<212> TYPE: PRT
<213> ORGANISM: Homo sapiens

<400> SEQUENCE: 22

Met Ser Leu Trp Leu Gly Ala Pro Val Pro Asp Ile Pro Pro Asp Ser
1               5                   10                  15

Ala Val Glu Leu Trp Lys Pro Gly Ala Gln Asp Ala Ser Ser Gln Ala
            20                  25                  30

Gln Gly Gly Ser Ser Cys Ile Leu Arg Glu Glu Ala Arg Met Pro His
        35                  40                  45

Ser Ala Gly Gly Thr Ala Gly Val Gly Leu Glu Ala Ala Glu Pro Thr
    50                  55                  60

Ala Leu Leu Thr Arg Ala Glu Pro Pro Ser Glu Pro Thr Glu Ile Arg
65                  70                  75                  80

Pro Gln Lys Arg Lys Gly Pro Ala Pro Lys Met Leu Gly Asn Glu
                85                  90                  95

Leu Cys Ser Val Cys Gly Asp Lys Ala Ser Gly Phe His Tyr Asn Val
            100                 105                 110

Leu Ser Cys Glu Gly Cys Lys Gly Phe Phe Arg Arg Ser Val Ile Lys
        115                 120                 125

Gly Ala His Tyr Ile Cys His Ser Gly Gly His Cys Pro Met Asp Thr
    130                 135                 140

Tyr Met Arg Arg Lys Cys Gln Glu Cys Arg Leu Arg Lys Cys Arg Gln
145                 150                 155                 160

Ala Gly Met Arg Glu Glu Cys Val Leu Ser Glu Glu Gln Ile Arg Leu
                165                 170                 175

Lys Lys Leu Lys Arg Gln Glu Glu Glu Gln Ala His Ala Thr Ser Leu
            180                 185                 190

Pro Pro Arg Ala Ser Ser Pro Pro Gln Ile Leu Pro Gln Leu Ser Pro
        195                 200                 205

Glu Gln Leu Gly Met Ile Glu Lys Leu Val Ala Ala Gln Gln Gln Cys
    210                 215                 220

Asn Arg Arg Ser Phe Ser Asp Arg Leu Arg Val Thr Pro Trp Pro Met
225                 230                 235                 240

Ala Pro Asp Pro His Ser Arg Glu Ala Arg Gln Gln Arg Phe Ala His
                245                 250                 255

Phe Thr Glu Leu Ala Ile Val Ser Val Gln Glu Ile Val Asp Phe Ala
            260                 265                 270

Lys Gln Leu Pro Gly Phe Leu Gln Leu Ser Arg Glu Asp Gln Ile Ala
        275                 280                 285

Leu Leu Lys Thr Ser Ala Ile Glu Val Met Leu Leu Glu Thr Ser Arg
    290                 295                 300

Arg Tyr Asn Pro Gly Ser Glu Ser Ile Thr Phe Leu Lys Asp Phe Ser
305                 310                 315                 320

Tyr Asn Arg Glu Asp Phe Ala Lys Ala Gly Leu Gln Val Glu Phe Ile
                325                 330                 335

Asn Pro Ile Phe Glu Phe Ser Arg Ala Met Asn Glu Leu Gln Leu Asn
            340                 345                 350

Asp Ala Glu Phe Ala Leu Leu Ile Ala Ile Ser Ile Phe Ser Ala Asp
        355                 360                 365

Arg Pro Asn Val Gln Asp Gln Leu Gln Val Glu Arg Leu Gln His Thr
    370                 375                 380

Tyr Val Glu Ala Leu His Ala Tyr Val Ser Ile His His Pro His Asp
385                 390                 395                 400

```
Arg Leu Met Phe Pro Arg Met Leu Met Lys Leu Val Ser Leu Arg Thr
            405                 410                 415
Leu Ser Ser Val His Ser Glu Gln Val Phe Ala Leu Arg Leu Gln Asp
        420                 425                 430
Lys Lys Leu Pro Pro Leu Leu Ser Glu Ile Trp Asp Val His Glu
435                 440                 445

<210> SEQ ID NO 23
<211> LENGTH: 1759
<212> TYPE: RNA
<213> ORGANISM: Homo sapiens

<400> SEQUENCE: 23
aggaaggagg gguggccuga ccccucggca gucccucccc ucagccuuuc cccaaauugc    60
uacuucucug gggcuccagg uccugcuugu gcucagcucc agcucacugg cuggccaccg   120
agacuucugg acaggaaacu gcaccauccu cuucucccag caaggggcu ccagagacug    180
cccacccagg aagucgggug gccugggau uggacagug ccuugguaau gaccagggcu     240
ccaggaagag augccuugu ggcuggggc cccugugccu gacauuccuc cugacucugc     300
gguggagcug uggaagccag cgcacagga ugcaagcagc caggcccagg gaggcagcag    360
cugcauccuc agagaggaag ccaggaugcc cacucugcu gggguacug caggggugg      420
gcuggaggcu gcagagccca cagcccugcu caccagggca gagccccuu cagaacccac    480
agagauccgu ccacaaaagc ggaaaaaggg gccagccccc aaaaugcugg ggaacgagcu   540
augcagcgug ugggggaca aggccucggg cuuccacuac aauguucuga gcugcgaggg    600
cugcaaggga uucuuccgcc gcagcgucau caagggagcg cacuacaucu gccacagugg   660
cggccacugc cccauggaca ccuacaugcg ucgcaagugc caggaguguc ggcuucgcaa   720
augccgucag gcuggcaugc gggaggagug uguccuguca aagaacaga uccgccugaa    780
gaaacugaag cggcaagagg aggaacaggc ucaugccaca uccuugcccc cagggcuuc    840
cucacccccc caaauccugc cccagcucag cccggaacaa cugggcauga ucgagaagcu   900
cgucgcugcc cagcaacagu guaaccggcg cuccuuuucu gaccggcuuc gagucacggu   960
gaugcuucug gagacaucuc ggagguacaa cccgggagu gagaguauca ccuuccucaa   1020
ggauuucagu uauaaccggg aagacuuugc caaagcaggg cugcaagugg aauucaucaa  1080
ccccaucuuc gaguucucca gggccaugaa ugagcugcaa cucaaugaug ccgaguuugc  1140
cuugcucauu gcuaucagca ucuucucugc agaccggccc aacgugcagg accagccuca  1200
gguagagagg cugcagcaca cauaugugga agcccugcau gccuacgucu ccauccacca  1260
uccccaugac cgacugaugu ucccacggau gcuaaugaaa cuggugagcc uccgacccu   1320
gagcagcguc cacucagagc aaguguuugc acugcgucug caggacaaaa agcucccacc  1380
gcugcucucu gagaucuggg augugcacga augacguuc uguccccaua uuucuguuu   1440
ucuuggccgg auggcugagg ccugguggcu gccuccuaga aguggaacag acugagaagg  1500
gcaaacauuc cugggagcug ggcaaggaga uccucccgug gcauuaaaag agagucaaag  1560
gguugcgagu uuuguggcua cugagcagug gagcccucgc uaacacugug cuguccuga   1620
agaucaugcu gaccccacaa acggaugggc cuggggggcca cuuugcacag gguucuccag  1680
agcccugccc auccgccuc caccacuucc uguuuucccc acagggcccc aagaaaaauu   1740
cuccacuguc aaaaaaaaa                                               1759
```

```
<210> SEQ ID NO 24
<211> LENGTH: 387
<212> TYPE: PRT
<213> ORGANISM: Homo sapiens

<400> SEQUENCE: 24

Met Ser Leu Trp Leu Gly Ala Pro Val Pro Asp Ile Pro Pro Asp Ser
1               5                   10                  15

Ala Val Glu Leu Trp Lys Pro Gly Ala Gln Asp Ala Ser Ser Gln Ala
            20                  25                  30

Gln Gly Gly Ser Ser Cys Ile Leu Arg Glu Glu Ala Arg Met Pro His
        35                  40                  45

Ser Ala Gly Gly Thr Ala Gly Val Gly Leu Glu Ala Ala Glu Pro Thr
    50                  55                  60

Ala Leu Leu Thr Arg Ala Glu Pro Pro Ser Glu Pro Thr Glu Ile Arg
65                  70                  75                  80

Pro Gln Lys Arg Lys Lys Gly Pro Ala Pro Lys Met Leu Gly Asn Glu
                85                  90                  95

Leu Cys Ser Val Cys Gly Asp Lys Ala Ser Gly Phe His Tyr Asn Val
            100                 105                 110

Leu Ser Cys Glu Gly Cys Lys Gly Phe Phe Arg Arg Ser Val Ile Lys
        115                 120                 125

Gly Ala His Tyr Ile Cys His Ser Gly His Cys Pro Met Asp Thr
    130                 135                 140

Tyr Met Arg Arg Lys Cys Gln Glu Cys Arg Leu Arg Lys Cys Arg Gln
145                 150                 155                 160

Ala Gly Met Arg Glu Glu Cys Val Leu Ser Glu Glu Gln Ile Arg Leu
                165                 170                 175

Lys Lys Leu Lys Arg Gln Glu Glu Glu Gln Ala His Ala Thr Ser Leu
            180                 185                 190

Pro Pro Arg Ala Ser Ser Pro Pro Gln Ile Leu Pro Gln Leu Ser Pro
        195                 200                 205

Glu Gln Leu Gly Met Ile Glu Lys Leu Val Ala Ala Gln Gln Gln Cys
    210                 215                 220

Asn Arg Arg Ser Phe Ser Asp Arg Leu Arg Val Thr Val Met Leu Leu
225                 230                 235                 240

Glu Thr Ser Arg Arg Tyr Asn Pro Gly Ser Glu Ser Ile Thr Phe Leu
                245                 250                 255

Lys Asp Phe Ser Tyr Asn Arg Glu Asp Phe Ala Lys Ala Gly Leu Gln
            260                 265                 270

Val Glu Phe Ile Asn Pro Ile Phe Glu Phe Ser Arg Ala Met Asn Glu
        275                 280                 285

Leu Gln Leu Asn Asp Ala Glu Phe Ala Leu Leu Ile Ala Ile Ser Ile
    290                 295                 300

Phe Ser Ala Asp Arg Pro Asn Val Gln Asp Gln Leu Gln Val Glu Arg
305                 310                 315                 320

Leu Gln His Thr Tyr Val Glu Ala Leu His Ala Tyr Val Ser Ile His
                325                 330                 335

His Pro His Asp Arg Leu Met Phe Pro Arg Met Leu Met Lys Leu Val
            340                 345                 350

Ser Leu Arg Thr Leu Ser Ser Val His Ser Glu Gln Val Phe Ala Leu
        355                 360                 365

Arg Leu Gln Asp Lys Lys Leu Pro Pro Leu Leu Ser Glu Ile Trp Asp
    370                 375                 380
```

Val His Glu
385

<210> SEQ ID NO 25
<211> LENGTH: 1748
<212> TYPE: RNA
<213> ORGANISM: Homo sapiens

<400> SEQUENCE: 25

| | | | | | |
|---|---|---|---|---|---|
| aucuuacuua | gggaccugcu | ggggugcggg | gaaaaggcgc | agucucggug | ggauugcgug | 60 |
| caggaggguc | ugguucuggc | uguggcggag | gagcauaaga | agacucugcg | guggagcugu | 120 |
| ggaagccagg | cgcacaggau | gcaagcagcc | aggcccaggg | aggcagcagc | ugcauccuca | 180 |
| gagaggaagc | caggaugccc | cacucugcug | ggggguacugc | aggggugggg | cuggaggcug | 240 |
| cagagcccac | agcccugcuc | accagggcag | agccccuuc | agaacccaca | gagauccguc | 300 |
| cacaaaagcg | gaaaaggggg | ccagccccca | aaaugcuggg | gaacgagcua | ugcagcgugu | 360 |
| gugggggacaa | ggccucgggc | uuccacuaca | auguucugag | cugcgagggc | ugcaagggau | 420 |
| ucuuccgccg | cagcgucauc | aagggagcgc | acuacaucug | ccacaguggc | ggccacugcc | 480 |
| ccauggacac | cuacaugcgu | cgcaagugcc | aggagugucg | gcuucgcaaa | ugccgucagg | 540 |
| cuggcaugcg | ggaggagugu | guccugucag | aagaacagau | ccgccugaag | aaacugaagc | 600 |
| ggcaagagga | ggaacaggcu | caugccacau | ccuugccccc | cagggcuucc | ucacccccc | 660 |
| aaauccugcc | ccagcucagc | ccggaacaac | ugggcaugau | cgagaagcuc | gucgcugccc | 720 |
| agcaacagug | uaaccggcgc | uccuuuucug | accggcuucg | agucacgccu | uggcccaugg | 780 |
| caccagaucc | ccauagccgg | gaggcccguc | agcagcgcuu | ugcccacuuc | acugagcugg | 840 |
| ccaucgucuc | ugugcaggag | auaguugacu | uugcuaaaca | gcuacccggc | uuccugcagc | 900 |
| ucagccggga | ggaccagauu | gcccugcuga | agaccucugc | gaucgaggug | augcuucugg | 960 |
| agacaucucg | gaggguacaac | ccugggagug | agaguaucac | cuuccucaag | gauuucaguu | 1020 |
| auaaccggga | agacuuugcc | aaagcagggc | ugcaagugga | auucaucaac | cccaucuucg | 1080 |
| aguucuccag | ggccaugaau | gagcugcaac | ucaaugaugc | cgaguuugcc | uugcucauug | 1140 |
| cuaucagcau | cuucucugca | gaccggccca | acgugcagga | ccagcuccag | guagagaggc | 1200 |
| ugcagcacac | auaugggguaa | gcccugcaug | ccuacgucuc | cauccaccau | ccccaugacc | 1260 |
| gacuauguu | cccacggaug | cuaaugaaac | uggugagccu | ccggacccug | agcagcguuc | 1320 |
| acucagagca | aguguuugca | cugcgucugc | aggacaaaaa | gcucccaccg | cugcucucug | 1380 |
| agaucuggga | ugugcacgaa | ugacuguucu | gucccauau | uuucuguuuu | cuuggccgga | 1440 |
| uggcugaggc | cugguggcug | ccuccuagaa | guggaacaga | cugagaaggg | caaacauucc | 1500 |
| ugggagcugg | gcaaggagau | ccuccgugg | cauuaaaaga | gagucaaagg | guucgcaguu | 1560 |
| uuguggcuac | ugagcagugg | agcccucgcu | aacacugugc | ugugucugaa | gaucaugcug | 1620 |
| accccacaaa | cggaugggcc | uggggggccac | uuugcacagg | guucuccaga | gcccugccca | 1680 |
| uccugccucc | accacuuccu | guuuuuccca | cagggcccca | agaaaaauuc | uccacuguca | 1740 |
| aaaaaaaa | | | | | | 1748 |

<210> SEQ ID NO 26
<211> LENGTH: 402
<212> TYPE: PRT
<213> ORGANISM: Homo sapiens

<400> SEQUENCE: 26

```
Met Pro His Ser Ala Gly Gly Thr Ala Gly Val Gly Leu Glu Ala Ala
1               5                   10                  15

Glu Pro Thr Ala Leu Leu Thr Arg Ala Glu Pro Pro Ser Glu Pro Thr
            20                  25                  30

Glu Ile Arg Pro Gln Lys Arg Lys Gly Pro Ala Pro Lys Met Leu
            35                  40                  45

Gly Asn Glu Leu Cys Ser Val Cys Gly Asp Lys Ala Ser Gly Phe His
50                  55                  60

Tyr Asn Val Leu Ser Cys Glu Gly Cys Lys Gly Phe Phe Arg Arg Ser
65                  70                  75                  80

Val Ile Lys Gly Ala His Tyr Ile Cys His Ser Gly Gly His Cys Pro
                85                  90                  95

Met Asp Thr Tyr Met Arg Arg Lys Cys Gln Glu Cys Arg Leu Arg Lys
                100                 105                 110

Cys Arg Gln Ala Gly Met Arg Glu Glu Cys Val Leu Ser Glu Glu Gln
                115                 120                 125

Ile Arg Leu Lys Lys Leu Lys Arg Gln Glu Glu Glu Gln Ala His Ala
            130                 135                 140

Thr Ser Leu Pro Pro Arg Ala Ser Ser Pro Pro Gln Ile Leu Pro Gln
145                 150                 155                 160

Leu Ser Pro Glu Gln Leu Gly Met Ile Glu Lys Leu Val Ala Ala Gln
                165                 170                 175

Gln Gln Cys Asn Arg Arg Ser Phe Ser Asp Arg Leu Arg Val Thr Pro
                180                 185                 190

Trp Pro Met Ala Pro Asp Pro His Ser Arg Glu Ala Arg Gln Gln Arg
                195                 200                 205

Phe Ala His Phe Thr Glu Leu Ala Ile Val Ser Val Gln Glu Ile Val
            210                 215                 220

Asp Phe Ala Lys Gln Leu Pro Gly Phe Leu Gln Leu Ser Arg Glu Asp
225                 230                 235                 240

Gln Ile Ala Leu Leu Lys Thr Ser Ala Ile Glu Val Met Leu Leu Glu
                245                 250                 255

Thr Ser Arg Arg Tyr Asn Pro Gly Ser Glu Ser Ile Thr Phe Leu Lys
                260                 265                 270

Asp Phe Ser Tyr Asn Arg Glu Asp Phe Ala Lys Ala Gly Leu Gln Val
            275                 280                 285

Glu Phe Ile Asn Pro Ile Phe Glu Phe Ser Arg Ala Met Asn Glu Leu
            290                 295                 300

Gln Leu Asn Asp Ala Glu Phe Ala Leu Leu Ile Ala Ile Ser Ile Phe
305                 310                 315                 320

Ser Ala Asp Arg Pro Asn Val Gln Asp Gln Leu Gln Val Glu Arg Leu
                325                 330                 335

Gln His Thr Tyr Val Glu Ala Leu His Ala Tyr Val Ser Ile His His
            340                 345                 350

Pro His Asp Arg Leu Met Phe Pro Arg Met Leu Met Lys Leu Val Ser
            355                 360                 365

Leu Arg Thr Leu Ser Ser Val His Ser Glu Gln Val Phe Ala Leu Arg
            370                 375                 380

Leu Gln Asp Lys Lys Leu Pro Pro Leu Leu Ser Glu Ile Trp Asp Val
385                 390                 395                 400

His Glu

<210> SEQ ID NO 27
```

<211> LENGTH: 1928
<212> TYPE: RNA
<213> ORGANISM: Homo sapiens

<400> SEQUENCE: 27

| | | | | | | |
|---|---|---|---|---|---|---|
| gauucuaacu | uagcuaagca | augcuacugg | agaccauagg | caaagccaag | guacagcuuc | 60 |
| agggaagucu | uuggugagcc | caucucucau | uaccaaggua | acgaagcgca | gacuccgggc | 120 |
| ccgggugggc | ggcaucacca | ccagguucac | gccgagaagg | agcuggagga | gagccgcccg | 180 |
| gcuccagccg | gaccgcuugc | ccgccaucac | cguuguaauc | uaugcagcaa | acaagcugga | 240 |
| acccgcuggg | uggcaccugc | aagcagccgc | ccggacgcac | ccacucugcg | guggagcugu | 300 |
| ggaagccagg | cgcacaggau | gcaagcagcc | aggcccaggg | aggcagcagc | ugcauccuca | 360 |
| gagaggaagc | caggaugccc | cacucugcug | gggguacugc | aggggugggg | cuggaggcug | 420 |
| cagagcccac | agcccugcuc | accagggcag | agccccuuc | agaacccaca | gagauccguc | 480 |
| cacaaaagcg | gaaaagggg | ccagccccca | aaaugcuggg | gaacgagcua | ugcagcgugu | 540 |
| guggggacaa | ggcucgggc | uuccacuaca | auguucugag | cugcgagggc | ugcaagggau | 600 |
| ucuuccgccg | cagcgucauc | aagggagcgc | acuacaucug | ccacaguggc | ggccacugcc | 660 |
| ccauggacac | cuacaugcgu | cgcaagugcc | aggagucg | gcuucgcaaa | ugccgucagg | 720 |
| cuggcaugcg | ggaggagugu | guccugcag | aagaacagau | ccgccugaag | aaacugaagc | 780 |
| ggcaagagga | ggaacaggcu | caugccacau | ccuugcccc | cagggcuucc | ucacccccc | 840 |
| aaauccugcc | ccagcucagc | ccggaacaac | ugggcaugau | cgagaagcuc | gucgcugccc | 900 |
| agcaacagug | uaaccggcgc | uccuuuucug | accggcuucg | agucacgccu | uggcccaugg | 960 |
| caccagaucc | ccauagccgg | gaggcccguc | agcagcgcuu | ugcccacuuc | acugagcugg | 1020 |
| ccaucgucuc | ugugcaggag | auaguugacu | uugcuaaaca | gcuacccggc | uuccugcagc | 1080 |
| ucagccggga | ggaccagauu | gcccugcuga | agaccucugc | gaucgaggug | augcuucugg | 1140 |
| agacaucucg | gagguacaac | ccugggagug | agaguaucac | cuuccucaag | gauuucaguu | 1200 |
| auaaccggga | agacuuugcc | aaagcagggc | ugcaagugga | auucaucaac | cccaucuucg | 1260 |
| aguucuccag | ggccaugaau | gagcugcaac | ucaaugaugc | cgaguuugcc | uugcucauug | 1320 |
| cuaucagcau | cuucucugca | gaccggccca | acgugcagga | ccagcuccag | guagagaggc | 1380 |
| ugcagcacac | auauguggaa | gcccugcaug | ccuacgucuc | cauccaccau | ccccaugacc | 1440 |
| gacugauguu | cccacggaug | cuaaugaaac | uggugagccu | ccggacccug | agcagcgucc | 1500 |
| acucagagca | aguuuugca | cugcgucugc | aggacaaaaa | gcucccaccg | cugcucucug | 1560 |
| agaucuggga | ugugcacgaa | ugacuguucu | guccccauau | uuucuguuuu | cuggccgga | 1620 |
| uggcugaggc | cugguggcug | ccuccuagaa | guggaacaga | cugagaaggg | caaacauucc | 1680 |
| ugggagcugg | gcaaggagau | ccuccgugg | cauuaaaaga | gagucaaagg | guugcgaguu | 1740 |
| uuguggcuac | ugagcagugg | agcccucgcu | aacacugugc | ugugucugaa | gaucaugcug | 1800 |
| accccacaaa | cggaugggcc | uggggcac | uuugcacagg | guucuccaga | gcccugccca | 1860 |
| uccugccucc | accacuuccu | guuuucccca | cagggcccca | agaaaauuc | uccacuguca | 1920 |
| aaaaaaaa | | | | | | 1928 |

<210> SEQ ID NO 28
<211> LENGTH: 453
<212> TYPE: PRT
<213> ORGANISM: Homo sapiens

<400> SEQUENCE: 28

```
Met Gln Gln Thr Ser Trp Asn Pro Leu Gly Gly Thr Cys Lys Gln Pro
1               5                   10                  15

Pro Gly Arg Thr His Ser Ala Val Glu Leu Trp Lys Pro Gly Ala Gln
            20                  25                  30

Asp Ala Ser Ser Gln Ala Gln Gly Gly Ser Ser Cys Ile Leu Arg Glu
                35                  40                  45

Glu Ala Arg Met Pro His Ser Ala Gly Gly Thr Ala Gly Val Gly Leu
        50                  55                  60

Glu Ala Ala Glu Pro Thr Ala Leu Leu Thr Arg Ala Glu Pro Pro Ser
65                  70                  75                  80

Glu Pro Thr Glu Ile Arg Pro Gln Lys Arg Lys Lys Gly Pro Ala Pro
                85                  90                  95

Lys Met Leu Gly Asn Glu Leu Cys Ser Val Cys Gly Asp Lys Ala Ser
                100                 105                 110

Gly Phe His Tyr Asn Val Leu Ser Cys Glu Gly Cys Lys Gly Phe Phe
            115                 120                 125

Arg Arg Ser Val Ile Lys Gly Ala His Tyr Ile Cys His Ser Gly Gly
130                 135                 140

His Cys Pro Met Asp Thr Tyr Met Arg Arg Lys Cys Gln Glu Cys Arg
145                 150                 155                 160

Leu Arg Lys Cys Arg Gln Ala Gly Met Arg Glu Glu Cys Val Leu Ser
            165                 170                 175

Glu Glu Gln Ile Arg Leu Lys Lys Leu Lys Arg Gln Glu Glu Glu Gln
                180                 185                 190

Ala His Ala Thr Ser Leu Pro Pro Arg Ala Ser Ser Pro Pro Gln Ile
        195                 200                 205

Leu Pro Gln Leu Ser Pro Glu Gln Leu Gly Met Ile Glu Lys Leu Val
210                 215                 220

Ala Ala Gln Gln Gln Cys Asn Arg Arg Ser Phe Ser Asp Arg Leu Arg
225                 230                 235                 240

Val Thr Pro Trp Pro Met Ala Pro Asp Pro His Ser Arg Glu Ala Arg
            245                 250                 255

Gln Gln Arg Phe Ala His Phe Thr Glu Leu Ala Ile Val Ser Val Gln
                260                 265                 270

Glu Ile Val Asp Phe Ala Lys Gln Leu Pro Gly Phe Leu Gln Leu Ser
        275                 280                 285

Arg Glu Asp Gln Ile Ala Leu Leu Lys Thr Ser Ala Ile Glu Val Met
    290                 295                 300

Leu Leu Glu Thr Ser Arg Arg Tyr Asn Pro Gly Ser Glu Ser Ile Thr
305                 310                 315                 320

Phe Leu Lys Asp Phe Ser Tyr Asn Arg Glu Asp Phe Ala Lys Ala Gly
            325                 330                 335

Leu Gln Val Glu Phe Ile Asn Pro Ile Phe Glu Phe Ser Arg Ala Met
                340                 345                 350

Asn Glu Leu Gln Leu Asn Asp Ala Glu Phe Ala Leu Leu Ile Ala Ile
        355                 360                 365

Ser Ile Phe Ser Ala Asp Arg Pro Asn Val Gln Asp Gln Leu Gln Val
370                 375                 380

Glu Arg Leu Gln His Thr Tyr Val Glu Ala Leu His Ala Tyr Val Ser
385                 390                 395                 400

Ile His His Pro His Asp Arg Leu Met Phe Pro Arg Met Leu Met Lys
            405                 410                 415
```

Leu Val Ser Leu Arg Thr Leu Ser Ser Val His Ser Glu Gln Val Phe
            420                 425                 430

Ala Leu Arg Leu Gln Asp Lys Lys Leu Pro Pro Leu Leu Ser Glu Ile
        435                 440                 445

Trp Asp Val His Glu
    450

<210> SEQ ID NO 29
<211> LENGTH: 2093
<212> TYPE: RNA
<213> ORGANISM: Homo sapiens

<400> SEQUENCE: 29

| | | | | | |
|---|---|---|---|---|---|
| ucgucaaguu | ucacgcuccg | ccccucuucc | ggacgugacg | caagggcggg | guugccggaa | 60 |
| gaaguggcga | aguuacuuuu | gagggauuuu | gaguagcggc | ggugugucag | gggcuaaaga | 120 |
| ggaggacgaa | gaaaagcaga | gcaagggaac | ccagggcaac | aggaguaguu | cacuccgcga | 180 |
| gaggccgucc | acgagacccc | cgcgcgcagc | caugagcccc | gcccccgcu | guugcuugga | 240 |
| gaggggcggg | accuggagag | aggcugcucc | gugacccccac | caugccucu | ccuaccacga | 300 |
| guucccugga | uacccccug | ccuggaaaug | gccccccuca | gccuggcgcc | ccuucuucu | 360 |
| cacccacugu | aaaggaggag | gguccggagc | cguggcccgg | gggguccggac | ccugaugucc | 420 |
| caggcacuga | ugaggccagc | ucagccugca | gcacagacug | ggucauccca | gaucccgaag | 480 |
| aggaaccaga | gcgcaagcga | agaagggcc | cagccccgaa | gaugcugggc | cacgagcuuu | 540 |
| gccgugucug | ugggacaag | gccuccggcu | uccacuacaa | cgugcucagc | ugcgaaggcu | 600 |
| gcaagggcuu | cuuccggcgc | aguguggucc | gugguggggc | caggcgcuau | gccugccggg | 660 |
| guggcggaac | cugccagaug | gacgcuuuca | ugcggcgcaa | guggccagcag | ugccggcugc | 720 |
| gcaagugcaa | ggaggcaggg | augagggagc | agugcguccu | uucugaagaa | cagauccgga | 780 |
| agaagaagau | ucggaaacaa | cagcagcagg | agucacaguc | acagucgcag | ucaccugugg | 840 |
| ggccgcaggg | cagcagcagc | ucagccucug | gccugggggc | uucccuggu | ggaucugagg | 900 |
| caggcagcca | gggcuccggg | gaaggcgagg | uguccagcu | aacagcggcu | caagaacuaa | 960 |
| ugauccagca | guugguggcg | gcccaacugc | agugcaacaa | acgcuccuuc | uccgaccagc | 1020 |
| ccaaagucac | gccuggcccc | cugggcgcag | accccccaguc | ccgagaugcc | cgccagcaac | 1080 |
| gcuuugccca | cuuucacggag | cuggccauca | ucucagucca | ggagaucgug | gacuucgcua | 1140 |
| agcaagugcc | ugguuuccug | cagcugggcc | gggaggacca | gaucgcccuc | cugaaggcau | 1200 |
| ccacuaucga | gaucaugcug | cuagagacag | ccaggcgcua | caaccacgag | acagagugua | 1260 |
| ucaccuucuu | gaaggacuuc | accuacagca | aggacgacuu | ccaccgugca | ggccugcagg | 1320 |
| uggaguucau | caaccccauc | uucgaguucu | cgcgggccau | gcggcggcug | ggccuggacg | 1380 |
| acgcugagua | cgcccugcuc | aucgccauca | acaucuucuc | ggccgaccgg | cccaacgugc | 1440 |
| aggagccggg | ccgcguggag | gcguugcagc | agcccuacgu | ggaggcgcug | cugccuaca | 1500 |
| cgcgcaucaa | gaggccgcag | gaccagcugc | gcuucccgcg | caugcucaug | aagcugguga | 1560 |
| gccugcgcac | gcugagcucu | gugcacucgg | agcaggucuu | cgccuugcgg | cuccaggaca | 1620 |
| agaagcugcc | gccucugcug | ucggagaucu | ggacguccca | cgagugaggg | gcuggccacc | 1680 |
| cagccccaca | gccuugccug | accacccucc | agcagauaga | cgccggcacc | ccuuccucuu | 1740 |
| ccuaggugg | aaggggcccu | gggccagccu | guagaccua | ucggcucuca | ucccuuggga | 1800 |
| uaagccccag | uccagguccca | ggaggcuccc | ucccugccca | gcgagucuuc | cagaagggu | 1860 |

```
                                   -continued
gaaaggguug caggucccga ccacugaccc uucccggcug cccucccucc ccagcuuaca    1920
ccucaagccc agcacgcagu gcaccuugaa cagagggagg ggaggaccca uggcucuccc    1980
cccuagcccg ggagaccagg gccuuccucu uccucugcuu uuauuuaaua aaaacuaaaa    2040
acagaaacag gaaauaaaaa uaugaauaca auccagcccg gagcuggagu gca           2093
```

<210> SEQ ID NO 30
<211> LENGTH: 461
<212> TYPE: PRT
<213> ORGANISM: Homo sapiens

<400> SEQUENCE: 30

```
Met Ser Ser Pro Thr Thr Ser Ser Leu Asp Thr Pro Leu Pro Gly Asn
1               5                   10                  15

Gly Pro Pro Gln Pro Gly Ala Pro Ser Ser Pro Thr Val Lys Glu
            20                  25                  30

Glu Gly Pro Glu Pro Trp Pro Gly Gly Pro Asp Pro Asp Val Pro Gly
        35                  40                  45

Thr Asp Glu Ala Ser Ser Ala Cys Ser Thr Asp Trp Val Ile Pro Asp
    50                  55                  60

Pro Glu Glu Glu Pro Glu Arg Lys Arg Lys Lys Gly Pro Ala Pro Lys
65                  70                  75                  80

Met Leu Gly His Glu Leu Cys Arg Val Cys Gly Asp Lys Ala Ser Gly
                85                  90                  95

Phe His Tyr Asn Val Leu Ser Cys Glu Gly Cys Lys Gly Phe Phe Arg
            100                 105                 110

Arg Ser Val Val Arg Gly Gly Ala Arg Arg Tyr Ala Cys Arg Gly Gly
        115                 120                 125

Gly Thr Cys Gln Met Asp Ala Phe Met Arg Arg Lys Cys Gln Gln Cys
    130                 135                 140

Arg Leu Arg Lys Cys Lys Glu Ala Gly Met Arg Glu Gln Cys Val Leu
145                 150                 155                 160

Ser Glu Glu Gln Ile Arg Lys Lys Lys Ile Arg Lys Gln Gln Gln Gln
                165                 170                 175

Glu Ser Gln Ser Gln Ser Gln Ser Pro Val Gly Pro Gly Ser Ser
            180                 185                 190

Ser Ser Ala Ser Gly Pro Gly Ala Ser Pro Gly Gly Ser Glu Ala Gly
        195                 200                 205

Ser Gln Gly Ser Gly Glu Gly Glu Gly Val Gln Leu Thr Ala Ala Gln
    210                 215                 220

Glu Leu Met Ile Gln Gln Leu Val Ala Ala Gln Leu Gln Cys Asn Lys
225                 230                 235                 240

Arg Ser Phe Ser Asp Gln Pro Lys Val Thr Pro Trp Pro Leu Gly Ala
                245                 250                 255

Asp Pro Gln Ser Arg Asp Ala Arg Gln Gln Arg Phe Ala His Phe Thr
            260                 265                 270

Glu Leu Ala Ile Ile Ser Val Gln Glu Ile Val Asp Phe Ala Lys Gln
        275                 280                 285

Val Pro Gly Phe Leu Gln Leu Gly Arg Glu Asp Gln Ile Ala Leu Leu
    290                 295                 300

Lys Ala Ser Thr Ile Glu Ile Met Leu Leu Glu Thr Ala Arg Arg Tyr
305                 310                 315                 320

Asn His Glu Thr Glu Cys Ile Thr Phe Leu Lys Asp Phe Thr Tyr Ser
                325                 330                 335
```

Lys Asp Asp Phe His Arg Ala Gly Leu Gln Val Glu Phe Ile Asn Pro
                340                 345                 350

Ile Phe Glu Phe Ser Arg Ala Met Arg Arg Leu Gly Leu Asp Asp Ala
            355                 360                 365

Glu Tyr Ala Leu Leu Ile Ala Ile Asn Ile Phe Ser Ala Asp Arg Pro
        370                 375                 380

Asn Val Gln Glu Pro Gly Arg Val Glu Ala Leu Gln Gln Pro Tyr Val
385                 390                 395                 400

Glu Ala Leu Leu Ser Tyr Thr Arg Ile Lys Arg Pro Gln Asp Gln Leu
                405                 410                 415

Arg Phe Pro Arg Met Leu Met Lys Leu Val Ser Leu Arg Thr Leu Ser
            420                 425                 430

Ser Val His Ser Glu Gln Val Phe Ala Leu Arg Leu Gln Asp Lys Lys
        435                 440                 445

Leu Pro Pro Leu Leu Ser Glu Ile Trp Asp Val His Glu
                450                 455                 460

<210> SEQ ID NO 31
<211> LENGTH: 1802
<212> TYPE: RNA
<213> ORGANISM: Homo sapiens

<400> SEQUENCE: 31
ucgucaaguu ucacgcuccg ccccucuucc ggacgugacg caagggcggg guugccggaa      60
gaaguggcga aguuacuuuu gaggguauuu gaguagcggc ggugugucag gggcuaaaga     120
ggaggacgaa gaaaagcaga gcaagggaac ccagggcaac aggaguaguu cacuccgcga     180
gaggccgucc acgagacccc cgcgcgcagc caugagcccc gcccccgcu guugcuugga     240 gaggggcggg accuggagag aggcugcucc gugaccccac caugccucu ccaccacga      300 guucccugga uaccccccug ccuggaaaug gcccccucca gccuggcgcc ccuucuucuu     360
cacccacugu aaaggaggag gguccggagc cguggcccgg ggguccggac ccugaugucc     420
caggcacuga ugaggccagc ucagccugca gcacagacug gggcgucuu ucugaagaac     480 agauccggaa gaagaagauu cggaaacaac agcagcagga gucacaguca caguccagu      540 caccugu ggg gccgcagggc agcagcagcu cagccucugg ccuggggcu uccccuggug     600 gaucugaggc aggcagccag ggcuccgggg aaggcgaggg uguccagcua acagcggcuc     660
aagaacuaau gauccagcag uuggugggcg gcccaacugc guugcaacaaa cgcuccuucu     720 ccgaccagcc caaagucacg cccuggcccc ugggcgcaga ccccagucc cgagaugccc     780 gccagcaacg cuuugcccac uucacggagc uggccaucau cucaguccag gagaucgugg     840
acuucgcuaa gcaagugccu gguuccugc agcgggccg ggaggaccag aucgcccucc     900
ugaaggcauc cacuaucgag aucaugcugc uagagacagc caggcgcuac aaccacgaga     960
cagaguguau caccuucuug aaggacuuca ccuacagcaa ggacgacuuc caccgugcag    1020
gccugcaggu ggaguucauc aaccccaucu ucgaguucuc gcgggccaug cggcggcugg    1080
gccuggacga cgcugaguac gcccugcuca ucgccaucaa caucuucucg gccgaccggc    1140
ccaacgugca ggagccgggc cgcguggagg cguugcagca gccuacgug gaggcgcugc    1200 uguccuacac gcgcaucaag aggccgcagg accagcugcg cuucccgcgc augcucauga    1260
agcuggugag ccugcgcacg cugagcucug cacucggga caggucuucu gccuugcggc    1320
uccaggacaa gaagcugccg ccucugcgu ccggagaucug ggacgccac gaguggggg     1380 cuggccaccc cagccccacag ccuugccuga ccacccucca gcagauagac gccggcaccc    1440

-continued

```
cuuccucuuc cuagggugga aggggcccug ggccgagccu guagaccuau cggcucucau    1500
cccuugggau aagccccagu ccaggucccag gaggcucccu cccugcccag cgagucuucc   1560
agaaggggug aaagggguugc agguccccgac cacugacccu ucccggcugc ccucccuccc  1620
cagcuuacac cucaagccca gcacgcagug caccuugaac agagggaggg gaggaccccau  1680 ggcucucccc ccuagcccgg gagaccaggg ccuuccucuu ccucugcuuu uauuuaauaa    1740
aaacuaaaaa cagaaacagg aaaauaaaau augaauacaa uccagcccgg agcuggagug    1800
ca                                                                   1802
```

<210> SEQ ID NO 32
<211> LENGTH: 364
<212> TYPE: PRT
<213> ORGANISM: Homo sapiens

<400> SEQUENCE: 32

```
Met Ser Ser Pro Thr Ser Ser Leu Asp Thr Pro Leu Pro Gly Asn
1               5                   10                  15

Gly Pro Pro Gln Pro Gly Ala Pro Ser Ser Pro Thr Val Lys Glu
                20                  25                  30

Glu Gly Pro Glu Pro Trp Pro Gly Pro Asp Pro Asp Val Pro Gly
            35                  40                  45

Thr Asp Glu Ala Ser Ser Ala Cys Ser Thr Asp Trp Gly Val Leu Ser
50                  55                      60

Glu Glu Gln Ile Arg Lys Lys Ile Arg Lys Gln Gln Gln Gln Glu
65                  70                  75                  80

Ser Gln Ser Gln Ser Gln Ser Pro Val Gly Pro Gln Gly Ser Ser Ser
                    85                  90                      95

Ser Ala Ser Gly Pro Gly Ala Ser Pro Gly Gly Ser Glu Ala Gly Ser
                100                 105                 110

Gln Gly Ser Gly Glu Gly Glu Gly Val Gln Leu Thr Ala Ala Gln Glu
                    115                 120                 125

Leu Met Ile Gln Gln Leu Val Ala Ala Gln Leu Gln Cys Asn Lys Arg
130                 135                 140

Ser Phe Ser Asp Gln Pro Lys Val Thr Pro Trp Pro Leu Gly Ala Asp
145                 150                 155                 160

Pro Gln Ser Arg Asp Ala Arg Gln Gln Arg Phe Ala His Phe Thr Glu
                    165                 170                 175

Leu Ala Ile Ile Ser Val Gln Glu Ile Val Asp Phe Ala Lys Gln Val
                180                 185                 190

Pro Gly Phe Leu Gln Leu Gly Arg Glu Asp Gln Ile Ala Leu Leu Lys
            195                 200                 205

Ala Ser Thr Ile Glu Ile Met Leu Leu Glu Thr Ala Arg Arg Tyr Asn
210                 215                 220

His Glu Thr Glu Cys Ile Thr Phe Leu Lys Asp Phe Thr Tyr Ser Lys
225                 230                 235                 240

Asp Asp Phe His Arg Ala Gly Leu Gln Val Glu Phe Ile Asn Pro Ile
                    245                 250                 255

Phe Glu Phe Ser Arg Ala Met Arg Arg Leu Gly Leu Asp Asp Ala Glu
                260                 265                 270

Tyr Ala Leu Leu Ile Ala Ile Asn Ile Phe Ser Ala Asp Arg Pro Asn
            275                 280                 285

Val Gln Glu Pro Gly Arg Val Glu Ala Leu Gln Gln Pro Tyr Val Glu
290                 295                 300
```

```
Ala Leu Leu Ser Tyr Thr Arg Ile Lys Arg Pro Gln Asp Gln Leu Arg
305                 310                 315                 320

Phe Pro Arg Met Leu Met Lys Leu Val Ser Leu Arg Thr Leu Ser Ser
            325                 330                 335

Val His Ser Glu Gln Val Phe Ala Leu Arg Leu Gln Asp Lys Lys Leu
        340                 345                 350

Pro Pro Leu Leu Ser Glu Ile Trp Asp Val His Glu
        355                 360

<210> SEQ ID NO 33
<211> LENGTH: 71
<212> TYPE: RNA
<213> ORGANISM: Homo sapiens

<400> SEQUENCE: 33
gccaacccag uguucagacu accuguucag gaggcucuca auguguacag uagucugcac        60
auugguuagg c                                                            71

<210> SEQ ID NO 34
<211> LENGTH: 110
<212> TYPE: RNA
<213> ORGANISM: Homo sapiens

<400> SEQUENCE: 34
aggaagcuuc uggagauccu gcuccgucgc cccaguguuc agacuaccug uucaggacaa        60
ugccguugua caguagucug cacauugguu agacugggca agggagagca                  110

<210> SEQ ID NO 35
<211> LENGTH: 80
<212> TYPE: RNA
<213> ORGANISM: Homo sapiens

<400> SEQUENCE: 35
cgggaaugcc gcggcgggga cggcgauugg uccguaugug ggugccacc ggccgccggc         60 uccgccccgg cccccgcccc                                                   80

<210> SEQ ID NO 36
<211> LENGTH: 110
<212> TYPE: RNA
<213> ORGANISM: Homo sapiens

<400> SEQUENCE: 36
uuggauguug gccuaguucu guguggaaga cuagugauuu uguuguuuuu agauaacuaa        60
aucgacaaca aaucacaguc ugccauaugg cacaggccau gccucuacag                  110

<210> SEQ ID NO 37
<211> LENGTH: 110
<212> TYPE: RNA
<213> ORGANISM: Homo sapiens

<400> SEQUENCE: 37
cuggauacag aguggaccgg cuggccccau cuggaagacu agugauuuug uuguugucuu        60
acugcgcuca acaacaaauc ccagucuacc uaauggugcc agccaucgca                  110

<210> SEQ ID NO 38
<211> LENGTH: 110
<212> TYPE: RNA
<213> ORGANISM: Homo sapiens
```

<400> SEQUENCE: 38
agauuagagu ggcugugguc uagugcugug uggaagacua gugauuuugu uguucugaug    60
uacuacgaca acaagucaca gccggccuca uagcgcagac ucccuucgac              110

<210> SEQ ID NO 39
<211> LENGTH: 71
<212> TYPE: DNA
<213> ORGANISM: Homo sapiens

<400> SEQUENCE: 39
gatccgacag tagcctgcac attagtcact tcctgtcagt aaccaatgtg cagactactg    60 tttttttgaat t                                                       71

<210> SEQ ID NO 40
<211> LENGTH: 73
<212> TYPE: DNA
<213> ORGANISM: Homo sapiens

<400> SEQUENCE: 40
gatccgccca gtgctcagac tacccgtgcc ttcctgtcag gaacaggtag tctgaacact    60 gggttttttga att                                                     73

<210> SEQ ID NO 41
<211> LENGTH: 69
<212> TYPE: DNA
<213> ORGANISM: Homo sapiens

<400> SEQUENCE: 41
gatccgcggc gggaacggcg atcggcccctt cctgtcagga ccaatcgccg tccccgccgt    60
ttttgaatt                                                           69

<210> SEQ ID NO 42
<211> LENGTH: 73
<212> TYPE: DNA
<213> ORGANISM: Homo sapiens

<400> SEQUENCE: 42
gatccgtgga agattagtga gtttattatc ttcctgtcag acaacaaaat cactagtctt    60 ccattttttga att                                                     73

<210> SEQ ID NO 43
<211> LENGTH: 14
<212> TYPE: PRT
<213> ORGANISM: Mus musculus

<400> SEQUENCE: 43

Thr Gln Gln Ile Arg Leu Gln Ala Glu Ile Phe Gln Ala Arg
1               5                   10

<210> SEQ ID NO 44
<211> LENGTH: 14
<212> TYPE: PRT
<213> ORGANISM: Homo sapiens

<400> SEQUENCE: 44

Ala Gln Gln Ile Arg Leu Gln Ala Glu Ala Phe Gln Ala Arg
1               5                   10

<210> SEQ ID NO 45
<211> LENGTH: 14

```
<212> TYPE: PRT
<213> ORGANISM: Artificial
<220> FEATURE:
<223> OTHER INFORMATION: Synthetic

<400> SEQUENCE: 45

Thr Ala Gln Ile Arg Leu Gln Ala Glu Ile Phe Gln Ala Arg
1               5                   10

<210> SEQ ID NO 46
<211> LENGTH: 14
<212> TYPE: PRT
<213> ORGANISM: Artificial
<220> FEATURE:
<223> OTHER INFORMATION: Synthetic

<400> SEQUENCE: 46

Thr Gln Ala Ile Arg Leu Gln Ala Glu Ile Phe Gln Ala Arg
1               5                   10

<210> SEQ ID NO 47
<211> LENGTH: 14
<212> TYPE: PRT
<213> ORGANISM: Artificial
<220> FEATURE:
<223> OTHER INFORMATION: Synthetic

<400> SEQUENCE: 47

Thr Gln Gln Ala Arg Leu Gln Ala Glu Ile Phe Gln Ala Arg
1               5                   10

<210> SEQ ID NO 48
<211> LENGTH: 14
<212> TYPE: PRT
<213> ORGANISM: Artificial
<220> FEATURE:
<223> OTHER INFORMATION: Synthetic

<400> SEQUENCE: 48

Thr Gln Gln Ile Ala Leu Gln Ala Glu Ile Phe Gln Ala Arg
1               5                   10

<210> SEQ ID NO 49
<211> LENGTH: 15
<212> TYPE: PRT
<213> ORGANISM: Artificial
<220> FEATURE:
<223> OTHER INFORMATION: Synthetic

<400> SEQUENCE: 49

Gln Thr Gln Gln Ile Arg Leu Gln Ala Glu Ile Phe Gln Ala Arg
1               5                   10                  15

<210> SEQ ID NO 50
<211> LENGTH: 13
<212> TYPE: PRT
<213> ORGANISM: Artificial
<220> FEATURE:
<223> OTHER INFORMATION: Synthetic

<400> SEQUENCE: 50

Gln Gln Ile Arg Leu Gln Ala Glu Ile Phe Gln Ala Arg
1               5                   10

<210> SEQ ID NO 51
<211> LENGTH: 57
<212> TYPE: DNA
```

```
<213> ORGANISM: Artificial
<220> FEATURE:
<223> OTHER INFORMATION: Synthetic shAPOE

<400> SEQUENCE: 51
ccgggaagga gttgaaggcc tacaactcga gttgtaggcc ttcaactcct tctttt        57

<210> SEQ ID NO 52
<211> LENGTH: 57
<212> TYPE: DNA
<213> ORGANISM: Artificial
<220> FEATURE:
<223> OTHER INFORMATION: Synthetic shAPOE

<400> SEQUENCE: 52
ccgggcagac actgtctgag caggtctcga gacctgctca gacagtgtct gctttt        57

<210> SEQ ID NO 53
<211> LENGTH: 57
<212> TYPE: DNA
<213> ORGANISM: Artificial
<220> FEATURE:
<223> OTHER INFORMATION: Synthetic shDNAJA

<400> SEQUENCE: 53
ccgggcgaga agtttaaact catatctcga gatatgagtt taaacttctc gctttt        57

<210> SEQ ID NO 54
<211> LENGTH: 57
<212> TYPE: DNA
<213> ORGANISM: Artificial
<220> FEATURE:
<223> OTHER INFORMATION: Synthetic shDNAJA4

<400> SEQUENCE: 54
ccggcctcga cagaaagtga ggattctcga gaatcctcac tttctgtcga ggtttt        57

<210> SEQ ID NO 55
<211> LENGTH: 30
<212> TYPE: DNA
<213> ORGANISM: Artificial
<220> FEATURE:
<223> OTHER INFORMATION: Synthetic ApoE Forward Primer

<400> SEQUENCE: 55
tcatgaggat ccatgaaggt tctgtgggct        30

<210> SEQ ID NO 56
<211> LENGTH: 29
<212> TYPE: DNA
<213> ORGANISM: Artificial
<220> FEATURE:
<223> OTHER INFORMATION: Synthetic ApoE Reverse Primer

<400> SEQUENCE: 56
tagcagaatt ctcagtgatt gtcgctggg        29

<210> SEQ ID NO 57
<211> LENGTH: 31
<212> TYPE: DNA
<213> ORGANISM: Artificial
<220> FEATURE:
<223> OTHER INFORMATION: Synthetic DNAJA4 Forward Primer

<400> SEQUENCE: 57
atccctggat ccatgtggga aagcctgacc c        31
```

<210> SEQ ID NO 58
<211> LENGTH: 31
<212> TYPE: DNA
<213> ORGANISM: Artificial
<220> FEATURE:
<223> OTHER INFORMATION: Synthetic DNAJA4 Reverse Primer

<400> SEQUENCE: 58
taccatgtcg actcatgccg tctggcactg c                          31

<210> SEQ ID NO 59
<211> LENGTH: 19
<212> TYPE: RNA
<213> ORGANISM: Artificial
<220> FEATURE:
<223> OTHER INFORMATION: Synthetic LRP1 target sequence

<400> SEQUENCE: 59
cgaggacgau gacugcuua                                        19

<210> SEQ ID NO 60
<211> LENGTH: 19
<212> TYPE: RNA
<213> ORGANISM: Artificial
<220> FEATURE:
<223> OTHER INFORMATION: Synthetic LRP1 target sequence

<400> SEQUENCE: 60
gcuaugaguu uaagaaguu                                        19

<210> SEQ ID NO 61
<211> LENGTH: 19
<212> TYPE: RNA
<213> ORGANISM: Artificial
<220> FEATURE:
<223> OTHER INFORMATION: Synthetic LRP8 target sequence

<400> SEQUENCE: 61
cgaggacgau gacugcuua                                        19

<210> SEQ ID NO 62
<211> LENGTH: 19
<212> TYPE: RNA
<213> ORGANISM: Artificial
<220> FEATURE:
<223> OTHER INFORMATION: Synthetic LRP8 target sequence

<400> SEQUENCE: 62
gaacuauuca cgccucauc                                        19

<210> SEQ ID NO 63
<211> LENGTH: 20
<212> TYPE: DNA
<213> ORGANISM: Artificial
<220> FEATURE:
<223> OTHER INFORMATION: Synthetic ApoE Forward Primer

<400> SEQUENCE: 63
tgggtcgctt ttgggattac                                       20

<210> SEQ ID NO 64
<211> LENGTH: 21
<212> TYPE: DNA
<213> ORGANISM: Artificial
<220> FEATURE:

```
<223> OTHER INFORMATION: Synthetic ApoE Reverse Primer

<400> SEQUENCE: 64
ttcaactcct tcatggtctc g                                      21

<210> SEQ ID NO 65
<211> LENGTH: 20
<212> TYPE: DNA
<213> ORGANISM: Artificial
<220> FEATURE:
<223> OTHER INFORMATION: Synthetic DNAJA4 Forward Primer

<400> SEQUENCE: 65
ccagcttctc ttcacccatg                                        20

<210> SEQ ID NO 66
<211> LENGTH: 20
<212> TYPE: DNA
<213> ORGANISM: Artificial
<220> FEATURE:
<223> OTHER INFORMATION: Synthetic DNAJA4 Reverse Primer

<400> SEQUENCE: 66
gccaatttct tcgtgactcc                                        20

<210> SEQ ID NO 67
<211> LENGTH: 19
<212> TYPE: DNA
<213> ORGANISM: Artificial
<220> FEATURE:
<223> OTHER INFORMATION: Synthetic GAPDH Forward Primer

<400> SEQUENCE: 67
agccacatcg ctcagacac                                         19

<210> SEQ ID NO 68
<211> LENGTH: 19
<212> TYPE: DNA
<213> ORGANISM: Artificial
<220> FEATURE:
<223> OTHER INFORMATION: Synthetic GAPDH Synthetic Primer

<400> SEQUENCE: 68
gcccaatacg accaaatcc                                         19

<210> SEQ ID NO 69
<211> LENGTH: 21
<212> TYPE: DNA
<213> ORGANISM: Artificial
<220> FEATURE:
<223> OTHER INFORMATION: Synthetic LRP1 Forward Primer

<400> SEQUENCE: 69
tttaacagca ccgagtacca g                                      21

<210> SEQ ID NO 70
<211> LENGTH: 19
<212> TYPE: DNA
<213> ORGANISM: Artificial
<220> FEATURE:
<223> OTHER INFORMATION: Synthetic LRP1 Reverse Primer

<400> SEQUENCE: 70
caggcagatg tcagagcag                                         19
```

```
<210> SEQ ID NO 71
<211> LENGTH: 20
<212> TYPE: DNA
<213> ORGANISM: Artificial
<220> FEATURE:
<223> OTHER INFORMATION: Synthetic LRP8 Forward Primer

<400> SEQUENCE: 71
gctaccctgg ctacgagatg                                                  20

<210> SEQ ID NO 72
<211> LENGTH: 20
<212> TYPE: DNA
<213> ORGANISM: Artificial
<220> FEATURE:
<223> OTHER INFORMATION: Synthetic LRP8 Reverse Primer

<400> SEQUENCE: 72
gattagggat gggctcttgc                                                  20

<210> SEQ ID NO 73
<211> LENGTH: 8
<212> TYPE: DNA
<213> ORGANISM: Artificial
<220> FEATURE:
<223> OTHER INFORMATION: Synthetic miRNA seed sequence

<400> SEQUENCE: 73 caguaguc                                                                8

<210> SEQ ID NO 74
<211> LENGTH: 8
<212> TYPE: DNA
<213> ORGANISM: Artificial
<220> FEATURE:
<223> OTHER INFORMATION: Synthetic miRNA seed sequence

<400> SEQUENCE: 74 ccaguguu                                                                8

<210> SEQ ID NO 75
<211> LENGTH: 8
<212> TYPE: DNA
<213> ORGANISM: Artificial
<220> FEATURE:
<223> OTHER INFORMATION: Synthetic miRNA seed sequence

<400> SEQUENCE: 75 ggcgggga                                                                8

<210> SEQ ID NO 76
<211> LENGTH: 31
<212> TYPE: DNA
<213> ORGANISM: Artificial
<220> FEATURE:
<223> OTHER INFORMATION: Synthetic Primer

<400> SEQUENCE: 76
agtacctcga ggggatccttt gagtcctact c                                    31

<210> SEQ ID NO 77
<211> LENGTH: 34
<212> TYPE: DNA
<213> ORGANISM: Artificial
<220> FEATURE:
<223> OTHER INFORMATION: Synthetic Primer
```

```
<400> SEQUENCE: 77
taattgcggc cgctcagaca gtgtctgcac ccag                           34

<210> SEQ ID NO 78
<211> LENGTH: 31
<212> TYPE: DNA
<213> ORGANISM: Artificial
<220> FEATURE:
<223> OTHER INFORMATION: Synthetic Primer

<400> SEQUENCE: 78
taatatctcg agatgtggga aagcctgacc c                              31

<210> SEQ ID NO 79
<211> LENGTH: 32
<212> TYPE: DNA
<213> ORGANISM: Artificial
<220> FEATURE:
<223> OTHER INFORMATION: Synthetic Primer

<400> SEQUENCE: 79
caattgcggc cgctcatgcc gtctggcact gc                             32

<210> SEQ ID NO 80
<211> LENGTH: 30
<212> TYPE: DNA
<213> ORGANISM: Artificial
<220> FEATURE:
<223> OTHER INFORMATION: Synthetic Primer

<400> SEQUENCE: 80
ttagcctcga gacgccgaag cctgcagcca                                30

<210> SEQ ID NO 81
<211> LENGTH: 35
<212> TYPE: DNA
<213> ORGANISM: Artificial
<220> FEATURE:
<223> OTHER INFORMATION: Synthetic Primer

<400> SEQUENCE: 81
ttactgcggc cgctgcgtga acttggtga atctt                           35

<210> SEQ ID NO 82
<211> LENGTH: 30
<212> TYPE: DNA
<213> ORGANISM: Artificial
<220> FEATURE:
<223> OTHER INFORMATION: Synthetic Primer

<400> SEQUENCE: 82
taatatctcg agcgtggtgc ggggcagcgt                                30

<210> SEQ ID NO 83
<211> LENGTH: 35
<212> TYPE: DNA
<213> ORGANISM: Artificial
<220> FEATURE:
<223> OTHER INFORMATION: Synthetic Primer

<400> SEQUENCE: 83
caattgcggc cgcttatctc tcataccagc tcaat                          35

<210> SEQ ID NO 84
<211> LENGTH: 43
```

<212> TYPE: DNA
<213> ORGANISM: Artificial
<220> FEATURE:
<223> OTHER INFORMATION: Synthetic Primer

<400> SEQUENCE: 84
gccagcgctg ggaactggca actggtcgct tttgggatta cct             43

<210> SEQ ID NO 85
<211> LENGTH: 43
<212> TYPE: DNA
<213> ORGANISM: Artificial
<220> FEATURE:
<223> OTHER INFORMATION: Synthetic Primer

<400> SEQUENCE: 85
cagcgggaga ccctgtcccc ataccagccg tcctcctggg gtg             43

<210> SEQ ID NO 86
<211> LENGTH: 43
<212> TYPE: DNA
<213> ORGANISM: Artificial
<220> FEATURE:
<223> OTHER INFORMATION: Synthetic Primer

<400> SEQUENCE: 86
tccccgcccc agccgtcctc acagggtgga ccctagttta ata             43

<210> SEQ ID NO 87
<211> LENGTH: 43
<212> TYPE: DNA
<213> ORGANISM: Artificial
<220> FEATURE:
<223> OTHER INFORMATION: Synthetic Primer

<400> SEQUENCE: 87
gggatcggtg gagaagtgcc tattgtgcaa ggggcggggg atg             43

<210> SEQ ID NO 88
<211> LENGTH: 43
<212> TYPE: DNA
<213> ORGANISM: Artificial
<220> FEATURE:
<223> OTHER INFORMATION: Synthetic Primer

<400> SEQUENCE: 88 gtaggggcg gggaacgtgt tatccgtgaa gaggtggcta ggg              43

<210> SEQ ID NO 89
<211> LENGTH: 43
<212> TYPE: DNA
<213> ORGANISM: Artificial
<220> FEATURE:
<223> OTHER INFORMATION: Synthetic Primer

<400> SEQUENCE: 89
cagggccaac ttagttccta acattctgtg cccttcagtg gat             43

<210> SEQ ID NO 90
<211> LENGTH: 43
<212> TYPE: DNA
<213> ORGANISM: Artificial
<220> FEATURE:
<223> OTHER INFORMATION: Synthetic Primer

<400> SEQUENCE: 90

-continued

```
acagtttgta tggactacta tcttaaatta tagcttgttt gga                43

<210> SEQ ID NO 91
<211> LENGTH: 43
<212> TYPE: DNA
<213> ORGANISM: Artificial
<220> FEATURE:
<223> OTHER INFORMATION: Synthetic Primer

<400> SEQUENCE: 91
taattattgc taaagaacta tgttttagtt ggtaatggtg taa                43

<210> SEQ ID NO 92
<211> LENGTH: 45
<212> TYPE: DNA
<213> ORGANISM: Artificial
<220> FEATURE:
<223> OTHER INFORMATION: Synthetic Primer

<400> SEQUENCE: 92
cagctgcacg gaccaggttc cataaaaaca ttgccagcta gtgag            45

<210> SEQ ID NO 93
<211> LENGTH: 22
<212> TYPE: DNA
<213> ORGANISM: Artificial
<220> FEATURE:
<223> OTHER INFORMATION: Synthetic primer

<400> SEQUENCE: 93
tgagtatttt tgtggcaact gc                                      22

<210> SEQ ID NO 94
<211> LENGTH: 18
<212> TYPE: DNA
<213> ORGANISM: Artificial
<220> FEATURE:
<223> OTHER INFORMATION: Synthetic primer

<400> SEQUENCE: 94
ctctgctggg aaagcggc                                           18

<210> SEQ ID NO 95
<211> LENGTH: 20
<212> TYPE: DNA
<213> ORGANISM: Artificial
<220> FEATURE:
<223> OTHER INFORMATION: Synthetic primer

<400> SEQUENCE: 95
caagcactct gcgaactgag                                         20

<210> SEQ ID NO 96
<211> LENGTH: 21
<212> TYPE: DNA
<213> ORGANISM: Artificial
<220> FEATURE:
<223> OTHER INFORMATION: Synthetic primer

<400> SEQUENCE: 96 aagttttga aggcaagatg c                                        21

<210> SEQ ID NO 97
<211> LENGTH: 23
<212> TYPE: DNA
<213> ORGANISM: Artificial
```

```
<220> FEATURE:
<223> OTHER INFORMATION: Synthetic primer

<400> SEQUENCE: 97
gcggtctggc agtaaaaact atc                                           23

<210> SEQ ID NO 98
<211> LENGTH: 23
<212> TYPE: DNA
<213> ORGANISM: Artificial
<220> FEATURE:
<223> OTHER INFORMATION: Synthetic primer

<400> SEQUENCE: 98
gtgaaacagc attgctgtca ctt                                           23

<210> SEQ ID NO 99
<211> LENGTH: 24
<212> TYPE: DNA
<213> ORGANISM: Artificial
<220> FEATURE:
<223> OTHER INFORMATION: Synthetic primer

<400> SEQUENCE: 99
ctaggccaca gaattgaaag atct                                          24

<210> SEQ ID NO 100
<211> LENGTH: 25
<212> TYPE: DNA
<213> ORGANISM: Artificial
<220> FEATURE:
<223> OTHER INFORMATION: Synthetic primer

<400> SEQUENCE: 100
gtaggtggaa attctagcat catcc                                         25

<210> SEQ ID NO 101
<211> LENGTH: 20
<212> TYPE: DNA
<213> ORGANISM: Artificial
<220> FEATURE:
<223> OTHER INFORMATION: Synthetic primer

<400> SEQUENCE: 101
gcctagccga gggagagccg                                               20

<210> SEQ ID NO 102
<211> LENGTH: 22
<212> TYPE: DNA
<213> ORGANISM: Artificial
<220> FEATURE:
<223> OTHER INFORMATION: Synthetic primer

<400> SEQUENCE: 102
tgtgacttgg gagctctgca gc                                            22

<210> SEQ ID NO 103
<211> LENGTH: 18
<212> TYPE: DNA
<213> ORGANISM: Artificial
<220> FEATURE:
<223> OTHER INFORMATION: Synthetic primer

<400> SEQUENCE: 103
gccgccccga ctgcatct                                                 18
```

```
<210> SEQ ID NO 104
<211> LENGTH: 20
<212> TYPE: DNA
<213> ORGANISM: Artificial
<220> FEATURE:
<223> OTHER INFORMATION: Synthetic primer

<400> SEQUENCE: 104
tcagtggagg gaaggaaatg                                              20

<210> SEQ ID NO 105
<211> LENGTH: 20
<212> TYPE: DNA
<213> ORGANISM: Artificial
<220> FEATURE:
<223> OTHER INFORMATION: Synthetic primer

<400> SEQUENCE: 105
ttcctgccct ggacacttac                                              20

<210> SEQ ID NO 106
<211> LENGTH: 22
<212> TYPE: DNA
<213> ORGANISM: Artificial
<220> FEATURE:
<223> OTHER INFORMATION: Synthetic primer

<400> SEQUENCE: 106
ttgtgcccag tcatagccga at                                           22

<210> SEQ ID NO 107
<211> LENGTH: 19
<212> TYPE: DNA
<213> ORGANISM: Artificial
<220> FEATURE:
<223> OTHER INFORMATION: Synthetic primer

<400> SEQUENCE: 107 cctttctcc ctgacaccg                                                19

<210> SEQ ID NO 108
<211> LENGTH: 19
<212> TYPE: DNA
<213> ORGANISM: Artificial
<220> FEATURE:
<223> OTHER INFORMATION: Synthetic primer

<400> SEQUENCE: 108
gcatccatct ggcaggttc                                               19

<210> SEQ ID NO 109
<211> LENGTH: 20
<212> TYPE: DNA
<213> ORGANISM: Artificial
<220> FEATURE:
<223> OTHER INFORMATION: Synthetic primer

<400> SEQUENCE: 109
aggtgagatg acaggagatc                                              20

<210> SEQ ID NO 110
<211> LENGTH: 57
<212> TYPE: DNA
<213> ORGANISM: Artificial
<220> FEATURE:
<223> OTHER INFORMATION: Synthetic
```

<400> SEQUENCE: 110
ccggccgact gatgttccca cggatctcga gatccgtggg aacatcagtc ggttttt          57

<210> SEQ ID NO 111
<211> LENGTH: 57
<212> TYPE: DNA
<213> ORGANISM: Artificial
<220> FEATURE:
<223> OTHER INFORMATION: Synthetic

<400> SEQUENCE: 111
ccgggcaact caatgatgcc gagttctcga gaactcggca tcattgagtt gcttttt          57

<210> SEQ ID NO 112
<211> LENGTH: 57
<212> TYPE: DNA
<213> ORGANISM: Artificial
<220> FEATURE:
<223> OTHER INFORMATION: Synthetic

<400> SEQUENCE: 112
ccggagagtg tatcaccttc ttgaactcga gttcaagaag gtgatacact cttttt          57

<210> SEQ ID NO 113
<211> LENGTH: 57
<212> TYPE: DNA
<213> ORGANISM: Artificial
<220> FEATURE:
<223> OTHER INFORMATION: Synthetic

<400> SEQUENCE: 113
ccgggaaggc atccactatc gagatctcga gatctcgata gtggatgcct tctttt          57

<210> SEQ ID NO 114
<211> LENGTH: 57
<212> TYPE: DNA
<213> ORGANISM: Artificial
<220> FEATURE:
<223> OTHER INFORMATION: Synthetic

<400> SEQUENCE: 114
ccgggcagac actgtctgag caggtctcga gacctgctca gacagtgtct gctttt          57

<210> SEQ ID NO 115
<211> LENGTH: 57
<212> TYPE: DNA
<213> ORGANISM: Artificial
<220> FEATURE:
<223> OTHER INFORMATION: Synthetic

<400> SEQUENCE: 115
ccgggcaact caatgatgct gagttctcga gaactcagca tcattgagtt gctttt          57

<210> SEQ ID NO 116
<211> LENGTH: 58
<212> TYPE: DNA
<213> ORGANISM: Artificial
<220> FEATURE:
<223> OTHER INFORMATION: Synthetic

<400> SEQUENCE: 116
ccggtgagat catgttgcta gaaacctcga ggtttctagc aacatgatct cattttg          58

<210> SEQ ID NO 117

```
<211> LENGTH: 57
<212> TYPE: DNA
<213> ORGANISM: Artificial
<220> FEATURE:
<223> OTHER INFORMATION: Synthetic

<400> SEQUENCE: 117
ccgggaggac actatgacgg aagtactcga gtacttccgt catagtgtcc tcttttt        57

<210> SEQ ID NO 118
<211> LENGTH: 20
<212> TYPE: DNA
<213> ORGANISM: Artificial
<220> FEATURE:
<223> OTHER INFORMATION: Synthetic primer

<400> SEQUENCE: 118
tgggtcgctt ttgggattac                                                 20

<210> SEQ ID NO 119
<211> LENGTH: 21
<212> TYPE: DNA
<213> ORGANISM: Artificial
<220> FEATURE:
<223> OTHER INFORMATION: Synthetic primer

<400> SEQUENCE: 119
ttcaactcct tcatggtctc g                                               21

<210> SEQ ID NO 120
<211> LENGTH: 19
<212> TYPE: DNA
<213> ORGANISM: Artificial
<220> FEATURE:
<223> OTHER INFORMATION: Synthetic primer

<400> SEQUENCE: 120
agccacatcg ctcagacac                                                  19

<210> SEQ ID NO 121
<211> LENGTH: 19
<212> TYPE: DNA
<213> ORGANISM: Artificial
<220> FEATURE:
<223> OTHER INFORMATION: Synthetic primer

<400> SEQUENCE: 121
gcccaatacg accaaatcc                                                  19

<210> SEQ ID NO 122
<211> LENGTH: 22
<212> TYPE: DNA
<213> ORGANISM: Artificial
<220> FEATURE:
<223> OTHER INFORMATION: Synthetic primer

<400> SEQUENCE: 122
gttataaccg ggaagacttt gc                                              22

<210> SEQ ID NO 123
<211> LENGTH: 21
<212> TYPE: DNA
<213> ORGANISM: Artificial
<220> FEATURE:
<223> OTHER INFORMATION: Synthetic primer

<400> SEQUENCE: 123
```

```
aaactcggca tcattgagtt g                                              21

<210> SEQ ID NO 124
<211> LENGTH: 22
<212> TYPE: DNA
<213> ORGANISM: Artificial
<220> FEATURE:
<223> OTHER INFORMATION: Synthetic primer

<400> SEQUENCE: 124
tttgagggta tttgagtagc gg                                             22

<210> SEQ ID NO 125
<211> LENGTH: 19
<212> TYPE: DNA
<213> ORGANISM: Artificial
<220> FEATURE:
<223> OTHER INFORMATION: Synthetic primer

<400> SEQUENCE: 125
ctctcgcgga gtgaactac                                                 19

<210> SEQ ID NO 126
<211> LENGTH: 20
<212> TYPE: DNA
<213> ORGANISM: Artificial
<220> FEATURE:
<223> OTHER INFORMATION: Synthetic primer

<400> SEQUENCE: 126
gaccctggag gctaaggact                                                20

<210> SEQ ID NO 127
<211> LENGTH: 20
<212> TYPE: DNA
<213> ORGANISM: Artificial
<220> FEATURE:
<223> OTHER INFORMATION: Synthetic primer

<400> SEQUENCE: 127
agagccttca tcttcgcaat                                                20

<210> SEQ ID NO 128
<211> LENGTH: 20
<212> TYPE: DNA
<213> ORGANISM: Artificial
<220> FEATURE:
<223> OTHER INFORMATION: Synthetic primer

<400> SEQUENCE: 128
gcacagtcaa ggccgagaat                                                20

<210> SEQ ID NO 129
<211> LENGTH: 20
<212> TYPE: DNA
<213> ORGANISM: Artificial
<220> FEATURE:
<223> OTHER INFORMATION: Synthetic primer

<400> SEQUENCE: 129
gccttctcca tggtggtgaa                                                20

<210> SEQ ID NO 130
<211> LENGTH: 19
<212> TYPE: DNA
```

```
<213> ORGANISM: Artificial
<220> FEATURE:
<223> OTHER INFORMATION: Synthetic primer

<400> SEQUENCE: 130
gcgctcagct cttgtcact                                               19

<210> SEQ ID NO 131
<211> LENGTH: 20
<212> TYPE: DNA
<213> ORGANISM: Artificial
<220> FEATURE:
<223> OTHER INFORMATION: Synthetic primer

<400> SEQUENCE: 131
ctccagccac aaggacatct                                              20

<210> SEQ ID NO 132
<211> LENGTH: 20
<212> TYPE: DNA
<213> ORGANISM: Artificial
<220> FEATURE:
<223> OTHER INFORMATION: Synthetic primer

<400> SEQUENCE: 132
gctctgccta catcgtggtc                                              20

<210> SEQ ID NO 133
<211> LENGTH: 18
<212> TYPE: DNA
<213> ORGANISM: Artificial
<220> FEATURE:
<223> OTHER INFORMATION: Synthetic primer

<400> SEQUENCE: 133
ctcatggccc agcatctt                                                18

<210> SEQ ID NO 134
<211> LENGTH: 19
<212> TYPE: DNA
<213> ORGANISM: Artificial
<220> FEATURE:
<223> OTHER INFORMATION: Synthetic primer

<400> SEQUENCE: 134
atggagcagg gaagaccac                                               19

<210> SEQ ID NO 135
<211> LENGTH: 19
<212> TYPE: DNA
<213> ORGANISM: Artificial
<220> FEATURE:
<223> OTHER INFORMATION: Synthetic primer

<400> SEQUENCE: 135
gtaggccgtg ccagaagtt                                               19

<210> SEQ ID NO 136
<211> LENGTH: 34
<212> TYPE: DNA
<213> ORGANISM: Artificial
<220> FEATURE:
<223> OTHER INFORMATION: Synthetic primer

<400> SEQUENCE: 136
tcatagctag cgcagagcca ggattcacgc cctg                              34
```

<210> SEQ ID NO 137
<211> LENGTH: 35
<212> TYPE: DNA
<213> ORGANISM: Artificial
<220> FEATURE:
<223> OTHER INFORMATION: Synthetic primer

<400> SEQUENCE: 137
tggtcctcga ggaaccttca tcttcctgcc tgtga                          35

<210> SEQ ID NO 138
<211> LENGTH: 30
<212> TYPE: DNA
<213> ORGANISM: Artificial
<220> FEATURE:
<223> OTHER INFORMATION: Synthetic primer

<400> SEQUENCE: 138
tagttacgcg tagtagcccc catctttgcc                                30

<210> SEQ ID NO 139
<211> LENGTH: 29
<212> TYPE: DNA
<213> ORGANISM: Artificial
<220> FEATURE:
<223> OTHER INFORMATION: Synthetic primer

<400> SEQUENCE: 139
aatcagctag cccctcagct gcaaagctc                                 29

<210> SEQ ID NO 140
<211> LENGTH: 29
<212> TYPE: DNA
<213> ORGANISM: Artificial
<220> FEATURE:
<223> OTHER INFORMATION: Synthetic primer

<400> SEQUENCE: 140
tagttacgcg tagtagcccc ctctttgcc                                 29

<210> SEQ ID NO 141
<211> LENGTH: 31
<212> TYPE: DNA
<213> ORGANISM: Artificial
<220> FEATURE:
<223> OTHER INFORMATION: Synthetic primer

<400> SEQUENCE: 141
aatcagctag cccttcagct gcaaagctct g                              31

TREATMENT AND DIAGNOSIS OF MELANOMA

CROSS REFERENCE TO RELATED APPLICATIONS

This application is a Continuation of U.S. patent application Ser. No. 15/650,480, filed Jul. 14, 2017, which is a Continuation of U.S. application Ser. No. 15/228,643, filed Aug. 4, 2016, Now U.S. Pat. No. 9,707,195, which is a Continuation of U.S. patent application Ser. No. 14/486,477, filed Sep. 15, 2014, now U.S. Pat. No. 9,526,710, which is a Continuation of International Application No. PCT/US2013/54690 filed Aug. 13, 2013, which claims priority to U.S. Provisional Application No. 61/682,339 filed Aug. 13, 2012 and U.S. Provisional Application No. 61/784,057 filed Mar. 14, 2013. The contents of the applications are incorporated herein by reference in their entirety.

FIELD OF THE INVENTION

This invention relates to diagnosis and treatment of migrating cancers and melanoma.

BACKGROUND OF THE INVENTION

Melanoma, a malignant tumor, develops from abnormal melanocytes in the lower epidermis and can metastasize to distant sites in the body via the blood and lymph systems. Although it accounts for less than 5% of skin cancer cases, melanoma is much more dangerous and responsible for a large majority of the deaths associated with skin cancer. Across the world the incidence of melanoma has been increasing at an alarming rate, with a lifetime risk of developing melanoma as high as 1/58 for males in the U.S. (Jemal et al., 2008, C A: Cancer J. Clin. 58:71-96). The mortality rate of malignant melanoma also continues to rise dramatically throughout the world. According to a 2006 WHO report, about 48,000 melanoma related deaths occur worldwide per year (Lucas et al. (2006) Environmental Burden of Disease Series. 13. World Health Organization. ISBN 92-4-159440-3). In the United States, it was estimated that almost 70,000 people were diagnosed with melanoma during 2010 and approximately 9,000 people would be expected to die from the disease (American Cancer Society; www.cancer.org).

Although some conventional cancer therapies have been used in treating metastatic melanoma, they are not effective. Metastatic melanoma therefore remains one of the most difficult cancers to treat and one of the most feared neoplasms. Accordingly, there is a need for new agents and methods for diagnosis and treatment of melanoma.

SUMMARY OF INVENTION

This invention addresses the above-mentioned need by providing agents and methods for diagnosis and treatment of melanoma. The invention is based, at least in part, on an unexpected discovery of a cooperative miRNA-protein network deregulated in metastatic melanoma. This network includes a number of metastasis suppressor factors and metastasis promoter factors.

In one aspect, the invention features a method for treating cancer, including administering to a subject in need thereof, a LXR agonist, wherein the LXR agonist is administered in an amount sufficient to increase the expression level or activity level of ApoE to a level sufficient to slow the spread of metastasis of the cancer.

In another aspect, the invention features a method for treating cancer, including administering to a subject in need thereof, an ApoE polypeptide in an amount sufficient to treat the cancer.

In another aspect, the invention features a method of slowing the spread of a migrating cancer, comprising administering to a subject in need thereof, a LXR agonist or an ApoE polypeptide.

In some embodiments of any of the aforementioned methods, the LXR agonist is a LXRβ agonist. In certain embodiments, the LXR agonist increases the expression level of ApoE at least 2.5-fold in vitro. In certain embodiments, the LXRβ agonist is selective for LXRβ over LXRα. In other embodiments, the LXRβ agonist has activity for LXRβ that is at least 2.5-fold greater than the activity of said agonist for LXRα. In some embodiments, the LXRβ agonist has activity for LXRβ that is at least 10-fold greater than the activity of said agonist for LXRα. In further embodiments, the LXRβ agonist has activity for LXRβ that is at least 100-fold greater than the activity of said agonist for LXRα. In certain embodiments, the LXR agonist has activity for LXRβ that is at least within 2.5-fold of the activity of said agonist for LXRα.

In some embodiments the migrating cancer is metastatic cancer. The metastatic cancer can include cells exhibiting migration and/or invasion of migrating cells and/or include cells exhibiting endothelial recruitment and/or angiogenesis. In other embodiments, the migrating cancer is a cell migration cancer. In still other embodiments, the cell migration cancer is a non-metastatic cell migration cancer.

The migrating cancer can be a cancer spread via seeding the surface of the peritoneal, pleural, pericardial, or subarachnoid spaces. Alternatively, the migrating cancer can be a cancer spread via the lymphatic system, or a cancer spread hematogenously.

In particular embodiments, the migrating cancer is a cell migration cancer that is a non-metastatic cell migration cancer, such as ovarian cancer, mesothelioma, or primary lung cancer.

In a related aspect, the invention provides a method for inhibiting or reducing metastasis of cancer comprising administering a LXR agonist or an ApoE polypeptide.

In another aspect, the invention provides a method for inhibiting proliferation or growth of cancer stem cells or cancer initiating cells, including contacting the cell with a LXR agonist or an ApoE polypeptide in an amount sufficient to inhibit proliferation or growth of said cell.

In yet another aspect, the invention provides a method of reducing the rate of tumor seeding of a cancer including administering to a subject in need thereof a LXR agonist or an ApoE polypeptide in an amount sufficient to reduce tumor seeding.

In still a further aspect, the invention provides a method of reducing or treating metastatic nodule-forming of cancer including administering to a subject in need thereof a LXR agonist or an ApoE polypeptide in an amount sufficient to treat said metastatic nodule-forming of cancer.

In other embodiments, the cancer is breast cancer, colon cancer, renal cell cancer, non-small cell lung cancer, hepatocellular carcinoma, gastric cancer, ovarian cancer, pancreatic cancer, esophageal cancer, prostate cancer, sarcoma, or melanoma. In some embodiments, the cancer is melanoma. In other embodiments, the cancer is breast cancer. In certain embodiments, the cancer is renal cell cancer. In further embodiments, the cancer is pancreatic cancer. In other embodiments, the cancer is non-small cell lung cancer. In some embodiments the cancer is colon cancer. In further embodiments, the cancer is ovarian cancer.

In other embodiments, the cancer is a drug resistant cancer. In further embodiments, the cancer is resistant to vemurafenib, dacarbazine, a CTLA4 inhibitor, a PD1 inhibitor, or a PDL1 inhibitor.

In some embodiments, the method comprises administering an LXR agonist selected from the list consisting of a compound of any one of Formula I-IV or any of compound numbers 1-39, or pharmaceutically acceptable salts thereof. In some embodiments, the LXR agonist is compound 1 or a pharmaceutically acceptable salt thereof. In other embodiments, the LXR agonist is compound 2 or a pharmaceutically acceptable salt thereof. In certain embodiments, the LXR agonist is compound 3 or a pharmaceutically acceptable salt thereof. In further embodiments, the LXR agonist is compound 12 or a pharmaceutically acceptable salt thereof. In some embodiments, the LXR agonist is compound 25 or a pharmaceutically acceptable salt thereof. In other embodiments, the LXR agonist is compound 38 or a pharmaceutically acceptable salt thereof. In further embodiments, the LXR agonist is compound 39 or a pharmaceutically acceptable salt thereof.

The method can further include administering an antiproliferative, wherein said LXR agonist and said antiproliferative are administered in an amount that together, is sufficient to slow the progression of migrating cancer. For example, the antiproliferative and LXR agonist can be administered within 28 days of each (e.g., within 21, 14, 10, 7, 5, 4, 3, 2, or 1 days) or within 24 hours (e.g., 12, 6, 3, 2, or 1 hours; or concomitantly) other in amounts that together are effective to treat the subject.

In some embodiments, the method comprises administering an ApoE polypeptide. The ApoE polypeptide fragment can increase the activity level or expression level of LRP1 or LRP8, and/or the ApoE polypeptide can bind to LRP1 or LRP8, the ApoE polypeptide can be the receptor binding region (RBR) of ApoE. The method can further include administering an antiproliferative, wherein said ApoE polypeptide and said antiproliferative are administered in an amount that together, is sufficient to slow the progression of migrating cancer. For example, the antiproliferative and ApoE polypeptide can be administered within 28 days of each (e.g., within 21, 14, 10, 7, 5, 4, 3, 2, or 1 days) or within 24 hours (e.g., 12, 6, 3, 2, or 1 hours; or concomitantly) other in amounts that together are effective to treat the subject.

In some embodiments, the pharmaceutical composition may further comprise an additional compound having antiproliferative activity. The additional compound having antiproliferative activity can be selected from the group of compounds such as chemotherapeutic and cytotoxic agents, differentiation-inducing agents (e.g. retinoic acid, vitamin D, cytokines), hormonal agents, immunological agents and anti-angiogenic agents. Chemotherapeutic and cytotoxic agents include, but are not limited to, alkylating agents, cytotoxic antibiotics, antimetabolites, vinca alkaloids, etoposides, and others (e.g., paclitaxel, taxol, docetaxel, taxotere, cis-platinum). A list of additional compounds having antiproliferative activity can be found in L. Brunton, B. Chabner and B. Knollman (eds). Goodman and Gilman's The Pharmacological Basis of Therapeutics, Twelfth Edition, 2011, McGraw Hill Companies, New York, N.Y.

The method may further include administering a antiproliferative compound selected from the group consisting of alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelin A receptor antagonist, retinoic acid receptor agonists, immuno-modulators, hormonal and antihormonal agents, photodynamic agents, tyrosine kinase inhibitors, antisense compounds, corticosteroids, HSP90 inhibitors, proteosome inhibitors (for example, NPI-0052), CD40 inhibitors, anti-CSI antibodies, FGFR3 inhibitors, VEGF inhibitors, MEK inhibitors, cyclin D1 inhibitors, NF-kB inhibitors, anthracyclines, histone deacetylases, kinesin inhibitors, phosphatase inhibitors, COX2 inhibitors, mTOR inhibitors, calcineurin antagonists, IMiDs, or other agents used to treat proliferative diseases. Examples of such compounds are provided in Tables 1.

In another aspect, the invention features a method for treating melanoma (e.g., metastatic melanoma) in a subject in need thereof. The method includes (a) increasing in the subject the expression level or activity level of a metastasis suppressor factor selected from the group consisting of DNAJA4, Apolipoprotein E (ApoE), LRP1, LRP8, Liver X Receptor (LXR, e.g., both LXR-alpha and LXR-beta), and miR-7 or (b) decreasing in the subject the expression level or activity level of a metastasis promoter factor selected from the group consisting of miR-199a-3p, miR-199a-5p, miR-1908, and CTGF.

In the method, the increasing step can be carried out by administering to the subject one or more of the followings: (i) a polypeptide having a sequence of DNAJA4, ApoE or an ApoE fragment, LRP1, LRP8, or LXR; (ii) a nucleic acid having a sequence encoding DNAJA4, ApoE, LRP1, LRP8, or LXR; (iii) a ligand for LRP1, LRP8, or LXR; and (iv) an RNAi agent encoding miR-7. Examples of the LRP1 or LRP8 ligand include the receptor binding portion of ApoE, anti-LRP1 or anti-LRP8 antibodies, and small molecule ligands. In one example, increasing the ApoE expression level can be carried out by increasing the activity level or expression level of LXR. Increasing the DNAJA4 expression level can also be carried out by increasing the activity level or expression level of LXR. The LXR activity level can be increased by administering to the subject a ligand of LXR, such as compounds of Formula I-IV as disclosed below. The increasing step can also be carried out by decreasing the expression level or activity level of a microRNA selected from the group consisting of miR-199a-3p, miR-199a-5p, and miR-1908. To this end, one can use a number of techniques known in the art, including, but not limited to, the miR-Zip technology, Locked Nucleic Acid (LNA), and antagomir technology as described in the examples below.

In another aspect, the invention provides a method for determining whether a subject has, or is at risk of having, metastatic melanoma. The method includes obtaining from the subject a sample; measuring in the sample (i) a first expression level of a metastasis promoter factor selected from the group consisting of miR-199a-3p, miR-199a-5p, miR-1908, and CTGF, or (ii) a second expression level of a metastasis suppressor factor selected from the group consisting of DNAJA4, ApoE, LRP1, LRP8, LXR, and miR-7; and comparing the first expression level with a first predetermined reference value, or the second expression level with a second predetermined reference value. The subject is determined to have, or to be at risk of having, metastatic melanoma if (a) the first expression level is above a first predetermined reference value or (b) the second expression level is below a second predetermined reference value. The first and second predetermined reference values can be obtained from a control subject that does not have metastatic melanoma. In one embodiment, the measuring step includes measuring both the first expression level and the second expression level. The sample can be a body fluid sample, a tumor sample, a nevus sample, or a human skin sample.

In a another aspect, the invention provides an array having a support having a plurality of unique locations, and any combination of (i) at least one nucleic acid having a sequence that is complementary to a nucleic acid encoding a metastasis promoter factor selected from the group consisting of miR-199a-3p, miR-199a-5p, miR-1908, and CTGF or a complement thereof, or (ii) at least one nucleic acid having a sequence that is complementary to a nucleic acid encoding a metastasis suppressor factor selected from the group consisting of DNAJA4, ApoE, LRP1, LRP8, LXR, and miR-7 or a complement thereof. Preferably, each nucleic acid is immobilized to a unique location of the support. This array can be used for metastatic melanoma diagnosis and prognosis.

Accordingly, the invention also provides a kit for diagnosing a metastatic potential of melanoma in a subject. The kit includes a first reagent that specifically binds to an expression product of a metastasis suppressor gene selected from the group consisting of DNAJA4, ApoE, LRP1, LRP8, LXR, and miR-7; or a second reagent that specifically binds to an expression product of a metastasis promoter gene selected from the group consisting of miR-199a-3p, miR-199a-5p, miR-1908, and CTGF. The second agent can be a probe having a sequence complementary to the suppressor or promoter gene or a complement thereof. The kit can further contain reagents for performing an immunoassay, a hybridization assay, or a PCR assay. In one embodiment, the kit contained the above-mentioned array.

In a another aspect, the invention provides a method of identifying a compound useful for treating melanoma or for inhibiting endothelial recruitment, cell invasion, or metastatic angiogenesis. The method includes (i) obtaining a test cell expressing a reporter gene encoded by a nucleic acid operatively liked to a promoter of a marker gene selected from the group consisting of miR-199a-3p, miR-199a-5p, miR-1908, and CTGF; (ii) exposing the test cell to a test compound; (iii) measuring the expression level of the reporter gene in the test cell; (iv) comparing the expression level with a control level; and (v) selecting the test compound as a candidate useful for treating melanoma or for inhibiting endothelial recruitment, cancer cell invasion, or metastatic angiogenesis, if the comparison indicates that the expression level is lower than the control level.

The invention provides another method of identifying a compound useful for treating melanoma or for inhibiting endothelial recruitment, cell invasion, or metastatic angiogenesis. The method includes (i) obtaining a test cell expressing a reporter gene encoded by a nucleic acid operatively liked to a promoter of a marker gene selected from the group consisting of DNAJA4, ApoE, LRP1, LRP8, LXR, and miR-7; (ii) exposing the test cell to a test compound; (iii) measuring the expression level of the reporter gene in the test cell; (iv) comparing the expression level with a control level; and (v) selecting the test compound as a candidate useful for treating melanoma or for inhibiting endothelial recruitment, cancer cell invasion, or metastatic angiogenesis, if the comparison indicates that the expression level is higher than the control level.

In the above-mentioned identification methods, the reporter gene can be a standard reporter gene (such as LaxZ, GFP, or luciferase gene, or the like), known in the art, or one of the aforementioned metastasis suppressor genes or metastasis promoter genes. In the methods, the control level can be obtained from a control cell that is the same as the test cell except that the control cell has not be exposed to the test compound.

In a another aspect, the invention provides a method for inhibiting endothelial recruitment, inhibiting tumor cell invasion, or treating metastatic cancer in a subject in need thereof, by administering to the subject an agent that inhibits expression or activity of CTGF. The subject can be one having a disorder characterized by pathological angiogenesis, including but not limited to cancer (e.g., metastatic melanoma), an eye disorder, and an inflammatory disorder. An example of the tumor cell is a metastatic melanoma cell. Examples of the agent include an antibody, a nucleic acid, a polypeptide, and a small molecule compound. In a preferred embodiment, the antibody is a monoclonal antibody.

In a another aspect, the invention provides a method for inhibiting endothelial recruitment, inhibiting tumor cell invasion, or treating metastatic cancer in a subject in need thereof, by administering to the subject an agent that increases expression or activity of miR-7. An example of the tumor cell is a metastatic melanoma cell. Examples of the agent include an antibody, a nucleic acid, a polypeptide, and a small molecule compound. In one example, the agent has miR-7 activity. The nucleic acid can be an oligonucleotide. And, the oligonucleotide can include a sequence selected from the group consisting of SEQ ID Nos. 36-38.

As used herein, "migrating cancer" refers to a cancer in which the cancer cells forming the tumor migrate and subsequently grow as malignant implants at a site other than the site of the original tumor. The cancer cells migrate via seeding the surface of the peritoneal, pleural, pericardial, or subarachnoid spaces to spread into the body cavities; via invasion of the lymphatic system through invasion of lymphatic cells and transport to regional and distant lymph nodes and then to other parts of the body; via haematogenous spread through invasion of blood cells; or via invasion of the surrounding tissue. Migrating cancers include metastatic tumors and cell migration cancers, such as ovarian cancer, mesothelioma, and primary lung cancer, each of which is characterized by cellular migration.

As used herein, "slowing the spread of migrating cancer" refers to reducing or stopping the formation of new loci; or reducing, stopping, or reversing the tumor load.

As used herein, "metastatic tumor" refers to a tumor or cancer in which the cancer cells forming the tumor have a high potential to or have begun to, metastasize, or spread from one location to another location or locations within a subject, via the lymphatic system or via haematogenous spread, for example, creating secondary tumors within the subject. Such metastatic behavior may be indicative of malignant tumors. In some cases, metastatic behavior may be associated with an increase in cell migration and/or invasion behavior of the tumor cells.

As used herein, "slowing the spread of metastasis" refers to reducing or stopping the formation of new loci; or reducing, stopping, or reversing the tumor load.

The term "cancer" refers to any cancer caused by the proliferation of malignant neoplastic cells, such as tumors, neoplasms, carcinomas, sarcomas, leukemias, lymphomas, and the like.

As used herein, "drug resistant cancer" refers to any cancer that is resistant to an antiproliferative in Table 2.

Examples of cancers that can be defined as metastatic include but are not limited to non-small cell lung cancer, breast cancer, ovarian cancer, colorectal cancer, biliary tract cancer, bladder cancer, brain cancer including glioblastomas and medullablastomas, cervical cancer, choriocarcinoma, endometrial cancer, esophageal cancer, gastric cancer, hematological neoplasms, multiple myeloma, leukemia, intraepithelial neoplasms, livercancer, lymphomas, neuroblastomas, oral cancer, pancreatic cancer, prostate cancer, sarcoma, skin cancer including melanoma, basocellular cancer, squamous cell cancer, testicular cancer, stromal tumors, germ cell tumors, thyroid cancer, and renal cancer.

"Proliferation" as used in this application involves reproduction or multiplication of similar forms (cells) due to constituting (cellular) elements.

"Cell migration" as used in this application involves the invasion by the cancer cells into the surrounding tissue and the crossing of the vessel wall to exit the vasculature in distal organs of the cancer cell.

By "cell migration cancers" is meant cancers that migrate by invasion by the cancer cells into the surrounding tissue and the crossing of the vessel wall to exit the vasculature in distal organs of the cancer cell.

"Non-metastatic cell migration cancer" as used herein refers to cancers that do not migrate via the lymphatic system or via haematogenous spread.

As used herein, "cell to cell adhesion" refers to adhesion between at least two cells through an interaction between a selectin molecule and a selectin specific ligand. Cell to cell adhesion includes cell migration.

A "cell adhesion related disorder" is defined herein as any disease or disorder which results from or is related to cell to cell adhesion or migration. A cell adhesion disorder also includes any disease or disorder resulting from inappropriate, aberrant, or abnormal activation of the immune system or the inflammatory system. Such diseases include but are not limited to, myocardial infarction, bacterial or viral infection, metastatic conditions, e.g. cancer. The invention further features methods for treating a cell adhesion disorder by administering a LXR agonist or ApoE polypeptide.

As used herein, "cancer stem cells" or "cancer initiating cells" refers to cancer cells that possess characteristics associated with normal stem cells, specifically the ability to give rise to all cell types found in a particular cancer sample. Cancer stem cells are therefore tumorgenic or tumor forming, perhaps in contrast to other non-tumorgenic cancer cells. Cancer stem cells may persist in tumors as a distinct population and cause cancer recurrence and metastasis by giving rise to new tumors.

As used herein, "tumor seeding" refers to the spillage of tumor cell clusters and their subsequent growth as malignant implants at a site other than the site of the original tumor.

As used herein, "metastatic nodule" refers to an aggregation of tumor cells in the body at a site other than the site of the original tumor.

The details of one or more embodiments of the invention are set forth in the description below. Other features, objects, and advantages of the invention will be apparent from the description and from the claims.

Figure 1A:
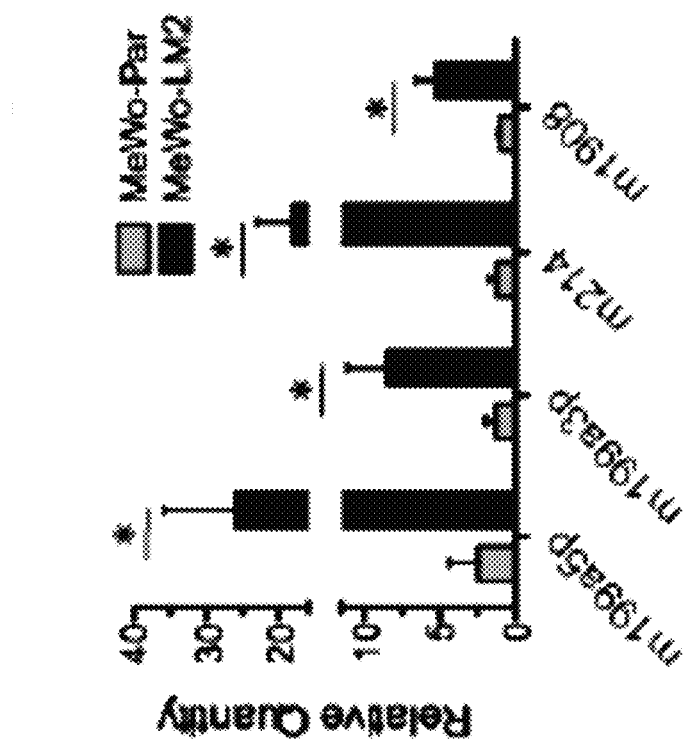
FIGS. 1A, 1B, 1C, 1D, 1E and 1F. Systematic Identification of miR-1908, miR-199a-3p, and miR-199a-5p as Endogenous Promoters of Human Melanoma Metastasis (1A) Heat map illustrating variance-normalized microarray expression values of miRNAs up-regulated in independent MeWo and A375 metastatic derivatives relative to their respective parental cells. Standard deviation changes from the mean of each heat map row are indicated by color map. (1B) miRNAs found to be up-regulated by microarray hybridization were validated by qRT-PCR in MeWo-LM2 metastatic derivatives. n=3. (1C) Bioluminescence imaging plot of lung metastatic colonization following intravenous injection of 4×104 parental MeWo cells over-expressing the precursors for miR-199a, miR-1908, miR-214, or a control hairpin. Lungs were extracted 63 days post-injection and H&E-stained. n=5. (1D) Bioluminescence imaging plot and H&E-stained lungs corresponding to lung metastasis following intravenous injection of 4×104 LM2 cells expressing a short hairpin (miR-Zip) inhibiting miR-1908 (m1908 KD), miR-199a-3p (m199a3p KD), miR-199a-5p (m199a5p KD), or a control sequence (shCTRL). Lungs were extracted and H&E-stained 49 days post-injection n=5-8. (1E) Lung colonization by 2×105 A375-LM3 metastatic derivatives with miR-Zip-induced silencing of miR-1908, miR-199a-3p, miR-199a-5p, or a control sequence was quantified at day 42 by bioluminescence imaging. n=5-8 (1F) The expression levels of miR-199a-3p, miR-199a-5p, and miR-1908 were determined in a blinded fashion by qRT-PCR in a cohort of non-metastatic (n=38) and metastatic (n=33) primary melanoma skin lesions from MSKCC patients. n=71. All data are represented as mean±SEM. $*p<0.05$, $p<0.01$, $*p<0.001$. See also FIG. 12.

Trans-well migration by 1×105 endothelial cells transduced with siRNAs targeting LRP8 or a control sequence in the presence of BSA (100 µM) or recombinant ApoE3 (100 µM). n=6-7. (6H) 1×105 endothelial cells were transduced with siRNAs targeting LRP8 or a control sequence, and trans-well chemotactic migration was assessed along an ApoE gradient. n=6-8. (6I) Endothelial recruitment into matrigel plugs, implanted subcutaneously above the ventral flank of mice, containing BSA (10 µg/mL), VEGF (400 ng/mL)+BSA (10 µg/mL), or VEGF (400 ng/mL)+recombinant ApoE3 (10 µg/mL). n=3-6.(6J) Blood vessel density within lung metastatic nodules formed following intravenous injection of 5×104 B16F10 mouse melanoma cells into wild-type or ApoE genetically null mice. Lung sections from FIG. 5M were immunohistochemically stained for MECA-32, and the percentage MECA-32 positive area within each metastatic nodule, outlined based on cell pigmentation, was quantified. n=17-20. All data are represented as mean±SEM. Scale bar, 100 µm.

FIGS. 7A, 7B, 7C, 7D, 7E, 7F, 7G, 7H, 7I AND 7K. Clinical and Therapeutic Cooperativity among miR-199a-3p, miR-199a-5p, and miR-1908 in Melanoma Metastasis (7A-7D). Kaplan-Meier curves for the MSKCC cohort (N=7I) representing metastasis-free survival of patients as a function of their primary melanoma lesion's miR-199a-3p (7A), miR-199a-5p (7B), miR-1908 (7C), or aggregate three miRNA expression levels (7D). Patients whose primary tumors' miRNA expression or aggregate miRNA expression levels (sum of the expression values of miR-199a-3p, miR-199a-5p, and miR-1908) were greater than the median for the population were classified as miRNA expression positive (red), while those whose primary tumors expressed the given miRNAs at a level below the median were classified as miRNA expression negative (blue). (7E) Lung metastasis by highly metastatic LM2 cells transfected with LNAs individually targeting each miR-1908, miR-199a-3p, or miR-199a-5p, a combination of LNAs targeting all three miRNAs, or a control LNA. 48 hours post-transfection, 1×105 cells were intravenously injected into immuno-deficient mice. n=5-6. (7F) Systemic metastasis by 1×105 MeWo-LM2 cells transfected with a control LNA (LNA-CTRL) or a cocktail of LNAs targeting miR-1908, miR-199a-3p, miR-199a-5p (LNA-3 miRNAs) 48 hours prior to intracardiac injection into athymic nude mice. n=5. (7G) Number of systemic metastatic foci arising from LNA-CTRL and LNA-3 miRNAs LM2 cells at day 28 post-intracardiac injection. n=5. (7H-7I) Bioluminescence signal quantification of bone metastasis (7H) and brain metastasis (7I) at day 28 post-intracardiac injection of LNA-CTRL and LNA-3 miRNAs LM2 cells. n=5. (7J) 4×104 highly metastatic MeWo-LM2 cells were tail-vein injected into immuno-compromised mice, and the mice were intravenously treated with a cocktail of in vivo-optimized LNAs targeting miR-1908, miR-199a-3p, and miR-199a-5p at a total dose of 12.5 mg/kg or a mock PBS control on a bi-weekly basis for four weeks. Lung colonization was assessed by bioluminescence imaging, and representative H&E-stained lungs extracted at day 56 are shown. n=5-6. (7K) Model of miRNA-dependent regulation of metastatic invasion, endothelial recruitment, and colonization in melanoma through targeting of ApoE-mediated melanoma cell LRP1 and endothelial cell LRP8 receptor signaling.

FIGS. 8A, 8B, 8C, 8D and 8E. MiRNA-dependent targeting of ApoE/LRP1 signaling promotes cancer cell invasion and endothelial recruitment through CTGF induction. (8A) A heat-map of variance-normalized CTGF expression levels, determined by qRT-PCR analysis, in (1) MeWo parental and MeWo-LM2 cells, (2) MeWo parental cells over-expressing miR-199a, miR-1908, or a control hairpin, and (3) MeWo parental cells transduced with short hairpins targeting ApoE or a control sequence. Color-map indicates the standard deviations change from the mean. (8B) CTGF levels in conditioned media from MeWo parental cells with ApoE knock-down determined by ELISA. n=6; p-values based on a one-sided student's t-test. (8C) CTGF levels, quantified by ELISA, in conditioned media from highly metastatic MeWo-LM2 cells treated with recombinant ApoE in the setting of LRP1 knock-down or a control knock-down. n=3-4; p-values based on a one-sided student's t-test. (8D-8E) Parental MeWo cells with shRNA-induced ApoE knock-down were (1) transfected with independent siRNAs targeting CTGF or a control sequence or (2) incubated in the presence of a CTGF neutralizing antibody (20 µg/mL) or an IgG control antibody (20 µg/mL), and the cells were subjected to cell invasion (8D) and endothelial recruitment (8E) assays. n=6-8; p-values based on a one-sided student's t-test; scale bar indicates 100 µM. All data are represented as mean±SEM.

Figures 9A, 9B, 9C:
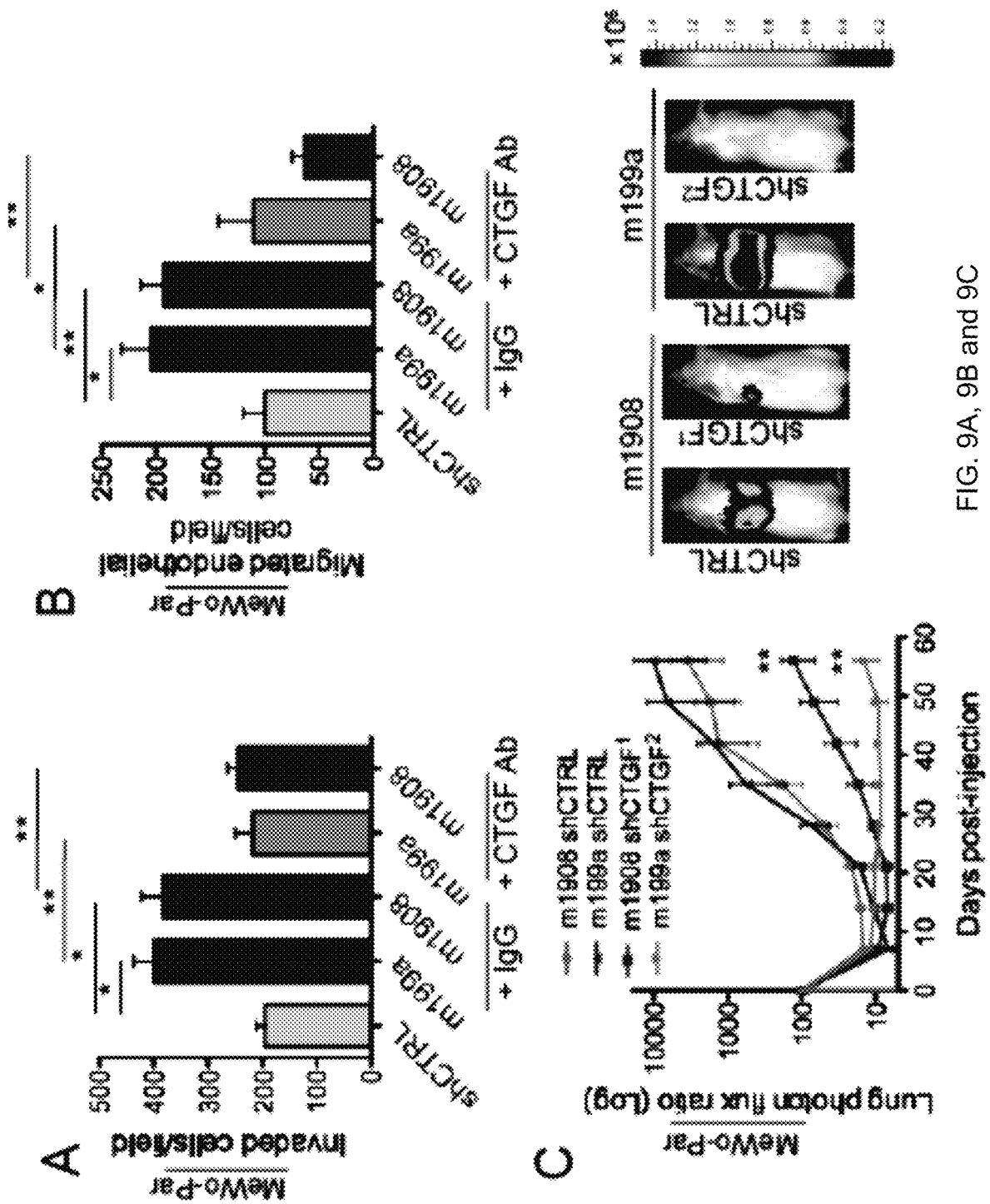

FIGS. 9A, 9B and 9C. CTGF mediates miRNA-dependent metastatic invasion, endothelial recruitment, and colonization. (9A) 1×105 parental MeWo cells expressing a control hairpin or over-expressing miR-199a or miR-1908 were subjected to a trans-well cell invasion assay in the presence of a blocking antibody targeting CTGF (20 µg/mL) or a control IgG antibody (20 µg/mL) as indicated in the figure. n=4-10; p-values based on a one-sided student's t-test. All data are represented as mean±SEM. (9B) Endothelial recruitment by parental MeWo cells expressing a control hairpin or over-expressing miR-199a or miR-1908. At the beginning of the assay, a neutralizing antibody targeting CTGF (20 µg/mL) or a control IgG antibody (20 µg/mL) were added to endothelial cells as indicated, and 1×105 endothelial cells were allowed to migrate towards 5×104 cancer cells in a trans-well migration assay. n=3-8; p-values based on a one-sided student's t-test. (9C) Bioluminescence imaging of lung metastasis by 5×104 parental MeWo cells knocked down for CTGF in the setting of miR-199a or miR-1908 over-expression. n=5-6; p-values obtained using a one-way Mann-Whitney t-test. All data are represented as mean±SEM.

FIGS. 10A, 10B, 10C, 10D and 10E. Treatment with the LXR agonist GW3965 elevates melanoma cell ApoE levels and suppresses cancer cell invasion, endothelial recruitment, and metastatic colonization. (10A-10B) Parental MeWo cells were incubated in the presence of DMSO or GW3965 at the indicated concentrations. After 48 hours, total RNA was extracted, and the levels of ApoE (10A) and DNAJA4 (10B) were determined by qRT-PCR. n=3. (10C) Cell invasion by 1×105 parental MeWo cells pre-treated with GW3965 or DMSO for 48 hours. n=6-7. p-values based on a one-sided student's t-test. All data are represented as mean±SEM. (10D) Endothelial recruitment by 5×104 parental MeWo cells pre-treated with GW3965 or DMSO for 48 hours. n=6-7. p-values based on a one-sided student's t-test. (10E) Mice were fed with grain-based chow diet containing GW3965 (20mg/kg) or a control diet. After 10 days, 4×104 parental MeWo cells were tail-vein injected into mice, and the mice were continuously fed with GW3965-containing chow or a control diet throughout the experiment. Lung colonization was assessed by bioluminescence imaging. n=5-6; p-values obtained using a one-way Mann-Whitney t-test All data are represented as mean±SEM.

Figures 11A, 11B:
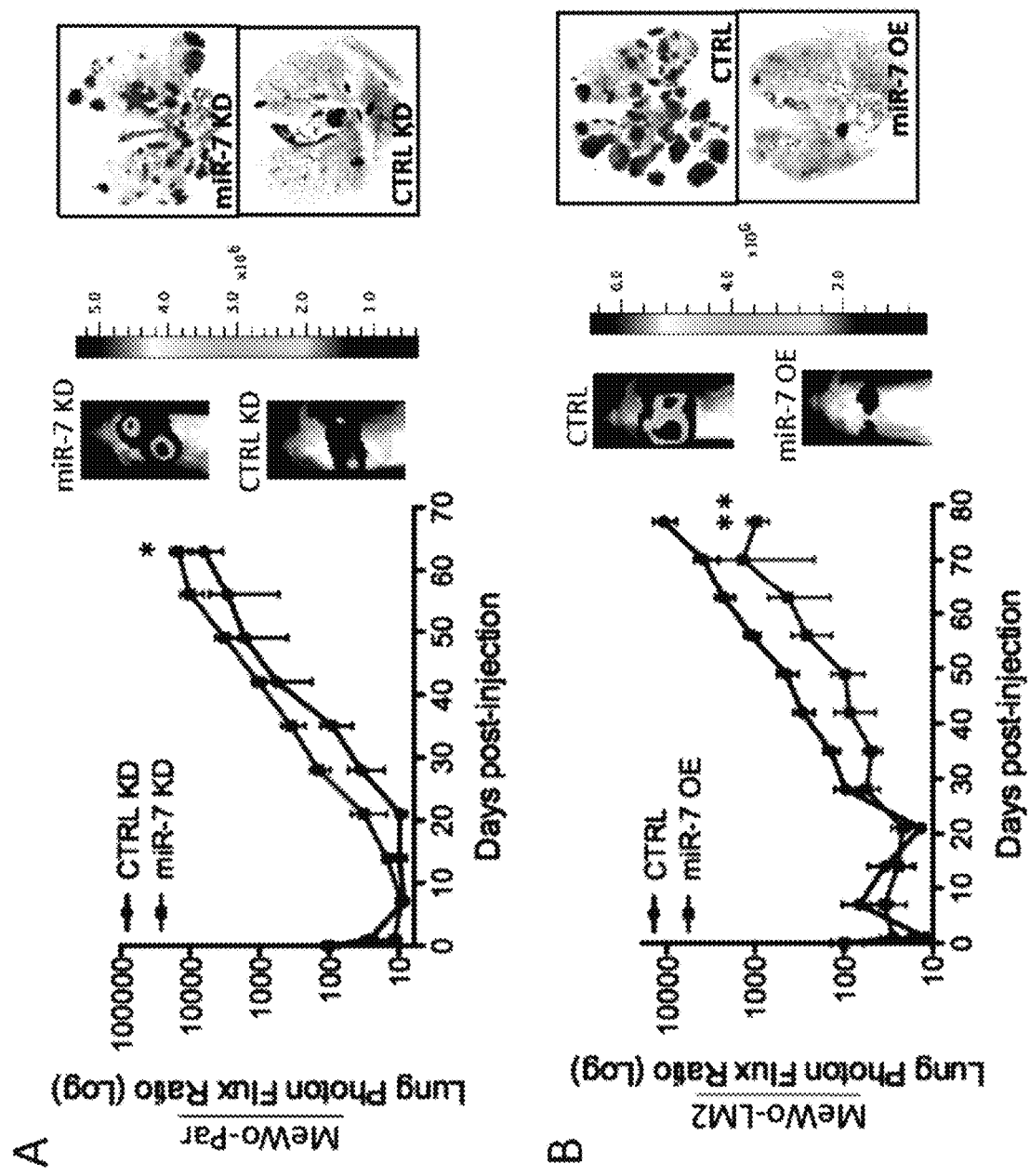

FIGS. 11A and 11B. Identification of miR-7 as an endogenous suppressor of melanoma metastasis. (11A) Bioluminescence imaging plot of lung metastatic colonization following intravenous injection of 4×104 parental MeWo cells expressing a short hairpin (miR-Zip) inhibiting miR-7 (miR-7 KD). Lungs were extracted 63 days post-injection and H&E-stained. n=5. (11B). Lung metastasis by 4×104 LM2 cells over-expressing the precursor for miR-7 or a control hairpin. Lung colonization was monitored weekly by bioluminescence imaging, and lungs were extracted at day 77 post-injection. n=5. All data are represented as mean±SEM; p-values were determined using a one-way Mann-Whitney t-test. *p<0.05, **p<0.01.

FIGS. 12A, 12B, 12C, 12D, 12E and 12F. In Vivo Selection For Highly Metastatic Human Melanoma Cell Line Derivatives and Identification of miR-199a-3p, miR-199a-5p, and miR-1908 as Metastasis-Promoter miRNAs (12A-12B) Bioluminescence imaging of lung metastasis and representative images of H&E-stained lungs corresponding to MeWo-LM2 (12A) and A375-LM3 metastatic derivatives (12B) and their respective parental cell lines. 4×104 MeWo-Par/MeWo-LM2 cells and 1×105 A375-Par/A375-LM3 cells were intravenously injected into NOD-SCID mice, and lungs were extracted and H&E stained on day 72 and day 49, respectively. n=4-5. (12C) Expression levels of miR-199a-5p, miR-199a-3p, miR-1908, and miR-214 were determined by qRT-PCR in A375-LM3 metastatic derivatives and their parental cells. n=3. (12D) Parental MeWo cells were transduced with retrovirus expressing a control hairpin or a pre-miRNA hairpin construct giving rise to miR-199a (both miR-199a-3p and miR-199a-5p), miR-1908, or miR-214. The expression levels of the target miRNAs were determined by qRT-PCR.12 n=3. (12E) H&E-stained lung sections from FIG. 1C were analyzed for the number of metastatic nodules resulting from parental MeWo cells over-expressing miR-199a, miR-1908, or a control hairpin. n=3. (12F) The number of metastatic nodules formed by LM2 cells with silenced expression of miR-199a-3p, miR-199a-5p, miR-1908, or a control sequence was analyzed in H&E-stained lung sections from FIG. 1D. n=3. All data are represented as mean±SEM.

FIGS. 13A, 13B, 13C, 13D, 13E, 13F, 13G and 13H. MiR-199a and miR-1908 Inhibit Proliferation in vitro and Selectively Promote Cell Invasion and Endothelial Recruitment (13A) 2.5×104 MeWo cells over-expressing miR-199a, miR-1908, or a control hairpin were seeded in triplicate, and viable cells were counted after 5 days. n=3. (13B) 1×105 poorly metastatic parental MeWo and highly metastatic LM2 cells were compared for their ability to invade though matrigel in a trans-well assay. n=3-4. (13C) 1×105 endothelial cells were seeded in a 6-well plate and allowed to form a monolayer. 2×105 parental MeWo cells over-expressing miR-199a, miR-1908, or a control hairpin were seeded on top of the endothelial monolayer and incubated for 30 minutes. Each monolayer was subsequently imaged, and the number of cancer cells adhering to endothelial cells was quantified. n=3. (13D) 1×106 parental MeWo cells over-expressing miR-199a, miR-1908, or a control hairpin were seeded in low adherent plates containing cell media supplemented with 0.2% methylcellulose. Following 48 hours in suspension, the numbers of dead and viable cells were quantified. n=3. (13E) 5×105 parental MeWo cells over-expressing miR-199a, miR-1908, or a control hairpin were seeded in a 6-well plate and incubated in low-serum media for 48 hours, after which the number of viable cells was quantified. n=4. (13F) Colony formation by parental MeWo cells over-expressing miR-199a, miR-1908, or a control hairpin. 50 cells were seeded in a 6-cm plate, and the number of colonies formed was quantified 2 weeks later. n=4. (13G) 5×104 parental MeWo and LM2 cells were seeded on the bottom of a well and assessed for their ability to recruit endothelial cells. n=6-8. (13H) Percentage blood vessel density, shown as a cumulative fraction plot, for metastatic nodules formed by parental MeWo cells over-expressing miR-199a, miR-1908, or a control hairpin. Lung sections from FIG. 1C were immunohistochemically double-stained for human vimentin and MECA-32, and the MECA-32 positive area relative to the total nodule area, given by human vimentin staining, was quantified using ImageJ. n=43 nodules (control); n=117 nodules (miR-199a OE); n=55 nodules (miR-1908 OE). All data are represented as mean±SEM. Scale bar, 100 μm.

FIGS. 14A, 14B, 14C, 14D, 14E, 14F, 14G. MiR-199a and miR-1908 Convergently and Cooperatively Target ApoE and DNAJA4 (14A) Venn diagram showing the integrative experimental approach that lead to the identification of putative target genes common to miR-199a-3p, miR-199a-5p, and miR-1908. Transcriptomic profiling of genes down-regulated by greater than 1.5-fold upon each miRNA over-expression were overlapped with genes up-regulated by more than 1.5-fold upon each miRNA silencing and with genes down-regulated by more than 1.5-fold in metastatic LM2 cells relative to their parental cell line. (14B, 14C, 14D) Expression levels of ApoE and DNAJA4 measured by qRT-PCR in parental MeWo cells over-expressing miR-199a, miR-1908, or a control hairpin (14B), in parental MeWo cells and their highly metastatic LM2 derivative cell line (14C), and in MeWo-LM2 cells with miR-Zip-based silencing of miR-199a-3p, miR-199a-5p, miR-1908, or a control sequence (14D). n=3. (14E) Heterologous luciferase reporter assays measuring the stability of miR-199a-3p, miR-199a-5p, or miR-1908 target site mutant ApoE and DNAJA4 3'UTR/CDS luciferase fusions in highly metastatic LM2 cells with inhibition of miR-199a-3p, miR-199a-5p, miR-1908, or a control sequence. n=3-4. (14F) MeWo-LM2 cells were transduced with retrovirus expressing a control vector or an over-expression vector giving rise to ApoE or DNAJA4. The expression levels of the target genes were determined by qRT-PCR. (14G) Expression levels of ApoE and DNAJA4, determined by qRT-PCR, in parental MeWo cells were transduced with lentiviral shRNAs targeting ApoE, DNAJA4, or a control sequence. All data are represented as mean±SEM.

FIGS. 15A, 15B, 15C, 15D, 15E, 15F, 15G, 15H, 15I and 15K. Epistatic Interactions between miR-199a/miR-1908 and ApoE/DNAJA4 (15A, 15B, 15C and 15D). MeWo-LM2 cells were transduced with lentiviral shRNAs targeting ApoE (15A, 15C), DNAJA4 (15B, 5D), or a control shRNA in the setting of miR-Zip-induced silencing of miR-1908 (15A, 15B), miR-199a-5p (15C, 15D), or a control sequence. The levels of the target genes were analyzed by qRT-PCR. (15E) Bioluminescence imaging of lung metastasis by 1×105 LM2 cells expressing a control hairpin or shRNAs (independent from the shRNAs used in FIG. 4E) targeting ApoE, DNAJA4, or a control sequence in the setting of miR-1908 inhibition. Representative bioluminescence images and H&E-stained lungs correspond to day 42 post-injection. n=5. (15F-15G) The expression levels of ApoE and DNAJA4 were analyzed by qRT-PCR in parental MeWo cells transduced with retrovirus expressing a control vector or an over-expression vector for ApoE or DNAJA4 in the setting of miR-1908 (15F) or miR-199a (15G) over-expression. (15H-15I). Parental MeWo cells over-expressing ApoE or DNAJA4 or expressing a control vector in the setting of miR-199a over-expression were examined for the invasion (15H) and endothelial recruitment (15I) phenotypes. n=7-8. (15J) Bioluminescence imaging of lung metastasis by 4×104 parental MeWo cells over-expressing ApoE or DNAJA4 or expressing a control vector in the setting of miR-1908 over-expression. Representative bioluminescence images and H&E-stained lungs correspond to day 56 post-injection n=4-8. (15K). Expression levels of ApoE and DNAJA4, determined by qRT-PCR, in highly metastatic A375-LM3 derivatives transduced with lentivirus expressing shRNA constructs targeting ApoE and DNAJA4 or a control sequence. All data are represented as mean±SEM. Scale bar, 100 μm.

FIGS. 16A, 16B, 16C, 16C, 16D, 16E, 16F, 16G, 16H and 16I. Extracellular ApoE Inhibits Melanoma Invasion and Endothelial Recruitment Phenotypes Independent of Any Effects on Cancer or Endothelial Cell Proliferation and Survival (16A) Extracellular ApoE levels were measured by ELISA in conditioned media from MeWo cells over-expressing miR-199a, miR-1908, or a control hairpin. n=3. (16B-16C) 3×104 MeWo-LM2 cells (16B) or endothelial cells (16C) were cultured in the presence of BSA (100 μM) or APOE (100 μM), and cell proliferation was monitored over time by counting the number of viable cells at each indicated time-point. n=3. (16D-16E) Survival of MeWo-LM2 cells (16D) or endothelial cells (16E) in the context of serum starvation in the presence of BSA (100 μM) or APOE (100 μM). n=3. (16F-16G) The mRNA expression levels of ApoE were assessed in parental MeWo cells transduced with lentivirus expressing a control hairpin or short hairpin constructs targeting DNAJA4 (16F) and in LM2 cells transduced with retrovirus expressing a control vector or an over-expression vector for DNAJA4 (16G). n=3. (H-I) LM2 cells transduced with retrovirus expressing a control vector or an over-expression vector for DNAJA4 were assessed for their ability to invade through matrigel (16H; n=6-8) and recruit endothelial cells in a trans-well assay (16I; n=4) in the presence of IgG (40m/mL) or 1D7 (40m/mL) ApoE neutralization antibodies. All data are represented as mean±SEM.

FIGS. 17A, 17B, 17C, 17D and 17E. ApoE Inhibits Cell Invasion and Endothelial Recruitment by Targeting Melanoma Cell LRP1 and Endothelial Cell LRP8 Receptors (17A) 1×105 LM2 cells transduced with siRNAs against LRP1 or a control sequence were analyzed for the ability to invade through matrigel. n=9-12. (17B) 1×105 MeWo-LM2 cells inhibited for miR-199a-5p or a control sequence were transfected with siRNAs targeting LRP1 or a control siRNA and examined for their matrigel invasion capacity. n=4. (17C) Representative H&E-stained lungs extracted at day 56 from NOD-SCID mice injected with MeWo-LM2 miR-1908 KD cells transduced with a control siRNA or siRNAs targeting LRP1 (See FIG. 6C). (17D-17E) 1×105 endothelial cells were transfected with siRNAs targeting LRP8 or a control sequence and allowed to trans-well migrate towards 5×104 MeWo-LM2 cells expressing a short control hairpin (17D; n=8) or 5×104 MeWo-LM2 cells inhibited for miR-199a-5p or a control sequence (17E; n=4). All data are represented as mean±SEM. Scale bar, 100 μm.

Figures 18A, 18B, 18C:
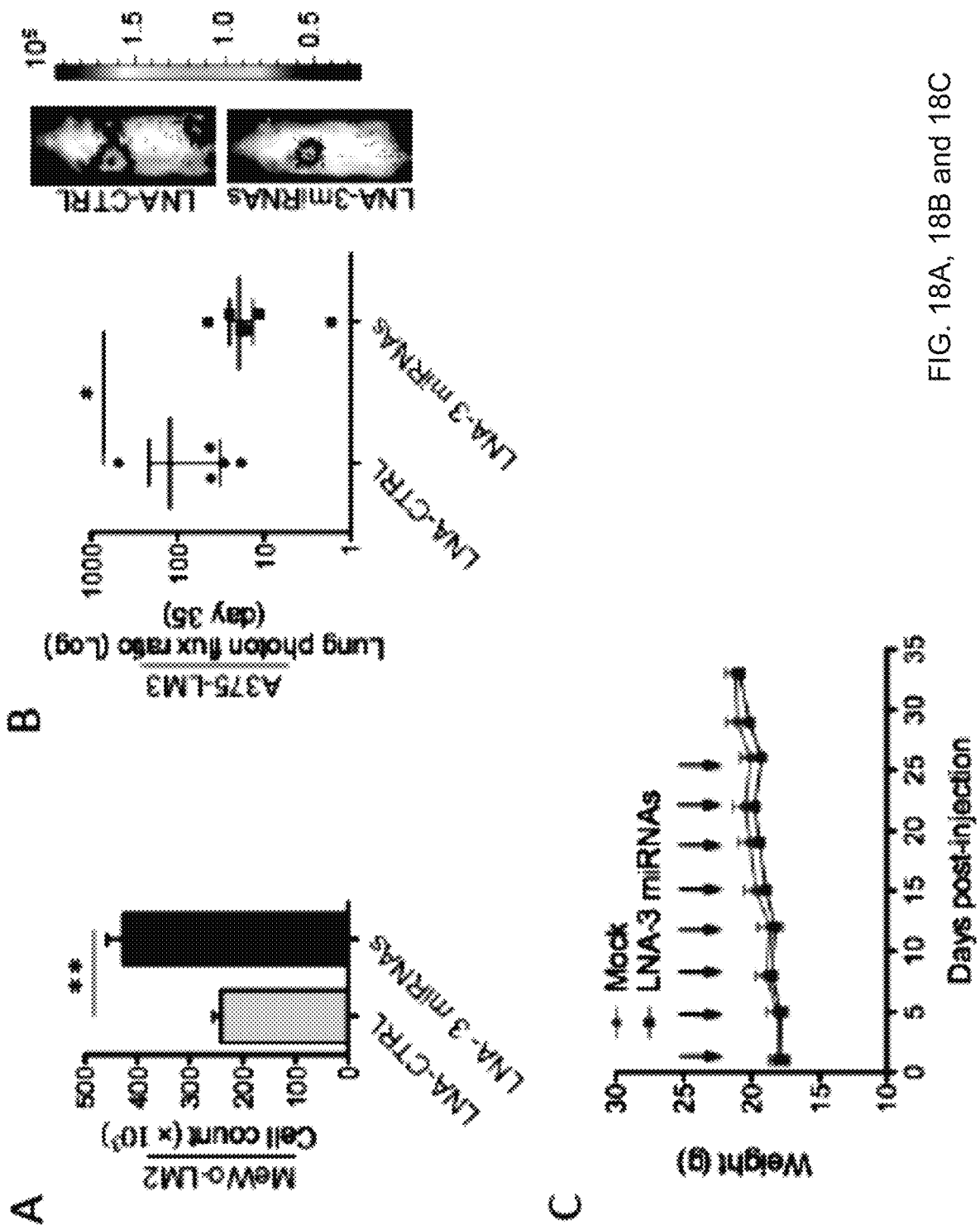

FIGS. 18A, 18B, and 18C. LNA-Based Inhibition of miR-199a and miR-1908 Suppresses Melanoma Metastasis (18A) In vitro cell proliferation by 2.5×104 MeWo-LM2 cells transduced with a control LNA or a cocktail of LNAs targeting miR-199a-3p, miR199a-5p and miR-1908. The number of viable cells was quantified after five days. n=3. (18B) Lung colonization by highly metastatic A375-LM3 derivatives transfected with a control LNA or a cocktail of LNAs targeting miR-199a-3p, miR199a-5p, and miR-1908. 48 hours post-transfection, 5×105 cells were injected intravenously into NOD-SCID mice, and lung colonization was determined by measuring bioluminescence 35 days later. n=5-6. (18C) The weight of mice treated with a cocktail of LNAs targeting the three miRNAs or a mock PBS control treatment (FIG. 7J) was monitored bi-weekly. n=5-6. All data are represented as mean±SEM.

FIGS. 19A, 19B, 19C, 19D, 19E, 19F and 19G. Activation of LXRβ Signaling Suppresses Melanoma Cell Invasion and Endothelial Recruitment. (19A) Heat-map depicting microarray-based expression levels of LXR and RXR isoforms in the NCI-60 melanoma cell line collection. The heat map for these genes is extracted from the larger nuclear hormone receptor family heat map (FIG. 20). Color-map key indicates the change in standard deviations for the expression value of each receptor relative to the average expression value of all microarray-profiled genes (>39,000 transcript variants) in each cell line. (19B) Cell invasion by 1×105 MeWo, 5×104 HT-144, 5×105 SK-Me1-2, and 5×104 SK-Mel-334.2 human melanoma cells. Cells were treated with DMSO, GW3965, T0901317, or Bexarotene at 1 μM for 72 hours and subjected to a trans-well matrigel invasion assay. n=4-8. (19C) 5×104 MeWo, HT-144, SK-Me1-2, and SK-Mel334.2 human melanoma cells were tested for their ability to recruit 1×105 endothelial cells in a trans-well migration assay, following treatment of the melanoma cells with DMSO, GW3965, T0901317, or Bexarotene at 1 μM for 72 hours. n=4-8. (19D-19E) 1×105 MeWo (19D) and 1×105 HT-144 (19E) melanoma cells expressing a control shRNA or shRNAs targeting LXRα or LXRβ were subjected to the cell invasion assay following treatment of the cells with DMSO, GW3965, or T0901317 at 1 μM for 72 hours. n=4-12. (19F-19G) 5×104 MeWo (19F) and 5×104 HT-144 (19G) cells, transduced with lentiviral shRNAs targeting LXRα or LXRβ or a control shRNA, were treated with DMSO, GW3965, or T0901317 at 1 μM for 72 hours and tested for their ability to recruit 1×105 endothelial cells in a trans-well migration assay. n=7-8. All data are represented as mean±SEM. Scale bar, 50 μm. *$p<0.05$, $p<0.01$, *$p<0.001$, ****$p<0.0001$.

FIGS. 20A, 20B, 20C, 20D, 20E, 20F and 20G. Analysis of Nuclear Hormone Receptor Expression in Melanoma and Effects of LXR and RXR Agonists on In Vitro Cell Growth, Related to FIG. 19(A-G). (20A) Heat-map showing microarray-based expression levels of all nuclear hormone receptor family members across the NCI-60 collection of melanoma lines. The expression levels of each receptor is presented as the number of standard deviations below or above the average expression levels of all genes (>39,000 transcript variants) detected by the microarray in each respective cell line. (20B) 2.5×104 MeWo, HT-144, or SK-Mel-334.2 human melanoma cells were seeded in 6-well plates and cultured in the presence of DMSO, GW3965, T0901317, or Bexarotene at 1 μM. Viable cells were counted on day 5 post-seeding. n=3-6. (20C) 2.5×104 MeWo, HT-144, or SK-Mel-334.2 cells were plated in triplicates and incubated in media containing DMSO, GW3965, T0901317, or Bexarotene at 1 μM for 5 days, after which the number of dead cells was quantified using trypan blue dead cell stain. n=3. (20D-20G) Relative expression of LXRα and LXRβ, determined by qRT-PCR, in MeWo (20D, 20E) and HT-144 (20F, 20G) human melanoma cells expressing a control shRNA or shRNAs targeting LXRα or LXRβ. All data are represented as mean±SEM.

FIGS. 21A, 21B, 21C, 21D, 21E, 21F, 21G, 21H, 21J, 21K and 21L. Therapeutic LXR Activation Inhibits Melanoma Tumor Growth. (21A-21B) Primary tumor growth by 5×104 B16F10 mouse melanoma cells subcutaneously injected into C57BL/6-WT mice. Following tumor growth to 5-10 mm3 in volume, mice were continuously fed a control chow or a chow supplemented with GW3965 (20 mg/kg/day or 100 mg/kg/day) (21A) or T0901317 (20 mg/kg/day) (21B). Representative tumor images shown correspond to tumors extracted at the final day (d12). n=10-18 (21A), 8-10 (21B). (21C-21E) Primary tumor growth by 1×106 MeWo (21C), 7.5×105 SK-Mel-334.2 (21D), and 2×106 SK-Mel-2 (21E) human melanoma cells subcutaneously injected into immunocompromised mice. Following tumor growth to 5-10 mm3 in volume, mice were randomly assigned to a control diet or a diet supplemented with GW3965 (20 mg/kg or 100 mg/kg, as indicated). Tumor images shown correspond to last day of measurements. n=6-34 (21C), 8 (21D), 5 (21E). (21F) 5×104 B16F10 cells were injected subcutaneously into C57BL/6-WT mice. Upon tumor growth to 150 mm3, mice were fed continuously with a control chow or a chow containing GW3965 (150 mg/kg), and tumor growth was measured daily. n=6-13. (21G-21I) Mouse overall survival following subcutaneous grafting of 5×104 B16F10 (21G), 1×106 MeWo (21H), and 7.5×105 SK-Mel-334.2 cells (21I) into mice that were administered a normal chow or a chow supplemented with GW3965 (100 mg/kg) upon formation of tumors measuring 5-10 mm3 in volume. n=6-9 (21F), 4-7(21H), 3-6 (21I). (21J, 21K, 21L) Tumor endothelial cell density, determined by immunohistochemical staining for the mouse endothelial cell antigen MECA-32 (21J), tumor cell proliferation, determined by staining for the proliferative marker Ki-67 (21K), and tumor cell apoptosis, determined by staining for cleaved caspase-3 (21L), in subcutaneous melanoma tumors formed by 1×106 MeWo human melanoma cells in response to mouse treatment with a control diet or a GW3965-supplemented diet (20 mg/kg) for 35 days. n=5. Tumor volume was calculated as (small diameter)2×(large diameter)/2. All data are represented as mean±SEM. Scale bars, 5 mm (21A, 21B, 21C, 21D), 50 µm (21J, 21K), 25 µm (21L).

Figures 21A, 21B, 21C, 21D, 21E, 21F, 21G, 21H, 21I:
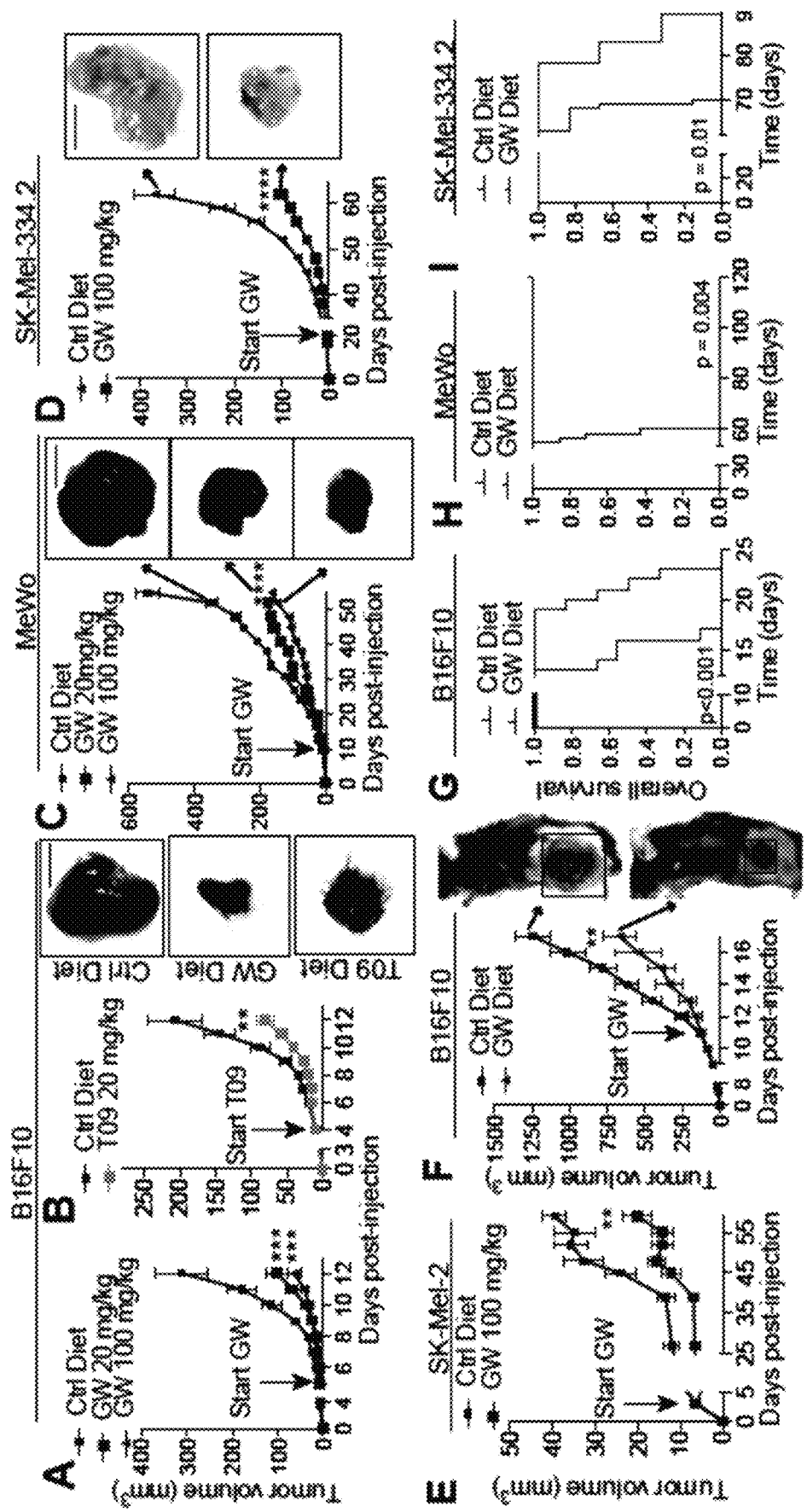
Figures 21J, 21K, 21L:
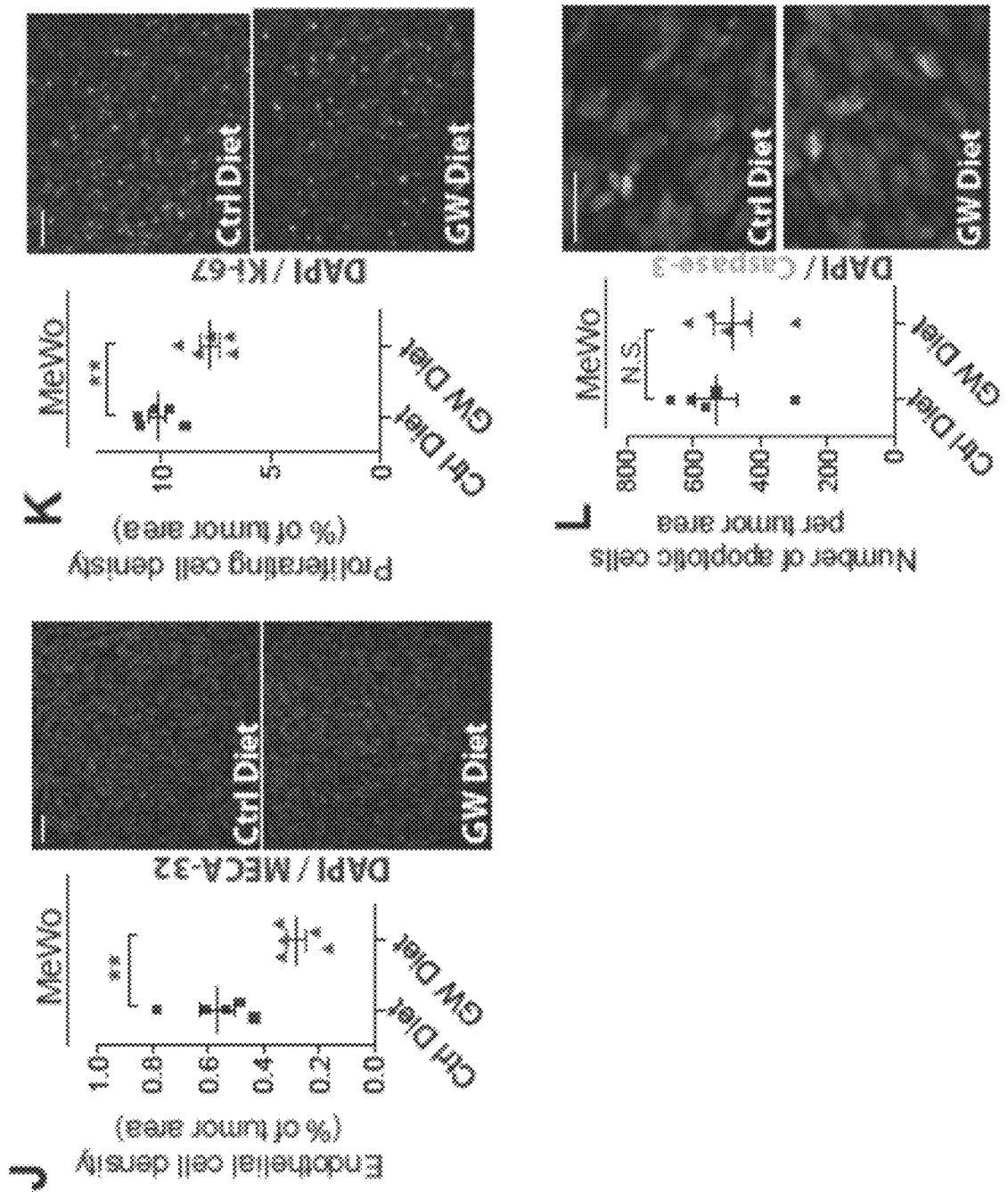
Figure 22:
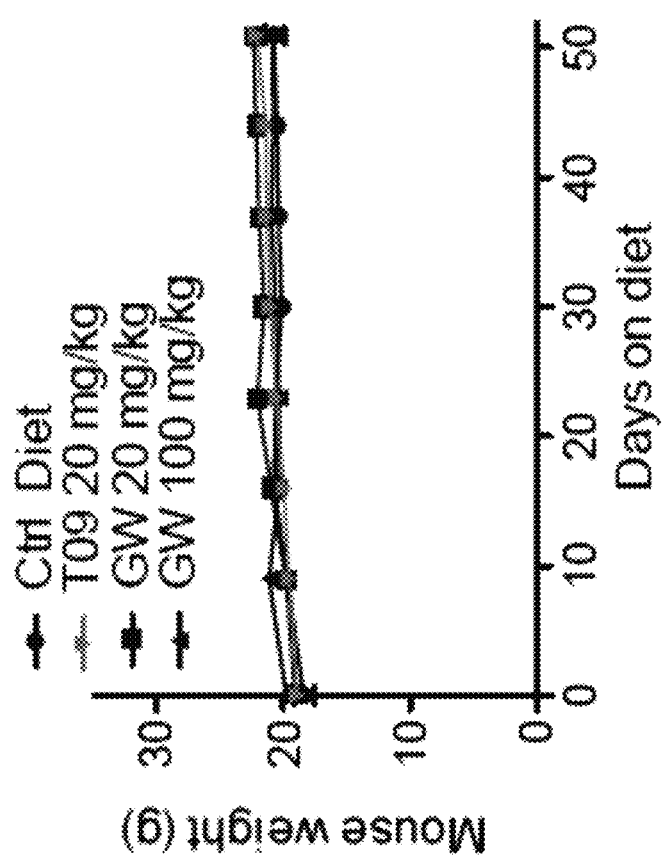

FIG. 22. LXRβ Agonism Suppresses Melanoma Tumor Growth, Related to FIG. 21(A-E). Weight measurements of mice fed a control diet or a diet supplemented with GW3965 (20 mg/kg/day or 100 mg/kg/day) or T0901317 (20 mg/kg) for 65 days. n=5-6.

FIGS. 23A, 23B, 23C, 23D, 23E, 23F, 23G, 23H, 23I, 23J and 23K. LXR Agonism Suppresses Melanoma Metastasis to the Lung and Brain. (23A) MeWo cells were pre-treated with DMSO or GW3965 (1 µM) for 48 hours and 4×104 cells were intravenously injected via the tail-vein into NOD Scid mice. Lung colonization was monitored by weekly bioluminescence imaging. Representative H&E-stained lungs correspond to the final day (d70) are shown. n=4-5. (23B-23C) Bioluminescence imaging of lung metastasis by 4×104 MeWo cells intravenously injected into NOD Scid mice that were fed a control chow or a chow containing GW3965 (20 mg/kg) or T0901317 (20 mg/kg) starting 10 days prior to cancer cell injection. Representative H&E-stained lungs correspond to final imaging day n=5-6. (23B-23C) Bioluminescence imaging of lung metastasis by 4×104 MeWo cells intravenously injected into NOD Scid mice that were fed a control chow or a chow containing GW3965 (20 mg/kg) or T0901317 (20 mg/kg) starting 10 days prior to cancer cell injection. Representative H&E-stained lungs correspond to final imaging day n=5-6. (23F) Systemic and brain photon flux following intracardiac injection of 1×105 MeWo brain metastatic derivative cells into athymic nude mice that were fed a control diet or a GW3965-supplemented diet (100 mg/kg) starting on day 0 post-injection. n=7. (23G) Schematic of experimental orthotopic metastasis model used to assess the ability of GW3965 treatment to suppress lung metastasis post-tumor excision. (23H) Ex-vivo lung photon flux, determined by bioluminescence imaging, in NOD Scid mice that were administered a control chow or a chow containing GW3965 (100 mg/kg) for 1 month following the excision of size-matched (~300-mm3 in volume) subcutaneous melanoma tumors formed by 1×106 MeWo melanoma cells. Representative lungs stained for human vimentin are also shown. n=7-9. (23I) 4×104 MeWo cells were intravenously injected into NOD Scid mice. Following initiation of metastases, detected by bioluminescence imaging on d42, mice were administered a control diet or a GW3965 diet (100 mg/kg) as indicated, and lung colonization progression was measured weekly. n=6. (23J) Number of macroscopic metastatic nodules in H&E-stained lungs extracted at the final day (d77) from NOD Scid mice administered a control diet or a diet supplemented with GW3965 (100 mg/kg), as indicated in (23I). n=4-5. (23K) Overall mouse survival following intravenous injection of 4×104 MeWo cells into NOD-Scid mice that were continuously fed a control chow or a GW3965-supplemented chow (20 mg/kg) starting 10 days prior to cancer cell injection. n=5-6. All data are represented as mean±SEM.

FIGS. 24A, 24B, 24C, 24D, 24E and 24F. Suppression of Genetically-Driven Melanoma Progression by LXR Activation Therapy. (24A) Overall survival of Tyr::CreER; BrafV600E/+; Ptenlox/+ C57BL/6 mice following general melanoma induction by intraperitoneal administration of 4-HT (25 mg/kg) on three consecutive days. After the first 4-HT injection, mice were randomly assigned to a control diet or a diet supplemented with GW3965 (100 mg/kg). n=10-11. (24B) Melanoma tumor burden, expressed as the percentage of dorsal skin area, measured on day 35 in Tyr::CreER; BrafV600E/+; Ptenlox/lox mice administered a control chow or a chow supplemented with GW3965 (100 mg/kg) upon melanoma induction as described in (24A). n=4-5. (24C) Number of macroscopic metastatic nodules to the salivary gland lymph nodes detected post-mortem in Tyr::CreER; BrafV600E/+; Ptenlox/lox mice that were fed a control chow or a chow containing GW3965 (100 mg/kg) following global induction of melanoma progression as described in (24A). n=7-8. (24D) Tumor growth following subcutaneous injection of 1×105 BrafV600E/+; Pten-/-; CDKN2A-/- primary melanoma cells into syngeneic C57BL/6-WT mice. Upon tumor growth to 5-10 mm3 in volume, mice were fed with a control chow or a chow supplemented with GW3965 (100 mg/kg). n=16-18. (24E) Overall survival of C57BL/6-WT mice subcutaneously injected with 1×105 BrafV600E/+; Pten-/-; CDKN2A-/- melanoma cells and treated with a GW3965 diet (100 mg/kg) or a control diet following tumor growth to 5-10 mm3 in volume. n=7-8. (24F) Lung colonization by 1×105 BrafV600E/+; Pten-/-; CDKN2A-/- primary melanoma cells intravenously injected into C57BL/6-WT mice. Immediately following cancer cell injection, mice were randomly assigned to a control diet or a GW3965-supplemented diet (100 mg/kg) for the remainder of the experiment. n=14-15. All data are represented as mean±SEM. Scale bar, 2 mm (24B), 5 mm (24D).

Figures 24A, 24B, 24C, 24D, 24E, 24F:
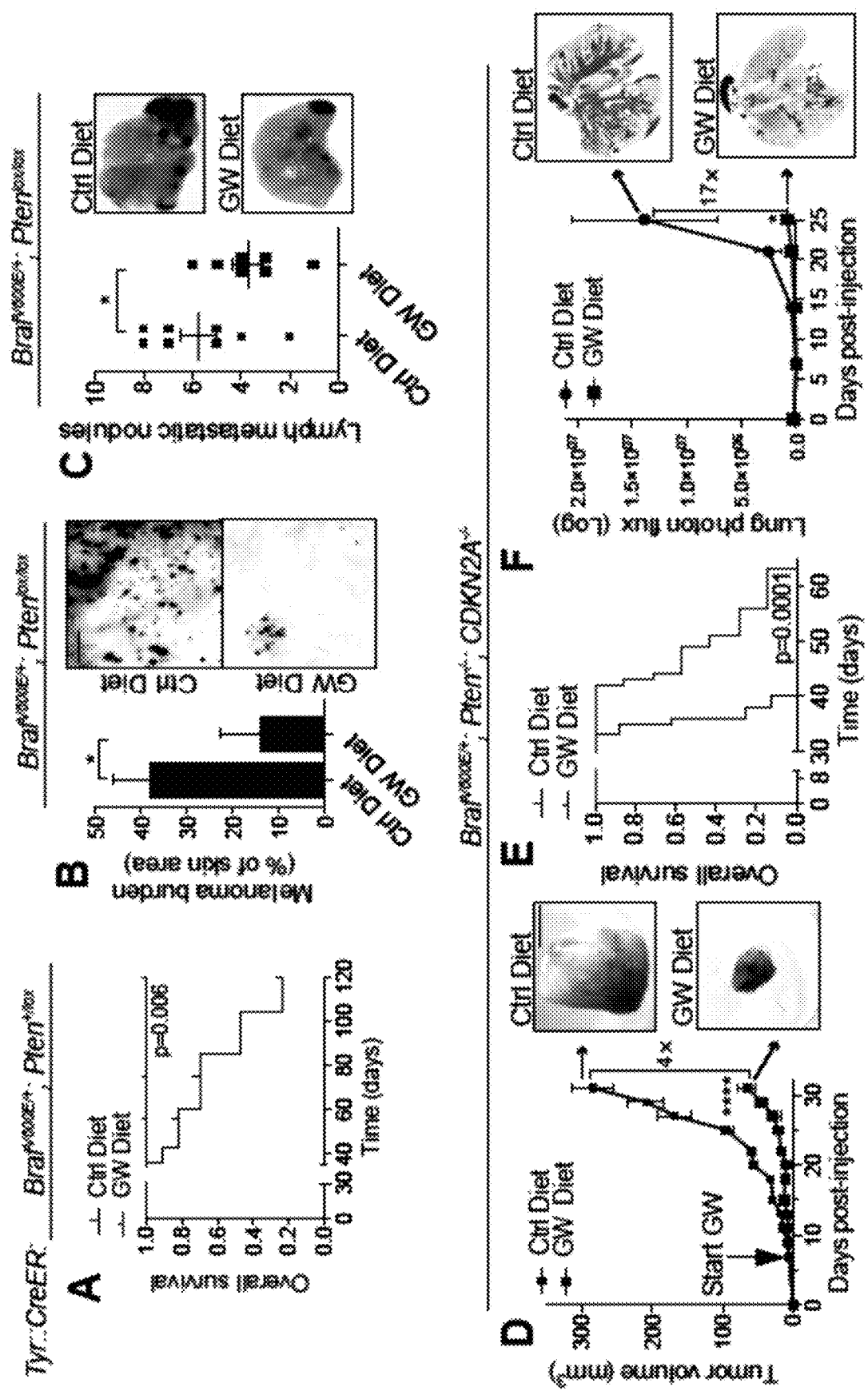
Figures 25A, 25B:
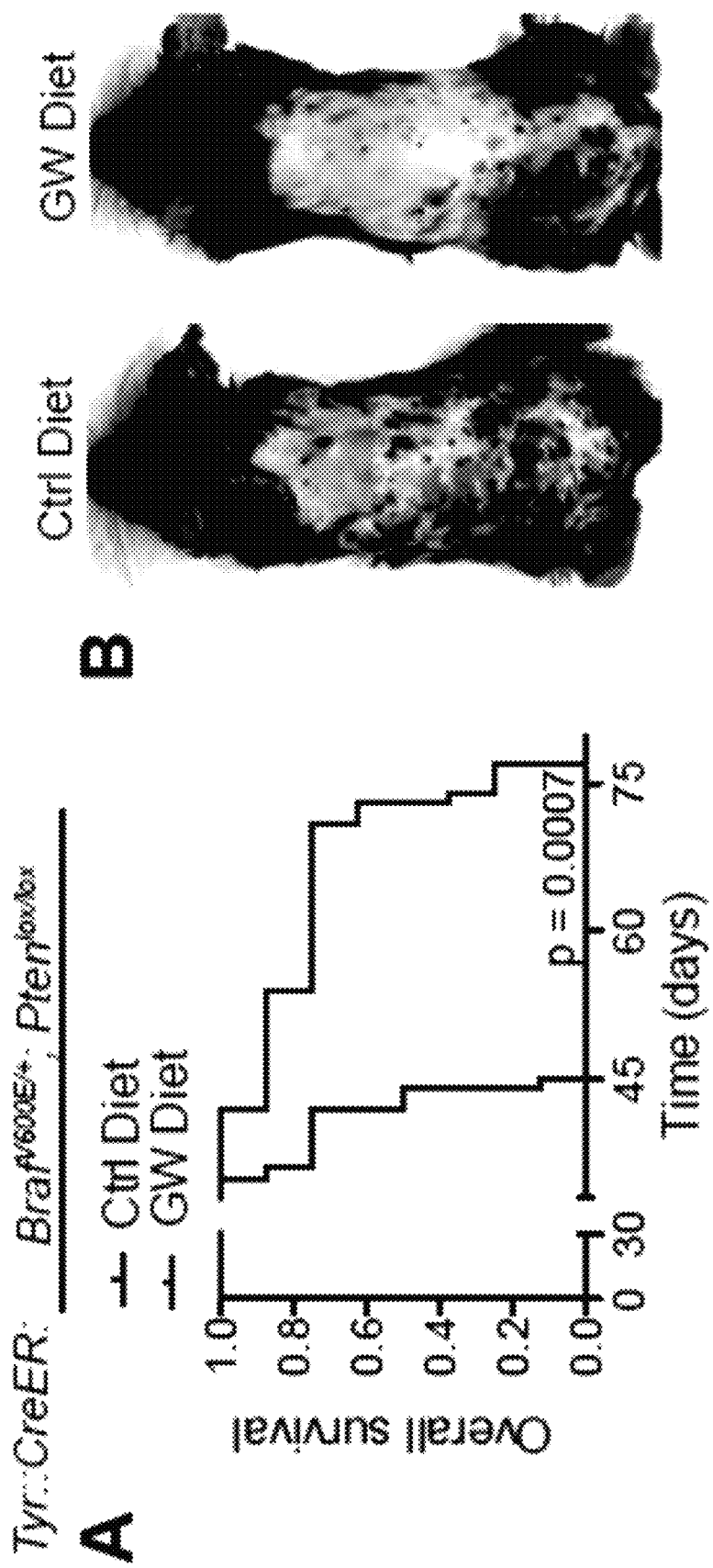

FIGS. 25A and 25B. LXR-Mediated Suppression of Melanoma Progression in a Genetically-Driven Melanoma Mouse Model, Related to FIG. 24(A-C). (25A) Overall survival of Tyr::CreER; BrafV600E/+; Ptenlox/lox C57BL/6 mice following general melanoma induction by intraperitoneal administration of 4-HT (25 mg/kg) on three consecutive days. After the first 4-HT injection, mice were randomly assigned to a control diet or a diet supplemented with GW3965 (100 mg/kg). n=7. (25B) Representative images of Tyr::CreER; BrafV600E/+; Ptenlox/lox C57BL/6 mice fed a control diet of GW3965-supplemented diet (100 mg/kg) taken 43 days following melanoma induction by intraperitoneal 4-HT administration.

FIG. 26. A List of the 50 most upregulated genes in MeWo human melanoma cells in response to GW3965 treatment.

FIGS. 27A, 27B, 27C, 27D, 27E, 27F, 27G, 27H, 27I, 27J and 27K. LXRβ Activation Induces ApoE Expression in Melanoma Cells; ApoE mediates LXRβ-Dependent Suppression of In Vitro Melanoma Progression Phenotypes. (27A, 27B, 27C) MeWo (27A), HT-144 (27B), and WM-266-4 (27C) human melanoma cells were treated with GW3965 or T0901317 at the indicated concentrations for 48 hours, and the expression levels of ApoE were analysed by qRT-PCR. n=3. (27D) Extracellular ApoE protein levels, quantified by ELISA, in serum-free conditioned media collected from HT-144 human melanoma cells treated with DMSO, GW3965, or T0901317 at 1 µM for 72 hours. n=3-4. (27E-27F) 5×10⁴ HT-144 cells, treated with DMSO, GW3965, or T0901317 at 1 µM for 72 hours, were tested for the cell invasion (27E) and endothelial recruitment phenotypes (27F) in the presence of an ApoE neutralization antibody (1D7) or an IgG control antibody added at 40 µg/mL to each trans-well at the start of the assay. n=4. (27G-27H) Cell invasion (27G) and endothelial recruitment (27F) by 1×10⁵ and 5×10⁴ MeWo cells, respectively, expressing a control shRNA or an shRNA targeting ApoE and treated with DMSO or GW3965 at 1 µM for 72 hours prior to each assay. n=7-8. (27I-27J) Relative ApoE expression, quantified by qRT-PCR, in MeWo (I) and HT-144 (27J) cells transduced with a control shRNA or shRNAs targeting LXRα or LXRβ and subsequently treated with DMSO, GW3965, or T0901317 at 1 µM for 48 hours. n=3-9. (27K) Extracellular ApoE protein levels, measured by ELISA, in serum-free conditioned media harvested from HT-144 cells transduced with a control shRNA or an shRNA targeting LXRα or LXRβ and treated with DMSO or GW3965 at 1 µM for 72 hours. n=3. All data are represented as mean±SEM. Scale bar, 50 µm.

FIGS. 28A, 28B, 28C, 28D, 28E, 28F, 28G, 28H and 28I. LXRβ Activation Suppresses Melanoma Invasion and Endothelial Recruitment by Transcriptionally Enhancing Melanoma-Cell ApoE Expression. (28A) Luciferase activity driven off the ApoE promoter fused downstream of multi-enhancer element 1 (ME.1) or multi-enhancer element 2 (ME.2) sequences and transfected into MeWo cells treated with DMSO, GW3965, or T0901317 at 1 µM for 24 hours. n=4-8. (28B) Extracellular ApoE protein levels were quantified by ELISA in serum-free conditioned media harvested from MeWo cells treated with DMSO, GW3965, or T0901317 at 1 µM for 72 hours. n=3-4. (28C) Cell invasion by 1×10⁵ MeWo cells pre-treated with DMSO, GW3965, or T0901317 at 1 µM for 72 hours. At the start of the assay, an ApoE neutralization antibody (1D7) or an IgG control antibody was added at 40 µg/mL to each trans-well, as indicated. n=7-8. (28D) 5×10⁴ MeWo cells, pre-treated with DMSO, GW3965, or T0901317 at 1 µM for 72 hours, were tested for their ability to recruit 1×10⁵ endothelial cells in the presence of 1D7 or IgG antibodies at 40 µg/mL. n=6-8. (28E) Extracellular ApoE protein levels, quantified by ELISA, in serum-free conditioned media from SK-Mel-334.2 primary human melanoma cells treated with DMSO or GW3965 at 1 µM for 72 hours. n=4. (28F-28G) 5×10⁴ SK-Mel-334.2 cells, pre-treated with GW3965 at 1 µM for 72 hours, were subjected to the cell invasion (28F) and endothelial recruitment (28G) assays in the presence of 1D7 or IgG antibodies at 40 µg/mL. n=7-8. (28H) Activity of the ApoE promoter fused to ME.1 or ME.2 enhancer elements was determined through measuring luciferase reporter activity in MeWo cells expressing a control shRNA or shRNAs targeting LXRα or LXRβ in the presence of DMSO or GW3965 (1 µM) for 24 hours. n=3-8. (28I) Extracellular ApoE protein levels, quantified by ELISA, were assessed in serum-free conditioned media collected from human MeWo melanoma cells expressing a control shRNA or shRNAs targeting LXRα or LXRβ in response to treatment with GW3965 or T0901317 (1 µM) for 72 hours. n=3-8. All data are represented as mean±SEM. Scale bar, 50 µm.

FIGS. 29A, 29B, 29C, 29D, 29E, 29F, 29G, 29H, 29I, 29J and 29K. Therapeutic Delivery of LXR Agonists Upregulates Melanoma-Derived and Systemic ApoE Expression. (29A-29B) ApoE expression levels, quantified by qRT-PCR, in subcutaneous tumors formed by B16F10 mouse melanoma cells injected into C57BL/6 mice. After 5-mm3 tumor formation, mice were fed a control diet or diet containing GW3965 (20 mg/kg) (29A) or T0901317 (20 mg/kg) (29B) for 7 days. n=3-4. (29C, 29D, 29E) ApoE transcript expression in primary tumors (29C), lung metastases (29D), and brain metastases (29E) formed by MeWo human melanoma cells grafted onto NOD Scid mice that were administered control chow or chow supplemented with GW3965 (20 mg/kg). ApoE levels were assessed on day 35 (29C), day 153 (29D), and day 34 (29E) post-injection of the cancer cells. n=3-5. (29F) Relative expression levels of LXRα, LXRβ, and ApoE were determined by qRT-PCR in B16F10 mouse melanoma cells expressing a control hairpin or an shRNA targeting mouse LXRα (sh_mLXRα), mouse LXRβ (sh_mLXRβ), or mouse ApoE (sh_mApoE). (29G-29H) ApoE (29G) and ABCA1 (29H) mRNA levels, measured by qRT-PCR, in B16F10 cells expressing a control shRNA or shRNAs targeting mouse LXRβ or mouse ApoE. The cells were treated with DMSO or GW3965 at 5 µM for 48 hours. n=3. (29I) ABCA1 mRNA levels, measured by qRT-PCR, in systemic white blood cells extracted from LXRα -/- or LXRβ -/- mice fed a control diet or a GW3965-supplemented diet (20 mg/kg) for 10 days. n=3-4. (29J) Relative expression of ApoE mRNA, expressed as the frequency of SAGE tags, in mouse skin and lung tissues was determined using the public mSAGE Expression Matrix database available through the NCI-funded Cancer Genome Anatomy Project (CGAP). (29K) Relative expression of ApoE mRNA, determined by qRT-PCR, in MeWo melanoma cells dissociated from lung metastatic nodules (LM2) or primary tumors relative to control unselected MeWo parental cells. n=3.

FIGS. 30A, 30B, 30C, 30D, 30E, 30F, 30G, 30H and 30I. LXRβ Agonism Suppresses Melanoma Tumor Growth and Metastasis by Inducing Melanoma-Derived and Systemic ApoE Expression. (30A) Western blot measurements of ApoE protein levels in adipose, lung, and brain tissue lysates extracted from wild-type mice fed with a control chow or a chow supplemented with GW3965 (20 mg/kg) or T0901317 (20 mg/kg) for 10 days. (30B) Quantification of ApoE protein expression based on western blots shown in (30A). Total tubulin was used as an endogenous control for normalization. n=3-5. (30C) Expression levels of ApoE, determined by qRT-PCR, in systemic white blood cells from mice fed a control diet or a diet supplemented with GW3965 or T0901317 at 20 mg/kg for 10 days. n=3-6. (30D) B16F10 control cells or B16F10 cells expressing shRNAs targeting mouse LXRα (sh_mLXRα) or mouse LXRβ (sh_mLXRβ) were subcutaneously injected into C57BL/6-WT, LXRα-/-, or LXRβ-/- mice. Once the tumors reached 5-10 mm3 in volume, mice were fed a control diet or a diet supplemented with GW3965 (20 mg/kg) for 7 days, after which final tumor volume was measured. Representative tumor images extracted at the end point are shown in the right panel. n=6-18. (30E) ApoE transcript levels, quantified by qRT-PCR, in systemic white blood cells extracted from LXRα−/− or LXRβ−/− mice fed a control diet or a GW3965-supplemented diet (20 mg/kg) for 10 days. n=3-5. (30F) Subcutaneous tumor growth by 5×104 B16F10 control cells or B16F10 cells expressing an shRNA targeting mouse ApoE (sh_mApoE) in C57BL/6-WT or ApoE−/− mice. Following the formation of tumors measuring 5-10 mm3 in volume, mice were fed a control diet or a diet supplemented with GW3965 (20 mg/kg) for 7 days, and final tumor volume was quantified. Representative images of tumors extracted at the final day of measurement (d12) are shown on the right. n=8-18. (30G) Lung colonization by 5×104 B16F10 cells transduced with a control shRNA or sh_mApoE and intravenously injected into C57BL/6-WT or ApoE−/− mice. Starting 10 days prior to cancer cell injection, mice were assigned to a control diet or a GW3965-supplemented diet (20 mg/kg) treatment. Lung metastasis was quantified on d22 by bioluminescence imaging. Representative lungs extracted at the end point (d22) are shown in the right panel. n=5-10. (30H) ApoE protein expression, determined by blinded immunohistochemical analysis, in non-metastatic (n=39) and metastatic (n=34) primary melanoma skin lesion samples obtained from patients at MSKCC. The fraction of ApoE-positively staining cell area was quantified as a percentage of total tumor area. (30I) Kaplan-Meier curves for the MSKCC cohort (n=71) depicting the metastasis-free survival of patients as a function of ApoE protein expression in patients' primary melanoma lesions. Melanomas that had ApoE levels above the median of the population were classified as ApoE-positive (pos), whereas tumors with ApoE expression below the median were classified as ApoE-negative (neg). All data are represented as mean±SEM. Scale bar, 5 mm (30D and 30F), 100 μm (30H).

FIGS. 31A, 31B, 31C, 31D, 31E, 31F, 31G, 31H and 31I. Activation of LXRβ Suppresses the In Vivo Growth of Melanoma Lines Resistant to Dacarbazine and Vemurafenib. (31A) In vitro cell growth by 2.5×104 B16F10 parental cells and in vitro-derived B16F10 DTIC-resistant cells in response to varying doses of dacarbazine (DTIC) added to the cell media for 4 days. n=3. (31B-31D) Tumor growth by 5×104 DTIC-sensitive B16F10 parental cells (31B) or 5×104 DTIC-resistant B16F10 cells (31C) subcutaneously injected into C57BL/6-WT mice. Following tumor growth to 5-10 mm3 in volume, mice were treated with dacarbazine (50 mg/kg, i.p., daily) or a control vehicle and randomly assigned to regular chow or a chow supplemented with GW3965 (100 mg/kg). Final day tumor volume measurements are shown in (31D). n=8-16 (31B), 7-8 (31C). (31E-31F) Tumor growth by DTIC-sensitive MeWo parental cells and in vivo-derived DTIC-resistant MeWo human melanoma cells in response to DTIC or GW3965 treatments. 5×105 cells were subcutaneously injected into NOD Scid gamma mice. After formation of tumors measuring 5-10 mm3 in volume, mice were blindedly assigned to a control treatment, a DTIC treatment (50 mg/kg, i.p., administered daily in 5-day cycles with 2-day off-treatment intervals), or a GW3965-supplemented diet treatment (100 mg/kg). Final day tumor measurements are show in (31F). n=6-8. (31G) Tumor growth by 2×106 SK-Mel-239 vemurafenib-resistant clone cells subcutaneously injected into NOD Scid gamma mice that were assigned to a control diet or a diet supplemented with GW3965 (100 mg/kg) subsequent to growth of tumors to 5-10 mm3 in volume. n=7-8. (31H) Overall mouse survival post-grafting of 2×106 SK-Mel-239 vemurafenib-resistant cells. Upon the growth of tumors to 5-10 mm3 in volume, mice were continuously fed a control diet or a diet supplemented with GW3965 (100 mg/kg). n=7. (31I) Experimentally derived model depicting the engagement of systemic and melanoma-autonomous ApoE by LXRβ activation therapy in mediating the suppression of melanoma progression phenotypes. Extracellular ApoE suppresses melanoma metastasis by coordinately inhibiting melanoma cell invasion and non-cell-autonomous endothelial recruitment through targeting melanoma-cell LRP1 and endothelial-cell LRP8 receptors, respectively. All data are represented as mean±SEM. Scale bar, 5 mm.

Figure 32:
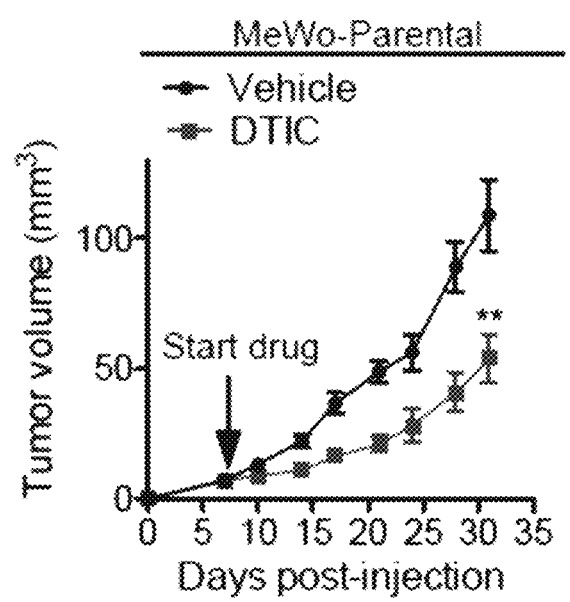
Figures 33A, 33B, 33C, 33D, 33E, 33F, 33G, 33H, 33I:
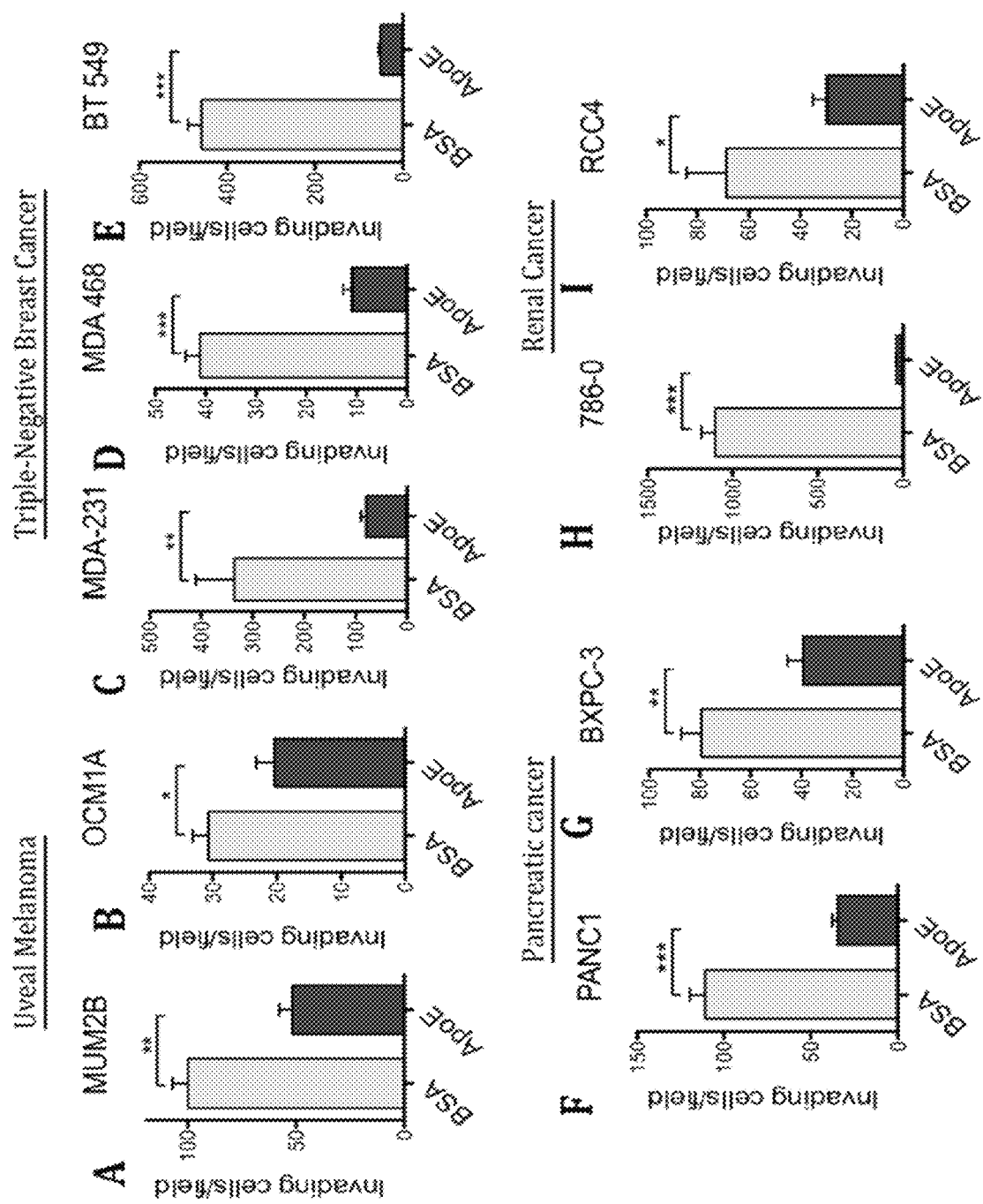

FIG. 32. Dacarbazine-Induced Suppression of Tumor Growth by Human Melanoma Cells. Tumor growth by 5×105 DTIC-sensitive MeWo parental cells subcutaneously injected into Nod SCID gamma mice. When tumors reached 5-10 mm3 volume, mice were treated with a control vehicle or DTIC (50 mg/kg, i.p., administered daily in 5-day cycles with 2-day off-treatment intervals), and tumor volume was measured twice a week. n=6.

FIGS. 33A, 33B, 33C, 33D, 33E, 33F, 33G, 33H and I. ApoE-mediated suppression of cell invasion across multiple cancer types. (33A-33B) 5×104 MUM2B and OCM1 human uveal melanoma cells, (33C-33E) 5×104 MDA-231, MDA-468, and BT 549 human triple-negative breast cancer cells, (33F-33G) 5×104 PANC1 and BXPC-3 human pancreatic cancer cells, and (33H-33I) 5×104 786-00 and RCC4 human renal cancer cells were tested for their ability to invade through matrigel-coated trans-well inserts in vitro. BSA or recombinant ApoE were added to the cell media at 100m/mL at the start of the assay. n=4. All data are represented as mean±SEM; *p<0.05, p<0.01, *p<0.001.

FIGS. 34A, 34B, 34C and 34D. Effects of LXR agonists LXR-623, WO-2007-002563 Ex. 19, WO-2010-0138598 Ex. 9, and SB742881 on ApoE expression in human melanoma cells. (34A-34D) MeWo human melanoma cells were treated with DMSO or the LXR agonists LXR-623 (34A), WO-2007-002563 (34B), WO-2010-0138598 (34C), or SB742881 (34D) at 500 nM, 1 μM, or 2 μM for 48 hours. The expression levels of ApoE were subsequently quantified by qRT-PCR. n=3. All data are represented as mean±SEM. *p<0.05, **p<0.01.

Figures 35A, 35B, 35C:
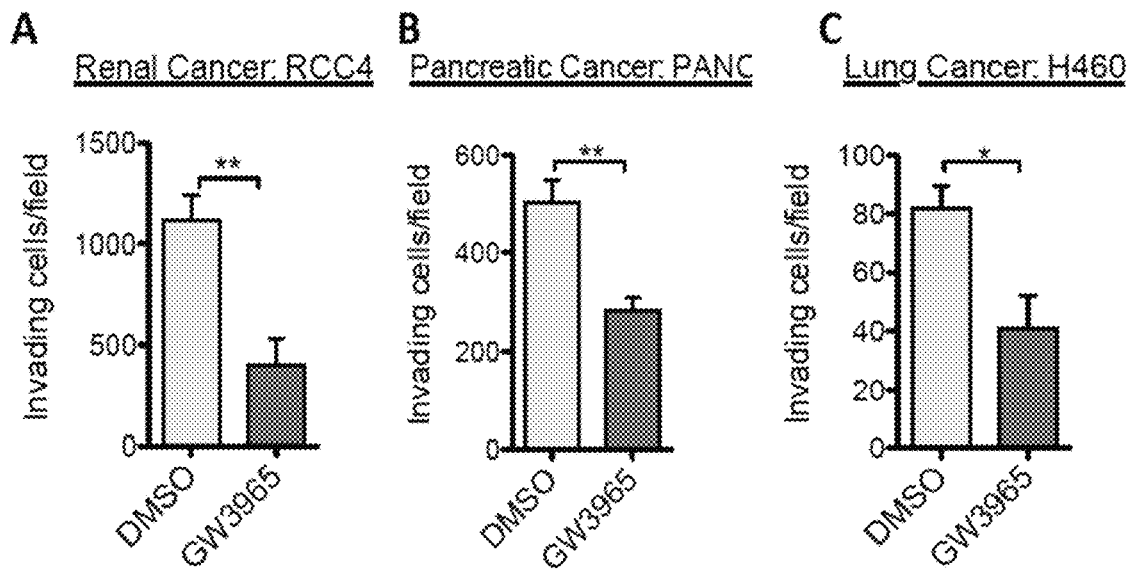

FIGS. 35A, 35B and 35C. Treatment with the LXR agonist GW3965 inhibits In Vitro tumor cell invasion of renal cancer, pancreatic cancer, and lung cancer. (35A, 35B, 35C) Trans-well matrigel invasion by 5×104 RCC human renal cancer cells (35A), 5×104 PANC1 human pancreatic cancer cells (35B), and 5×104 H460 human lung cancer cells (35C) that were treated with DMSO or GW3965 at 1 μM for 72 hours prior to the assay. n=4. All data are represented as mean±SEM. *p<0.05, **p<0.01.

Figure 36:
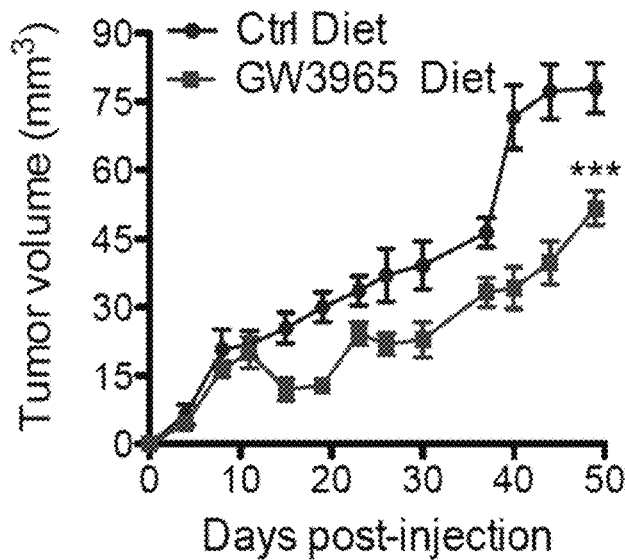

FIG. 36. Treatment with the LXR agonist GW3965 inhibits breast cancer tumor growth In Vivo. Primary tumor growth by 2×106 MDA-468 human breast cancer cells injected into the mammary fat pads of NOD Scid gamma mice. Two days prior to cancer cell injection, the mice were assigned to a control diet treatment or a diet supplemented with GW3965 (75 mg/kg) and maintained on the corresponding diet throughout the experiment. n=8. All data are represented as mean±SEM. ***p<0.001.

Figures 37A, 37B:
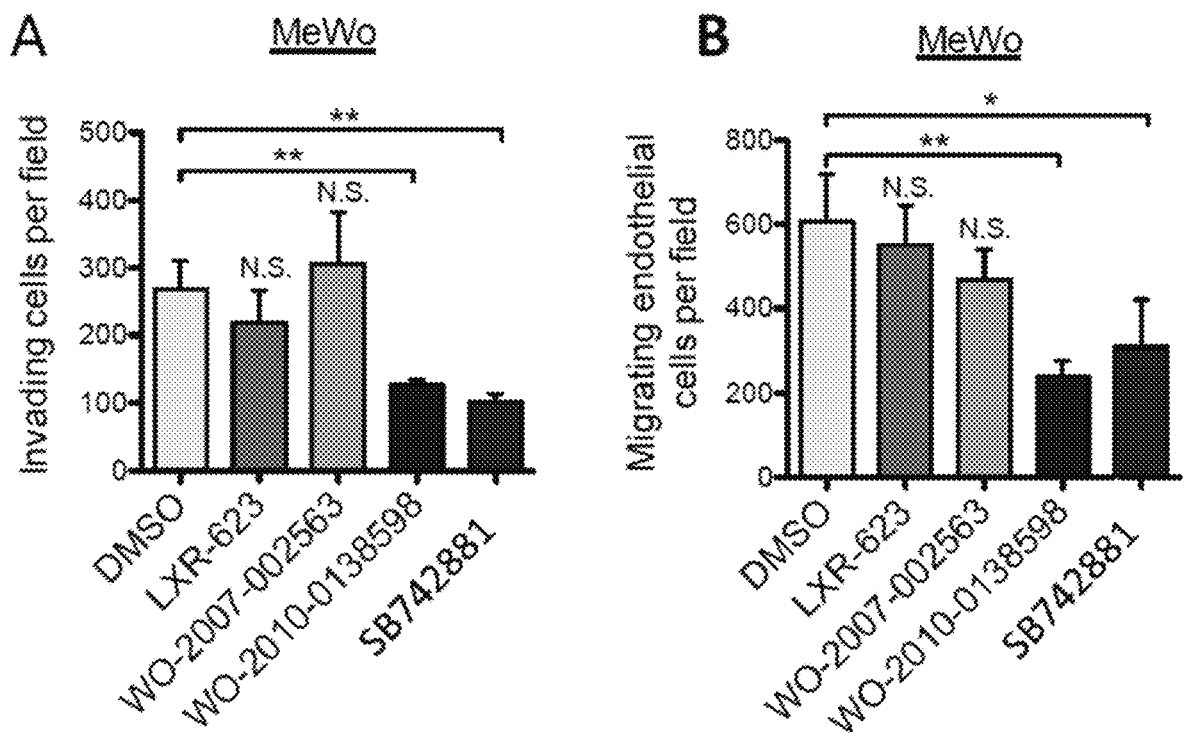
Figures 38A, 38B, 38C, 38D:
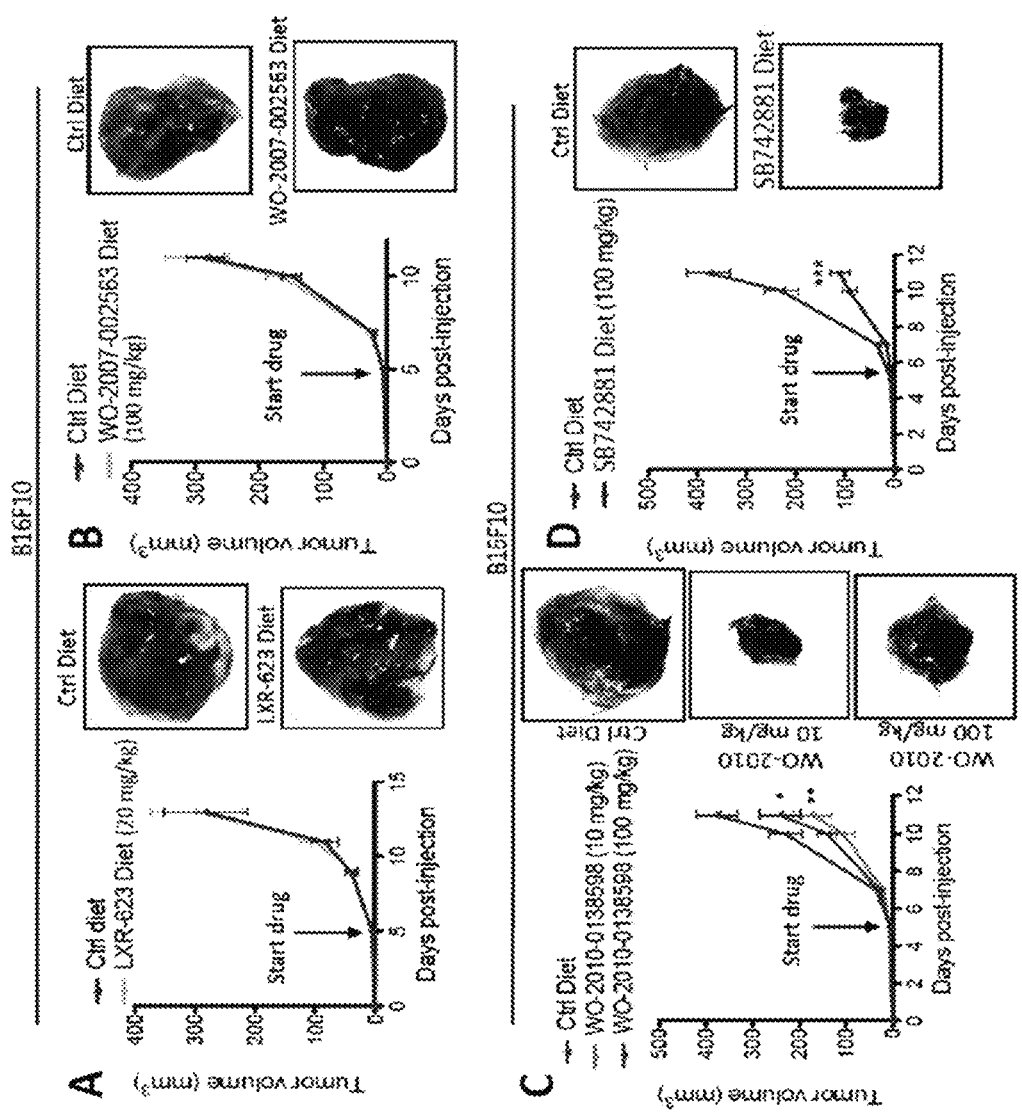

FIGS. 37A and 37B. Effects of LXR agonists LXR-623, WO-2007-002563 Ex. 19, WO-2010-0138598 Ex. 9, and SB742881 on in vitro melanoma progression phenotypes. (37A) Cell invasion by 1×105 MeWo human melanoma cells pre-treated with DMSO, LXR-623, WO-2007-002563

Ex. 19, WO-2010-0138598 Ex. 9, or SB742881 at 1 µM each for 72 hours. The number of cells invading into the basal side of matrigel-coated trans-well inserts was quantified. n=5. (37B) Endothelial recruitment by 5×104 MeWo cells pre-treated with DMSO, LXR-623, WO-2007-002563 Ex. 19, WO-2010-0138598 Ex.9, or SB742881 at 1 µM each for 72 hours. Cancer cells were seeded at the bottom of a 24-well plate. Endothelial cells were seeded in a trans-well insert fitted into each well and allowed to migrate towards the cancer cells. The number of endothelial cells migrating to the basal side of each trans-well insert was quantified. n=4-5. All data are represented as mean±SEM. *p<0.05, **p<0.01.

FIGS. 38A, 38B, 38C and 38D. Effects of LXR agonists LXR-623, WO-2007-002563 Ex. 19, WO-2010-0138598 Ex. 9, and SB742881 on in vivo tumor growth. (38A, 38B, 38C, 38D) Tumor growth by 5×104 B16F10 mouse melanoma cells subcutaneously injected into 7-week-old C57BL/6 mice. After tumors reached 5-10 mm3 in volume, the mice were randomly assigned to a control diet treatment, an LXR-623-supplemented diet treatment at 20 mg/kg/day (38A) a WO-2007-002563 Ex. 19-supplemented diet treatment at 100 mg/kg/day (38B), a WO-2010-0138598 Ex. 19-supplemented diet treatment at 10 mg/kg/day or 100 mg/kg/day (38C), or an SB742881-supplemented diet treatment at 100 mg/kg/day (38D). n=8-10. All data are represented as mean±SEM.

DETAILED DESCRIPTION OF THE INVENTION

The present invention features methods for preventing or reducing aberrant proliferation, differentiation, or survival of cells. For example, compounds of the invention may be useful in reducing the risk of, or preventing, tumors from increasing in size or from reaching a metastatic state. The subject compounds may be administered to halt the progression or advancement of cancer. In addition, the instant invention includes use of the subject compounds to reduce the risk of, or prevent, a recurrence of cancer.

Metastatic progression requires that sets of effector proteins involved in common cellular phenotypes be coherently expressed (Gupta and Massagué, 2006 Cell 127, 679-695; Hanahan and Weinberg, 2011 Cell 144, 646-674; Talmadge and Fidler, 2010 Cancer Res. 70, 5649-5669; Hynes, 2003 Cell 113, 821-823). Such concerted expression states are apparent in gene expression profiles of primary breast cancers that metastasize (Wang et al., 2005 Lancet 365, 671-679), as well as profiles of human cancer cell clones that display enhanced metastatic activity (Kang et al., 2003 Cancer Cell 3, 537-549; Minn et al., 2005 Nature 436, 518-524). In recent years, post-transcriptional regulation has emerged as a pervasive and robust mode of concerted expression-state and phenotype-level control. The most studied class of post-transcriptional regulators with metastatic regulatory activity are small non-coding RNAs (miR-NAs) (Bartel, 2009 Cell 136, 215-233; Fabian et al., 2010 Annu. Rev. Biochem, 79, 351-379; Filipowicz et al., 2008 Nat. Rev. Genet. 9, 102-114). Metastasis promoter miRNAs (Ma et al., 2007 Nature 449, 682-688; Huang et al., 2008 Nat. Cell Biol. 10, 202-210) and suppressor miRNAs (Tavazoie et al., 2008 Nature 451, 147-152) were originally discovered in breast cancer. Subsequent studies revealed many more miRNAs with regulatory roles in the tumorigenesis and metastasis of other cancer types (Hatziapostolou et al., 2011 Cell 147, 1233-1247; Hurst et al., 2009 Cancer Res. 69, 7495-7498; Olson et al., 2009 Genes Dev. 23, 2152-2165; Zhang et al., 2010 Oncogene 29, 937-948) In many cases, the expression levels of these miRNAs in human cancer samples have supported their experimental roles in metastasis. Thus, deregulated miRNA expression (Garzon et al., 2010 Nat. Rev. Drug Discov. 9, 775-789; Lujambio and Lowe, 2012 Nature 482, 347-355) and, more recently, deregulated expression of long non-coding RNAs (Calin et al., 2007 Nat. Rev. Cancer 6, 857-866; Gupta et al., 2010 Nature 464, 1071-1076; Guttman et al., 2009 Nature 458, 223-227; Huarte et al., 2010.Cell 142, 409-419; Loewer et al., 2010 Nat. Genet. 42, 1113-1117) as well as non-coding pseudogenes competing for endogenous miRNA binding (Poliseno et al., 2010 Nature 465, 1033-1038) appear to be pervasive features of human cancer. Clues regarding the robust control exerted by specific miRNAs on metastatic progression came from early work showing that concerted targeting of multiple metastasis genes by a single metastasis suppressor miRNA was responsible for the dramatic metastasis suppression effects (Tavazoie et al., 2008 Nature 451, 147-152). Such divergent gene targeting by miRNAs has appeared to be a defining feature of these regulators.

At a conceptual level, the need for divergent regulation of gene expression in cancer is readily understood. A miRNA could exert robust metastatic suppression by virtue of its ability to target multiple genes required for metastasis. The miRNA's silencing through genetic or epigenetic mechanisms would readily promote cancer progression by de-repressing multiple promoters of metastasis (Png et al., 2011 Nature 481, 190-194). A role for convergent regulation of a single gene by multiple metastasis regulatory miRNAs is more nuanced. This scenario would emerge if there existed a key gene that acted as a robust suppressor of metastatic progression. Convergent and cooperative targeting of this gene by multiple miRNAs could achieve maximal silencing of such a key metastasis suppressor gene. This scenario, as opposed to genetic deletion, may be seen in cases where complete loss of a target gene could not be tolerated by the cell, and the gene would be required at low levels to mediate metabolic actions, for example. Given this possibility, a search for cooperative metastasis promoter miRNAs may uncover novel genes that are pivotal for metastasis suppression and may provide therapeutic insights into more effective treatments for metastasis prevention.

As disclosed herein, via a systematic, in vivo selection-based approach, a set of miRNAs were identified to be deregulated in multiple independent metastatic lines derived from multiple patients with melanoma—a highly prevalent cancer with increasing incidence (Garbe and Leiter, 2009 Clin. Dermatol. 27, 3-9). As disclosed herein, miR-1908, miR-199a-3p, and miR-199a-5p act as robust endogenous promoters of melanoma metastasis through convergent targeting of the metabolic gene ApoE and the heat-shock protein DNAJA4. Through loss-of-function, gain-of-function, and epistatic analyses, a cooperative miRNA network that maximally silences ApoE signaling is delineated. Cancer cell-secreted ApoE inhibits metastatic invasion and endothelial recruitment, which is mediated through its actions on distinct receptors on melanoma and endothelial cells. These miRNAs display significant prognostic capacity in identifying patients that develop melanoma metastatic relapse, while therapeutic delivery of LNAs targeting these miRNAs significantly inhibits melanoma metastasis. The current lack of effective therapies for the prevention of melanoma metastasis after surgical resection (Garbe et al., 2011 Oncologist 16, 5-24) requires an improved molecular and mechanistic understanding of melanoma metastatic progression. To this end, the findings disclosed herein reveal a number of key novel non-coding and coding genes involved in melanoma progression and offer a novel avenue for both identifying patients at high-risk for melanoma metastasis and treating them.

Listed below are the nucleic acid and amino acid sequences of the members of the above-mentioned network and a number of other sequences.

APOE-RNA sequence (SEQ ID NO: 1)

gggatccttgagtcctactcagccccagcggaggtgaaggacgtccttccccaggagccgactggccaatcacaggcaggaagatgaag gttctgtgggctgcgttgctggtcacattcctggcaggatgccaggccaaggtggagcaagcggtggagacagagccggagcccgagct gcgccagcagaccgagtggcagagcggccagcgctgggaactggcactgggtcgctifigggattacctgcgctgggtgcagacactgt ctgagcaggtgcaggaggagctgctcagctcccaggtcacccaggaactgagggcgctgatggacgagaccatgaaggagttgaaggc ctacaaatcggaactggaggaacaactgaccccggtggcggaggagacgcgggcacggctgtccaaggagctgcaggcggcgcagg cccggctgggcgcggacatggaggacgtgtgcggccgcctggtgcagtaccgcggcgaggtgcaggccatgctcggccagagcacc gaggagctgcgggtgcgcctcgcctcccacctgcgcaagctgcgtaagcggctcctccgcgatgccgatgacctgcagaagcgcctgg cagtgtaccaggccggggcccgcgagggcgccgagcgcggcctcagcgccatccgcgagcgcctggggccccctggtggaacaggg ccgcgtgcgggccgccactgtgggctccctggccggccagccgctacaggagcgggcccaggcctggggcgagcggctgcgcgcgc ggatggaggagatgggcagccggacccgcgaccgcctggacgaggtgaaggagcaggtggcggaggtgcgcgccaagctggagga gcaggcccagcagatacgcctgcaggccgaggccttccaggcccgcctcaagagctggttcgagcccctggtggaagacatgcagcgc cagtgggccgggctggtggagaaggtgcaggctgccgtgggcaccagcgccgcccctgtgcccagcgacaatcactgaacgccgaag cctgcagccatgcgaccccacgccaccccgtgcctcctgcctccgcgcagcctgcagcgggagaccctgtcccgccccagccgtcctc ctggggtggaccctagtttaataaagattcaccaagtttcacgcaaaaaaaaaaaaaaaaaaaaaaaaaaaaaaaaaaaaaaaaaaaaa APOE-Amino acid sequence (SEQ ID NO: 2)

mkvlwaallv tflagcqakv eqavetepep elrqqtewqs gqrwelalgr fwdylrwvqt lseqvqeell ssqvtqelra lmdetmkelk aykseleeql tpvaeetrar lskelqaaqa rlgadmedvc qrlvqyrgev qamlqqstee lrvrlashlr klrkrllrda ddlqkrlavy qagaregaer glsairerlg plveqgrvra atvgslagqp lqeraqawge rlrarmeemg srtrdrldev keqvaevrak leeqaqqirl qaeafqarlk swfeplvedm qrqwaglvek vqaavgtsaa pvpsdnh (Underlined residues 136-150 represent the LRP-binding domain of Apo E)

DNAJA4 isoform 1-RNA sequence (SEQ ID NO: 3)

aguccccacccuucggcgcagggcuccggccaacacagcccuccaggccgccuacucuccagccagccggcuccacggacccacg gaagggcaaggggcggccucggggcggcgggacaguugucggagggcgccuccaggcccaagccgccuucuccggccccc gccauggcccggggcggcagucagagcuggagcuccggggaaucagacgggcagccaaaggagcagacgcccgagaagcccag acacaagauggugaaggagacccaguacuaugacaucugggcgugaagcccagcgcgucccggaggagaucaagaaggccu aucggaagcuggcgcucaaguaccacccggacaagaacccggaugagggcgagaaguuuaaacucauaucccaggcauaugaa gugcuuucagauccaaagaaaagggauguuuaugaccaaggcggagagcaggcaauuaaagaaggaggcucaggcagcccca gcuucucuucacccauggacaucuuugacauguucuuggugguggugacggauggcuagagagagaagaggcaagaaug uuguacaccaguuaucuguaacucuugaagaucuauauaauggagucacgaagaaauuggcccuccagaaaaauguaauuug ugagaaaugugaaggugüüggugggaagaagggaucgguggagaagugcccgcugugcaaggggcggggaugcagaucca cauccagcagaucgggccgggcauggüacagcagauccagaccgugugcaucgagugcaagggccaggggugagcgcaucaac cccaaggaccgcugcgagagcugcagcggggccaaggugauccgugagaagaagauuaucgagguacauguugaaaagguua ugaaagaugggcaaaagauacuauuucauggagaaggagaucaggagccugagcuggagccuggugaugucauaauugugcu ugaucagaaggaucauagugucuuucagagacgaggccaugacuugaucaugaaaaugaaauucagcuuucugaagcucuu uguggcuucaagaagacgauaaaaacauuggacaaucgaauucuuguuauuacauccaaagcaggugaggugauaaagcacg gggaccugagaugcgugcgcgaugaaggaaugcccaucuacaaagcaccccuggaaaagggauucugaucaucaguuuuu aguaaucuuccugaaaaacacuggcuuucucuggaaaagcuuccucagcuggaagcuuuacucccuccucgacagaaaguga -continued ggauuacagaugacauggaucagguggagcugaaggaguuuugucccaaugagcagaacuggcgucagcacagggaggccua cgaggaggacgaagacgggccccaggcuggagugcagugccagacggcaugacguggugcggggcagcguggccccaccgga cuagcacaugaugaauguaaaguuggcacaaugaaaaugacaucgcuuaauggccuugcguuugggaugcccuguguaug uguucagcauucuuaauugcugagugucuuuuuggcuuucuuuugguuguaacuuaaguuauagcuuaauuuauauuua aauguuuuaaguauaaaucaccucuagucugcauauggaaucuguucauuucuauuucaggauauacuuuugagauguca gugauugcaccaauacuuugugcuucuaguggcuuugccauaauucagugucaccaauaaggcacagcccaguuagcagcuu agccccccuagcaaaccccaaggcacaaagugggcauccugacucaucucuaggucuguggucuuccccucuucccuggca gaguuauugagggcaugaucucagggcugcuaagauaacauuucugaggauucuagaugauccucuuaaagaauaaaagcac auccguggaucggacauggcugcaugugccugcuuaacagggccaacuuaguuccuacuguucugugcccuucagugaaug gaacgugagugucugaucaucucuuuggaaguuuucugaaccuuccaagcucugugguggaggacaaaccagguguuugaauc auaugcugauaacuguuugccugugacccucacaccuuguucuucaggguuuaaugauuuucuguugacaacuuuugcaa ugcuuucccaccaaagugcuuacuuguaaagaaaacuaaauccuucugugucccggcagccucagugcagcaacagaagcca agggagaaugcugcugguuuggcccauggcacagccagcuucucugaccaguaauccggggugacuugagggucugcaaagg cauagaacuccccaguguuuuccaccucauucucccagauugagcucccuuccaaggaucguuccucucauugcacagccau auuacaaaggguuccugcucaagugaauguuugguuaagaacuucgcugaguuccacuguggauuacaguuuguauggacu acuacuguaaauuauagcuuguuuggagggauauuaguucauauuuuauucaugacagguagacuacaauucgaacuuagg guuaccucagucuuuagccauuacugcuuauuucuuuucccaagucacaaaaaacuuguaagcugcugggeuuaaagcagag gccaccugucagaucuaccucuaccccuuauuugguuacauggcaccugagaguuucacucagaccagggaucuuccuuaggag ggucaaagugcagaucagaccaugcagguaaggugaaccagcugcacggaccagguucccgcaaaacauugccagcuagugag gcauaauuugcucaaaguauagaaacagcccaccugugcccacuuugaccauuggugaggauagauauaaaaucacuucuucc aacgaagccuaggugaaaaucuauuuauaaauggaccacaacucggggugucguuuugugcugugacuuccuaauuauug cuaaagaacuacuguuuaguuggaauggugaaaauuacauucagcuccuucuugucauauaaaaggaauuuggagggug ucgcuuaaaauuuuauuccaccuguacauuugucacuuuaaaauuaaauugagcugguaugagagauaaaaaaaaaaaaaa aaaa DNAJA4 isoform 1-Amino acid sequence (SEQ ID NO: 4)

marggsqsws sgesdgqpke qtpekprhkm vketqyydil gvkpsaspee ikkayrklal kyhpdknpde gekfldisqa yevlsdpkkr dvydqggeqa ikeggsgsps fsspmdifdm ffggggrmar errgknvvhq lsvtledlyn gvtkklalqk nvicekcegv ggkkgsvekc plckgrgmqi hiqqigpgmv qqiqtvciec kgqgerinpk drcescsgak virekkiiev hvekgmkdgq kilfhgegdq epelepgdvi ivldqkdhsv fqrrghdlim kmkiqlseal cgfkktikti dnrilvitsk agevikhgdl revrdegmpi ykaplekgil iiqflvifpe khwlsleklp qleallpprq kvritddmdq velkefcpne qnwrqhreay eededgpqag vqcqta DNAJA4 isoform 2-RNA sequence (SEQ ID NO: 5)

gugaccgugacgcgcgagcgggcggcgggggcgcgggccaggggcgcgggccagggugccggcaggggcguccggggcgcu cugaccggccucgcccgccccccccgcagacacaagauggugaaggagacccaguacuaugacaucugggcugaagcccag cgcgucccggaggagaucaagaaggccuaucggaagcuggcgcucaaguaccacccggacaagaacccggaugagggcgaga aguuuaaacucauaucccaggcauaugaagugcuuucagauccaaagaaaagggauguuuaugaccaaggcggagagcaggc aauuaagaaggaggcucaggcagcccccagcuucucuucacccauggacaucuuugacauguucuuuggguggugguggacgg auggcuagagagagaagaggcaagaaugungacaccaguuaucuguaacucuugaagaucuauauaauggagucacgaaga aauuggccccuccagaaaaaaugcucgaaauuggugagaaaugugaaggguguuggcugggaagaagggaucgguggagaagugcccgc -continued

```
ugugcaaggggcggggaugcagauccacauccagcagaucgggccgggcaugguacagcagauccagaccgugugcaucga gugcaagggccagggugagcgcaucaaccccaaggaccgcugcgagagcugcagcggggccaaggugauccgugagaagaag auuaucgagguacauguugaaaaagguaugaaagaugggcaaaagauacuauuucauggagaaggagaucaggagccugagc uggagccuggugaugucauaauugugcuugaucagaaggaucauagugucuuucagagacgaggccaugacuugaucauga aaaugaaaauucagcuuucugaagcucuuugugcuucaagaagacgauaaaaacauuggacaaucgaauucuuguuauuac auccaaagcaggugaggugauaaagcacggggaccugagaugcgugcgcgaugaaggaaugcccaucuacaaagcaccccugg aaaaagggauucugaucauacaguuuuuaguaaucuuuccugaaaaacacuggcuuucucuggaaaagcuuccucagcugga agcuuuacuccccuccucgacagaaagugaggauuacagaugacaucaaggugagcugaaggaguuuugucccaaugag cagaacuggcgucagcacaggggggccuacgaggaggacgaagacgggcccaggcuggagugcagugccagacggcaugac guggugcggggcagcgugggccccaccggacuagcacaugaugauaauaaaaguuggcacaaugaaaaugacaucgcuuuaaug gccuugguuuggaugauccugaugugugugugugugucagcauucuuaauugcugagugucuuuuggcuuuucuuuugguuguua acuuaaguuauagcuuaauuuauauuuaaauguuuuaaguauaaaucaccucuagucugcauauggaaucuguucauuucua uuuucaggauauacuuuugagaugucagaugauuugcaccaauacuuuugugcuucuaguggcuuugccauaauucagugucac caauaaggcacagcccaguuagcagcuuagccccccugcaaaccccaaggcacaaaguggcaauccugacucaucucuaggu cuguggauuucuuccccucuuccccuuggcagagaauuauugagggcaugauacucagggcugcuaagauaacauuucugaggauuc uagaugauccucuuaaagaauaaaagcacauccgugauucggacauggcugcauaugccugcuuaacagggccaacuuaguu ccuacuguucugugccccuucagguggauggaacgugagugucugaucaucucucuggaaguuucugaaccuccaagcuc ugguggaggacaaaccagguguuugaaucauaugcugauaacuguuugccugugacccucacaccuuguucuucaggguuu uaaugauuuucuguugacaacuuuugcaaugcuuucccaccaaagugcuuacuuguaaagaaaacuaaauccuucuguguccc ccggcagccucagugcagcaacagaagccaagggagaaugcugcugguuggcccauggcacagccagcuucucugaccagua auccgggggugacuugagggucugcaaaggcauagaacuccccagugguuccaccucauucucccagauugagcuccccuucc aaaggaucguccucucauugcacagccauauuacaaaggguuccugcucaagugauguuuugguaagaacuucgcugagu uccacguggauuacaguuuguauggacuacuacuguaaauuauagcuuguuugagggauauuagucauuauuuuauuca ugacagguagacuacaauucgaacuuaggguuaccucaguccuuuagccauuacugcuuauuucuuuuccccaagucacaaaa aacuuguaagcugcugggguuaaagcagaggccaccugucagaucuacccuacccuuauuuggauacauggcaccugagaguu ucacucagaccagggaucuuccuuaggagggucaaagugcagaucagaccaugcagguaaggugaaccagcugcacggaccag guucccgcaaaacauugccagcuagugaggcauaauuugcucaaaguauagaaacagcccaccuguggcccacuuugaccauug gugaggauagauauaaaaucacuucuuccaacgaagccuaggugaaaaucuauuuauaaauggaccacaacucggggugc guuuugugcugugacuuccuaauuauugcuaaagaacuacuguuuaguuggguaauggguaaaauuacauucagcucccuu cuugucauauaaaaggaauuuggagggugucgcuuaaaauuuuauuccaccuguacauuugucacuuuaaaauuaaaauuga gcugguaugagagauaaaaaaaaaaaaaaaa
```

DNAJA4 isoform 2-Amino acid sequence (SEQ ID NO: 6)

```
mvketqyydi lgvkpsaspe eikkayrkla lkyhpdknpd egekfklisq ayevlsdpkk rdvydqggeq aikeggsgsp
sfsspmdifd mffggggrma rerrgknvvh qlsvtledly ngvtkklalq knvicekceg vggkkgsvek cplckgrgmq
ihiqqigpgm vqqiqtvcie ckgqgerinp kdrcescsga kvirekkiie vhvekgmkdg qkilfhgegd qepelepgdv
iivldqkdhs vfqrrghdli mkmkiqlsea lcgfkktikt ldnrilvits kagevikhgd lrcvrdegmp iykaplekgi
liiqflvifp ekhwlslekl pqleallppr qkvritddmd qvelkefcpn eqnwrqhrea yeededgpqa gvqcqta
```

DNAJA4 isoform 3-RNA sequence (SEQ ID NO: 7)

```
acauuucagcaagcuggcuaaagacaugugggaaagccugacccuggauucaggucaaaucucagcacucacaagauuuaaac
ucauauucccaggcauaugaagugcuuucagauccaaagaaaaggauguuuaugaccaaggcggagagcaggcaauuaaagaa
ggaggcucaggcagccccagcuucucuucacccauggacaucuuugacauguucuuuggugguggugacggauggcuaga
```

-continued

```
gagagaagaggcaagaauguuguacaccaguuaucuguaacucuugaagaucuauauaauggagucacgaagaaauuggccc
uccagaaaaauguaauuugugagaaaugugaaggguguuggugggaagaagggaucgguggagaagugcccgcugugcaagg
ggcggggggaugcagauccacauccagcagaucgggccgggcauggguacagcagauccagaccgugugcaucgagugcaaggg
ccagggugagcgcaucaaccccaaggaccgcugcgagagcugcagcggggccaaggugauccgugagaagaagauuaucgag
guacauguugaaaaaggguaugaaagaugggcaaaagauacuauuucauggagaaggagaucaggagccugagcuggagccug
gugaugucauaauugugcuugaucagaaggaucauagugucuuucagagacgaggccaugacuugaucaugaaaaaugaaaau
ucagcuuucugaagcucuuuguggcuucaagaagacgauaaaaacauuggacaaucgaauucuguuauuacauccaaagca
ggugaggugauaaagcacggggaccugagaugcgugcgcgaugaaggaaugcccaucuacaaagcaccccuggaaaaaggga
uucugaucauacaguuuuuaguaaucuuccugaaaaacacuggcuuucucuggaaaagcuuccucagcuggaagcuuuacu
cccuccucgacagaaagugaggauuacagaugacauggaucagguggagcugaaggaguuuugucccaaugagcagaacugg
cgucagcacagggaggccuacgaggaggacgaagacgggccccaggcuggagugcagugccagacggcaugacguggugcgg
ggcagcugggccccaccggacuagcacaugaugaauguaaaaguuggcacaaugaaaaugacaucgcuuuaauggccuugugu
uugggaugucucuguaugugucagcauucuuaauugcugagugucuuuugucuuucuuuugguuguaacuuaaguu
auagcuuaauuuauauuuaaaauguuuuaaguauaaaucaccucuagucugcauauggaaucuguucauuucuauuucagga
uauacuuuugagaugucagugauugcaccaauacuuugugcuucuaguggcuuugccauaauucagugucaccaauaaggca
cagcccaguuagcagcuuagcccccuagcaaaccccaaggcacaaaguggggcauccugacucaucucuaggucuguggguuuc
uccccucuucccuuggcagaguuauugagggcaugaucucagggcugcuaagauaacauuucugaggauucuagaugauccu
cuuaaagaauaaaagcacauccguggaucggacauggcugcaugugccugcuuaacagggccaacuuaguuccuacuguucu
gugcccuucagugggauggaacgugagugucugaucaucucucuuggaaguuuucugaaccuuccaagcucuguggugagga
caaaccagucguuugaaucauaugcugauaacuguuugccugugacccucacaccuuguucuucagggguuuuaaugauuuucu
guugacaacuuuugcaaugcuuuccccaccaaagugcuuacuuguaaagaaaaacuaaauccuucuguguccccggcagccucag
ugcagcaacagaagccaagggagaaugcugcugguuuggcccauggcacagccagcuucucugaccaguaauccggggugac
uugagggucugcaaaggcauagaacucccagguguuuccacccucauucucccagauugagcucccuuccaaaggaucguuc
cucucauugcacagccauauuacaaaggguuuccugcucaagugauguuuuggaaagaacuucgcugaguuccacuguggau
uacaguuuguauggacuacuacuguaaauuauagcuuguuuggagggauauuagucauuauuuuauucaugacagguagac
uacaauucgaacuuagggguuaccucagucuuuagccauuacugcuuauuucuuuuccccaagucacaaaaaacuuguaagcu
gcugggguuaaagcagaggccaccugucagaucuacccuacccuuauuugguuacauggcaccugagaguuucacucagacca
gggaucuuccuuaggagggucaaagugcagaucagaccaugcagguaaggugaaccagcugcacggaccagguucccgcaaa
acauugccagcuaguggaggcauaauuugcucaaaguauagaaacagcccaccugugcccacuuugaccauuggugaggauag
auauaaaaucacuucuuccaacgaagccuaggugaaaaucuauuauaaaauggaccacaacucugggggucguuuugugc
ugugacuuccuaauuauugcuaaagaacuacguuuaguuggaauggguaaaauuacauucagcuccuucuugucauaua
aaaggaauuuggaggggugucgcuuaaaauuuuauuccaccuguacauuugucacuuuaaauuaaaauugagcugguaugag
agauaaaaaaaaaaaaaaaaaa
```

DNAJA4 isoform 3-Amino acid sequence
(SEQ ID NO: 8)

```
mwesltldsg qisaltrfkl isqayevlsd pkkrdvydqg geqaikeggs gspsfsspmd ifdmffgggg rmarerrgkn
vvhqlsvtle dlyngvtkkl alqknvicek cegvggkkgs vekcplckgr gmqihiqqig pgmvqqiqtv cieckgqger
inpkdrcesc sgakvirekk iievhvekgm kdgqkilfhg egdqepelep gdviivldqk dhsvfqrrgh dlimkmkiql
sealcgfkkt iktldnrilv itskagevik hgdlrcvrde gmpiykaple kgiliiqflv ifpekhwlsl eklpqleall
pprqkvritd dmdqvelkef cpneqnwrqh reayeededg pqagvqcqta
```

-continued

LRP1-RNA sequence (SEQ ID NO: 9)

cagcggugcgagcuccaggcccaugcacugaggaggcggaaacaaggggagccccagagcuccaucaagcccccuccaaagg cuccccuacccgguccacgcccccaccccccucccccgccuccucccaauugugcauuuuugcagccggaggcggcuccgag auggggcugugagcuucgcccgggggagggggaaagagcagcgaggagugaagcgggggggugggugaaggguuuggauu ucggggcaggggcgcaccccgucagcaggcccuccccaaggggcucggaacucuaccucuucacccacgccccuggugcgc uuugccgaaggaaagaauaagaacagagaaggaggagggggaaaggaggaaaaggggacccccccaacuggggggggugaag gagagaaguagcaggaccagaggggaaggggcugcugcuugcaucagcccacaccaugcugaccccgccguugcuccugcug cugcccugcucucagcucuggucgcggcggcuaucgacgccccuaagacuugcagccccaagcaguuugccugcagagauca aauaaccuguaucucaaagggcuggcggugcgacggugagagggacugcccagacggaucugacgaggcccugagauuugu ccacagaguaaggcccagcgaugccagccaaacgagcauaacugccgggguacugagcugugugguucccaugucccgccucug caaugggguccaggacugcauggacggcucagaugaggggcccacugccgagagcuccaaggcaacugcucucgccugggc ugccagcaccauugugucccccacacucgaugggcccaccugcuacugcaacagcagcuuucagcuucaggcagauggcaagac cugcaaagauuuugaugagugcucagugacggcaccugcagccagcuaugcaccaacacagacggcuccuucauaugugc ugugugaaggauaccuccugcagccggauaaccgcuccugcaaggccaagaacgagccaguagaccggccccugugcugu ugauagccaacucccagaacaucuuggccacguaccugaguggggcccaggugucuaccaucacaccuacgagcacgcggcag accacagccauggacuucagcuaugccaacgagaccguaugcugggugcauguugggacagugcugcucagacgcagcuca agugugcccgcaugccuggccuaaagggcuucguggaugagcacaccaucaacaucucccucagucugcaccacguggaacag auggccaucgacuggcugacaggcaacuucuacuuuguggaugacaucgaugauaggaucuuugucugcaacagaaaugggg acacaugugucacauugcuagaccuggaacucuacaaccccaagggcauugcccuggacccugccauggggaaggugacuuuu cacugacuaugggcagaucccaaaggguggaacgcugugacauggaugggcagaaccgcaccaagcucgucgacagcaagauug uguuccucauggcaucacgcuggaccuggucagccgccuugucuacugggcagaugccuaucggacuauauugaagugg uggacuaugagggcaagggccgccagaccaucauccagggcauccugauugagcaccuguacggccugacugugu uugagaa uuaucucuaugccaccaacucggacaaugccaaugcccagcagaagacgagugugauccgugugaaccgcuuuaacagcaccg aguaccagguugucacccggguggacaagggguggugcccuccacaucuaccaccagaggcgucagccccgagugaggagcca ugccugugaaaacgaccaguaugggaagccggguggcugcucugacaucugccugcuggccaacagccacaaggcgcggacc ugccgcugccguuccggcuucagccuggggcagugacgggaagucaugcaagaagccggagcaugagcuguuccucguguaug gcaagggccggccaggcaucauccggggcauggauauggggggccaaggucccggaugagcacaugaucccccauugaaaaccu caugaaccccgagcccuggacuuccacgcugagaccggcuucaucuacuuugccgacaccaccagcuaccucauuggccgcc agaagauugauggcacugagcgggagaccauccugaaggacggcauccacaaugugggagggugugccguggacuggaugg gagacaaucuguacuggacggacgaugggcccaaaaagacaaucagcguggccaggcuggagaaagcugcucagacccgcaag acuuuaaucgagggcaaaaugacacaccccagggcuauuguggguggauccacucaaugggguggaugua cuggacagacuggg aggaggaccccaaggacagucggcguggggcggcuggagagggcguggauggauggcucacaccgagacaucuuugucaccuc caagacagugcuuuggcccaaugggcuaagccuggacaucccggcuggggcgccucuacuggguggaugccuucuacgaccgc aucgagacgauacugcucaauggcacagaccggaagauugugaugaaggaguccugagcugaaccacgccuuuggccugug uc accauggcaacuaccucuucuggacugaguaucggaguggcagugucuaccgcuuggaacgggguguaggaggcgcaccccc cacugugacccuucugcgcagugagcgggccccccaucuuugagauccgaauguaugaugcccagcagcagcaaguuggcacca acaaaugccggguga acaauggcggcugcagcagccugugcuuugccaccccugggagccgccagugcgccugugcugagga ccaggug uuggacgcagacggcgucacuugcuuggcgaacccauccuacgugccuccaccccagugccagccaggcgaguuu gccugugccaacagccgcugcauccaggagcgcuggaagugugacggagacaacgauugccuggacaacagugaugaggccc cagcccucugccaucagcacaccugcccccucggaccgauucaagugcgagaacaaccggugcauccccaaccgcuggcucugc -continued gacggggacaaugacugugggaacagugaagaugaguccaaugccacuuguucagcccgccaccugcccccccaaccaguucuc cugugccagugggccgcugcaucccaucuccuggacgugugaucuggaugacgacuguggggaccgcucugaugagucugc uucgugugccuaucccaccugcuuccccugacucaguuuaccugcaacaauggcagauguaucaacaucaacuggagaugcg acaaugacaaugacugugggggacaacagugacgaagccggcugcagccacuccuguucuagcacccaguucaagugcaacagc gggcguugcauccccgagcacuggaccugcgaugggggacaaugacugcggagacuacagugaugagacacacgccaacugcac caaccaggccacgaggcccccuggugggcugccacacugaugaguuccagugccggcuggauggacuaugcauccccccugcgg uggcgcugcgaugggggacacugacugcauggacuccagcgaugagaagagcugugagggagugacccacgucugcgauccca gugucaaguuuggcugcaaggacucagcucggugcaucagcaaagcguggggugugugauggcgacaaugacugugaggaua acucggacgaggagaacugcgaguccuggccugcaggccacccucgcacccuugugccaacaacaccucagucugccugccc ccugacaagcugugugauggcaacgacgacuguggcgacggcucagaugagggcgagcucugcgaccagugcucucugaaua acgguggcugcagccacaacugcucaguggcaccuggcgaaggcauugugugguuccugcccucggggcauggagcuggggcc cgacaaccacaccugccagauccagagcuacugugccaagcaucucaaaugcagccaaaagugcgaccagaacaaguucagcgu gaagugcuccugcuacagggcuggguccuggaaccugacggcgagagcugccgcagccuggaccccuucaagccguucauc auuucuccaaccgccaugaaauccggcgcaucgaucuucacaaaggagacuacagcguccuggugcccggccugcgcaacac caucgcccuggacuuccaccucagccagagcgcccucuacuggaccgacgugguggaggacaagaucuaccgcgggaagcugc uggacaacggagcccugacuaguuucgaggugugauucaguauggccuggccacacccgagggccuggcuguagacuggau ugcaggcaacaucuacuggguggagaguaaccuggaucagaucgagguggccaagcuggaugggacccuccggaccacccug cuggccggugacauugagcacccaagggcaaucgcacuggauccccgggaugggauccuguuuggacagacugggaugcca gccugccccgcauugaggcagccuccaugagugggggcugggcgccgcaccgugcaccgggagaccggcucugggggcuggcc caacgggcucaccguggacuaccuggagaagcgcauccuuuggauugacgccaggucagaugccauuuacucagcccguuac gacggcucuggccacauggaggugcuucggggacacgaguuccugucgcacccguuugcagugacgcuguacggggggag gucuacuggacugacuggcgaacaaacacacuggcuaaggccaacaaguggaccggccacaaugucaccgugguacagaggac caacacccagcccuuugaccugcaggguguaccaccccuccccgccagcccauggcuccaauccccugugaggccaaugggggcc agggccccugcucccaccugugucucaucaacuacaaccggaccgugccugcgccugcccccaccucaugaagcuccacaag gacaacaccaccugcuaugaguuuaagaaguccugcuguacgcacgucagauggagauccgaggugugggaccuggaugcuc ccuacuacaacuacaucaucuccuucacggugcccgacaucgacaacgucacagugcuagacuacgaugcccgcgagcagcgu guguacugg ucugacgugcggacacaggccaucaagcgggccuucaucaacggcacaggcguggagacagucgucucugcag acuugccaaaugcccacgggcuggcugugga cugggucucccgaaaccuguucuggacaagcuaugacaccaauaagaagcag aucaaugugggcccggcuggauggcuccuucaagaacgcaguggugcagggccuggagcagcccccauggccuugucgccacc cucugcguggaagcucuacuggaccgaugguga caacaucagcauggccaacauggauggcagcaaucgcacccugcucuu caguggccagaagggccccgugggccuggcuauugcauucccugaaagcaaacucuacuggaucagcuccgggaaccauacca ucaaccgcugcaaccuggaugggagugggcuggaggucaucgaugccaugcggagccagcugggcaaggccaccgcccuggc caucauggggggacaagcugguggugggcugaucaggugucggaaaagaugggcacaugcagcaaggcugacgcucgggcucc guggccuucggaacagcaccacccuggugaugcacaugaaggucuaugacgagagcauccagcuggaccauaagggcaccaa ccccugcagugucaacaacggugacugcucccagcucugccugcccacgucagagacgacccgcuccugcaugugcacagccg gcuauagccuccggagugggccagcaggccugcgagggcguaggguccuuucuccuguacucuguugcaugagggaaucaggg gaauucccuggaucccaaugacaagucagaugcccuggucccagugccgggaccucgcuggcugucggcaucgacuucca cgcugaaaaugacaccaucuacugggguggacauggggccugagcacgaucagccgggccaagcgggaccagacguggcgugaa gacguggugaccaauggcauuggccgugugggagggcauugcaguggacuggaucgcaggcaacaucuacuggacagaccagg gcuuugaugucaucgaggucgcccggcucaauggcuccuuccgcuacgugguucucccagggucuagacaagccccgggc caucaccguccacccggagaaagggguacuuguucuggacugaguggggucaguauccgcguauugagcggucucggcuagau -continued ggcacggagcguguggugcuggucaacgucagcaucagcuggcccaacggcaucucaguggacuaccaggaugggaagcugu acuggugcgaugcacggacagacaagauugaacggaucgaccuggagacaggugagaaccgcgagguggu ucuguccagcaa caacauggacauguuucagugucuguguuugaggauuucaucuacuggagugacaggacucaugccaacggcucuaucaag cgcgggagcaaagacaaugccacagacuccgugcccugcgaaccggcaucggcguccagcuuaaagacaucaaagucuucaa ccgggaccggcagaaaggccaacgugugcgcgguggccaauggcgggugccagcagcugugccuguaccggggccguggg cagcgggccugcgccugugcccacgggaugcuggcugaagacggagcaucgugccgcgaguaugccggcuaccugcucuacu cagagcgcaccauucucaagaguauccaccugucggaugagcgcaaccucaaugcgcccgugcagcccuucgaggacccugag cacaugaagaacgucaucgcccuggccuuugacuaccgggcaggcaccucucccgggcaccccaaucgcaucuucuucagcga cauccacuuugggaacauccaacagaucaacgacgauggcuccaggaggauccacauguggaaaacgugggcuccguggaag gccuggccuaucaccguggcugggacacucucuauuggacaagcuacacgacauccaccaucacgcgccacacaguggaccag acccgcccaggggccuucgagcgugagaccgucaucacuaugucuggagaugaccacccacgggccuucguuuuggacgagu gccagaaccucauguucuggaccaacuggaaugagcagcauccagcaucaugcgggcggcgcucucgggagccaaugccu gacccuuaucgagaaggacauccguaccccc aauggccuggccaucgaccaccgugccgagaagcucuacuucucugacgcca cccuggacaagaucgagcggugcgaguaugacggcucccaccgcuaugugauccaaaagucagagccuguccaccccuucgg gcuggccguguauggggagcacauuuucuggacugacuggggugcggcgggcagugcagcgggccaacaagcacgugggcag caacaugaagcugcugcgcguggacaucccccagcagcccauggg caucaucgccguggccaacgacaccaacagcugugaac ucucuccaugccgaaucaacaacgguggcugccaggaccugugucugcucacucaccagggccaugucaacugcucaugccga ggggccgaauccuccaggaugaccucaccugccgagcggugaauuccucuugccgagcacaagaugaguuugagugugcca auggcgagugcaucaacuucagccugaccugcgacggcgucccccacugcaaggacaaguccgaugagaagccauccuacugc aacucccgccgcugcaagaagacuuuccggcagugcagcaauggcgcuguguguccaacaugcuguggugcaacgggccg acgacuguggggauggcucugacgagaucccuugcaacaagacagccuguggguguggcgaguccgcugccgggacgggac cugcaucgggaacuccagccgcugcaaccaguuugugg auugugaggacgccucagaugagaugaacugcagugccaccgac ugcagcagcuacuuccgccugggcgugaagggcgugcucuuccagcccugcgagcggaccucacucugcuacgcacccagcu gggugugugauggcgccaaugacugugggg acuacagugaugagcgcgacugcccaggugugaaacgccccagaugcccucu gaauuacuucgccugcccuaguggggcgcugcaucccc augagcuggacgugugacaaagaggaugacugugaacauggcgag gacgagacccacugcaacaaguucugcucagaggcccaguuugagugccagaaccaucgcugcaucuccaagcaguggcugug ugacggcagcgaugacugugggggauggcucagacgaggcugcucacugugaaggcaagacgugcggcccccuccuccuucucc ugcccuggcacccacgugugcgucccccgagcgcuggcucugugacggugacaaagacugugcugauggugcagacgagagca ucgcagcugguugcuuguacaacagcacuugugacgaccgugaguucaugugccagaaccgccagugcaucccca agcacuu cgugugugaccacgaccgugacugugcagauggcucugaugaguccccgagugugaguacccgaccugcggccccagugag uuccgcgugccaauggggcgcugucugagcucccgccagugggagugugauggcgagaaugacugccacgaccagagugacg aggcucccaagaacccacacugcaccagccaagagcacaagugcaaugccucgucacaguuccugugcagcaguggg cgcugu guggcugaggcacugcucugcaacggccaggaugacuguggcgacagcucggacgagcgguggcugccacaucaaugagugue ucagccgcaagcucaguggcugcagccaggacugugaggaccucaagaucggcuucaagugccgcugucgcccuggcuuccg gcugaaggacgacggccggacgugugcugauguggacgagugcagcaccaccuuccccugcagccagcgcugcaucaacacuc auggcagcuauaagugucuguguguggagggcuaugcaccccgcggcggcgacccccacagcugcaaggcugugacugacga ggaaccguuucugaucuucgccaaccgguacuaccugcgcaagcucaaccuggacgggccaacuacacguuacuuaagcagg gccugaacaacgccguugccuuggauuuugacuaccgagagcagaugaucuacuggacagaugugaccacccagggcagcau gauccgaaggaugcaccuuaacgggagcaaugugcaggu ccuacaccguacaggccucagcaaccccgaugggcuggcugug gacuggguggguggcaaccuguacuggguagcgacaaaggccgggacaccaucgaggugccaagcucaauggggccuaucgga -continued cggugcuggucagcucuggccuccgugagcccagggcucuggugguggaugugcagaaugggu accuguacuggacagacu ggggugaccauucacugaucggccgcaucggcauggaugggu ccagccgcagcgucaucguggacaccaagaucacauggcc caauggccugacgcuggacuaugucacugagcgcaucuacugggccgacgcccgcgaggacua cauugaauuugccagccug gauggcuccaaucgccacguugugcugagccaggacaucccgcacaucuuugcacugacccug uuugaggacuacgucuacu ggaccgacugggaaacaaaguccauuaaccgagcccacaagaccacgggcaccaacaaaacgc uccucaucagcacgcugcacc ggcccauggaccugcaugucuuccaugcccugcgccagccagacgugcccaaucaccccugca aggucaacaaugguggcugc agcaaccugugccugcugucccccggggagggcacaaaugugccugccccaccaacuucuacc uggcagcgaugggcgcac cugugugccaacugcacggcuagccaguuuguaugcaagaacgacaagugcauccccuucgg uggaagugugacaccgag gacgacugcggggaccacucagacgagcccccggacugcccugaguucaagugccggcccgga caguuccagugcuccacagg uaucugcacaaacccugccuucaucgcgauggcgacaaugacugccaggacaacagugacgag gccaacugugacauccacg ucugcuugcccagucaguucaaaugcaccaacaccaaccgcuguauuccggcaucuuccgcug caaugggcaggacaacugc ggagaugggaggaugagagggacugccccgaggugaccugcgcccccaaccaguuccagugcu ccauuaccaaacggugca uccccccgggucugggucugcgaccgggacaaugacugugggauggcagugaugagcccgcca acugcacccagaugaccug uggugugga cgaguuccgcugcaaggauucgggccgcugcaucccagcgcguuggaagugug acggagaggaugacugugg ggauggcucggaugagcccaaggaagagugugaugaacgcaccgugagccauaccaguuccgc ugcaagaacaaccgcug gggccccaaaugcacccagcaggugugugcgggcuacugugccaacaacagcaccugcacugucaaccagggcaaccagcccc agugccgaugccuaccggcuuccugggcgaccgcugccaguaccggcagugcucuggcuacugugagaacuuuggcacaug ccagauggcugcugauggcucccgacaaugccgcugcacugccuacuuugagggaucgaggugugaggugaacaagugcagc cgcugucucgaaggggccuguguggucaacaagcagaguggggaugucaccugcaacugcacggauggccgggugccccca gcugucugaccugcgucggccacugcagcaauggcggcuccuguaccaugaacagcaaaaugaugccugagugccagugccc accccacaugacagggccccggugugaggagcacgucuucagccagcagcagccaggacauauagccuccauccuaauccccuc ugcuguugcugcugcugcugguucguggugccggagugguauucgguauaagcggcgaguccaaggggcuaagggcuucc agcaccaacggaugaccaacggggccaugaacguggagauuggaaaccccaccuacaagauguacgaaggcggagagccugau gaugugggaggccuacuggacgcugacuuugcccuggacccugacaagcccaccaacuucaccaaccccguguaugccacacu cuacaugggggccauggcagucgccacucccuggccagcacggacgagaagcgagaacuccugggccggggcccugaggac gagauaggggaccccuuggcauagggcccugcccgucggacugccccagaaagccuccugcccccugccggugaaguccuu cagugagccccuccccagccagcccuuccuuggccccgccgaugauauaaaugua aaaaaugaaggaauuacauuuuauaugug agcgagcaagccggcaagcgagcacaguauuauuucuccauccccucccugccugucccuuggcaccccaugcugccuucag ggagacaggcagggagggcuuggggcugcaccuccuacccucccaccagaacgcaccccacugggagagcugguggugcagc cuuccccucccuguauaagacacuuugccaaggcucucccucucgccccaucccugcuugcccgcucccacagcuuccugag ggcuaauucugggaagggagaguucuuugcugccccugucggaagacguggcucugggugagguaggcgggaaaggaugg aguguuuaguucuuggggggaggccaccccaaaccccagccccaacuccaggggcaccaugagauggccaugcucaaccccc cucccagacaggccccuccugucuccaggccccaccgagguucccagggcuggagacuucucugguaaacauuccuccag ccuccccucccuggggacgccaaggaggugggccacacccaggaagggaaagcgggcagccccguuuggggacgugaacg uuuuaauaauuuuugcugaauuccuuuacaacuaaauaacacagauauuguuauaauaaaauuguaaaaaaaaaaaaaaaa
aa LRP1-Amino acid sequence (SEQ ID NO: 10)

mltppllll1 pllsalvaaa idapktcspk qfacrdqitc iskgwrcdge rdcpdgsdea peicpqskaq rcqpnehncl gtelcvpmsr lcngvqdcmd gsdegphcre lqgncsrlgc qhhcvptldg ptcycnssfq lqadgktckd fdecsvygtc sqlctntdgs ficgcvegyl lqpdnrscka knepvdrppv lliansqnil atylsgaqvs titptstrqt tamdfsyane tvcwvhvgds aaqtqlkcar mpglkgfvde htinisls1h hveqmaidwl tgnfyfvddi ddrifvenrn gdtcvtlldl elynpkgial dpamgkvfft dygqipkver cdmdgqnrtk lvdskivfph gitldlvsrl vywadayldy ievvdyegkg rqtiiqgili ehlygltvfe nylyatnsdn anaqqktsvi rvnrfnstey qvvtrvdkgg alhiyhqrrq prvrshacen dqygkpggcs dicllanshk artcrcrsgf slgsdgksck kpehelflvy gkgrpgiirg mdmgakvpde hmipienlmn praldfhaet gfiyfadtts yligrqkidg teretilkdg ihnvegvavd wmgdnlywtd dgpkktisva rlekaaqtrk tliegkmthp raivvdping wmywtdweed pkdsrrgrle rawmdgshrd ifytsktylw pnglsldipa grlywydafy drietillng tdrkivyegp elnhafglch hgnylfwtey rsgsvyrler gvggapptvt lirserppif eirmydaqqq qvgtnkcrvn nggcsslcla tpgsrqcaca edqvldadgv tclanpsyvp ppqcqpgefa cansrciqer wkcdgdndcl dnsdeapalc hqhtcpsdrf kcennrcipn rwlcdgdndc gnsedesnat csartcppnq fscasgrcip iswtcdlddd cgdrsdesas cayptcfplt qftcnngrci ninwrcdndn dcgdnsdeag cshscsstqf kcnsgrcipe hwtcdgdndc gdysdethan ctnqatrppg gchtdefqcr ldglciplrw rcdgdtdcmd ssdekscegv thvcdpsvkf gckdsarcis kawvcdgdnd cednsdeenc eslacrppsh pcanntsycl ppdklcdgnd dcgdgsdege lcdqcslnng gcshncsvap gegivcscpl gmelgpdnht cqiqsycakh lkcsqkcdqn kfsvkcscye gwvlepdges crsldpfkpf iifsnrheir ridlhkgdys vlvpglrnti aldfhlsqsa lywtdvvedk iyrgklldng altsfevviq yglatpegla vdwiagniyw vesnldqiev akldgtirtt llagdiehpr aialdprdgi lfwtdwdasl prieaasmsg agrrtvhret gsggwpnglt -continued vdylekrilw idarsdaiys arydgsghme vlrghefish pfavtlygge vywtdwrtnt lakankwtgh nytyvqrtnt
qpfdlqvyhp srqpmapnpc eanggqgpcs hiclinynrt vscacphlmk lhkdnttcye fkkfflyarq meirgvdlda
pyynyiisft vpdidnytvl dydareqrvy wsdvrtqaik rafingtgve tvvsadlpna hglavdwvsr nlfwtsydtn
kkqinvarld gsfknavvqg leqphglvvh plrgklywtd gdnismanmd gsnrtllfsg qkgpvglaid fpesklywis
sgnhtinrcn ldgsglevid amrsqlgkat alaimgdklw wadqvsekmg tcskadgsgs vvirnsttly mhmkvydesi
qldhkgtnpc synngdcsql clptsettrs cmctagyslr sgqqacegvg sfllysvheg irgipldpnd ksdalvpvsg
tslavgidfh aendtiywvd mglstisrak rdqtwredvy tngigrvegi avdwiagniy wtdqgfdvie varingsfry
vvisqgldkp raitvhpekg ylfwtewgqy priersrldg tervylvnys iswpngisvd yqdgklywcd artdkierid
letgenrevy lssnnmdmfs vsvfedfiyw sdrthangsi krgskdnatd svplrtgigy qlkdikvfnr drqkgtnvca
vanggcqqlc lyrgrgqrac acahgmlaed gascreyagy llysertilk sihlsdernl napvqpfedp ehmknviala
fdyragtspg tpnriffsdi hfgniqqind dgsrritive nvgsveglay hrgwdtlywt syttstitrh tvdqtrpgaf
eretvitmsg ddhprafvld ecqnlmfwtn wneqhpsimr aalsganylt liekdirtpn glaidhraek lyfsdatldk
ierceydgsh ryvilksepv hpfglavyge hifwtdwvrr avqrankhvg snmkllrvdi pqqpmgiiav andtnscels
perinnggcq dlcllthqgh vncscrggri lqddltcrav nsscraqdef ecangecinf sltcdgvphc kdksdekpsy
cnsrrckktf rqcsngrcvs nmlwcngadd cgdgsdeipc nktacgvgef rcrdgtcign ssrcnqfvdc edasdemncs
atdcssyfrl gykgylfqpc ertslcyaps wvcdgandcg dysderdcpg vkrprcpiny facpsgrcip mswtcdkedd
cehgedethc nkfcseaqfe cqnhrciskq wlcdgsddcg dgsdeaahce gktcgpssfs cpgthycype rwlcdgdkdc
adgadesiaa gclynstcdd refmcqnrqc ipkhfvcdhd rdcadgsdes peceyptcgp sefrcangrc lssrqwecdg
endchdqsde apknphctsq ehkcnassqf lcssgrcvae allcngqddc gdssdergch ineclsrkls gcsqdcedlk
igfkercrpg frlkddgrtc advdecsttf pcsqrcinth gsykcicveg yaprggdphs ckavtdeepf lifanryylr
klnldgsnyt llkqglnnav aldfdyreqm iywtdvttqg smirrmhlng snvqvlhrtg lsnpdglavd wvggnlywcd
kgrdtievsk ingayrtylv ssglrepral vvdvqngyly wtdwgdhsli grigmdgssr svivdtkitw pngltldyvt
eriywadare dyiefasldg snrhyvlsqd iphifaltlf edyvywtdwe tksinrahkt tgtnktllis tlhrpmdlhv
fhalrqpdvp nhpckvnngg csnlcllspg gghkcacptn fylgsdgrtc vsnctasqfv ckndkcipfw wkcdteddcg
dhsdeppdcp efkcrpgqfq cstgictnpa ficdgdndcq dnsdeancdi hyclpsqfkc tntnrcipgi frcngqdncg
dgederdcpe vtcapnqfqc sitkrcipry wvcdrdndcv dgsdepanct qmtcgvdefr ckdsgrcipa rwkcdgeddc
gdgsdepkee cdertcepyq frcknnrcvp grwqcdydnd cgdnsdeesc tprpcsesef scangrciag rwkcdgdhdc
adgsdekdct prcdmdqfqc ksghciplrw rcdadadcmd gsdeeacgtg vrtcpldefq cnntickpla wkcdgeddcg
dnsdenpeec arfvcppnrp frckndrycl wigrqcdgtd ncgdgtdeed cepptahtth ckdkkeficr nqrclssslr
cnmfddcgdg sdeedcsidp kltscatnas icgdearcvr tekaaycacr sgfhtvpgqp gcqdineclr fgtcsqlcnn
tkgghlcsca rnfmkthntc kaegseyqvl yiaddneirs lfpghphsay eqafqgdesv ridamdvhvk agrvywtnwh
tgtisyrslp paappttsnr hrrqidrgvt hlnisglkmp rgiaidwvag nvywtdsgrd vievaqmkge nrktlisgmi
dephaivvdp lrgtmywsdw gnhpkietaa mdgtlretly qdniqwptgl avdyhnerly wadaklsvig siringtdpi
vaadskrgls hpfsidvfed yiygvtyinn rvfkihkfgh splvnitggl shasdvvlyh qhkqpevtnp cdrkkcewlc
llspsgpvct cpngkrldng tcypvpsptp ppdaprpgtc nlqcfnggsc flnarrqpkc rcqprytgdk celdqcwehc
rnggtcaasp sgmptcrcpt gftgpkctqq vcagycanns tctvnqgnqp qcrclpgflg drcqyrqcsg ycenfgtcqm
aadgsrqcrc tayfegsrce vnkcsrcleg acvvnkqsgd vtcnctdgrv apscltcvgh csnggsctmn skmmpecqcp
phmtgprcee hvfsqqqpgh iasiliplll llllvlvagv vfwykrrvqg akgfqhqrmt ngamnveign ptykmyegge
pddyggllda dfaldpdkpt nftnpvyatl ymgghgsrhs lastdekrel lgrgpedeig dpla LRP8 isoform 1-RNA sequence (SEQ ID NO: 11)

gcuggcggcggccgcccagggccggggccgcgcgcccagccugagcccgccccgccgccgagcgucaccgaaccugcuugaaa ugcagccgaggagccggggcgggcggcagcggcggcggcggcggcggcggggcagcggcaaccccggcgccgcggcaagga cucggagggcugagacgcggcggcggcggcgcggggagcgcggggcgcggcggccggagccccgggcccgccaugggccucc ccgagccgggccucuccggcuucggcgcugcugcugcugcugcugcugcugcugcugcagccagcaucuugcggc ggcagcggcugauccgcugcucggcggccaagggccggccaaggauugcgaaaaggaccaauuccagugccggaacgagcgc ugcaucccucugugaggaugcgacgaggacgaugacugcuuagaccacagcgacgaggacgacugcccaagaagaccug ugcagacagugacuucaccugugacaacggccacugcauccacgaacggguggaagugugacggcgaggaggagugaccugau ggcuccgaugagucccgaggccacuugcaccaagcaggugugnuccugcagagaagcugagcugnuggacccaccagccacaagu guguaccugccucgugcgcugcgacggggagaaggacugcgagggguggagcggaugaggccggcugugucauuagucgg ccccgcacgaguuccagugcggcaaccgcucgugccuggccgccguguucgugugcgacggcgacgacgacguguggugacgg cagcgaugagcgcggcugugcagacccggccucgcggccccgcgaguuccgcugcggcggcgauggcggcggcgccugcauc ccggagcgcuggucugcgaccgccaguuugacugcgaggaccgccucggacgaggcagccgagcucgcggccguccgggcc ccggggccacgucccgcgcccgccgccuggccaccgccucccaguucgccugccgcagcggcgagugcgugcaccugggcug gcgcugcgacggcgaccgcgacugcaaagacaaaucggacgaggccgacugcccacugggccacugccguggggacgaguucc agugugggggauggggacaugugccuugcaaucaagcacugcaaccaggagcaggacuguccagaugggagugaugaagcugg cugccuacaggggcugaacgagugucugcacaacaauggcggcugcucacacaucugcacugaccucaagauuggcuuugaa ugcacgugcccagcaggcuuccagcuccuggaccagaagaccugngcgacauugaugagugcaaggacccagaugccugca gccagaucugugucaauuacaagggcuauuuuaagugugaggucucacccccggcuacgagaugggaccuacugaccaagaacug caaggcugcugcugggcaagagcccaucccuaaucuucaccaacggcacgaggugcggaggaucgaccuggugagcggaacu auucacgccucaucccaugcucaagaaugucgugagcacauagaugggaagugucacccaaucgcaucuacggguggugaccu cuccuaccguaagaucuauagcgccuacauggacaaggccagugacccgaaagagcaggaggucucuauugacgacagccgaacuugc acucuccagagggccuggcagugacgugugnuccacaagcacaucuacuggacugacucgggcaauaagaccaucucagggucc acaguugauggnggcgcgcgacgcacucucuucagccguaaccucagugaaccccggggccaucgcuguugaccccccugcgag gguucauguauuggucugacugggggggaccagaggccaagauugagaaaucuggggcucaacgggugggugaccggcaaacacugg uguuccagacaauauuugaaugggcccaacggaaucacccuggaucugcugagccagcgccuuguagucugggguagacuccaaagccuacac caacugnuccagcauugacuucagugaggcaacagaaagaacgcugauccucuccaccugaccuuccugagccacccuuuuugggau agcucugunuugaggacaaggguguucuggacagaccuggagaacgaggccauuuucagugcaaaucggcucaauggccuggaa ancuccauccuggcugagaaccucaacaacccacaugacauugcaucuuccaugagcucgaagcagccaagagccucagaugc cugcgagcugagugccagccuaaaggaggcugugaaauaccgguccuuccugcuccucagaucuccagccacucucccaag uacacaugugccuguccugacacaauguggcuggguccagacaugaagaggagucuaccgagcaccucaaucuaccucaacuac gacguuagcuucuaccaugagcgaggaccaguaccugccaccacaagacgccccccgggaccaccgunccacagauccaccuaccagaa ccacagcacaagaagacaccaagccugacagcugcaguccccaagcucaguuagnugucccccagggcucccagcaucgagcccgucuac ccuaagcccugcaaccagcaaccacucccagcacuaugcaaaugaagacaguaagaugggcucaacagucacugccgcguuua ucgggaucaucgugcccauagugguguauagccccuccugucaugaguggauaccugaucggagaaacuggaagcggaagaa caccaaaagcaugaauuungacaacccagucuacaggaaaacaacagaagaagaagacgaagagagcuccauauagggagaac ugcucagauuggccaugucuauccuucagcaaucagcagcuuugaucgcccacugugggcagagcccuguuccuuggggagacc agagaaccggaagacccagcccgcccucaaggagcuuuuugucuugcggggaaccaaggucacagcugcaccaaucccc gaagaacccucuuuccgagcugccugucgucaaauccaagcgaguggcauuaagccuugaagauguggacuacccugagga uggauucaccccuuggugccucauggaauucagucccaugcacuacacucugggugauaugacuggaugaauggguuuc uauauauggguuucugungangugunauguungugugngugganuunuuuuuaaannunungnugnggaaagguaaccacaaaguu augaugaacugcaaacauccaaaggaugugagaguuuuucuauguauaauguuuuauacacuuuuuaacugguugcacuacc caugaggaauucguggaauggcuacugcugacuaacaugaugcacauaaccaaauggggggccaauggcacaguaccuuacuca ucauuuaaaaacuauauuuacagaagauguuuggpuugcugggggggcuuuuuuagguuuuggggcauuuguuuuuguaa auaagaugauuaugcuuuguggcuauccaucaacauaaguaaaaaaaaaaaaaaacacuucaacucccucccccauuuagau uauuuauuaacauauuuuaaaaaucagaugaguucuauaaauaauuuagagaagugagaguauuuauuuuuggcauguuug gcccaccacacagacucugugugugugugugugugugugugugucuauaugugacagaaaaaucguagagaagaggca caucuauggcuacuguucaaauacauaaagauaaauuuauuuucacacaguccacaaggggguauaucuguaguuuucagaa aagccuuuggaaaucuggaucagaaaauagauaccauggggguuugugcaauuauguaguaaaaaaggcaaaucuuuucaccucu ggcuauccugagaccccaggaagucaggaaaagccuuucagcucacccauggcugcugugacuccuaccagggcuuucuug gcuuggcgaaggucaguguacagacauuccaugguaccagagugcucagaaacucaagauaggauaugccucacccucagc uacuccuuguuuaaaguucagcucuuugaguaacuucuucaauuucuuucaggacacuuggguugaauucaguaaguuuc cucugaagcacccugaagggugccauccuuacagagcuaaguggagacguuuccagaucagcccaaguuuacuauauagagacu ggcccaggcacugaaugucuaggacaugcuguggaugaagauaaagauggugggaauagguuuuaucacaucucuuauuucuc uuuucccccuuacucucuuccauuucuuuaugugggggaaacauuuuaagguaauaaauuagguuacuuuuaccaucauauguuuca uauagaugaaacuaauuuuuggcuuaagucagaacaacuggccaaaauugaagucauauuugagggggaaauggcauacgc aauauuauauuauuuggauauuuauguuucacacaggaauuugguuuacugcuuuguaaauaaaaggaaaaacuccgggguau auguauagauguucuucauuauagacaucuucuuugcuuuucuuggccuuggggggaggaaggggagaagugcucuuuucuac uuguggggucucccauuggaaacauaaaauccuauaguccccagaaggauuucagucccccaguggcuuucccauccaaagagaaaga guuugaguuucuuaacucugcuguucgcccacuuacucccacuagacaaccagggacaaggugcaacauggaaguguuugac uuaaguaggagcagaggagcugcaucuaaucucaucauaccuggaacuugacacacuuaagcaaaugccuucccaucccuacc ugccagaugcccccaacucaaugaaguuggaugucucaccagcuugauaccccuuugaauuuucagucagacauucuggaguu cuagcauccuguaccuaggaccuuccucugugucacucuuggccuccuaaaacucuaagaaaauaacuauauucuggagcuug ggcagugguguuuugcauaauccagcaaucuccucaugacaugcaugugugauaguccugaaacauucauugagaggguaaa ugcaguugaccuagaaugaccaauaccaaacagaauuuuaagaacagguggccaacuccuauggagcuuacucacauauuacu auucuuuuaagaacggaaaguaaaauuauuuuugacugaagaaaaauagaugacagugaaaaacauggaaaugauacucaaaaca agugacuuuuucuguaaccuuccaaagaaacugaauuuuccaaggaauuaaaugauaacaguggcuaaaggcauaguuucuaa acuuucaguaagauccuggcauucacagaaaaaaaugaugaauggggucuggacauacagccugagaucucaaaaugacaaug aaauucacaacuuuuucucagagacauucauguuuccugcauaugcuacaacugcaguuugaaaagaggcagcaauggggagca acccuuuacaagaaacaaauugugauauauucauguguuggacggcaguaaauaagaugaaaccugaggagucagauccaccu ucccccauucauagaggcuuuucagccucauuugagguacaguuacauaucuuuugccuuuugcccccgugcauagcuauc uacagccaaucacagaucacagagucacuggacuauagagcuggaaggaagcucagagacaaugccaaggggggcagaaaauuu aucagaagccagucccagugcguuuccuccauuuccuucugcaggaagacuauuuugggcugccugaacauuguaucaaacc ugcuaccuauacuauggucuaccuuuccuccaguggaauuacaaaggcacuaacugaaaugccuucuagaaacagagaaaacg aaacuguacuuauuuacucuugauacacagauuauuuauaaaacagauugaaguaaccuguuaacuggcaaaaagagaaugag aucggauuuaaauguauggcaguaagccuauugaucccuccaguuaucucaguaugacugcaguauauucauucacuaaaa ccacucacuagauaccaacuacacaccuggcacugcagauguaaaggucagucacacauguucugacuuuacagaguucacag uagcaguggaggaugauauaugugggaaacaaaaaaggcauugauucuauucagagcacguuagggcucaaggagagagggg gucuuuccaccuaagaaaugaggaauagggucaucauagaagugaccuuaagucuuaaaaauuaagaaggggauuccaagcu gcuucagacagagacacaucgagcuaaaacacagaggguaugaaagagcacagggacuuuaggaauugcacaguucauucuaac aggaacaaaaggcucaagggggggcaagaaaugaggcuguauggaaagagauucaauguaagcacuuuauaaaauagauuaau -continued uucugauucaaugaagcauuucuugaucauugugu acaaggcacuacaugcaucauggaaaauucauuaggaugcauugcca gcacuuugcagaacugauauuauucagccucaagcuuuccaguggccaaagggaaaugcugacugcuuuucauauauuugag ucaaagauuuuuuauauggucaaugaagacuaauauaagggcagugggauuuucacagaugcaugccauguugucgagagcc ucuuagauuuucucaacugugagaaagaaaaacgaaaaugu ugaagacguugagucuggagagggga uacuaaucacuguc aguugggcacugguggg aaug gggaaauggcacaggaaugcaagccucuccaccc uaccccc cgaacuccagccauacacuca ucguuucacaaaauauaaaugaguuagcauuaaaauguuucagaguaaauaauuccuuuucccgaaaugcaug aagauag agu aacagacuucucacacuguauuuuuagggu auggagaauuuagaagguuaaagaauu acugcuucaauuuuucaguuaaaaa aaaaucaggaagcucucguucauucaggcuaugcaccaugugcacagucaagaauuagcagaaacccucugcauuuacaaacac uuugugcuauaaaaaaguaauuuuuaaaaagccacgugugugugugugu auauauauauauauauauauuuaaagccaag guuuugauacuuuuuuacaaaaacuacaagagaaaacaaauauaccugu ccaaaccauauacuuuuaaaagagcauu uuuuuu uccauacaagcuguuguuaauuggggguaaagugcugauuugcaaacuucaucaaauuguucccaagug gauucuccuug uuugucuccccuaccaaccccaaaguuaccauauuu gauguaagaaucaggcauguuagaauguugu gucacacuaacuga uucugcucuuuuugucuugucauucaaguccguuagcuucuguacgcggugcccuuugcagucgguguc ucuuccagag gcgaggggg cugaggauggggugcugcaucucacuagcuauacuggcaucaucuu gguaaacugaaaaccaaauggg acau uuguaaaaucagugcacuguuucuagagagaguuaaauuc auuuaaaaaaaaa LRP8 isoform 1-Amino acid sequence
(SEQ ID NO: 12)

mglpepgplr llalllllll llllqlqhla aaaadpllgg qgpakdcekd qfqcrnerci psvwrcdedd dcldhsdedd cpkktcadsd ftcdnghcih erwkcdgeee cpdgsdesea tctkqvcpae klscgptshk cvpaswrcdg ekdceggade agcaticaph efqcgnrscl aavfvcdgdd dcgdgsderg cadpacgpre frcggdggga ciperwvcdr qfdcedrsde aaelcgrpgp gatsapaaca tasqfacrsg ecvhlgwrcd gdrdckdksd eadcplgtcr gdefqcgdgt cvlaikhcnq eqdcpdgsde agclqglnec lhnnggcshi ctdlkigfec tcpagfqlld qktcgdidec kdpdacsqic vnykgyfkce cypgyemdll tknckaaagk spsliftnrh evrridlvkr nysrlipmlk nvvaldveva tnriywcdls yrkiysaymd kasdpkeqev lideqlhspe glavdwvhkh iywtdsgnkt isvatvdggr rrtlfsrnls epraiavdpl rgfmywsdwg dqakieksgl ngvdrqtivs dniewpngit ldllsqrlyw vdsklhqlss idfsggnrkt lisstdflsh pfgiavfedk vfwtdlenea ifsanringl eisilaenln nphdivifhe lkqprapdac elsvqpnggc eylclpapqi sshspkytca cpdtmwlgpd mkrcyrapqs tstttlastm trtvpattra pgttvhrsty qnhstetpsl taavpssysv prapsispst lspatsnhsq hyanedskmg stvtaavigi ivpivviall cmsgyliwrn wkrkntksmn fdnpvyrktt eeedelhi grtaqighvy paaissfdrp lwaepclget repedpapal kelfvlpgep rsqlhqlpkn plselpvvks krvalsledd gip LRP8 isoform 2-RNA sequence
(SEQ ID NO: 13)

gcuggcggcggccgcccagggccggggccgcgcgcccagccugagcccgccccgccgccgagcgucaccgaaccugcuugaaa ugcagccgaggagccggggcggg cggcagcgg cggcggcggcggcggcggggg cagcggcaaccccggcgccgcggcaagga cucggagggcugagacgcggcggcggcggcgcgggg agcgcggggcgcggcggccgg agccccgggcccgccaugggccucc ccgagccgggcccucuccggcuucuggcgcugcugcugcugcugcugcugcugcugcugcagcuccagcauccuugcggc ggcagcggcugauccgcugcucggcggccaagggccggccaaggauugcgaaaaggaccaauuccagugccggaacgagcgc ugcaucccucugugugg agaugcgacgaggacgaugacug cuuagaccacagcgacgaggacgacugcccaagaagaccug ugcagacagugacuucaccugugacaacggccacugcauccacgaacgguggaagugugacggcgaggaggagugcccugau ggcuccgaugaguccgaggccacuugcaccaagcaggugugucc ugcagagaagcugagcuguggacccaccagccacaagu guguaccugccucguggcgcugcgacgggg agaaggacugcgaggguggagcggaugaggccggcugugcuaccuggcuga acgagugucugcacaacaauggcggcug cucacacaucugcacugaccucaagauuggcuuugaaugcacgugcccagcaggc uuccagcuccuggaccagaagaccuguggcgacauugaugagugcaaggacccagaugccugcagccagaucuguguc aauu acaagggcuauuuuaagugugaguguacccuggcuacgagauggaccuacugaccaagaacugcaaggcugcu gcuggcaa gagcccaucccuaaucuucaccaaccggcacgaggugcggaggaucgaccuggugaagcggaacuauucacgccucaucccca ugcucaagaaugucguggcacuagaugugGaaguugccaccaaucgcaucuacggugugaccucuccuaccguaagaucua uagcgccuacauggacaaggccagugacccgaaagagcaggagguccucauugacgagcaguugcacucccagagggccug gcaguggacuggguccacaagcacaucuacggacugacucgggcaauaagaccaucucaguggccacaguugauggugcc gccgacgcacucucuucagccguaaccucagugaaccccgggccaucgcuguugaccccugcgagggucauguauuggc ugacugggggaccaggccaagauugagaaaucugggcucaacgguguggaccggcaaacacuggugucagacaauauugaa uggcccaacggaaucacccuggaucugcugagccagcgcuuguacugggguagacuccaagcuacaccaacugccagcauuga cuucagguggaggcaacagaaagacgcugaucuccuccacugacuuccugagccacccuuuugggauagcuguguuugaggac aaggguguucuggacagaccuggagaacgaggccauuucagugcaaaucggcucaauggccuggaaaucuccauccuggcug agaaccucaacaacccacaugacauugucaucuuccaugagcugaagcagccaagagcuccagaugccgugugagcugagugc cagccuaauggaggcugugaauaccugugccuuccugcuccucagaucuccagccacucucccaaguacacaugugccugcc ugacacaaugugcugggguccagacaugaagaggugcuaccgagcaccucaaucuaccucaacuacgacguuagcuucuacca ugacgaggacaguaccugccaccacaagagccccgggaccaccguccacagauccaccuaccagaaccacagcacagagacac caagccugacagcugcagucccaagcucaguuagugucccagggcucccagcaucagcccgucuacccuaagcccugcaacc agcaaccacucccagcacuaugcaaaugaagacaguaagauggcucaacagucacugccgcuguuaucgggaucaucgugcc cauaguggugauagccuccugugcaugauggauaccugaucuggagaaacuggaagcggaagaacaccaaaagcaugaau uuugacaacccagucuacaggaaaacaacagaagaagaagacgaagaugagcuccauauagggagaacugcucagauuggcca ugucuauccugcagcaaucagcagcuuugaucgcccacuguggcagagcccugucuuggggagaccagagaaccggaagac ccagccccugcccucaaggagcuuuugucuugccgggggaaccaaggucacagcugcaccaaacucccgaagaaccucuuuc cgagcugccugucgucaaauccaagcgaguggcauuaagccuugaagaugauggacuacccgaggaugggaucaccccuu cgugccucauggaauucaguccccaugcacuacacucuggaugguguaugacuggaugaauggguuucuauauaugggucug ugugaguguaugugugugugauuuuuuuuuaaauuuauguugcggaaagguaaccacaaaguuaugaugaacugcaaa cauccaaaggaugugagaguuuucuauguauaauguuuuauacacuuuuuaacgguugcacucccaugaggaauucgu ggaauggcuacugcugacuaacaugaugcacauaaccaaaugggggccaauggcacaguaccuuacucaucauuuaaaaacua uauuuacagaagauguuuggugcugggggggcuuuuuagguuuuggggcauuuguuuuuguaaauaagaugauuaug cuuugugggcuauccaucaacauaaguaaaaaaaaaaaaaaaaacuucaacuccucccccauuuagauuauuuauuaacauau uuuaaaaaucgaugaguucuauaaauaauuuagagaagugagaguauuuauuuuuggcauguuuggcccaccacacagacu cugugugguaugugugugggguuauauguguaugugugugacagaaaaaucuguagagaagaggcacaucuauggcuacugu ucaaauacauaaagauaaauuuauuucacacaguccacaaggggguauaucuuguaguuuucagaaaagccuuuggaaaucu ggaucagaaaauagauaccauggguuugugcaauuaguaguaaaaaggcaaaucuuucaccucuggcuauccugagacc ccaggaagucaggaaaagccuuucagcucacccauggcugcuguggacuccuaccagggcuuucuggcuuuggcgaagguca guguacagacauuccauggaccagaguucagaaacucaagauaggauaugccucacccucagcuacuccuuguuuaaag uucagcucuuugaguaacuucuucaauuucuuucaggacacuugggugaauucaguaaguuuccucugaagcacccugaag ggugccauccuuacagagcuaagguggagacguuuccagaucagcccaaguuuacauagagacuggcccaggcacugaaugu cuaggacaugcuguggaugaagauaaagaugguggaauaggguuuaucacaucucuauuucucuuuucccuuacucucua ccauuccuuuaugugggggaaacauuuuaagguaauaaauagguuacuuaccaucauauguucauauagaugaaacuaauuu uuggcuuaagucagaacaacuggccaaaauugaagucauauuugagggggaaauggcauacgcaauauuauauuauauugg auauuuauguucacacaggaauuugguuuacugcuuuguaaauaaaaggaaaaacuccggguauauguauagauguucuuca uuauagacaucuucuuugcuuuucuuggccuugggggaggaagggagaagugcucuuuucuacuugugggggucucccauug gaaacauaauccuauagucccagaaggauucaguccccaguggcuuucccauccaaagagaaagaguuugaguuucuuaacuc -continued ugcuguucugccacuuacucccacuagacaaccagggacaaggugcaacauggaaguguuugacuuaaguaggagcagagga gcugcaucuaaucucaucauaccuggaacuugacacacuuaagcaaaugccuucccaucccuaccugccagaugcccccaacuc aaugaaguuggaugucucaccagcuugauacccuuugaauuuucagucagacauucuggaguucuagcauccuguaccuagg accuuccucugugucacucuuggccuccuaaacucuaagaaaauaacuauauucuggagcuugggcagugguguuuugcauaa uccagcaaucuccucaugacaugcaugguugauaguccugaaacauucauugagaggguaaaugcaguugaccuagaauga ccaauaccaaacagaauuuuaagaacaggugggccaacuccuauggagcuuacucacauauuacuauucuuuuaagaacggaaa guaaauuauuuuugacugaagaaaaaugaugacagugaaaaacauggaaauguacucaaaacaagugacuuuuucuguaacc uccaaagaaacugaauuuuccaaggaauuaaaugauaacaguggcuaaggcauaguuucuaaacuuucaguaagauccugg cauucacagaaaaaaugaugaauggggucuggacauacagccugagaucucaaaaugacaaugaaauucacaacuuuuucuc agagacauucauguuccugcauaugcuacaacugcaguuugaaagaggcagcaaugggagcaacccuuuacaagaaacaaau ugugauauauucauguguuggacggcaguaaauaagaugaaaccugaggagucagauccaccuuccccauucauagaggcu uuucagccucauuugagguacaguuacauaucuuuugccuuuugcccccgugcauagcuaucuacagccaaucacagauca cagaucacuggacauauagagcuggaaggaagcucagagacaaugccaaggggcagaaaauuuaucagaagccagucccagu gcguuccuccauuccuucugcaggaagacuauuugggcugccugaacauuguaucaaaccugcuaccauacuaugguc uaccuuccuccagugg aauucaaaggcacuaacugaaaugccuucuagaaacagagaaaacgaaacuguacuuauuuacuc uugauacacagauuauuuauaaaacagauugaaguaaccuguuaacuggcaaaaagagaaugagaucggauuuaaaauguaug gcaguaaguccuauugaucccuccagauаucucaguaugacugсaguaиauucauucauaaaaccacucacuagauaccaac uacacaccuggcacugcagaugaaaaggucagucacacauguucugacuuuacagaguucacaguagcaguggaggaugaua uauguggaaacaaaaaaggcauugauucuauucagagcacuguuagggcucaaaggagagaggggucuuuccaccuaagaaa ugaggaauagggucaucauagaagugaccuuaagucuuaaaaauuaagaaggggauuccaagcugcuucagacagagacaca ucgagcuaaaacacagaggguagaaagagcacagggacuuuaggaauugcacaguucauucuaacaggaacaaaaggcucaag gggggcaagaaaugaggcuguauggaaagagauucaacuguaagcacuuuauaaaauagauuaauuucugauucaaugaagca uuucuugaucauuguguacaaggcacuacaugcaucauggaaaauucauuaggaugcauugccagcacuuugcagaacugau auuauucagccucaagcuuuccaguggccaaagggaaaugcugacugcuuuucauauauuugagucaaagauuuuuuauaug gucaaugaagacuaauauaagggcaguggga uuuucacagaugcaugccauguugcgagagccucuuagauuuucucaacu gugagaagaaaacgaaaauguugaagacguugagucuggagaggggauacuaaucacuguccaguugggcacugguggga aug gggaaauggcacaggaaugcaagccucuccacccuaccccccgaacuccagccauacacucaucguuucacaaaauauaaa ugaguuagcauuaaaugu uucagaguaaauaauuccuuuucccgaaaugcaugaagauagaguaacagacuucucacacugu auuuuuagggu au ggagaauuuagaagguaaagaauuacugcuucaauuuuucaguuaaaaaaaaaucaggaagcucuguu cauucaggcuaugcaccaugugcacagucaagaauuagcagaaacccucugcauuuacaaacacuuugugcuauaaaaaagua auuuuuaaaagccacguguguguguguauauauauauauauauauauauuuaaagccaagguuuugauacuuuuuuac aaaaacuacaagagaaaacaaauauaccuguccaaaccauauacuuuuaaaagagcauuuuuuuuuccauacaagcuguuguu aauuggggguaaagugcugauuugcaaacuucaucaaauugucccaaguggauucuccuuguuugucucccccuaccaac cccaaaguuaccauauuugauguaagaaucaggcauguuagaauguugugucacacuaacugaиucugсucuuuuugucuug ucauucaaguuccguuagcuucuguacgcggugcccuuugcagucuggugucucuuccagaggcgaggggcugaggauggg ggugcugcaucucacuagcuauacuggcaucaucuugguaaacugaaaaccaaauguggacauuuguaaaaucagugcacug uuucuagagagagauuaaauucauuuaaaaaaaa LRP8 isoform 2-Amino acid sequence (SEQ ID NO: 14)

mglpepgplr llalllllll lllqlqhla aaadpllgg qgpakdcekd qfqcrnerci psywrcdedd dcldhsdedd cpkktcadsd ftcdnghcih erwkcdgeee cpdgsdesea tctkqvcpae klscgptshk cvpaswrcdg ekdceggade agcatwlnec lhnnggcshi ctdlkigfec tcpagfqlld qktcgdidec kdpdacsqic vnykgyfkce cypgyemdll -continued tknckaaagk spsliftnrh evrridlvkr nysrlipmlk nvvaldveva tnriywcdls yrkiysaymd kasdpkeqev
lideqlhspe glavdwvhkh iywtdsgnkt isvatvdggr rrtlfsrnls epraiavdpl rgfmywsdwg dqakieksgl
ngvdrqtivs dniewpngit ldllsqrlyw vdsklhqlss idfsggnrkt lisstdflsh pfgiavfedk vfwtdlenea
ifsanringl eisilaenln nphdivifhe lkqprapdac elsvqpnggc eylclpapqi sshspkytca cpdtmwlgpd
mkrcyrapqs tstttlastm trtvpattra pgttvhrsty qnhstetpsl taavpssysy prapsispst lspatsnhsq
hyanedskmg stvtaavigi ivpivviall cmsgyliwrn wkrkntksmn fdnpvyrktt eeededelhi grtaqighvy
paaissfdrp lwaepclget repedpapal kelfylpgep rsqlhqlpkn plselpvvks krvalsledd gip LRP8 isoform 3-RNA sequence (SEQ ID NO: 15)

gcuggcggcggccgcccagggccggggccgcgcgcccagccugagcccgccccgccgccgagcgucaccgaaccugcuugaaa
ugcagccgaggagccggggcgggcggcagcggcggcggcggcggcgggggcagcggcaaccccggcgccgcggcaagga
cucggagggcugagacgcggcggcggcggcgcggggagcgcggggcgcggcggccggagccccgggcccgccaugggccucc
ccgagccgggcccucuccggcuucuggcgcugcugcugcugcugcugcugcugcugcugcagcuccagcaucuugcggc
ggcagcggcugauccgcugcucggcggccaagggccggccaaggauugcgaaaaggaccaauuccagugccggaacgagcgc
ugcaucccccucuguguggagaugcgacgaggacgaugacugcuuagaccacagcgacgaggacgacugccccaagaagaccug
ugcagacagugacuucaccugugacaacggccacugcauccacgaacgguggaagugugacggcgaggaggaguguccugau
ggcuccgaugaguccgaggccacuugcaccaagcaggugugucugcagagaagcugagcuguggacccaccagccacaagu
guguaccugccucguggcgcugcgacggggagaaggacugcgaggguggagcggaugaggccggcugugcuaccucacugg
gcaccugccguggggacgaguuccaguguggggaugggacauguguccuugcaaucaagcacugcaaccaggagcaggacug
uccagaugggagugaugaagcuggcugccuacaggggcugaacgagugucugcacaacaauggcggcugcucacacaucugc
acugaccucaagauuggcuuugaaugcacgugcccagcaggcuuccagcuccuggaccagaagaccuguggcgacauugaug
agugcaaggacccagaugccugcagccagaucugugucaauuacaagggcuauuuuaagugugagugcuacccuggcuacga
gauggaccuacugaccaagaacugcaaggcugcugcuggcaagagcccaucccuaaucuucaccaaccggcacgaggugcgga
ggaucgaccuggugaagcggaacuauucacgccucauccccaugcucaagaaugucguggcacuagauguggaaguugccac
caaucgcaucuacuggugugaccucuccuaccguaagaucuauagcgccuacauggacaaggccagugacccgaaagagcagg
agguccucauugacgagcaguugcacucuccagagggccuggcaguggacugggucccacaagcacaucuacuggacugacuc
gggcaauaagaccaucucaguggccacaguugaugguggccgccgacgcacucucuucagccguaaccucagugaaccccggg
ccaucgcuguugacccccugcgaggguucauguauuggucugacuggggggaccaggccaagauugagaaaucugggcucaa
cggugugggaccggcaaacacuggugucagacaauauugaauggcccaacggaaucacccuggaucugcugagccagcgcuug
uacugguagacuccaagcuacaccaacuguccagcauugacuucaguggaggcaacagaaagacgcugaucuccuccacuga
cuuccugagccacccuuuugggauagcuguguuugaggacaagguguucuggacagaccuggagaacgaggccauuuucag
ugcaaaucggcucaauggccuggaaaucuccauccuggcugagaaccucaacaacccacaugacauugucaucuuccaugagc
ugaagcagccaagagcuccagaugccugugagcugaguguccagccuaauggaggcugugaauaccugugccuuccugcucc
ucagaucuccagccacucucccaaguacacaugugccuguccugacacaauguggcuggguccagacaugaagaggugcuacc
gagaugcaaaugaagacaguaagaugggcucaacagucacugccgcuguuaucgggaucaucgugcccauaguggugauagc
ccuccugugcaugaguggauaccugaucuggagaaacuggaagcggaagaacaccaaaagcaugaauuuugacaacccagucu
acaggaaaacaacagaagaagaagacgaagaugagcuccauauagggagaacugcucagauuggccaugucuauccugcacga
guggcauuaagccuugaagaugauggacuacccugaggaugggaucacccccuucgugccucauggaauucagucccaugca
cuacacucuggaugguguaugacuggaugaaugguuucuauauaugggucugugugaguguaugugugugugugauuuu
uuuuuuaaauuuauguugcggaaagguaaccacaaaguuaugaugaacugcaaacauccaaaggaugugagaguuuuucuau
guauaauguuuuauacacuuuuuaacugguugcacuacccaugaggaauucguggaauggcuacugcugacuaacaugaugc -continued acauaaccaaauggggggccaauggcacaguaccuuacucaucauuuaaaaacuauauuuacagaagaugu uuggu ugcuggg ggggcuuuuuaggu u uuggggcauu uguu uuuuguaaauaagaugau uau gcuu uguggcuauccaucaacauaaguaaa aaaaaaaaaaaaacacuucaacucccucccccauuuagauuauuuauuaacauauuuuaaaaaucagaugaguucuauaaauaa uuuagagaagugagaguauuuauuuuuggcauguuuggcccaccacacagacucuguguguguaugugugu uuauaugu guaugugugugacagaaaaaucuguagagaagaggcacaucuauggcuacuguucaaauacauaaagauaaauuuauuuuca cacaguccacaaggggu auaucuugu aguuuucagaaaagccuuuggaaaucuggaucagaaaauagauaccaugguuugug caauuauguaguaaaaaaggcaaaucuuuucaccucuggcuauuccugagaccccaggaagucaggaaaagccuuucagcuca cccauggcugcugugacuccuaccagggcuuucuggcuuuggcgaaggucaguguacagacauuccaugguaccagagugc ucagaaacucaagauaggauaugccucacccucagcuacuccuuguuuuaaaguucagcucuuugaguaacuucuucaauuu cuuucaggacacuuggguugaauucaguaaguuuccucugaagcacccugaagggugccauccuuacagagcuaaguggaga cguuccagaucagcccaaguuuacuauagagacuggcccaggcacugaaugucuaggacaugcugu ggaugaagauaaaga uggu ggaauagguuuaucacaucucuuauuucucuuuuccccuuacucucuaccauuuccuuuauguggggaaacauuuu aagguaauaaauagguuacuuaccaucauaugu ucauauagaugaaacuaauuuuuggcuuaaguc agaacaacuggccaaaa uugaagucauauuugaggggggaaauggcauacgcaauauuauauuauauuggauauuuauguucacacaggaauuuggu u uacugcuuuguaaauaaaggaaaaacuccgggu auauguauagauguucuucauuauagacaucuucuuugcu uuucuug gccuuggggg aggaagggagaagugcucuuu ucuacuuguggggucucccauuggaaacauaauccuauagucccagaagga uucaguccccaguggcuuucccauccaaagagaaagaguuugaguuucuuaacucugcuguucgccacuu acucccacuag acaaccagggacaaggugcaacauggaaguguuugacuuaaguaggagcagaggagcugcaucuaaucucaucauaccugga acuugacacacuuaagcaaaugccuucccaucccuaccugccagaugcccccaacucaaugaaguuggaugucucaccagcuu gauacccuuugaauuuucagucagacauucuggaguucuagcauccuguaccuaggaccuuccucugugucacucuuggccu ccuaaacucuaagaaaauaacuauauucuggagcuugggcaguguguuuugcauaauccagcaaucuccucaugacaugcau guguugauaguccugaaacauucauugagagggu aaaugcaguugaccuagaaugaccaauaccaaacagaauuuuaagaaca ggu ggccaacuccuauggagcuuacucacauauuacuauucuuuuaagaacggaaaguaaaauuauuuu ugacugaagaaaa augaugacagugaaaaacauggaaaugu acucaaaacaagugacuuuucuguaaccuuccaaagaaacugaauuuuccaagg aauuaaaugauaacagu ggcuaaggcauaguuucaaacuuucaguaagauccuggcauucacagaaaaaaaugaugaaugg ggucuggacauacagccugagaucucaaaaugacaaugaaauucacaacuuuuucucagagacauucauguuuccugcauau gcuacaacugcaguuugaaagaggcagcaagggagcaacccuuuacaagaaacaaauugugauauauucauguguuggacg gcaguaaauaagaugaaaccugaggagucagauccaccuuccccauucauagaggcuuuucagccucauuuugagguacag uuacauaucuuuugccuuuugcccccgugcauagcuaucuacagccaaucacagaucacagagucacuggacuauagagcug gaaggaagcucagagacaaugccaagggggcagaaaauuuaucagaagccagucccagugcguuuccuccauuuccuucugca ggaagacuauuuugggcugccugaacauuguaucaaaccugcuaccauacuauggucuaccuuuccuccaguggaauuaca aaggcacuaacugaaaugccuucuagaaacagagaaaacgaaacuguacuuauuuacucuugauacacagauuauuuauaaaa cagauugaaguaaccuguuaacuggcaaaaagagaaugagaucggauuuaaaauguauggcaguaagccuauugaucccucc aguuaucucaguaugacugcaguauauucauucacuaaaaccacucacuagauaccaacuacacaccuggcacugcagaugua aaggucagucacacauguucugacuuuacagaguucacaguagcaguggaggaugauauaugu ggaaacaaaaaaggcauug auucuauucagagcacuguagggcucaaaggagagaggggucuuuccaccuaagaaaugaggaauagggucaucauagaag ugaccuuaagucuuaaaaauuaagaaggggauuccaagcugcuucagacagagacacaucgagcuaaaacacagagguaugaa agagcacagggacuuuaggaauugcacaguucauucuaacaggaacaaaaggcucaaggggggcaagaaaugaggcuguaug gaaagagauucaauguaagcacuuuauaaaauagauuaauuucugauucaaugaagcauuucuugaucauuguguacaaggc acuacaugcaucauggaaaauucauuaggaugcauugccagcacuuugcagaacugauauuauucagccucaagcuuuccag uggccaaagggaaaugcugacugcuuuucauauauuugagucaaagauuuuuuauauggucaaugaagacuaauauaagggc

```
agugggauuuucacagaugcaugccauguugucgagagccucuuagauuuucucaacugugagaaagaaaaacgaaaauguu gaagacguugagucuggagaggggauacuaaucacugucccaguugggcacuggugggaauggggaaauggcacaggaaugc aagccucuccacccuaccccccgaacuccagccauacacucaucguuucacaaaauauaaaugaguuagcauuaaauguuucag aguaaauaaauuccuuuucccgaaaugcaugaagauagaguaacagacuucucacacuguauuuuuagggguaggagaauuua gaagguuaaagaauuacugcuucaauuuuucaguuaaaaaaaaaucaggaagcucuguucauucaggcuaugcaccaugugc acagucaagaauuagcagaaacccucugcauuucaaacacuuugugcuauaaaaaguaauuuuuaaaaagccacgugugug uguguguauauauauauauauauauauuuaaagccaagguuuugauacuuuuuuacaaaaacuacaagagaaaacaaaua uaccuguccaaaccauauacuuuuaaaagagcauuuuuuuuuuccauacaagcuguuguuaauuuggggguaaagugcugauu ugcaaacuucaucaaauuguucccaaguggauucuccuuguuugucuccccuaccaaccccaaaguuaccauauuugaugua agaaucaggcauguuagaauguugugucacacuaacugauucugcucuuuuugucuugucauucaaguuccguuagcuucu guacgcggugcccuuugcagucggugucucuuccagaggcgaggggcugaggaugggugcugcaucucacuagcuaua cuggcaucaucuugguaaacugaaaaccaaaugggacauuuguaaaaucagugcacuguuucuagagagagauuaaauuca uuuaaaaaaaa
```

LRP8 isoform 3-Amino acid sequence (SEQ ID NO: 16)

```
mglpepgpplr llallllll lllllqlqhla aaaadpllgg qgpakdcekd qfqcrnerci psvwrcdedd dcldhsdedd cpkktcadsd ftcdnghcih erwkcdgeee cpdgsdesea tctkqvcpae klscgptshk cvpaswrcdg ekdceggade agcatslgtc rgdefqcgdg tcvlaikhcn qeqdcpdgsd eagclqglne clhnnggcsh ictdlkigfe ctcpagfqll dqktcgdide ckdpdacsqi cvnykgyfkc ecypgyemdl ltknckaaag kspsliftnr hevrridlvk rnysrlipml knvvaldvev atnriywcdl syrkiysaym dkasdpkeqe vlideqlhsp eglavdwvhk hiywtdsgnk tisvatvdgg rrrtlfsrnl sepraiavdp lrgfmywsdw gdqakieksg lngvdrqtiv sdniewpngi tldllsqrly wvdsklhqls sidfsggnrk tlisstdfls hpfgiavfed kvfwtdlene aifsanring leisilaenl nnphdivifh elkqprapda celsvqpngg ceylclpapq isshspkytc acpdtmwlgp dmkrcyrdan edskmgstvt aavigiivpi vviallcmsg yliwrnwkrk ntksmnfdnp vyrktteeed edelhigrta qighvypary alsleddglp
```

LRP8 isoform 4-RNA sequence (SEQ ID NO: 17)

```
gcuggcggcggccgcccagggccggggccgcgcgcccagccugagcccgccccgccgccgagcgucaccgaaccugcuugaaa ugcagccgaggagccggggcgggcggcagcggcggcggcggcggcggcggggggcagcggcaaccccggcgccgcggcaagga cucggagggcugagacgcggcggcggcggcgcggggagcgcggggcgcggcggccggagccccgggcccgccaugggccucc ccgagccgggccccucuccggcuucuggcgcugcugcugcugcugcugcugcugcugcugcagcuccagcaucuugcggc ggcagcggcugauccgcugcucggcggccaagggccggccaaggauugcgaaaaggaccaauuccagugccggaacgagcgc ugcaucccucuguguggagaugcgacgaggacgaugacugcuuagaccacagcgacgaggacgacugccccaagaagaccug ugcagacagugacuucaccugugacaacggccacugcaucccgaacggguggaaguguugacggcgaggaggagaguguccugau ggcuccgaugaguccgaggccacuugcaccaagcaggugugucugcagagaagcugagcuguggacccaccagccacaagu guguaccugccucguggcgcugcgacggggagaaggacugcgaggguggagcggaugaggccggcugugcuaccuugugcg ccccgcacgaguuccagugcggcaaccgcucgugccuggccgccguguucgugugcgacggcgacgacugguggacgg cagcgaugagcgcggcugugcagaccggccucgggccccgcgaguuccgcugcggcggcgauggcggcggcgccugcauc ccggagcgcuggggucugcgaccgccaguuugacugcgaggaccgcucggacgaggcagccgagcucugcggccguccgggcc ccggggccacguccgcgcccgccgccugcgccaccgccucccaguucgccugccgcagcggcgagugcgugcaccugggcug gcgcugcgacggcgaccgcgacugcaaagacaaaucggacgaggccgacugcccacuggggcaccugccgggggacgaguucc aguguggggaugggacauguguccuugcaaucaagcacugcaaccaggagcaggacuguccagauggagugaugaagcugg cugccuacaggggcugaacgagugucucgcacaacaauggcggcugcucacacaucugcacugaccucaagauuggcuuugaa
```

-continued ugcacgugcccagcaggcuuccagcuccuggaccagaagaccuguggcgacauugaugaugcaaggacccagaugccugca gccagaucugugucaauuacaagggcuauuuuaaguguagugcuacccuggcuacgagauggaccuacugaccaagaacug caaggcugcugcuggcaagagcccaucccuaaucuucaccaaccggcacgaggugcggaggaucgaccuggugaagcggaacu auucacgccucaucccaugcucaagaaugucguggcacuagaugugaaguugccaccaaucgcaucuacggugugaccu cuccuaccguaagaucuauagcgccuacauggacaaggccagugacccgaaagagcaggagguccucauugacgagcaguugc acucuccagagggccuggcaguggacuggguccacaagcacaucuacuggacugacucgggcaauaagaccaucucaguggcc acaguugauggugccgccgacgcacucucuucagccguaaccucagugaaccccgggccaucgcuguugaccccccugcgag gguucauguauggucugacugggggggaccaggccaagauugagaaaucugggcucaacgguguggaccggcaaacacugg ugucagacaauauugaauggcccaacggaaucacccuggaucugcugagccagcgcuuguacuggguagacuccaagcuacac caacuguccagcauugacuucaguggaggcaacagaaagacgcugaucuccuccacugacuuccugagccacccuuuugggau agcuguguugaggacaaggguguucggacagaccuggagaacgaggccauuucagugcaaaucggcucaauggccuggaa aucuccauccuggcugagaaccucaacaacccacaugacauugucaucuuccaugagcugaagcagccaagagcuccagaugc cugugagcugaguguccagccuaauggaggcugugaauaccugaccuuccugcuccucagaucuccagccacucucccaag uacacaugugccuguccugacacaauguggcuggguccagacaugaagaggugcuaccgagcaccucaaucuaccucaacuac gacguuagcuucuaccaugacgaggacaguaccugccaccacaagagcccccgggaccaccguccacagauccaccuaccagaa ccacagcacagagacaccaagccugacagcugcaguccccaagcucaguuagugucccagggcucccagcaucagcccgucuac ccuaagcccugcaaccagcaaccacucccagcacaugcaaaugaagacaguaagauggggcucaacagucacugccgcuguua ucgggaucaucgugcccauaguggugauagcccuccugugcaugaguggauaccugaucuggagaaacuggaagcggaagaa caccaaaagcaugaauuuugacaacccagucuacaggaaaacaacagaagaagaagacgaagaugagcuccauauagggagaac ugcucagauuggccaugucuauccugcacgaguggcauuaagccuugaagaugauggacuacccugaggaugggaucacccc cuucgugccucauggaauucaguccccaugcacuacacucuggauggguguaugacuggaugaaugggguuucuauauauggggu cugugugaguguaugugugugugugauuuuuuuuuaaauuuauguugcggaaagguaaccacaaaguuaugaugaacugc aaacauccaaaggaugugagaguuuucuaguauaaauguuuuauacacuuuuuaacgguugcacuacccaugaggaauuc guggaauggcuacugcugacuaacaugaugcacauaaccaaaugggggccaauggcacaguaccuuacucaucauuuuaaaaac uauauuuacagaagauguuuggugcuggggggcuuuuuagguuuuggggcauuuguuuuuuguaaauaagaugauua ugcuuuguggcuauccaucaacauaaguaaaaaaaaaaaaaaaaacacuucaacucccucccccauuuagauuauuuauuaaca uauuuuaaaaaucagaugaguucuauaaauaauuuagagaagugagaguauuuauuuuuggcauguuuggcccaccacacag acucugugugugugugugugguuuauaugugugugugugugacagaaaaaucuguagagaagaggcacaucuauggcuac uguucaaauacauaaagauaaauuuauuuucacacaguccacaaggggauaucuuguaguuuucagaaaagccuuuggaaa ucuggaucagaaaauagauaccaugguuuguguccaauuaguguaaaaaaggcaaaucuuuucaccucuggcuauuccgag accccaggaagucaggaaaagccuuucagcucacccauggcugcugugacuccuaccagggcuuucuuggcuuuggcgaagg ucaguguacagacauuccauggguaccagagugcucagaaacucaagauaggauaugccucacccucagcuacuccuuguuuua aaguucagcucuuugaguaacuucuucaauuucuuucaggacacuugggugaauucaguaaguuucccucugaagcacccug aagggugccauccuuacagagcuaaguggagacguuuccagaucagcccaaguuuacauagagacuggcccaggcacgaa ugucuaggacaugcuggaugaagauaaagaugguggaauagguuuuaucacaucucuauuucucuuuucccuuacuc ucuaccauuccuuuaugugggaaacauuuuaagguaauaaauagguuacuuaccaucauauguucauauagaugaaacua auuuuuggcuuaagucagaacaacuggccaaaauugaagucauauuugagggggaaauggcauacgcaauauuauauuaua uuggauauuuauguucacacaggaauuugguuuacugcuuugaaauaaaaggaaaaacuccggguauauguauagauguu cuucauuauagacaucuucuuugcuuuucuuggccuuggggaggaagggagaagugcucuuuucuacuuguggggucucc cauuggaaacauaauccuauagucccagaaggauucaguccccaguggcuuucccauccaaagagaaagaguuugaguuucu uaacucugcuguuucugccacuuacucccacuagacaaccagggacaaggugcaacauggaaguguuugacuuaaguaggagc -continued agaggagcugcaucuaaucucaucauaccuggaacuugacacacuuaagcaaaugccuucccaucccuaccugccagaugccc
ccaacucaaugaaguuggaugucucaccagcuugauacccuuugaauuuucagucagacauucuggaguucuagcauccugu
accuaggaccuuccucuguqucacucuuggccuccuaaacucuaagaaaauaacuauauucuggagcuugggcagugguguuu
ugcauaauccagcaaucuccucaugacaugcaugguugauagccugaaacauucaugagaggguaaaugcaguugaccu
agaaugaccaauaccaaacagaauuuuaagaacaggugggccaacuccuauggagcuuacucacauauuacuauucuuuaaga
acggaaaguaaaauuauuuugacugaagaaaaaugaugacagugaaaaacauggaaauguacucaaaacaagugacuuuuuc
uguaaccuuccaagaaacugaauuuuccaaggaauuaaaugauaacaguggcuaaggcauaguuucuaaacuuucaguaaga
uccuggcauucacagaaaaaaaugaugaauggggucuggacauacagccugagaucucaaaaugacaaugaaauucacaacuu
uuucucagagacauucauguuuccugcauaugcuacaacugcaguuugaaagaggcagcaaugggagcaacccuuuacaaga
aacaaauugugauauauucaugauguuggacggcaguaaaauaagaugaaaccugaggagucagauccaccuuccccauucaua
gaggcuuuucagccucauuuugagguacaguuacauaucuuuugccuuuugcccccgugcauagcuaucuacagccaaucac
agaucacagagucacuggacuauagagcuggaaggaagcucagagacaaugccaaggggggcagaaaauuuaucagaagccagu
cccagugcguuccuccauuuccuucugcaggaagacuauuuugggcugccgaacauuguaucaaaccugcuaccuauacu
auggucuaccuuuccuccaguggaauuacaaaggcacuaacugaaaugccuucuagaaacagagaaaacgaaacuguacuuau
uuacucuugauacacagauuauuuauaaaacagauugaaguaaccuguuaacuggcaaaaagagaaugagaucggauuuaaa
uguauggcaguaaguccuauugaucccuccaguuaucucaguaugacugcaguauauucauucacuaaaaccacucacuaga
uaccaacuacacaccuggcacugcagauguaaaggucagucacacauguucugacuuuacagaguucacaguagcaguggagg
augauauaugugggaaacaaaaaaggcauugauucuauucagagcacuguaagggcucaaaggagagagggucuuuuccaccu
aagaaaugaggaauagggucaucauagaagugaccuuaagucuuaaaaauuaagaaggggauuccaagcugcuucagacaga
gacacaucgagcuaaaacacagagguaugaaagagcacagggacuuuuaggaauugcacaguucauucuaacaggaacaaaagg
cucaaggggggcaagaaaugaggcuguauggaaagagauucaaguuaagcacuuuauaaaauagauuaauuucugauucauu
gaagcauuucuugaucauuguguacaaggcacuacaugcaucauggaaaauucauuaggaugcauugccagcacuuugcaga
acugauauuauucagccucaagcuuuccaguggccaaagggaaaugcugacugcuuuucauauauuuugagucaaagauuuuu
uauauggucaaugaagacuaauauaagggcagugggauuuucacagaugcaugccauguugucgagagcccucuuagauuuuc
ucaacugugagaaagaaaaacgaaaauguugaagacguugagucuggagaggggauacuaaucacuguccaguugggcacug
gugggaaugggaaauggcacaggaaugcaagccucuccacccuaccccccgaacuccagccauacacucaucguuucacaaa
auauaaaugaguuagcauuaaauguuucagaguaaauaauuccuuuucccgaaaugcaugaagauagaguaacagacuucuc
acacuguauuuuaggguauggagaauuuagaagguuaaagaauuacugcuucaauuuucaguuaaaaaaaaaucaggaag
cucuguucauucaggcuaugcaccaugugcacagucaagaauuagcagaaacccucugcauuuacaaacacuuugugcuauaa
aaaaguaauuuuaaaaagccacgugugugugugugugugugugugugugugugugugugugugugugaugauuuuaagccaagguuuugauacuu
uuuuacaaaaacuacaagagaaacaaauauaccuguccaaaccauauacuuuuaaaagagcauuuuuuuuccauacaagcu
guuguuaauuuggggguaaagugcugauuugcaaacuucaucaaauuguucccaaguggauucuccuuguuugucuccccc
uaccaaccccaaaguuaccauauuugauguaagaaucaggcauguuagaauguugugucacacuaacugauucugcucuuuu
ugucuugcauucaaguuccguuagcuucuguacgcggugcccuuugcagucggugucucuuccagaggcgaggggggcug
aggaugggggugcugcaucucacuagcuauacuggcaucaucuugguaaacugaaaaccaaauguggacauuuguaaaaucag
ugcacuguuucuagagagagauuaaauucauuuaaaaaaaa LRP8 isoform 4-Amino acid sequence
                                                                                                      (SEQ ID NO: 18)
mglpepgplr llalllllll llllqlqhla aaaadpllgg qgpakdcekd qfqcrnerci psvwrcdedd dcldhsdedd
cpkktcadsd ftcdnghcih erwkcdgeee cpdgsdesea tctkqvcpae klscgptshk cvpaswrcdg ekdceggade
agcaticaph efqcgnrscl aavfvcdgdd dcgdgsderg cadpacgpre frcggdggga ciperwvcdr qfdcedrsde -continued aaelcgrpgp gatsapaaca tasqfacrsg ecvhlgwrcd gdrdckdksd eadcplgtcr gdefqcgdgt cvlaikhcnq eqdcpdgsde agclqglnec lhnnggcshi ctdlkigfec tcpagfqlld qktcgdidec kdpdacsqic vnykgyfkce cypgyemdll tknckaaagk spsliftnrh evrridlvkr nysrlipmlk nvvaldveva tnriywcdls yrkiysaymd kasdpkeqev lideqlhspe glavdwvhkh iywtdsgnkt isvatvdggr rrtlfsrnls epraiavdpl rgfmywsdwg dqakieksgl ngvdrqtivs dniewpngit ldllsqrlyw vdsklhqlss idfsggnrkt lisstdflsh pfgiavfedk vfwtdlenea ifsanringl eisilaenln nphdivifhe lkqprapdac elsvqpnggc eylclpapqi sshspkytca cpdtmwlgpd mkrcyrapqs tstttlastm trtvpattra pgttvhrsty qnhstetpsl taavpssysv prapsispst lspatsnhsq hyanedskmg stvtaavigi ivpivviall cmsgyliwrn wkrkntksmn fdnpvyrktt eeededelhi grtaqighvy parvalsled dglp CTGF-RNA sequence (SEQ ID NO: 19)

aaacucacacaacaacucuuccccgcugagaggagacagccagugcgacuccacccuccagcucgacggcagccgccccggccg acagccccgagacgacagcccggcgcgucccgguccccaccuccgaccaccgccagcgcuccaggccccgccgcuccccgcucg ccgccaccgcgcccuccgcuccgcccgcagugccaaccaugaccgccgccaguaugggccccguccgcgucgccuucgugguc cuccucgcccucugcagccggccggccgucggccagaacugcagcgggccgugccggugcccggacgagccggcgccgcgcu gcccggcgggcgugagccucgugcuggacggcugcggcugcugccgcgucugcgccaagcagcugggcgagcugugcaccga gcgcgaccccugcgacccgcacaagggccucuucugugacuucggcuccccggccaaccgcaagaucggcgugugcaccgcca aagauggugcucccugcaucuucgguggUacgguguaccgcagcggagaguccuuccagagcagcugcaaguaccagugcac gugccuggacggggcgguggggcugcaugccccugugcagcauggacguucgucugcccagcccugacugccccuucccgagg agggucaagcugcccgggaaaugcugcgaggagugggugugugacgagcccaaggaccaaaccgugguugggccugcccucg cggcuuaccgacuggaagacacguuuggcccagacccaacuaugauuagagccaacugccugguccagaccacagaguggagc gccuguuccaagaccugugggaugggcaucuccacccggguuaccaaugacaacgccuccugcaggcuagagaagcagagccg ccugugcauggucaggccuugcgaagcugaccuggaagagaacauuaagaagggcaaaaagugcauccguacucccaaaaucu ccaagccuaucaaguuugagcuuucuggcugcaccagcaugaagacauaccgagcuaaauucuguggaguauguaccgacgg ccgaugcugcacccccacagaaccaccacccugccgguggaguucaagugcccugacggcgaggucaugaagaagaacauga uguucaucaagaccugugccugccauuacaacugucccggagacaaugacaucuuugaaucgcuguacuacaggaagaugua cggagacauggcaugaagccagagagugagagacauuaacucauuagacuggaacuugaacugauucacaucucauuuuucc guaaaaaugauuucaguagcacaaguuauuuaaaucuguuuuucuaacuggggggaaaagauucccacccaauucaaaacauu gugccaugucaaacaaauagucuaucaaccccagacacugguuugaagaauguuaagacuugacaguggaacuacauuaguac acagcaccagaauguauauuaaggugugggcuuuaggagcagugggagggguaccagcagaaagguuaguaucaucagauagca ucuuauacgaguaauaugccugcuauuugaaguguaauugagaaggaaaauuuuagcgugcucacugaccugccuguagccc cagugacagcuaggaugugcauucuccagccaucaagagacugagucaaguuguuccuuaagucagaacagcagacucagcuc ugacauucugauucgaaugacacuguucaggaaucggaauccugucgauuagacuggacagcuuguggcaagugaauuugcc uguaacaagccagauuuuuuaaaauuuauauuguaaauauugugugugugugugugugguauauauauauauauguacag uuaucuaaguuaauuuaaaguuguuugugccuuuuuauuuuuguuuuuaaugcuuugauauuucaauguuagccucaauu ucugaacaccauagguagaauguaaagcuugucugaucguucaaagcaugaaauggauacuuauauggaaauucugcucaga uagaaugacaguccgucaaaacagauuguuugcaaaggggaggcaucaguguccuuggcaggcugauuucuagguaggaaau gugguagccucacuuuuaaugaacaaauggccuuuauuaaaaacugagugacucuauauagcugaucaguuuuuucaccugg aagcauuuguuucuacuuugauaugacuguuuuucggacaguuuauuuguugagagugugaccaaaaguuacauguuugca ccuuucuaguugaaaauaaaguguauauuuuuucuauaaaaaaaaaaaaaaaaa CTGF-Amino Acid sequence (SEQ ID NO: 20)

mtaasmgpvr vafvvllalc srpavgqncs gpercpdepa prcpagvslv ldgcgccrvc akqlgelcte rdpcdphkgl
fcdfgspanr kigvctakdg apcifggtvy rsgesfqssc kyqctcldga vgcmplcsmd vrlpspdcpf prrvklpgkc
ceewvcdepk dqtvvgpala ayrledtfgp dptmirancl vqttewsacs ktcgmgistr vtndnascrl ekqsrlcmvr
pceadleeni kkgkkcirtp kiskpikfel sgctsmktyr akfcgvctdg rcctphrttt lpvefkcpdg evmkknmmfi
ktcachyncp gdndifesly yrkmygdma LXR-a isoform 1: RNA sequence (SEQ ID NO: 21)

aggaaggagggguggccugaccccucggcaguccucccccucagccuuuccccaaauugcuacuucucuggggcuccagguc
cugcuugugcucagcuccagcucacuggcuggccaccgagacuucuggacaggaaacugcaccauccucuucucccagcaagg
gggcuccagagacugcccacccaggaagucugguggccugggauuuggacagugccuugguaaugaccagggcuccaggaa
gagauguccuuguggcuggggccccugugccugacauuccuccugacucugcgguggagcugugaagccaggcgcacag
gaugcaagcagccaggcccagggaggcagcagcugcauccucagagaggaagccaggaugccccacucugcuggggguacug
cagggguggggcuggaggcugcagagcccacagcccugcucaccagggcagagccccuucagaacccacagagauccgucca
caaaagcggaaaaaggggccagcccccaaaaugcuggggaacgagcuaugcagcgugugugggggacaaggccucgggcuucc
acuacaauguucugagcugcgagggcugcaagggauucuuccgccgcagcgucaucaagggagcgcacuacaucugccacag
uggcggccacugccccauggacaccuacaugcgucgcaagugccaggagugucggcuucgcaaaugccgucaggcuggcaug
cgggaggagugugaccugucagaagaacagauccgccugaagaaacugaagcggcaagaggaggaacaggcucaugccacauc
cuugcccccagggcuuccucaccccccaaauccugcccagcucagcccggaacaacugggcaugaucgagaagcucgucg
cugcccagcaacaguguaaccggcgcuccuuuucugaccggcuucgagucacgccuuggcccauggcaccagauccccauagc
cgggaggcccgucagcagcgcuuugcccacuucacugagcuggccaucgucucugugcaggagauaguugacuuugcuaaac
agcuacccggccuuccugcagcucagccggaggaccagauugcccugcugaagaccucugcgaucgaggugaugcuucugga
gacaucucggagguacaacccugggagugagaguauccaccuuccucaaggauuucaguuauaaccgggaagacuuugccaaa
gcagggcugcaaguggaauucaucaaccccaucuucgaguucuccagggccaugaaugagcugcaacucaaugaugccgagu
uugccuugcucauugcuaucagcaucuucucugcagaccggcccaacgugcaggaccagcuccagguagagaggcugcagca
cacauauguggaagcccugcaugccuacgucuccauccaccauccccaugaccgacugauguucccacggaugcuaaugaaac
uggugagccuccggacccugagcagcguccacucagagcaagucuuugcacgcgucucaggacaaaaagcucccaccgcug
cucucugagaucugggaugugcacgaaugacuguucugccccauauuuucuguuuucuuggccggauggcugaggccugg
uggcugccuccuagaaguggaacagacugagaagggcaaacauuccugggagcugggcaaggagauccucccguggcauuaa
aagagagucaaaggguugcgaguuuuguggcuacugagcaguggagcccucgcuaacacugugcugugucugaagaucaug
cugaccccacaaacggauggggccuggggggccacuuugcacagggguucuccagagcccugcccauccugccuccaccacuuccu
guuuucccacagggccccaagaaaaauucuccacugucaaaaaaaaaa LXR-a (NR1H3) isoform 1: Amino acid sequence (SEQ ID NO: 22)

mslwlgapvp dippdsavel wkpgaqdass qaqggsscil reearmphsa ggtagvglea aeptalltra eppsepteir
pqkrkkgpap kmlgnelcsv cgdkasgfhy nvlscegckg ffrrsvikga hyichsgghc pmdtymrrkc qecrlrkcrq
agmreecvls eeqirlkklk rqeeeqahat slppraspp qilpqlspeq lgmieklvaa qqqcnrrsfs drirvtpwpm
apdphsrear qqrfahftel aivsvqeivd fakqlpgflq lsredqiall ktsaievmll etsrrynpgs esitflkdfs
ynredfakag lqvefinpif efsramnelq lndaefalli aisifsadrp nvqdqlqver lqhtyvealh ayvsihhphd
rlmfprmlmk lvslrtlssv hseqvfalrl qdkklpplls eiwdvhe LXR-a (NR1H3) isoform 2: RNA sequence (SEQ ID NO: 23)

aggaaggagggguggccugaccccucggcaguccucccccucagccuuuccccaaauugcuacuucucuggggcuccagguc
cugcuugugcucagcuccagcucacuggcuggccaccgagacuucuggacaggaaacugcaccauccucuucucccagcaagg gggcuccagagacugcccacccaggaagucuggugg ccuggggauuuggacagugccuugguaaugaccagggcuccaggaa gagaugccuuguggcuggggg ccccugugccugacauuccuccugacucugcgguggagcugug gaagccaggcgcacag gaugcaagcagccaggcccagggaggcagcagcugcauccucagagaggaagccaggaugccccacucugcgggggu acug caggggugggg cuggaggcugcagagcccacagcccugcucaccagggcagagcccccuucagaacccacagagauccgucca caaaagcggaaaaaggggccagcccccaaaaugcugggg aacgagcuaugcagcgug uguggggacaaggccucgggcuucc acuacaauguucugagcugcgagggcugcaagggauucuuccgccgcagcgucaucaagggagcgcacuacaucugccacag uggcggccacugccccauggacaccuacaugcgucgcaagugccaggagugucggcuucgcaaaugccgucaggcuggcaug cgggaggagugugu ccugucagaagaacagauccgccugaagaaacugaagcggcaagaggaggaacaggcucaugccacauc cuugcccccagggcuuccucacc ccccaaauccugcccagcucagcccggaacaacugggcaugaucgagaagcucgucg cugcccagcaacagugua accggcgcuccuuuucugaccggcuucgagucacggugaugcuucuggagacaucucggaggua caacccugggagugagaguauca ccuuccucaaggauuucag uuauaaccgggaagacuuugccaaagcagggcugcaagug gaauucaucaaccccaucuucgaguucuccagggccaugaaugagcugcaacucaaugaugccgaguuugccuugcucauug cuaucagcaucuucucugcagaccggcccaacgug caggaccagcuccagguagagaggcugcagcacacauauguggaagcc cugcaugccuacgucuccauccaccauccccaugaccgacgauguucccacggaugcuaaugaaacuggugagccuccggac ccugagcagcgu ccacucagagcaagu guuugcacugcgucugcaggacaaaaagcucccaccgcugcucucugagaucugg gaugugcacg aaugacuguucugucccc auauuuucuguuuucuggccggauggcugaggccuggug gcugccuccuaga aguggaacagacugagaagggcaaacauuccugggagcuggg caaggagauccucccg uggcauuaaaagagaguc aaaggg uugcgaguuuuguggcuacug agcagug gagcccucgcuaacacugugcugu gucugaagaucaugcugaccccacaaacgg auggg ccugggggc cacuuugcacag ggu ucuccagagcccugcccauccugccuccaccacuuccuguuuu ucccacaggg ccccaagaaaaauucuccacugucaaaaaaaaa LXR-a (NR1H3) isoform 2 : Amino acid sequence
(SEQ ID NO: 24)
mslwlgapvp dippdsavel wkpgaqdass qaqggsscil reearmphsa ggtagvglea aeptalltra eppsepteir pqkrkkgpap kmlgnelcsv cgdkasgfhy nvlscegckg ffrrsvikga hyichsgghc pmdtymrrkc qecrlrkcrq agmreecvls eeqirlkklk rqeeeqahat slpprasspp qilpqlspeq lgmieklvaa qqqcnrrsfs drlrvtvmll etsrrynpgs esitflkdfs ynredfakag lqvefinpif efsramnelq lndaefalli aisifsadrp nvqdqlqver lqhtyvealh ayvsihhphd rlmfprmlmk lvslrtlssv hseqvfalrl qdkklpplls eiwdvhe LXR-a (NR1H3) isoform 3 : RNA sequence
(SEQ ID NO: 25)
aucuuacuuagggaccugcuggggugcggggaaaaggcgcagucucgguggg auugcgugcaggagggucgugg ucuggcu gug gcggaggagcauaagaagacucugcgguggagcugug gaagccaggcgcacaggaugcaagcagccaggcccagggagg cagcagcugcauccucagagaggaagccaggaugccccacucugcgggggu acugcaggggug gggcuggaggcugcagag cccacagcccugcucaccagggcagagcccccuucagaacccacagagauccgucca caaaagcggaaaaaggggccagcccc aaaaugcugggg aacgagcuaugcagcgug uguggggacaaggccucgggcuuccacuacaauguucugagcugcgagggcu gcaagggauucuuccgccgcagcgucaucaagggagcgcacuacaucugccacagug gcggccacugccccauggacaccuac augcgucgcaagugccaggagugucggcuucgcaaaugccgucaggcuggcaugcgggaggagugugu ccugucagaagaac agauccgccugaagaaacugaagcggcaagaggaggaacaggcucaugccacauccuugcccccagggcuuccucacccccc caaauccugcccagcucagcccggaacaacugggcaugaucgagaagcucgucgcugcccagcaacagugua accggcgcuc cuuuucugaccggcuucgagucacgccuuggcccauggaccagauccccauagccggg aggcccgucagcagcgcuuugcc cacuucacgagcuggccaucgucucugugcaggagauaguugacuuugcuaaacagcuaccc ggcuuccugcagcucagcc ggg aggaccagauugcccugcugaagaccucgcgaucgaggugaugcuucuggagacaucucggagguacaacccugggag ugagaguauca ccuuccucaaggauuucag uuauaaccgggaagacuuugccaaagcagggcugcaagug gaauucaucaac -continued

```
cccaucuucgaguucuccaggggccaugaaugagcugcaacucaaugaugccgaguuugccuugcucauugcuaucagcaucu ucucugcagaccggcccaacgugcaggaccagcuccagguagagaggcugcagcacacauaugguggaagcccugcaugccuac gucuccauccaccauccccaugaccgacugauguucccacggaugcuaaugaaacuggugagccuccggacccugagcagcgu ccacucagagcaaguguuugcacugcgucugcaggacaaaaagcucccaccgcugcucucugagaucugggaugugcacgaa ugacuguucuguccccauauuuucuguuuucuuggccggauggcugaggccuggugcugccuccuagaaguggaacagac ugagaagggcaaacauuccugggagcugggcaaggagauccucccguggcauuaaaagagagucaaagggguugcgaguuuug uggcuacugagcaguggagcccucgcuaacacugugcugugucugaagaucaugcugaccccacaaacggaugggccugggg gccacuuugcacagggguucuccagagcccugcccauccugccuccaccacuuccuguuuuucccacagggccccaagaaaaau ucuccacugucaaaaaaaa
```

LXR-a (NR1H3) isoform 3: Amino acid sequence (SEQ ID NO: 26)

```
mphsaggtag vgleaaepta lltraeppse pteirpqkrk kgpapkmlgn elcsvcgdka sgfhynvlsc egckgffrrs vikgahyich sgghcpmdty mrrkcqecrl rkcniagmre ecvlseeqir lkklkrqeee qahatslppr assppqilpq lspeqlgmie klvaaqqqcn rrsfsdrlry tpwpmapdph srearqqrfa hftelaivsv qeivdfakql pgfiqlsred qiallktsai evmlletsrr ynpgsesitf lkdfsynred fakaglqvef inpifefsra mnelqlndae falliaisif sadrpnvqdq lqverlqhty vealhayvsi hhphdrlmfp rmlmklvslr tlssvhseqv falrlqdkkl ppllseiwdv he
```

LXR-a (NR1H3) isoform 4: RNA sequence (SEQ ID NO: 27)

```
gauucuaacuuagcuaagcaaugcuacuggagaccauaggcaaagccaaggu acagcuucagggaagucuuuggugagcccca ucucucauuaccaagguaacgaagcgcagacuccgggcccggguggg cggcaucaccaccagguucacgccgagaaggagcug gaggagagccgcccggcuccagccggaccgcuugcccgccaucaccguug uaaucuaugcagcaaacaagcuggaacccgcug ggguggcaccugcaagcagccgcccggacgcacccacucugcgguggagcugu ggaagccaggcgcacaggaugcaagcagcca ggcccagggaggcagcagcugcauccucagagaggaagccaggaugcccc acucugcgggggguacugcaggggugggcug gaggcugcagagcccacagcccugcucaccaggggcagagcccccuucagaacccacagagauccguccacaaaagcggaaaaag gggccagcccccaaaaugcuggggaacgagcuaugcagcgugugugggga caaggccucgggcuuccacuacaauguucuga gcugcgagggcugcaagggauucuuccgccgcagcgucaucaagggagcg cacuacaucugccacaguggcggccacugccc cauggacaccuacaugcgucgcaagugccaggagugucggcuucgcaaaug ccgucaggcuggcaugcgggaggagugugnc cugucagaagaacagauccgccugaagaaacugaagcggcaagaggaggaa caggcucaugccacauccuugcccccagggc uuccucaccccccaaauccugccccagcucagcccggaacaacugggcaug aucgagaagcucgucgcugcccagcaacagu guaaccggcgcuccuuucugaccggcuucgagucacgccuuggcccaug gcaccagauccccauagccggggaggcccguca gcagcgcuuugcccacuucacugagcuggccaucgucucugugcaggagau aguugacuuugcuaaacagcuacccggcuuc cugcagcucagccgggaggaccagauugcccugcugaagaccucugcga ucgaggugaugcuucggagacaucucggaggu acaacccugggagugagaguaucaccuuccucaaggauuucaguuauaa ccgggaagacuuugccaaagcagggcugcaagu ggaauucaucaaccccaucuucgaguucuccagggccaugaaugagc ugcaacucaaugaugccgaguuugccuugcucauu gcuaucagcaucuucucugcagaccggcccaacgugcaggaccagcuc cagguagagaggcugcagcacacauaugguggaagc ccugcaugccuacgucuccauccaccauccccaugaccgacugauguuc ccacggaugcuaaugaaacuggugagccuccgga cccugagcagcgucccacucagagcaaguguuugcacugcgucugcagga caaaaagcucccaccgcugcucucugagaucugg gaugugcacgaaugacuguucugucccc auauuuucuguuuucuuggccggauggcugaggccuggugcugccuccuaga aguggaacagacugagaagggcaaacauuccugggagcugggcaaggagau ccucccguggcauuaaaagagagucaaaggg uugcgaguuuuguggcuacugagcaguggagcccucgcuaacacugugc ugugucugaagaucaugcugaccccacaaacgg aug ggccuggggg ccacuuugcacagggguucuccagagcccugcccaucc ugccuccaccacuuccuguuuuucccacaggg ccccaagaaaaauucuccacugucaaaaaaaa
```

LXR-a (NR1H3) isoform 4: Amino acid sequence (SEQ ID NO: 28)

mqqtswnplg gtckqppgrt hsavelwkpg aqdasssqaqg gsscilreea rmphsaggta gvgleaaept alltraepps
epteirpqkr kkgpapkmlg nelcsvcgdk asgfhynvls cegckgffrr svikgahyic hsgghcpmdt ymrrkcqecr
lrkcrqagmr eecvlseeqi rlkklkrqee eqahatslpp rassppqilp qlspeqlgmi eklvaaqqqc nrrsfsdrlr
vtpwpmapdp hsrearqqrf ahftelaivs vqeivdfakq lpgflqlsre dqiallktsa ievmlletsr rynpgsesit
flkdfsynre dfakaglqve finpifefsr amnelqlnda efalliaisi fsadrpnvqd qlqverlqht yvealhayvs
ihhphdrlmf prmlmklvsl rtlssvhseq vfalrlqddk lppllseiwd vhe LXR-b (NR1H2) isoform 1: RNA sequence (SEQ ID NO: 29)

ucgucaaguuucacgcuccgccccucuuccggacgugacgcaagggcgggguugccggaagaaguggcgaaguuacuuuuga
ggguauuugaguagcggcggugugucaggggcuaaagaggaggacgaagaaaagcagagcaagggaacccagggcaacagga
guaguucacuccgcgagaggccguccacgagaccccccgcgcgcagccaugagccccgcccccgcuguugcuuggagaggggc
gggaccuggagagaggcugcuccgugaccccaccauguccucuccuaccacgaguucccuggauaccccccugccuggaaaug
gccccccucagccuggcgccccuucuucuucacccacugaaaggaggagggguccggagccgugugccccgggggguccggaccc
ugaugucccaggcacugaugaggccagcucagccugcagcacagacugggucaucccagaucccgaagaggaaccagagcgca
agcgaaagaagggcccagccccgaagaugcugggccacgagcuuugccgugucguggggacaaggccuccggcuuccacua
caacgugcucagcugcgaaggcugcaagggcuucuuccggcgcagugugguccguggugggggccaggcgcuaugccugccg
gggugggcggaaccugccagaugacgcuuucaugcggcgcaagugccagcagugccggcugcgcaagugcaaggaggcaggg
augagggagcagugcguccuuucugaagaacagauccggaagaagaagauucggaaacaacagcagcaggagucacagucaca
gucgcagucaccugugggggccgcagggcagcagcagcucagccucugggccuggggcuuccccugguggaucugaggcaggc
agccagggcuccggggaaggcgaggguguccagcuaacagcggcucaagaacuaaugauccagcaguuggugcggcccaac
ugcagugcaacaaacgcuccuucuccgaccagcccaaagucacgcccuggccccuggcgcagaccccagucccgagaugccc
gccagcaacgcuuugcccacuucacggagcuggccaucaucucaguccaggagaucguggacuucgcuaagcaagugccugg
uuuccugcagcugggccgggaggaccagaucgccccucugaaggcauccacuaucgagaucaugcugcuagagacagccagg
cgcuacaaccacgagacagaguguaucaccuucuugaaggacuucaccuacagcaaggacgacuuccaccgugcaggccugca
ggaggaguucaucaaccccaucuucgaguucucgcgggccaugcggcggcugggccuggacgacgcugaguacgcccugcuc
aucgccaucaacaucuucucggccgaccggcccaacgugcaggagccgggccgcguggaggcguugcagcagcccuacgugg
aggcgcugcuguccuacacgcgcaucaagaggccgcaggaccagcugcgcuucccgcgcaugcucaugaagcuggugagccu
gcgcacgcugagcucugugcacucggagcaggucuucgccuugcggcuccaggacaagaagcugccgccucugcugucggag
aucugggacguccacgagugagggcuggccacccagcccacagccuugccugaccacccucagcagauagacgccggcac
cccuuccucuuccuaggguggaaggggcccugggccgagccuguagaccuaucggcucucauccccuugggauaagccccagu
ccaggyccaggaggcuccccucccugcccagcgagucuuccagaagggggugaaagggguugcagguccccgaccacugacccuucc
cggcugcccuccuccccagcuuacaccucaagcccagcacgcagugcaccuugaacagagggagggggagacccauggcucu
cccccccuagcccgggagaccagggccuuccucuuccucugcuuuuauuuaauaaaaacuaaaaacagaaacaggaaauaaaa
uaugaauacaauccagcccgggagcuggagugca LXR-b (NR1H2) isoform 1: Amino acid sequence (SEQ ID NO: 30)

mssptsssld tplpgngppq pgapssspv keegpepwpg gpdpdvpgtd eassacstdw vipdpeeepe rkrkkgpapk
mlghelcrvc gdkasgfhyn vlscegckgf frrsvvrgga rryacrgggt cqmdafmrrk cqqcrlrkck eagmreqcvl
seeqirkkki rkqqqesqs qsqspvgpqg ssssasgpga spggseagsq gsgegegvql taaqelmiqq lvaaqlqcnk
rsfsdqpkvt pwplgadpqs rdarqqrfah ftelaiisvq eivdfakqvp gflqlgredq iallkastie imlletarry nhetecitfl
kdftyskddf hraglqvefi npifefsram rrlglddaey alliainifs adrpnvqepg rvealqqpyv eallsytrik
rpqdqlrfpr mlmklvslrt lssvhseqvf alrlqdkklp pllseiwdvh e LXR-b (NR1H2) isoform 2: RNA sequence (SEQ ID NO: 31)

ucgucaaguuucacgcuccgccccucuuccggacgugacgcaagggcggggüugccggaagaaguggcgaaguuacuuuuga
ggguauuugaguagcggcggugugucaggggcuaaagaggaggacgaagaaaagcagagcaagggaacccagggcaacagga
guaguucacuccgcgagaggccguccacgagaccccgcgcgcagccaugagccccgcccccgcuguugcuuggagaggggc
gggaccuggagagaggcugcuccgugaccccaccaugucccucuccuaccacgaguucccuggauaccccccugccuggaaaug
gccccccucagccuggcgccccuucuucuucacccacugaaaggagggggucggagccguggcccggggguccggaccc
ugaugucccaggcacugaugaggccagcucagccugcagcacagacuggggcguccuuucugaagaacagauccggaagaag
aagauucggaaacaacagcagcaggagucacagucacagucgcagucaccgugggggccgcagggcagcagcagcucagccuc
ugggccuggggcuuccccugguggaucugaggcaggcagccagggcuccggggaaggcgagggugccagcuaacagcggc
ucaagaacuaaugauccagcaguugguggcggcccaacugcagugcaacaaacgcuccuucuccgaccagcccaaagucacgc
ccuggccccugggcgcagaccccagucccgagaugcccgccagcaacgcuuugcccacuucacggagcuggccaucaucuca
guccaggagaucguggacuucgcuaagcaagugccugguuuccugcagcugggccgggaggaccagaucgcccuccugaagg
cauccacuaucgagaucaugcugcuagagacagccaggcgcuacaaccacgagacagaguguauccaccuucuugaaggacuuc
accuacagcaaggacgacuuccaccgugcaggccugcaggguggaguucaucaaccccaucuucgaguucucgcgggccaugcg
gcggcugggccuggacgacgcugaguacgcccugcucaucgccaucaacaucuucucggccgaccggcccaacgugcaggagc
cgggccgcguggaggcguugcagcagcccuacguggaggcgcugcugucccuacacgcgcaucaagaggccgcaggaccagcu
gcgcuucccgcgcaugcucaugaagcuggugagccugcgcacgcugagcucugugcacucggagcaggucuucgccuugcgg
cuccaggacaagaagcugccgccucugcugucggagaucugggacguccacgagugaggggcuggccacccagcccacagcc
uugccugaccacccuccagcagauagacgccggcacccccuuccucuuccuagggguggaaggggcccugggccgagccuguag
accuaucggcucucaucccuugggauaagccccaguccaggüccaggaggcucccucccugcccagcgagucuuccagaaggg
gugaaagggüucagguccegaccacugacccuuccggcugccuccuccccagcuuacaccucaagcccagcacgcagug
caccuugaacagaggggagggaggacccauggcucuccccccüagcccgggagaccagggccuuccucuuccucugcuuuüa
uuuaauaaaaacuaaaaacagaaacaggaaaauaaaauaugaauacaauccagcccggagcuggagugca LXR-b (NR1H2) isoform 2 : Amino acid sequence (SEQ ID NO: 32)

msspttssld tplpgngppq pgapsssptv keegpepwpg gpdpdvpgtd eassacstdw gvlseeqirk kkirkqqqqe
sqsqsqspvg pqgssssasg pgaspggsea gsqqsgegeg vqltaaqelm iqqlvaaqlq cnkrsfsdqp kvtpwplgad
pqsrdarqqr fahftelaii svqeivdfak qvpgflqlgr edqiallkas tieimlleta rrynheteci tflkdftysk ddfhraglqv
efinpifefs ramrrlgldd aeyalliain ifsadrpnvq epgrvealqq pyveallsyt rikrpqdqlr fprmlmklvs
lrtlssvhse qvfalrlqdk klppllseiw dvhe has-miR-199a-1 sequence (SEQ ID NO: 33)

GCCAACCCAGUGUUCAGACUACCUGUUCAGGAGGCUCUCAAUGUGUACAGUAGUC
UGCACAUUGGUUAGGC has-miR-199a-2 sequence (SEQ ID NO: 34)

AGGAAGCUUCUGGAGAUCCUGCUCCGUCGCCCCAGUGUUCAGACUACCUGUUCAG
GACAAUGCCGUUGUACAGUAGUCUGCACAUUGGUUAGACUGGGCAAGGGAGAGC
A has-miR-1908 sequence (SEQ ID NO: 35)

CGGGAAUGCCGCGGCGGGGACGGCGAUUGGUCCGUAUGUGUGGUGCCACCGGCCG
CCGGCUCCGCCCCGGCCCCCGCCCC has-miR-7-1 sequence (SEQ ID NO: 36)

UUGGAUGUUGGCCUAGUUCUGUGUGGAAGACUAGUGAUUUUGUUGUUUUUAGAU
AACUAAAUCGACAACAAAUCACAGUCUGCCAUAUGGCACAGGCCAUGCCUCUACA
G has-miR-7-2 sequence (SEQ ID NO: 37)

CUGGAUACAGAGUGGACCGGCUGGCCCCAUCUGGAAGACUAGUGAUUUUGUUGU
UGUCUUACUGCGCUCAACAACAAAUCCCAGUCUACCUAAUGGUGCCAGCCAUCGC
A

```
has-miR-7-3 sequence
                                                                           (SEQ ID NO: 38)
AGAUUAGAGUGGCUGUGGUCUAGUGCUGUGUGGAAGACUAGUGAUUUUGUUGUU
CUGAUGUACUACGACAACAAGUCACAGCCGGCCUCAUAGCGCAGACUCCCUUCGA
C miR-Zip 199a-3p sequence
                                                                           (SEQ ID NO: 39)
GATCCGACAGTAGCCTGCACATTAGTCACTTCCTGTCAGTAACCAATGTGCAGACTA
CTGTTTTTTGAATT miR-Zip 199a-5p sequence
                                                                           (SEQ ID NO: 40)
GATCCGCCCAGTGCTCAGACTACCCGTGCCTTCCTGTCAGGAACAGGTAGTCTGA
ACACTGGGTTTTTGAATT miR-Zip 1908 sequence
                                                                           (SEQ ID NO: 41)
GATCCGCGGCGGGAACGGCGATCGGCCCTTCCTGTCAGGACCAATCGCCGTCCCCG
CCGTTTTTGAATT miR-Zip 7 sequence
                                                                           (SEQ ID NO: 42)
GATCCGTGGAAGATTAGTGAGTTTATTATCTTCCTGTCAGACAACAAAATCACTAGT
CTTCCATTTTTGAATT
```

The members of this network can be used as targets for treating metastatic melanoma. In addition, the members can be used a biomarkers for determining whether a subject has, or is at risk of having, a metastatic melanoma or for determining a prognosis or surveillance of patient having the disorder. Accordingly, the present invention encompasses methods of treating metastatic melanoma by targeting one or more of the members, methods of determining the efficacy of therapeutic regimens for inhibiting the cancer, and methods of identifying anti-cancer agent. Also provided are methods of diagnosing whether a subject has, or is at risk for having, metastatic melanoma, and methods of screening subjects who are thought to be at risk for developing the disorder. The invention also encompasses various kits suitable for carrying out the above mentioned methods.

ApoE Polypeptides

The term "polypeptide or peptide" as used herein includes recombinantly or synthetically produced fusion or chimeric versions of any of the aforementioned metastasis suppressors, having the particular domains or portions that are involved in the network. The term also encompasses an analog, fragment, elongation or derivative of the peptide (e.g. that have an added amino-terminal methionine, useful for expression in prokaryotic cells).

"Apolipoprotein polypeptide or ApoE polypeptide" as used herein means a peptide, drug, or compound that mimics a function of the native apolipoprotein either in vivo or in vitro including apolipoprotein analogs, fragments, elongations or derivatives that are a peptide of between 10 and 200 amino acid residues in length, such peptides can contain either natural, or non-natural amino acids containing amide bonds. Apolipoprotein peptide fragments may be modified to improve their stability or bioavailability in vivo as known in the art and may contain organic compounds bound to the amino acid side chains through a variety of bonds.

In one aspect, our invention is a method for using an isolated apoEp1.B peptide having the amino acid sequence TQQIRLQAEIFQAR (murine)(SEQ. ID. No.43) or AQQ-IRLQAEAFQAR (human)(SEQ. ID. No.44) or an analog, fragment, elongation or derivative of the peptide. The invention also includes a nucleic acid molecule encoding the apoEpI.B peptide, or an analog, fragment, elongation or derivative thereof.

The term "analog" includes any peptide having an amino acid residue sequence substantially identical to the native peptide in which one or more residues have been conservatively substituted with a functionally similar residue and which displays the ability to mimic the native peptide. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite activity. Analogs of the peptides include peptides having the following sequences: TAQIRLQAEIFQAR (SEQ.ID.NO.:45); TQAIRLQAEIFQAR (SEQ.ID.NO.:46); TQQARLQAEIFQAR (SEQ.ID.NO.:47) and TQQ-IALQAEIFQAR (SEQ.ID.NO.:48).

"Derivative" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject peptide having an amino acid residue sequence shorter than that of a peptide whose amino acid residue sequence is shown herein.

The term "elongation" refers to any subject peptide having an amino acid sequence longer by one or two amino acids (either at the carboxy or amino terminal end) than that of a peptide of the present invention. Preferably, the elongation occurs at the amino terminal end. Fragments and elongations of the peptides include peptides that have the following sequences: QTQQIRLQAEIFQAR (SEQ.ID.NO.:49) and QQIRLQAEIFQAR (SEQ.ID.NO.:50).

ApoE polypeptides and methods for their preparation are described in U.S. Pat. No. 6,652,860, incorporated herein by reference.

LXR Agonists

The methods of the invention can include administering a LXR agonist for the prevention and treatment of metastasis. The LXR agonist can be a compound according to the Formula I, II, III, or IV shown below.

Formula I is provided below:

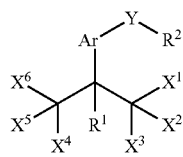

Formula I or a pharmaceutically acceptable salt thereof, wherein
Ar is an aryl group;
$R^1$ is a member selected from the group consisting of
—OH, —CO$_2$H, —O—(C$_1$-C$_7$)alkyl, —OC(O)—, —(C$_1$-C$_7$)heteroalkyl, —OC(O)—(C$_1$-C$_7$)heteroalkyl, —NH$_2$, —NH(C$_1$-C$_7$) alkyl, —N((C$_1$-C$_7$)alkyl)$_2$ and —NH—S(O)$_2$(C$_1$-C$_5$)alkyl;
$R^2$ is a member selected from the group consisting of
(C$_1$-C$_7$)alkyl, (C$_1$-C$_7$)heteroalkyl, aryl and aryl (C$_1$-C$_7$) alkyl;
$X^1$, $X^2$, $X^3$, $X^4$, $X^5$ and $X^6$ are each independently a member selected from the group consisting of:
H, (C$^1$-C$^5$)alkyl, (C$^1$-C$^5$)heteroalkyl, F and Cl, with the proviso that no more than three of $X^1$ through $X^6$ are H, (C$^1$-C$^5$)alkyl, (C$^1$-C$^5$)heteroalkyl; and
Y is a divalent linking group selected from the group consisting of:
—N(R$^{12}$)S(O)$_m$—, —N(R$^{12}$)S(O)$_m$N(R$^{13}$)—, —N(R$^{12}$)C(O)—, —N(R$^{12}$)C(O)N(R$^{13}$)—, —N(R$^{12}$)C(S)— and —N(R$^2$)C(O)O—;
wherein R$^{12}$ and R$^{13}$ are each independently selected from the group consisting of:
H, (C$_1$-C$_7$)alkyl, (C$_1$-C$_7$)heteroalkyl, aryl and aryl(C$_1$-C$_7$) alkyl, and optionally when Y is —N(R$^{12}$)S(O)$_m$— or —N(R$^{12}$)S(O)$_m$N(R$^{13}$)—, R$^{12}$ forms a five- or six-membered ring fused to Ar or to R$^2$ through covalent attachment to Ar or to R$^2$, respectively; and the subscript m is an integer of from 1 to 2;
with the proviso that when R$^1$ is OH, and —Y—R$^2$ is —N(R$^{12}$)S(O)$_m$—R$^2$ or —N(R$^{12}$)C(O)N(R$^{13}$)—R$^2$ and is attached to a position para to the quaternary carbon attached to Ar, and when R$^2$ is phenyl, benzyl, or benzoyl, then i) at least one of R$^{12}$ or R$^{13}$ is other than hydrogen and contains an electron-withdrawing substituent, or ii) R$^2$ is substituted with a moiety other than amino, acetamido, di(C$_1$-C$_7$)alkylamino, (C$_1$-C$_7$)alkylamino, halogen, hydroxy, nitro, or (C$_1$-C$_7$)alkyl, or iii) the benzene ring portion of R$^2$ is substituted with at least three independently selected groups in addition to the Y group or point of attachment to Y.

In some embodiments, Y is —N(R12)S(O)2- and R1 is OH.

Accordingly, the compounds of Formula I include but are not limited the compound with the structure shown below:

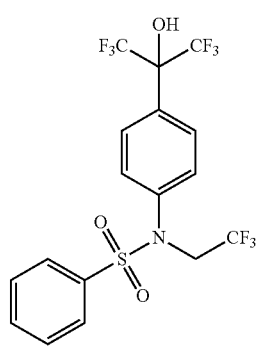

Compounds of Formula I can be synthesized as described by U.S. Pat. No. 6,316,503, incorporated herein by reference.

Formula II is provided below:

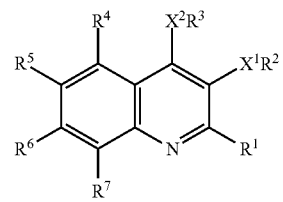

Formula II wherein:
$R^1$ is -H;
$X^1$ is a bond, C$_1$ to C$_5$ alkyl, —C(O)—, —C(=CR$^8$R$^9$)—, —O—, —S(O)$_t$—, —NR$^8$—, —CR$^8$R$^9$—, —CHR$^{23}$, —CR$^8$(CR$^9$)—, —C(CR$^8$)$_2$—, —CR$_8$(OC(O)R$^9$)—, —C=NOR$^9$—, —C(O)NR$^8$—, —CH$_2$O—, —CH$_2$S—, —CH$_2$NR$^8$—, —OCH$_2$—, —SCH$_2$—, —NR$^8$CH$_2$—, or

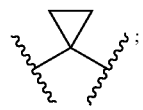 [SMILES: *C1(*)CC1]

$R^2$ is H, C$_1$ to C$_6$alkyl, C$_2$to C$_6$alkenyl, C$_2$to C$_6$alkynyl, C$_3$ to C$_6$ cycloalkyl, —CH$_2$OH, C7 to C$_{11}$ arylalkyl, phenyl, naphthyl, C$_1$ to C$_3$ perfluoroalkyl, CN, C(O)NH$_2$, CO$_2$R$^{12}$ or phenyl substituted independently by one or more of the groups independently selected from C$_1$ to C$_3$ alkyl, C$_2$to C$_4$ alkenyl, C$_2$ to C$_4$ alkynyl, C$_1$ to C$_3$ alkoxy, C$_1$ to C$_3$ perfluoroalkyl, halogen, —NO$_2$, —NR$^8$R$^9$, —CN, —OH, and C$_1$ to C$_3$alkyl substituted with 1 to 5 fluorines, or R$^2$ is a heterocycle selected from the group consisting of pyridine, thiophene, benzisoxazole, benzothiophene, oxadiazole, pyrrole, pyrazole, imidazole, and furan, each of which may be optionally substituted with one to three groups independently selected from $C_1$ to $C_3$ alkyl, $C_1$ to $C_3$ alkoxy, $C_1$ to $C_3$ perfluoroalkyl, halogen, $-NO_2$, $-NR^8R^9$, $-CN$, and $C_1$ to $C_3$alkyl substituted with 1 to 5 fluorines;

$X^2$ is a bond or $-CH_2-$;

$R^3$ is phenyl, naphthyl, or phenyl or naphthyl substituted independently by one to four groups independently selected from $C_1$ to $C_3$ alkyl, hydroxy, phenyl, acyl, halogen, $-NH2$, $-CN$, $-NO_2$, $C_1$ to $C_3$ alkoxy, $C_1$ to $C_3$perfluoroalkyl, $C_1$ to $C_3$ alkyl substituted with 1 to 5 fluorines, $NR^{14}R^{15}$, $-C(O)R^{10}$, $-C(O)NR^1R^{11}$, $-C(O)NR^{11}A$, $-C\equiv CR^8$, $-CH=CHR^8$, $-WA$, $-C\equiv CA$, $-CH=CHA$, $-WYA$, $-WYNR^{11}-A$, $-WYR^{10}$, $-WY(CH2)_jA$, $-WCHR^{11}(CH2)_jA$, $-W(CH2)_jA$, $-W(CH2)_jR^{10}$, $-CHR^{11}W(CH_2)_jR^{10}$, $-CHR^{11}W(CH_2)_jA$, $-CHR^{11}NR^{12}YA$, $-CHR^{11}NR^{12}YR^{10}$, pyrrole, $-W(CH_2)_jA(CH_2)_kD(CH_2)_pZ$, $-W(CR^{18}R^{19})A(CH_2)_kD(CH_2)_pZ$, $-(CH_2)_jWA(CH_2)_kD(CH_2)_pZ$, $-CH=CHA(CH2)_kD(CH2)pZ$, $-C\equiv CA(CH_2)_kD(CH_2)_pZ$, $-W(CH_2)_jC\equiv CA(CH_2)_kD(CH2)_pZ$, and $-W(CH_2)_jZ$, or $R^3$ is a heterocycle selected from pyrimidine, thiophene, furan, benzothiophene, indole, benzofuran, benzimidazole, benzothiazole, benzoxazole, and quinoline, each of which may be optionally substituted with one to three groups independently selected from $C_1$ to $C_3$alkyl, $C_1$ to $C_3$ alkoxy, hydroxy, phenyl, acyl, halogen, $-NH_2$, $-CN$, $-NO_2$, $C_1$ to $C_3$ perfluoroalkyl, $C_1$ to $C_3$ alkyl substituted with 1 to 5 fluorines, $-C(O)R^{10}$, $-C(O)NR^{10}R^{11}$, $-C(O)NR^{11}A$, $-C\equiv CR^8$, $-CH=CHR^8$, $-WA$, $-C\equiv CA$, $-CH=CHA$, $-WYA$, $-WYR^{10}$, $-WY(CH_2)_jA$, $-W(CH_2)_jA$, $-W(CH_2)_jR^{10}$, $-CHR^{11}W(CH_2)_jR^{10}$, $-CHR^{11}W(CH_2)_jA$, $-CHR^{11}NR^{12}YA$, $-CHR^{11}NR^{12}Y^{10}$, $-WCHR^{11}(CH_2)_jA$, $-W(CH_2)_jA(CH_2)_kD(CH_2)_pZ$, $-W(CR^{18}R^{19})A(CH_2)_kD(CH_2)_pZ$, $-(CH_2)_jWA(CH_2)_kD(CH_2)_pZ$, $-CH=CHA(CH_2)_kD(CH_2)_pZ$, $-C\equiv CA(CH_2)_kD(CH_2)_pZ$, $-W(CH_2)_jC\equiv CA(CH_2)_kD(CH_2)_pZ$, and $-W(CH_2)_jZ$;

W is a bond, -0-, $-S-$, $-S(O)-$, $-S(O)_2-$, $-NR^{11}-$, or $-N(COR^{12})-$;

Y is $-CO-$, $-S(O)^2-$, $-CONR^{13}-$, $CONR^{13}CO-$, $-CONR^{13}SO_2-$, $-C(NCN)-$, $-CSNR^{13}$, $-C(NH)NR^{13}$, or $-C(O)O-$;

j is 0 to 3;
k is 0 to 3;
t is 0 to 2;

D is a bond, $-CH=CH-$, $-C\equiv C-$, $-C=$, $-C(O)-$, phenyl, $-O-$, $-NH-$, $-S-$, $-CHR^{14}-$, $-CR^{14}R^{15}-$, $-OCHR^{14}-$, $-OCR^{14}R^{15}-$, or $-CH(OH)CH(OH)-$;

p is 0 to 3;

Z is $-CO_2R^{11}$, $-CONR^{10}R^{11}$, $-C(NR^{10})NR^{11}R^{12}$, $-CONH_2NH_2$, $-CN$, $-CH_2OH$, $-NR^{16}R^{17}$, phenyl, $CONHCH(R^{20})COR^{12}$, phthalimide, pyrrolidine-2,5dione, thiazolidine-2,4-dione, tetrazolyl, pyrrole, indole, oxazole, 2-thioxo-1,3-thiazolinin-4-one, $C_1$ to $C_7$ amines, $C_3$ to $C_7$ cyclic amines, or $C_1$ to $C_3$ alkyl substituted with one to two OH groups; wherein said pyrrole is optionally substituted with one or two substituents independently selected from the group consisting of $-CO_2CH_3$, $-CO_2H$, $-COCH_3$, $-CONH_2$, and $-CN$;

wherein said $C_1$ to $C_7$amines are optionally substituted with one to two substituents independently selected from the group consisting of $-OH$, halogen, $-OCH_3$, and $-C\equiv CH$;

wherein said phenyl is optionally substituted with $CO_2R^{11}$, and wherein said $C_3$ to $C_7$ cyclic amines are optionally substituted with one or two substituents independently selected from the group consisting of $-OH$ $-CH_2OH$, $C_1$ to $C_3$ alkyl, $-CH_2OCH_3$, $-CO_2CH_3$, and $-CONH_2$, and wherein said oxazole is optionally substituted with $CH_2CO_2R^{11}$;

A is phenyl, naphthyl, tetrahydronaphthyl, indan or biphenyl, each of which may be optionally substituted by one to four groups independently selected from halogen, $C_1$ to $C_3$ alkyl, $C_2$ to $C_4$ alkenyl, $C_2$ to $C_4$ alkynyl, acyl, hydroxy, halogen, $-CN$, $-NO_2$, $-CO_2R^{11}$, $-CH_2CO_2R^{11}$, phenyl, $C_1$ to $C_3$perfluoroalkoxy, $C_1$ to $C_3$ perfluoroalkyl, $-NR^{10}R^{11}$, $-CH_2NR^{10}R^{11}$, $-SR^{11}$, $C_1$ to $C_6$ alkyl substituted with 1 to 5 fluorines, $C_1$ to $C_3$alkyl substituted with 1 to 2-OH groups, $C_1$ to $C_6$ alkoxy optionally substituted with 1 to 5 fluorines, or phenoxy optionally substituted with 1 to 2 $CF_3$ groups; or A is a heterocycle selected from pyrrole, pyridine, pyridine-N-oxide, pyrimidine, pyrazole, thiophene, furan, quinoline, oxazole, thiazole, imidazole, isoxazole, indole, benzo[1,3]-dioxole, benzo[1,2,5]-oxadiazole, isochromen-l-one, benzothiophene, benzofuran,2,3-di-5 hydrobenzo[1,4]-dioxine, bitheinyl, quinazolin-2,4-9[3H]dione, and 3-H-isobenzofuran-1-one, each of which may be optionally substituted by one to three groups independently selected from halogen, $C_1$ to $C_3$ alkyl, acyl, hydroxy, $-CN$, $-NO_2$, $C_1$ to $C_3$perfluoroalkyl, $-NR^{10}R^{11}$, $-CH_2NR^{10}R^{11}$, $-SR^{11}$, $C_1$ to $C_3$ alkyl substituted with 1 to 5 fluorines, and $C_1$ to $C_3$ alkoxy optionally substituted with 1 to 5 fluorines;

$R^4$, $R^5$, and $R^6$ are each, independently, $-H$ or $-F$;

$R^7$ is $C_1$ to $C_4$ alkyl, $C_1$ to $C_4$ perfluoroalkyl, halogen, $-NO_2$, $-CN$, phenyl or phenyl substituted with one or two groups independently selected from halogen, $C_1$ to $C_2$alkyl and OH;

provided that if $X_1R^2$ forms hydrogen, then $R^3$ is selected from:

(a) phenyl substituted by $-W(CH_2)_jA(CH_2)_kD(CH_2)_pZ$, $-W(CR^{18}R^{19})A(CH_2)_kD(CH_2)_pZ$, $-(CH_2)_jWA(CH_2)_kD(CH_2)_pZ$, $-CH=CHA(CH_2)_kD(CH_2)_pZ$, $-C\equiv CA(CH_2)_kD(CH_2)_pZ$, or $-W(CH_2)_jC\equiv CA(CH_2)_kD(CH_2)_pZ$, wherein the phenyl moiety is further optionally substituted with one or two groups independently selected from $C_1$ to $C_2$ alkyl, $C_1$ to $C_2$perfluoroalkyl, halogen, and CN; and (b) a heterocycle selected from pyrimidine, thiophene, and furan, each of which is substituted by one of $-W(CH_2)_jA(CH_2)_kD(CH_2)_pZ$, $-W(CR^{18}R^{19})A(CH_2)_kD(CH_2)_pZ$, $-(CH_2)_jWA(CH_2)_kD(CH_2)_pZ$, $-CH=CHA(CH_2)_kD(CH_2)_pZ$, $-C\equiv CA(CH_2)_kD(CH_2)_pZ$, or $-W(CH_2)_jC\equiv CA(CH_2)_kD(CH_2)_pZ$;

each $R^8$ is independently-H, or $C_1$ to $C_3$alkyl;
each $R^9$ is independently-H, or $C_1$ to $C_3$alkyl;
each $R^{10}$ is independently-H, $-CH$, $C_1$ to $C_3$alkoxy, $C_1$ to $C_7$ alkyl, $C_3$ to $C_7$ alkenyl, $C_3$ to $C_7$ alkynyl, $C_3$ to $C_7$ cycloalkyl, $-CH_2CH_2OCH_3$, 2-methyl-tetrahydro-furan, 2-methyl-tetrahydro-pyran, 4-methyl-piperidine, morpholine, pyrrolidine, or phenyl optionally substituted with one or two $C_1$ to $C_3$alkoxy groups, wherein said $C_1$ to $C_7$ alkyl is optionally substituted with 1, 2 or 3 groups independently selected from $C_1$ to $C_3$ alkoxy, $C_1$ to $C_3$thioalkoxy, and CN;

each $R^{11}$ is independently-H, $C_1$ to $C_3$alkyl or $R^{22}$; or $R^{10}$ and $R^{11}$, when attached to the same atom, together with said atom form:

a 5 to 7 membered saturated ring, optionally substituted by 1 to 2 groups independently selected from $C_1$ to $C_3$ alkyl, OH and $C_1$-$C_3$alkoxy; or a 5 to 7 membered ring containing 1 or 2 heteroatoms, optionally substituted by 1 to 2 groups independently selected from $C_1$ to $C_3$alkyl, OH and $C_1$-$C_3$ alkoxy;

each $R^{12}$ is independently-H, or $C_1$ to $C_3$alkyl;

each $R^{13}$ is independently-H, or $C_1$ to $C_3$alkyl;

each $R^{14}$ and $R^{15}$ is, independently, $C_1$ to $C_7$ alkyl, $C_3$ to $C_8$ cycloalkyl, $C_2$ to $C_7$ alkenyl, $C_2$ to $C_7$ alkynyl, —CH, —F, $C_7$ to $C_{14}$arylalkyl, where said arylalkyl is optionally substituted with 1 to 3 groups independently selected from $NO_2$, $C_1$ to $C_6$ alkyl, $C_1$ to $C_3$perhaloalkyl, halogen, $CH_2CO_2R^{11}$, phenyl and $C_1$ to $C_3$ alkoxy, or $R^{12}$ and $R^{15}$ together with the atom to which they are attached can form a 3 to 7 membered saturated ring;

each $R^{16}$ and $R^{17}$ is, independently, hydrogen, $C_1$ to $C_3$ alkyl, $C_1$ to $C_3$alkenyl, $C_1$ to $C_3$ alkynyl, phenyl, benzyl or $C_3$ to $C_8$ cycloalkyl, wherein said $C_1$ to $C_3$ alkyl is optionally substituted with one OH group, and wherein said benzyl is optionally substituted with 1 to 3 groups selected from $C_1$ to $C_3$alkyl and $C_1$ to $C_3$alkoxy; or $R^{16}$ and $R^{17}$, together with the atom to which they are attached, can form a 3 to 8 membered heterocycle which is optionally substituted with one or two substituents independently selected from the group consisting of $C_1$ to $C_3$alkyl, —OH, $CH_2OH$, —$CH_2OCH_3$, —$CO_2CH_3$, and -$CONH_2$;

each $R^{18}$ and $R^{19}$ is, independently, $C_1$ to $C_3$alkyl;

each $R^{20}$ is independently H, phenyl, or the side chain of a naturally occurring alpha amino acid;

each $R^{22}$ is independently arylalkyl optionally substituted with $CH_2COOH$; and each $R_{23}$ is phenyl;

or a pharmaceutically acceptable salt thereof.

Compounds of Formula II can be synthesized as described in U.S. Pat. No. 7,576,215, incorporated herein by reference. The compound of formula II can be any of compounds 26-32, or a pharmaceutically acceptable salt thereof.

26

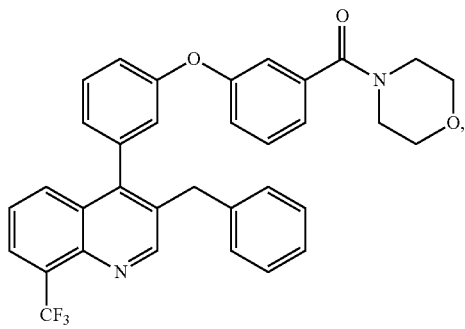

27

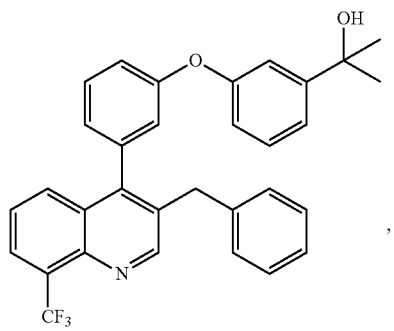

28

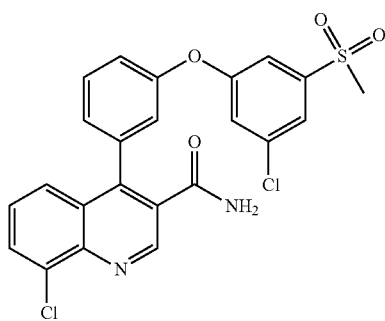

29

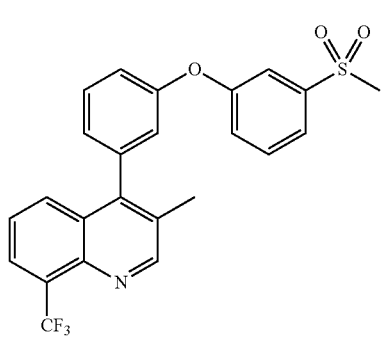

30

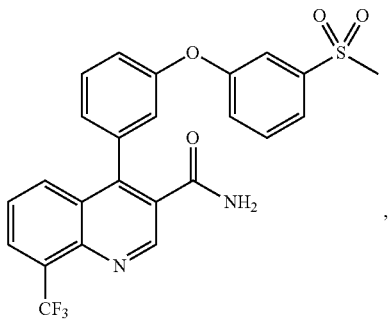

31

32

Formula III is provided below:

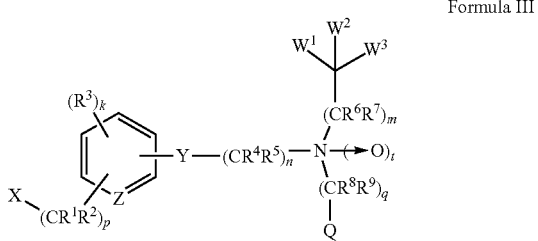

Formula III wherein:

X is selected from hydrogen, $C_1$-$C_8$ alkyl, halo, —$OR^{10}$, —$NR^{10}R^{11}$, nitro, cyano, —$COOR^{10}$, or —$COR^{10}$.

Z is CH, $CR^3$ or N, wherein when Z is CH or $CR^3$, k is 0-4 and t is 0 or 1, and when Z is N, k is 0-3 and t is 0;

Y is selected from —O—, —S—, —N($R^{12}$)—, and —C($R^4$)($R^5$)—;

$W^1$ is selected from $C_1$-$C_6$ alkyl, $C_0$-$C_6$ alkyl, $C_3$-$C_6$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{12}$, —$C_0$-$C_6$alkyl-C(O)$SR^{12}$, —$C_0$-$C_6$alkyl-$CONR^{13}R^{14}$, —$C_0$-$C_6$ alkyl-$COR^{15}$, —$C_0$-$C_6$ alkyl—$NR^{13}R^{14}$, —$C_0$-$C_6$ alkyl-$SR^{12}$, —$C_0$-$C_6$alkyl-$OR^{12}$, —$C_0$-$C_6$alkyl-$SO_3H$, —$C_0$-$C_6$alkyl-$SO_2NR^{13}R^{14}$, —$C_0$-$C_6$alkyl-$SO_2R^{12}$, —$C_0$-$C_6$alkyl-$SOR^{15}$, —$C_0$-$C_6$alkylOCOR^{15}$, —$C_0$-$C_6$alkyl-OC(O)$NR^{13}R^{14}$, —$C_0$-$C_6$alkyl-OC(O)$OR^{15}$, —$C_0$-$C_6$ alkyl-$NR^{13}C(O)OR^{15}$, —$C_0$-$C_6$ alkyl-$NR^{13}C(O)NR^{13}R^{14}$ and —$C_0$-$C_6$ alkyl-$NR^{13}COR^{15}$, where said $C_1$-$C_6$ alkyl, is optionally unsubstituted or substituted by one or more halo substituents;

$W^2$ is selected from H, halo, $C_1$-$C_6$alkyl, $C_2$-$C_6$alkenyl, $C_2$-$C_6$ alkynyl, —$C_0$-$C_6$ alkyl-$NR^{13}R^{14}$, —$C_0$-$C_6$alkyl-$SR^{12}$, —$C_0$-$C_6$ alkyl-$OR^{12}$, —$C_0$-$C_6$alkyl$CO_2R^{12}$, —$C_0$-$C_6$alkyl-C(O)$SR^{12}$, —$C_0$-$C_6$ alkyl$CONR^{13}R^{14}$, —$C_0$-$C_6$alkyl-$COR^{15}$, —$C_0$-$C_6$ alkylOCOR^{15}$, —$C_0$-$C_6$alkyl-OCONR^{13}R^{14}$, —$C_0$-$C_6$alkyl-$NR^{13}CONR^{13}R^{14}$, —$C_0$-$C_6$ alkyl-$NR^{13}COR^{15}$, —$C_0$-$C_6$alkyl-Het, —$C_0$-$C_6$alkyl-Ar and —$C_0$-$C_6$alkyl-$C_3$-$C_7$ cycloalkyl, wherein said $C_1$-$C_6$ alkyl is optionally unsubstituted or substituted by one or more halo substituents, and wherein the $C_3$-$C_7$cycloalkyl, Ar and Het moieties of said —$C_0$-$C_6$alkyl-Het, —$C_0$-$C_6$alkyl-Ar and —$C_0$-$C_6$alkyl-$C_3$-$C_7$cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$alkyl-$CO2R^{12}$, —$C_0$-$C_6$ alkyl-C(O)$SR^{12}$, —$C_0$-$C_6$alkyl-$CONR^{13}R^{14}$, —$C_0$-$C_6$alkyl-$COR^{15}$, —$C_0$-$C_6$alkyl-$NR^{13}R^{14}$, —$C_0$-$C_6$alkyl-$SR^{12}$, —$C_0$-$C_6$alkyl-$OR^{12}$, —$C_0$-$C_6$ alkyl-$SO_3H$, —$C_0$-$C_6$alkyl-$SO_2NR^{13}R^{14}$, —$C_0$-$C_6$alkyl-$SO_2R^{12}$, —$C_0$-$C_6$alkyl-$SOR^{15}$, —$C_0$-$C_6$alkyl-OCOR^{15}$, —$C_0$-$C_6$alkylOC(O)$NR^{13}R^{14}$, —$C_0$-$C_6$alkyl-OC(O)$OR^{15}$, —$C_0$-$C_6$alkyl-$NR^{13}C(O)OR^{15}$, —$C_0$-$C_6$alkyl-$NR^{13}C(O)NR^{13}R^{14}$, and —$C_0$-$C_6$alkyl-$NR^{13}COR^{15}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{13}R^{14}$, —$C_0$-$C_6$alkyl$SR^{12}$, —$C_0$-$C_6$alkyl-$OR^{12}$, —$C_0$-$C_6$alkyl-$CO_2R^{12}$, —$C_0$-$C_6$alkyl-C(O)$SR^{12}$, —$C_0$-$C_6$alkyl-$CONR^{13}R^{14}$, —$C_0$-$C_6$alkyl-$COR^{15}$, —$C_0$-$C_6$alkyl-OCOR^{15}$, —$C_0$-$C_6$ alkyl-$OCONR^{13}R^{14}$, —$C_0$-$C_6$alkyl$NR^{13}CONR^{13}R^{14}$, —$C_0$-$C_6$alkyl-$NR^{13}COR^{15}$, —$C_0$-$C_6$alkyl-Het, —$C_1$-$C_6$alkyl-Ar and —$C_1$-$C_6$alkyl-$C_3$-$C_7$cycloalkyl, wherein said $C_1$-$C_6$ alkyl is optionally unsubstituted or substituted by one or more halo substituents;

Q is selected from $C_3$-$C_8$cycloalkyl, Ar and Het; wherein said $C_3$-$C_8$cycloalkyl, Ar and Het are optionally unsubstituted or substituted with one or more groups independently selected from halo, cyano, nitro, $C_1$-$C_6$alkyl, $C_3$-$C_6$alkenyl, $C_3$-$C_6$alkynyl, —$C_0$-$C_6$alkyl$CO_2R^{12}$, —$C_0$-$C_6$ alkyl-C(O)$SR^{12}$, —$C_0$-$C_6$alkylCONR^{13}R^{14}$, —$C_0$-$C_6$ alkyl-$COR^{15}$, —$C_0$-$C_6$alkyl$NR^{13}R^{14}$, —$C_0$-$C_6$alkyl-$SR^{12}$, —$C_0$-$C_6$alkyl-$OR^{12}$, —$C_0$-$C_6$ alkyl-$SO_3H$, —$C_0$-$C_6$ alkyl-$SO_2NR^{13}R^{14}$, —$C_0$-$C_6$alkyl-$SO_2R_{12}$, —$C_0$-$C_6$alkyl-$SOR^{15}$, —$C_0$-$C_6$alkyl-OCOR^{15}$, —$C_0$-$C_6$alkyl-OC(O)$NR^{13}R^{14}$, —$C_0$-$C_6$alkyl-OC(O)$OR^{15}$, —$C_0$-$C_6$alkyl$NR^{13}C(O)OR^{15}$, —$C_0$-$C_6$ alkyl-$NR^{13}C(O)NR^{13}R^{14}$, and —$C_0$-$C_6$alkyl-$NR^{13}COR^{15}$, where said $C_1$-$C_6$alkyl is optionally unsubstituted or substituted by one or more halo substituents;

p is 0-8;

n is 2-8;

m is 0 or 1;

q is 0 or 1;

t is 0 or 1;

each $R^1$ and $R^2$ are independently selected from H, halo, $C_1$-$C_6$alkyl, $C_3$-$C_6$alkenyl, $C_3$-$C_6$ alkynyl, —$C_0$-$C_6$alkyl-$NR^{13}R^{14}$, —$C_0$-$C_6$alkyl-$OR^{12}$, —$C_0$-$C_6$ alkyl-$SR^{12}$, —$C_1$-$C_6$alkyl-Het, —$C_1$-$C_6$alkyl-Ar and —$C_1$-$C_6$alkyl-$C_3$-$C_7$cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$alkenyl, $C_3$-$C_6$alkynyl, —$C_0$-$C_6$alkyl-Ar, —$C_0$-$C_6$alkyl-Het, —$C_0$-$C_6$alkyl-$C_3$-$C_7$cycloalkyl, —$C_0$-$C_6$alkyl-$CO2R^{12}$, —$C_0$-$C_6$alkyl-C(O)$SR^{12}$, —$C_0$-$C_6$alkyl-$CONR^{13}R^{14}$, —$C_0$-$C_6$alkyl-$COR^{15}$, —$C_0$-$C_6$alkyl-$NR^{13}R^{14}$, —$C_0$-$C_6$alkyl-$SR^{12}$, —$C_0$-$C_6$alkyl-$OR^{12}$, —$C_0$-$C_6$alkyl-$SO_3H$, —$C_0$-$C_6$alkylSO_2NR^{13}R^{14}$, —$C_0$-$C_6$ alkyl-$SO_2R^{12}$, —$C_0$-$C_6$alkylSOR^{15}$, —$C_0$-$C_6$alkyl-OCOR^{15}$, —$C_0$-$C_6$ alkyl-OC(O)$NR^{13}R^{14}$, —$C_0$-$C_6$alkyl-OC(O)$OR^{15}$, —$C_0$-$C_6$alkyl-$NR^{13}C(O)OR^{15}$, —$C_0$-$C_6$alkyl-$NR^{13}C(O)NR^{13}R^{14}$, and —$C_0$-$C_6$alkyl-$NR^{13}COR^{15}$, wherein said $C_1$-$C_6$alkyl is optionally unsubstituted or substituted by one or more halo substituents;

each $R^4$ and $R^5$ is independently selected from H, halo, $C_1$-$C_6$alkyl, —$C_0$-$C_6$alkyl-Het, —$C_0$-$C_6$alkyl-Ar and —$C_0$-$C_6$alkyl-$C_3$-$C_7$cycloalkyl;

$R^6$ and $R^7$ are each independently selected from H, halo, $C_1$-$C_6$ alkyl, —$C_0$-$C_6$alkyl-Het, —$C_0$-$C_6$ alkyl-Ar and —$C_0$-$C_6$alkyl-$C_3$-$C_7$cycloalkyl;

$R^8$ and $R^9$ are each independently selected from H, halo, $C_1$-$C_6$ alkyl, —$C_0$-$C_6$alkyl-Het, —$C_0$-$C_6$ alkyl-Ar and —$C_0$-$C_6$alkyl-$C_3$-$C_7$ cycloalkyl;

$R^{10}$ and $R^{11}$ are each independently selected from H, $C_1$-$C_{12}$ alkyl, $C_3$-$C_{12}$alkenyl, $C_3$-$C_{12}$alkynyl, —$C_0$-$C_8$alkyl-Ar, —$C_0$-$C_8$ alkyl-Het, —$C_0$-$C_8$ alkyl-$C_3$-$C_7$ cycloalkyl, —$C_0$-$C_8$ alkyl-O—Ar, —$C_0$-$C_8$alkyl-O-Het, —$C_0$-$C_8$ alkyl-O-$C_3$-$C_7$cycloalkyl, —$C_0$-$C_8$alkyl-S(O)$_x$-$C_0$-$C_6$alkyl, —$C_0$-$C_8$alkyl-S(O)$_x$—Ar, —$C_0$-$C_8$ alkyl-S(O)$_x$-Het, —$C_0$-$C_8$ alkyl-S(O)$_x$-$C_3$-$C_7$cycloalkyl, —$C_0$-$C_8$alkyl-NH—Ar, —$C_0$-$C_8$alkyl-NH-Het, —$C_0$-$C_8$alkyl-NH-$C_3$-

C₇cycloalkyl, —C₀-C₈alkyl-N(C₁-C₄ alkyl)-Ar, —C₀-C₈alkyl-N(C₁-C₄alkyl)-Het, —C₀-C₈alkyl-N(C₁-C₄alkyl-C₃-C₇cycloalkyl, —C₀-C₈alkyl-Ar, —C₀-C₈alkyl-Het and —C₀-c₈alkyl-C₃-C₇cycloalkyl, where x is 0, 1, or 2, or R¹⁰ and R¹¹, together with the nitrogen to which they are attached, form a 4-7 membered heterocyclic ring which optionally contains one or more additional heteroatoms selected from N, O, and S, wherein said C₁-C₁₂alkyl, C₃-C₁₂ alkenyl, or C₃-C₁₂alkynyl is optionally substituted by one or more of the substituents independently selected from the group halo, —OH, —SH, —NH₂, —NH(unsubstituted C₁-C₆alkyl), —N(unsubstituted C₁-C₆ alkyl)(unsubstituted C₁-C₆alkyl), unsubstituted —OC₁-C₆ alkyl, —CO₂H, —CO₂(unsubstituted C₁-C₆ alkyl), —CONH₂, —CONH (unsubstituted C₁-C₆ alkyl), —CON(unsubstituted C₁-C₆ alkyl)(unsubstituted C₁-C₆ alkyl), —SO₃H, —SO₂NH₂, —SO₂NH(unsubstituted C₁-C₆alkyl) and —SO₂N(unsubstituted C₁-C₆alkyl)(unsubstituted C₁-C₆ alkyl);

R¹² is selected from H, C₁-C₆ alkyl, C₃-C₆alkenyl, C₃-C₆alkynyl, -C₀-C₆alkyl-Ar, —C₀-C₆alkyl-Het and —C₀-C₆alkyl-C₃-C₇cycloalkyl;

each R¹³ and each R¹⁴ are independently selected from H, C₁-C₆alkyl, C₃-C₆alkenyl, C₃-C₆alkynyl, —C₀-C₆alkyl-Ar, —C₀-C₆alkyl-Het and-C₀-C₆alkyl-C₃-C₇cycloalkyl, or R¹³ and R¹⁴ together with the nitrogen to which they are attached form a 4-7 membered heterocyclic ring which optionally contains one or more additional heteroatoms selected from N, O, and S;

and R¹⁵ is selected from C₁-C₆alkyl, C₃-C₆ alkenyl, C₃-C₆alkynyl, —C₀-C₆alkyl-Ar, —C₀-C₆ alkyl-Het and —C₀-C₆ alkyl-C₃-C₇ cycloalkyl;

or a pharmaceutically acceptable salt thereof.

In some embodiments, X is hydrogen, p is 0, t is 0, Z is CH, and Y is —O—.

In further embodiments, X is hydrogen, p is 0, t is 0, Z is CH, and Y is —O—, W¹ and W² are phenyl, W³ is hydrogen, q is 1, and R⁸ and R⁹ are hydrogen.

In other embodiments, X is hydrogen, p is 0, t is 0, Z is CH, and Y is —O—, W¹ and W² are phenyl, W³ is hydrogen, q is 1, R⁸ and R⁹ are hydrogen, and Q is Ar.

Accordingly, the compounds of Formula III include but are not limited the compounds with structures shown below GW3965 2 and SB742881 25:

2

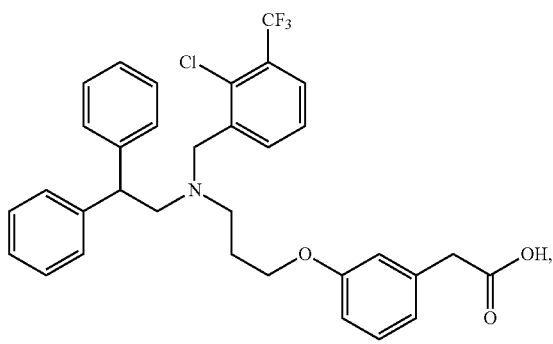

25

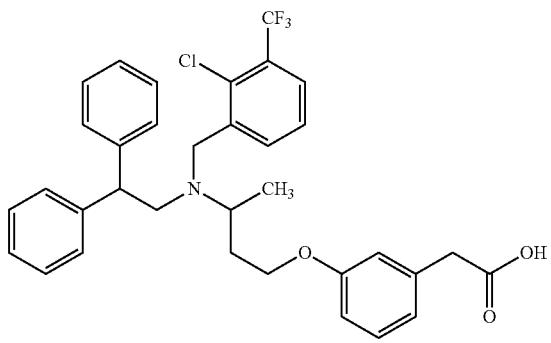

Compounds of Formula III can be synthesized as described in U.S. Pat. Nos. 7,365,085 and 7,560,586 incorpoarated herein by reference.

Formula IV is shown below:

Formula IV

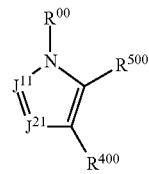

or a pharmaceutically acceptable salt thereof, wherein:
J¹¹ is-N═ and J²¹ is —CR³⁰⁰—, or J¹¹ is —CR²⁰⁰— and J21 is ═N—;
R⁰⁰ G¹, G²¹, or Rᴺ;
R²⁰⁰ is G¹, G²¹, or Rᶜ;
R³⁰⁰ and R⁴⁰⁰ are independently Rᶜ or Q, provided one and only one of R³⁰⁰, R⁴⁰⁰, and
R⁵⁰⁰ is
Q;
Q is C₃₋₆ cycloalkyl, heteroaryl or heterocyclyl, each optionally substituted with 1 to 4Rᵠ, or Q is —X—Y—Z; wherein each Rᵠ is independently aryloxy, aralkyloxy, aryloxyalkyl, arylC₀-C₆alkylcarboxy, C(R¹¹⁰)═C(R¹¹⁰)—COOH, oxo, ═S, —Z, —Y'—Z, or —X—Y—Z, wherein each Rᵠ is optionally substituted with 1 to 4 R⁸⁰;
R⁵⁰⁰ is G¹ G²¹, Q, or Rᶜ; provided that only one of R⁰⁰, R²⁰⁰, and R⁵⁰⁰ is G¹ and only one of R⁰⁰, N═, and R⁵⁰⁰ is G²¹;
G²¹ is -J⁰-K°, wherein J⁰ and K⁰ are independently aryl or heteroaryl, each optionally substituted with one to four Rᴷ groups; each Rᴷ is independently hydrogen, halogen, CR¹¹⁰═CR¹¹⁰COOR¹¹⁰, nitro, —Z, —Y—Z, or —X—Y—Z;
G¹ is -L¹⁰-R, wherein L¹⁰ is a bond, L⁵⁰, L⁶⁰, -L⁵⁰-L⁶⁰-L⁵⁰-, or -L⁶⁰-L⁵⁰-L⁵⁰-, wherein
each L⁵⁰ is independently —[C(R¹⁵⁰)₂]ₘ—;
each L⁶⁰ is independently —CS—, —CO—, —SO₂—, —O—, —CON(R¹¹⁰)—, —CONR¹¹⁰N(R¹¹⁰)—, —C(═NR¹¹⁰)—, —C(NOR¹¹)—, —C(═N—N(R¹¹⁰)₂)—, —C₃-C₈cycloalkyl-, or -heterocyclyl-, wherein the) cycloalkyl or heterocyclyl is optionally substituted with one to 4 R¹⁴⁰ groups; or
or each L⁶⁰ is independently C₂-C₆ alidiyl, wherein the alidiyl chain is optionally interrupted by —C(R¹⁰⁰)₂—, —C(R¹¹⁰)₂C(R¹¹⁰)ᵤ—, —C(R¹¹)C (R¹¹⁰)—, —C($R^{110}$)$_2$O—, —C($R^{110}$)$_2$NR$^{110}$—, —C≡C—, —O—, —S—, —N(RO)CO—, —N($R^{100}$)CO$_2$—, —CON($R^{110}$)—, —CO—, —CO$_2$—, —OC(=O)—, —OC(=O)N($R^{100}$)—, —SO$_2$—, —N($R^{100}$)SO$_2$—, or —SO$_2$N($R^{100}$);

R is aryl, heterocyclyl, heteroaryl or —(C$_3$-C$_6$)cycloalkyl, wherein R is optionally substituted with 1 to 4 $R^A$, wherein each $R^A$ is independently halogen, nitro, heterocyclyl, C$_1$-C$_6$ alkyl, C$_2$-C$_6$ alkenyl, C$_2$-C$_6$ alkynyl, C$_3$-C$_8$ cycloalkyl, (C$_3$-C$_8$ cycloalkyl)-C$_1$-C$_6$ alkyl-, (C$_3$-C$_8$ cycloalkenyl)-C$_1$-C$_6$ alkyl-, (C$_3$-C$_8$ cycloalkyl)-C$_1$C$_6$ alkenyl-, arylalkyl, aryloxy, arylC$_{1-6}$ alkoxy, C$_1$-C$_6$ haloalkyl, SO$_2$R$^{110}$, OR$^{110}$, SR$^{110}$, N$_3$, SOR$^{110}$, COR$^{110}$, SO$_2$N(R$^{110}$)$_2$, SO$_2$NR$^{110}$COR$^{110}$, C≡N, C(O)OR$^{110}$, CON(R$^{110}$)$_2$, —CON(R$^{110}$)OR$^{110}$, OCON(R$^{110}$)$_2$, —NR$^{110}$COR$^{110}$, NR$^{110}$CON(R$^{110}$)$_2$, NR$^{110}$COOR$^{110}$, —C(=N—OH)R$^{110}$, —C(=S)N(R$^{110}$)$_2$, —S(=O)N(R$^{110}$)$_2$, —S(=O)OR$^{110}$, —N(R$^{110}$)S(=O)$_2$R$^{110}$, —C(=O)N(R$^{110}$)N(R$^{110}$)$_2$, —OC(=O)—R$^{110}$, —OC(=O)—OR$^{110}$ or N(R$^{11}$)$_2$, wherein each $R^A$ is optionally substituted with 1 to 4 groups which independently are -halogen, —C$_1$-C$_6$ alkyl, aryloxy, C$_{0-6}$ alkylSO$_2$R$^{110}$, C$_{0-6}$ alkylCOOR$^{110}$, C$_{1-6}$ alkoxyaryl, C$_1$-C$_6$ haloalkyl, —SO$_2$R$^{110}$, —OR$^{110}$, —SR$^{110}$, —N$_3$, —SO$_2$R$^{110}$, —COR$^{110}$, —SO$_2$N(R$^{110}$)$_2$, —SO$_2$NR$^{110}$COR$^{110}$, —C≡N, —C(O)OR$^{110}$, —CON(R$^{110}$)$_2$, —CON(R$^{110}$)OR$^{110}$, —OCON(R$^{110}$)$_2$, —NR$^{110}$COR$^{110}$, —NR$^{110}$CON(R$^{110}$)$_2$, —NR$^{110}$COOR$^{110}$, or —N(R$^{110}$)$_2$;

$R^N$ is -L$^{31}$-R$^{60}$, wherein L$^{31}$ is a bond, —X$^3$(CH$_z$)$_n$—X$^3$—, —(CH$_2$)$_m$—X3-(CH$_2$)$_n$— or —(CH$_2$)$_{1+w}$—Y$^3$—(CH$_2$)$_w$—, wherein each w is independently 0-5: and each X$^3$ is independently a bond, —C(R$^{110}$)$_2$—, —C(R$^{110}$)$_2$—, —C(R$^{110}$)=C(R$^{110}$)—, —C≡C—, —CO—, —CS—, —CONR$^{100}$—, —C(=N)(R$^{100}$)—, —C(=N—OR$^{110}$)—, —C[=N—N(R$^{110}$)$_2$], —CO$_2$—, —SO$_2$—, or —SO$_2$N(R$^{110}$)—; and Y$^3$ is —O—, —S—, —NR$^{70}$—, —N(R$^{100}$)CO—, —N(R$^{110}$)CO2-, —OCO—, —OC(=O)N (R$^{100}$)—, —NR$^{100}$CONR$^{100}$—, —N(R$^{110}$)SO$_2$—, or —NR$^{100}$CSNR$^{100}$—;

or L$^{31}$ is C$_{2-6}$ alidiyl chain wherein the alidiyl chain is optionally interrupted by —C(R$^{110}$)$_2$—, C(R$^{110}$)$_2$C(R$^{110}$)$_2$—, —C(R$^{110}$)=C(R$^{110}$)—, —C(R$^{110}$)$_2$O—, —C(R$^{110}$)$_2$NR$^{110}$—, —C≡C—, —O—, —S—, —N(R$^{100}$)CO—, —N(R$^{100}$)CO$_2$—, —CON(R$^{100}$)—, —CO—, —CO$_2$—, —OC(=O)—,—OC(=O)N(R$^{110}$)—, —SO$_2$—, —N(R$^{100}$)SO$_2$—, or —SO$_2$N(R$^{100}$); and R$^{60}$ is C$_1$-C$_6$ alkyl, C$_1$-C$_6$ halo alkyl, aryl, C$_3$-C$_8$ cycloalkyl, heteroaryl, heterocyclyl, —CN, —C(=O)R$^{110}$, —C(=O)OR$^{110}$, —C(=O)N(R$^{110}$)$_2$, —N(R$^{110}$)$_2$, —SO$_2$R$^{110}$, —S(=O)$_2$N(R$^{110}$)$_2$, —C(=O)N(R$^{110}$)N(R$^{110}$)$_2$, or —C(=O)N(R$^{11}$)(OR$^{110}$), wherein the aryl, heteroaryl, cycloalkyl, or heterocyclyl is optionally substituted with 1 to 4 R$^{60a}$, wherein
each R$^{60a}$ is independently —Z, —Y'—Z, or-X—Y—Z;
each $R^C$ is independently -L$^{30}$-R$^{70}$, wherein
each L$^{30}$ is independently a bond or —(CH$_2$)$_m$—V$^{10}$—(CH$_2$)$_n$—, wherein
V$^{10}$ is —C(R$^{110}$)$_2$—, —C(R$^{110}$)$_2$C(R$^{110}$)$_2$—, —C(R$^{110}$)=C(R$^{110}$)—, —C(R$^{110}$)$_2$O—, —C(R$^{110}$)$_2$NR$^{110}$—, —C≡C—, —O—, —S—, —NR$^{10}$—, —N(R$^{100}$)CO—, —N(R$^{100}$)CO2-, —OCO—, —CO—, —CS—, —CONR$^{100}$—, —C(=N—R$^{110}$)—, —C(=N—OR$^{110}$)—, —C[=N—N(R$^{110}$)$_2$], —CO$_2$—, —OC(=O)—, —OC(=O)N(R$^{100}$)—, SO$_2$—, —N(R$^{100}$)SO$_2$—, —SO$_2$N (R$^{100}$)—, —NR$^{100}$CONR$^{100}$—, —NR$^{100}$CSNR$^{100}$—, C$_3$-C$_6$cycloalkyl, or C$_3$-C$_6$ cyclohaloalkyl; or each L$^{30}$ is independently C$_2$-C$_6$ alidiyl, wherein the alidiyl chain is optionally interrupted by —C(R$^{110}$)$_2$—, —C(R$^{110}$)$_2$C(R$^{110}$)$_2$—, —C(R$^{110}$)C(R$^{110}$)—, —C(R$^{110}$)$_2$O—, —C(R$^{110}$)$_2$NR$^{110}$—, —C≡C—, —O—, —S—, —N(R$^{100}$)CO—, —N(R$^{100}$)CO$_2$—, NR$^{110}$—, —CON(R$^{100}$)—, —CO—, —CO$_2$—, —O(C=O)—, —O(C=O)N(R$^{100}$)—, —SO$_2$—, —N(R$^{100}$)SO$_2$—, or —SO$_2$N(R$^{100}$)—;

each R$^{70}$ is independently hydrogen, halogen, nitro, aryl, heteroaryl, heterocyclyl, —Z, —Y—Z, or —X—YZ, wherein the aryl, heteroaryl, and heterocyclyl, are each optionally substituted with 1 to 4 R$^{70a}$, wherein each R$^{70a}$ is independently aryloxy, aralkyloxy, aryloxyalkyl, arylC$_o$-C$_6$alkylcarboxy, C(R$^{110}$)=C(R$^{110}$)COOH, oxo, —Z, —Y'—Z, or —X—Y—Z, wherein each R$^{70a}$ is optionally substituted with 1 to 4 R$^{80}$, and wherein each R$^{80}$ is independently halogen, C$_1$-C$_6$ alkyl, C$_1$-C$_6$ alkoxy, C$_1$-C$_8$haloalkyl, C$_1$-C$_8$ haloalkyl(OR$^{110}$, C$_0$-C$_6$ alkylOR$^{110}$, C$_0$-C$_6$ alkylCON(R$^{110}$)$_2$, C$_0$-C$_6$ alkylCOR$^{110}$, C$_0$-C$_6$ alkylCOOR$^{110}$, or C$_0$-C$_6$ alkylSO$_2$R$^{110}$;

each R$^{100}$ is independently —R$^{110}$, —C(=O)R$^{110}$, —CO$_2$R$^{110}$, or —SO$_2$R$^{110}$;

each R$^{110}$ is independently -hydrogen, —C$_1$-C$_6$ alkyl, C$_2$-C$_6$ alkenyl, C$_1$-C$_6$ alkynyl, —C$_1$-C$_6$ haloalkyl, or —N(R$^{12}$)$_2$, wherein any of R$^{110}$ is optionally substituted with 1 to 4 radicals of R$^{120}$;

each R$^{120}$ is independently halogen, cyano, nitro, oxo, —B(OR$^{130}$), C$_0$-C$_6$ alkylN(R$^{13}$)$_2$, C$_1$-C$_6$haloalkyl, C$_1$-C$_6$ alkyl, C$_1$-C$_6$ alkoxy, (C$_0$-C$_6$ alkyl)C=O(OR$^{130}$), C$_0$-C$_6$ alkylOR$^{130}$, C$_0$-C$_6$ alkylCOR$^{130}$, C$_0$-C$_6$alkylSO$_2$R$^{130}$, C$_0$-C$_6$alkylCON(R$^{13}$)$_2$, C$_0$-C$_6$alkylCONR$^{130}$OR$^{130}$, C$_0$-C$_6$alkylS0$_2$N(R$^{130}$)$_2$, C$_0$-C$_6$alkylSR$^{130}$, C$_0$-C$_6$ haloalkylOR$^{130}$, C$_0$-C$_6$alkylCN, —C$_0$-C$_6$alkyN(R$^{13}$)$_2$, —NR$^{13}$S0$_2$R$^{13}$, or —OC$_{o-6}$ alkylCOOR$^{130}$;

each R$^{130}$ is independently hydrogen, C$_1$-C$_6$ alkyl, C$_2$-C$_6$ alkenyl, or C$_2$-C$_6$ alkynyl;

each R$^{140}$ is independently C$_1$-C$_6$ alkyl, C$_1$-C$_6$ alkoxy, halogen, C$_1$-C$_6$ haloalkyl, C$_0$-C$_6$ alkylCON(R$^{110}$)$_0$, C$_0$-C$_6$ alkylCONR$^{110}$R$^{10}$, C$_0$-C$_6$ alkylOR$^{110}$, or C$_0$-C$_6$ alkylCOOR$^{110}$; and each R$^{150}$ is independently hydrogen, halogen, OR$^{130}$, (C$_1$-C$_6$)alkyl or (C$_1$-C$_6$)haloalkyl, wherein
each alkyl is optionally substituted with at least one group which are each independently halogen, cyano, nitro, azido, OR$^{130}$, C(O)R$^{130}$, C(O)OR$^{13}$C(O)N(R$^{130}$)$_2$, N(R$^{130}$)$_2$, N(R$^{130}$)C(O)R$^{130}$, N(R$^{130}$)S(O)$_2$R$^{130}$, —OC(O)OR$^{130}$, OC(O)N(R$^{130}$)$_2$, N(R$^{130}$)C(O)OR$^{130}$, N(R$^{130}$)C(O)N(R$^{130}$), SR$^{130}$, S(O)R$^{130}$, S(O)$_2$R', or S(O)$_2$N(R$^{130}$)$_2$; or two R$^{150}$ (bonded to same or different atoms) can be taken together to form a C3-C6 cycloalkyl;

each X is independently —O—, —S—, or —N(R$^{100}$)—;
each Y is independently —[C(R$^{150}$)$_2$]$_p$—, or —C$_2$-C$_6$ alkenyl, wherein p is 1, 2, 3, 4, 5, or 6;
each Y' is independently —[C(R$^{150}$)$_2$]$_p$—, —C$_2$-C$_6$ alkenyl C$_3$-C$_8$ cycloalkyl, or heterocyclyl, wherein the cycloalkyl or heterocyclyl is optionally substituted with 1 to 3 Z groups;

each Z is independently —H, halogen, —OR$^{110}$, —SR$^{110}$, —C(=O)R$^{110}$, —C(=O)R$^{110}$, —C(=O)N(R$^{110}$)$_2$, —N(R$^{100}$)$_2$, —N$_3$, —NO$_2$, —C(=N—OH)R$^{110}$, —C(=S)N(R$^{110}$)$_2$, —CN, —S(=O)R$^{110}$, —S(=O)N(R$^{110}$)$_2$, —S(=O)OR$^{110}$, —S(=O)₂R¹¹⁰, S(=O)₂N(R¹¹⁰)₂, —NR¹¹⁰COR¹¹⁰, —N(R¹¹⁰)C(=O)N(R¹¹⁰)₂, —N(R¹¹⁰)COOR¹¹⁰, —N(R¹¹⁰)S(=O)₂R¹¹⁰, —C(=O)N(R¹¹⁰)N(R¹¹⁰)₂, —C(=O)N(R¹¹⁰)(OR¹¹⁰), —OC(=O)—R¹¹⁰, —OC(=O)—OR¹¹⁰, or —OC(=O)—N(R¹¹⁰)₂; and each m and n is independently 0, 1, 2, 3, 4, 5, or 6.

In some embodiments the compound of Formula IV has a structure of Formula V or VI:

Formula V

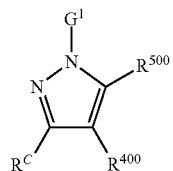

Formula VI

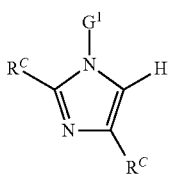

In other embodiments the compound of Formula VI has a structure of Formula VII:

Formula VII

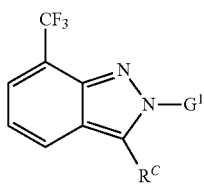

In yet other embodiments the compound of Formula VI has a structure of Formula VIII:

Formula VIII

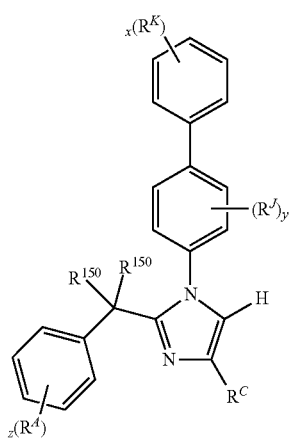

In still further embodiments the compound of Formula VI has a structure of Formula IX:

Formula IX

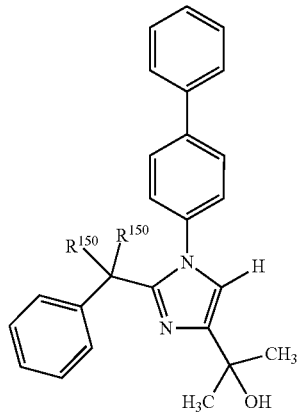

Accordingly, the compounds of Formula IV which can be useful in the methods of the invention include, but are not limited to, compounds having the structures are shown below, and pharmaceutically acceptable salts thereof:

3

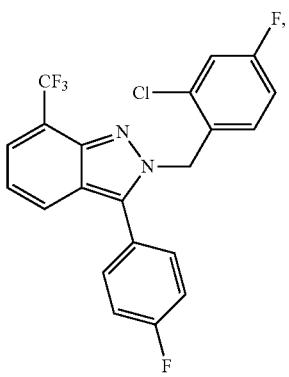

4

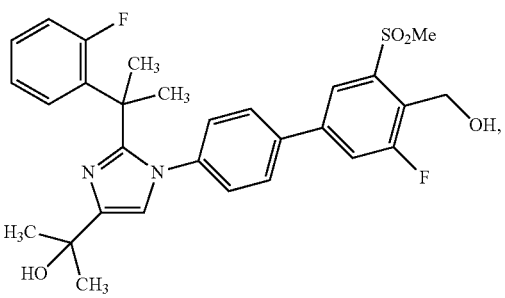

5

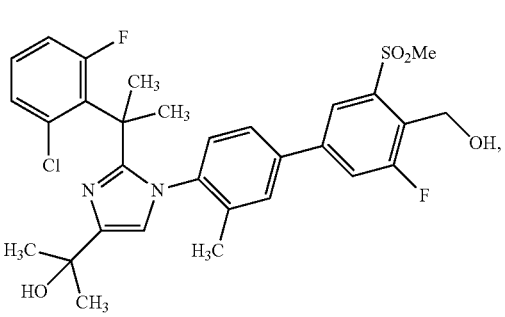

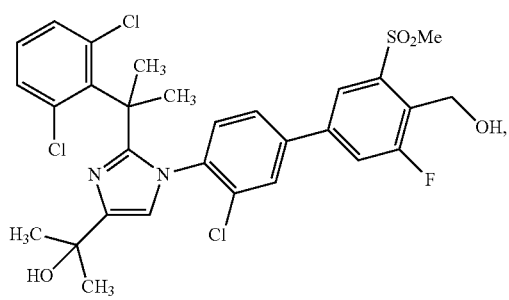
6
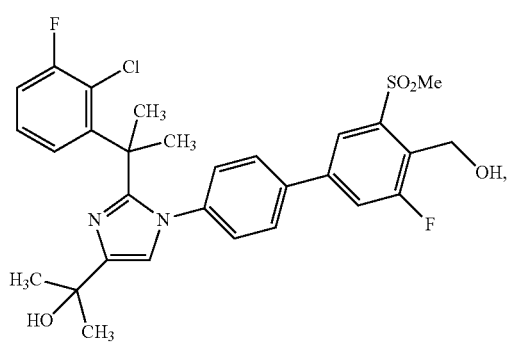
7
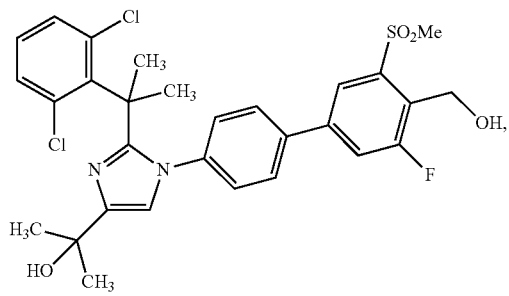
8
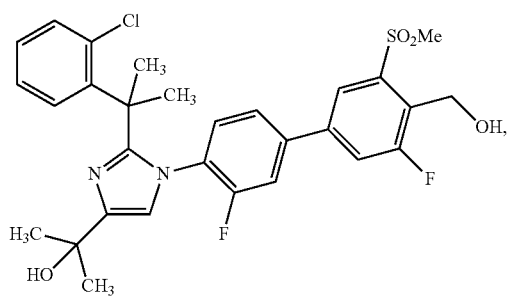
9
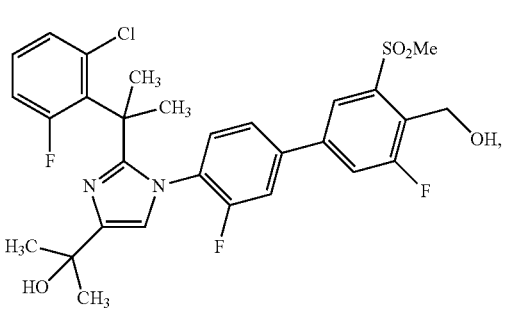
10
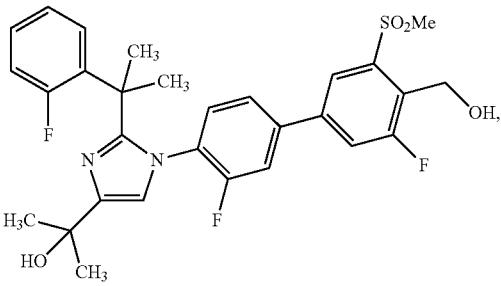
11
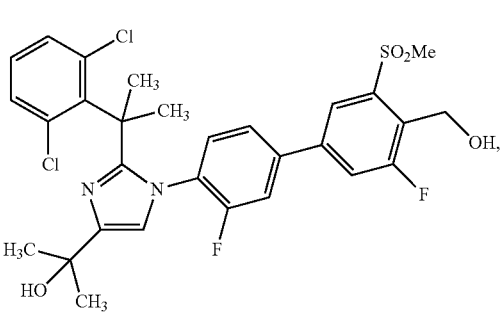
12
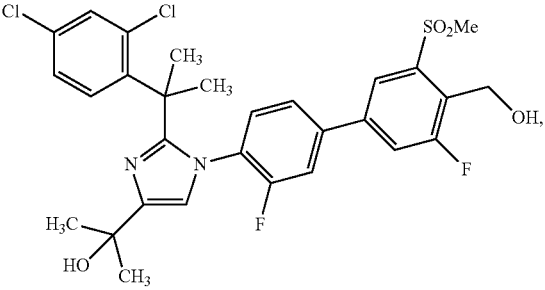
13
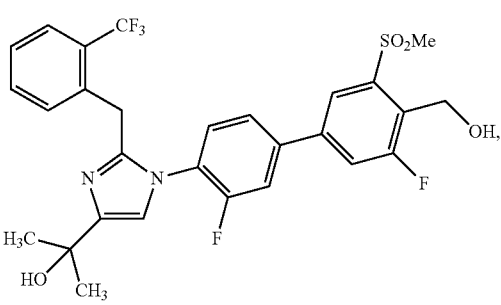
14
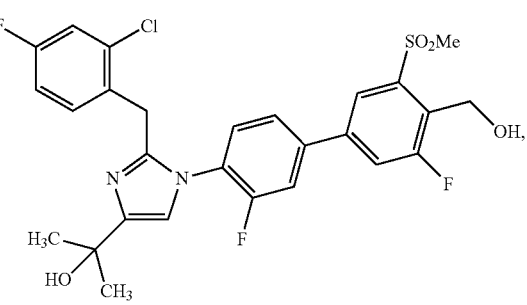
15

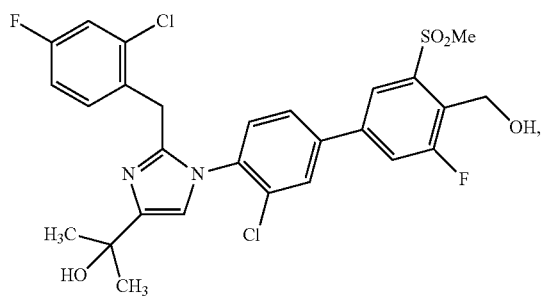
16
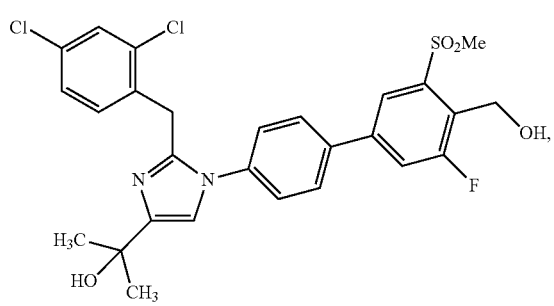
17
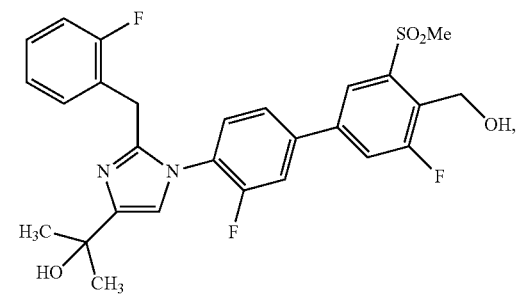
18
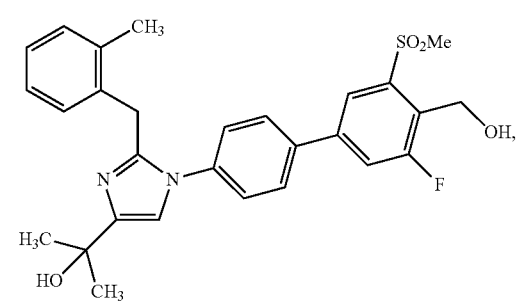
19
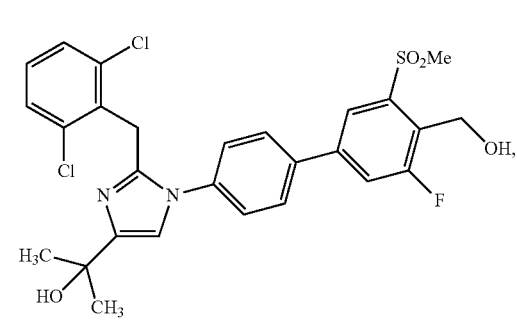
20
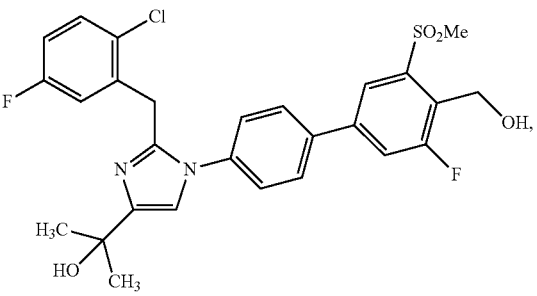
21
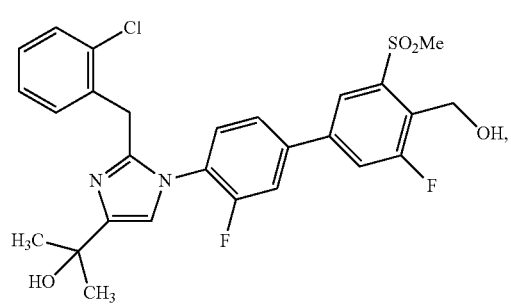
22
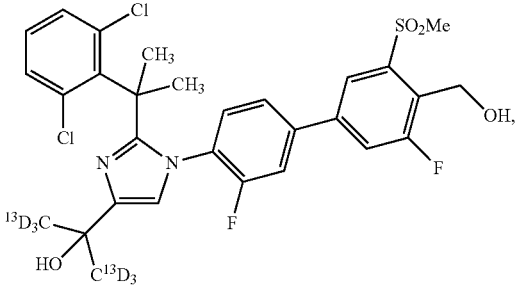
23
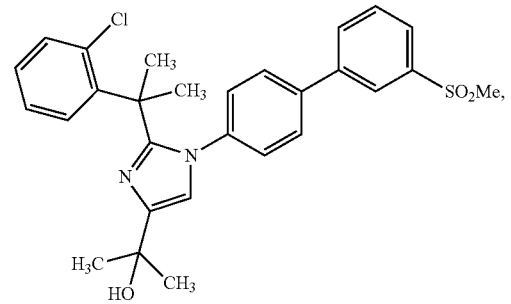
38

-continued

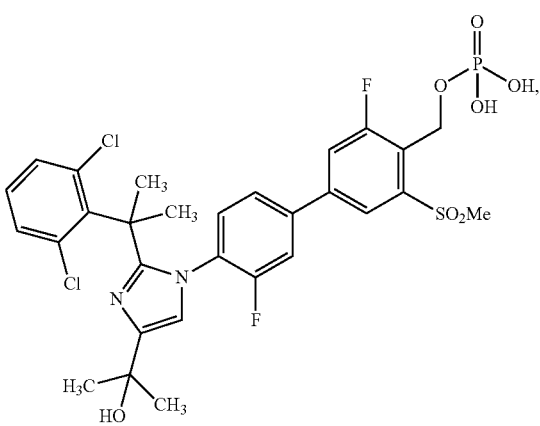

39 and selected from the list comprising:
33 2-(1-(3 chloro-3'-fluoro-4'-(hydroxymethyl)-5'-(methylsulfonyl)biphenyl-4-yl)-2-(2-(2,6dichlorophenyl) propan-2-yl)-1H-imidazol-4-yl)propan-2-ol; 34 2-(2-(2(2-chloro-3-fluorophenyl)propan-2-yl)-1-(3'-fluoro-4'-(hydroxymethyl)-5'(methylsulfonyl)biphenyl -4-yl)-1H-imidazol-4-yl)propan-2-ol; 35 2-(2-(2 (2,6-dichlorophenyl)propan-2-yl)-1-(3'-fluoro-4'-(hydroxymethyl)-5'(methylsulfonyl)biphenyl-4-yl)-1H-imidazol-4-yl)propan-2-ol; 36 2-(2-(2(2,6-dichlorophenyl)propan-2-yl)-1-(3,3 '-difluoro-4'-(hydroxymethyl)-5'(methylsulfonyl)biphenyl-4-yl)-1H-imidazol-4-yl)propan-2-ol;and 37 2-(2-[1(2,6-dichlorophenyl)ethyl]-1-[3,3'-difluoro-4'-(hydroxymethyl)-5'(methylsul fonyl)biphenyl-4-yl]-1H-imidazol-4-yl) propan-2-ol. Compound 12 is also known as WO2010 0138598 Ex. 9. Compound 38 is also known WO2007 002563 Ex. 19. Compound 39 is also known as WO2012 0135082.

Compounds of Formula IV can be synthesized as described in PCT publication No. US2010/0069367 and WO2010/138598 incorpoarated herein by reference.

The LXR agonist that can be used for the treatment and/or prevention of metastasis can be compound 24, or a pharmaceutically acceptable salt thereof.

24

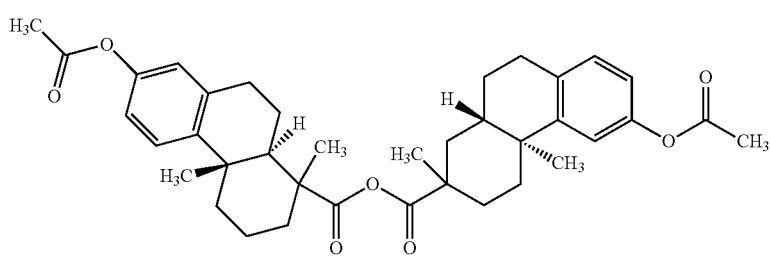

In further embodiments compounds that can be used for the treatment and/or prevention of metastasis can be found in the PCT publications in the list consisting of:

WO2006/094034, WO2008/049047, WO2009/020683, WO2009/086138, WO2009/086123, WO2009/086130, WO2009/086129, WO2007/002559, WO2007/002563, WO2007/081335, WO2006/017055, WO2006/102067, WO2009/024550, US2006/074115, US2006/135601, WO2009/021868, WO2009/040289, WO2007/047991, WO2007/050425, WO2006/073363, WO2006/073364, WO2006/073365, WO2006/073366, WO2006/073367, US2009/0030082, WO2008/065754, JP2008/179562, WO2007/092065, US2010/0069367, U.S. Pat. Nos. 7,998, 995, and 7,247,748, WO2010/138598, U.S. Pat. No. 7,365, 085, U.S. 75/776,215, U.S. 63/136,503, US2004/0072868, US2005/0107444, US2005/0113580, US2005/0131014, US2005/0282908, US2009/0286780, incorporated herein by reference.

LXRα and LXRβ, initially discovered by multiple groups at roughly the same time (Apfel et al., 1994; Willy et al., 1995; Song et al., 1994; Shinar et al., 1994; Teboul et al., 1995), belong to a family of nuclear hormone receptors that are endogenously activated by cholesterol and its oxidized derivatives to mediate transcription of genes involved in maintaining glucose, cholesterol, and fatty acid metabolism (Janowski et al., 1996; Calkin and Tontonoz, 2012). Given the intricate link between lipid metabolism and cancer cell growth (Cairns et al., 2011), the ubiquitous expression of LXRβ in melanoma is unlikely to be coincidental, allowing melanoma cells to synthesize lipids and lipoprotein particles to sustain their growth. At the same time, however, such stable basal expression levels make LXRβ an ideal therapeutic target, as exemplified by the broad-ranging responsiveness of melanoma cells to LXRβ activation therapy.

Compounds have been shown to have selectivity for LXRβ or LXRα. This selectivity may allow for increased activity and/or decreased off target effects. Examples of compounds with selectivity towards LXRβ or LXRα are shown in Table 1.

TABLE 1

$EC_{50}$ values for selected compounds against LXRα and LXRβ

| Compound | $EC_{50}$ - LXRα (nM) | $EC_{50}$ - LXRβ (nM) |
| --- | --- | --- |
| GW3965 2 | 200 | 40 |
| SB742881 25 | 74 | 25 |
| TO901317 1 | 20 | 50 |
| LXR-623 3 | 179 | 24 |
| 12 | <100 | 11 |
| 38 | 101-1000 | 630 |

As used herein, reference to the activity of an LXR agonist at LXRα and LXRβ refer to the activity as measured using the ligand sensing assay (LiSA) described in Spencer et al. Journal of Medicinal Chemistry 2001, 44, 886-897, incorporated herein by reference. In some embodiments, the LXR agonist has an EC50 of less than 1 µM in the ligand sensing assay (e.g., 0.5 nm to 500 nM, 10 nM to 100 nM). For example, the methods of the invention can be performed using an LXRβ agonist having activity for LXRβ that is at least 3-fold greater than the activity of the agonist for LXRα, or having activity for LXRβ that is at least 10-fold greater than the activity of the agonist for LXRα, or having activity for LXRβ that is at least 100-fold greater than the activity of said agonist for LXRα, or having activity for LXRβ that is at least within 3-fold of the activity of the agonist for LXRα. The term "greater activity" in the LiSA assay assay refers to a lower EC50. For example, GW3965 2 has approximately 6-fold greater activity for LXRβ (EC50=30) compared to LXRα (EC50=190).

As used herein, the term "increases the level of ApoE expression in vitro" refers to certain LXR agonists capable of increasing the level of ApoE expression 2.5-fold in the qPCR assay of Example 21 at a concentration of less than 5 µM (e.g., at a concentration of 100 nM to 2 µM, at a concentration of less than or equal to 1 µM). The LXR agonists exhibiting this in vitro effect can be highly efficacious for use in the methods of the invention.

The term "alkyl" used is the present application relates a saturated branched or unbranched aliphatic univalent substituent. The alkyl substituent has 1 to 100 carbon atoms, (e.g., 1 to 22 carbon atoms, 1 to 10 carbon atoms 1 to 6 carbon atoms, 1 to 3 carbon atoms). Accordingly, examples of the alkyl substituent include methyl, ethyl, n-propyl, isopropyl, n-butyl, isobutyl, sec-butyl, tert-butyl, n-pentyl and n-hexyl.

The term "alkoxy" represents a chemical substituent of formula —OR, where R is an optionally substituted C1-C6 alkyl group, unless otherwise specified. In some embodiments, the alkyl group can be substituted, e.g., the alkoxy group can have 1, 2, 3, 4, 5 or 6 substituent groups as defined herein.

The term "alkoxyalkyl" represents a heteroalkyl group, as defined herein, that is described as an alkyl group that is substituted with an alkoxy group. Exemplary unsubstituted alkoxyalkyl groups include between 2 to 12 carbons. In some embodiments, the alkyl and the alkoxy each can be further substituted with 1, 2, 3, or 4 substituent groups as defined herein for the respective group.

As used herein, the term "cycloalkyl" refers to a monocyclic, bicyclic, or tricyclic substituent, which may be saturated or partially saturated, i.e. possesses one or more double bonds. Monocyclic substituents are exemplified by a saturated cyclic hydrocarbon group containing from 3 to 8 carbon atoms. Examples of monocyclic cycloalkyl substituents include cyclopropyl, cyclobutyl, cyclopentyl, cyclopentenyl, cyclohexyl, cyclohexenyl, cycloheptyl and cyclooctyl. Bicyclic fused cycloalkyl substituents are exemplified by a cycloalkyl ring fused to another cycloalkyl ring. Examples of bicyclic cycloalkyl substituents include, but are not limited to decalin, 1,2,3,7,8,8a-hexahydro-naphthalene, and the like. Tricyclic cycloalkyl substituents are exemplified by a cycloalkyl bicyclic fused ring fused to an additional cycloalkyl substituent.

The term "alkylene" used is the present application relates a saturated branched or unbranched aliphatic bivalent substituent (e.g. the alkylene substituent has 1 to 6 carbon atoms, 1 to 3 carbon atoms). Accordingly, examples of the alkylene substituent include methylene, ethylene, trimethylene, propylene, tetramethylene, isopropylidene, pentamethylene and hexamethylene.

The term "alkenylene or alkenyl" as used in the present application is an unsaturated branched or unbranched aliphatic bivalent substituent having a double bond between two adjacent carbon atoms (e.g. the alkenylene substituent has 2 to 6 carbon atoms, 2 to 4 carbon atoms). Accordingly, examples of the alkenylene substituent include but are not limited to vinylene, 1-propenylene, 2-propenylene, methylvinylene, 1-butenylene, 2-butenylene, 3-butenylene, 2-methyl-l-propenylene, 2-methyl-2-propenylene, 2-pentenylene, 2-hexenylene.

The term "alkynylene or alkynyl" as used is the present application is an unsaturated branched or unbranched aliphatic bivalent substituent having a tripple bond between two adjacent carbon atoms(e.g. the alkynylene substituent has 2 to 6 carbon atoms 2 to 4 carbon atoms). Examples of the alkynylene substituent include but are not limited to ethynylene, 1-propynylene, 1-butynylene, 2-butynylene, 1-pentynylene, 2-pentynylene, 3-pentynylene and 2-hexynylene.

The term "alkadienylene" as used is the present application is an unsaturated branched or unbranched aliphatic bivalent substituent having two double bonds between two adjacent carbon atoms(e.g. the alkadienylene substituent has 4 to 10 carbon atoms). Accordingly, examples of the alkadienylene substituent include but are not limited to 2,4-pentadienylene, 2,4-hexadienylene, 4-methyl-2,4-pentadienyl ene, 2,4-heptadienylene, 2, 6-heptadi enyl ene, 3-methyl-2,4-hexadienylene, 2,6-octadienylene, 3-methyl-2,6-heptadienylene, 2-methyl-2,4-heptadienylene, 2,8-nonadienylene, 3-methyl-2,6-octadienylene, 2,6-decadienylene, 2,9-decadienylene and 3,7-dimethyl-2,6-octadienylene substituents.

The term "heteroaliphatic substituent or heteroalkyl", as used herein, refers to a monovalent or a bivalent substituent, in which one or more carbon atoms have been substituted with a heteroatom, for instance, with an oxygen, sulfur, nitrogen, phosphorus or silicon atom, wherein the nitrogen and sulfur atoms may optionally be oxidized, and the nitrogen heteroatom may optionally be quaternized. The heteroatom(s) O, N and S may be placed at any interior position of the heteroaliphatic substituent. Examples include —CH2—CH2-O—CH3, —CH2-CH2-NH—CH3, —CH2-CH2-N(CH3)-CH3, —CH2-S—CH2-CH3, —S(O)—CH3, —CH2-CH2-S(O)2-CH3, —CH═CH—O—CH3, —CH2-CH═N—OCH3, and —CH═CH—N(CH3)—CH3. A heteroaliphatic substituent may be linear or branched, and saturated or unsaturated.

In one embodiment, the heteroaliphatic substituent has 1 to 100, (e.g 1 to 42 carbon atoms). In yet another embodiment, the heteroaliphatic substituent is a polyethylene glycol residue.

As used herein, "aromatic substituent or aryl" is intended to mean any stable monocyclic, bicyclic or polycyclic carbon ring of up to 10 atoms in each ring, wherein at least one ring is aromatic, and may be unsubstituted or substituted. Examples of such aromatic substituents include phenyl, p-toluenyl (4-methylphenyl), naphthyl, tetrahydronaphthyl, indanyl, biphenyl, phenanthryl, anthryl or acenaphthyl. In cases where the aromatic substituent is bicyclic and one ring is non-aromatic, it is understood that attachment is via the aromatic ring.

The term "alkylaryl substituents or arylalkyl" refers to alkyl substituents as described above wherein one or more bonds to hydrogen contained therein are replaced by a bond to an aryl substituent as described above. It is understood that an arylalkyl substituents is connected to the carbonyl group if the compound of the invention through a bond from the alkyl substituent. Examples of arylalkyl substituents include, but are not limited to, benzyl (phenylmethyl), p-trifluoromethylbenzyl (4-trifluoromethylphenylmethyl), 1-phenyl ethyl, 2-phenyl ethyl, 3-phenylpropyl, 2-phenylpropyl and the like.

The term "heteroaromatic substituent or heteroaryl" as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic heteroaromatic substituents include phenyl, pyridine, pyrimidine or pyridizine rings that are
  a) fused to a 6-membered aromatic (unsaturated) heterocyclic ring having one nitrogen atom;
  b) fused to a 5- or 6-membered aromatic (unsaturated) heterocyclic ring having two nitrogen atoms;
  c) fused to a 5-membered aromatic (unsaturated) heterocyclic ring having one nitrogen atom together with either one oxygen or one sulfur atom; or
  d) fused to a 5-membered aromatic (unsaturated) heterocyclic ring having one heteroatom selected from O, N or S.

Heteroaryl groups within the scope of this definition include but are not limited to: benzoimidazolyl, benzofuranyl, b enzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The aliphatic, heteroaliphatic, aromatic and heteroaromatic substituents can be optionally substituted one or more times, the same way or differently with any one or more of the following substituents including, but not limited to: aliphatic, heteroaliphatic, aromatic and heteroaromatic substituents, aryl, heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO2; —CN; —CF3; —CH2CF3; —CHCl2; —CH2OH; —CH2CH2OH; —CH2NH2; —CH2SO2CH3; —C(O)Rx; —CO2(Rx); —CON(Rx)2; —OC(O)Rx; —OCO2Rx; —OCON(Rx)2; —N(RX)2; —S(O)Rx; —S(O)2Rx; —NRx (CO)Rx wherein each occurrence of Rx independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, (alkyl)aryl or (alkyl)heteroaryl substituents described above and herein may be substituted or unsubstituted. Additionally, it will be appreciated, that any two adjacent substituents taken together may represent a 4, 5, 6, or 7-membered substituted or unsubstituted alicyclic or heterocyclic substituents. Additional examples of generally applicable substituents are illustrated by the specific embodiments shown below.

The terms "halo" and "halogen" refer to a halogen atom selected from the group consisting of F, Cl, Br and I.

The term "halogenated alkyl substituent, haloalkyl" refers to an alkyl substituents as defined above which is substituted with at least one halogen atom. In an embodiment, the halogenated alkyl substituent is perhalogenated. In another embodiment, perfluoroalkyl refers to the halogenated alkyl substituent is a univalent perfluorated substituent of formula $C_nF_{2n+1}$. For example, the halogenated alkyl substituent may have 1 to 6 carbon atoms, (e.g. 1 to 3 carbon atoms). Accordingly, examples of the alkyl group include trifluoromethyl, 2,2,2-trifluoroethyl, n-perfluoropropyl, n-perfluorobutyl and n-perfluoropentyl.

The term "amino," as used herein, represents —N(RN1)2, wherein each RN1 is, independently, H, OH, NO2, N(RN2)2, SO2ORN2, SO2RN2, SORN2, an N-protecting group, alkyl, alkenyl, alkynyl, alkoxy, aryl, alkaryl, cycloalkyl, alkcycloalkyl, heterocyclyl (e.g., heteroaryl), alkheterocyclyl (e.g., alkheteroaryl), or two RN1 combine to form a heterocyclyl or an N-protecting group, and wherein each RN2 is, independently, H, alkyl, or aryl. In a preferred embodiment, amino is —NH2, or —NHRN1, wherein RN1 is, independently, OH, NO2, NH2, NRN22, SO2ORN2, SO2RN2, SORN2, alkyl, or aryl, and each RN2 can be H, alkyl, or aryl. The term "aminoalkyl," as used herein, represents a heteroalkyl group, as defined herein, that is described as an alkyl group, as defined herein, substituted by an amino group, as defined herein. The alkyl and amino each can be further substituted with 1, 2, 3, or 4 substituent groups as described herein for the respective group. For example, the alkyl moiety may comprise an oxo (=O) substituent.

As used herein, the term "aryloxy" refers to aromatic or heteroaromatic systems which are coupled to another residue through an oxygen atom. A typical example of an O-aryl is phenoxy. Similarly, "arylalkyl" refers to aromatic and heteroaromatic systems which are coupled to another residue through a carbon chain, saturated or unsaturated, typically of C1-C8, C1-C6, or more particularly C1-C4 or C1-C3 when saturated or C2-C8, C2-C6, C2-C4, or C2-C3 when unsaturated, including the heteroforms thereof. For greater certainty, arylalkyl thus includes an aryl or heteroaryl group as defined above connected to an alkyl, heteroalkyl, alkenyl, heteroalkenyl, alkynyl or heteroalkynyl moiety also as defined above. Typical arylalkyls would be an aryl(C6-C12)alkyl(C1-C8), aryl(C6-C12)alkenyl(C2-C8), or aryl(C6-C12)alkynyl(C2-C8), plus the heteroforms. A typical example is phenylmethyl, commonly referred to as benzyl.

Typical optional substituents on aromatic or heteroaromatic groups include independently halo, CN, NO2, CF3, OCF3, COOR', CONR'2, OR', SR', SOR', SO2R', NR'2, NR'(CO)R',NR'C(O)OR', NR'C(O)NR'2, NR'SO2NR'2, or NR'SO2R', wherein each R' is independently H or an optionally substituted group selected from alkyl, alkenyl, alkynyl, heteroalkyl, heteroalkenyl, heteroalkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl and arylalkyl.

Optional substituents on a non-aromatic group (e.g., alkyl, alkenyl, and alkynyl groups), are typically selected from the same list of substituents suitable for aromatic or heteroaromatic groups, except as noted otherwise herein. A non-aromatic group may also include a substituent selected from =O and =NOR' where R' is H or an optionally substituted group selected from alkyl, alkenyl, alkynyl, heteroalkyl, heteroalkenyl, heteralkynyl, heteroaryl, and aryl (all as defined above).

In general, a substituent group (e.g., alkyl, alkenyl, alkynyl, or aryl (including all heteroforms defined above) may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. However, alkyl substituted by aryl, amino, halo and the like would be included. For example, where a group is substituted, the group may be substituted with 1, 2, 3, 4, 5, or 6 substituents. Optional substituents include, but are not limited to: C1-C6 alkyl or heteroaryl, C2-C6 alkenyl or heteroalkenyl, C2-C6 alkynyl or heteroalkynyl, halogen; aryl, heteroaryl, azido(—N3), nitro (—NO2), cyano (—CN), acyloxy(—OC(=O)R'), acyl (—C(=O)R'), alkoxy (—OR'), amido (—NR'C(=O)R" or —C(=O)NRR'), amino ('NRR'), carboxylic acid (—CO2H), carboxylic ester (—CO2R'), carbamoyl (—OC(=O)NR'R" or —NRC(=O)OR'), hydroxy (—OH), isocyano (—NC), sulfonate (—S(=O)2OR), sulfonamide (—S(=O)2NRR' or —NRS(=O)2R'), or sulfonyl ('S(=O)2R), where each R or R' is selected, independently, from H, C1-C6 alkyl or heteroaryl, C2-C6 alkenyl or heteroalkenyl, 2C-6C alkynyl or heteroalkynyl, aryl, or heteroaryl. A substituted group may have, for example, 1, 2, 3, 4, 5, 6, 7, 8, or 9 substituents.

The term "heterocyclyl, heterocyclic, or Het" as used herein represents cyclic heteroalkyl or heteroalkenyl that is, e.g., a 3-, 4-, 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like.

Some of the compounds of the present invention can comprise one or more stereogenic centers, and thus can exist in various isomeric forms, e.g. stereoisomers and/or diastereomers. Thus, the compounds of the invention and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided. Moreover, when compounds of the invention exist in tautomeric forms, each tautomer is embraced herein.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Treatment Methods

As disclosed herein, miR-1908, miR-199a-3p, miR-199a-5p, and CTGF were identified as endogenous metastasis promoters of metastatic invasion, endothelial recruitment, and colonization in melanoma while DNAJA4, ApoE, LRP1, LRP8, LXR, and miR7 function as metastasis suppressors or inhibitors of the same process. In addition, it was found that these miRNAs convergently target ApoE and the heat-shock factor DNAJA4. Cancer-secreted ApoE suppresses invasion and endothelial recruitment by activating melanoma cell LRP1 and endothelial LRP8 receptors, respectively. DNAJA4, in turn, induces ApoE expression. These miRNAs strongly predict human metastatic outcomes. Pre-treatment with locked nucleic acids (LNAs) targeting miR-199a-3p, miR-199a-5p, and miR-1908 inhibits metastasis to multiple organs, while therapeutic delivery of these LNAs significantly suppresses human melanoma cell metastasis in a mouse model.

Accordingly, this invention provides methods for treating melanoma via increasing in the subject the expression level or activity level of one of the metastasis suppressors. This increasing can be achieved by, among others, forced expression of one or more of the metastasis suppressors DNAJA4, ApoE, LRP1, and LRP8, or decreasing the expression level or activity level of one or more miR-199a-3p, miR-199a-5p, and miR-1908. In addition, the treatment can be achieved by decreasing the expression level or activity level of one or more of the metastasis promoters.

The invention also provides methods for treating in a subject an angiogenic disorder or a disorder of angiogenesis. The terms "angiogenic disorder," "disorder of angiogenesis," and "angiogenesis disorder" are used interchangeably herein, and refer to a disorder characterized by pathological angiogenesis. A disorder characterized by pathological angiogenesis refers to a disorder where abnormal or aberrant angiogenesis, alone or in combination with others, contributes to causation, origination, or symptom of the disorder. Examples of this disorder include various cancers (e.g., vascularized tumors), eye disorders, inflammatory disorders, and others.

Typical vascularized tumors that can be treated with the method include solid tumors, particularly carcinomas, which require a vascular component for the provision of oxygen and nutrients. Exemplary solid tumors include, but are not limited to, carcinomas of the lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, Kaposi's sarcoma, and sarcomas.

A number of disorders or conditions, other than cancer, also can be treated with the above-described method. Examples include arthritis, rheumatoid arthritis, psoriasis, atherosclerosis, diabetic retinopathy, age-related macular degeneration, Grave's disease, vascular restenosis (including restenosis following angioplasty), arteriovenous malformations (AVM), meningioma, hemangioma, neovascular glaucoma, chronic kidney disease, diabetic nephropathy, polycystic kidney disease, interstitial lung disease, pulmonary hypertension, chronic obstructive pulmonary disease (COPD), emphysema, autoimmune hepatitis, chronic inflammatory liver disease, hepatic cirrhosis, cutaneous T-cell lymphoma, rosacea, and basal cell carcinoma.

Other treatment targets include those described in, e.g., US Applications 2009004297, 20090175791, and 20070161553, such as angiofibroma, atherosclerotic plaques, corneal graft neovascularization, hemophilic joints, hypertrophic scars, Osler-Weber syndrome, pyogenic granuloma retrolental fibroplasia, scleroderma, trachoma, vascular adhesions, synovitis, dermatitis, various other inflammatory diseases and disorders, and endometriosis.

Forced Expression of Metastasis Suppressors

Both polypeptides of the aforementioned metastasis suppressors (e.g., DNAJA4, ApoE, LRP1, LRP8, and LXR) and nucleic acid encoding the polypeptides can be used to practice the invention. While many polypeptide preparations can be used, a highly purified or isolated polypeptide is preferred. The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (e.g., glycosylation or phosphorylati on).

The polypeptide "of this invention" includes recombinantly or synthetically produced fusion or chimeric versions of any of the aforementioned metastasis suppressors, having the particular domains or portions that are involved in the network. The term also encompasses polypeptides that have an added amino-terminal methionine (useful for expression in prokaryotic cells).

Within the scope of this invention are fusion proteins containing one or more of the afore-mentioned sequences and a heterologous sequence. A "chimeric" or "fusion" refers to the combination of amino acid sequences of different origin in one polypeptide chain by in-frame combination of their coding nucleotide sequences. The term explicitly encompasses internal fusions, i.e., insertion of sequences of different origin within a polypeptide chain, in addition to fusion to one of its termini. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

An "isolated" or "purified" polypeptide refers to a polypeptide that has been separated from other proteins, lipids, and nucleic acids with which it is naturally associated. The polypeptide can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide described in the invention can be purified from a natural source, produced by recombinant DNA techniques, or by chemical methods.

A "recombinant" polypeptide refers to a polypeptide produced by recombinant DNA techniques; i.e., produced from cells transformed by an exogenous DNA construct encoding the desired polypeptide. A "synthetic" polypeptide refers to a polypeptide prepared by chemical synthesis. The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified.

"Overexpression" refers to the expression of a RNA or polypeptide encoded by a nucleic acid introduced into a host cell, wherein the RNA or polypeptide or protein is either not normally present in the host cell, or wherein the RNA or polypeptide is present in said host cell at a higher level than that normally expressed from the endogenous gene encoding the RNA or polypeptide.

The amino acid composition of each of the above-mentioned polypeptides may vary without disrupting their functions—the ability to up-regulate the above-mentioned network (e.g., increase the activation level of the ApoE/LRP signaling pathway), thereby inhibiting metastasis to multiple organs. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in one of the above-described polypeptides (e.g., SEQ ID NOs: 2, 4, 6, 8, 10, 12, 14, 16, and 18) is preferably replaced with another amino acid residue from the same side chain family. Alternatively, mutations can be introduced randomly along all or part of the sequences, such as by saturation mutagenesis, and the resultant mutants can be screened for the ability to up-regulate the above-mentioned network or ApoE/LRP signaling pathway, and trigger the respective cellular response to identify mutants that retain the activity as descried below in the examples.

A functional equivalent of a polypeptide of this invention refers to a derivative of the polypeptide, e.g., a protein having one or more point mutations, insertions, deletions, truncations, a fusion protein, or a combination thereof. It retains substantially the activity to of the above-mentioned polypeptide. The isolated polypeptide of this invention can contain the sequence of one of SEQ ID NOs: 2, 4, 6, 8, 10, 12, 14, 16, and 18, or a functional equivalent or fragment thereof. In general, the functional equivalent is at least 75% (e.g., any number between 75% and 100%, inclusive, e.g., 70%, 80%, 85%, 90%, 95%, and 99%) identical to one of SEQ ID NOs: 2, 4, 6, 8, 10, 12, 14, 16, and 18.

A polypeptide described in this invention can be obtained as a recombinant polypeptide. To prepare a recombinant polypeptide, a nucleic acid encoding it can be linked to another nucleic acid encoding a fusion partner, e.g., glutathione-s-transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention. Alternatively, the polypeptide of the invention can be chemically synthesized (see e.g., Creighton, "Proteins: Structures and Molecular Principles," W. H. Freeman & Co., NY, 1983). For additional guidance, skilled artisans may consult Ausubel et al. (Current Protocols in Molecular Biology and Short Protocols in Molecular Biology, 3rd Ed. 1987 & 1995), Sambrook et al. (Molecular Cloning, A Laboratory Manual, Cold Spring Harbor Press, Cold Spring Harbor, N.Y., 1989), and chemical synthesis Gait, M.bJ. Ed. (Oligonucleotide Synthesis, IRL Press, Oxford, 1984).

Due to their functions as cellular protein or membrane protein, DNAJA4, LRP1, LRP8, and LXR can be associated with, e.g., conjugated or fused to, one or more of an amino acid sequence comprising a cell-penetrating peptide (CPP) sequence, and the like. In this manner, a composition of the invention as discussed below can include a transport enhancer. A cell-penetrating peptide (CPP) generally consists of less than 30 amino acids and has a net positive charge. CPPs internalize in living animal cells in an endocytotic or receptor/energy-independent manner. There are several classes of CPPs with various origins, from totally protein-derived CPPs via chimeric CPPs to completely synthetic CPPs. Examples of CPPs are known in the art. See, e.g., U.S. Application Nos. 20090099066 and 20100279918. It is know that CPPs can delivery an exogenous protein into various cells.

All of naturally occurring versions, genetic engineered versions, and chemically synthesized versions of the above-mentioned polypeptides can be used to practice the invention disclosed therein. Polypeptides obtained by recombinant DNA technology may have the same amino acid sequence as a naturally occurring version (e.g., one of SEQ ID NOs: 2, 4, 6, 8, 10, 12, 14, 16, and 18) or a functionally equivalent thereof. They also include chemically modified versions. Examples of chemically modified polypeptides include polypeptides subjected to conformational change, addition or deletion of a side chain, and those to which a compound such as polyethylene glycol has been bound. Once purified and tested by standard methods or according to the method described in the examples below or other methods known in the art, the polypeptides can be included in suitable composition.

For expressing the above-mentioned factors, the invention provides a nucleic acid that encodes any of the polypeptides mentioned above. Preferably, the nucleotide sequences are isolated and/or purified. A nucleic acid refers to a DNA molecule (e.g., but not limited to, a cDNA or genomic DNA), an RNA molecule (e.g., but not limited to, an mRNA), or a DNA or RNA analog. A DNA or RNA analog can be synthesized from nucleotide analogs. The nucleic acid molecule can be single-stranded or double-stranded. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The terms "RNA," "RNA molecule," and "ribonucleic acid molecule" are used interchangeably herein, and refer to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA also can be chemically synthesized. DNA and RNA can be single-stranded (i.e., ssRNA and ssDNA, respectively) or multi-stranded (e.g., double-stranded, i.e., dsRNA and dsDNA, respectively).

The present invention also provides recombinant constructs having one or more of the nucleotide sequences described herein. Example of the constructs include a vector, such as a plasmid or viral vector, into which a nucleic acid sequence of the invention has been inserted, in a forward or reverse orientation. In a preferred embodiment, the construct further includes regulatory sequences, including a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook et al. (2001, Molecular Cloning: A Laboratory Manual, Cold Spring Harbor Press).

Examples of expression vectors include chromosomal, nonchromosomal and synthetic DNA sequences, e.g., derivatives of or Simian virus 40 (SV40), bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the polypeptides described above can be inserted into an appropriate restriction endonuclease site(s) by procedures known in the art. Such procedures and related sub-cloning procedures are within the scope of those skilled in the art.

The nucleic acid sequence in the aforementioned expression vector is preferably operatively linked to an appropriate transcription control sequence (promoter) to direct mRNA synthesis. Examples of such promoters include: the retroviral long terminal (LTR) or SV40 promoter, the *E. coli* lac or trp promoter, the phage lambda PL promoter, and other promoters known to control expression of genes in prokaryotic or eukaryotic cells or viruses. The expression vector can also contain a ribosome binding site for translation initiation, and a transcription terminator. The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in *E. coli.*

The vector containing the appropriate nucleic acid sequences as described above, as well as an appropriate promoter or control sequence, can be employed to transform an appropriate host to permit the host to express the polypeptides described above. Such vectors can be used in gene therapy. Examples of suitable expression hosts include bacterial cells (e.g., *E. coli, Streptomyces, Salmonella typhimurium*), fungal cells (yeast), insect cells (e.g., *Drosophila* and *Spodoptera frugiperda* (519)), animal cells (e.g., CHO, COS, and HEK 293), adenoviruses, and plant cells. The selection of an appropriate host is within the scope of those skilled in the art. In some embodiments, the present invention provides methods for producing the above mentioned polypeptides by transfecting a host cell with an expression vector having a nucleotide sequence that encodes one of the polypeptides. The host cells are then cultured under a suitable condition, which allows for the expression of the polypeptide.

Decreasing Expression or Activity Level of Metastasis Promoters

As mentioned above, one can use an inhibitory agent that decreases the expression or activity level of miR-199a-3p, miR-199a-5p, miR-1908, or CTGF in treating melanoma. An inhibitory agent (i.e., inhibitor) can be a nucleic acid, a polypeptide, an antibody, or a small molecule compound. In one example, the inhibitor functions at a level of transcription, mRNA stability, translation, protein stability/degradation, protein modification, and protein binding.

A nucleic acid inhibitor can encode a small interference RNA (e.g., an RNAi agent) that targets one or more of the above-mentioned genes, e.g., CTGF, and inhibits its expression or activity. The term "RNAi agent" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein or RNA) is down-regulated. Generally, an interfering RNA ("iRNA") is a double stranded short-interfering RNA (siRNA), short hairpin RNA (shRNA), or single-stranded micro-RNA (miRNA) that results in catalytic degradation of specific mRNAs, and also can be used to lower or inhibit gene expression.

The term "short interfering RNA" or "siRNA" (also known as "small interfering RNAs") refers to an RNA agent, preferably a double-stranded agent, of about 10-50 nucleotides in length, preferably between about 15-25 nucleotides in length, more preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

The term "miRNA" or "microRNA" refers to an RNA agent, preferably a single-stranded agent, of about 10-50 nucleotides in length, preferably between about 15-25 nucleotides in length, more preferably about 17, 18, 19, 20, 21, 22, 23, 24, or 25 nucleotides in length, which is capable of directing or mediating RNA interference. Naturally-occurring miRNAs are generated from stem-loop precursor RNAs (i.e., pre-miRNAs) by Dicer. The term "Dicer" as used herein, includes Dicer as well as any Dicer orthologue or homologue capable of processing dsRNA structures into siRNAs, miRNAs, siRNA-like or miRNA-like molecules. The term microRNA (or "miRNA") is used interchangeably with the term "small temporal RNA" (or "stRNA") based on the fact that naturally-occurring microRNAs (or "miRNAs") have been found to be expressed in a temporal fashion (e.g., during development).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

Within the scope of this invention is utilization of RNAi featuring degradation of RNA molecules (e.g., within a cell). Degradation is catalyzed by an enzymatic, RNA-induced silencing complex (RISC). A RNA agent having a sequence sufficiently complementary to a target RNA sequence (e.g., the above-mentioned CTGF gene) to direct RNAi means that the RNA agent has a homology of at least 50%, (e.g., 50%, 60%, 70%, 80%, 90%, 95%, 98%, 99%, or 100% homology) to the target RNA sequence so that the two are sufficiently complementary to each other to hybridize and trigger the destruction of the target RNA by the RNAi machinery (e.g., the RISC complex) or process. A RNA agent having a "sequence sufficiently complementary to a target RNA sequence to direct RNAi" also means that the RNA agent has a sequence sufficient to trigger the translational inhibition of the target RNA by the RNAi machinery or process. A RNA agent also can have a sequence sufficiently complementary to a target RNA encoded by the target DNA sequence such that the target DNA sequence is chromatically silenced. In other words, the RNA agent has a sequence sufficient to induce transcriptional gene silencing, e.g., to down-modulate gene expression at or near the target DNA sequence, e.g., by inducing chromatin structural changes at or near the target DNA sequence.

The above-mentioned polynucleotides can be delivered using polymeric, biodegradable microparticle or microcapsule delivery devices known in the art. Another way to achieve uptake of the polynucleotides is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of naked DNA (i.e., without a delivery vehicle) to an intramuscular, intradermal, or subcutaneous site is another means to achieve in vivo expression.

siRNA, miRNA, and asRNA (antisense RNA) molecules can be designed by methods well known in the art. siRNA, miRNA, and asRNA molecules with homology sufficient to provide sequence specificity required to uniquely degrade any RNA can be designed using programs known in the art, including, but not limited to, those maintained on websites for AMBION, Inc. and DHARMACON, Inc. Systematic testing of several designed species for optimization of the siRNA, miRNA, and asRNA sequence can be routinely performed by those skilled in the art. Considerations when designing short interfering nucleic acid molecules include, but are not limited to, biophysical, thermodynamic, and structural considerations, base preferences at specific positions in the sense strand, and homology. These considerations are well known in the art and provide guidelines for designing the above-mentioned RNA molecules.

An antisense polynucleotide (preferably DNA) of the present invention can be any antisense polynucleotide so long as it possesses a base sequence complementary or substantially complementary to that of the gene encoding a component of the aforementioned network. The base sequence can be at least about 70%, 80%, 90%, or 95% homology to the complement of the gene encoding the polypeptide. These antisense DNAs can be synthesized using a DNA synthesizer.

The antisense DNA of the present invention may contain changed or modified sugars, bases or linkages. The antisense DNA, as well as the RNAi agent mentioned above, may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like. The inhibitory action of the antisense DNA can be examined using a cell-line or animal based gene expression system of the present invention in vivo and in vitro.

The above-discussed nucleic acids encoding one or more of the polypeptides mentioned above or RNAi agents can be cloned in a vector for delivering to cells in vitro or in vivo. For in vivo uses, the delivery can target a specific tissue or organ (e.g., skin). Targeted delivery involves the use of vectors (e.g., organ-homing peptides) that are targeted to specific organs or tissues after systemic administration. For example, the vector can have a covalent conjugate of avidin and a monoclonal antibody to a liver specific protein.

In certain embodiments, the present invention provides methods for in vivo expression the above-mentioned metastasis suppressors. Such method would achieve its therapeutic effect by introduction of nucleic acid sequences encoding any of the factors into cells or tissues of a human or a non-human animal in need of inhibiting endothelial recruitment, cancer cell invasion, or metastatic angiogenesis. Delivery of the nucleic acid sequences can be achieved using a recombinant expression vector such as a chimeric virus or a colloidal dispersion system. Preferred for therapeutic delivery of the nucleic acid sequences is the use of targeted liposomes.

Various viral vectors which can be utilized for gene therapy disclosed herein include, adenovirus, adeno-associated virus (AAV), herpes virus, vaccinia, or, preferably, an RNA virus such as a retrovirus and a lentivirus. Preferably, the retroviral vector is a lentivirus or a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes.

All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using a target-specific antibody or hormone that has a receptor in the target. Those of skill in the art will recognize that specific polynucleotide sequences can be inserted into the retroviral genome or attached to a viral envelope to allow target specific delivery of the retroviral vector.

Another targeted system for delivery of nucleic acids is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA, and intact virions can be encapsulated within the aqueous interior and delivered to cells in a biologically active form. Methods for efficient gene transfer using a liposome vehicle are known in the art. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Exemplary phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

When used in vivo, it is desirable to use a reversible delivery-expression system. To that end, the Cre-loxP or FLP/FRT system and other similar systems can be used for reversible delivery-expression of one or more of the above-described nucleic acids. See WO2005/112620, WO2005/039643, U.S. Applications 20050130919, 20030022375, 20020022018, 20030027335, and 20040216178. In particular, the reversible delivery-expression system described in US Application NO 20100284990 can be used to provide a selective or emergency shut-off.

In another example, the above-mentioned inhibitory agent can be a polypeptide or a protein complex, such as an antibody. The term "antibody" refers to an immunoglobulin molecule or immunologically active portion thereof, i.e., an antigen-binding portion. Examples include, but are not limited to, a protein having at least one or two, heavy (H) chain variable regions (VH), and at least one or two light (L) chain variable regions (VL). The VH and VL regions can be further subdivided into regions of hypervariability, termed "complementarity determining regions" ("CDR"), interspersed with regions that are more conserved, termed "framework regions" (FR). As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, and IgG4), delta, epsilon and mu constant region genes, as well as the myriad immunoglobulin variable region genes.

The term "antigen-binding portion" of an antibody (or "antibody portion") refers to one or more fragments of an antibody that retain the ability to specifically bind to an antigen (e.g., LRP1, LRP8, and CTGF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85: 5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

Antibodies that specifically bind to one of the above-mentioned target proteins (e.g., CTGF) can be made using methods known in the art. This antibody can be a polyclonal or a monoclonal antibody. In one embodiment, the antibody can be recombinantly produced, e.g., produced by phage display or by combinatorial methods. In another embodiment, the antibody is a fully human antibody (e.g., an antibody made in a mouse which has been genetically engineered to produce an antibody from a human immunoglobulin sequence), a humanized antibody, or a non-human antibody, for example, but not limited to, a rodent (mouse or rat), goat, primate (for example, but not limited to, monkey), rabbit, or camel antibody. Examples of methods to generate humanized version of antibodies include, but are not limited to, CDR grafting (Queen et al., U.S. Pat. No. 5,585,089; Riechmann et al., Nature 332:323 (1988)), chain shuffling (U.S. Pat. No. 5,565,332); and veneering or resurfacing (EP 592,106; EP 519,596); Padlan, Molecular Immunology 28(415):489-498 (1991); Studnicka et al., Protein Engineering 7(6):805-814 (1994); Roguska. et al., PNAS 91:969-973 (1994)). Examples of methods to generate fully human antibodies include, but are not limited to, generation of antibodies from mice that can express human immunoglobulin genes and use of phage-display technology to generate and screen human immunoglobulin gene libraries.

An "isolated antibody" is intended to refer to an antibody that is substantially free of other antibodies having different antigenic specificities (e.g., an isolated antibody that specifically binds CTGF is substantially free of antibodies that specifically bind antigens other than such an antigen). Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by the heavy chain constant region genes. The phrases "an antibody recognizing an antigen" and "an antibody specific for an antigen" are used interchangeably herein with the term "an antibody which binds specifically to an antigen." As used herein, the term "high affinity" for an IgG antibody refers to an antibody having a KD of 10-7 M or less, preferably 10-8 M or less, more preferably 10-9 M or less and even more preferably 10-10 M or less for a target antigen. However, "high affinity" binding can vary for other antibody isotypes. For example, "high affinity" binding for an IgM isotype refers to an antibody having a KD of 10-7 M or less, more preferably 10-8 M or less.

In one example, a composition contains a monoclonal antibody that neutralizes CTGF. In one embodiment, this antibody can be a fully human antibody, a humanized antibody, or a non-human antibody, for example, but not limited to, a rodent (mouse or rat), goat, primate (for example, but not limited to, monkey), rabbit, or camel antibody. In one embodiment, one or more amino-acids of this monoclonal monoclonal antibody may be substituted in order to alter its physical properties. These properties include, but are not limited to, binding specificity, binding affinity, immunogenicity, and antibody isotype. Pharmaceutical compositions containing fully human or humanized versions of the above described antibodies can be used for treating melanoma or for inhibiting endothelial recruitment, cancer cell invasion, or metastatic angiogenesi s.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental animal or animal suitable as a disease model. A subject to be treated for a disorder can be identified by standard diagnosing techniques for the disorder. Optionally, the subject can be examined for mutation, expression level, or activity level of one or more of the miR-199a-3p, miR-199a-5p, miR-1908, and CTGF mentioned above by methods known in the art or described above before treatment. If the subject has a particular mutation in the gene, or if the gene expression or activity level is, for example, greater in a sample from the subject than that in a sample from a normal person, the subject is a candidate for treatment of this invention.

To confirm the inhibition or treatment, one can evaluate and/or verify the inhibition of endothelial recruitment or resulting angiogenesis using technology known in the art before and/or after the administering step. Exemplary technologies include angiography or arteriography, a medical imaging technique used to visualize the inside, or lumen, of blood vessels and organs of the body, can generally be done by injecting a radio-opaque contrast agent into the blood vessel and imaging using X-ray based techniques such as fluoroscopy.

"Treating" or "treatment" as used herein refers to administration of a compound or agent to a subject who has a disorder with the purpose to cure, alleviate, relieve, remedy, delay the onset of, prevent, or ameliorate the disorder, the symptom of a disorder, the disease state secondary to the disorder, or the predisposition toward the disorder. An "effective amount" or "therapeutically effective amount" refers to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The expression "effective amount" as used herein, refers to a sufficient amount of the compound of the invention to exhibit the desired therapeutic effect. The exact amount required will vary from subject to subject, depending on the species, age, and general condition of the subject, the particular therapeutic agent and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the anticancer activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

A therapeutic agent can be administered in vivo or ex vivo, alone or co-administered in conjunction with other drugs or therapy, i.e., a cocktail therapy. As used herein, the term "co-administration" or "co-administered" refers to the administration of at least two agent(s) or therapies to a subject. For example, in the treatment of tumors, particularly vascularized, malignant tumors, the agents can be used alone or in combination with, e.g., chemotherapeutic, radiotherapeutic, apoptopic, anti-angiogenic agents and/or immunotoxins or coaguligands. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In an in vivo approach, a compound or agent is administered to a subject. Generally, the compound is suspended in a pharmaceutically-acceptable carrier (such as, for example, but not limited to, physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) can increase the efficiency of delivery, particularly for oral delivery.

Compositions

Within the scope of this invention is a composition that contains a suitable carrier and one or more of the therapeutic agents described above. The composition can be a pharmaceutical composition that contains a pharmaceutically acceptable carrier, a dietary composition that contains a dietarily acceptable suitable carrier, or a cosmetic composition that contains a cosmetically acceptable carrier.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, sodium lauryl sulfate, and D&C Yellow #10.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts, include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; natural and synthetic phospholipids, such as soybean and egg yolk phosphatides, lecithin, hydrogenated soy lecithin, dimyristoyl lecithin, dipalmitoyl lecithin, distearoyl lecithin, dioleoyl lecithin, hydroxylated lecithin, lysophosphatidylcholine, cardiolipin, sphingomyelin, phosphatidylcholine, phosphatidyl ethanolamine, diastearoyl phosphatidylethanolamine (DSPE) and its pegylated esters, such as DSPE-PEG750 and, DSPE-PEG2000, phosphatidic acid, phosphatidyl glycerol and phosphatidyl serine. Commercial grades of lecithin which are preferred include those which are available under the trade name Phosal® or Phospholipon® and include Phosal 53 MCT, Phosal 50 PG, Phosal 75 SA, Phospholipon 90H, Phospholipon 90G and Phospholipon 90 NG; soy-phosphatidylcholine (SoyPC) and DSPE-PEG2000 are particularly preferred; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The above-described composition, in any of the forms described above, can be used for treating melanoma, or any other disease or condition described herein. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally comprise one or more excipients or diluents. In some preferred embodiments, the topical formulations include a material that would enhance absorption or penetration of the active agent(s) through the skin or other affected areas.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incompatibility, instability, allergic response, and the like. The carrier enables an active agent and optional component to be delivered to the skin at an appropriate concentration(s). The carrier thus can act as a diluent, dispersant, solvent, or the like to ensure that the active materials are applied to and distributed evenly over the selected target at an appropriate concentration. The carrier can be solid, semi-solid, or liquid. The carrier can be in the form of a lotion, a cream, or a gel, in particular one that has a sufficient thickness or yield point to prevent the active materials from sedimenting. The carrier can be inert or possess dermatological benefits. It also should be physically and chemically compatible with the active components described herein, and should not unduly impair stability, efficacy, or other use benefits associated with the composition.

Combination Therapies

In some embodiments, the pharmaceutical composition may further comprise an additional compound having antiproliferative activity. The additional compound having antiproliferative activity can be selected from a group of antiproliferative agents including those shown in Table 2.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

By "antiproliferative agent" is meant any antiproliferative agent, including those antiproliferative agents listed in Table 2, any of which can be used in combination with a LXR agonist to treat the medical conditions recited herein. Antiproliferative agents also include organo-platine derivatives, naphtoquinone and benzoquinone derivatives, chrysophanic acid and anthroquinone derivatives thereof.

TABLE 2

| | | |
|---|---|---|
| Alkylating agents | Busulfan | Chlorambucil |
| | dacarbazine | procarbazine |
| | ifosfamide | altretamine |
| | hexamethylmelamine | estramustine phosphate |
| | thiotepa | mechlorethamine |
| | dacarbazine | streptozocin |
| | lomustine | temozolomide |
| | cyclophosphamide | Semustine |
| Platinum agents | spiroplatin | lobaplatin (Aeterna) |
| | tetraplatin | satraplatin (Johnson Matthey) |
| | ormaplatin | BBR-3464 (Hoffmann-La Roche) |
| | iproplatin | |
| | ZD-0473 (AnorMED) | SM-11355 (Sumitomo) |
| | oxaliplatin | AP-5280 (Access) |
| | carboplatin | cisplatin |
| Antimetabolites | azacytidine | trimetrexate |
| | Floxuridine | deoxycoformycin |
| | 2-chlorodeoxyadenosine | pentostatin |
| | 6-mercaptopurine | hydroxyurea |
| | 6-thioguanine | decitabine (SuperGen) |
| | cytarabine | clofarabine (Bioenvision) |
| | 2-fluorodeoxy cytidine | irofulven (MGI Pharma) |

TABLE 2-continued

| | | |
|---|---|---|
| | methotrexate | DMDC (Hoffmann-La Roche) |
| | tomudex | ethynylcytidine (Taiho) |
| | fludarabine | gemcitabine |
| | raltitrexed | capecitabine |
| Topoisomerase inhibitors | amsacrine | exatecan mesylate (Daiichi) |
| | epirubicin | quinamed (ChemGenex) |
| | etoposide | gimatecan (Sigma-Tau) |
| | teniposide or mitoxantrone | diflomotecan (Beaufour-Ipsen) |
| | 7-ethyl-10-hydroxy-camptothecin | TAS-103 (Taiho) |
| | dexrazoxanet (TopoTarget) | elsamitrucin (Spectrum) |
| | pixantrone (Novuspharma) | J-107088 (Merck & Co) |
| | rebeccamycin analogue (Exelixis) | BNP-1350 (BioNumerik) |
| | BBR-3576 (Novuspharma) | CKD-602 (Chong Kun Dang) |
| | rubitecan (SuperGen) | KW-2170 (Kyowa Hakko) |
| | irinotecan (CPT-11) | hydroxycamptothecin (SN-38) |
| | topotecan | |
| Antitumor antibiotics | valrubicin | azonafide |
| | therarubicin | anthrapyrazole |
| | idarubicin | oxantrazole |
| | rubidazone | losoxantrone |
| | plicamycin | MEN-10755 (Menarini) |
| | porfiromycin | GPX-100 (Gem Pharmaceuticals) |
| | mitoxantrone (novantrone) | Epirubicin |
| | amonafide | mitoxantrone |
| | | doxorubicin |
| Antimitotic agents | colchicine | E7010 (Abbott) |
| | vinblastine | PG-TXL (Cell Therapeutics) |
| | vindesine | IDN 5109 (Bayer) |
| | dolastatin 10 (NCI) | A 105972 (Abbott) |
| | rhizoxin (Fujisawa) | A 204197 (Abbott) |
| | mivobulin (Warner-Lambert) | LU 223651 (BASF) |
| | cemadotin (BASF) | D 24851 (ASTAMedica) |
| | RPR 109881A (Aventis) | ER-86526 (Eisai) |
| | TXD 258 (Aventis) | combretastatin A4 (BMS) |
| | epothilone B (Novartis) | isohomohalichondrin-B (PharmaMar) |
| | T 900607 (Tularik) | |
| | T 138067 (Tularik) | ZD 6126 (AstraZeneca) |
| | cryptophycin 52 (Eli Lilly) | AZ10992 (Asahi) |
| | vinflunine (Fabre) | IDN-5109 (Indena) |
| | auristatin PE (Teikoku Hormone) | AVLB (Prescient NeuroPharma) |
| | BMS 247550 (BMS) | azaepothilone B (BMS) |
| | BMS 184476 (BMS) | BNP-7787 (BioNumerik) |
| | BMS 188797 (BMS) | CA-4 prodrug (OXiGENE) |
| | taxoprexin (Protarga) | dolastatin-10 (NIH) |
| | SB 408075 (GlaxoSmithKline) | CA-4 (OXiGENE) |
| | Vinorelbine | docetaxel |
| | Trichostatin A | vincristine |
| | | paclitaxel |
| Aromatase inhibitors | aminoglutethimide | YM-511 (Yamanouchi) |
| | atamestane (BioMedicines) | formestane |
| | letrozole | exemestane |
| | anastrazole | |
| Thymidylate synthase inhibitors | pemetrexed (Eli Lilly) | nolatrexed (Eximias) |
| | ZD-9331 (BTG) | CoFactor ™ (BioKeys) |
| DNA antagonists | trabectedin (PharmaMar) | edotreotide (Novartis) |
| | glufosfamide (Baxter International) | mafosfamide (Baxter International) |
| | albumin + 32P (Isotope Solutions) | apaziquone (Spectrum Pharmaceuticals) |
| | thymectacin (NewBiotics) | O6 benzyl guanine (Paligent) |
| Farnesyltransferase inhibitors | arglabin (NuOncology Labs) | tipifarnib (Johnson & Johnson) |
| | lonafarnib (Schering-Plough) | perillyl alcohol (DOR BioPharma) |
| | BAY-43-9006 (Bayer) | |
| Pump inhibitors | CBT-1 (CBA Pharma) | zosuquidar trihydrochloride (Eli Lilly) |
| | tariquidar (Xenova) | |
| | MS-209 (Schering AG) | biricodar dicitrate (Vertex) |
| Histone acetyltransferase inhibitors | tacedinaline (Pfizer) | pivaloyloxymethyl butyrate (Titan) |
| | SAHA (Aton Pharma) | |
| | MS-275 (Schering AG) | depsipeptide (Fujisawa) |
| Metalloproteinase inhibitors | Neovastat (Aeterna Laboratories) | CMT-3 (CollaGenex) |
| | marimastat (British Biotech) | BMS-275291 (Celltech) |
| Ribonucleoside reductase inhibitors | gallium maltolate (Titan) | tezacitabine (Aventis) |
| | triapine (Vion) | didox (Molecules for Health) |
| TNF alpha agonists/antagonists | virulizin (Lorus Therapeutics) | revimid (Celgene) |
| | CDC-394 (Celgene) | |
| Endothelin A receptor antagonist | atrasentan (Abbott) | YM-598 (Yamanouchi) |
| | ZD-4054 (AstraZeneca) | |
| Retinoic acid receptor agonists | fenretinide (Johnson & Johnson) | alitretinoin (Ligand) |
| | LGD-1550 (Ligand) | |

TABLE 2-continued

| | | |
|---|---|---|
| Immunomodulators | interferon<br>oncophage (Antigenics)<br>GMK (Progenics)<br>adenocarcinoma vaccine (Biomira)<br>CTP-37 (AVI BioPharma)<br>IRX-2 (Immuno-Rx)<br>PEP-005 (Peplin Biotech)<br>synchrovax vaccines (CTL Immuno)<br>melanoma vaccine (CTL Immuno)<br>p21 RAS vaccine (GemVax)<br>MAGE-A3 (GSK)<br>nivolumab (BMS)<br>abatacept (BMS) | dexosome therapy (Anosys)<br>pentrix (Australian Cancer Technology)<br>ISF-154 (Tragen)<br>cancer vaccine (Intercell)<br>norelin (Biostar)<br>BLP-25 (Biomira)<br>MGV (Progenics)<br>β-alethine (Dovetail)<br>CLL therapy (Vasogen)<br>Ipilimumab (BMS),<br>CM-10 (cCam Biotherapeutics)<br>MPDL3280A (Genentech) |
| Hormonal and antihormonal agents | estrogens<br>conjugated estrogens<br>ethinyl estradiol<br>chlortrianisen<br>idenestrol<br>hydroxyprogesterone caproate<br>medroxyprogesterone<br>testosterone<br>testosterone propionate;<br>fluoxymesterone<br>methyltestosterone<br>diethylstilbestrol<br>megestrol<br>bicalutamide<br>flutamide<br>nilutamide | dexamethasone<br>prednisone<br>methylprednisolone<br>prednisolone<br>aminoglutethimide<br>leuprolide<br>octreotide<br>mitotane<br>P-04 (Novogen)<br>2-methoxyestradiol (EntreMed)<br>arzoxifene (Eli Lilly)<br>tamoxifen<br>toremofine<br>goserelin<br>Leuporelin<br>bicalutamide |
| Photodynamic agents | talaporfin (Light Sciences)<br>Theralux (Theratechnologies)<br>motexafin gadolinium (Pharmacyclics) | Pd-bacteriopheophorbide (Yeda)<br>lutetium texaphyrin (Pharmacyclics)<br>hypericin |
| Kinase Inhibitors | imatinib (Novartis)<br>leflunomide (Sugen/Pharmacia)<br>ZD1839 (AstraZeneca)<br>erlotinib (Oncogene Science)<br>canertinib (Pfizer)<br>squalamine (Genaera)<br>SU5416 (Pharmacia)<br>SU6668 (Pharmacia)<br>ZD4190 (AstraZeneca)<br>ZD6474 (AstraZeneca)<br>vatalanib (Novartis)<br>PKI166 (Novartis)<br>GW2016 (GlaxoSmithKline)<br>EKB-509 (Wyeth)<br>trastuzumab (Genentech)<br>OSI-774 (Tarceva ™)<br>CI-1033 (Pfizer)<br>SU11248 (Pharmacia)<br>RH3 (York Medical)<br>Genistein<br>Radicinol<br>Met-MAb (Roche)<br>SR-27897 (CCK A inhibitor, Sanofi-Synthelabo)<br>tocladesine (cyclic AMP agonist, Ribapharm)<br>alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-100 (gal3 antagonist, GlycoGenesys)<br>G17DT immunogen (gastrin inhibitor, Aphton)<br>efaproxiral (oxygenator, Allos Therapeutics)<br>PI-88 (heparanase inhibitor, Progen)<br>tesmilifene (histamine antagonist, YM BioSciences)<br>histamine (histamine H2 receptor agonist, Maxim)<br>tiazofurin (IMPDH inhibitor, Ribapharm)<br>cilengitide (integrin antagonist, Merck KGaA)<br>SR-31747 (IL-1 antagonist, Sanofi-Synthelabo) | EKB-569 (Wyeth)<br>kahalide F (PharmaMar)<br>CEP-701 (Cephalon)<br>CEP-751 (Cephalon)<br>MLN518 (Millenium)<br>PKC412 (Novartis)<br>Phenoxodiol (Novogen)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone)<br>Tyrphostins<br>Gefitinib (Iressa)<br>PTK787 (Novartis)<br>EMD 72000 (Merck)<br>Emodin<br>Radicinol<br>Vemurafenib (B-Raf enzyme inhibitor, Daiichi Sankyo)<br>ceflatonin (apoptosis promotor, ChemGenex)<br>BCX-1777 (PNP inhibitor, BioCryst)<br>ranpirnase (ribonuclease stimulant, Alfacell)<br>galarubicin (RNA synthesis inhibitor, Dong-A)<br>tirapazamine (reducing agent, SRI International)<br>N-acetylcysteine (reducing agent, Zambon)<br>R-flurbiprofen (NF-kappaB inhibitor, Encore)<br>3CPA (NF-kappaB inhibitor, Active Biotech)<br>seocalcitol (vitamin D receptor agonist, Leo)<br>131-I-TM-601 (DNA antagonist, TransMolecular)<br>eflornithine (ODC inhibitor, ILEX Oncology) |

TABLE 2-continued

| | |
|---|---|
| CCI-779 (mTOR kinase inhibitor, Wyeth) | minodronic acid (osteoclast inhibitor, Yamanouchi) |
| exisulind (PDE V inhibitor, Cell Pathways) | indisulam (p53 stimulant, Eisai) |
| CP-461 (PDE V inhibitor, Cell Pathways) | aplidine (PPT inhibitor, PharmaMar) |
| AG-2037 (GART inhibitor, Pfizer) | gemtuzumab (CD33 antibody, Wyeth Ayerst) |
| WX-UK1 (plasminogen activator inhibitor, Wilex) | PG2 (hematopoiesis enhancer, Pharmagenesis) |
| PBI-1402 (PMN stimulant, ProMetic LifeSciences) | Immunol ™ (triclosan oral rinse, Endo) |
| bortezomib (proteasome inhibitor, Millennium) | triacetyluridine (uridine prodrug, Wellstat) |
| SRL-172 (T cell stimulant, SR Pharma) | SN-4071 (sarcoma agent, Signature BioScience) |
| TLK-286 (glutathione S transferase inhibitor, Telik) | TransMID-107 ™ (immunotoxin, KS Biomedix) |
| PT-100 (growth factor agonist, Point Therapeutics) | PCK-3145 (apoptosis promotor, Procyon) |
| midostaurin (PKC inhibitor, Novartis) | doranidazole (apoptosis promotor, Pola) |
| bryostatin-1 (PKC stimulant, GPC Biotech) | CHS-828 (cytotoxic agent, Leo) |
| CDA-II (apoptosis promotor, Everlife) | trans-retinoic acid (differentiator, NIH) |
| SDX-101 (apoptosis promotor, Salmedix) | MX6 (apoptosis promotor, MAXIA) |
| rituximab (CD20 antibody, Genentech | apomine (apoptosis promotor, ILEX Oncology) |
| carmustine | urocidin (apoptosis promotor, Bioniche) |
| Mitoxantrone | Ro-31-7453 (apoptosis promotor, La Roche) |
| Bleomycin | brostallicin (apoptosis promotor, Pharmacia) |
| Absinthin | β-lapachone |
| Chrysophanic acid | gelonin |
| Cesium oxides | cafestol |
| BRAF inhibitors, PDL1 inhibitors | kahweol |
| MEK inhibitors | caffeic acid |
| bevacizumab | Tyrphostin AG |
| angiogenesis inhibitors | PD-1 inhibitors |
| dabrafenib | CTLA-4 inhibitors |
| | sorafenib |
| | BRAF inhibitors |

Diagnosis and Prognosis Methods

The above-describe genes can be used in determining whether a subject has, or is at risk of having, metastatic melanoma. Alternatively, they can be used for determining a prognosis of such a disorder in a subject.

Diagnosis Methods

In one aspect, the invention provides qualitative and quantitative information to determine whether a subject has or is predisposed to metastatic melanoma or other disease characterized by endothelial recruitment, cancer cell invasion, or metastatic angiogenesis. A subject having such a disorder or prone to it can be determined based on the expression levels, patterns, or profiles of the above-described genes or their products (mRNAs, microRNAs, or polypeptides) in a test sample from the subject. In other words, the products can be used as markers to indicate the presence or absence of the disorder. Diagnostic and prognostic assays of the invention include methods for assessing the expression level of the products. The methods allow one to detect the disorder. For example, a relative increase in the expression level of one or more promoters (i.e., miR-199a-3p, miR-199a-5p, miR-1908, and CTGF) is indicative of presence the disorder. Conversely, a lower expression level or a lack of the expression is indicative lack of the disorder.

The presence, level, or absence of, an mRNA, microRNA, or polypeptide product in a test sample can be evaluated by obtaining a test sample from a test subject and contacting the test sample with a compound or an agent capable of detecting the nucleic acid (e.g., RNA or DNA probe) or polypeptide. The "test sample" includes tissues, cells and biological fluids isolated from a subject, as well as tissues, cells and fluids present within a subject. The level of expression of a gene(s) of interest can be measured in a number of ways, including measuring the RNA encoded by the gene.

Expressed RNA samples can be isolated from biological samples using any of a number of well-known procedures. For example, biological samples can be lysed in a guanidinium-based lysis buffer, optionally containing additional components to stabilize the RNA. In some embodiments, the lysis buffer can contain purified RNAs as controls to monitor recovery and stability of RNA from cell cultures. Examples of such purified RNA templates include the Kanamycin Positive Control RNA from PROMEGA (Madison, Wis.), and 7.5 kb Poly(A)-Tailed RNA from LIFE TECHNOLOGIES (Rockville, Md.). Lysates may be used immediately or stored frozen at, e.g., −80° C.

Optionally, total RNA can be purified from cell lysates (or other types of samples) using silica-based isolation in an automation-compatible, 96-well format, such as the RNEASY purification platform (QIAGEN, Inc., Valencia, Calif.). Other RNA isolation methods are contemplated, such as extraction with silica-coated beads or guanidinium. Further methods for RNA isolation and preparation can be devised by one skilled in the art.

The methods of the present invention can be performed using crude samples (e.g., blood, serum, plasma, or cell lysates), eliminating the need to isolate RNA. RNAse inhibitors are optionally added to the crude samples. When using crude cellular lysates, it should be noted that genomic DNA can contribute one or more copies of a target sequence, e.g., a gene, depending on the sample. In situations in which the target sequence is derived from one or more highly expressed genes, the signal arising from genomic DNA may not be significant. But for genes expressed at low levels, the background can be eliminated by treating the samples with DNAse, or by using primers that target splice junctions for subsequent priming of cDNA or amplification products.

The level of RNA corresponding to a gene in a cell can be determined both in situ and in vitro. RNA isolated from a test sample can be used in hybridization or amplification assays that include, Southern or Northern analyses, PCR analyses, and probe arrays. A preferred diagnostic method for the detection of RNA levels involves contacting the isolated RNA with a nucleic acid probe that can hybridize to the RNA encoded by the gene. The probe can be a full-length nucleic acid or a portion thereof, such as an oligonucleotide of at least 10 nucleotides in length and sufficient to specifically hybridize under stringent conditions to the RNA.

In one format, RNA (or cDNA prepared from it) is immobilized on a surface and contacted with the probes, for example, by running the isolated RNA on an agarose gel and transferring the RNA from the gel to a membrane, such as nitrocellulose. In another format, the probes are immobilized on a surface and the RNA (or cDNA) is contacted with the probes, for example, in a gene chip array. A skilled artisan can adapt known RNA detection methods for detecting the level of RNA.

The level of RNA (or cDNA prepared from it) in a sample encoded by a gene to be examined can be evaluated with nucleic acid amplification, e.g., by standard PCR (U.S. Pat. No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), and in situ PCR (Thaker V. Methods Mol Biol. 115:379-402, 1999), or any other nucleic acid amplification method, followed by the detection of the amplified molecules using techniques known in the art. In another embodiment, the methods of the invention further include contacting a control sample with a compound or agent capable of detecting the RNA of a gene and comparing the presence of the RNA in the control sample with the presence of the RNA in the test sample.

The above-described methods and markers can be used to assess the risk of a subject for developing melanoma. In particular, the invention can be applied to those in high risk cohort who already have certain risks so as to gain critical insight into early detection. A change in levels of miR gene products associated with melanoma can be detected prior to, or in the early stages of, the development of transformed or neoplastic phenotypes in cells of a subject. The invention therefore also provides a method for screening a subject who is at risk of developing melanoma, comprising evaluating the level of at least one gene product, or a combination of gene products, associated with melanoma in a biological sample obtained form the subject's skin. Accordingly, an alteration in the level of the gene product, or combination of gene products, in the biological sample as compared to the level of a corresponding gene product in a control sample, is indicative of the subject being at risk for developing melanoma. The biological sample used for such screening can include skin tissue that is either normal or suspected to be cancerous. Subjects with a change in the level of one or more gene products associated with melanoma are candidates for further monitoring and testing. Such further testing can comprise histological examination of tissue samples, or other techniques within the skill in the art.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder, e.g., melanoma.

Prognosis Methods

The diagnostic methods described above can identify subjects having, or at risk of developing, a melanoma. In addition, changes in expression levels and/or trends of the above-mentioned genes in a biological sample, e.g., peripheral blood samples, can provide an early indication of recovery or lack thereof. For example, a further increase (or decline) or persistently-altered gene expression levels of the promoter genes (or inhibitor genes) indicate a poor prognosis, i.e., lack of improvement or health decline. Accordingly, these genes allow one to assess post-treatment recovery of melanoma. The analysis of this select group of genes or a subset thereof indicates outcomes of the conditions.

The prognostic assays described herein can be used to determine whether a subject is suitable to be administered with an agent (e.g., an agonist, antagonist, peptidomimetic, protein, peptide, nucleic acid, small molecule, or other drug candidate) to treat melanoma or other disorders associated with endothelial recruitment, cancer cell invasion, or metastatic angiogenesis. For example, such assays can be used to determine whether a subject can be administered with a chemotherapeutic agent.

Thus, also provided by this invention is a method of monitoring a treatment for a cellular proliferative disorder in a subject. For this purpose, gene expression levels of the genes disclosed herein can be determined for test samples from a subject before, during, or after undergoing a treatment. The magnitudes of the changes in the levels as compared to a baseline level are then assessed. A decrease in the expression of the above-mentioned promoter genes (miR-199a-3p, miR-199a-5p, miR-1908, and CTGF) after the treatment indicates that the subject can be further treated by the same treatment. Similarly, an increase in the inhibitors (DNAJA4, ApoE, LRP1, and LRP8) also indicates that the subject can be further treated by the same treatment. Conversely, further increase or persistent high expression levels of one or more of the promoter genes is indicate lack of improvement or health decline.

Information obtained from practice of the above assays is useful in prognostication, identifying progression of, and clinical management of diseases and other deleterious conditions affecting an individual subject's health status. In preferred embodiments, the foregoing diagnostic assays provide information useful in prognostication, identifying progression of and management of melanoma and other conditions characterized by endothelial recruitment, cancer cell invasion, or metastatic angiogenesis. The information more specifically assists the clinician in designing chemotherapeutic or other treatment regimes to eradicate such conditions from the body of an afflicted subject, a human.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer after treatment, while the average patient with the same cancer has only a 25% probability of being cured.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" a target includes determining the amount of the target present, as well as determining whether it is present or absent.

Arrays

Also provided in the invention is a biochip or array. The biochip/array may contain a solid or semi-solid substrate having an attached probe or plurality of probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

"Attached" or "immobilized" as used herein to refer to a nucleic acid (e.g., a probe) and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

The solid substrate can be a material that may be modified to contain discrete individual sites appropriate for the attachment or association of the probes and is amenable to at least one detection method. Examples of such substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate can be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The array/biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide. The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography. Detailed discussion of methods for linking nucleic acids to a support substrate can be found in, e.g., U.S. Pat. Nos. 5,837,832, 6,087,112, 5,215,882, 5,707,807, 5,807,522, 5,958,342, 5,994,076, 6,004,755, 6,048,695, 6,060,240, 6,090,556, and 6,040,138.

In some embodiments, an expressed transcript (e.g., a transcript of a microRNA gene described herein) is represented in the nucleic acid arrays. In such embodiments, a set of binding sites can include probes with different nucleic acids that are complementary to different sequence segments of the expressed transcript. Examples of such nucleic acids can be of length of 15 to 200 bases, 20 to 100 bases, 25 to 50 bases, 40 to 60 bases. Each probe sequence can also include one or more linker sequences in addition to the sequence that is complementary to its target sequence. A linker sequence is a sequence between the sequence that is complementary to its target sequence and the surface of support. For example, the nucleic acid arrays of the invention can have one probe specific to each target microRNA gene. However, if desired, the nucleic acid arrays can contain at least 2, 5, 10, 100, 200, 300, 400, 500 or more probes specific to some expressed transcript (e.g., a transcript of a microRNA gene described herein).

Kits

In another aspect, the present invention provides kits embodying the methods, compositions, and systems for analysis of the polypeptides and microRNA expression as described herein. Such a kit may contain a nucleic acid described herein together with any or all of the following: assay reagents, buffers, probes and/or primers, and sterile saline or another pharmaceutically acceptable emulsion and suspension base. In addition, the kit may include instructional materials containing directions (e.g., protocols) for the practice of the methods described herein. For example, the kit may be a kit for the amplification, detection, identification or quantification of a target mRNA or microRNA sequence. To that end, the kit may contain a suitable primer (e.g., hairpin primers), a forward primer, a reverse primer, and a probe.

In one example, a kit of the invention includes one or more microarray slides (or alternative microarray format) onto which a plurality of different nucleic acids (each corresponding to one of the above-mentioned genes) have been deposited. The kit can also include a plurality of labeled probes. Alternatively, the kit can include a plurality of polynucleotide sequences suitable as probes and a selection of labels suitable for customizing the included polynucleotide sequences, or other polynucleotide sequences at the discretion of the practitioner. Commonly, at least one included polynucleotide sequence corresponds to a control sequence, e.g., a normalization gene or the like. Exemplary labels include, but are not limited to, a fluorophore, a dye, a radiolabel, an enzyme tag, that is linked to a nucleic acid primer.

In one embodiment, kits that are suitable for amplifying nucleic acid corresponding to the expressed RNA samples are provided. Such a kit includes reagents and primers suitable for use in any of the amplification methods described above. Alternatively, or additionally, the kits are suitable for amplifying a signal corresponding to hybridization between a probe and a target nucleic acid sample (e.g., deposited on a microarray).

In addition, one or more materials and/or reagents required for preparing a biological sample for gene expression analysis are optionally included in the kit. Furthermore, optionally included in the kits are one or more enzymes suitable for amplifying nucleic acids, including various polymerases (RT, Taq, etc.), one or more deoxynucleotides, and buffers to provide the necessary reaction mixture for amplification.

Typically, the kits are employed for analyzing gene expression patterns using mRNA or microRNA as the starting template. The RNA template may be presented as either total cellular RNA or isolated RNA; both types of sample yield comparable results. In other embodiments, the methods and kits described in the present invention allow quantitation of other products of gene expression, including tRNA, rRNA, or other transcription products.

Optionally, the kits of the invention further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

The kits optionally contain distinct containers for each individual reagent and/or enzyme component. Each component will generally be suitable as aliquoted in its respective container. The container of the kits optionally includes at least one vial, ampule, or test tube. Flasks, bottles and other container mechanisms into which the reagents can be placed and/or aliquoted are also possible. The individual containers of the kit are preferably maintained in close confinement for commercial sale. Suitable larger containers may include injection or blow-molded plastic containers into which the desired vials are retained. Instructions, such as written directions or videotaped demonstrations detailing the use of the kits of the present invention, are optionally provided with the kit.

In a further aspect, the present invention provides for the use of any composition or kit herein, for the practice of any method or assay herein, and/or for the use of any apparatus or kit to practice any assay or method herein.

A "test sample" or a "biological sample" as used herein may mean a sample of biological tissue or fluid that comprises nucleic acids. Such samples include, but are not limited to, tissue or body fluid isolated from animals. Biological samples may also include sections of tissues such as biopsy and autopsy samples, frozen sections taken for histological purposes, blood, plasma, serum, sputum, stool, tears, mucus, urine, effusions, amniotic fluid, ascitic fluid, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

The term "body fluid" or "bodily fluid" refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C. Suitable body fluids are acellular fluids. "Acellular" fluids include body fluid samples in which cells are absent or are present in such low amounts that the miRNA level determined reflects its level in the liquid portion of the sample, rather than in the cellular portion. Such acellular body fluids are generally produced by processing a cell-containing body fluid by, for example, centrifugation or filtration, to remove the cells. Typically, an acellular body fluid contains no intact cells however, some may contain cell fragments or cellular debris. Examples of acellular fluids include plasma or serum, or body fluids from which cells have been removed.

The term "gene" used herein refers to a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto. The term also includes pseudogenes, which are dysfunctional relatives of known genes that have lost their protein-coding ability or are otherwise no longer expressed in a cell.

"Expression profile" as used herein refers to a genomic expression profile, e.g., an expression profile of microRNAs. Profiles may be generated by any convenient means for determining a level of a nucleic acid sequence e.g., quantitative hybridization of microRNA, cRNA, etc., quantitative PCR, ELISA for quantification, and the like, and allow the analysis of differential gene expression between two samples. A subject or patient sample, e.g., cells or a collection thereof, e.g., tissues, is assayed. Samples are collected by any convenient method, as known in the art. Nucleic acid sequences of interest are nucleic acid sequences that are found to be predictive, including the nucleic acid sequences of those described herein, where the expression profile may include expression data for 5, 10, 20, 25, 50, 100 or more of, including all of the listed nucleic acid sequences. The term "expression profile" may also mean measuring the abundance of the nucleic acid sequences in the measured samples.

"Differential expression" refers to qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type that may be detectable by standard techniques. Some genes will be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, Northern analysis, and RNase protection.

"Nucleic acid" or "oligonucleotide" or "polynucleotide" as used herein refers to at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

The term "primer" refers to any nucleic acid that is capable of hybridizing at its 3' end to a complementary nucleic acid molecule, and that provides a free 3' hydroxyl terminus which can be extended by a nucleic acid polymerase. As used herein, amplification primers are a pair of nucleic acid molecules that can anneal to 5' or 3' regions of a gene (plus and minus strands, respectively, or vice-versa) and contain a short region in between. Under appropriate conditions and with appropriate reagents, such primers permit the amplification of a nucleic acid molecule having the nucleotide sequence flanked by the primers. For in situ methods, a cell or tissue sample can be prepared and immobilized on a support, such as a glass slide, and then contacted with a probe that can hybridize to RNA. Alternative methods for amplifying nucleic acids corresponding to expressed RNA samples include those described in, e.g., U.S. Pat. No. 7,897,750.

The term "probe" as used herein refers to an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

"Stringent hybridization conditions" as used herein refers to conditions under which a first nucleic acid sequence (e.g., probe) hybridizes to a second nucleic acid sequence (e.g., target), such as in a complex mixture of nucleic acids. Stringent conditions are sequence-dependent and be different in different circumstances, and can be suitably selected by one skilled in the art. Stringent conditions may be selected to be about 5-10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C. However, several factors other than temperature, such as salt concentration, can influence the stringency of hybridization and one skilled in the art can suitably select the factors to accomplish a similar stringency.

As used herein the term "reference value" refers to a value that statistically correlates to a particular outcome when compared to an assay result. In preferred embodiments, the reference value is determined from statistical analysis of studies that compare microRNA expression with known clinical outcomes. The reference value may be a threshold score value or a cutoff score value. Typically a reference value will be a threshold above (or below) which one outcome is more probable and below which an alternative threshold is more probable.

In one embodiment, a reference level may be one or more circulating miRNA levels expressed as an average of the level of the circulating miRNA from samples taken from a control population of healthy (disease-free) subjects. In another embodiment, the reference level may be the level in the same subject at a different time, e.g., before the present assay, such as the level determined prior to the subject developing the disease or prior to initiating therapy. In general, samples are normalized by a common factor. For example, acellular body fluid samples are normalized by volume body fluid and cell-containing samples are normalized by protein content or cell count. Nucleic acid samples may also be normalized relative to an internal control nucleic acid.

As disclosed herein, the difference of the level of one or more polypeptides or RNAs (mRNAs or microRNAs) is indicative of a disease or a stage thereof. The phrase "difference of the level" refers to differences in the quantity of a particular marker, such as a nucleic acid, in a sample as compared to a control or reference level. For example, the quantity of a particular biomarker may be present at an elevated amount or at a decreased amount in samples of patients with a neoplastic disease compared to a reference level. In one embodiment, a "difference of a level" may be a difference between the quantity of a particular biomarker present in a sample as compared to a control (e.g., reference value) of at least about 1%, 2%, 3%, 5%, 10%, 15%, 20%, 25%, 30%, 35%, 40%, 50%, 60%, 75%, 80% 100%, 150%, 200%, or more. In one embodiment, a "difference of a level" may be a statistically significant difference between the quantities of a biomarker present in a sample as compared to a control. For example, a difference may be statistically significant if the measured level of the biomarker falls outside of about 1.0 standard deviation, about 1.5 standard deviations, about 2.0 standard deviations, or about 2.5 stand deviations of the mean of any control or reference group. With respect to miRNA measurement, the level may be measured from real-time PCR as the Ct value, which may be normalized to a ΔCt value as described in the Examples below.

Drug Screening

The invention provides a method for identifying a compound that are useful for treating melanoma or for inhibiting endothelial recruitment, cell invasion, or metastatic angiogenesis.

Candidate compounds to be screened (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. 1994, J. Med. Chem. 37:2678-2685; and Lam, 1997, Anticancer Drug Des. 12:145. Examples of methods for the synthesis of molecular libraries can be found in, e.g., DeWitt et al., 1993, PNAS USA 90:6909; Erb et al., 1994, PNAS USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Scott and Smith 1990, Science 249:386-390; Devlin, 1990, Science 249:404-406; Cwirla et al., 1990, PNAS USA 87:6378-6382; Felici 1991, J. Mol. Biol. 222:301-310; and U.S. Pat. No. 5,223,409).

To identify a useful compound, one can contact a test compound with a system containing test cells expressing a reporter gene encoded by a nucleic acid operatively liked to a promoter of a marker gene selected from the above-mentioned metastasis promoters or suppressors. The system can be an in vitro cell line model or an in vivo animal model. The cells can naturally express the gene, or can be modified to express a recombinant nucleic acid. The recombinant nucleic acid can contain a nucleic acid coding a reporter polypeptide to a heterologous promoter. One then measures the expression level of the miRNA, polypeptide, or reporter polypeptide.

For the polypeptide, the expression level can be determined at either the mRNA level or at the protein level. Methods of measuring mRNA levels in a cell, a tissue sample, or a body fluid are well known in the art. To measure mRNA levels, cells can be lysed and the levels of mRNA in the lysates or in RNA purified or semi-purified from the lysates can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out using tissue sections or unlysed cell suspensions, and detectably (e.g., fluorescent or enzyme) labeled DNA or RNA probes. Additional mRNA-quantifying methods include RNA protection assay (RPA) and SAGE. Methods of measuring protein levels in a cell or a tissue sample are also known in the art.

To determine the effectiveness of a candidate compound to treat melanoma or inhibiting endothelial recruitment, cell invasion, or metastatic angiogenesis, one can compare the level obtained in the manner described above with a control level (e.g., one obtained in the absence of the candidate compound). The compound is identified as being effective if (i) a metastasis suppressor's level is lower than a control or reference value or (ii) a metastasis promoter's level is higher than the control or reference value. One can further verify the efficacy of a compound thus-identified using the in vitro cell culture model or an in vivo animal model as disclosed in the example below.

EXAMPLES

Example 1

Materials and Methos

This example descibes materials and methos used in EXAMPLES 2-11 below.

Compounds

TABLE 3

Compound Names

| Compound # | Compound Name |
|---|---|
| 1 | T0901317 |
| 2 | GW3965 |
| 3 | LXR-623 |
| 12 | WO-2010-0138598 Ex. 9 or WO-201000138598 |
| 25 | SB742881 |
| 38 | WO-2007-002563 Ex. 19 or WO-2007-002563 |

Animal Studies

All mouse experiments were conducted in agreement with a protocol approved by the Institutional Animal Care and Use Committee (IACUC) at The Rockefeller University. 6-8-week old age-matched and sex-matched mice were used for primary tumor growth and metastasis assays as previously described (Minn et al., 2005; Tavazoie et al., 2008). See Extended Experimental Procedures.

Cell Culture

All cancer cell lines were cultured as previously described (Tavazoie et al., 2008). 293T and human umbilical vein endothelial cells (HUVEC's) were maintained in standard conditions. miRNA and gene knock-down/over-expression studies in cell lines and in vitro functional assays are detailed in Extended Experimental Procedures.

Microarray Hybridization

In order to identify miRNAs deregulated across highly metastatic derivatives, small RNAs were enriched from total RNA derived from MeWo and A375 cell lines and profiled by LC sciences. In order to identify potential gene targets of miR-199a-3p, miR-199a-5p, and miR-1908, total RNA from MeWo cell lines was labeled and hybridized onto Illumina HT-12 v3 Expression BeadChip arrays by The Rockefeller University genomics core facility. See Extended Experimental Procedures for thresholds and criteria used to arrive at miRNA and mRNA targets.

Analysis of miRNA Expression in Human Melanoma Skin Lesions

All human clinical samples used in this study were obtained, processed, and analyzed in accordance with IRB guidelines. Total RNA was extracted from paraffin-embedded cross-sections of primary melanoma skin lesions previously resected from patients at MSKCC, and specific miRNA expression levels were analyzed in a blinded fashion using TaqMan miRNA Assays (Applied Biosystems). Kaplan-Meier curves representing each patient's metastasis-free-survival data as a function of primary tumor miRNA expression values were generated using the GraphPad Prism software package.

In Vivo LNA Therapy

Following tail-vein injection of $4 \times 10^4$ MeWo-LM2 cells, NOD-SCID mice were treated intravenously twice a week for four weeks with in vivo-optimized LNAs (Exiqon) antisense to miR-199a-3p, miR-199a-5p, and miR-1908 at a combinatorial dose of 12.5 mg/kg delivered in 0.1 mL of PBS.

Histology

For gross macroscopic metastatic nodule visualization, 5-μm-thick lung tissue sections were H&E stained. For in vivo endothelial content analyses, lung sections were double-stained with antibodies against MECA-32 (Developmental Studies Hybridoma Bank, The University of Iowa, IA), which labels mouse endothelial cells, and human vimentin (Vector Laboratories), which labels human melanoma cells. See Extended Experimental Procedures.

Data Analysis

All data are represented as mean±SEM. The Kolmogorov-Smirnov test was used to determine significance of differences in metastatic blood vessel density cumulative distributions. The prognostic power of the miRNAs to predict metastatic outcomes was tested for significance using the Mantel-Cox log-rank test. The one-way Mann-Whitney t-test was used to determine significance values for non-Gaussian bioluminescence measurements. For all other comparisons, the one-sided student's t-test was used. P values<0.05 were deemed to be statistically significant.

In Vivo Selection, Experimental Metastasis, and Primary Tumor Growth Assays

All mouse experiments were conducted in agreement with a protocol approved by the Institutional Animal Care and Use Committee (IACUC) at The Rockefeller University. To generate multiple metastatic derivatives from two independent human melanoma cell lines, in vivo selection was performed as previously described (Minn et al., 2005 Nature 436, 518-524; Pollack and Fidler, 1982 J. Natl. Cancer Inst. 69, 137-141). In brief, $1 \times 10^6$ pigmented MeWo or non-pigmented A375 melanoma parental cells were resuspended in 0.1 mL of PBS and intravenously injected into 6-8-week old immunocompromised NOD-SCID mice. Following lung metastases formation, nodules were dissociated and cells were propagated in vitro, giving rise to first generation of lung metastatic derivatives (LM1). The LM1 cells were then subjected to another round of in vivo selection by injecting $2 \times 10^5$ cells via the tail-vein into NOD-SCID mice, giving rise to metastatic nodules, whose subsequent dissociation yielded second generation of lung metastatic derivatives (LM2). For the A375 cell line, a third round of in vivo selection was performed, yielding the highly metastatic A375-LM3 derivatives.

In order to monitor metastasis in vivo through bioluminescence imaging, A375 and MeWo parental cells and their metastatic derivatives were transduced with a retroviral construct expressing a luciferase reporter (Ponomarev et al., 2004 Eur J Nucl Med Mol Imaging 31, 740-751). For all metastasis experiments, lung or systemic colonization was monitored over time and quantified through non-invasive bioluminescence imaging as previously described (Minn et al., 2005). To determine whether in vivo selection had been achieved, $4 \times 10^4$ MeWo parental or MeWo-LM2 cells and $1 \times 10^5$ A375 parental or A375-LM3 cells were resuspended in 0.1 mL of PBS and injected via the lateral tail vein into 6-8-week old NOD-SCID mice. For experimental metastasis assays testing the effects of putative promoter miRNAs on lung colonization, $4 \times 10^4$ MeWo parental cells over-expressing miR-199a, miR-1908, miR-214, or a control hairpin, $4 \times 10^4$ MeWo-LM2 cells with silenced expression of miR-199a-3p, miR-199a-5p, miR-1908, or a control sequence, and $2 \times 10^5$ A375-LM3 cells inhibited for miR-199a-3p, miR-199a-5p, miR-1908, or a control sequence were resuspended in 0.1 mL of PBS and tail-vein injected into 6-8-week old NOD-SCID mice. For epistasis experiments, $1 \times 10^5$ MeWo-LM2 cells expressing an shRNA targeting ApoE, DNAJA4, or a control sequence or siRNA inhibiting LRP1 or a control sequence in the setting of miRNA inhibition were intravenously injected into 6-8-week old NOD-SCID mice. For ApoE pre-treatment experiments, MeWo-LM2 cells were incubated in the presence of ApoE or BSA at 100 μg/mL at 37° C. After 24 hours, $4 \times 10^4$ cells were injected via the tail-vein into 7-week old NOD-SCID mice.

To determine the effect of pre-treating highly metastatic melanoma cells with LNAs targeting miR-199a-3p, miR-199a-5p, and miR-1908 on metastasis, MeWo-LM2 cells were transfected with each LNA individually, a cocktail of LNAs targeting all three miRNAs, or a control LNA. After 48 hours, 1×10$^5$ cells, resuspended in 0.1 mL of PBS, were administered intravenously into 7-week old NOD-SCID mice for lung metastatic colonization studies or through intracardiac injection into 7-week old athymic nude mice for systemic metastasis assays. To determine the effect of genetic deletion of ApoE on metastasis, 8-week old C57BL/6-WT or C57BL/6-ApoE−/− mice were intravenously injected with 5×10$^4$ B 16F10 mouse melanoma cells. For primary tumor growth studies, 1×10$^6$ parental MeWo cells over-expressing miR-199a, miR-1908, or a control hairpin were mixed 1:1 with matrigel and subcutaneously injected into the lower right flank of 6-week old immunodeficient NOD-SCID mice. Animals were palpated weekly for tumor formation, after which sizeable tumors were measured twice a week. Tumor volume was calculated as (small diameter)$^2$×(large diameter)/2.

Lentiviral miRNA Inhibition and Gene Knock-Down 293T cells were seeded in a 10-cm plate and allowed to reach 60% confluency. Prior to transfection, the cell media was replaced with fresh antibiotic-free DMEM media supplemented with 10% FBS. 6 μg of vector A, 12 μg of vector K, and 12 μg of the appropriate miR-Zip (System Biosciences, Mountain View, Calif.) or shRNA plasmid construct (MSKCC HTS Core Facility, New York, N.Y.) were co-transfected using 60 μL of TransIT-293 transfection reagent (MIR 2700, Minis Bio LLC, Madison, Wis.). The cells were incubated at 37° C. for 48 hours, and the virus was harvested by spinning the cell media for 10 minutes at 2000 g followed by virus filtration through a 0.45 μm filter. 1×10$^5$ cancer cells were transduced with 2 mL of the appropriate virus in the presence of 10 μg/mL of polybrene (TR-1003-G, Millipore, Billerica, Mass.) for 6 hrs. After 48 hours, 2 μg/mL of puromycin (P8833, Sigma-Aldrich, St Louis, Mo.) was added to the cell media for lentiviral selection. The cells were kept in puromycin selection for 72 hours. The following miR-Zip sequences were used:

miR-Zip-199a-3p:
5'-GATCCGACAGTAGCCTGCACATTAGTCACTTCCTGTCAGTAACCAA

TGTGCAGACTACTGTTTTTGAATT-3' miR-Zip-199a-5p:
5'-GATCCGCCCAGTGCTCAGACTACCCGTGCCTTCCTGTCAGGAACAG

GTAGTCTGAACACTGGGTTTTTGAATT-3' miR-Zip-1908
5'-GCCGTTTTTGAATT-3'

The following shRNA sequences were used:

shAPOE$^1$:
5'CCGGGAAGGAGTTGAAGGCCTACAACTCGAGTTGTAGGCCTTCAACTC

CTTCTTTTT3' shAPOE$^2$:
5'CCGGGCAGACACTGTCTGAGCAGGTCTCGAGACCTGCTCAGACAGTGT

CTGCTTTTT3' shDNAJA4$^1$:
5'CCGGGCGAGAAGTTTAAACTCATATCTCGAGATATGAGTTTAAACTTC

TCGCTTTTT3' shDNAJA4$^2$:
5'CCGGCCTCGACAGAAAGTGAGGATTCTCGAGAATCCTCACTTTCTGTC

GAGGTTTTT3'

Retroviral miRNA and Gene Over-Expression

6 μg of vector VSVG, 12 μg of vector Gag-Pol, and 12 μg of pBabe plasmid containing the coding sequences of human ApoE, DNAJA4, or an empty vector or miR-Vec containing the precursor sequence of miR-199a, miR-214, miR-1908, or a control hairpin were co-transfected into 60%-confluent 293T cells using 60 μL of TransIT-293 transfection reagent. The cells were incubated at 37° C. for 48 hours, after which the virus was harvested and transduced into cancer cells in the presence of 10 μg/mL of polybrene for 6 hours. After 48 hours, 2 μg/mL of puromycin or 10 μg/mL of blasticidin (15205, Sigma-Aldrich, St Louis, Mo.) were added to the cell media for retroviral selection. The cells were kept in puromycin selection for 72 hours or in blasticidin selection for 7 days. The following cloning primers were used for over-expression of the coding sequences of ApoE and DNAJA4:

ApoE_CDS_Fwd:
5'-TCATGAGGATCCATGAAGGTTCTGTGGGCT-3'

ApoE_CDS_Rev:
5'-TAGCAGAATTCTCAGTGATTGTCGCTGGG-3'

DNAJA4_CDS_Fwd:
5'-ATCCCTGGATCCATGTGGGAAAGCCTGACCC-3'

DNAJA4_CDS_Rev:
5'-TACCATGTCGACTCATGCCGTCTGGCACTGC-3'

LNA-Based miRNA Knock-Down

LNAs complimentary to mature miR-199a-3p, miR-199a-5p, miR-1908, or a control sequence (426917-00, 426918-00, 426878-00, and 1990050, respectively; Exiqon, Vedbaek, Denmark) were transfected at a final concentration of 50 nM into 50% confluent MeWo-LM2 cancer cells cultured in antibiotics-free media using lipofectamine™ 2000 transfection reagent (11668-09, Invitrogen, Carlsbad, Calif.). After 8 hours, the transfection media was replaced with fresh media. After 48 hours, 1×10$^5$ cells were injected intravenously into NOD-SCID mice to assess lung metastatic colonization or through intracardiac injection into athymic nude mice to assess systemic metastasis. For cell invasion and endothelial recruitment in vitro assays, the cells were used 96 hours post-transfection.

siRNA-Based mRNA Knock-Down siRNAs targeting LRP1, LRP8, VLDLR, LDLR, or a control seqeuence were transfected into cancer cells or HUVEC's at a final concentration of 100 nM using lipofectamine™ 2000 transfection reagent. After 5 hours, the transfection media was replaced with fresh media. The cells were subjected to matrigel invasion and endothelial recruitment assays 96 hours post-transfection. Cells transduced with siRNAs targeting LRP1 or a control sequence in the setting of miRNA inhibition were tail-vein injected for lung colonization assays 72 hours post-transfecton. Control non-targeting siRNAs were obtained from Dharmacon. The following LRP1 and LRP8 target sequences were used:

siLRP1¹:
5'-CGAGGACGAUGACUGCUUA-3';

siLRP1²:
5'-GCUAUGAGUUUAAGAAGUU-3';

siLRP8¹:
5'-CGAGGACGAUGACUGCUUA-3';

siLRP8²:
5'-GAACUAUUCACGCCUCAUC-3'.

Cell Proliferation Assay

To determine the effects of miR-199a or miR-1908 overexpression and combinatorial LNA-induced miRNA inhibition on cell proliferation, $2.5 \times 10^4$ cells were seeded in triplicate in 6-well plates, and viable cells were counted after 5 days. To assess the effects of recombinant ApoE addition on melanoma cell or endothelial cell proliferation, $3 \times 10^4$ melanoma MeWo-LM2 cells or endothelial cells were incubated in the presence of ApoE (100 µM) or BSA (100 µM). Viable cells were counted after 8, 24, 48, 72, and 120 hours.

Matrigel Invasion Assay

Cancer cells were serum-starved in 0.2% FBS DMEM-based media for 12 hours. Trans-well invasion chambers (354480, BD Biosciences, Bedford, Mass.) were pre-equilibrated prior to beginning the assay by adding 0.5 mL of starvation media to the top and bottom chambers. After 30 minutes, the media in the top chamber was removed, and 0.5 mL of media containing $1 \times 10^5$ cancer cells was added into each matrigel-coated trans-well insert and incubated at 37° C. for 24 hours. For neutralization antibody and/or recombinant protein experiments, antibody/recombinant protein was added to each well at the start of the assay at the following concentrations as indicated in the figures: 5-40 µg/mL anti-ApoE 1D7 (Heart Institute, University of Ottawa), 5-40 µg/mL anti-IgG (AB-108-C, R&D Systems, Minneapolis, Minn.), 100 µM recombinant human ApoE3 (4696, BioVision, Mountain View, Calif.), and 100 µM BSA (A2153, Sigma-Aldrich). Upon completion of the assay, matrigel-coated inserts were washed with PBS, the cells at the top side of each insert were scraped off, and the inserts were fixed in 4% paraformaldehyde for 15 minutes. The inserts were then cut out and mounted onto slides using VectaShield mounting medium containing DAPI (H-1000, Vector Laboratories, Burlingame, Calif.). The basal side of each insert was imaged using an inverted fluorescence microscope (Zeiss Axiovert 40 CFL) at 5× magnification, taking three representative images for each insert. The number of invaded cells was quantified using ImageJ (NIH).

Endothelial Recruitment Assay $5 \times 10^4$ cancer cells were seeded into 24-well plates approximately 24 hours prior to the start of the assay. HUVEC's were grown to 80% confluency and serum starved in EGM-2 media supplemented with 0.2% FBS for 16 hours. HUVEC's were then pulsed with Cell Tracker Red CMTPX dye (C34552, Invitrogen) for 45 minutes. Meanwhile, cancer cells were washed with PBS, 0.5 mL of 0.2% FBS EGM-2 media was added to each well, and a 3.0 µm HTS Fluoroblock insert (351151, BD Falcon, San Jose, Calif.) was placed into each well. $1 \times 10^5$ HUVEC's, resuspended in 0.5 mL of starvation media, were seeded into each trans-well insert, and the recruitment assay was allowed to proceed for 16-18 hours at 37° C. For neutralization antibody and/or recombinant protein experiments, antibody/protein was then added to each well at the appropriate concentration as indicated in the figures: 40 µg/mL anti-ApoE 1D7, 40 µg/mL anti-IgG, 100 µM rhApoE3, and 100 µM BSA. Upon completion of the assay, the inserts were processed and analyzed as described for the matrigel invasion assay above (See Matrigel Invasion Assay).

Endothelial Migration Assay

Serum-starved HUVEC's were pulsed with Cell Tracker Red CMTPX dye for 45 minutes and seeded into HTS Fluoroblock trans-well inserts at a concentration of $1 \times 10^5$ HUVEC's in 0.5 mL starvation media per each insert. The assay was allowed to proceed for 16-18 hours at 37° C., and the inserts were processed and analyzed as described above (See Matrigel Invasion Assay).

Chemotaxis Assay

HUVEC's were serum-starved in 0.2% FBS EGM-2 media for 16 hours and labeled with Cell Tracker Red CMTPX dye for 45 minutes. Meanwhile, the indicated amounts (1-5 µg) of recombinant human ApoE3 or BSA were mixed with 250 µL of matrigel (356231, BD Biosciences) and allowed to solidify at the bottom of a 24-well plate for 30 min. 250 µL of HUVEC EGM-2 media containing 0.2% FBS was then added to each matrigel-coated well, and 3.0 µM HTS Fluoroblock inserts were fitted into each well. $1 \times 10^5$ HUVEC's, resuspended in 0.5 mL of starvation media, were seeded into each insert and allowed to migrate along the matrigel gradient for 16-18 hours at 37° C. Upon completion of the assay, the inserts were mounted on slides and analyzed as described above (See Matrigel Invasion Assay).

Endothelial Adhesion Assay

HUVEC's were seeded in 6-well plates and allowed to form monolayers. Cancer cells were serum starved in 0.2% FBS DMEM-based media for 30 minutes and pulsed with Cell Tracker Green CMFDA dye (C7025, Invitrogen) for 45 minutes. $2 \times 10^5$ cancer cells, resuspended in 0.5 mL starvation media, were seeded onto each endothelial monolayer. The cancer cells were allowed to adhere to the HUVEC monolayers for 30 minutes at 37° C. The endothelial monolayers were then washed gently with PBS and fixed with 4% paraformaldehyde for 15 minutes. Each well was then coated with PBS, and 8 images were taken for each endothelial monolayer using an inverted Fluorescence microscope (Zeiss Axiovert 40 CFL) at 10× magnification. The number of cancer cells adhering to HUVEC's was quantified using ImageJ.

Anoikis Assay $1 \times 10^6$ MeWo cells over-expressing miR-199a, miR-1908, or a control hairpin were seeded in low adherent plates containing cell media supplemented with 0.2% methylcellulose. Following 48 hours in suspension, the numbers of dead and viable cells were counted using trypan blue.

Serum Starvation Assay

To determine the effects of miR-199a and miR-1908 on melanoma cell serum starvation capacity, $1 \times 10^5$ MeWo parental cells over-expressing miR-199a, miR-1908, or a control hairpin were seeded in quadruplicate into 6-well plates and incubated in 0.2% FBS starvation DMEM-based media for 48 hours, after which the number of viable cells was counted using trypan blue. To determine the effect of recombinant ApoE3 addition on the survival of melanoma cells or endothelial cells in serum starvation conditions, $3 \times 10^4$ MeWo-LM2 cells or endothelial cells were incubated in the presence of ApoE3 (100 µM) or BSA (100 µM) in low serum conditions (0.2% FBS). The number of viable cells was counter after 8, 16, and 24 hours.

Colony Formation Assay

Fifty MeWo parental cells over-expressing miR-199a, miR-1908, or a control hairpin were seeded in quadruplicate into 6-cm plates. After two weeks, the cells were washed with PBS, fixed with 6% glutaraldehyde, and stained with 0.5% crystal violet. The number of positive-staining colonies was counted.

miRNA Microarray Hybridization

For identification of miRNAs showing deregulated expression across highly metastatic melanoma cell line derivatives, total RNA from multiple independent metastatic derivatives and their respective parental MeWo and A375 cell populations was used to enrich for small RNAs which were then labelled and hybridized onto microfluidic custom microarray platforms by LC sciences. The arrays were designed to detect 894 mature miRNAs corresponding to the miRNA transcripts listed in Sanger miRBase Release 13.0. Out of all the probes analyzed, those corresponding to 169 miRNAs yielded signal above a background threshold across the multiple cell lines analyzed. The raw signal intensities, corresponding to probe hybridization, were median-normalized for each cell line. A threshold of 2-fold or higher up-regulation of median-normalized expression values were used in order to identify miRNAs commonly induced in multiple metastatic derivatives for two independent human melanoma cell lines.

Microarray-Based Gene Target Prediction for miR-199a and miR-1908

In order to identify potential genes targeted by miR-199a-3p, miR-199a-5p, and miR-1908, total RNA was extracted from MeWo cell lines with loss- or gain-of-function of each miRNA and submitted to the genomics core facility at The Rockefeller University for hybridization onto Illumina HT-12 v3 Expression BeadChip microarrays. The raw signal intensities, corresponding to probe hybridization, were then median-normalized for each cell line sample. Three sets of microarray profile comparisons were generated: (1) MeWo control cells relative to MeWo cells over-expressing miR-199a or miR-1908, (2) MeWo-LM2 control cells relative to MeWo-LM2 cells expressing a short hairpin (miR-Zip) targeting miR-199a-3p, miR-199a-5p, or miR-1908, and (3) MeWo parental cells relative to MeWo-LM2 cells. Based on the median-normalized expression values from these arrays, the following criteria were used to arrive at possible target genes common to miR-199a and miR-1908: (1) Genes down-regulated by more than 1.5 fold upon individual over-expression of each miR-199a and miR-1908, (2) Genes up-regulated by more than 1.5 fold upon inhibition of either both miR-199a-3p and miR-1908 or both miR-199a-5p and miR-1908, and (3) genes down-regulated by more than 1.5 fold in LM2 cells, which express physiologically higher levels of the three miRNAs, relative to MeWo parental cells.

Analysis of miRNA and mRNA Expression in Cell Lines

Total RNA was extracted from various cell lines using the miRvana kit (AM1560, Applied Biosystems, Austin, Tex.). The expression levels of mature miRNAs were quantified using the Taqman miRNA expression assay (4427975-0002228, Applied Biosystems). RNU44 was used as an endogenous control for normalization. For mRNA expression analyses, 600 ng of total RNA was reverse transcribed using the cDNA First-Strand Synthesis Kit (18080-051, Invitrogen), and roughly 200 ng of the resulting cDNA was then mixed with SYBR green PCR Master Mix (4309155, Applied Biosystems) and the appropriate primers. Each reaction was performed in quadruplicate, and mRNA expression was quantified by performing real-time PCR amplification using an ABI Prism 7900HT Real-Time PCR System (Applied Biosystems). GAPDH was used as an endogenous control for normalization. The following primers were used:

```
ApoE_Fwd:
5'-TGGGTCGCTTTTGGGATTAC-3'

ApoE_Rev:
5'-TTCAACTCCTTCATGGTCTCG-3'

DNAJA4_Fwd:
5'-CCAGCTTCTCTTCACCCATG-3'

DNAJA4_Rev:
5'-GCCAATTTCTTCGTGACTCC-3'

GAPDH_Fwd:
5'-AGCCACATCGCTCAGACAC-3'

GAPDH_Rev:
5'-GCCCAATACGACCAAATCC-3'

LRP1_Fwd:
5'-TTTAACAGCACCGAGTACCAG-3'

LRP1_Rev:
5'CAGGCAGATGTCAGAGCAG-3'

LRP8_Fwd:
5'-GCTACCCTGGCTACGAGATG-3'

LRP8_Rev:
5'-GATTAGGGATGGGCTCTTGC-3'
```

ELISA

Conditioned cancer cell media was prepared by incubating cells in 0.2% FBS serum starvation DMEM-based media for 24 hours. ApoE levels in conditioned media were determined using the APOE ELISA kit (IRAPKT031, Innovative Research, Novi, Mich.).

Luciferase Reporter Assays

Heterologous luciferase reporter assays were performed as previously described (Tavazoie et al., 2008). In brief, full-length 3'UTRs and CDS's of ApoE and DNAJA4 were cloned downstream of a renilla luciferase reporter into the psiCheck2 dual luciferase reporter vector (C8021, Promega, Madison, Wis.). $5\times10^4$ parental MeWo cells, MeWo-LM2 cells, MeWo cells over-expressing miR-199a, miR-1908, or a control hairpin, and MeWo-LM2 cells expressing a miR-Zip hairpin targeting miR-199a-3p, miR-199a-5p, miR-1908, or a control sequence were transfected with 100 ng of the respective specific reporter constructs using TransiT-293 transfection reagent. Twenty-four hours post-transfection, the cells were lysed, and the ratio of renilla to firefly luciferase expression was determined using the dual luciferase assay (E1910, Promega). Putative miRNA binding sites in each target construct were identified by alignment to the complimentary miRNA seed sequences (miR-199a-3p: 5'-CAGUAGUC-3'; miR-199a-5p: 5'-CCAGUGUU-3'; miR-1908: 5'-GGCGGGGA-3'). The miRNA complimentary sites on each target construct were mutated using the QuickChange Multi Site-Directed Mutagenesis Kit (200514, Agilent Technologies, Santa Clara, Calif.). Based on miRNA seed sequence complimentarity analysis, the CDS of ApoE was mutated at position 141 (CTG to ACT), the 3'UTR of ApoE was mutated at positions 83 (GCC to ATA) and 98 (CTG to ACA), the CDS of DNAJA4 was mutated at positions 373 (CGC to TAT) and 917 (CTG to AGA), and the 3'UTR of DNAJA4 was mutated at positions 576 (CTG to ACA), 1096 (CTG to TCT), 1396 (CGC to TGT), and 1596 (CTG to TGT). The following primers were used to clone the 3'UTR's and CDS's of ApoE and DNAJA4:

```
ApoE_CDS_Fwd:
5'-AGTACCTCGAGGGGATCCTTGAGTCCTACTC-3'

APOE_CDS_Rev:
5'-TAATTGCGGCCGCTCAGACAGTGTCTGCACCCAG-3'

DNAJA4_CDS_Fwd:
5'-TAATATCTCGAGATGTGGGAAAGCCTGACCC-3'

DNAJA4_CDS_Rev:
5'-CAATTGCGGCCGCTCATGCCGTCTGGCACTGC-3'

APOE_3'UTR_Fwd:
5'-TTAGCCTCGAGACGCCGAAGCCTGCAGCCA-3'

APOE_3'UTR_Rev:
5'-TTACTGCGGCCGCTGCGTGAAACTTGGTGAATCTT-3'

DNAJA4_3'UTR_Fwd:
5'-TAATATCTCGAGCGTGGTGCGGGGCAGCGT-3'

DNAJA4_3'UTR_Rev:
5'-CAATTGCGGCCGCTTATCTCTCATACCAGCTCAAT-3'
```

The following primers were used to mutagenize the miRNA binding sites on each target:

```
APOE_CDS_mut:
5'-GCCAGCGCTGGGAACTGGCAACTGGTCGCTTTTGGGATTACCT-3'

APOE_3'UTR_mut1:
5'-CAGCGGGAGACCCTGTCCCCATACCAGCCGTCCTCCTGGGGTG-3'

APOE_3'UTR_mut2:
5'-TCCCCGCCCCAGCCGTCCTCACAGGGTGGACCCTAGTTTAATA-3'

DNAJA4_CDS_mut1:
5'-GGGATCGGTGGAGAAGTGCCTATTGTGCAAGGGGCGGGGATG-3'

DNAJA4_CDS_mut2:
5'-GTAGGGGCGGGGAACGTGTTATCCGTGAAGAGGTGGCTAGGG-3'

DNAJA4_3'UTR_mut1:
5'-CAGGGCCAACTTAGTTCCTAACATTCTGTGCCCTTCAGTGGAT-3'

DNAJA4_3'UTR_mut2:
5'-ACAGTTTGTATGGACTACTATCTTAAATTATAGCTTGTTTGGA-3'

DNAJA4_3'UTR_mut3:
5'-TAATTATTGCTAAAGAACTATGTTTTAGTTGGTAATGGTGTAA-3'

DNAJA4_3'UTR_mut4:
5'-CAGCTGCACGGACCAGGTTCCATAAAAACATTGCCAGCTAGTGAG-3'
```

Analysis of miRNA Expression in Human Melanoma Skin Lesions

All human clinical samples used in this study were obtained, processed, and analyzed in accordance with institutional IRB guidelines. Paraffin-embedded cross-sections of primary melanoma skin lesions from 71 human patients were obtained from MSKCC. The samples were de-paraffinized by five consecutive xylene washes (5 minutes each). Following de-paraffinization, the malignancy-containing region was identified by H&E staining, dissected, and total RNA was extracted from it using the RecoverAll Total Nucleic Acid Isolation Kit (AM1975, Applied Biosystems). The expression levels of mature miR-199a-3p, miR-199a-5p, and miR-1908 in each sample were quantified in a blinded fashion using the Taqman miRNA assay. RNU44 was used as an endogenous control for normalization. The expression levels of each miRNA were compared between primary melanomas with propensity to metastasize and primary melanomas that did not metastasize. Kaplan-Meier curves were plotted using metastasis-free survival data of patients as a function of the expression levels for each miRNA in each patient's tumor. Metastatic recurrence to such sites as lung, brain, bone, and soft tissue were previously documented and allowed for a retrospective analysis of the relationship between the expression levels of identified miRNAs and metastatic recurrence.

Histology

Animals were perfused with PBS followed by fixation with 4% paraformaldehyde infused via intracardiac and subsequently intratracheal injection. The lungs were sectioned out, incubated in 4% paraformaldehyde at 4° C. overnight, embedded in paraffin, and sliced into 5-µm-thick increments. For gross macroscopic metastatic nodule visualization, lung sections were H&E stained. For endothelial content analysis in metastatic nodules formed by human melanoma MeWo cells in mice, representative lung sections were double-stained with primary antibodies against MECA-32 (Developmental Studies Hybridoma Bank, The University of Iowa, IA), which labels mouse endothelial cells, and human vimentin (VP-V684, Vector Laboratories), which labels human melanoma cells. Various Alexa Flour dye-conjugated secondary antibodies were used to detect primary antibodies. To determine the blood vessel density within metastatic nodules, fluorescence was measured using a Zeiss laser scanning confocal microscope (LSM 510), and the MECA-32 signal within each metastatic nodule, outlined based on co-staining with human vimentin, was quantified in a blinded fashion using ImageJ (NIH). For endothelial content analysis in metastatic nodules formed by mouse B16F10 mouse melanoma cells in wild type and ApoE genetically null mice, representative lung sections were stained for MECA-32, and the MECA-32 signal within each nodule, demarcated based on cell pigmentation, was quantified in a blinded fashion. The collective vessel area, given as the percentage area covered by blood vessels relative to the total area of each metastatic nodule, was obtained by background subtraction (rolling ball radius of 1 pixel) and use of a pre-determined threshold as a cut-off. A metastatic nodule was defined as any region of greater than 2000 µm$^2$ total area. For large nodules, minimum of four representative images were obtained, and their average blood vessel density was calculated.

In Vivo Matrigel Plug Assay

10 µg/mL recombinant human ApoE3 (4696, BioVision), 10 µg/mL BSA (A2153, Sigma Aldrich), or 400 ng/ml VEGF were mixed with matrigel (356231, BD Biosciences) as indicated. 400 µL of matrigel containing the indicated recombinant proteins were injected subcutaneously just above the ventral flank of immunocompromised NOD-SCID mice. Plugs were extracted on day 3 post-injection and fixed in 4% paraformaldehyde for 48 hours. Plugs were then paraffin-embedded and sectioned at 5-µm-thick increments. Plug cross-sectional sections were immunohistochemically stained using a primary antibody against the mouse endothelial antigen MECA-32 (Developmental Studies Hybridoma Bank, The University of Iowa, IA), detected by peroxidase-conjugated secondary antibody, and subsequently visualized by DAB oxidization. To quantify the extent of endothelial cell invasion into each matrigel plug, the number of endothelial cells was counted in 4-5 random fields for each plug, and the average number of endothelial cells per given plug area was calculated.

Tissue Culture

The SK-Mel-334 primary human melanoma line was established from a soft tissue metastasis of a Braf-mutant melanoma of a patient at the MSKCC. Following minimum expansion in vitro, the cells were in vivo selected (Pollack and Fidler, 1982) to generate the lung-metastatic derivatives SK-Mel-334.2. The SK-Mel-239 vemurafenib-resistant clone (C1) was a gift from Poulikos Poulikakos (Mount Sinai Medical School) and the B-Raf$^{V600E/+}$; Pten$^{-/-}$; CDKN2A$^{-/-}$ primary murine melanoma cell line was generously provided by Marcus Rosenberg (Yale University). All other cell lines used were purchased from ATCC.

ApoE Elisa

Extracellular ApoE levels in serum-free conditioned media from melanoma cells treated with DMSO, GW3965, or T0901317 (1 µM each) were quantified using the ApoE ELISA kit (Innovative Research) at 72 hours following treatment.

Western Blotting

Mouse lung and brain tissue samples were homogenized on ice in RIPA buffer (Sigma-Aldrich) supplemented with protease inhibitors (Roche). Mouse adipose tissue was homogenized on ice in TNET buffer (1.5 mM Tris pH 7.5, 150 mM NaCl, 2 mM EDTA 1% triton, protease inhibitors). Total protein lysate (2 µg) was separated by SDS-PAGE, transferred to PVDF membrane, and blotted with an anti-mouse ApoE (ab20874, Abcam) and anti-tubulin α/β (2148, Cell Signaling) antibodies.

ApoE Expression Analysis in Melanoma Clinical Samples

All clinical sample procurement, processing, and analyses were performed in strict agreement with IRB guidelines. Primary melanoma skin lesions were previously resected from patients at the MSKCC, formalin-fixed, paraffin-embedded, and sectioned into 5-µm-thick slides. ApoE protein expression was assessed by double-blinded immunohistochemical analysis using the D6E10 anti-ApoE antibody (ab1906, Abcam).

Histochemistry

Animals were intracardially perfused with PBS followed by 4% paraformaldehyde (PFA). Fixed lungs were embedded in paraffin and sectioned into 5-µm-thick increments. Macroscopic lung metastatic nodules were visualized by H&E staining. For analysis of tumor endothelial cell content, proliferation, and apoptosis, primary tumor paraffin-embedded sections were stained with antibodies against MECA-32 (Developmental Studies Hybridoma Bank, University of Iowa), KI-67 (ab15580, Abcam), and cleaved caspase-3 (9661, Cell Signaling), respectively.

Tail-Vein Metastasis Assays

Melanoma cells used for in vivo metastasis assays were transduced with a stably expressed retroviral construct encoding a luciferase reporter gene (Ponomarev et al., 2004), allowing us to monitor the in vivo progression of melanoma cells by bioluminescence imaging. The following numbers of melanoma cells, resuspended in 100 µL of PBS, were injected intravenously via the tail-vein: $4 \times 10^4$ MeWo cells, $2.5 \times 10^5$ HT-144 cells, $2 \times 10^5$ SK-Mel-334.2 cells, $5 \times 10^4$ B 16F10 cells, and $1 \times 10^5$ YUMM cells. The MeWo, HT-144, and SK-Mel-334.2 cells were injected into 6-8 week-old sex-matched NOD scid mice, while the B16F10 and YUMM cells were injected into 6-8 week-old sex-matched C57BL/6 mice. In all experiments assessing at the effects of GW3965 on metastasis formation, mice were pre-treated on a control diet or a GW3965-supplemented diet (20 mg/kg) for 10 days. To assess the effect of GW3965 treatment on brain metastasis, $1 \times 10^5$ MeWo brain-metastatic derivatives were injected intracardially into athymic nude mice. Immediately following injection, mice were randomly assigned to a control diet or GW3965-supplemented diet (100 mg/kg). To determine whether oral delivery of GW3965 can inhibit the progression of incipient metastasis, NOD Scid mice were intravenously injected with $4 \times 10^4$ MeWo cells and the cells were allowed to colonize the lungs for 42 days, after which mice were blindly assigned to a control diet or a GW3965-supplemented diet (100 mg/kg) treatment.

Orthotopic Metastasis Assays

To determine the effect of GW3965 treatment on lung colonization by melanoma cells dissociated from an orthotopic site, $1 \times 10^6$ MeWo cells expressing a luciferase reporter were subcutaneously injected into both lower flanks of NOD Scid mice. Upon the formation of tumors measuring ~300 mm$^3$ in volume, the tumors were excised and the mice were randomly assigned to a control diet or a GW3965-supplemented diet (100 mg/kg) treatment. One month after tumor excision, the lungs were extracted and lung colonization was measured by ex vivo bioluminescence imaging. To histologically confirm the extent of melanoma lung colonization, lungs were then fixed in 4% PFA overnight, paraffin-embedded, section into 5-µM increments and stained for human vimentin (VP-V684, Vector Laboratories).

Generation of Dacarbazine-Resistant Melanoma Cells

Dacarbazine-resistant B16F10 mouse melanoma cells were generated by continuously culturing the cells in the presence of DTIC (D2390, Sigma-Aldrich, St. Louis, Mo.). First, the cells were treated with 500 µg/mL DTIC for one week. Following this initial DTIC treatment, the remaining (~10%) viable cells were allowed to recover for one week, after which 750 µg/mL of DTIC was added to the cell media for 5 days. Subsequent to this high-dose treatment, the cells were allowed to recover in the presence of low-dose DTIC (100 µg/mL) for one week. The cells were then continuously cultured in cell media containing 200 µg/mL DTIC for at least one month prior to grafting the cells into mice. DTIC was added to fresh cancer cell media every 3 days. For tumor growth experiments, $5 \times 10^4$ B16F10 parental and DTIC-resistant cells were subcutaneously injected into the lower flank of 7-week-old C57BL/6 mice. Following formation of small tumors measuring 5-10 mm$^3$ in volume, the mice were randomly assigned to the following treatment groups: (1) control diet+vehicle, i.p.; (2) control diet+DTIC i.p. (50 mg/kg); (3) GW3965-supplemented diet (100 mg/kg)+vehicle i.p.. DTIC was dissolved in the presence of citric acid (1:1 by weight) in water and administered daily by intraperitoneal injection.

The DTIC-resistant MeWo human melanoma cell line clone was generated following DTIC treatment of mice bearing MeWo tumors measuring 600-800 mm$^3$ in volume. After initial tumor shrinkage in response to daily DTIC dosing (50 mg/kg, i.p.) during the first two weeks, the tumors eventually developed resistance and resumed growth, at which point tumor cells were dissociated and the DTIC-resistant MeWo cell line was established. The cells were expanded in vitro in the presence of DTIC (200 µg/mL) for one week, after which $5 \times 10^5$ DTIC-resistant MeWo cells were re-injected into 8-week old Nod SCID gamma mice. Following growth of tumors to 5-10 mm$^3$ in volume, mice were blindly assigned to the following treatment groups: (1) control diet; (2) control diet+DTIC (50 mg/kg); (3) GW3965-supplemented diet (100 mg/kg). To determine the effect of DTIC on tumor growth by parental unselected MeWo cells, $5 \times 10^5$ MeWo cells were subcutaneously injected into Nod SCID gamma mice, and the mice were treated with a control vehicle or DTIC (50 mg/kg) subsequent to formation of tumors measuring 5-10 mm$^3$ in volume. DTIC was administered daily, as described above, in cycles consisting of 5 consecutive daily treatments interspersed by 2-day off-treatment intervals. Tumor growth was measured twice a week.

Genetically-Initiated Model of Melanoma Progression

The Tyr::CreER; B-Raf$^{V600E/+}$; Pten$^{lox/+}$/Tyr::CreER; B-Raf$^{V600E/+}$; Pten$^{lox/lox}$ conditional model of melanoma progression was previously established and characterized by Dankort et al. (2009). Briefly, melanoma in these mice was induced at 6 weeks of age by intraperitoneally injecting 4-HT (H6278, 70% isomer, Sigma-Aldrich, St Louis, Mo.) at 25 mg/kg administered in peanut oil on three consecutive days. The 4-HT stock solution was prepared by dissolving it in 100% EtOH at 50 mg/mL by heating at 45° C. for 5 min and mixing. Once dissolved, the stock 4-HT solution was then diluted by 10-fold in peanut oil, yielding a 5 mg/mL 4-HT working solution that was then injected into mice. After the first 4-HT injection, mice were blindedly assigned to receive either a control diet or a diet supplemented with GW3965 (100 mg/kg). Mice were examined three times a week for the presence and progression of melanoma lesions. At day 35, dorsal skin samples were harvested from control-treated and GW3965-treated mice, fixed in 4% PFA and photographed at 10×. The percentage of pigmented melanoma lesion area out of the total skin area was quantified using ImageJ. For survival analyses, mice were monitored daily for melanoma progression and euthanized according to a standard body condition score, taking into account initial signs of moribund state and discomfort associated with the progression of melanoma burden. Post-mortem, the lungs, brains, and salivary glands were harvested and examined for the presence of macroscopic melanoma lesions.

Mouse Genotyping

All mouse genotyping was performed using standard PCR conditions, as recommended by Jackson Labs. The following genotyping primers were used for the respective PCR reactions:

```
Tyr::CreER; B-Raf^V600E/+; Pten^lox/+ and
Tyr::CreER; B-Raf^V600E/+; Pten^lox/lox mice:
B-Raf Forward:
5'-TGA GTA TTT TTG TGG CAA CTG C-3'

B-Raf Reverse:
5'-CTC TGC TGG GAA AGC GGC-3'

Pten Forward:
5'-CAA GCA CTC TGC GAA CTG AG-3'

Pten Reverse:
5'-AAG TTT TTG AAG GCA AGA TGC-3'

Cre Transgene Forward:
5'-GCG GTC TGG CAG TAA AAA CTA TC-3'

Cre Transgene Reverse:
5'-GTG AAA CAG CAT TGC TGT CAC TT-3'

Internal Positive Control Forward:
5'-CTA GGC CAC AGA ATT GAA AGA TCT-3'

Internal Positive Control Reverse:
5'-GTA GGT GGA AAT TCT AGC ATC ATC C-3'

ApoE-/-mice:
Common Forward:
5'-GCC TAG CCG AGG GAG AGC CG-3'

Wild-type Reverse:
5'-TGT GAC TTG GGA GCT CTG CAG C-3'

Mutant_Reverse:
5'-GCC GCC CCG ACT GCA TCT-3'

LXRα-/-mice:
Common Forward:
5'-TCA GTG GAG GGA AGG AAA TG-3'

Wild-type_Reverse:
5'-TTC CTG CCC TGG ACA CTT AC-3'

Mutant_Reverse:
5'-TTG TGC CCA GTC ATA GCC GAA T-3'

LXRβ-/-mice:
Common Forward:
5'-CCT TTT CTC CCT GAC ACC G-3'

Wild-type Reverse:
5'-GCA TCC ATC TGG CAG GTT C-3'

Mutant Reverse:
5'-AGG TGA GAT GAC AGG AGA TC-3'
```

Cell Proliferation and Viability Assay:

To determine the effects of GW3965, T0901317, and Bexarotene on in vitro cell growth, 2.5×10$^4$ melanoma cells were seeded in triplicate in 6-well plates and cultured in the presence of DMSO, GW3965, T0901317, or Bexarotene at 1 μM each. After 5 days, the number of viable and dead cells was counted using the trypan blue dye (72-57-1, Sigma-Aldrich), which selectively labels dead cells.

Cell Invasion Assay

The cell invasion assay was performed as previously described in detail (Pencheva et al., 2012) using a trans-well matrigel invasion chamber system (354480, BD Biosciences). In brief, various melanoma cells were cultured in the presence of DMSO, GW3965, T0901317, or Bexarotene at 1 μM for 56 hours, after which melanoma cells were switched to starvation media (0.2% FBS) for 16 hours in the presence of each drug. Following starvation, cells were seeded into matrigel-coated trans-well inserts, and the invasion assay was allowed to proceed for 24 hours at 37° C. For ApoE antibody neutralization experiments, 40 μg/mL 1D7 anti-ApoE blocking antibody (Heart Institute, University of Ottawa, Ottawa, Canada) or 40 μg/mL anti-IgG control antibody (AB-108-C, R&D Systems, Minneapolis, Minn.) was added to each trans-well insert at the start of the assay.

Endothelial Recruitment Assay

The endothelial recruitment assay was carried out as previously described (Pencheva et al., 2012; Png et al., 2012). Melanoma cells were treated with DMSO, GW3965, T0901317, or Bexarotene at 1 μM for 56 hours, after which 5×10$^4$ cells were seeded in a 24-well plate in the presence of each drug and allowed to attach for 16 hours prior to starting the assay. HUVEC cells were serum-starved overnight in EGM-2 media containing 0.2% FBS. The following day, 1×10$^5$ HUVEC cells were seeded into a 3.0 μm HTS Fluoroblock trans-well migration insert (351151, BD Falcon, San Jose, Calif.) fitted into each well containing cancer cells at the bottom. The HUVEC cells were allowed to migrate towards the cancer cells for 20 hours at 37° C., after which the inserts were processed as previously described (Pencheva et al., 2012). For ApoE antibody neutralization experiments, 40 μg/mL 1D7 anti-ApoE blocking antibody (Heart Institute, University of Ottawa, Ottawa, Canada) or 40 μg/mL anti-IgG control antibody (AB-108-C, R&D Systems, Minneapolis, Minn.) was added to each trans-well insert at the start of the assay.

Lentiviral shRNA-Based Gene Knockdown shRNAs were integrated into lentiviral particles that were prepared by transfection of 6 μg of vector A, 12 μg of vector K, and 12 μg of shRNA plasmid into HEK-293T packaging cells, as previously described (Pencheva et al., 2012; Png et al., 2012). Lentiviral shRNA transduction was performed in the presence of 10 µg/mL of polybrene (TR-1003-G, Millipore, Billerica, Mass.) for 6 hours, as described previously (Pencheva et al., 2012). The cells were expanded for 72 hours after transduction and lentiviral selection was performed by culturing the cells in the presence of 2 µg/mL of puromycin (P8833, Sigma-Aldrich) for 72 hours.

The following shRNA sequences were used:

```
Human:
sh₁LXRα:
5'-CCGGCCGACTGATGTTCCCACGGATCTCGAGATCCGTGGGAACAT

CAGTCGGTTTTT-3' sh₂LXRα:
5'-CCGGGCAACTCAATGATGCCGAGTTCTCGAGAACTCGGCATCATT

GAGTTGCTTTTT-3' sh₁LXRβ:
5'-CCGGAGAGTGTATCACCTTCTTGAACTCGAGTTCAAGAAGGTGAT

ACACTCTTTTT-3' sh₂LXRβ:
5'-CCGGGAAGGCATCCACTATCGAGATCTCGAGATCTCGATAGTGGA

TGCCTTCTTTTT-3' shApoE:
5'-CCGGGCAGACACTGTCTGAGCAGGTCTCGAGACCTGCTCAGACAG

TGTCTGCTTTTT-3'

Mouse:
sh_mLXRα:
5'-CCGGGCAACTCAATGATGCTGAGTTCTCGAGAACTCAGCATCATT

GAGTTGCTTTTT-3' sh_mLXRβ:
5'-CCGGTGAGATCATGTTGCTAGAAACCTCGAGGTTTCTAGCAACAT

GATCTCATTTTTG-3' sh_mApoE:
5'-CCGGGAGGACACTATGACGGAAGTACTCGAGTACTTCCGTCATAG

TGTCCTCTTTTT-3'
```

Gene Expression Analysis by qRT-PCR:

RNA was extracted from whole cell lysates using the Total RNA Purification Kit (17200, Norgen, Thorold, Canada). 600 ng of total RNA was then reverse transcribed into cDNA using the cDNA First-Strand Synthesis Kit (18080-051, Invitrogen), and quantitative real-time PCR amplification was performed as previously described (Pencheva et al., 2012) using an ABI Prism 7900HT Real-Time PCR System (Applied Biosystems, Austin, Tex.). Each PCR reaction was carried out in quadruplicates. Gene expression was normalized to GAPDH, which was used as an endogenous control.

The following primers were used:

```
Human:
ApoE Forward:
5'-TGGGTCGCTTTTGGGATTAC-3'

ApoE Reverse:
5'-TTCAACTCCTTCATGGTCTCG-3'

GAPDH Forward:
5'-AGCCACATCGCTCAGACAC-3'

GAPDH Reverse:
5'-GCCCAATACGACCAAATCC-3'

LXRα_Fwd:
5'-GTTATAACCGGGAAGACTTTGC-3'

LXRα_Rev:
5'-AAACTCGGCATCATTGAGTTG-3'

LW_Fwd:
5'-TTTGAGGGTATTTGAGTAGCGG-3'

LW_Rev:
5'-CTCTCGCGGAGTGAACTAC-3'

Mouse:
ApoE Forward:
5'-GACCCTGGAGGCTAAGGACT-3'

ApoE Reverse:
5'-AGAGCCTTCATCTTCGCAAT-3'

GAPDH Forward:
5'-GCACAGTCAAGGCCGAGAAT-3'

GAPDH_Reverse:
5'-GCCTTCTCCATGGTGGTGAA-3'

LXRα Forward:
5'-GCGCTCAGCTCTTGTCACT-3'

LXRα Reverse:
5'-CTCCAGCCACAAGGACATCT-3'

LXRβ Forward:
5'-GCTCTGCCTACATCGTGGTC-3'

LXRβ Reverse:
5'-CTCATGGCCCAGCATCTT-3'

ABCA1 Forward:
5'-ATGGAGCAGGGAAGACCAC-3'

ABCA1 Reverse:
5'-GTAGGCCGTGCCAGAAGTT-3'
```

ApoE Promoter Activity Assay

The ApoE promoter, consisting of a sequence spanning 980 base pairs upstream and 93 base pairs downstream of the ApoE gene, was cloned into a pGL3-Basic vector (E1751, Promega Corporation, Madison, Wis.) upstream of the firefly luciferase gene using NheI and SacI restriction enzymes. Then, multi-enhancer elements 1 (ME.1) and 2 (ME.2) were cloned directly upstream of the ApoE promoter using MluI and SacI restriction enzymes. To assess ApoE promoter- and ME.1/ME.2-driven transcriptional activation by LXR agonists, $5\times10^4$ MeWo cells were seeded into a 24-well plate. The following day, 100 ng of pGL3-ME.1/ME.2-ApoE promoter construct and 2 ng of pRL-CMV renilla luciferase construct (E2261, Promega) were co-transfected into cells in the presence of DMSO, GW3965, or T0901317 at 1 µM, each condition in quadruplicate. To assess transcriptional activation by LXRα or LXRβ, $5\times10^4$ MeWo cells expressing a control shRNA or shRNA targeting LXRα or LXRβ were seeded into a 24-well plate. The following day, 200 ng of pGL3-ME.1/ME.2-ApoE promoter construct and 2 ng of pRL-CMV renilla luciferase were co-transfected into cells in the presence of DMSO, GW3965, or T0901317 at 1 M, each condition in quadruplicate. After 24 hours, cells were lysed, and cell lysate was analyzed for firefly and renilla luciferase activity using the Dual Luciferase Assay System (E1960, Promega) and a Bio-Tek Synergy NEO Microplate Reader. Firefly luciferase signal was normalized to renilla luciferase signal and all data are expressed relative to the luciferase activity ratio measured in the DMSO-treated control cells.

The following cloning primers were used:

```
ApoE-promoter Forward:
5'-TCA TAG CTA GCG CAG AGC CAG GAT TCA CGC CCT
G-3'

ApoE-promoter Reverse:
5'-TGG TCC TCG AGG AAC CTT CAT CTT CCT GCC TGT
GA-3'

ME.1 Forward:
5'-TAG TTA CGC GTA GTA GCC CCC ATC TTT GCC-3'

ME.1 Reverse:
5'-AAT CAG CTA GCC CCT CAG CTG CAA AGC TC-3'

ME.2 Forward:
5'-TAG TTA CGC GTA GTA GCC CCC TCT TTG CC-3'

ME.2_Reverse:
5'-AAT CAG CTA GCC CTT CAG CTG CAA AGC TCT G-3'
```

Tumor Histochemistry

Tumors were excised from mice and fixed in 4% paraformaldehyde at 4° C. for 48 hours. Then, tumors were paraffin-embedded and sectioned into 5-μm-thick increments. For endothelial cell content analysis in tumors, tumor sections were stained with a primary antibody against the mouse endothelial cell marker MECA-32 (Developmental Studies Hybridoma Bank, The University of Iowa, IA) and counterstained with DAPI nuclear stain. To determine tumor cell proliferation and apoptosis, tumor sections were stained with antibodies against the proliferative marker Ki-67 (Abcam, ab15580, Cambridge, Mass.) and the apoptotic marker cleaved caspase-3 (9661, Cell Signaling, Danvers, Mass.), respectively. Various Alexa Flour dye-conjugated secondary antibodies were used to detect primary antibodies. Fluorescence was measured using inverted fluorescence microscope (Zeiss Axiovert 40 CFL) at 5× magnification for MECA-32 and Ki-67 staining and 10× magnification for cleaved caspase-3 staining. Endothelial cell content density and tumor proliferation rate were quantified by calculating the average percentage of MECA-32 or Ki-67 positively-staining area out of the total tumor area. Tumor apoptosis was measured by counting the number of cleaved caspase-3 expressing cells per given tumor area.

Analysis of ApoE Expression in Primary Melanoma Lesions

Human primary melanoma skin samples were resected from melanoma patients at MSKCC, formalin-fixed, embedded in paraffin, and sectioned into 5-μm-thick increments. To determine ApoE protein expression, the samples were first de-paraffinized by two consecutive xylene washes (5 minutes each), and rehydrated in a series of ethanol washes (100%, 95%, 80%, and 70% EtOH). ApoE antigen was retrieved by incubating the samples in the presence of proteinase K (5 μg/mL) for 20 minutes at room temperature. To quench endogenous peroxidase activity, the slides were incubated in 3% $H_2O_2$ solution. The slides were then blocked in three consecutive Avidin, Biotin, and horse serum block solutions for 15 min each at room temperature (SP-2001, Vector Laboratories, Burlingame, Calif.). ApoE was detected by staining with D6E10 anti-ApoE antibody (ab1908, Abcam), which was used at a 1:100 dilution in PBS at 4° C. overnight. The primary antibody was then recognized by incubating the slides in a peroxidase-conjugated secondary antibody (PK-4002, Vector Laboratories) and exposed by DAB (SK-4105, Vector Laboratories) oxidation reaction. The slides were imaged at 10× magnification and analysed in a double-blinded manner. ApoE expression was quantified by counting the number of DAB-positive cells and measuring the area of extracellular ApoE staining. Total ApoE staining signal was expressed as the percentage staining area per given tumor area, determined based on matched H&E-stained slides for each sample. Kaplan-Meier curves depicting patients' metastasis-free survival times were generated by plotting each patient's relapse-free survival data as a function of ApoE expression in that patient's primary melanoma lesion. Patients whose tumors had ApoE levels lower than the median ApoE expression of the population were classified as ApoE-negative, whereas patients whose melanomas expressed ApoE above the median were classified as ApoE-positive. Previously documented patients' history of metastatic recurrence to sites such as lung, brain, bone, soft and subcutaneous tissues, and skin enabled us to retrospectively determine the relationship between ApoE expression at a primary melanoma site and metastatic relapse.

Example 2

Figure 1B:
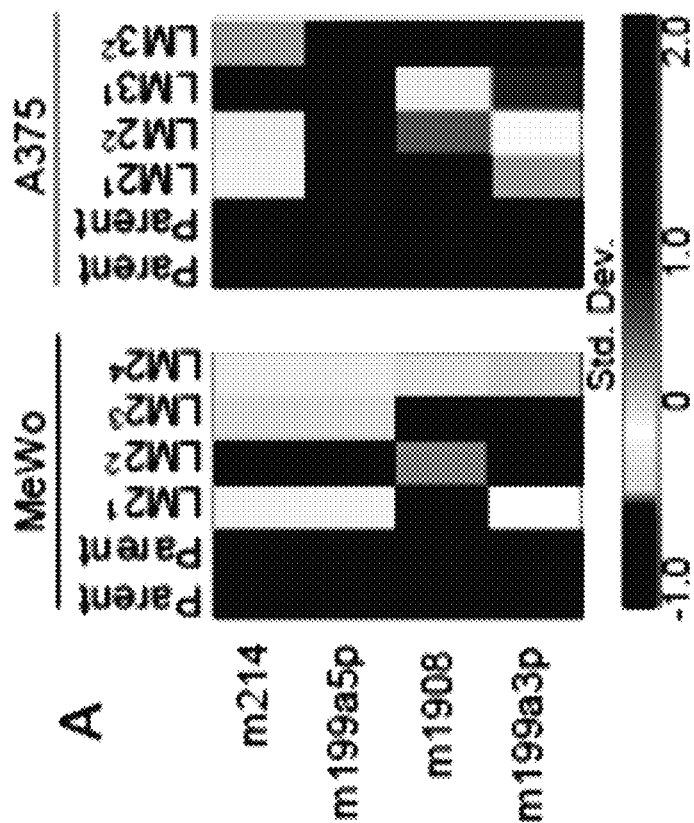
Figures 1C, 1D:
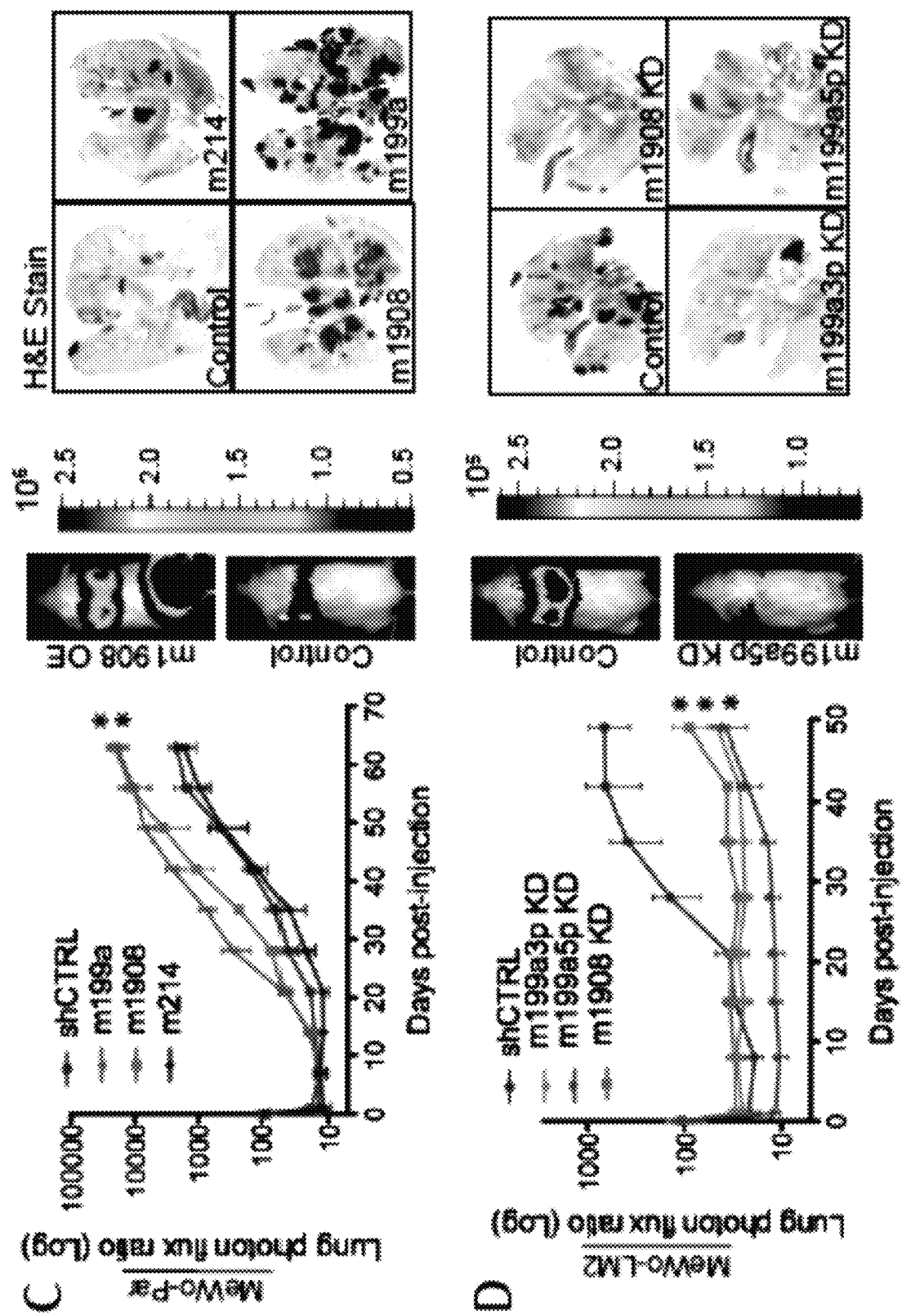
Figures 12A, 12B, 12C, 12D:
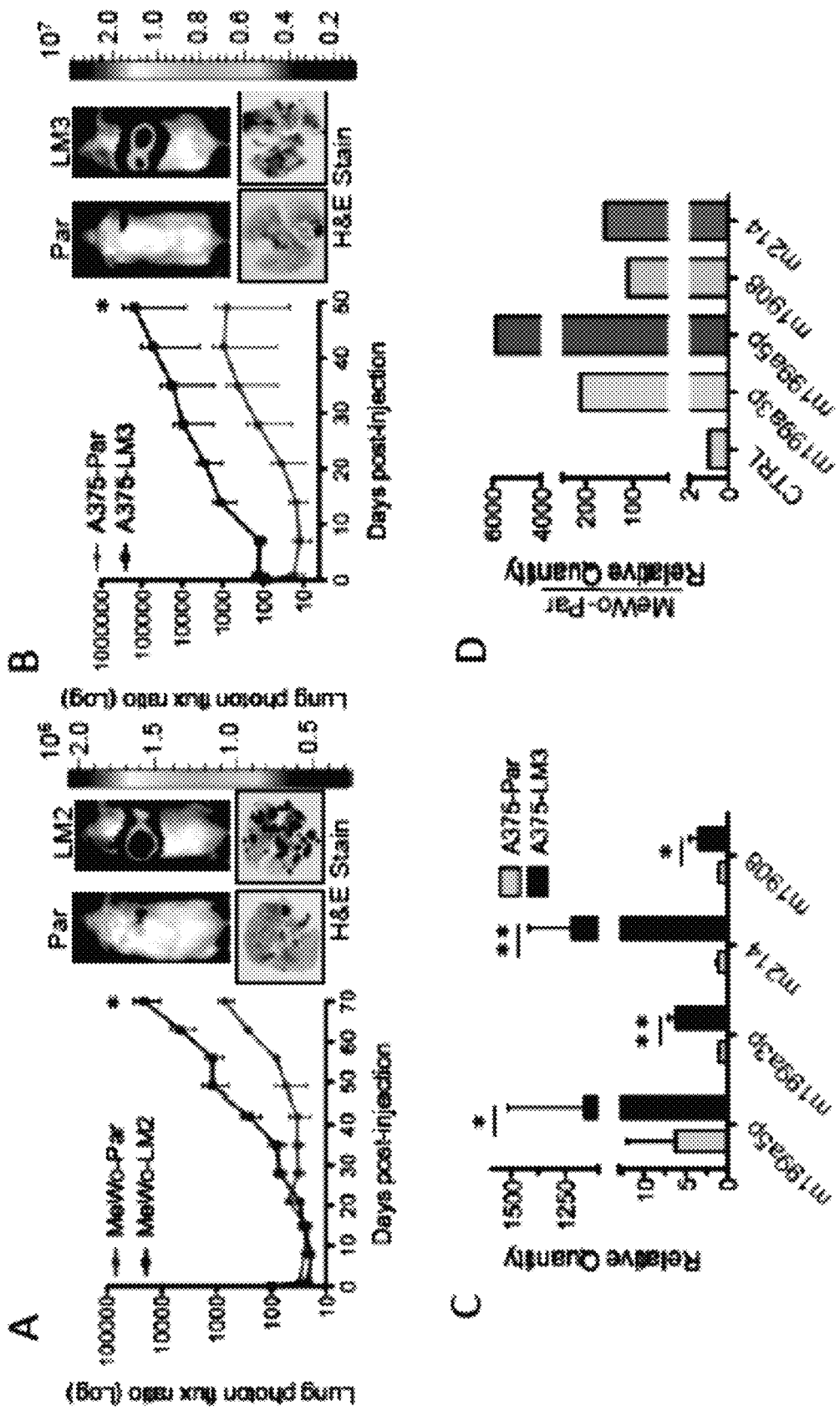
Figure 12E:
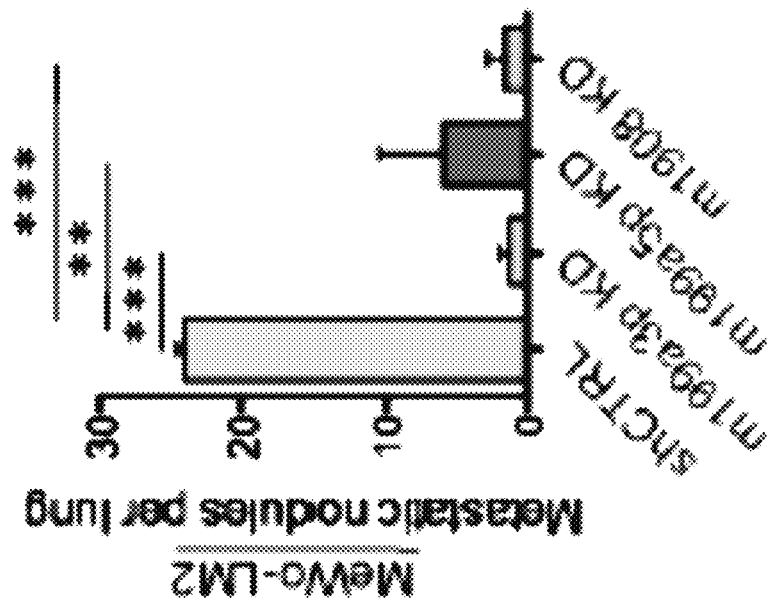

Endogenous Mir-1908, Mir-199a-3p, And Mir-199a-5p Promote Human Melanoma Metastasis In order to identify miRNA regulators of melanoma metastasis, in vivo selection (Pollack and Fidler, 1982) was utilized with the pigmented MeWo and non-pigmented A375 human melanoma cell lines to generate multiple second (LM2) and third generation (LM3) lung metastatic derivatives. Comparison of the metastatic potential of the MeWo-LM2 and A375-LM3 lines showed these derivatives to metastasize significantly more efficiently than their respective parental populations in lung colonization assays (FIGS. 12A-B). Hybridization-based small RNA profiling of 894 mature miRNAs followed by quantitative stem-loop PCR (qRT-PCR) revealed four miRNAs (miR-1908, miR-199a-3p, miR-199a-5p, and miR-214) to be upregulated greater than two-fold in multiple A375 and MeWo metastatic derivatives relative to their respective parental cells (FIGS. 1A-B, 12C). The significant induction of miR-199a-3p, miR-199a-5p, miR-214, and miR-1908 across multiple metastatic derivatives suggested a metastasis-promoting role for these miRNAs. Retrovirally mediated transduction and over-expression of the precursors for miR-199a-3p and miR-199a-5p (over-expressed concomitantly as the miR-199a hairpin) and miR-1908 lead to a robust increase in lung metastatic colonization based on both bioluminescence signal quantification and gross lung histology (FIG. 1C, 12D; 9.64-fold increase, P=0.016 for miR-1908; 8.62-fold increase, P=0.028 for miR-199a), while miR-214 over-expression did not significantly affect metastasis. Importantly, over-expression of each miR-199a and miR-1908 increased the number of metastatic nodules formed (FIG. 12E), consistent with a role for these miRNAs in metastatic initiation. These findings also revealed miR-199a and miR-1908 to be sufficient for enhanced metastatic colonization.

Figure 12F:
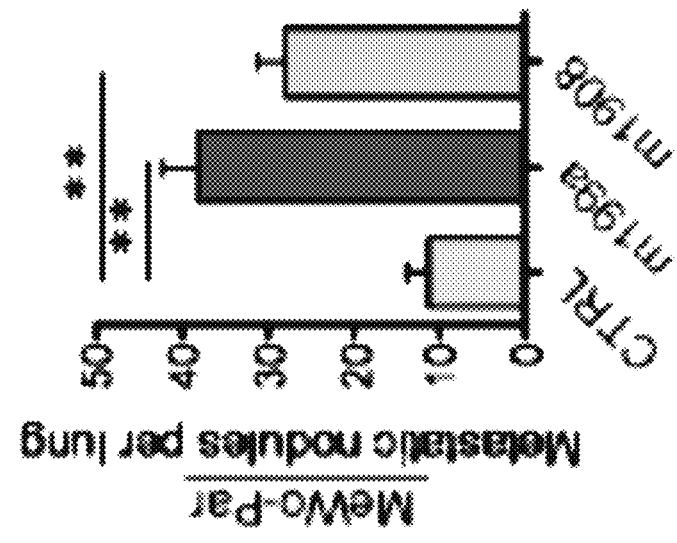

Next, assays were carried out to examine if endogenous levels of these miRNAs promote metastasis. To this end, miR-1908 and each of the two miRNAs arising from the miR-199a hairpin (miR-199a-3p and miR-199a-5p) were inhibited in the highly metastatic cells through miR-Zip technology. Individual inhibition of each of these miRNAs suppressed metastatic colonization by more than 7-fold (FIG. 1D; P=0.047 for miR-1908 inhibition; P=0.010 for miR-199a-3p inhibition; P=0.015 for miR-199a-5p inhibition) and dramatically decreased the number of metastatic nodules formed (FIG. 12F).

Figures 1E, 1F:
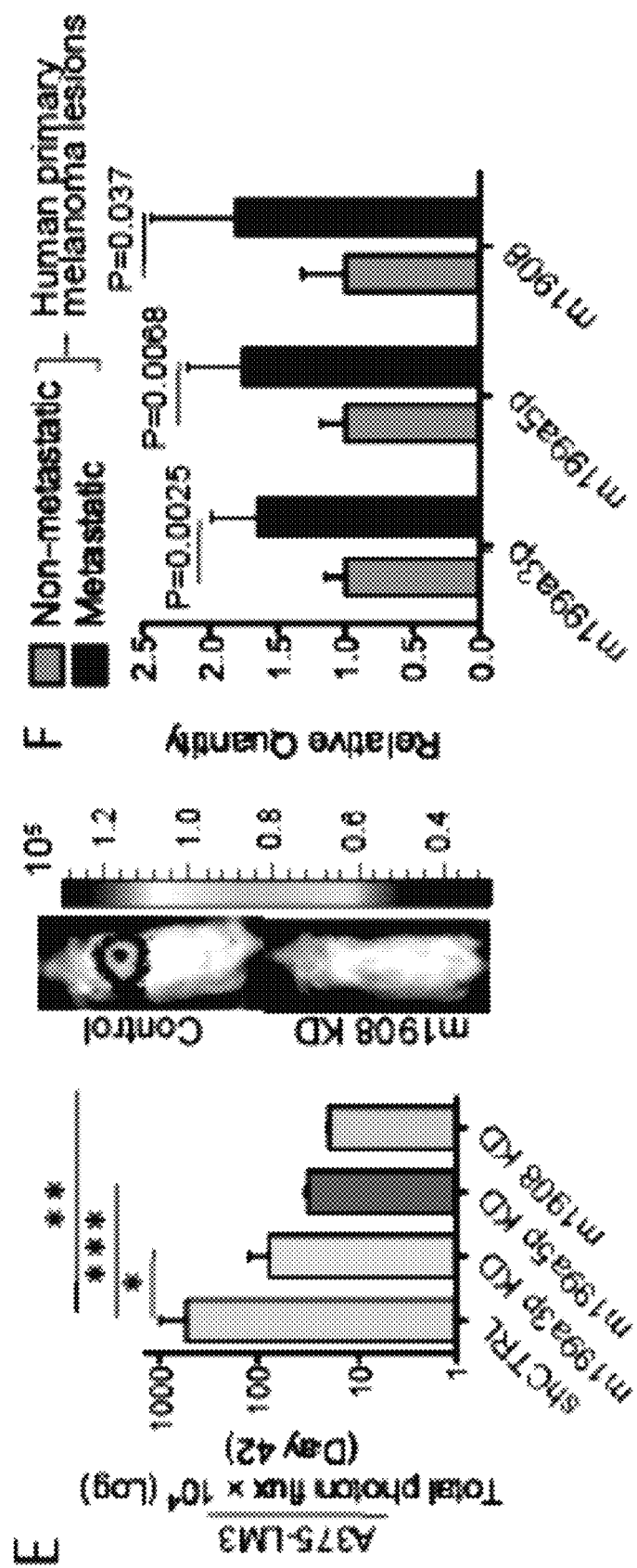

To determine whether these miRNAs also promote metastasis in an independent cell line, their expression was silenced in the A375 metastatic derivative cell line. Indeed, inhibition of miR-1908, miR-199a-3p, or miR-199a-5p significantly reduced the lung colonization capacity of metastatic A375-LM3 cells (FIG. 1E), establishing these three miRNAs as endogenous promoters of metastasis by human melanoma cells.

Given the robust functional roles of miR-1908, miR-199a-3p, and miR-199a-5p in promoting melanoma metastasis in a mouse model of human cell metastasis, further assays were carried out to examine whether expression of these miRNAs correlates with the capacity of human primary melanoma lesions to metastasize. To this end, 71 primary melanoma skin lesions obtained from Memorial Sloan-Kettering Cancer Center (MSKCC) patients were analyzed in a blinded fashion for the expression levels of miR-1908, miR-199a-3p, and miR-199a-5p through qRT-PCR. Consistent with the above functional studies, all three miRNAs were significantly induced in primary melanomas that had metastasized relative to those that had not (FIG. 1F; P=0.037 for miR-1908; P=0.0025 for miR-199a-3p; P=0.0068 for miR-199a-5p), suggesting that upregulated expression of these miRNAs in primary lesions is an early event predictive of melanoma cancer progression.

Example 3

Mir-1908, Mir-199a-3p, and Mir-199a-5p Promote Cell Invasion and Endothelial Recruitment In this Examiner, assays were carried out to determine the cellular mechanisms by which miR-1908, miR-199a-3p, and miR-199a-5p regulate metastasis.

Figures 13A, 13B, 13C, 13D, 13E, 13F, 13G:
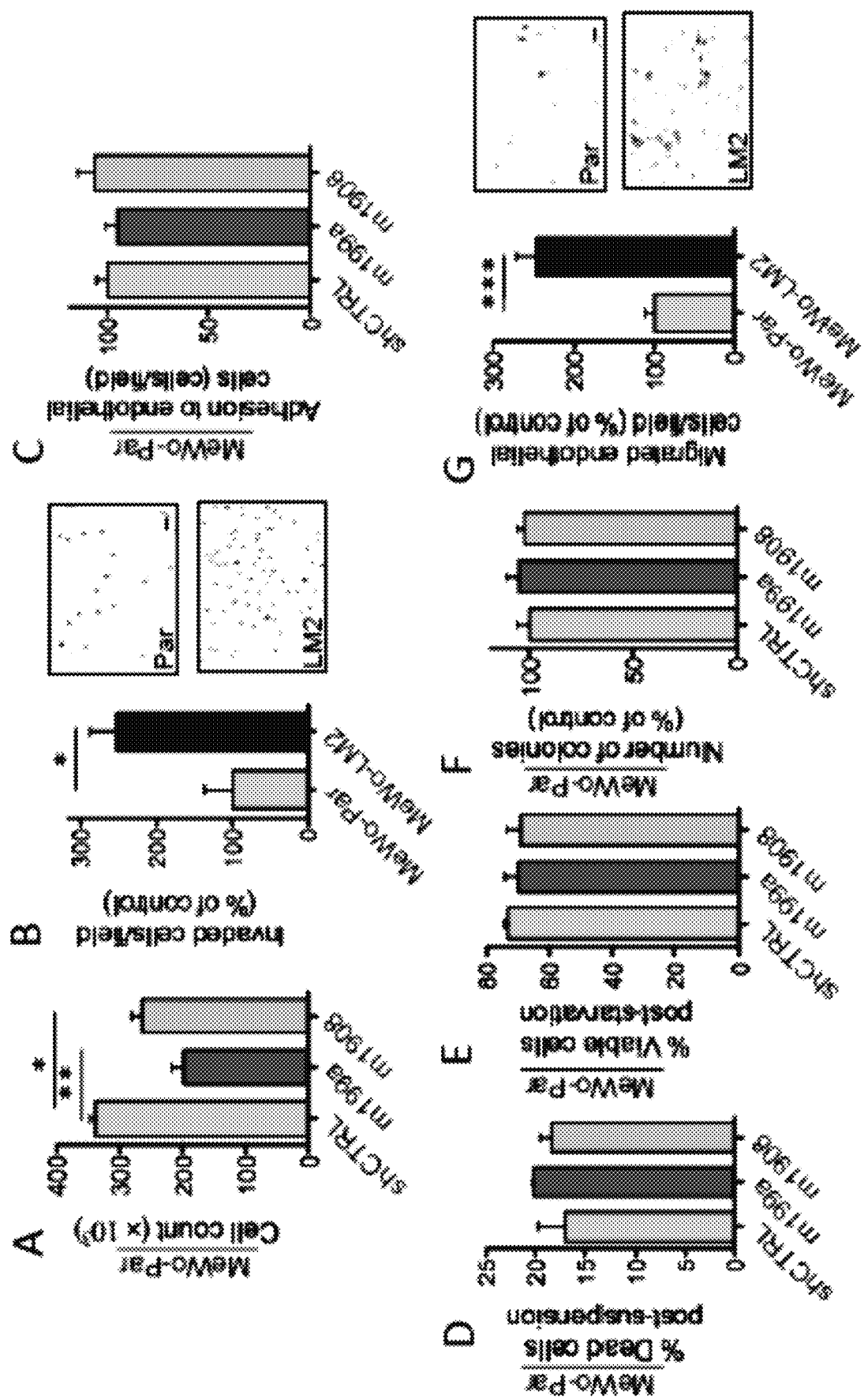

First, it was examined if these miRNAs promote metastasis by enhancing proliferation or tumor growth. Contrary to this, over-expression of each miRNA reduced cell proliferation (FIG. 13A). More importantly, miR-1908 over-expression did not increase primary tumor growth, while miR-199a over-expression actually lead to a significant decrease (35%; P<0.001) in tumor volume (FIG. 2A), indicating that the pro-metastatic effects of miR-1908 and miR-199a are not secondary to tumor growth promotion or enhanced cell proliferation.

Next, it was examined whether these miRNAs regulate cell invasion, a key metastatic phenotype. Metastatic LM2 cells, which express higher levels of these miRNAs, displayed significantly increased matrigel invasion capacity relative to their less metastatic parental population (FIG. 13B). Accordingly, over-expression of miR-199a and miR-1908 individually enhanced the ability of parental MeWo cells to invade through matrigel (FIG. 2B; three-fold increase for miR-199; two-fold increase for miR-1908). Conversely, individual inhibition of miR-199a-3p, miR-199a-5p, and miR-1908 significantly decreased the invasive capacity of MeWo-LM2 (FIG. 2C) as well as A375-LM3 (FIG. 2D) metastatic melanoma cell derivatives.

Figures 2A, 2B, 2C, 2D, 2E:
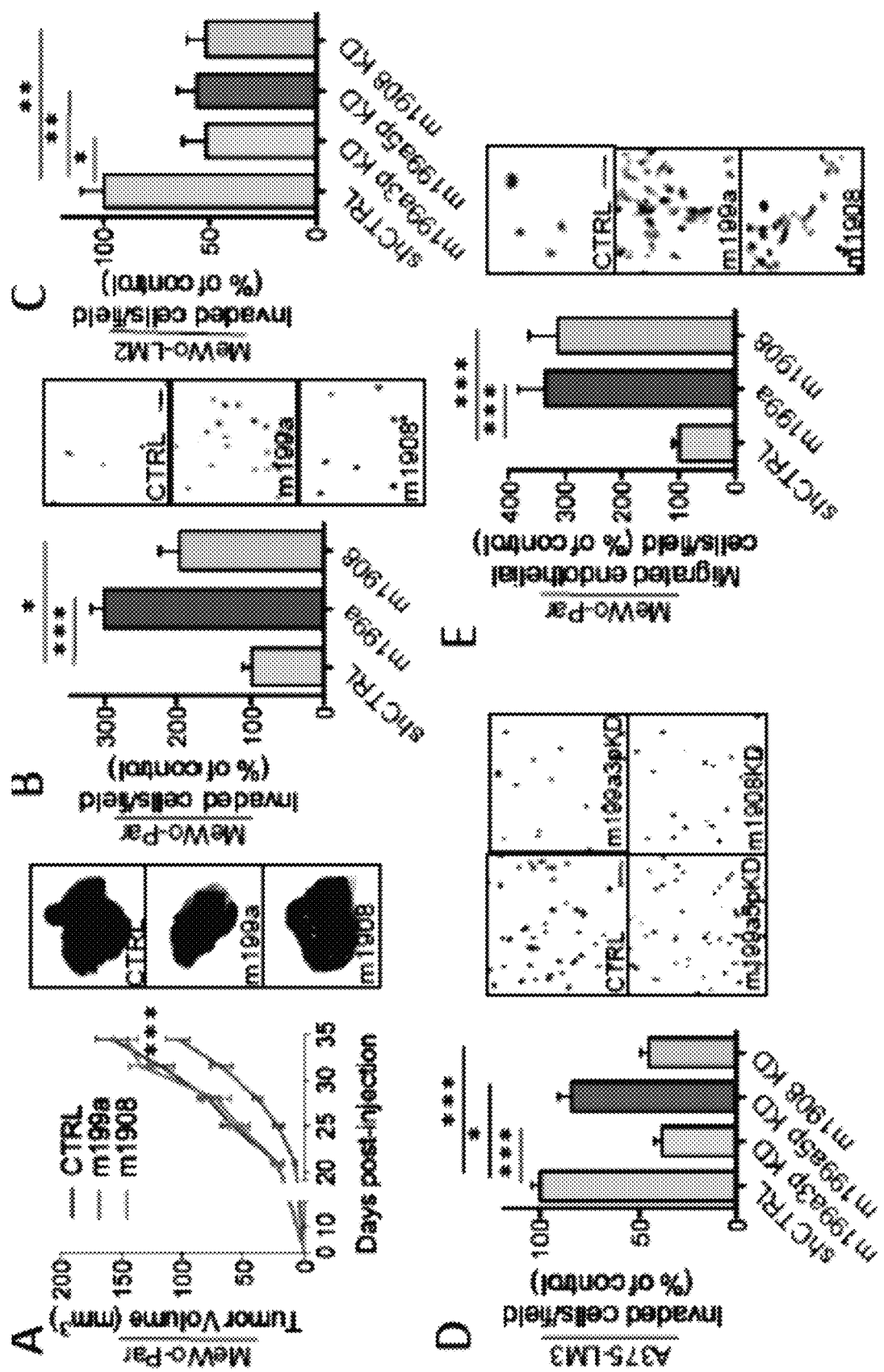
FIGS. 2A, 2B, 2C, 2D, 2E, 2F, 2G and 2H. MiR-1908, miR-199a-3p, and miR-199a-5p Display Dual Cell-Autonomous/Non-Cell-Autonomous Roles in Regulating Melanoma Metastatic Progression (2A) 1×106 parental MeWo cells over-expressing miR-199a, miR-1908, or a control hairpin were injected subcutaneously into immuno-deficient mice, and primary tumor volume was monitored over time. n=4-6. (2B) 1×105 parental MeWo cells over-expressing miR-199a, miR-1908, or a control hairpin were allowed to invade through a trans-well matrigel-coated insert for 24 hours, and the number of cells invaded into the basal side of each insert was quantified. n=7. (2C-2D) 1×105 highly metastatic MeWo-LM2 (2C) and A375-LM3 (2D) cells with miR-Zip-induced inhibition of miR-199a-3p, miR-199a-5p, miR-1908, or a control sequence were subjected to the cell invasion assay. n=6-8. (2E) 5×104 MeWo cells over-expressing miR-199a, miR-1908, or a control hairpin were seeded on the bottom of a well, and 1×105 human umbilical vein endothelial cells (HUVEC's) were allowed to migrate towards the cancer cells for 16 hours through a trans-well insert. Endothelial recruitment capacity was measured by quantifying the number of HUVEC's migrated to the basal side of each insert. n=7. (2F-2G) Endothelial recruitment by 5×104 MeWo-LM2 (2F) and A375-LM3 (2G) cells inhibited for miR-199a-3p, miR-199a-5p, miR-1908, or a control sequence. n=6-10. (2H) Cumulative fraction plot of the percentage blood vessel density distribution for metastatic nodules formed following intravenous injection of 2×105 highly metastatic MeWo-LM2 cells depleted for miR-199-3p, miR-199a-5p, miR-1908, or a control sequence. Lung sections were immunohistochemically double-stained for human vimentin (blue) and MECA-32 (red), and the percentage MECA-32 positive area within each metastatic nodule, demarcated based on vimentin staining, was quantified. n=211 nodules (control KD); n=60 nodules (m199a3p KD); n=138 nodules (m199a5p KD); n=39 nodules (m1908 KD). All data are represented as mean±SEM. Scale bar, 100 µm. See also FIG. 13.
Figures 2F, 2G, 2H:
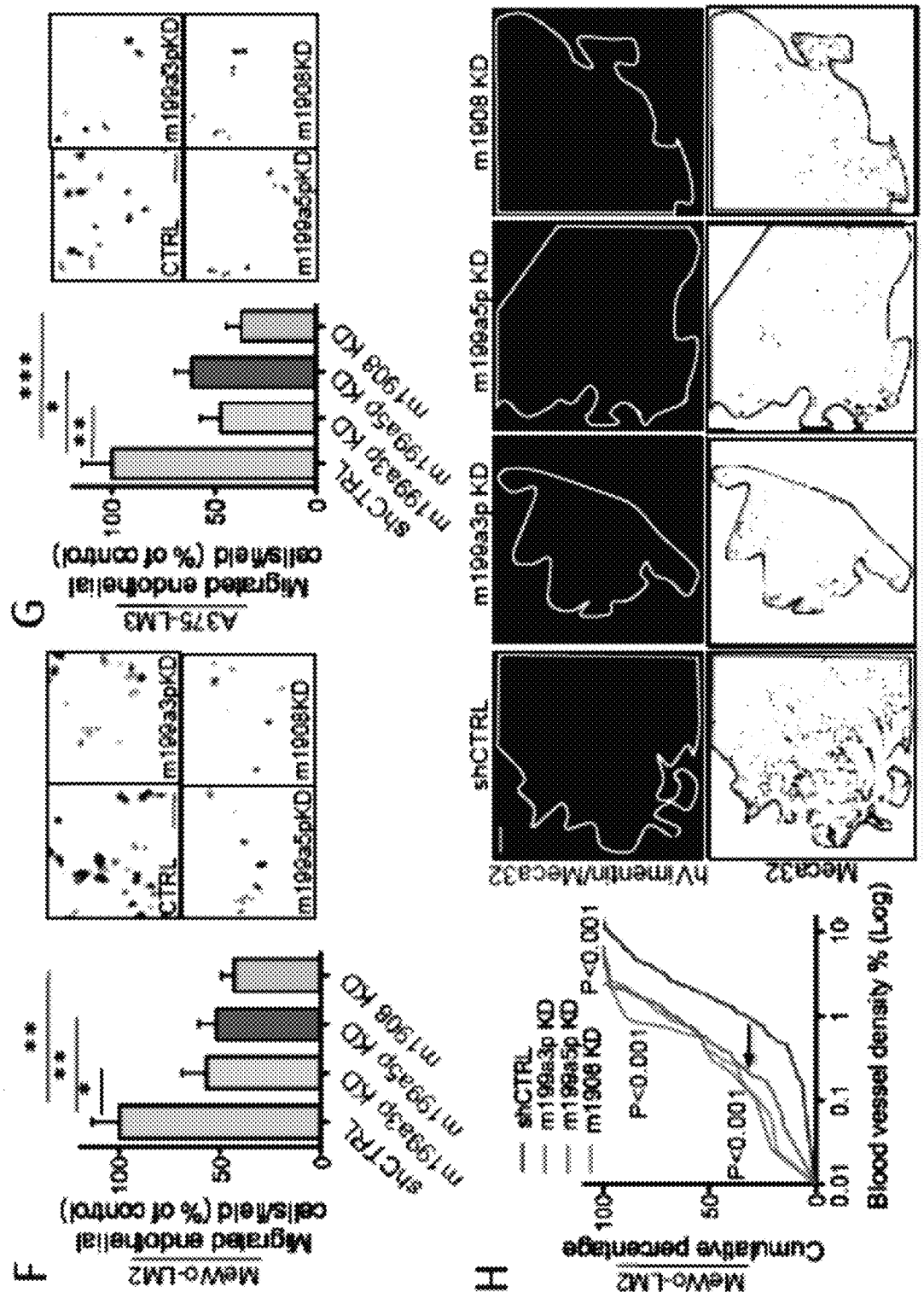

Given the robust effects of these miRNAs on metastatic progression, further analyses were conducted to examiner whether they may regulate any additional pro-metastatic phenotypes. While over-expression of miR-199a or miR-1908 did not modulate melanoma cell adhesion to endothelial cells (FIG. 13C), resistance to anoikis (FIG. 13D), survival in the setting of serum starvation (FIG. 13E), or colony formation (FIG. 13F), each miRNA dramatically enhanced (more than three-fold increase) the ability of parental MeWo cells to recruit endothelial cells in trans-well endothelial recruitment assays (FIG. 2E). Consistent with this, metastatic Mewo-LM2 cells, which physiologically over-express miR-199a and miR-1908, were more efficient at recruiting endothelial cells relative to their parental cells (FIG. 13G). Conversely, inhibition of miR-199a-3p, miR-199a-5p, or miR-1908 in the metastatic MeWo-LM2 (FIG. 2F) as well as A375-LM3 cells (FIG. 2G) suppressed endothelial recruitment, consistent with the requirement and sufficiency of these miRNAs for enhanced endothelial recruitment capacity of metastatic melanoma cells.

To determine whether endogenous miR-199a-3p, miR-199a-5p, and miR-1908 regulate endothelial recruitment by metastatic cells in vivo, assays were carried out to examine metastatic blood vessel density by performing co-immunostaining for human vimentin, which labels human MeWo melanoma cells, and mouse endothelial cell antigen (MECA-32), which labels mouse endothelial cells. Strikingly, inhibition of miR-199a-3p, miR-199a-5p, or miR-1908 individually led to pronounced decreases (an average of 3-fold for miR-199a-3p and miR-199a-5p and 4.7-fold for miR-1908) in blood vessel density within metastatic nodules (FIG. 2H; P<0.001 for miR-199a-3p; P<0.001 for miR-199a-5p; and P<0.001 for miR-1908), revealing a role for these miRNAs in promoting metastatic endothelial content and metastatic angiogenesis. Conversely, over-expression of each miRNA in poorly metastatic melanoma cells dramatically increased metastatic blood vessel density (FIG. 13H). These findings reveal miR-199a-3p, miR-199a-5p, and miR-1908 as necessary and sufficient for enhanced invasion and endothelial recruitment during melanoma progression.

Example 4

Mir-1908, Mir-199a-3p, and Mir-199a-5p Convergently and Cooperatively Target Apoe and DNAJA4

In this example, a systematic and unbiased approach was employed to identify the direct molecular targets of these miRNAs.

Figures 14A, 14B, 14C, 14D:
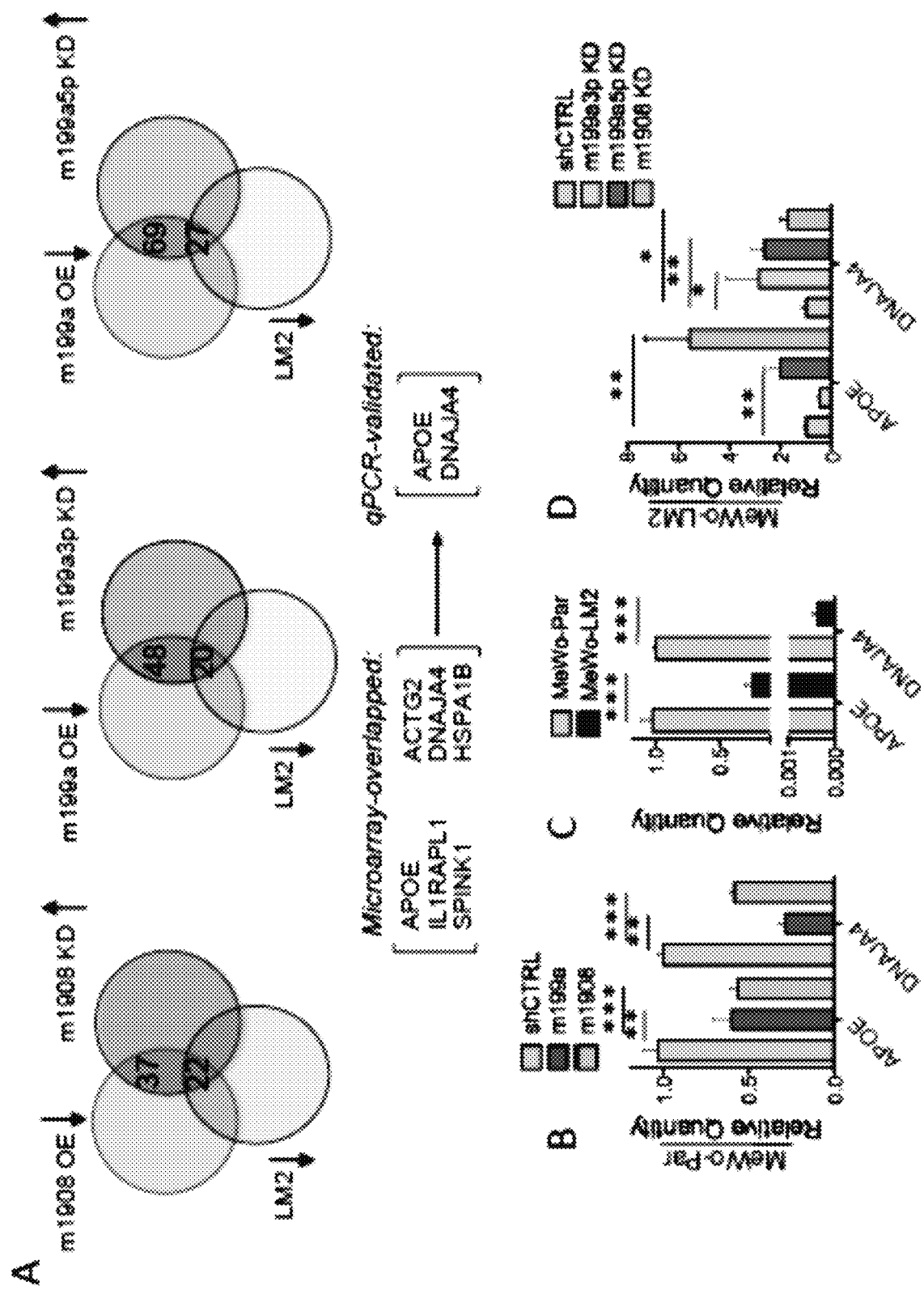

Since miR-1908, miR-199a-3p, and miR-199a-5p mediate the same sets of in vitro and in vivo phenotypes and miR-199a-5p and miR-199a-3p arise from the same precursor hairpin, it was hypothesized that the pro-metastatic phenotypes of these miRNAs may arise through silencing of common target genes. Given that mammalian miRNAs act predominantly by destabilizing target mRNA transcripts (Guo et al., 2010 Nature 466, 835-840), transcriptomic profiling of melanoma cells was performed in the context of both loss- and gain-of-function for each miRNA. This revealed a small set of genes that were repressed by both miR-199a and miR-1908 and that also displayed lower levels in the metastatic LM2 derivatives, which express higher endogenous levels of these miRNAs (FIG. 14A). Quantitative RT-PCR validated two genes, the metabolic gene Apolipoprotein E (ApoE) and the heat-shock protein DNAJA4, as significantly modulated by miR-199a and miR-1908 and dramatically silenced in the highly metastatic LM2 cells (FIGS. 3A and 14B-D).

Figure 3:
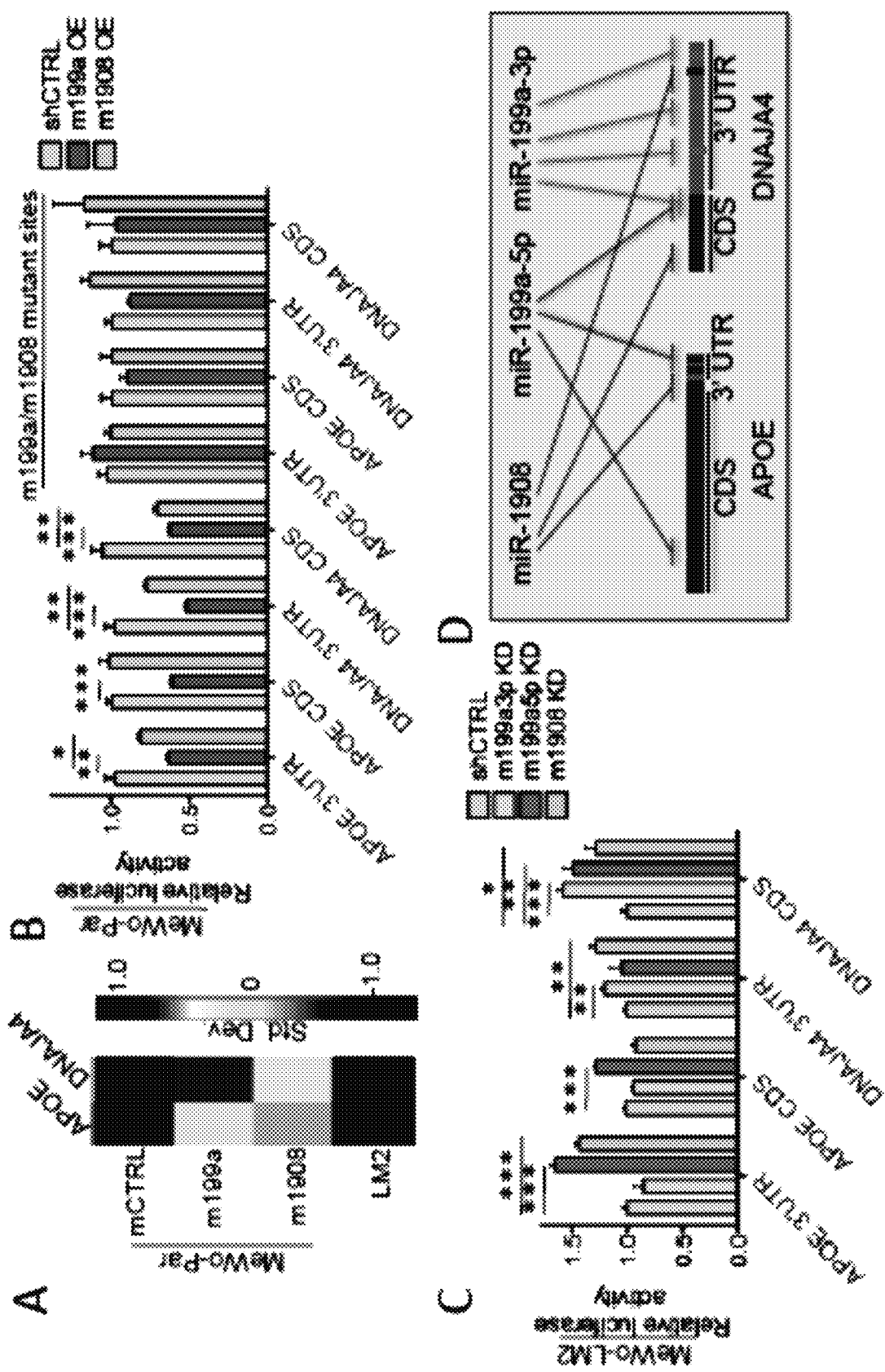
FIGS. 3A, 3B, 3C, 3D, 3E, 3F, 3G, 3H and 3I. Identification of ApoE and DNAJA4 as Common Target Genes of miR-199a and miR-1908 (3A) Heat map depicting mRNA levels of ApoE and DNAJA4, measured by qRT-PCR, in poorly metastatic MeWo cells over-expressing miR-199a, miR-1908, or a control hairpin and in highly metastatic MeWo-LM2 cells. Color map illustrates standard deviation changes from the mean of each heat map column. (3B) Heterologous luciferase reporter assays measuring the stability of wild-type ApoE and DNAJA4 3'UTR/CDS luciferase fusions or miRNA target-site mutant ApoE and DNAJA4 3'UTR/CDS fusions in parental MeWo cells over-expressing miR-199a, miR-1908, or a control hairpin. n=3-4. (3C) Stability of wild-type ApoE and DNAJA4 3'UTR/CDS luciferase fusions in MeWo-LM2 cells with silenced expression of miR-199a-3p, miR-199a-5p, miR-1908, or a control sequence. n=4. (3D) Schematic of experimentally derived model of ApoE and DNAJA4 3'UTR/CDS targeting by miR-199a-3p, miR-199a-5p, and miR-1908. (3E) Luciferase activity of wild-type and miRNA target-site mutant ApoE and DNAJA4 3'UTR/CDS luciferase fusions in highly metastatic MeWo-LM2 derivatives and their poorly metastatic parental cell line. n=4. (3F) Matrigel invasion capacity by 1×105 MeWo-LM2 cells expressing a control vector or over-expressing ApoE or DNAJA4. n=4. (3G) Endothelial recruitment ability by 5×104 MeWo-LM2 cells transduced with a control vector or an over-expression vector for ApoE or DNAJA4. n=6. (3H-3I) Poorly metastatic parental MeWo cells transduced with lentiviral short hairpins targeting ApoE, DNAJA4, or a control sequence were assessed for their matrigel invasion capacity (3H) and ability to recruit endothelial cells (3I). n=6-8. All data are represented as mean±SEM. Scale bar, 100 µm. See also FIG. 14.
Figures 3E, 3F, 3G, 3H, 3I:
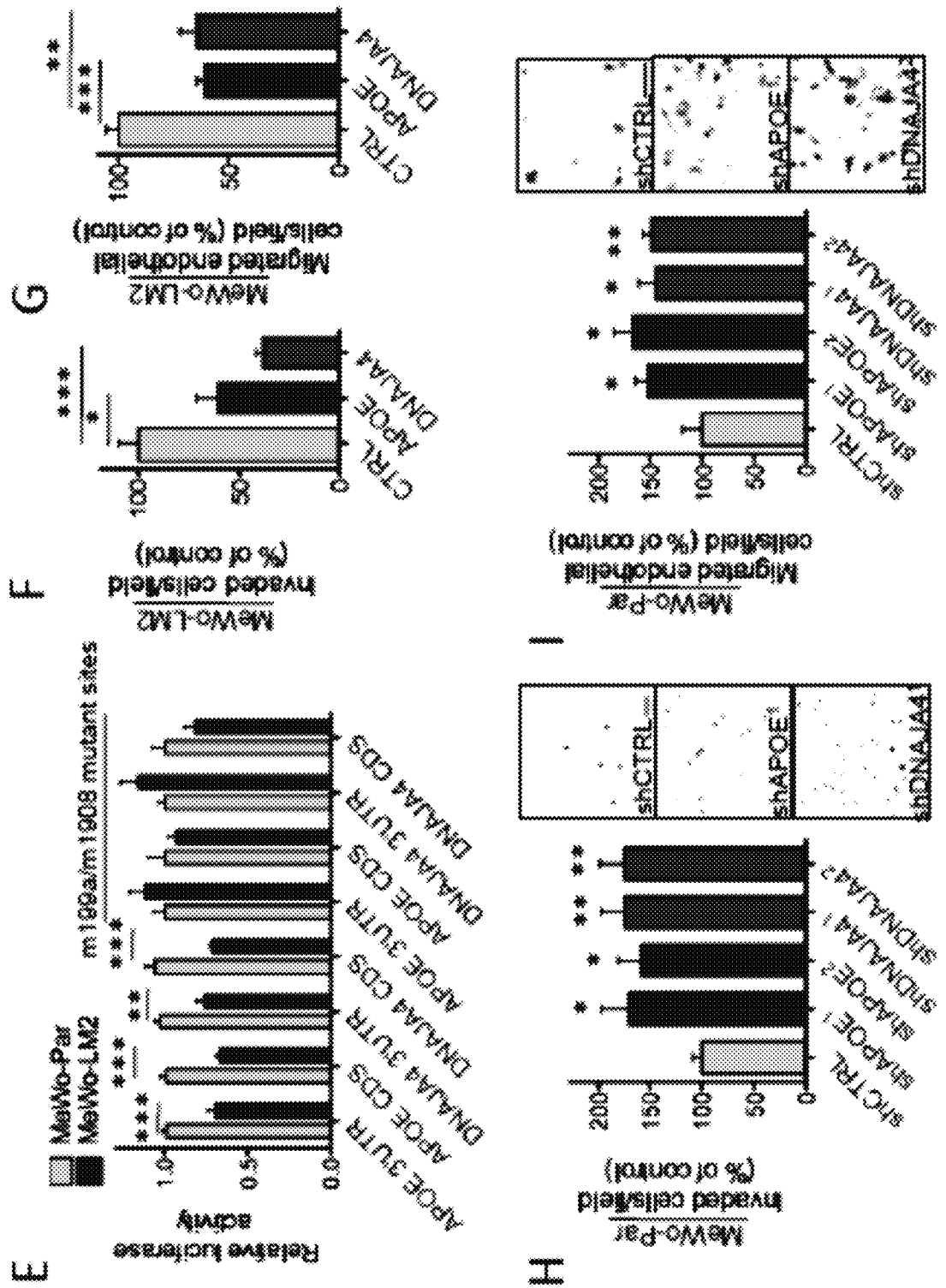

To determine whether ApoE and DNAJA4 are directly targeted by miR-1908, miR-199a-3p, and miR-199a-5p, the effects of each miRNA on the stability of its putative targets were examined through heterologous luciferase reporter assays. Interestingly, over-expression of miR-199a repressed the stability of the 3' untranslated region (UTR) and coding sequence (CDS) of both ApoE and DNAJA4, while over-expression of miR-1908 destabilized the 3'UTR of ApoE and the 3'UTR and CDS of DNAJA4. Consistent with direct targeting, mutating the miRNA complementary sequences on each target abrogated miRNA-mediated regulation (FIG. 3B). In a direct test of endogenous targeting, individual miRNA inhibition in metastatic LM2 cells resulted in increased target stability (FIG. 3C) that was abrogated upon mutating the miRNA target sites (FIG. 14E), revealing ApoE to be directly targeted by miR-1908 and miR-199a-5p and DNAJA4 to be directly targeted by all three miRNAs (FIG. 3D). Importantly, the CDS' s and 3'UTR's of both of these genes were less stable in the highly metastatic LM2 cells, which express physiologically higher levels of the three regulatory miRNAs, indicating that endogenous targeting of ApoE and DNAJA4 by these miRNAs is relevant to melanoma metastasis (FIG. 3E).

Figures 14E, 14F, 14G:
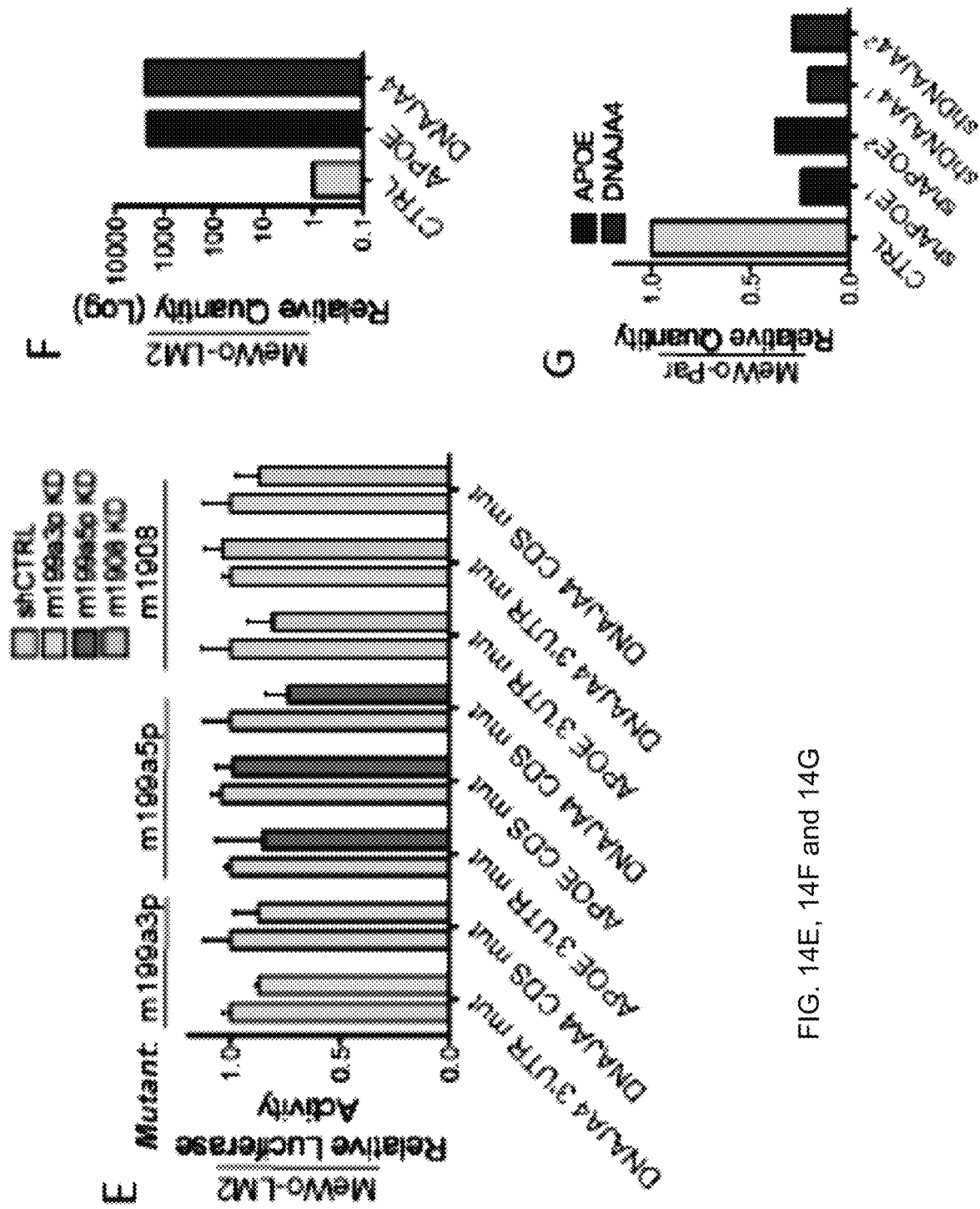

Given the molecular convergence of miR-199a-3p, miR-199a-5p, and miR-1908 onto common target genes, it was next examined whether these targets, ApoE and DNAJA4, could mediate the metastatic phenotypes conferred by these miRNAs. Over-expression of each gene in the metastatic LM2 cells led to pronounced reductions in cell invasion and endothelial recruitment phenotypes (FIGS. 3F-G, 14F). Conversely, knock-down of ApoE or DNAJA4 in the poorly metastatic cells using independent hairpins significantly enhanced cell invasion and endothelial recruitment (FIGS. 3H-I, 4G), revealing ApoE and DNAJA4 to act as endogenous suppressors of these pro-metastatic phenotypes— consistent with their targeting by the above mentioned metastasis-promoting miRNAs.

Example 5

Figures 4A, 4B, 4C, 4D, 4E, 4F:
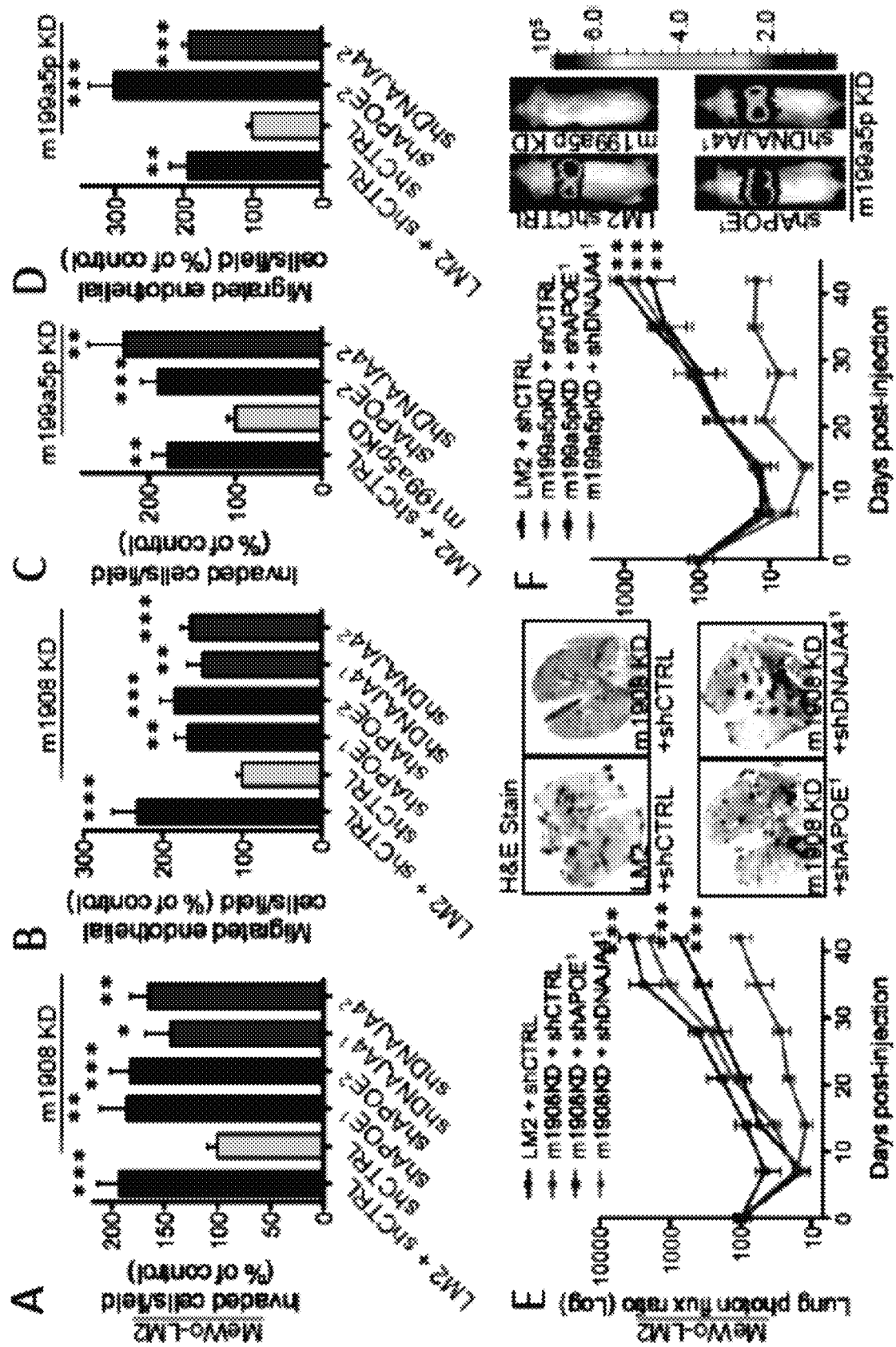
FIGS. 4A, 4B, 4C, 4D, 4E, 4F, 4G, 4H, 4I, 4J and 4K. Direct Targeting of ApoE and DNAJA4 by miR-199a and miR-1908 Promotes Metastatic Invasion, Endothelial Recruitment, and Colonization (4A-4D) Highly metastatic LM2 cells expressing a control shRNA or shRNAs targeting ApoE or DNAJA4 in the context of miR-1908 inhibition (m1908 KD; 4A, 4B) or miR-199a-5p inhibition (m199a5p KD; 4C, 4D) were subjected to the cell invasion (4A, 4C) and endothelial recruitment assays (4B, 4D). n=6-8. (4E-4F) Bioluminescence imaging plot and H&E-stained lungs representative of lung metastasis after intravenous injection of 1×105 LM2 cells expressing a control hairpin or hairpins targeting ApoE, DNAJA4, or a control sequence in the setting of miR-1908 silencing (4E) or miR-199a-5p silencing (4F). n=5. (4G-4H) Parental MeWo cells over-expressing ApoE or DNAJA4 or expressing a control vector in the context of miR-1908 over-expression were analyzed for the matrigel invasion (4G) and endothelial recruitment (4H) phenotypes. (4I-4J) A375-LM3 derivatives expressing a control shRNA or shRNAs targeting ApoE and DNAJA4 were transduced with a cocktail of LNAs targeting miR-199a-3p, miR-199a-5p, and miR-1908 or a control LNA and analyzed in the matrigel invasion (4I) and endothelial recruitment (4J) assays. n=4. (4K) Blood vessel density distribution, represented in a cumulative fraction plot, for metastatic nodules formed by MeWo-LM2 cells inhibited for miR-1908 and transduced with shRNAs targeting ApoE, DNAJA4, or a control sequence. Lung sections from FIG. 4E were immunocytochemically double-stained for human vimentin (blue) and the endothelial marker MECA-32 (red). The percentage MECA-32 positive area within each vimentin-positive nodule was quantified. n=39 nodules (shCTRL); n=97 (shAPOE1); n=38 (shAPOE2); n=200 (shDNAJA41); n=19 (shDNAJA42). All data are represented as mean±SEM. Scale bar, 100 µm. See also FIG. 15.
Figures 4G, 4H, 4I, 4J, 4K:
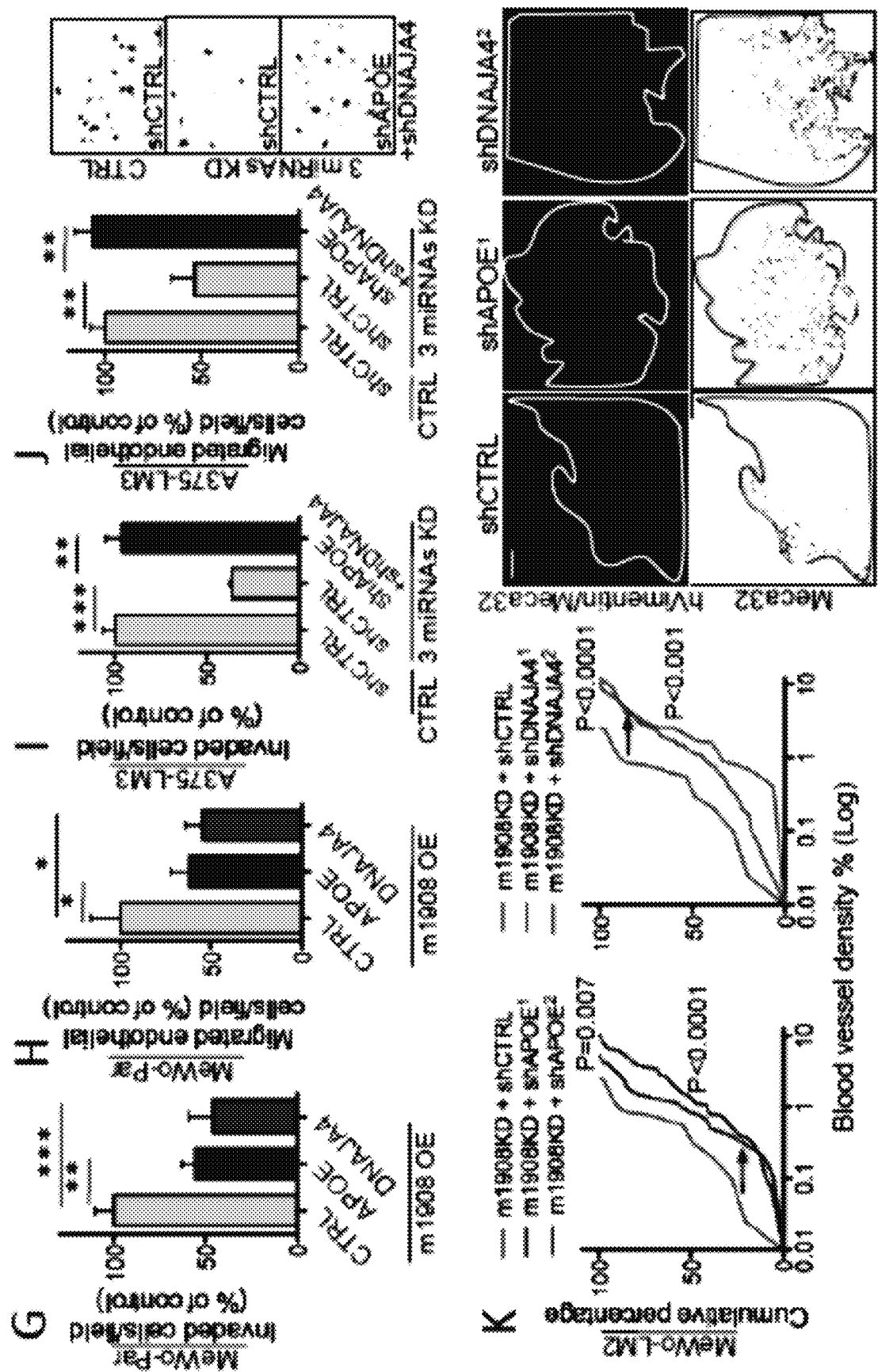
Figures 15A, 15B, 15C, 15D, 15E, 15F, 15G:
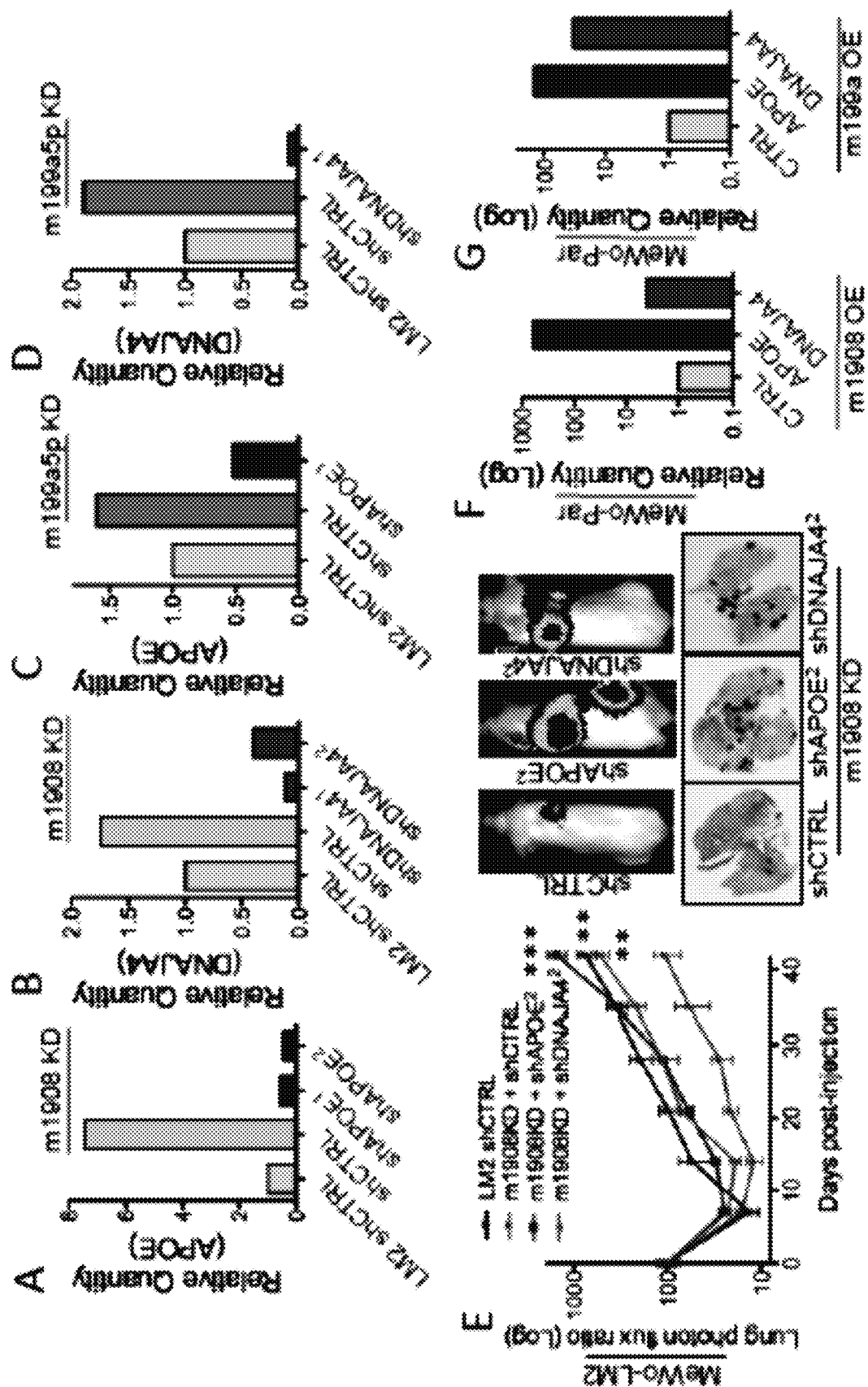
Figures 15H, 15I, 15J, 15K:
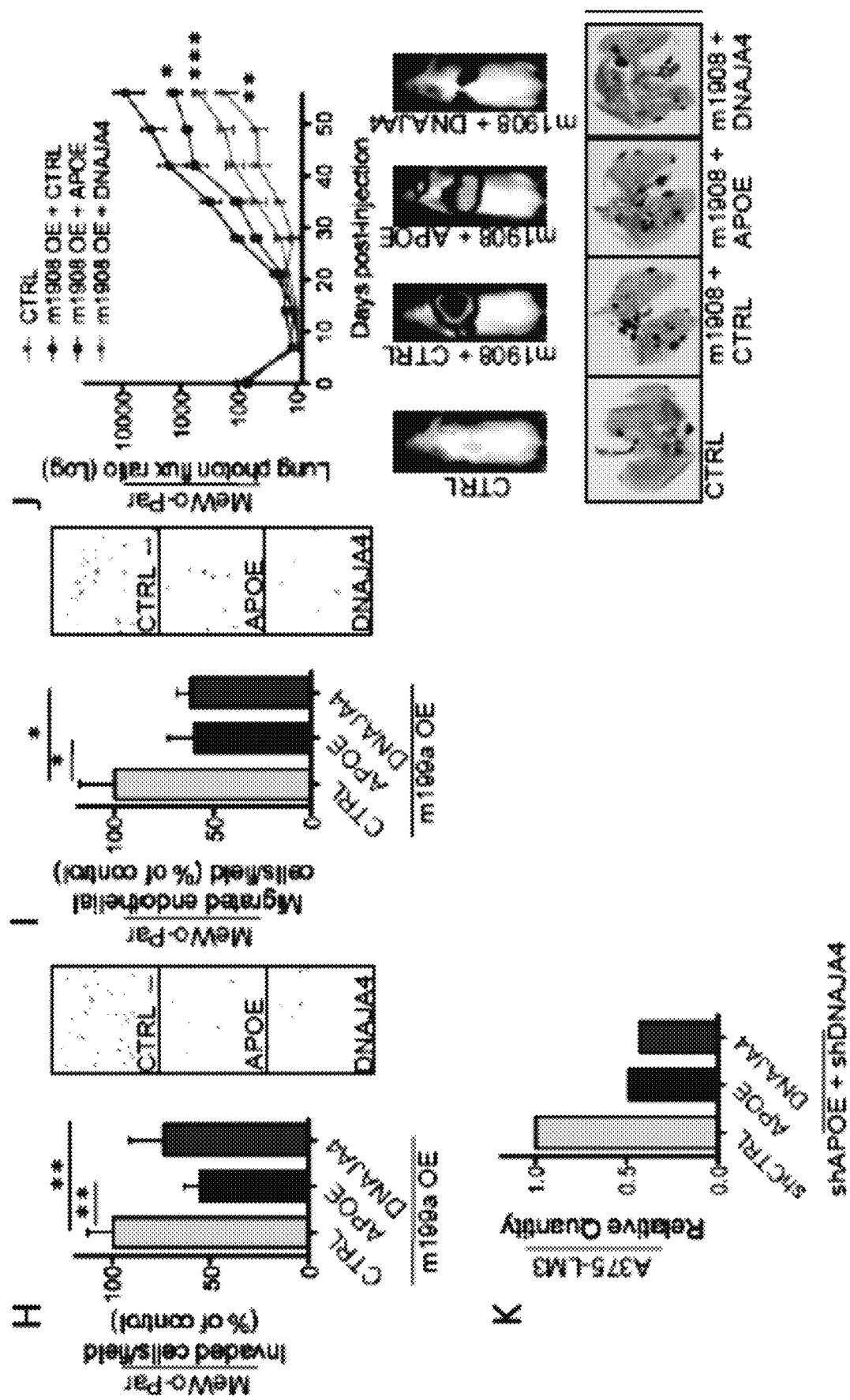

ApoE and DNAJA4 Mediate miR-199a- and miR-1908-Dependent Metastatic Invasion, Endothelial Recruitment, and Colonization To determine whether ApoE and DNAJA4 are the direct biological effectors downstream of miR-199a and miR-1908, assays were carried out to examine whether these two target genes epistatically interact with each miRNA. As expected, miRNA silencing reduced the invasion and endothelial recruitment capacity of highly metastatic melanoma cells. Importantly, knock-down of ApoE or DNAJA4 in the setting of miRNA inhibition significantly occluded the suppression of invasion (FIGS. 4A and 4C) and endothelial recruitment (FIGS. 4B and 4D) upon silencing of each miRNA. Strikingly, knock-down of either of these genes in cells depleted for miR-1908 or miR-199a-5p fully rescued the dramatic suppression of metastatic colonization resulting from miRNA inhibition (FIG. 4E-F, 15E). Conversely, over-expression of ApoE or DNAJA4 in cells over-expressing miR-1908 (FIG. 4G-H, 15F) or miR-199a (FIG. 15G-I) was sufficient to suppress cell invasion and endothelial recruitment. Additionally, ApoE or DNAJA4 over-expression was sufficient to inhibit miRNA-mediated metastatic colonization (FIG. 15J). Importantly, ApoE and DNAJA4 were also required for miRNA-dependent enhanced cell invasion and endothelial recruitment by the highly metastatic A375-LM3 cells (FIGS. 4 I-J, 15K).

To determine whether ApoE and DNAJA4 also regulate miRNA-dependent metastatic endothelial recruitment in vivo, co-immunostaining of melanoma metastases (human vimentin) and endothelial cells (MECA-32) was performed in lung metastatic nodules formed by cells knocked-down for each of these genes in the context of miRNA inhibition. Notably, knock-down of ApoE or DNAJA4 resulted in a significant (>3.5-fold) increase in metastatic blood vessel density in metastases arising from cells with miRNA silencing (FIG. 4K, P<0.01 for both ApoE and DNAJA4 knock-down cells). These findings reveal ApoE and DNAJA4 as direct downstream effectors of miRNA-dependent metastatic invasion, colonization, and endothelial recruitment phenotypes induced by these pro-metastatic miRNAs in melanoma.

Example 6

Figures 5A, 5B, 5C, 5D, 5E, 5F, 5G:
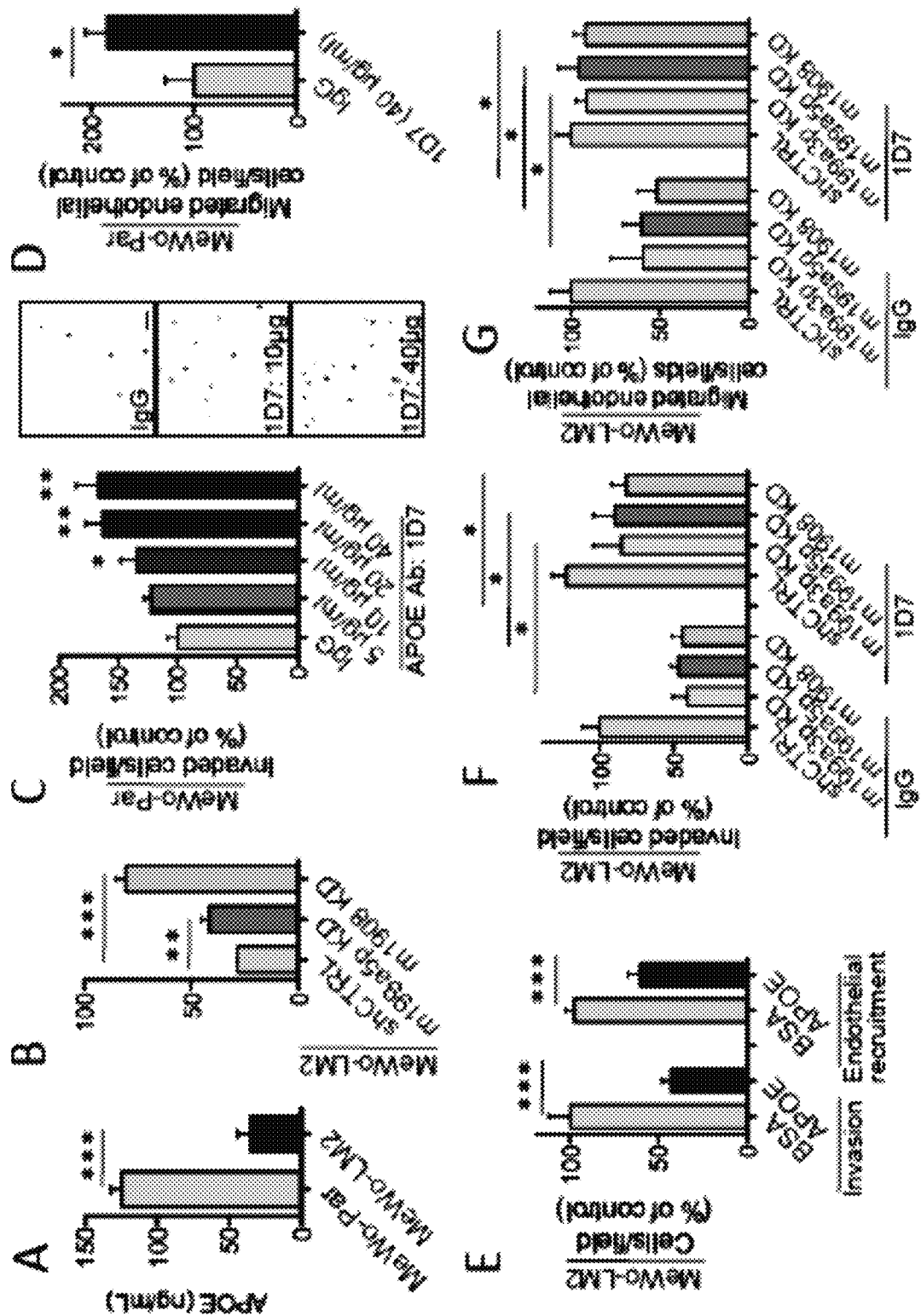
FIGS. 5A, 5B, 5C, 5D, 5E, 5F, 5G, 5H, 5I, 5J, 5K, 5L and 5M. Melanoma-Cell Secreted ApoE Inhibits Melanoma Invasion and Endothelial Recruitment, while Genetic Deletion of ApoE Accelerates Metastasis (5A-5B) Extracellular ApoE levels quantified by ELISA in conditioned media from MeWo-LM2 metastatic derivatives and their parental cells (5A) and LM2 cells silenced for miR-199a-5p, miR-1908, or a control sequence (5B). n=3. (5C) ApoE-neutralizing antibody 1D7 (10-40 µg/mL) or IgG (40 µg/mL) was added to the cell media, and matrigel invasion by parental MeWo cells was assessed. n=4-6. (5D) Endothelial recruitment by parental MeWo cells in the presence of 1D7 (40 µg/mL) or a control IgG antibody (40 µg/mL). n=4. (5E) The matrigel invasion and endothelial recruitment phenotypes were assessed in LM2 cells in the presence of bovine serum albumin (BSA) (100 µM) or recombinant ApoE3 (100 µM) added to the cell media. n=7-10. (5F-5G) LM2 cells with silenced expression of miR-199a-3p, miR-199a-5p, miR-1908, or a control sequence were examined for matrigel invasion capacity (5F) and endothelial recruitment ability (5G) in the presence of IgG or ApoE-neutralizing 1D7 antibodies (40 µg/mL). n=5-6. (5H) ApoE levels quantified by ELISA in conditioned media from parental MeWo cells transduced with shRNAs targeting DNAJA4 or a control sequence. n=3. (5I-5J) Parental MeWo cells with shRNA-induced silencing of DNAJA4 were analyzed for the matrigel invasion (5I) and endothelial recruitment (5J) phenotypes in the presence of either BSA (100 µM) or recombinant ApoE3 (100 µM). n=4. (5K) Array-based ApoE expression levels in nevi (n=9), primary melanomas (n=6), and distant melanoma metastases samples (n=19). (5L) Highly metastatic MeWo-LM2 cells were incubated in the presence of recombinant ApoE3 or BSA at 100 µg/mL. After 24 hours, 4×104 cells were intravenously injected into NOD-SCID mice, and lung colonization was monitored by bioluminescence imaging. n=6. (5M) Lung metastasis by 5×104 B16F10 mouse melanoma cells intravenously injected into ApoE genetically null C57BL/6 mice or their wild-type control littermates. Lung bioluminescence quantification and representative H&E-stained lungs correspond to 19 days post-injection. n=8-18. All data are represented as mean±SEM. Scale bar, 100 µm.
Figures 16A, 16B, 16C, 16D, 16E, 16F:
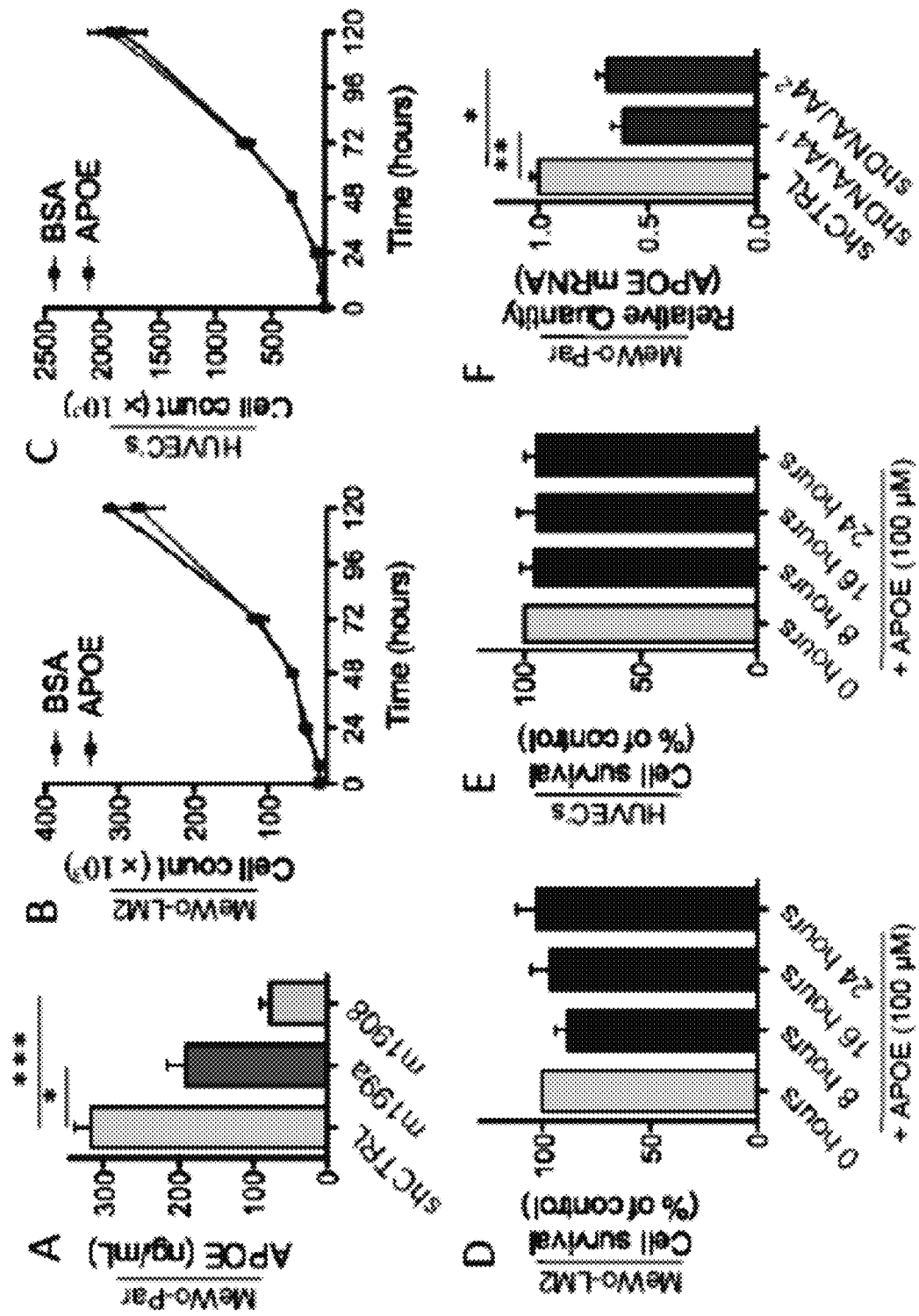

Melanoma Cell-Secreted Apoe Is Both a Necessary and Sufficient Mediator of Invasion and Endothelial Recruitment, While Genetic Deletion of Apoe Promotes Metastasis ApoE is a secreted factor. As such, it was examined whether melanoma-cell secreted ApoE could suppress invasion and endothelial recruitment. Accordingly, extracellular ApoE levels, detected by ELISA, were 3.5-fold lower in metastatic LM2 cells—which express higher levels of miR-199a and miR-1908—than their less metastatic parental cells (FIG. 5A). Secreted ApoE levels were also significantly suppressed by endogenous miR-199a and miR-1908 (FIGS. 5B and 16A).

Next, inhibiting ApoE through use of a neutralizing antibody (1D7) that recognizes the receptor-binding domain of ApoE enhanced both cell invasion (FIG. 5C; 1.68-fold increase) and endothelial recruitment (FIG. 5D; 1.84-fold increase) by parental MeWo cells, which express high endogenous levels of ApoE (FIG. 14C). Conversely, addition of recombinant human ApoE significantly suppressed invasion and endothelial recruitment by metastatic LM2 cells (FIG. 5E), which exhibit low endogenous ApoE levels (FIG. 14C). Importantly, recombinant ApoE addition did not affect melanoma cell or endothelial cell in vitro proliferation (FIG. 16B-C) or survival in serum starvation conditions (FIG. 16D-E), indicating that suppression of these phenotypes by recombinant ApoE is not secondary to a decrease in proliferation or impaired survival. Consistent with ApoE being epistatically downstream of miR-199a and miR-1908, neutralization of ApoE with the ApoE neutralizing antibody 1D7 significantly abrogated the suppressed invasion and endothelial recruitment phenotypes seen with inhibition of each miRNA (FIGS. 5F-G). The above findings reveal melanoma cell-secreted ApoE as a necessary and sufficient suppressor of miRNA-dependent invasion and endothelial recruitment phenotypes in melanoma.

Figures 5H, 5I, 5J, 5K, 5L, 5M:
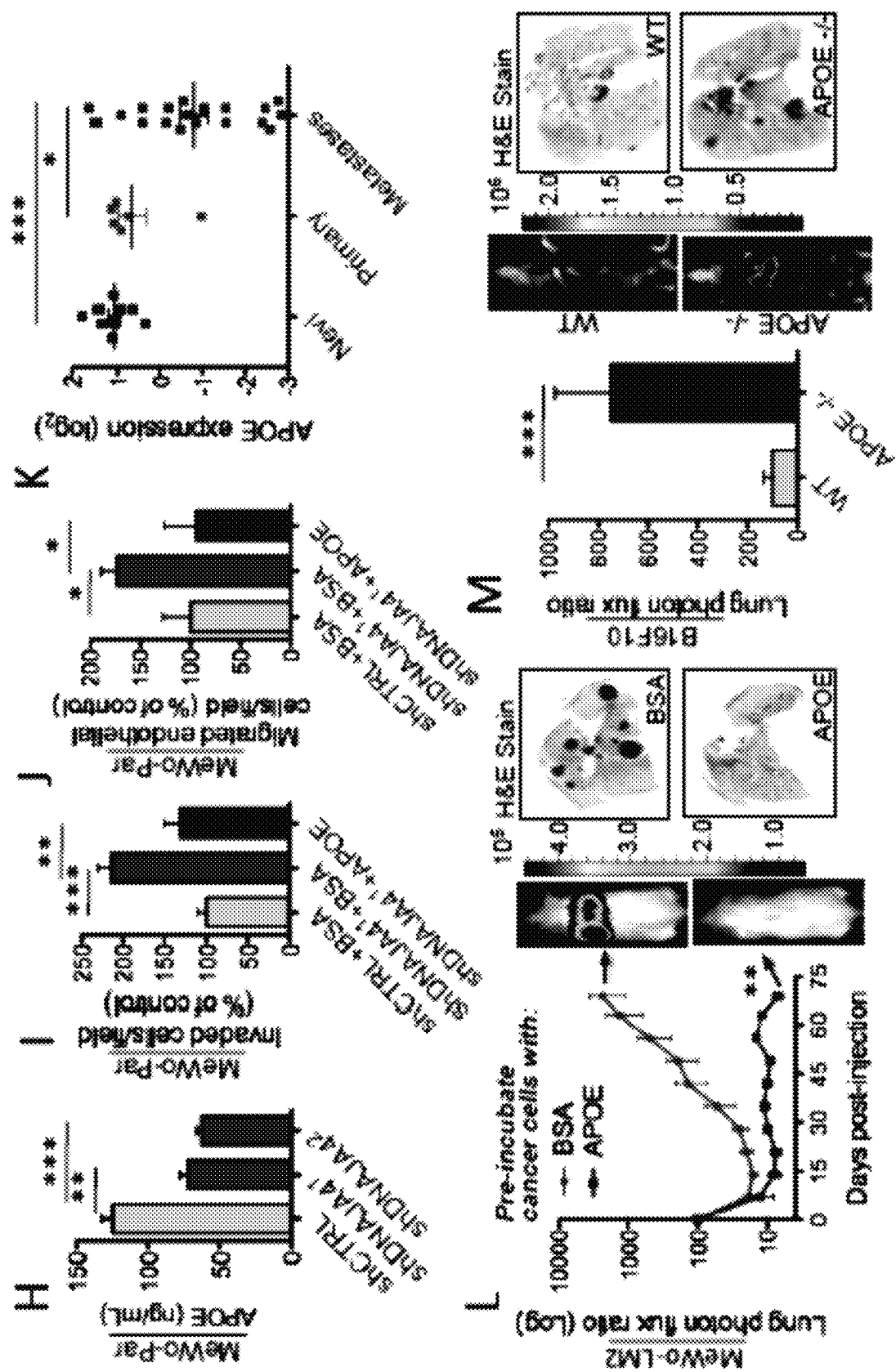
Figures 16G, 16H, 16I:
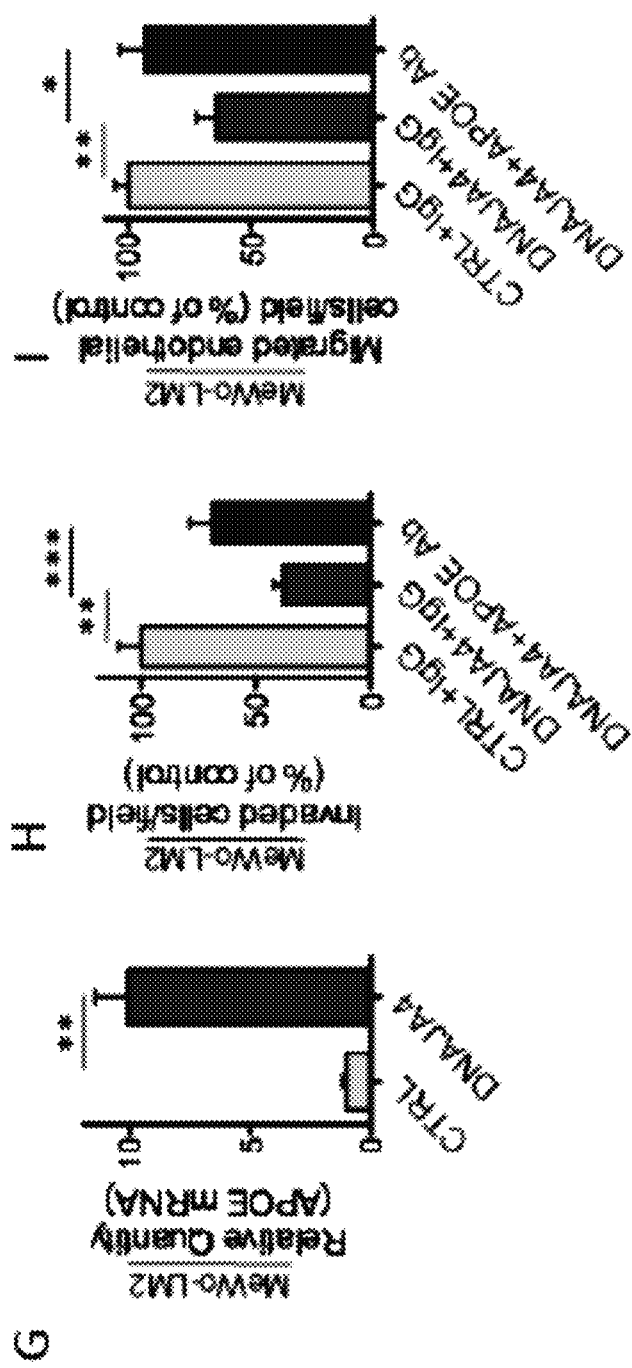

Further assays were carried out to investigate the mechanism by which DNAJA4, a poorly characterized heat-shock protein, mediates endothelial recruitment and invasion. Given the phenotypic commonalities displayed by ApoE and DNAJA4, it was hypothesized that DNAJA4 may play a regulatory role and enhance ApoE levels. Indeed, knock-down of DNAJA4 reduced both ApoE transcript levels (FIG. 16F) as well as secreted ApoE levels (FIG. 5H), while DNAJA4 over-expression substantially elevated ApoE expression (FIG. 16G). Consistent with DNAJA4 acting upstream of ApoE, addition of recombinant ApoE abrogated the enhanced cell invasion and endothelial recruitment phenotypes seen with DNAJA4 knock-down (FIG. 5I-J). Conversely, the suppression of invasion and endothelial recruitment seen with DNAJA4 over-expression phenotypes were significantly occluded by antibody neutralization of ApoE (FIGS. 16H-I). These findings reveal DNAJA4 to suppress melanoma invasion and endothelial recruitment through positive regulation of ApoE expression and resulting secretion.

In view of the regulatory convergence of three metastasis-promoting miRNAs and the DNAJA4 gene on ApoE, assays were carried out to determine whether ApoE expression correlates with human melanoma progression. To this end, published array-based expression data for ApoE (Haqq et al., 2005 Proc. Natl. Acad. Sci. USA 102, 6092-6097) was analyzed in nevi, primary, and metastatic lesions. Consistent with a metastasis-suppressive role, ApoE levels were significantly lower in distal organ metastases relative to primary ($P<0.025$) and nevi lesions ($P<0.0003$) (FIG. 5K).

Given its significant correlation with human melanoma progression, it was next examined whether increasing ApoE signaling in melanoma cells could have therapeutic efficacy in suppressing melanoma metastasis. More specifically, metastatic MeWo-LM2 cells were pre-incubated with recombinant ApoE or BSA for 24 hours prior to injection into mice. Strikingly, pre-treatment of cancer cells with ApoE robustly suppressed metastatic colonization by over 300-fold (FIG. 5L). This dramatic suppression of metastasis by ApoE pre-incubation of melanoma cells reflects that the effects of ApoE on melanoma cells are pivotal for metastatic initiation, as cells pre-treated with ApoE exhibit reduced invasive ability, which is needed to initiate metastatic events leading to lung colonization.

Given the robust influence exerted by ApoE on metastasis and metastatic phenotypes, as well as its strong association with human melanoma progression, further assays were carried out to investigate the impact of genetic deletion of systemic ApoE on melanoma progression in an immunocompetent mouse model of melanoma metastasis. Consistent with a major suppressive role for extracellular ApoE in metastasis, B16F10 mouse melanoma cells injected into the circulation exhibited a greater than 7-fold increase in metastatic colonization in ApoE genetically null mice compared to their wild-type littermates (FIG. 5M). These findings establish systemic and cancer-secreted ApoE as a robust suppressor of human and mouse melanoma metastasis.

Example 7

Extracellular ApoE Divergently Targets Melanoma Cell LRP1 and Endothelial Cell LRP8 Receptors In this example, assays were carried out to investigate the molecular mechanisms by which ApoE suppresses metastasis.

Figures 6A, 6B, 6C, 6D, 6E, 6F:
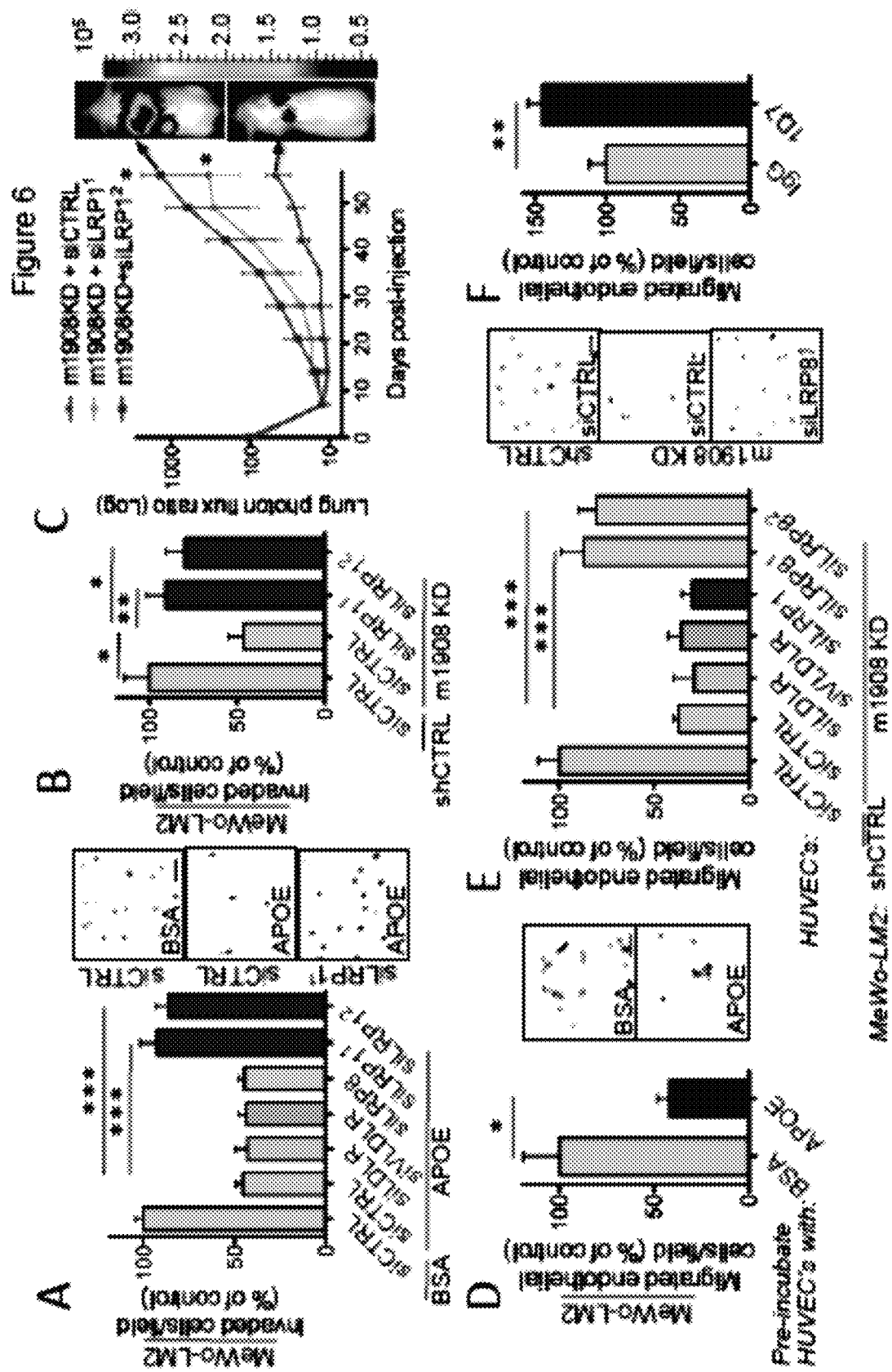
FIGS. 6A, 6B, 6C, 6D, 6E, 6F, 6G, 6H, 6I and 6J. Identification of Distinct Melanoma and Endothelial Cell Receptors that Mediate the Effects of ApoE on Melanoma Invasion and Endothelial Recruitment (6A) Matrigel invasion capacity was examined in 1×105 LM2 cells transduced with siRNAs targeting LDLR, VLDLR, LRP8, LRP1, or a control sequence in the presence of either BSA (100 µM) or recombinant ApoE3 (100 µM). n=4-7. (6B) 1×105 MeWo-LM2 cells transduced with short hairpins targeting miR-1908 or a control sequence were transfected with siRNAs targeting LRP1 or a control siRNA and subjected to the matrigel invasion assay. n=4. (6C) Bioluminescence imaging of lung colonization by 1×105 LM2 cells transduced with siRNAs targeting LRP1 or a control sequence in the setting of miR-1908 inhibition. n=5. (6D) 1×105 endothelial cells pre-incubated with BSA (100 µM) or recombinant ApoE3 (100 µM) for 24 hours were analyzed for the endothelial recruitment phenotype by 5×105 LM2 cells. n=3-4. (6E) 1×105 endothelial cells were transduced with siRNAs targeting LDLR, VLDLR, LRP1, LRP8, or a control sequence and allowed to migrate in a trans-well system towards LM2 cells inhibited for miR-1908 or a control sequence. n=4-12. (6F) Trans-well migration by 1×105 endothelial cells in the presence of IgG (40 µg/mL) or 1D7 antibodies (40 µg/mL) added to the cell media. n=6-8. (6G)

In order to identify the ApoE receptor(s) that mediate(s) invasion, down all four known ApoE receptors, VLDLR, LRP1, LRP8, and LDLR (Hatters et al., 2006 Trends Biochem. Sci. 31, 445-454; Hauser et al., 2011 Prog. Lipid Res. 50, 62-74) were knocked in melanoma cells. Interestingly, knock-down of LRP1, but not the other ApoE receptors, abolished the cell invasion suppression effect induced by recombinant ApoE (FIG. 6A). Importantly, knock-down of LRP1 in metastatic LM2 cells, which display low levels of ApoE, only modestly increased cell invasion (FIG. 17A), suggesting the effects of LRP1 to be mediated by endogenous ApoE.

Figures 17A, 17B, 17C, 17D, 17E:
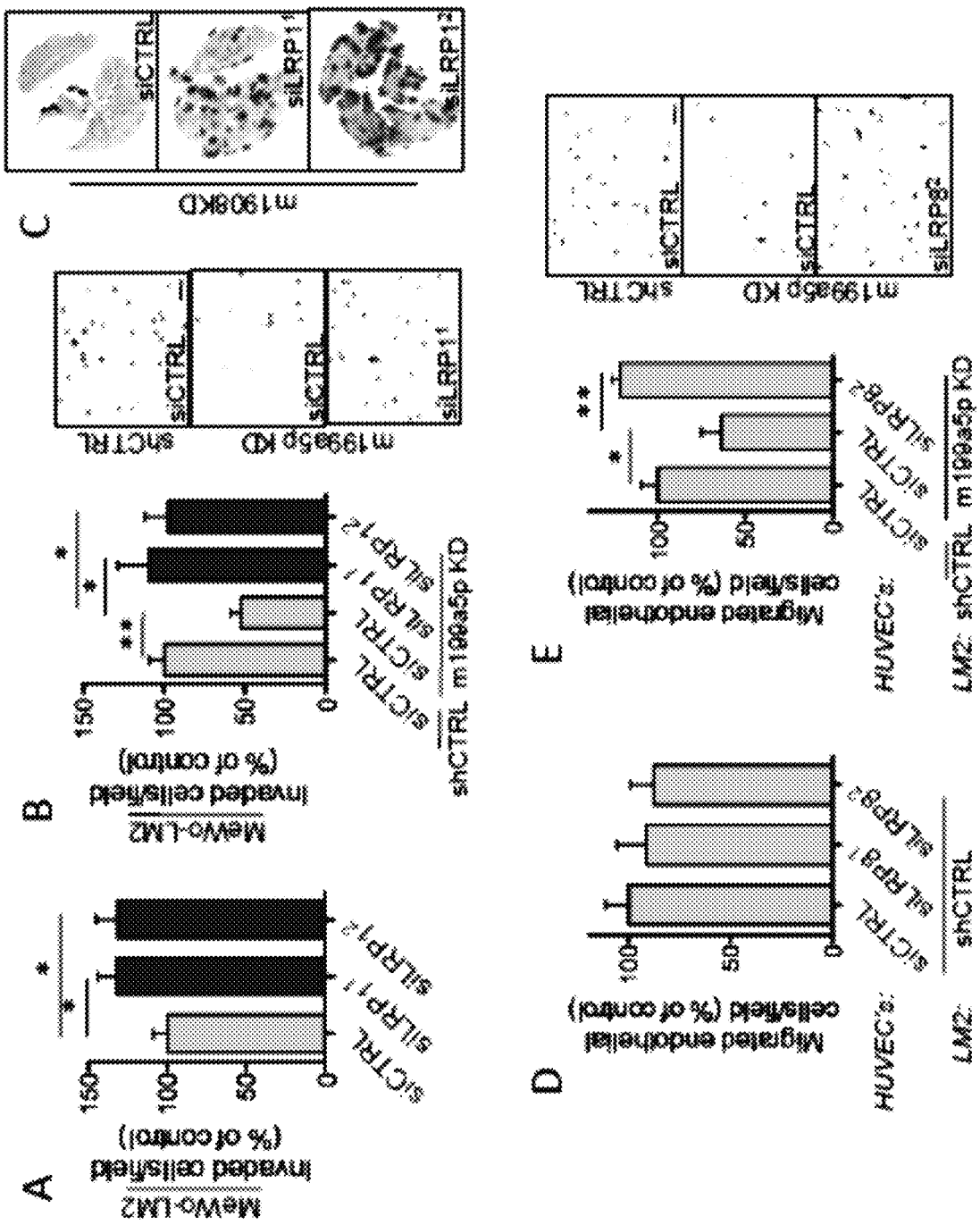

To determine if LRP1 also mediates the miRNA-dependent effects on invasion and metastatic colonization, LRP1 was knocked down in the context of miRNA inhibition. LRP1 knock-down in the setting of miRNA silencing rescued the suppressed invasion phenotype arising from miRNA inhibition (FIGS. 6B, 17B). Consistent with these in vitro results, LRP1 knock-down significantly enhanced in vivo metastatic colonization by LM2 cells silenced for miR-1908 (FIG. 6C, 17C). These findings reveal LRP1 to be epistatically downstream of miRNA/ApoE-dependent melanoma invasion and metastatic colonization.

While the invasion phenotype reflects the cell-autonomous effects of ApoE on melanoma cells, the endothelial recruitment phenotype suggests a non-cell-autonomous role of cancer-expressed ApoE directly on endothelial cells. Consistent with this, pre-treatment of endothelial cells with ApoE significantly reduced their ability to migrate towards highly metastatic cancer cells (FIG. 6D). In order to identify the ApoE receptor(s) on endothelial cells that mediate(s) the endothelial recruitment phenotype, all four known ApoE receptors were knocked down on endothelial cells. Interestingly, unlike for cancer cell invasion, knock-down of endothelial LRP8, but not any of the other receptors, selectively and significantly abrogated the inhibition of endothelial recruitment caused by miRNA silencing (FIGS. 6E, 17D-E). These findings are consistent with the LRP8 receptor being the downstream endothelial mediator of miRNA/ApoE-dependent effects on endothelial recruitment.

Figures 6G, 6H, 6I, 6J:
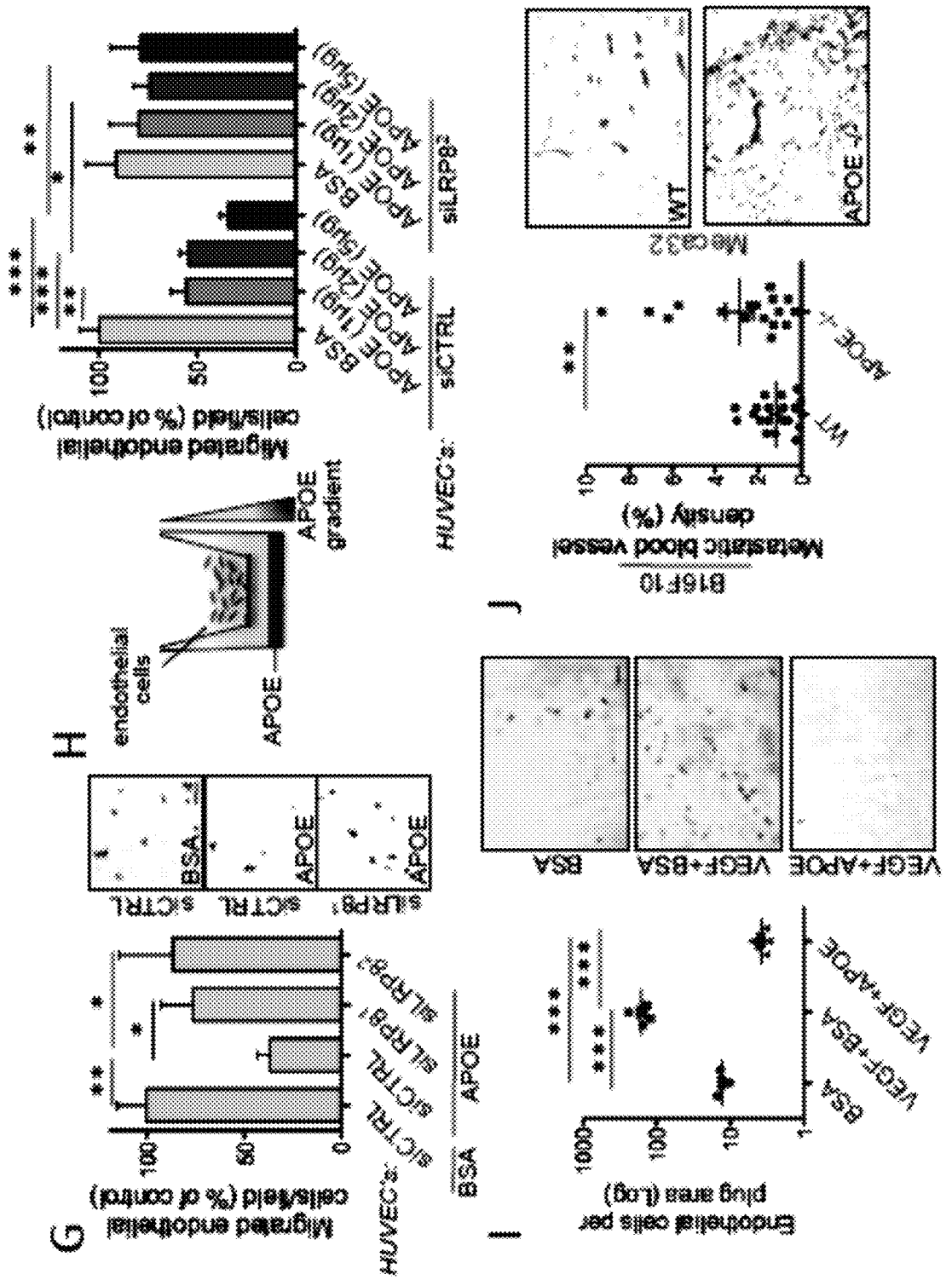

Next, assays were carried out to examine whether ApoE/LRP8 signaling might also regulate general endothelial migration in a cancer cell-free system. Accordingly, antibody neutralization of ApoE, which is present in endothelial cell media, significantly enhanced endothelial migration (FIG. 6F), while recombinant ApoE was sufficient to inhibit endothelial migration in a trans-well assay (FIG. 6G) and a gradient-based chemotactic assay (FIG. 6H) in an endothelial cell LRP8 receptor-dependent manner. Importantly, addition of ApoE lead to a dramatic (greater than 40-fold) suppression of VEGF-induced endothelial recruitment in vivo into subcutaneous matrigel plugs (FIG. 6I).

Given the requirement and sufficiency of ApoE in mediating endothelial recruitment, further assays were carried out to examine whether systemic ApoE might regulate metastatic angiogenesis. Consistent with the robust suppression of metastatic endothelial content by melanoma cell-secreted ApoE (FIG. 4K), genetically null ApoE mice displayed higher blood vessel densities within their lung metastatic nodules formed by B16F10 mouse melanoma cells compared to their wild-type littermates (FIG. 6J; 2.41-fold increase, $P=0.0055$). Taken together, the above findings reveal dual cell-autonomous/non-cell-autonomous roles for ApoE in metastasis suppression through divergent signaling mediated by melanoma cell LRP1 and endothelial cell LRP8 receptors.

Example 8

MiR-199a-3p, miR-199a-5p, and miR-1908 as Robust Prognostic and Therapeutic Targets in Melanoma Metastasis To examine whether the metastasis promoter miRNAs described herein could serve as clinical predictors of metastatic outcomes, the expression levels of miR-199a-3p, miR-199a-5p, and miR-1908 were quantified in a blinded fashion by qRT-PCR in a cohort of human melanoma samples obtained from patients at MSKCC. The relationships between the levels of these miRNAs in primary melanoma lesions and metastatic relapse outcomes were then determined.

Figures 7A, 7B, 7C, 7D, 7E:
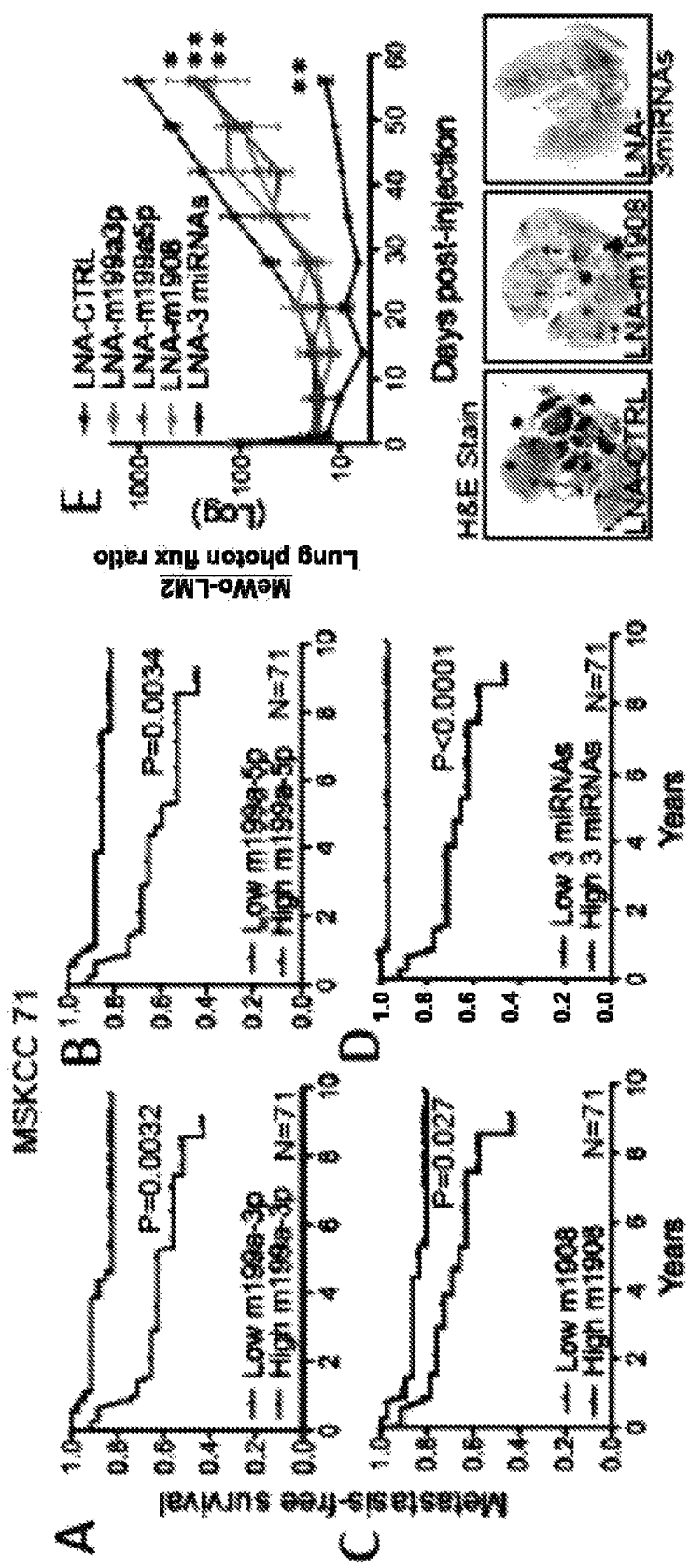

Importantly, patients whose primary melanoma lesions expressed higher (greater than the median for the population) levels of miR-199a-3p, miR-199a-5p, or miR-1908 were more likely to develop distal metastases and exhibited significantly shorter metastasis-free survival times than patients whose primary melanomas expressed lower levels of each of these miRNAs (FIGS. 7A-C, P=0.0032 for miR-199a-3p, P=0.0034 for miR-199a-5p, and P=0.027 for miR-1908). Strikingly, the aggregate expression levels of the three miRNAs displayed the strongest prognostic capacity in stratifying patients at high risk from those with very low risk for metastatic relapse (FIG. 7D, P<0.0001). These clinical findings are consistent with functional cooperativity between these miRNAs in the regulation of cancer progression and suggest utility for these molecules as clinical prognostic biomarkers of melanoma metastasis.

In light of the current lack of effective treatment options for the prevention of melanoma metastasis and the strong prognostic value of the three regulatory miRNAs in melanoma metastasis, these miRNAs therapeutically targeted using antisense LNA therapy (Elmer et al., 2008(a); Elmer et al., 2008(b)). Highly metastatic MeWo-LM2 cells pre-treated with LNA oligonucleotides antisense to mature miR-199a-3p, miR-199a-5p, or miR-1908 exhibited roughly a four-fold decrease in metastatic activity. Given clinical evidence for cooperativity among these miRNAs, the impact of silencing all three miRNAs on metastatic progression was examined. Remarkably, co-transfection of LNAs against all three miRNAs suppressed metastatic colonization by over seventy-fold, revealing dramatic synergy and cooperativity between endogenous miR-199a-3p, miR-199a-5p, and miR-1908 (FIG. 7E, P=0.004). Importantly, inhibition of these miRNAs with triple LNA pre-treatment did not result in decreased in vitro proliferation (FIG. 18A), indicating that the dramatic metastasis suppression phenotype is not secondary to impaired proliferation. Combinatorial LNA-mediated miRNA targeting in the independent A375 metastatic derivative line also significantly inhibited lung colonization (FIG. 18B).

Figures 7F, 7G, 7H, 7I, 7J:
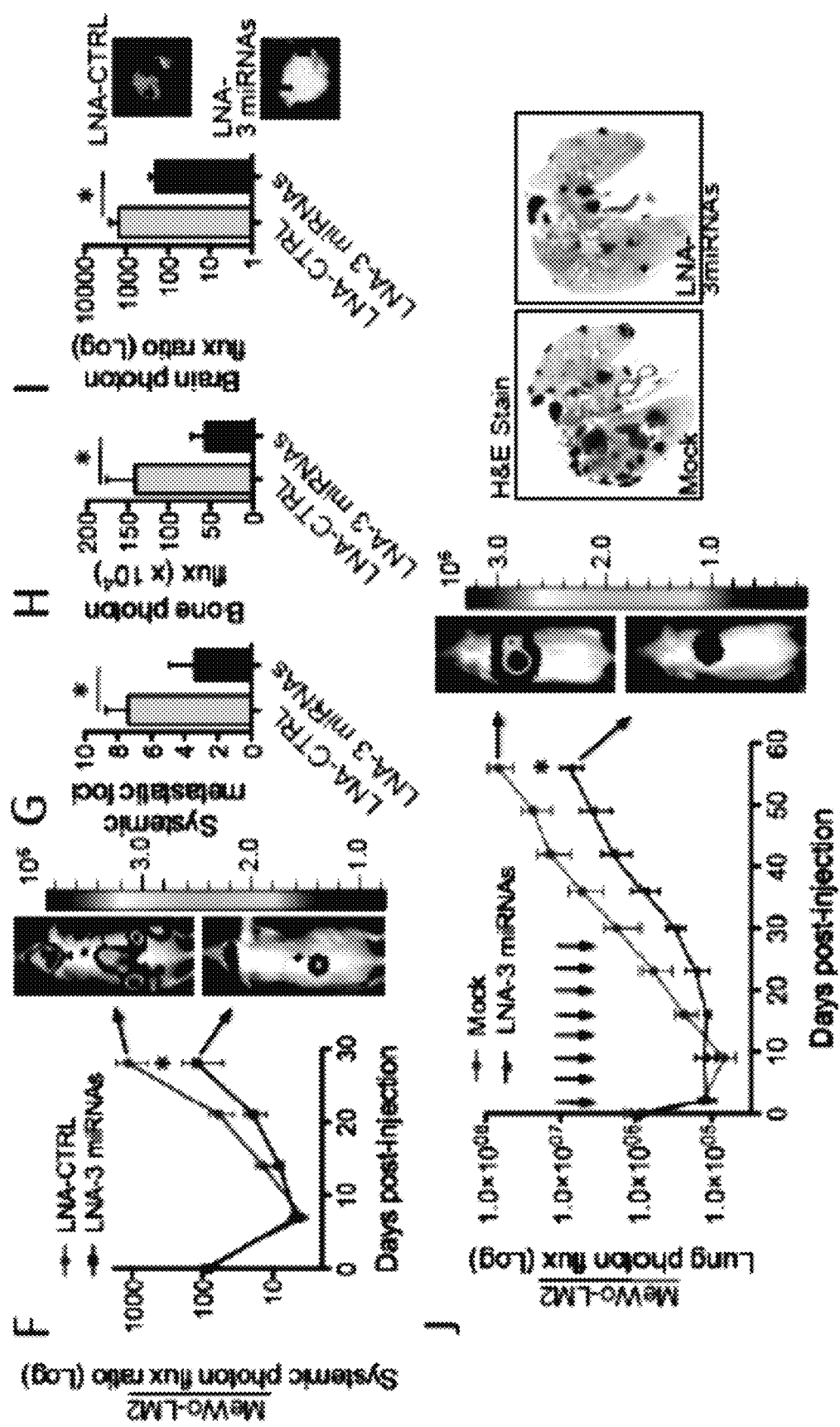

Next, it was examined whether combinatorial LNA-induced miRNA inhibition could suppress systemic melanoma metastasis to multiple distant organs. Indeed, intracardiac injection of highly metastatic melanoma cells pre-treated with a cocktail of LNAs targeting the three regulatory miRNAs revealed endogenous miR-199a-3p, miR-199a-5p, and miR-1908 to promote systemic melanoma metastasis (FIG. 7F). Combinatorial LNA-mediated inhibition of the three miRNAs lead to a reduction in the number of systemic metastatic foci (FIG. 7G) in distal sites such as the brain and bone (FIGS. 7H-I).

Figure 7K:
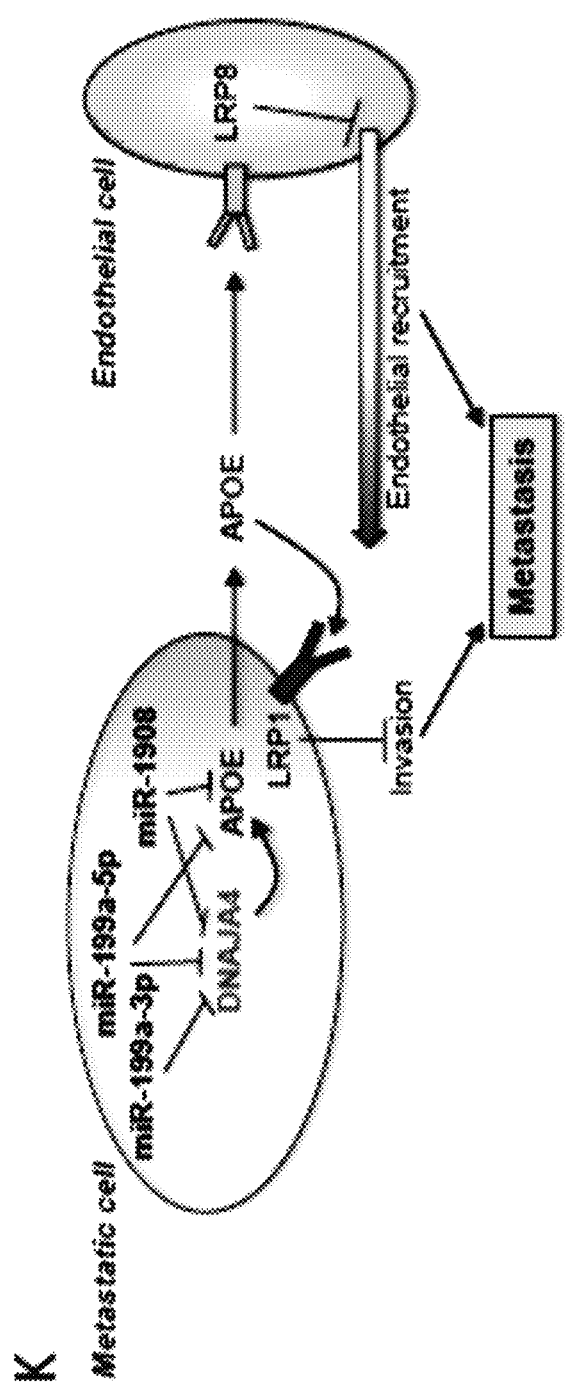

Further assays were carried out to examine the therapeutic efficacy of systemically administered in vivo-optimized LNAs in melanoma metastasis prevention. To this end, highly metastatic MeWo-LM2 cells were injected into mice. The following day, mice were intravenously treated with LNAs targeting miR-199a-3p, miR-199a-5p, and miR-1908 at a low total dose (12.5 mg/kg) on a bi-weekly basis for four weeks. Notably, combinatorial LNA treatment reduced lung colonization by 9-fold (FIG. 7J, P=0.031) without any apparent signs of toxicity (FIG. 18C). Taken together, the above findings reveal a novel miRNA-dependent regulatory network that converges on ApoE signaling to control cell-autonomous and non-cell-autonomous features of melanoma metastatic progression (FIG. 7K). The above basic studies have identified a set of miRNAs with powerful prognostic and therapeutic potential in the clinical management of melanoma.

Figures 8A, 8B, 8C, 8D, 8E:
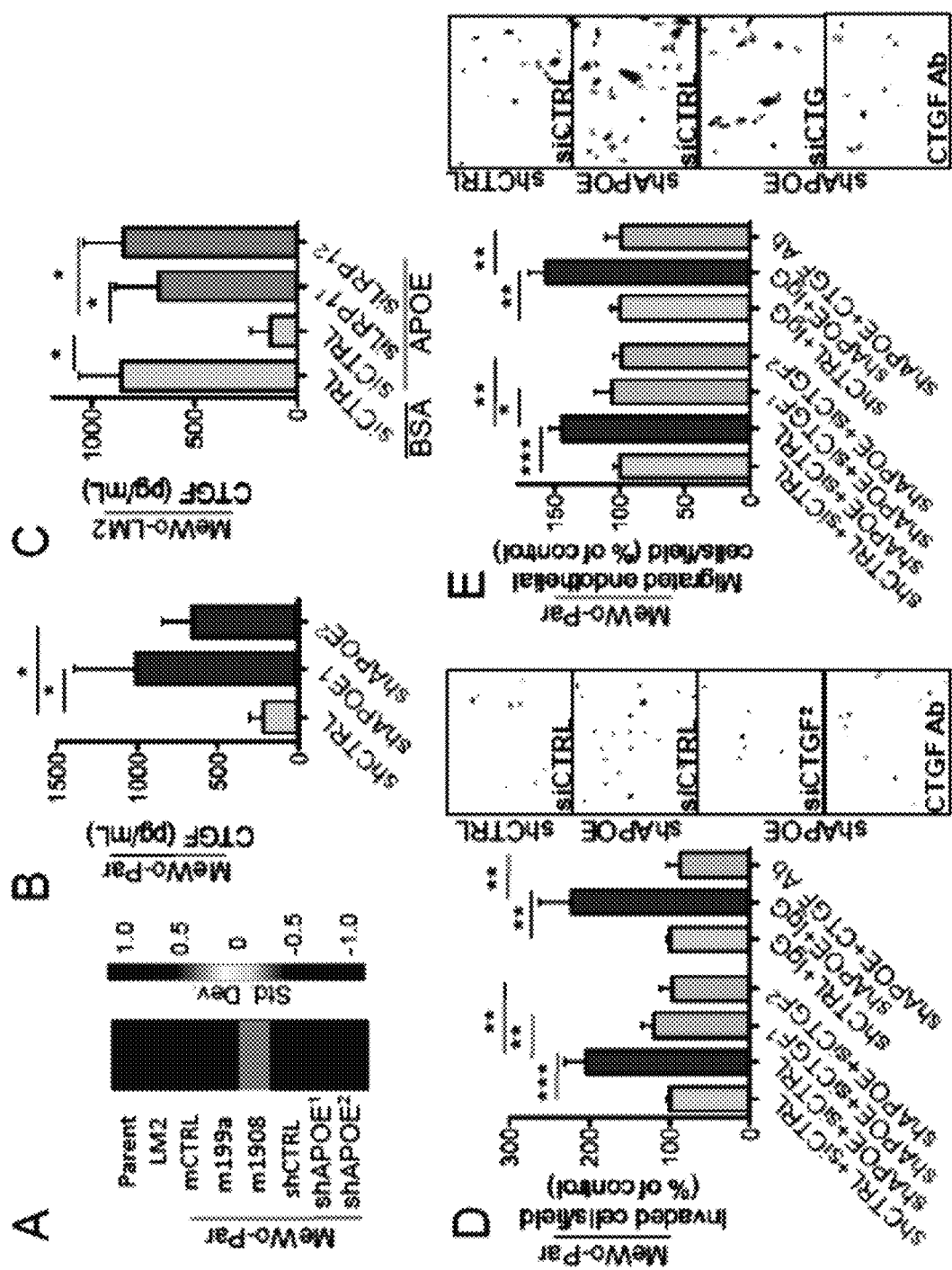

Example 9 miRNA-Dependent Targeting of Apoe/LRP 1 Signaling Promotes Cancer Cell Invasion and Endothelial Recruitment through CTGF Induction In this example, Connective Tissue Growth Factor (CTGF) was identified as a down-stream mediator of ApoE/LRP1 signaling in cancer cell invasion and endothelial recruitment. CTGF expression level, as determined by qRT-PCR analysis and ELISA, is mediated by ApoE/LRP1 signaling (FIGS. 8A, 8B, and 8C). Additionally, ApoE/LRP1 regulated cancer cell invasion and endothelial recruitment are mediated by CTGF (FIG. 8D, 8E).

Example 10

CTGF Mediates miRNA-Dependent Metastatic Invasion, Endothelial Recruitment, and Colonization In this Examiner, assays were carried out to investigate whether CTGF mediates miRNA-dependent invasion and endothelial recruitment. Briefly, trans-well cell invasion and endothelial recruitment assays were performed on parental MeWo cells over-expressing miR-199a or miR-1908 in the presence of a blocking antibody targeting CTGF. Indeed, it was found that mir-199a and mir-1908 dependent metastatic invasion and endothelial recruitment are mediated by CTGF (FIGS. 9A and 9B). In order to investigate whether in vivo melanoma metastasis (metastatic colonization) is mediated by CTGF, bioluminescence imaging was performed on lung metastasis by 5×104 parental MeWo cells knocked down for CTGF in the setting of miR-199a or miR-1908 over-expression. Knock-down of CTGF in this setting resulted in significant reduction of in vivo melanoma metastasis (FIG. 9C).

Example 11

Figures 10A, 10B, 10C, 10D, 10E:
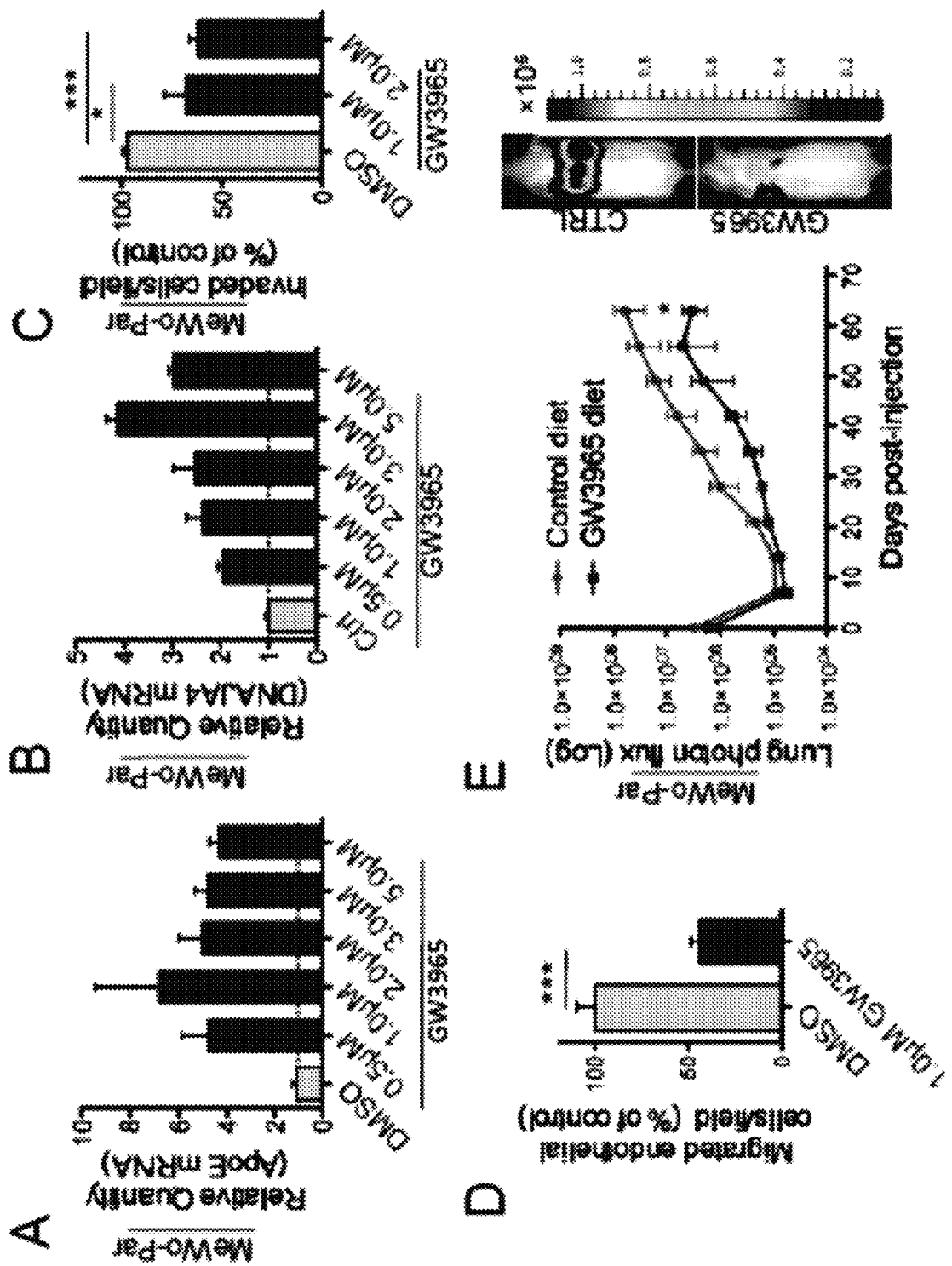

Treatment with LXR Agonist GW3965 Elevates Melanoma Cell ApoE and DNAJA4 Levels and Suppresses Cancer Cell Invasion, Endothelial Recruitment, and Metastatic Colonization Small molecule agonists of the Liver X Receptor (LXR) have previously been shown to increase Apo E levels. To investigate whether increasing Apo-E levels via LXR activation resulted in therapeutic benefit, assays were carried out to assess the effect of the LXR agonist GW3965 [chemical name: 3-[3-[N-(2-Chloro-3-trifluoromethylbenzyl)-(2,2-diphenylethyl)amino]propyloxy] phenylacetic acid hydrochloride) on Apo-E levels, tumor cell invasion, endothelial recruitment, and in vivo melanoma metastasis (FIG. 10). Incubation of parental MeWo cells in the presence of therapeutic concentrations of GW3965 increased expression of ApoE and DNAJA4 (FIGS. 10A and 10B). Pre-treatment of MeWO cells with GW3965 decreased tumor cell invasion (FIG. 10C) and endothelial recruitment (FIG. 10D). To test whether GW3965 could inhibit metastasis in vivo, mice were administered a grain-based chow diet containing GW3965 (20mg/kg) or a control diet, and lung metastasis was assayed using bioluminescence after tail-vein injection of $4 \times 10^4$ parental MeWo cells into the mice (FIG. 10E). Oral administration of GW3965 to the mice in this fashion resulted in a significant reduction in in vivo melanoma metastasis (FIG. 10E).

Example 12

Identification of Mir-7 as an Endogenous Suppressor of Melanoma Metastasis

In this example, miR-7 was identified as an endogenous suppressor of melanoma metastasis (FIG. 11). To test whether miR-7 suppresses melanoma metastasis in vivo, its expression was knocked down in parental MeWo cells using miR-Zip technology (FIG. 11A). Bioluminescence imaging plot of lung metastatic colonization following intravenous injection of 4×104 parental MeWo cells expressing a short hairpin (miR-Zip) inhibitor of miR-7 (miR-7 KD) significantly increased lung metastasis in vivo (FIG. 11A). Conversely, overexpression of miR-7 in LM2 cells significantly reduced lung metastasis in vivo (FIG. 11B).

The complexity of cancer requires the application of systematic analyses (Pe'er and Hacohen, 2011). Via a systematic global approach, a cooperative network of miRNAs was uncovered. The miRNAs are i) upregulated in highly metastatic human melanoma cells, ii) required and sufficient for metastatic colonization and angiogenesis in melanoma, and iii) robust pathologic predictors of human melanoma metastatic relapse. Through a transcriptomic-based and biologically guided target identification approach, miR-1908, miR-199a-3p, and miR-199a-5p were found to convergently target the heat shock factor DNAJA4 and the metabolic gene ApoE. The requirement of each individual miRNA for metastasis indicates that these three convergent miRNAs are non-redundant in promoting melanoma metastasis, while the robust synergistic metastasis suppression achieved by combinatorial miRNA inhibition reveals functional cooperativity between these miRNAs, presumably achieved through maximal silencing of ApoE and DNAJA4. The identification of ApoE as a gene negatively regulated by three metastasis promoter miRNAs, positively regulated by a metastasis suppressor gene (DNAJA4), and silenced in clinical metastasis samples highlights the significance of this gene as a suppressor of melanoma progression.

Example 13

Identification of LXRβ Signaling as a Novel Therapeutic Target in Melanoma

Figures 19A, 19B, 19C:
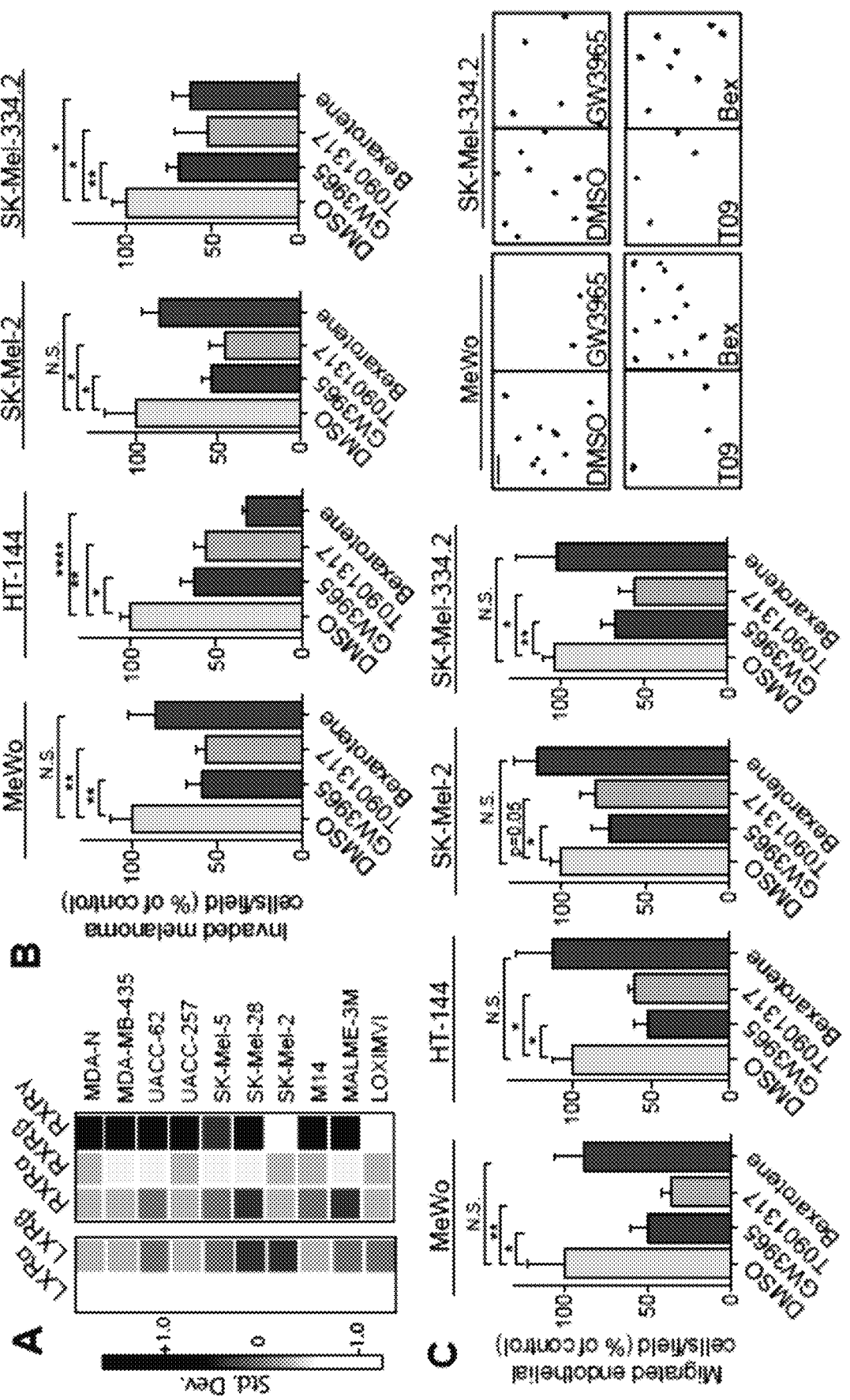
Figures 19D, 19E, 19F, 19G:
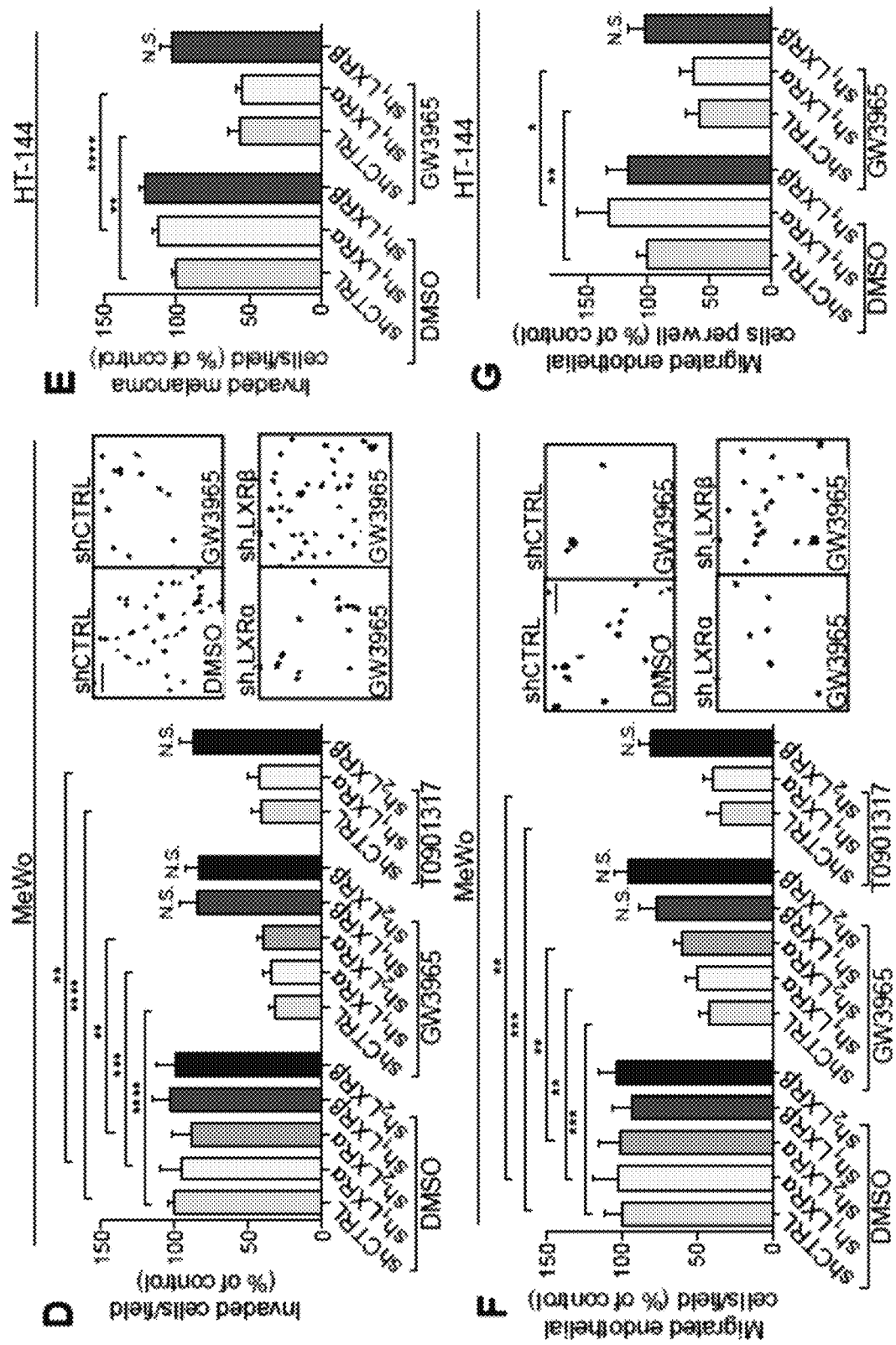
Figure 20A:
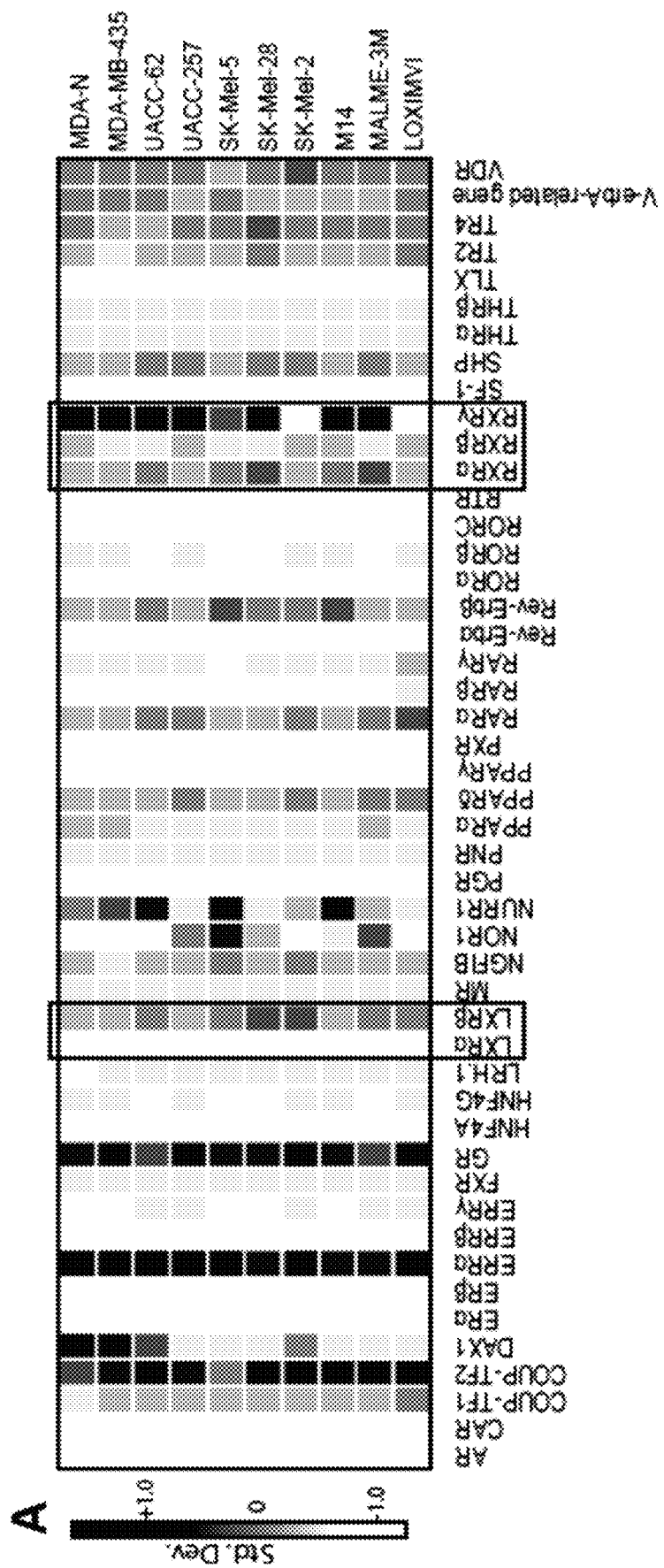

To identify nuclear hormone receptors that show broad expression in melanoma, we examined the expression levels of all nuclear hormone receptor family members across the NCI-60 collection of human melanoma cell lines. Several receptors exhibited stable expression across multiple melanoma lines, suggesting that they could represent novel potential targets in melanoma (FIGS. 19A and 20A). Notably, out of these, liver-X receptors (LXRs) were previously shown to enhance ApoE transcription in adipocytes and macrophages (Laffitte et al., 2001), while pharmacologic activation of RXRs was found to drive ApoE expression in pre-clinical Alzheimer's models (Cramer et al., 2012).

Given the recently uncovered metastasis-suppressive role of ApoE in melanoma (Pencheva et al., 2012), the ubiquitous basal expression of LXRβ and RXRα in melanoma, and the availability of pharmacologic agents to therapeutically activate LXRs and RXRs, we investigated whether activation of LXRs or RXRs in melanoma cells might inhibit melanoma progression phenotypes. In light of the established roles of nuclear hormone receptors such as ER and AR in regulating breast and prostate cancer cell proliferation, we first examined whether pharmacologic agonism of LXRs or RXRs in melanoma cells affects in vitro cell growth.

Figures 20B, 20C, 20D, 20E, 20F, 20G:
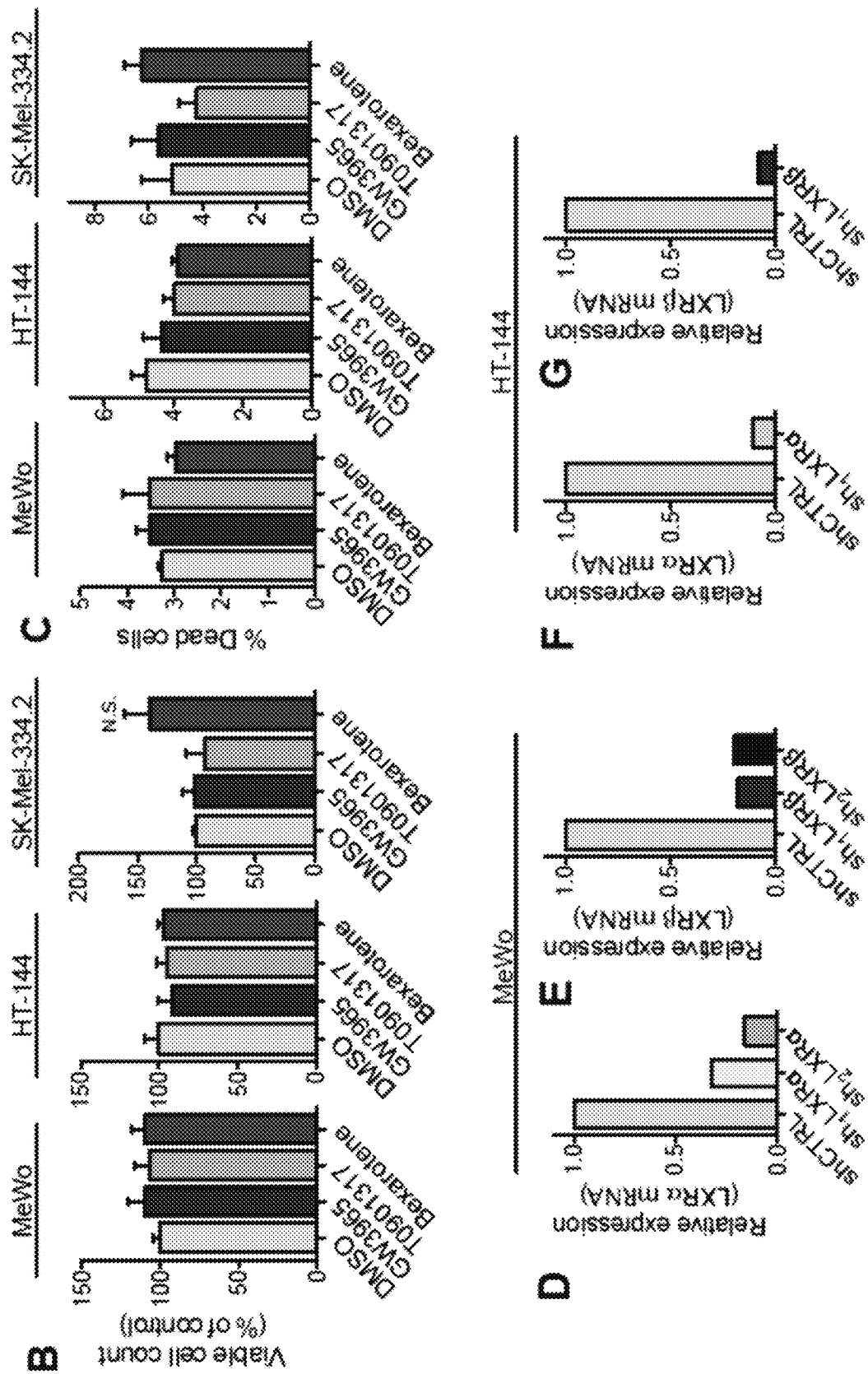

Treatment of melanoma cells with two structurally-distinct LXR agonists, GW3965 2 or T0901317 1, or the RXR agonist bexarotene did not affect cell proliferation or cell viability rates (FIG. 20B-C). We next assessed the effects of LXR or RXR activation on cell invasion and endothelial recruitment—phenotypes displayed by metastatic melanoma and metastatic breast cancer populations (Pencheva et al., 2012; Png et al., 2012). Treatment of the mutationally diverse MeWo (B-Raf/N-Ras wild-type), HT-144 (B-Raf mutant), and SK-Mel-2 (N-Ras mutant) human melanoma lines as well as the SK-Mel-334.2 (B-Raf mutant) primary human melanoma line with GW3965 2 or T0901317 1 consistently suppressed the ability of melanoma cells to invade through matrigel and to recruit endothelial cells in trans-well assays (FIG. 19B-C). In comparison, treatment with bexarotene suppressed invasion only in half of the melanoma lines tested and it did not significantly affect the endothelial recruitment phenotype (FIGS. 19B-C).

Given the superiority of LXR over RXR agonism in broadly inhibiting both cell invasion and endothelial recruitment across multiple melanoma lines, we investigated the requirement for LXR signaling in mediating the suppressive effects of LXR agonists. Knockdown of melanoma LXRβ, but not LXRα, abrogated the ability of GW3965 2 and T0901317 1 to suppress invasion and endothelial recruitment (FIG. 19D-G and FIGS. 20D-G), revealing melanoma-cell LXRβ to be the functional target of LXR agonists in eliciting the suppression of these in vitro phenotypes. Our molecular findings are consistent with LXRβ being the predominant LXR isoform expressed by melanoma cells (FIG. 19A, $P<0.0001$).

The ubiquitous basal expression of LXRβ in melanoma is likely reflective of the general role that LXRs play in controlling lipid transport, synthesis, and catabolism (Calkin and Tontonoz, 2013). While such stable LXRβ expression would be key to maintaining melanoma cell metabolism and growth, it also makes LXR signaling an attractive candidate for broad-spectrum therapeutic targeting in melanoma.

Example 14

Therapeutic Delivery of LXR Agonists Suppresses Melanoma Tumor Growth

LXR agonists were originally developed as oral drug candidates for the purpose of cholesterol lowering in patients with dyslipidemia and atherosclerosis (Collins et al., 2002; Joseph and Tontonoz, 2003). These compounds were abandoned clinically secondary to their inability to reduce lipid levels in large-animal pre-clinical models (Groot et al., 2005).

Given the robust ability of GW3965 2 and T0901317 1 to suppress in vitro melanoma progression phenotypes (FIG. 19B-C), we investigated whether therapeutic LXR activation could be utilized for the treatment of melanoma. Indeed, oral administration of GW3965 2 or T0901317 1 at low doses (20 mg/kg), subsequent to formation of subcutaneous tumors measuring 5-10 mm3 in volume, suppressed tumor growth by the aggressive B16F10 mouse melanoma cells in an immunocompetent model by 67% and 61%, respectively (FIG. 21A-B). Administration of a higher LXR agonist dose (100 mg/kg) led to an 80% reduction in tumor growth (FIG. 21A), consistent with dose-dependent suppressive effects.

Oral administration of GW3965 2 also robustly suppressed tumor growth by the MeWo (70% inhibition) and SK-Mel-2 (49% inhibition) human melanoma cell lines, as well as the SK-Mel-334.2 primary human melanoma line (73% inhibition) (FIG. 21C-E and FIG. 22A).

Encouraged by the robust tumor-suppressive impact of LXR agonists on small tumors (5-10 mm3) (FIG. 21A-E), we next investigated whether LXR activation therapy could inhibit the growth of large (~150 mm3) tumors.

We found that treatment with GW3965 2 led to a roughly 50% reduction in the growth of established large B16F10 tumors (FIG. 21F). Importantly, therapeutic delivery of GW3965 2 subsequent to tumor establishment substantially prolonged the overall survival time of immunocompetent mice injected with mouse B16F10 cells, immunocompromised mice bearing tumor xeongrafts derived from the human MeWo established melanoma line, as well as the SK-Mel.334-2 primary human melanoma line (FIG. 21G-I). These findings are consistent with broad-spectrum responsiveness to LXR activation therapy across melanotic and amelanotic established melanoma tumors of diverse mutational subtypes: B-Raf and N-Ras wild-type (B16F10 and MeWo; FIG. 21A-C), B-Raf mutant (SK-Mel-334.2; FIG. 21D), and N-Ras mutant (SK-Mel-2; FIG. 21E).

We next sought to determine the cell biological phenotypes regulated by LXR agonists in suppressing tumor growth. Consistent with the inhibitory effects of GW3965 2 on endothelial recruitment by melanoma cells in vitro, GW3965 2 administration led to a roughly 2-fold reduction in the endothelial cell content of tumors (FIG. 21J). This effect was accompanied by a modest decrease (23%) in the number of actively proliferating tumor cells in vivo (FIG. 21K) without a change in the number of apoptotic cells (FIG. 21L). These results suggest that, in addition to reducing local tumor invasion, LXR activation suppresses melanoma tumor growth primarily through inhibition of tumor angiogenesis with a resulting reduction in in vivo proliferation.

Example 15

Figures 23A, 23B, 23C, 23D, 23E, 23F:
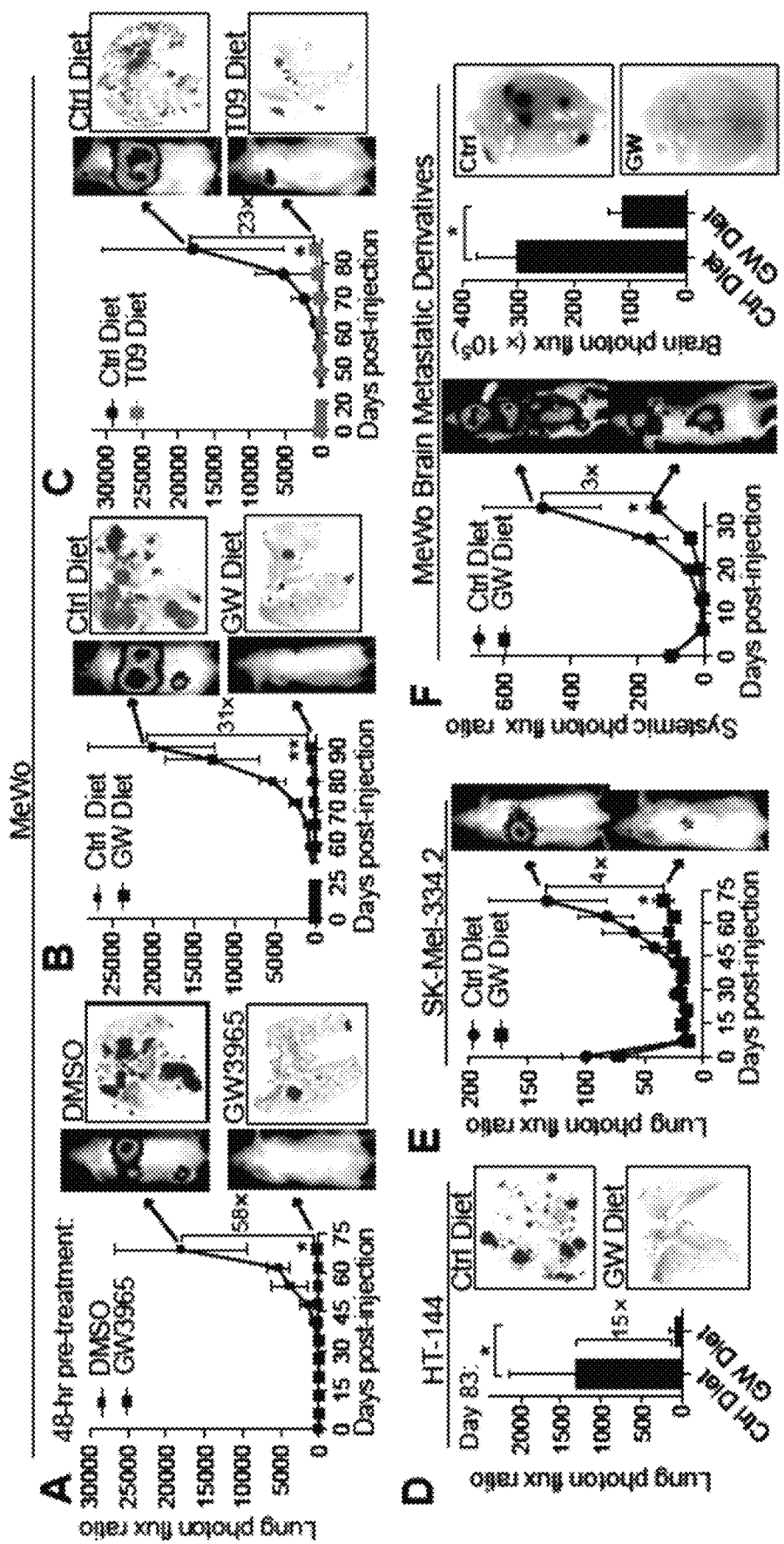

LXR Agonism Suppresses Melanoma Metastasis to the Lung and Brain and Inhibits the Progression of Incipient Metastases The strong suppressive effects of LXR agonists on melanoma tumor growth motivated us to examine whether LXR activation could also suppress metastatic colonization by melanoma cells. To this end, pre-treatment of human MeWo melanoma cells with GW3965 2 led to a more than 50-fold reduction in their metastatic colonization capacity (FIG. 23A). In light of this dramatic inhibitory effect, we next assessed the ability of orally administered LXR agonists to suppress metastasis. Immunocompromised mice that were orally administered GW3965 2 or T0901317 1 experienced 31-fold and 23-fold respective reductions in lung metastatic colonization by human MeWo cells (FIG. 23B-C). Treatment with GW3965 2 also suppressed metastatic colonization by the HT-144 melanoma line (FIG. 23D) as well as the SK-Mel-334.2 primary melanoma line (FIG. 23E).

GW3965 2 is a lipophilic molecule that can efficiently cross the blood brain barrier and potently activate LXR signaling in the brain. Consistent with this, oral delivery of GW3965 2 was previously shown to improve amyloid plaque pathology and memory deficits in pre-clinical models of Alzheimer's disease (Jiang et al., 2008). We thus wondered whether LXR agonism could exhibit therapeutic activity in the suppression of melanoma brain metastasis—a dreaded melanoma outcome in dire need of effective therapies (Fonkem et al., 2012). Notably, oral administration of GW3965 2 inhibited both systemic dissemination and brain colonization following intracardiac injection of brain-metastatic melanoma cells derived from the MeWo parental line (FIG. 23F). These results reveal robust metastasis suppression by LXR activation therapy across multiple melanoma lines and in multiple distal organ metastatic sites.

Figures 23G, 23H, 23I, 23J, 23K:
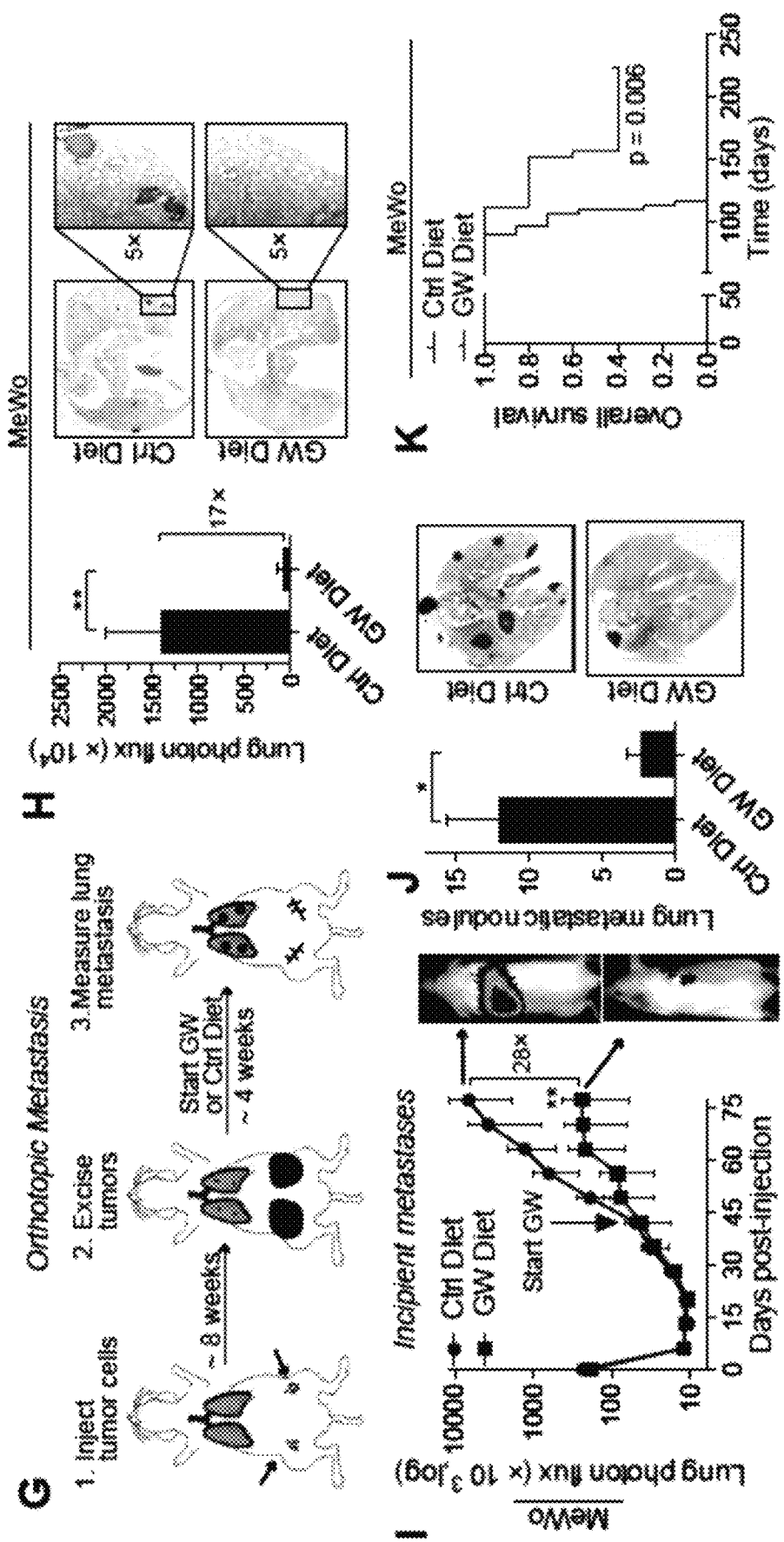

Encouraged by the robust effects observed in suppressing metastasis formation (FIG. 23A-F), we next sought to determine whether LXR activation therapy could halt the progression of melanoma cells that had already metastatically disseminated. We first tested the ability of GW3965 2 to reduce lung colonization by melanoma cells disseminating from an orthotopic site following removal of the primary tumor (FIG. 23G). Importantly, oral administration of GW3965 2 post-tumor excision inhibited lung colonization by disseminated melanoma cells by 17-fold (FIG. 23H). Remarkably, treatment of mice with GW3965 2 also dramatically suppressed (28-fold) colonization by incipient lung metastases that had progressed 8-fold from the baseline at seeding (FIG. 23I). Consistent with LXR activation inhibiting metastatic initiation, GW3965 2 treatment decreased the number of macroscopic metastatic nodules formed (FIG. 23J). Finally, treatment of mice with GW3965 2 in this 'adjuvant' pre-clinical context significantly prolonged their survival times following metastatic colonization (FIG. 23K).

Example 16

LXR Activation Reduces Melanoma Progression and Metastasis in a Genetically-Driven Mouse Model of Melanoma Roughly 60% of human melanoma tumors are marked by activating mutations in the Braf oncogene, with one single amino acid variant, B-RafV600E, being the predominant mutation found (Davies et al., 2002). Nearly 20% of melanomas exhibit activating mutations in B-Raf with concurrent silencing of the Pten tumor-suppressor, which drives progression to a malignant melanoma state (Tsao et al., 2004; Chin et al., 2006). Recently, Tyrosinase (Tyr)-driven conditional B-Raf activation and Pten loss were shown to genetically cooperate in driving mouse melanoma progression (Dankort et al., 2009).

To determine whether LXR activation could suppress melanoma progression in this genetically-initiated model, we induced melanomas in Tyr::CreER; B-RafV600E/+; Ptenlox/+ and Tyr::CreER; B-RafV600E/+; Ptenlox/lox mice by intraperitoneal administration of 4-hydroxytamoxifen (4-HT). Notably, oral administration of GW3965 2 following melanoma initiation attenuated tumor progression and significantly extended the overall survival times of both PTEN heterozygous Tyr::CreER; B-RafV600E/+; Ptenlox/+ and PTEN homozygous Tyr::CreER; B-RafV600E/+; Ptenlox/lox mice (FIG. 24A-B and FIG. 25A-B). Next, we examined the ability of GW3965 2 to suppress melanoma metastasis in this genetic context. While we did not detect macroscopic metastases in the lungs or brains of 4-HT-treated Tyr::CreER; B-Raf$^{V600E/+}$; Pten$^{lox/lox}$ control mice, we consistently observed melanoma metastases to the salivary gland lymph nodes. Importantly, Tyr::CreER; B-Raf$^{V600E/-}$; Pten$^{lox/lox}$ mice treated with GW3965 2 exhibited a decrease in the number of lymphatic metastases detected post-mortem (FIG. 24C). These findings indicate that LXR activation inhibits orthotopic metastasis in a genetically-driven melanoma model, in addition to its suppressive effects on primary melanoma tumor progression.

The cooperativity between B-Raf activation and Pten loss in driving melanoma progression can be further enhanced by inactivation of CDKN2A, a cell cycle regulator frequently mutated in familial melanomas (Hussussian et al., 1994; Kamb et al., 1994). We thus examined the effect of LXR activation on B-Raf$^{V600E/+}$; Pten$^{-/-}$; CDKN2A$^{-/-}$ melanomas, allowing us to test the therapeutic efficacy of LXR agonism in a more aggressive genetically-driven melanoma progression model. Importantly, therapeutic delivery of GW3965 2 robustly inhibited tumor growth and lung metastasis by B-Raf$^{V600E/+}$; Pten$^{-/-}$; CDKN2A$^{-/-}$ primary mouse melanoma cells injected into syngeneic immunocompetent mice and extended the overall survival of mice bearing B-Raf$^{V600E/+}$; Pten$^{-/-}$; CDKN2A$^{-/-}$ melanoma burden (FIG. 24D-F). Taken together, the robust suppression of melanoma progression across independent xenograft and genetically-induced immunocompetent melanoma mouse models that exhibit the diverse mutational profiles of human melanomas motivates the clinical testing of LXR activation therapy.

Example 17

Pharmacologic Activation of LXRβ Suppresses Melanoma Phenotypes by Transcriptionally Inducing Melanoma-Cell ApoE expression We next sought to determine the downstream molecular target of LXRβ that mediates suppression of melanoma progression. To this end, we transcriptomically profiled human MeWo melanoma cells treated with the LXR agonist GW3965 2.

Figures 27A, 27B, 27C, 27D, 27E, 27F:
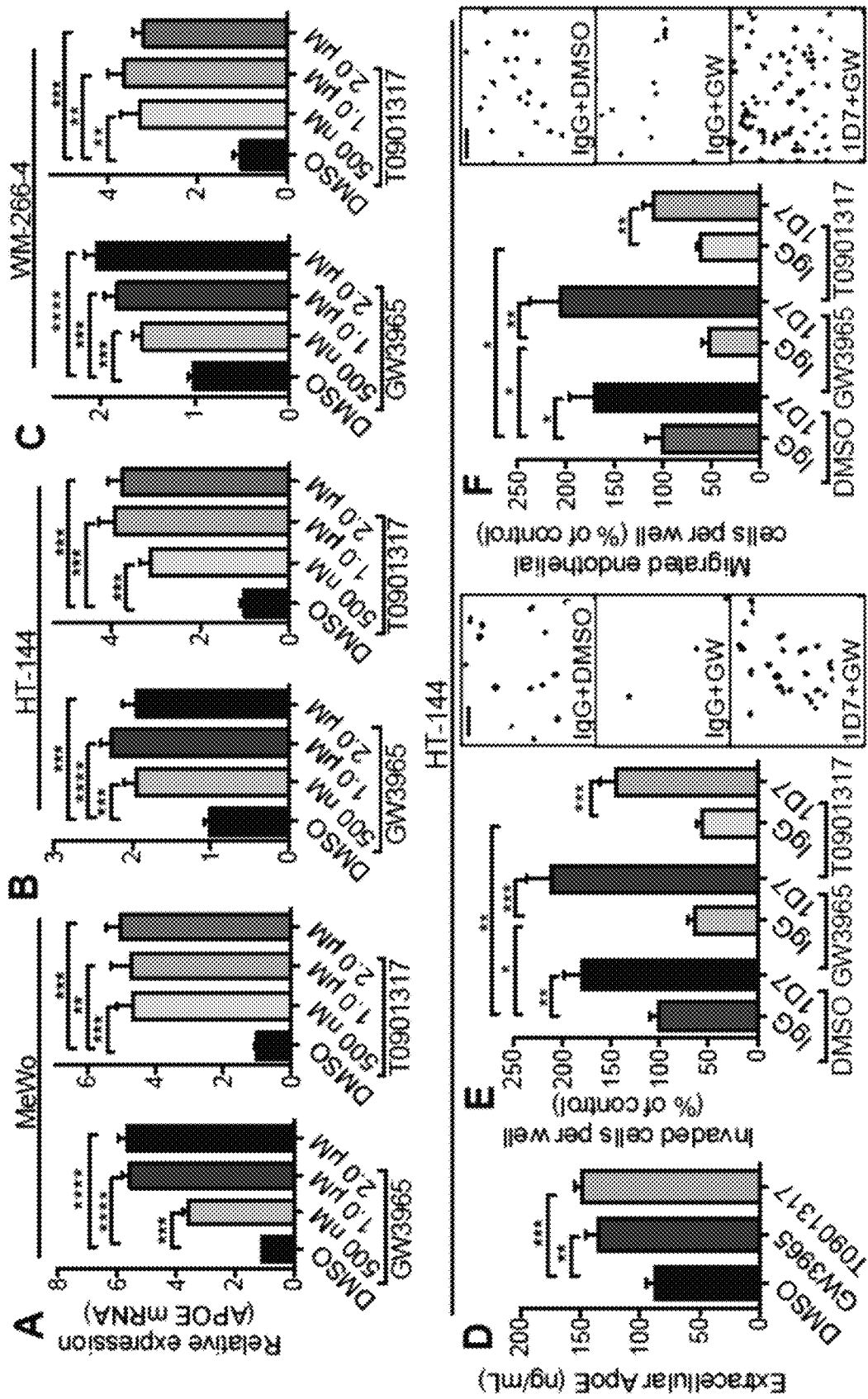

Out of the 365 genes that were significantly induced in response to LXR activation, we identified ApoE, a previously validated transcriptional target of LXRs in macrophages and adipocytes (Laffitte et al., 2001), as the top upregulated secreted factor in melanoma cells (FIG. 26). Quantitative real-time PCR (qRT-PCR) validation revealed robust upregulation of ApoE transcript expression following treatment with independent LXR agonists across multiple human melanoma lines (FIG. 27A-C).

Figures 28A, 28B, 28C, 28D, 28E, 28F, 28G:
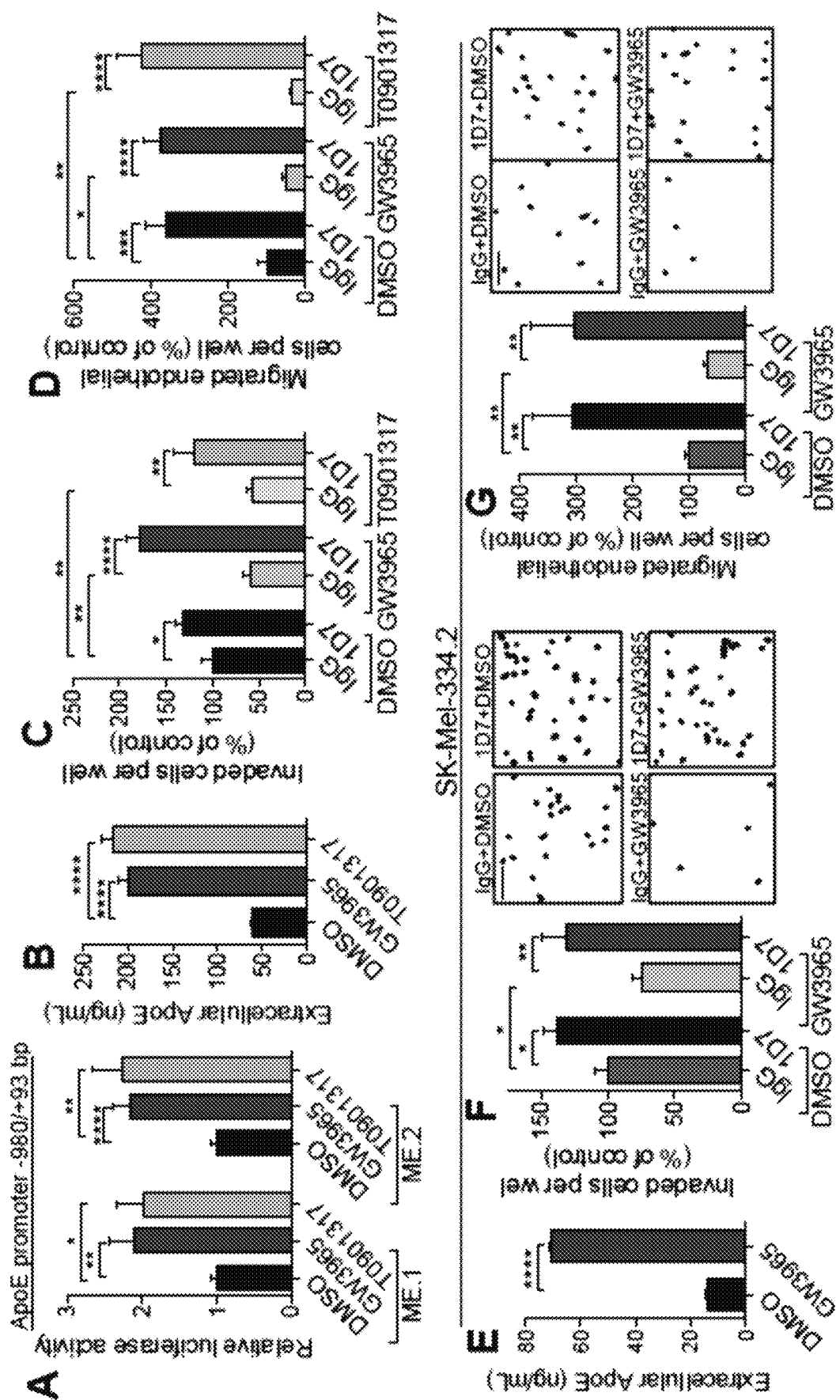
Figures 28H, 28I:
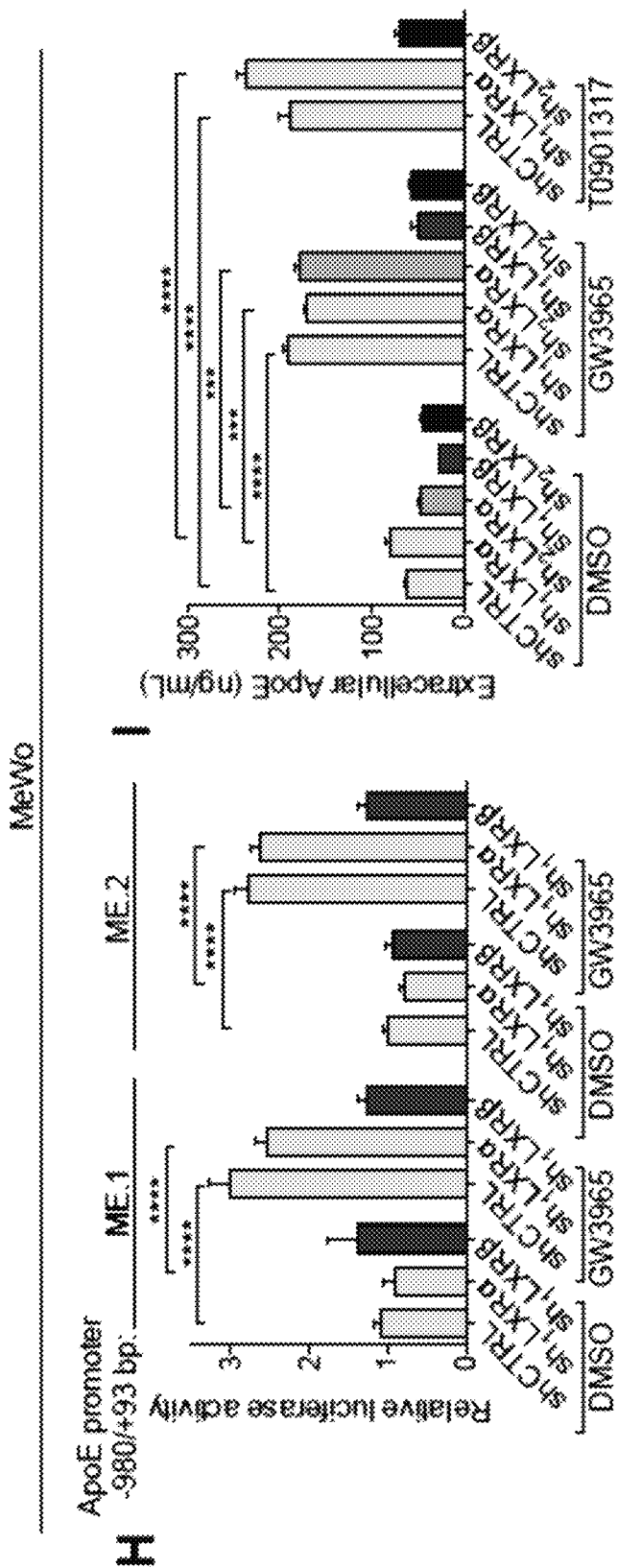

In light of the previously reported metastasis-suppressive function of ApoE in melanoma (Pencheva et al., 2012), we investigated whether LXRβ activation suppresses melanoma progression through transcriptional induction of ApoE. Indeed, GW3965 2 and T0901317 1 were found to enhance the melanoma cell-driven activity of a luciferase reporter construct containing the ApoE promoter fused to either of two previously characterized LXR-binding multi-enhancer elements (ME.1 or ME.2) (Laffitte et al., 2001) (FIG. 28A). Importantly, this transcriptional induction resulted in elevated levels of secreted ApoE protein (FIG. 28B). Consistent with direct LXRβ targeting of ApoE in melanoma cells, neutralization of extracellular ApoE with an antibody fully blocked the LXRβ-mediated suppression of cell invasion and endothelial recruitment and further enhanced these phenotypes relative to the control IgG treatment (FIG. 28C-G and FIG. 27D-F), revealing the effects of LXR agonism to be modulated by extracellular ApoE.

Figures 27G, 27H, 27I, 27J, 27K:
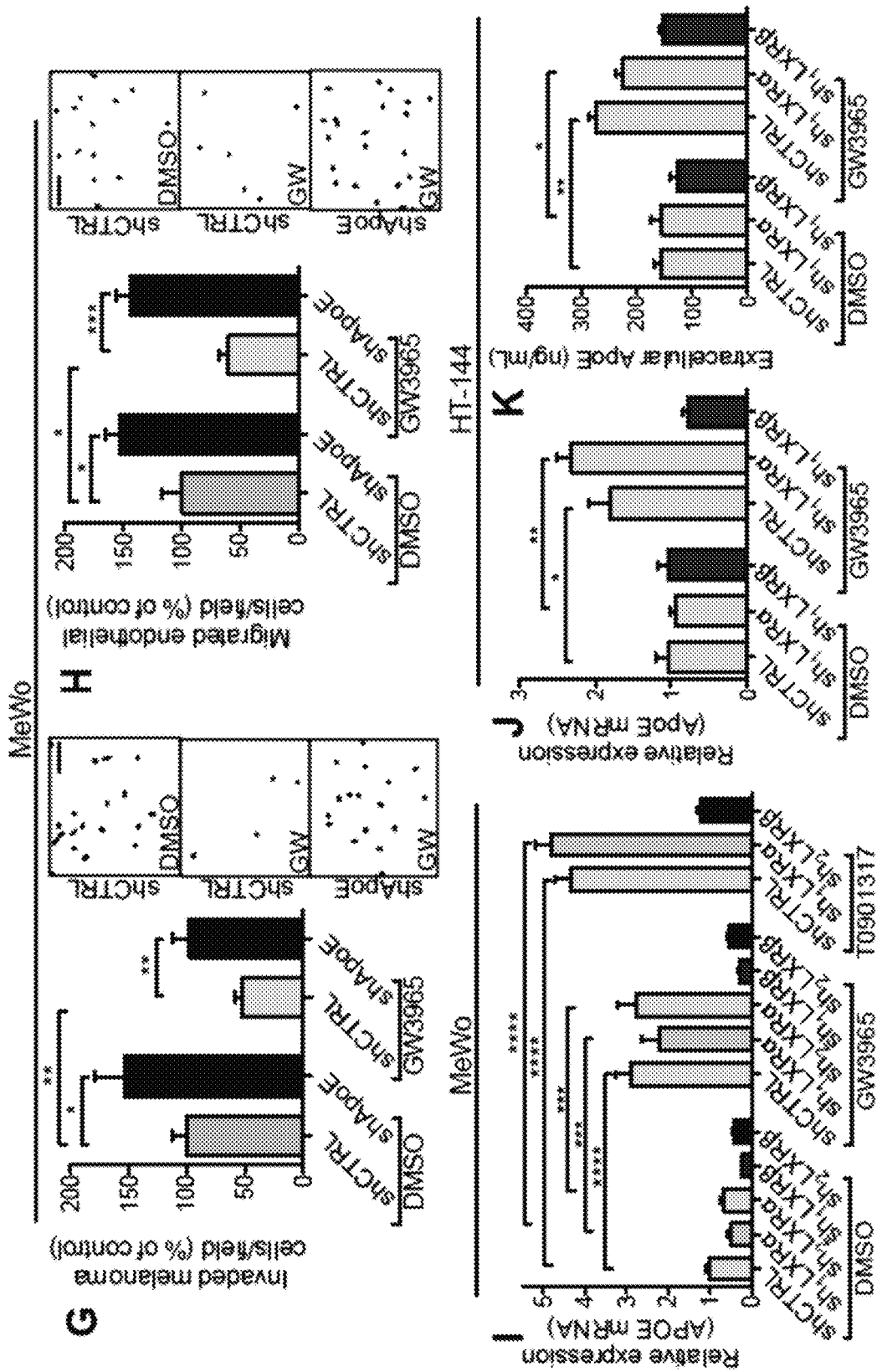

Additionally, molecular knockdown of ApoE in melanoma cells also blocked the GW3965 2-mediated suppression of cell invasion and endothelial recruitment phenotypes (FIG. 27G-H). In agreement with this, melanoma cell depletion of LXRβ, but not LXRα, abrogated the ability of GW3965 2 and T0901317 1 to upregulate ApoE transcription and ultimately protein expression (FIG. 28H-I and FIG. 27I-K). Collectively, these findings indicate that pharmacologic activation of LXRβ, the predominant LXR isoform expressed by melanoma cells, suppresses cell-intrinsic invasion and endothelial recruitment by melanoma cells through transcriptionally activating ApoE expression in melanoma cells.

Example 18

Engagement of Melanoma-Derived and Systemic ApoE by LXRβ Activation Therapy

The LXRβ-induced suppression of key melanoma phenotypes by extracellular ApoE in vitro suggested that the suppressive effects of LXR agonists in vivo might be further augmented by the activation of LXRs in peripheral tissues, which could serve as robust sources of extracellular ApoE.

Importantly, such non-transformed tissues would be less vulnerable to developing resistance to LXR activation therapy, allowing for chronic ApoE induction in patients. We thus investigated whether therapeutic LXR agonism suppresses melanoma progression by inducing ApoE derived from melanoma cells or systemic tissues. Consistent with LXRβ agonism increasing ApoE expression in melanoma cells in vivo, ApoE transcript levels were upregulated in melanoma primary tumors as well as in melanoma lung and brain metastases dissociated from mice that were fed an LXR agonist-supplemented diet (FIG. 29A-E). Importantly, treatment of mice with either GW3965 2 or T0901317 1 significantly elevated ApoE protein expression in systemic adipose, lung, and brain tissues of mice (FIGS. 30A-B) and also upregulated ApoE transcript levels in circulating white blood cells (FIG. 30C). These results indicate that LXR activation therapy induces both melanoma-cell and systemic tissue ApoE expression in vivo.

To determine the in vivo requirement of melanoma-derived and systemic LXR activation for the tumor-suppressive effects of orally administered LXR agonists, we first tested the ability of GW3965 2 to suppress tumor growth by B16F10 mouse melanoma cells depleted of LXRβ.

Figures 29A, 29B, 29C, 29D, 29E, 29F, 29G, 29H:
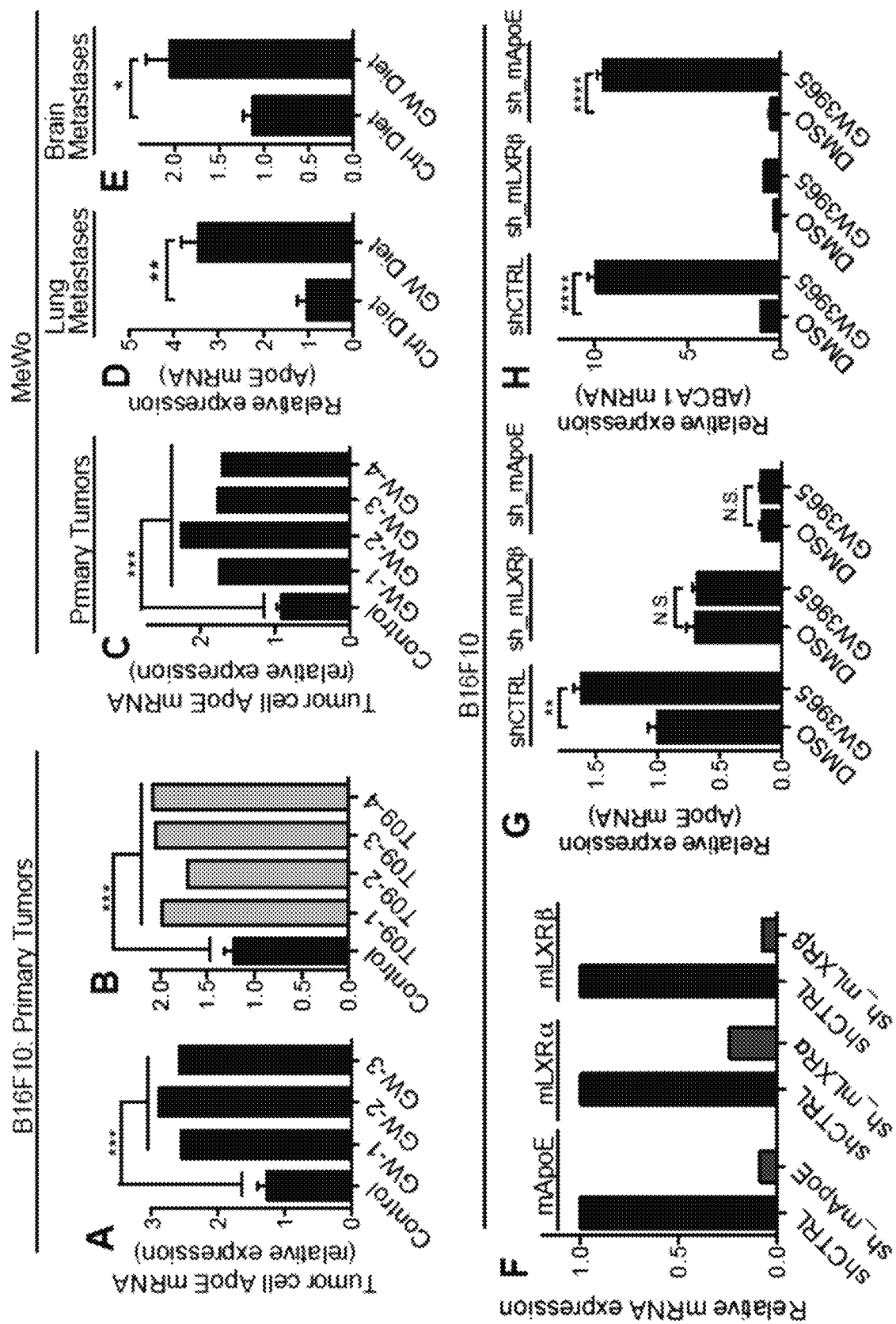
Figure 29I:
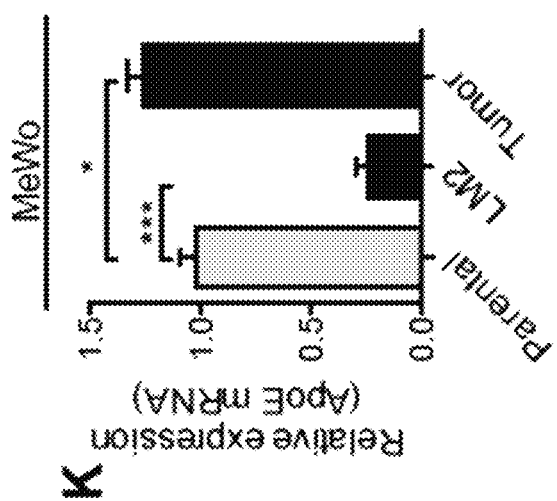
Figure 29J:
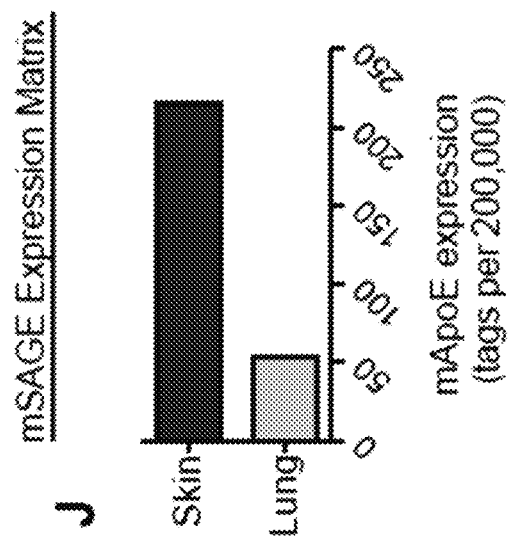
Figure 29K:
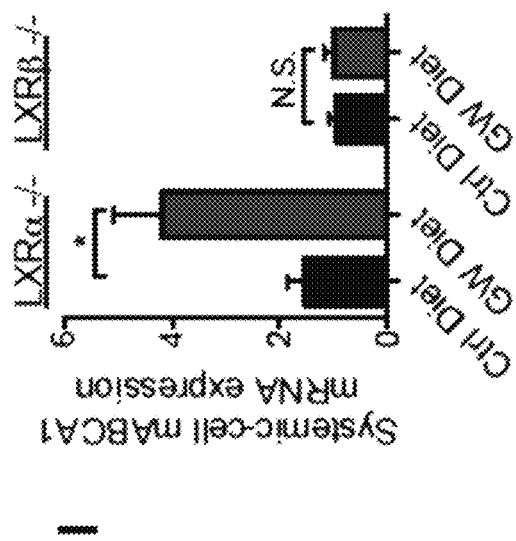
Figures 30A, 30B, 30C, 30D, 30E, 30F:
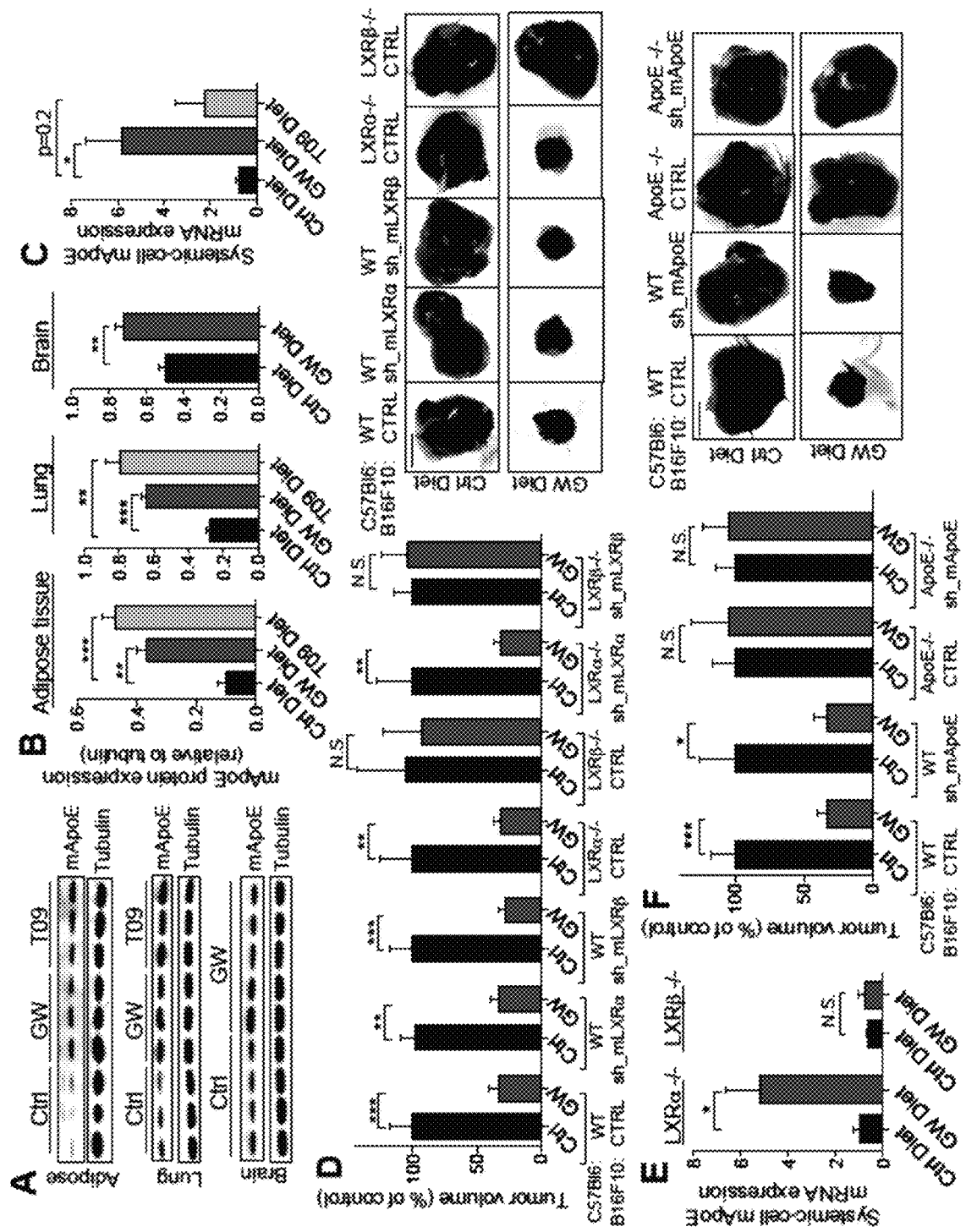

Consistent with our findings in human melanoma cells, knockdown of mouse melanoma-cell LXRβ abrogated the GW3965-mediated induction of ApoE expression (FIG. 29F-H). Despite this, melanoma-cell LXRβ knockdown was unable to prevent the suppression of tumor growth by GW3965 2 (FIG. 29D), implicating a role for systemic LXR activation in tumor growth inhibition by GW3965 2. To identify the LXR isoform that mediates this non-tumor autonomous suppression of melanoma growth by LXR agonists, we examined the effects of GW3965 2 on tumors implanted onto LXRα or LXRβ genetically null mice. Interestingly, genetic ablation of systemic LXRβ blocked the ability of GW3965 to suppress melanoma tumor growth, while LXRα inactivation had no effect on tumor growth inhibition by GW3965 (FIG. 6D). Importantly, the upregulation of systemic ApoE expression by GW3965 2, an agonist with 6-fold greater activity towards LXRβ than LXRα, was abrogated in LXRβ −/−, but not in LXRα−/− mice (FIG. 30E and FIG. 29I). These results indicate that ApoE induction by GW3965 2 in peripheral tissues is predominantly driven by systemic LXRβ activation. In agreement with this, we find systemic LXRβ to be the primary molecular target and effector of GW3965 2 in mediating melanoma tumor growth suppression.

We next examined whether ApoE is required for the in vivo melanoma-suppressive effects of LXR agonists. Consistent with the lack of an impact for melanoma-cell LXRβ knockdown on the tumor-suppressive activity of GW3965 2, depletion of melanoma-cell ApoE did not prevent tumor growth inhibition by GW3965 2 neither (FIG. 29F-H and FIG. 30F). These findings suggest that the tumor suppressive effects of GW3965 2 might be primarily mediated through ApoE induction in systemic tissues.

Figures 30G, 30H, 30I:
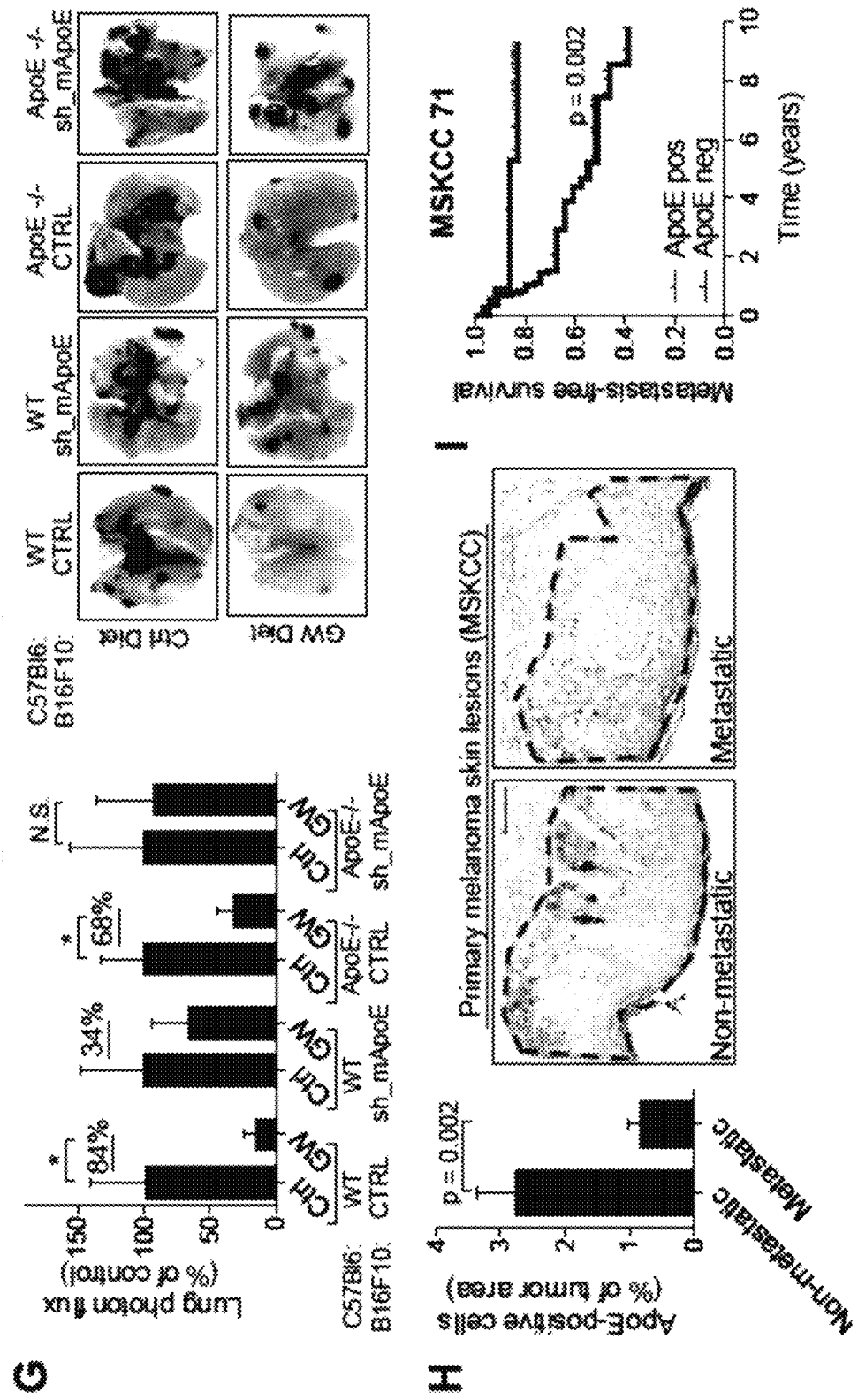

Indeed, GW3965 2 was completely ineffective in suppressing tumor growth in mice genetically inactivated for ApoE (FIG. 30F), revealing systemic ApoE as the downstream effector of systemic LXRβ in driving melanoma tumor growth suppression. Interestingly, in contrast to primary tumor growth regulation, knockdown of melanoma-cell ApoE partially prevented the metastasis-suppressive effect of GW3965 2 (FIG. 30G). Similarly, genetic inactivation of ApoE only partially prevented the metastasis suppression elicited by GW3965 2 as well (FIG. 30G). The GW3965-driven inhibition of metastasis was completely blocked only in the context of both melanoma-cell ApoE knockdown and genetic inactivation of systemic ApoE (FIG. 30G), indicative of a requirement for both melanoma-derived and systemic ApoE engagement by LXRβ in suppressing metastasis. We thus conclude that the effects of LXRβ activation on primary tumor growth are elicited primarily through systemic ApoE induction, while the effects of LXRβ agonism on metastasis are mediated through ApoE transcriptional induction in both melanoma cells and systemic tissues.

The identification of ApoE as the sole downstream mediator of the LXRβ-induced suppression of melanoma phenotypes further highlights the importance of this gene as a suppressor of melanoma progression. To determine whether ApoE expression is clinically prognostic of melanoma metastatic outcomes, we assessed ApoE protein levels by performing blinded immunohistochemical analysis on 71 surgically resected human primary melanoma lesions.

We found that patients whose melanomas had metastasized exhibited roughly 3-fold lower ApoE expression in their primary tumors relative to patients whose melanomas did not metastasize (FIG. 30H, P=0.002). Remarkably, ApoE expression levels in patients' primary melanoma lesions robustly stratified patients at high risk from those at low risk for metastatic relapse (FIG. 30I, P=0.002). These observations are consistent with previous findings that revealed significantly lower levels of ApoE in distant melanoma metastases relative to primary lesions (Pencheva et al., 2012). Collectively, this work indicates that ApoE, as a single gene, could likely act as a prognostic and predictive biomarker in primary melanomas to identify patients that i.) are at risk for melanoma metastatic relapse and as such ii.) could obtain clinical benefit from LXRβ agonist-mediated ApoE induction.

Ecample 19

LXRβ Activation Therapy Suppresses the Growth of Melanomas Resistant to Dacarbazine and Vemurafenib Encouraged by the robust ability of LXRβ activation therapy to suppress melanoma tumor growth and metastasis across a wide range of melanoma lines of diverse mutational backgrounds, we next sought to determine whether melanomas that are resistant to two of the mainstay clinical agents used in the management of metastatic melanoma— dacarbazine and vemurafenib—could respond to LXRβ-activation therapy.

Figures 31A, 31B, 31C, 31D, 31E, 31F:
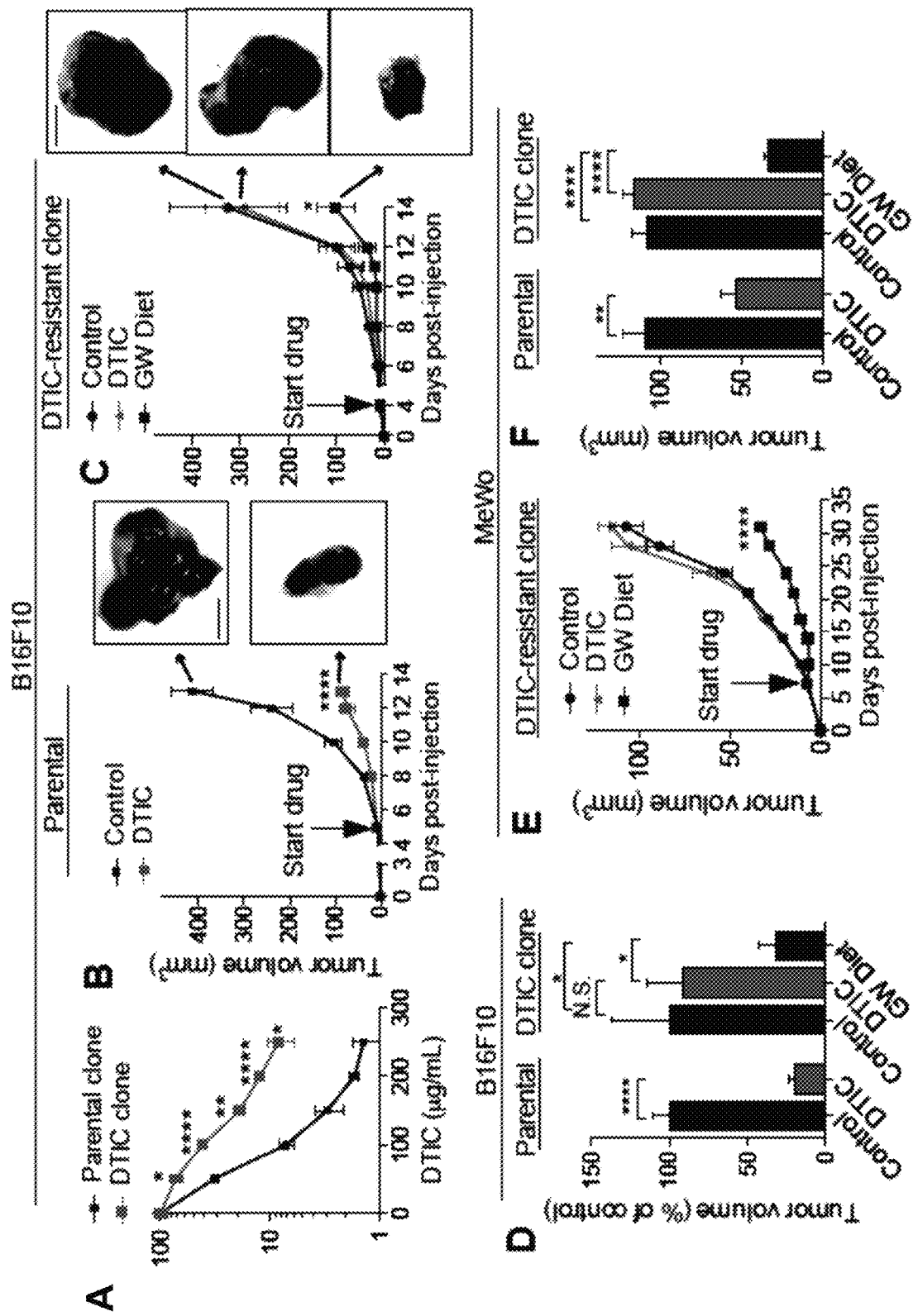

To this end, we generated B16F10 clones resistant to dacarbazine (DTIC) by continuously culturing melanoma cells in the presence of DTIC for two months. This yielded a population of cells that exhibited a 7-fold increase in viability in response to high-dose DTIC treatment compared to the parental B16F10 cell line (FIG. 31A). To confirm that this in vitro-derived DTIC clone was also resistant to DTIC in vivo, we assessed the effects of dacarbazine treatment on tumor growth.

While dacarbazine significantly suppressed the growth of the DTIC-sensitive parental line (FIG. 31B), it did not affect tumor growth by B16F10 DTIC-resistant cells (FIG. 31C). GW3965 2 robustly suppressed tumor growth by the DTIC-resistant B16F10 melanoma clone by more than 70% (FIGS. 31C-D). Importantly, oral delivery of GW3965 2 also strongly inhibited the growth of in vivo-derived DTIC-resistant human melanoma tumors formed by the independent MeWo cell line (FIG. 31E-F and FIG. 32A).

These results reveal that LXRβ agonism is effective in suppressing multiple melanoma cell populations that are resistant to dacarbazine—the only FDA-approved cytotoxic chemotherapeutic in metastatic melanoma. Our findings have important clinical implications for melanoma treatment since all stage IV patients who are treated with dacarbazine ultimately progress by developing tumors that are resistant to this agent.

Figures 31G, 31H, 31I:
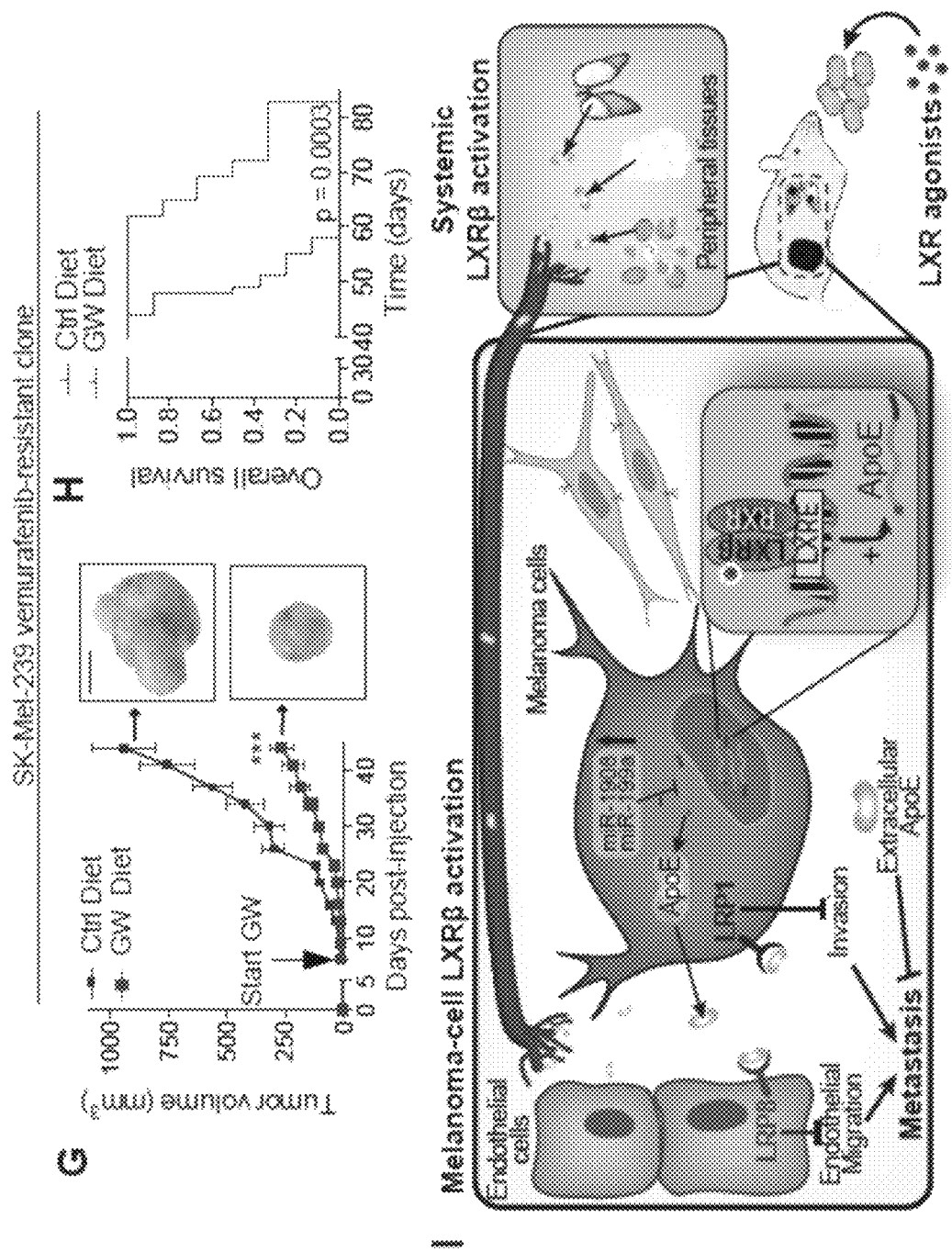

We tested the impact of LXRβ activation therapy on melanoma cells resistant to the recently approved B-Raf kinase inhibitor, vemurafenib—a regimen that shows activity against B-Raf-mutant melanomas (Bollag et al., 2010; Sosman et al., 2012). Numerous investigators have derived melanoma lines resistant to vemurafenib (Poulikakos et al., 2011; Shi et al., 2012, Das Thakur et al., 2013). GW3965 2 treatment suppressed the growth of the previously derived SK-Mel-239 vemurafenib-resistant line by 72% (FIG. 31G) and significantly prolonged the survival of mice bearing vemurafenib-resistant melanoma burden (FIG. 31H). Our findings from combined pharmacologic, molecular and genetic studies in diverse pre-clinical models of melanoma establish LXRβ targeting as a novel therapeutic approach that robustly suppresses melanoma tumor growth and metastasis through the transcriptional induction of ApoE—a key suppressor of melanoma invasion and metastatic angiogenesis (Pencheva et al., 2012; FIG. 31I).

Example 20

Treatment with ApoE Inhibits Tumor Cell Invasion and Endothelial Recruitment Across Multiple Cancer Types, Including Breast Cancer, Renal Cell Cancer and Pancreatic Cancer In order to determine if ApoE treatment could be effective for treating cancer types in addition to melanoma, in vitro assays were performed to assess the effect of ApoE treatment on several different cancer cell lines, including breast cancer, renal cell cancer, and pancreatic cancer cell lines (FIG. 33).

The ability of cancer cells to invade through matrigel in vitro was tested by using a trans-cell matrigel invasion chamber system (354480, BD Biosciences). Various cancer cell lines were serum-starved overnight in media containing 0.2% FBS. The following day, invasion chambers were pre-equilibrated prior to the assay by adding 0.5 mL of starvation media to the top and bottom wells. Meanwhile, cancer cells were trypsinized and viable cells were counted using the trypan blue dead cell exclusion dye. Cancer cells were then resuspended at a concentration of 1×105 cells/1 mL starvation media, and 0.5 mL of cell suspension, containing 5×10$^4$ cells, was seeded into each trans-well. To determine the effect of recombinant ApoE on cancer cell invasion, human recombinant ApoE3 (4696, Biovision) or BSA were added to each trans-well at 100 μg/mL at the start of the assay. The invasion assay was allowed to proceed for 24 hours at 37° C. Upon completion of the assay, the inserts were washed in PBS, the cells that did not invade were gently scraped off from the top side of each insert using q-tips, and the cells that invaded into the basal insert side were fixed in 4% PFA for 15 minutes at room temperature. Following fixation, the inserts were washed in PBS and then cut out and mounted onto slides using VectaShield mounting medium containing DAPI nuclear stain (H-1000, Vector Laboratories). The basal side of each insert was imaged using an inverted fluorescence microscope (Zeiss Axiovert 40 CFL) at 5× magnification, and the number of DAPI-positive cells was quantified using ImageJ.

Indeed, treatment with ApoE inhibited both tumor cell invasion and endothelial recruitment across all three of these cancer types (FIG. 33A-I).

Example 21

LXR agonists LXR-623, WO-2007-002563 Ex. 19, WO-2010-0138598 Ex. 9, and SB742881, Induce ApoE Expression in Human Melanoma Cells Given that ApoE activation by treatment with LXR agonists GW3965 2 and T0901317 1 resulted in therapeutic benefit for inhibiting tumor growth and metastasis, we next examined the ability of other LXR agonists to induce ApoE expression in human melanoma cell lines (FIG. 34).

To determine the effect of the various LXR agonists (LXR-623, WO-2007-002563 Ex. 19, WO-2010-0138598 Ex. 9, and SB742881 on ApoE expression in melanoma cells, 1×10$^5$ human MeWo melanoma cells were seeded in a 6-well plate. The following day, DMSO or the respective LXR agonist was added to the cell media at a concentration of 500 nM, 1 μM, or 2 μM, as indicated, and the cells were incubated in the presence of DMSO or the drug for 48 hours at 37° C. The total amount of DMSO added to the cell media was kept below 0.2%. RNA was extracted from whole cell lysates using the Total RNA Purification Kit (17200, Norgen). For every sample, 600 ng of RNA was reverse transcribed into cDNA using the cDNA First-Strand Synthesis kit (Invitrogen). Approximately 200 ng of cDNA was mixed with SYBR® green PCR Master Mix and the corresponding forward and reverse primers specific for detection of human ApoE. Each reaction was carried out in quadruplicates, and ApoE mRNA expression levels were measured by quantitative real-time PCR amplification using an ABI Prism 7900HT Real-Time PCR System (Applied Biosystems). The relative ApoE expression was determined using the ΔΔCt method. GAPDH was used as an endogenous control for normalization purposes.

Figures 34A, 34B, 34C, 34D:
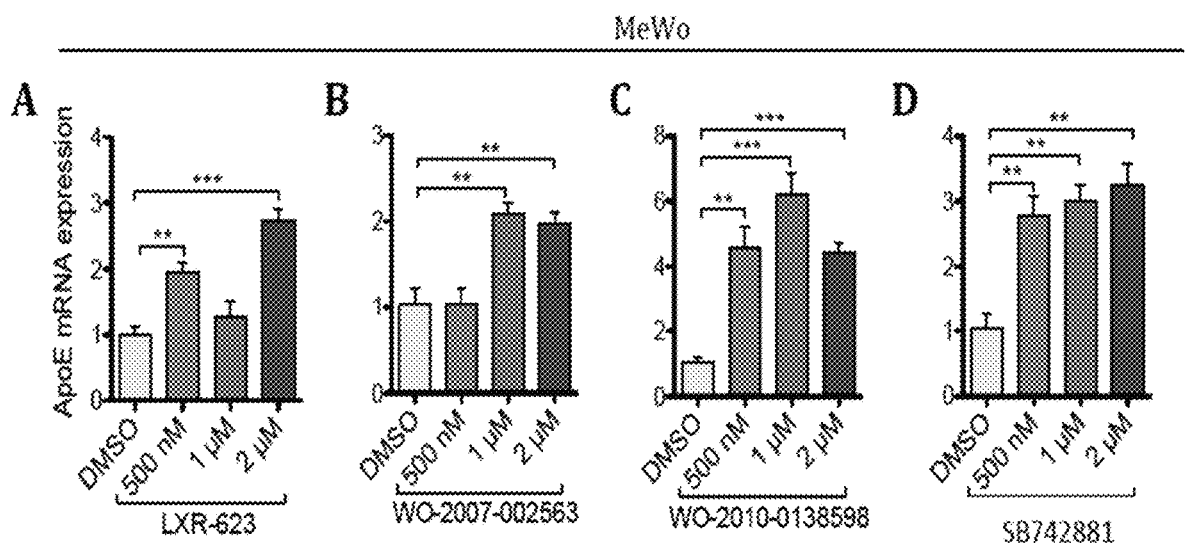

Indeed, treatment with the LXR agonists LXR-623, WO-2007-002563 Ex. 19, WO-2010-0138598 Ex. 9, and SB742881 all led to varied degrees of ApoE expression induction. (FIG. 34A-C).

Example 22

Treatment with the LXR Agonist GW3965 Inhibits In Vitro Tumor Cell Invasion of Renal Cancer, Pancreatic Cancer, and Lung Cancer We have demonstrated that treatment with LXR agonists resulted in inhibition of melanoma tumor cell invasion. Given that this effect is mediated by activation of ApoE expression, we hypothesized that treatment with LXR agonists would result in inhibition of in vitro tumor cell invasion in breast cancer, pancreatic cancer, and renal cancer, since these cancer types were responsive to ApoE treatment. In order to test this hypothesis, we performed in vitro tumor cell invasion assays by treating breast cancer, pancreatic cancer, and renal cell cancer cell lines with the LXR agonist GW3965 2 (FIG. 35).

Various cell lines (5×10$^4$ RCC human renal cancer cells, 5×10$^4$ PANC1 human pancreatic cancer cells, and 5×10$^4$ H460 human lung cancer cells) were treated with DMSO or GW3965 at 1 μM for 56 hours. The cells were serum starved for 16 hours in 0.2% FBS media in the presence of DMSO or GW3965. Following serum starvation, the cells were subjected to the trans-well invasion assay using a matrigel invasion chamber system (354480, BD Biosciences). Invasion chambers were pre-equilibrated prior to the assay by adding 0.5 mL of starvation media to the top and bottom wells. Meanwhile, cancer cells were trypsinized and viable cells were counted using trypan blue. Cancer cells were then resuspended at a concentration of 1×10$^5$ cells/1 mL starvation media, and 0.5 mL of cell suspension, containing 5×10$^4$ cells, was seeded into each trans-well. The invasion assay was allowed to proceed for 24 hours at 37° C. Upon completion of the assay, the inserts were washed in PBS, the cells that did not invade were gently scraped off from the top side of each insert using q-tips, and the cells that invaded into the basal insert side were fixed in 4% PFA for 15 minutes at room temperature. Following fixation, the inserts were washed in PBS and then cut out and mounted onto slides using VectaShield mounting medium containing DAPI nuclear stain (H-1000, Vector Laboratories). The basal side of each insert was imaged using an inverted fluorescence microscope (Zeiss Axiovert 40 CFL) at 5× magnification, and the number of DAPI-positive cells was quantified using ImageJ.

Indeed, treatment with GW3965 2 resulted in inhibition of tumor cell invasion in all three cancer types tested (FIG. 35A-C). This further demonstrated the broad therapeutic potential of LXR agonists for treating various cancer types.

Example 23

Treatment with the LXR Agonist GW3965 Inhibits Breast Cancer Tumor Growth In Vivo We have demonstrated that LXR agonists inhibit in vitro cancer progression phenotypes in breast cancer, pancreatic cancer, and renal cancer. To investigate if LXR agonist treatment inhibits breast cancer primary tumor growth in vivo, mice injected with MDA-468 human breast cancer cells were treated with either a control diet or a diet supplemented with LXR agonist GW3965 2 (FIG. 36).

To determine the effect of orally delivered GW3965 2 on breast cancer tumor growth, 2×10$^6$ MDA-468 human breast cancer cells were resuspended in 50 μL PBS and 50 μL matrigel and the cell suspension was injected into both lower memory fat pads of 7-week-old Nod Scid gamma female mice. The mice were assigned to a control diet treatment or a GW3965-supplemented diet treatment (75 mg/kg/day) two days prior to injection of the cancer cells. The GW3965 2 drug compound was formulated in the mouse chow by Research Diets, Inc. Tumor dimensions were measured using digital calipers, and tumor volume was calculated as (small diameter)$^2$×(large diameter)/2.

Treatment with GW3965 resulted in significant reduction in breast cancer tumor size in vivo (FIG. 36).

Example 24

Effects of Treatment with LXR Agonists LXR-623, WO-2007-002563 Ex. 19, WO-2010-0138598 Ex. 9, and SB742881 on In Vitro Melanoma Progression Phenotypes We have demonstrated the ability of various LXR agonists to induce ApoE expression with varying potency in melanoma cells (FIG. 34). Since the therapeutic effect of LXR agonists on cancer is via activation of ApoE expression, we hypothesized that the therapeutic potency of any given LXR agonist is directly correlated with its ability to induce ApoE expression. To confirm this, we quantified the effect of treatment with various LXR agonists on in vitro endothelial recruitment and tumor cell invasion of melanoma cells. As shown in FIG. 37, the degree to which LXR agonists inhibit in vitro cancer progression phenotypes is related to the LXR agonist's ApoE induction potency.

Cell Invasion: MeWo human melanoma cells were treated with DMSO, LXR-623, WO-2007-002563 Ex. 19, WO-2010-0138598 Ex. 9, or SB742881 at 1 µM each for 56 hours. The cells were then serum starved for 16 hours in 0.2% FBS media in the presence of each corresponding drug or DMSO. Following serum starvation, the cells were subjected to the trans-well invasion assay using a matrigel invasion chamber system (354480, BD Biosciences). Invasion chambers were pre-equilibrated prior to the assay by adding 0.5 mL of starvation media to the top and bottom wells. Meanwhile, cancer cells were trypsinized and viable cells were counted using trypan blue. Cancer cells were then resuspended at a concentration of $2\times10^5$ cells/1 mL starvation media, and 0.5 mL of cell suspension, containing $1\times10^5$ cells, was seeded into each trans-well. The invasion assay was allowed to proceed for 24 hours at 37° C. Upon completion of the assay, the inserts were washed in PBS, the cells that did not invade were gently scraped off from the top side of each insert using q-tips, and the cells that invaded into the basal insert side were fixed in 4% PFA for 15 minutes at room temperature. Following fixation, the inserts were washed in PBS, cut out, and mounted onto slides using VectaShield mounting medium containing DAPI nuclear stain (H-1000, Vector Laboratories). The basal side of each insert was imaged using an inverted fluorescence microscope (Zeiss Axiovert 40 CFL) at 5× magnification, and the number of DAPI-positive cells was quantified using ImageJ.

Endothelial Recruitment: MeWo human melanoma cells were treated with DMSO, LXR-623, WO-2007-002563 Ex. 19, WO-2010-0138598 Ex. 9, or SB742881 at 1 µM each for 56 hours. Subsequently, $5\times10^4$ cancer cells were seeded into 24-well plates in the presence of each drug or DMSO and allowed to attach for 16 hours prior to starting the assay. Human umbilical vein endothelial cells (HUVEC cells) were serum-starved in 0.2% FBS-containing media overnight. The following day, $1\times10^5$ HUVEC cells were seeded into a 3.0 µm HTS Fluoroblock insert (351151, BD Falcon) fitted into each well containing the cancer cells at the bottom. The HUVEC cells were allowed to migrate towards the cancer cells for 20 hours, after which the inserts were washed in PBS, fixed in 4% PFA, labeled with DAPI, and mounted on slides. The basal side of each insert was imaged using an inverted fluorescence microscope (Zeiss Axiovert 40 CFL) at 5× magnification, and the number of DAPI-positive cells was quantified using ImageJ.

LXR agonists that potently induce ApoE expression (e.g. WO-2010-0138598 Ex. 9 and SB742881) are more effective at inhibiting cancer progression phenotypes (FIG. 37) than lower potency LXR agonists. This further demonstrates that the therapeutic benefit of LXR agonist treatment for cancer is a result of ApoE induction.

Example 25

Treatment with LXR Agonists Inhibit Melanoma Tumor Growth In Vivo

We have demonstrated that LXR agonists that induce ApoE expression inhibit in vitro tumor activity. To confirm if these agonists inhibit melanoma tumor growth in vivo, mice that were injected with B16F10 melanoma cells were treated with either LXR-623, WO-2007-002563 Ex. 19, WO-2010-0138598 Ex. 9, or SB742881.

To assess the effect of orally administered LXR-623, WO-2007-002563 Ex. 19, WO-2010-0138598 Ex. 9, or SB742881 on melanoma tumor growth, $5\times10^4$ B16F10 mouse melanoma cells were resuspended in 50 µL PBS and 50 µL matrigel and the cell suspension was subcutaneously injected into both lower dorsal flanks of 7-week-old C57BL/6 mice. The mice were palpated daily for tumor formation and after detection of tumors measuring 5-10 m³ in volume, the mice were assigned to a control chow or a chow containing each respective LXR agonist: LXR-623 (20 mg/kg/day), WO-2007-002563 Ex. 19 (100 mg/kg/day), WO-2010-0138598 Ex. 9 (10 mg/kg/day or 100 mg/kg/day), or SB742881 (100 mg/kg/day). The LXR drug compounds were formulated in the mouse chow by Research Diets, Inc. Tumor dimensions were measured using digital calipers, and tumor volume was calculated as (small diameter)$^2\times$(large diameter)/2.

Consistent with our in vitro data, LXR agonists that potently induce ApoE expression in vitro (WO-2010-0138598 Ex. 9, and SB742881) significantly inhibited melanoma primary tumor growth in vivo (FIG. 38). This is also consistent with our results demonstrating that other LXR agonists which potently induce ApoE expression (GW3965 2, T0901317 1) also inhibit primary tumor growth in vivo (FIG. 21).

Accordingly, the above examples focused on characterizing the molecular and cellular mechanisms by which it exerts its effects. To this end, it was found that ApoE targets two distinct, yet homologous, receptors on two diverse cell types. ApoE acting on melanoma cell LRP1 receptors inhibits melanoma invasion, while its action on endothelial cell LRP8 receptors suppresses endothelial migration. The results from loss-of-function, gain-of-function, epistasis, clinical correlation, and in vivo selection derivative expression analyses give rise to a model wherein three miRNAs convergently target a metastasis suppressor network to limit ApoE secretion, thus suppressing ApoE/LRP1 signaling on melanoma cells and ApoE/LRP8 signaling on endothelial cells (FIG. 7K). Although the above systematic analysis has identified ApoE and DNAJA4 as key targets and direct mediators of the metastatic phenotypes regulated by these miRNAs, it cannot be excluded that the three miRNAs may individually retain additional target genes whose silencing may contribute to metastatic progression. The ability of ApoE or DNAJA4 knock-down to fully rescue the metastasis suppression phenotypes seen with individual miRNA silencing, however, strongly suggests that these genes are the key mediators of the miRNA-dependent effects on metastasis.

The above results reveal combined molecular, genetic, and in vivo evidence for a required and sufficient role for ApoE in the suppression of melanoma metastatic progression. ApoE can distribute in the circulatory system both in a lipoprotein-bound and a lipid-free state (Hatters et al., 2006). While it has been shown that lipid-free recombinant ApoE is sufficient to suppress melanoma invasion and endothelial migration, it is possible that ApoE contained in lipoprotein particles could also suppress melanoma invasion and endothelial recruitment. The ability of recombinant ApoE to inhibit these pro-metastatic phenotypes, as well as the increased melanoma invasion and endothelial recruitment phenotypes seen with antibody-mediated ApoE neutralization suggests that the ApoE molecule itself is the key mediator of these phenotypes. Consistent with the findings disclosed herein, a synthetic peptide fragment of ApoE was previously found to inhibit endothelial migration through unknown mechanisms (Bhattacharjee et al., 2011). The findings disclosed herein are consistent with a role for melanoma cell-secreted and systemic endogenous ApoE in inhibiting endothelial recruitment, which is not secondary to impaired endothelial cell growth.

The above-described molecular, genetic, and in vivo studies reveal a role for endogenous cancer-derived ApoE in the modulation of endothelial migration and cancer angiogenesis through endothelial LRP8 receptor signaling. This robust non-cell-autonomous endothelial recruitment phenotype mediated by ApoE/LRP8 signaling suggests that ApoE may also modulate metastatic angiogenesis in other cancer types, and such a general role for ApoE in cancer angiogenesis biology remains to be explored. ApoE is a polymorphic molecule with well-established roles in lipid, cardiovascular, and neurodegenerative disorders. Its three major variants, ApoE2, ApoE3, and ApoE4, display varying representations in the human population, with ApoE3 being the most common variant (Hatters et al., 2006). The three isoforms differ at residues 112 and 158 in the N-terminal domain, which contains the ApoE receptor-binding domain. These structural variations are thought to give rise to distinct functional attributes among the variants. Consistent with this, the three ApoE isoforms differ in their binding affinity for members of the LDL receptor family, lipoprotein-binding preferences, and N-terminus stability. Namely, ApoE2 has 50- to 100-fold attenuated LDL receptor binding ability compared to ApoE3 and ApoE4 (Weisgraber et al., 1982), while ApoE4, unlike the other two variants, preferentially binds to large lower-density lipoproteins (Weisgraber et al., 1990) and exhibits the lowest N-terminus stability (Morrow et al., 2000). These functional differences confer pathophysiological properties to select ApoE isoforms. While ApoE3, found in 78% of the population, is considered a neutral allele, ApoE2 is associated with type III hyperlipoprotenemia (Hatters et al., 2006) and ApoE4 represents the major known genetic risk factor for Alzheimer's disease (Corder et al., 1993) and also correlates with a modest increase in the risk of developing cardiovascular disease (Luc et al., 1994). Given that the multiple human melanoma cell lines analyzed in the above study are homozygous for the ApoE3 allele, as well as the ability of recombinant ApoE3 to inhibit melanoma invasion and endothelial recruitment, the above findings are consistent with ApoE3 being sufficient and required for the suppression of melanoma metastatic progression. However, it will be of interest in the future to determine whether ApoE2 and ApoE4 can modulate these pro-metastatic phenotypes to a similar extent as ApoE3 and whether specific ApoE genotypes confer enhanced risk of melanoma metastatic progression.

Besides surgical resection of primary melanoma lesions, there are currently no effective therapies for the prevention of melanoma metastasis with interferon therapy increasing overall survival rates at 5 years by a meager 3% based on meta-analyses, while phase III trial data demonstration of significant survival benefits is still outstanding (Garbe et al., 2011). The dramatic enhancement of melanoma metastatic progression in the context of genetic ablation of systemic ApoE suggests that modulating ApoE levels may have significant therapeutic implications for melanoma—a disease that claims approximately 48,000 lives a year globally (Lucas et al., 2006). Given the robust ability of ApoE to suppress melanoma invasion, endothelial migration, metastatic angiogenesis, and metastatic colonization, therapeutic approaches aimed at pharmacological induction of endogenous ApoE levels may significantly reduce melanoma mortality rates by decreasing metastatic incidence.

The above-described unbiased in vivo selection based approach led to discovery of deregulated miRNAs that synergistically and dramatically promote metastasis by cancer cells from independent patients' melanoma cell lines representing both melanotic and amelanotic melanomas. While miR-1908 has not been previously characterized, miR-199a has been implicated in hepatocellular carcinoma (Hou et al., 2011; Shen et al., 2010) and osteosarcoma (Duan et al., 2011) that, contrary to melanoma, display downregulation of miR-199a expression levels. These differences are consistent with the established tissue-specific expression profiles of miRNAs in various cancer types. The identification of miR-199a as a promoter of melanoma metastasis is supported by a previous clinical association study revealing that increased miR-199a levels correlate with uveal melanoma progression (Worley et al., 2008), suggesting that induced miR-199a expression may be a defining feature of metastatic melanoma regardless of site of origin. Previous studies have implicated additional miRNAs in promoting melanoma metastatic progression such as miR-182 (Segura et al., 2009), miR-214 (which was upregulated in metastatic melanoma cells, but it did not functionally perform in the above studies; Penna et al., 2011), and miR-30b/miR-30d (Gaziel-Sovran et al., 2011). Each of these miRNAs have been reported to only modestly modulate melanoma metastasis, leading to 1.5- to 2-fold increased or decreased metastasis modulation upon miRNA over-expression or knockdown, respectively. In contrast, over-expression of either miR-199a or miR-1908 enhanced metastasis by 9-fold (FIG. 1C), while combinatorial miRNA knock-down synergistically suppressed melanoma metastasis by over 70-fold (FIG. 7E). Therefore, the study disclosed herein represents the first systematic discovery of multiple miRNAs that convergently and robustly promote human melanoma metastasis, as well as the first to assign dual cell-autonomous/non-cell-autonomous roles to endogenous metastasis-regulatory miRNAs in cancer.

Previous systematic analysis of miRNAs in breast cancer revealed primarily a decrease in the expression levels of multiple microRNAs in in vivo selected metastatic breast cancer cells (Tavazoie et al., 2008). Those findings were consistent with the subsequent discovery of many additional metastasis suppressor miRNAs in breast cancer (Shi et al., 2010; Wang and Wang, 2011), the identification of a number of miRNAs as direct transcriptional targets of the p53 tumour suppressor (He et al., 2007), the downregulation of miRNAs in breast cancer relative to normal tissues (Calin and Groce, 2006; Iorio et al., 2005), the downregulation of drosha and dicer in breast cancer (Yan et al., 2011) and metastatic breast cancer (Grelier et al., 2011), as well as the pro-tumorigenic and pro-metastatic effects of global miRNA silencing through dicer knock-down (Kumar et al., 2007; Kumar et al., 2009; Martello et al., 2010; Noh et al., 2011). In contrast to breast cancer, the above findings in melanoma reveal a set of miRNAs upregulated in metastatic human melanoma, raising the intriguing possibility that miRNA processing may actually act in a pro-tumorigenic or pro-metastatic manner in melanoma. Consistent with this, dicer is required for melanocytic development (Levy et al., 2010), and dicer expression was recently found to positively correlate with human melanoma progression in a clinico-pathological study (Ma et al., 2011). These findings, when integrated with the findings disclosed here, motivate future studies to investigate the functional requirement for dicer (Bernstein et al., 2001) in melanoma metastasis.

The establishment of in vivo selection models of melanotic and amelanotic melanoma metastasis has allowed one to identify the cellular phenotypes displayed by highly metastatic melanoma cells. The work reveals that, in addition to enhanced invasiveness, the capacity of melanoma cells to recruit endothelial cells is significantly enhanced in highly metastatic melanoma cells relative to poorly metastatic melanoma cells. Additionally, it was found that three major post-transcriptional regulators of metastasis strongly mediate endothelial recruitment. It was further found that the downstream signaling pathway modulated by these miRNAs also regulates endothelial recruitment. These findings reveal endothelial recruitment to be a defining feature of metastatic melanoma cells. Enhanced endothelial recruitment capacity was also recently found to be a defining feature of metastatic breast cancer, wherein suppression of metastasis by miR-126 was mediated through miRNA targeting of two distinct signaling pathways that promote endothelial recruitment (Png et al., 2012). In breast cancer, endothelial recruitment increased the likelihood of metastatic initiation rather than tumor growth. Similarly, the melanoma metastasis promoter miRNAs studied here dramatically enhanced metastatic colonization, without enhancing primary tumor growth, and increased the number of metastatic nodules—consistent with a role for these miRNAs and their regulatory network in metastatic initiation rather than tumor growth promotion. Taken together, these findings are consistent with endothelial recruitment into the metastatic niche acting as a promoter of metastatic initiation and colonization in these distinct epithelial cancer types. Such a non-canonical role for endothelial cells in cancer progression would contrast with the established role of endothelial cells in angiogenic enhancement of blood flow spurring enhanced tumor growth. Endothelial cells are known to play such non-canonical roles in development by supplying cues to neighboring cells during organogenesis (Lammert et al., 2001). Such cues have also been recently shown to promote organ regeneration (Ding et al., 2011; Ding et al., 2010; Kobayashi et al., 2010). Future work is needed to determine the metastasis stimulatory factors provided by endothelial cells that catalyze metastatic initiation.

The ability of miR-199a-3p, miR-199a-5p, and miR-1908 to individually predict metastasis-free survival in a cohort of melanoma patients indicates the significance of each miRNA as a clinical predictor of melanoma cancer progression. Importantly, the dramatic and highly significant capacity of the three miRNA aggregate signature (FIG. 7D) to stratify patients at high risk from those at essentially no risk for metastatic relapse reveals both the cooperativity of these miRNAs, as well as their clinical potential as melanoma biomarkers (Sawyers, 2008) for identifying the subset of patients that might benefit from miRNA inhibition therapy. Therapeutic miRNA targeting has gained momentum through the use of in vivo LNAs that have been shown to antagonize miRNAs in mice (Elmer et al., 2008(b); Krutzfeldt et al., 2005; Obad et al., 2011) and primates (Elmer et al., 2008(a)) and are currently being tested in human clinical trials. The powerful prognostic capacity of the three miRNAs, proof-of-principle demonstration of robust synergistic metastasis prevention achieved by treating highly metastatic melanoma cells with a cocktail of LNAs targeting miR-199a-3p, miR-199a-5p, and miR-1908 (FIG. 7E), as well as the metastasis suppression effect of therapeutically delivered in vivo-optimized LNAs targeting these miRNAs (FIG. 7J) motivate future clinical studies aimed at determining the therapeutic potential of combinatorially targeting these pro-metastatic and pro-angiogenic miRNAs in patients at high risk for melanoma metastasis—an outcome currently lacking effective chemotherapeutic options.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated in their entireties.

The invention claimed is:

1. A method of treating ovarian cancer in a subject in need thereof, the method comprising administering to the subject an LXRβ agonist selected from:

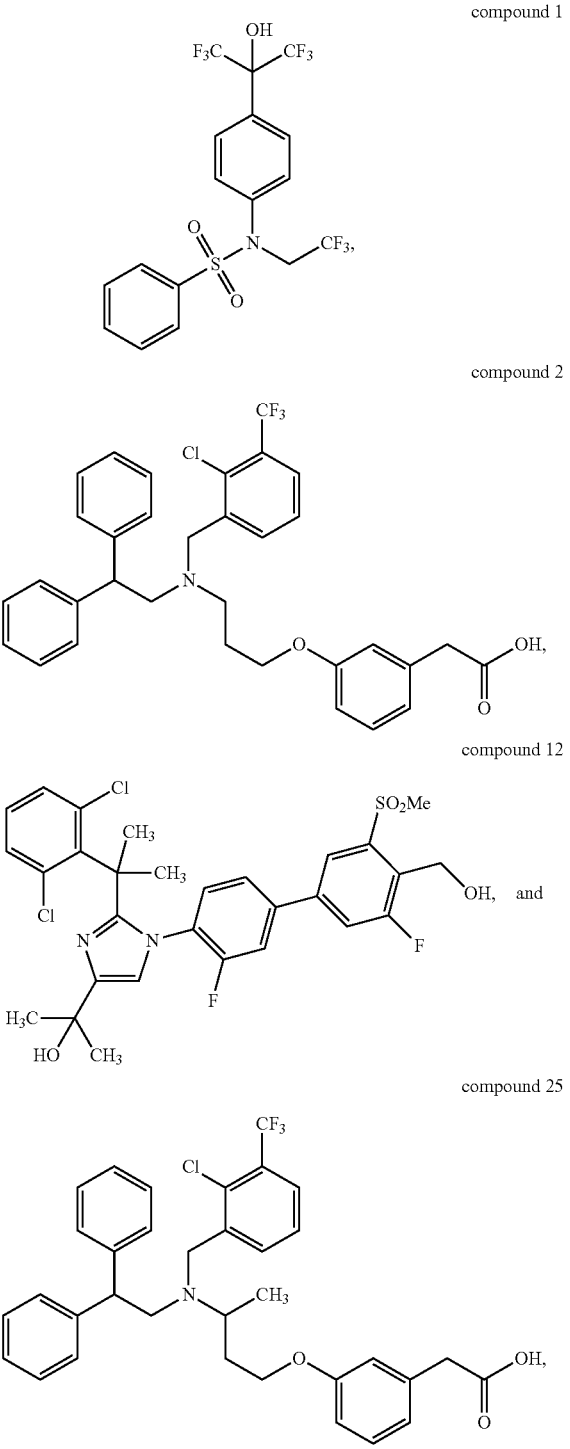

or a pharmaceutically acceptable salt thereof in an amount sufficient to suppress the invasion of surrounding tissue by the ovarian cancer and/or suppress metastatic colonization of the ovarian cancer.

2. The method of claim 1, wherein the LXRβ agonist is compound 1, or a pharmaceutically acceptable salt thereof.

3. The method of claim 1, wherein the LXRβ agonist is compound 2, or a pharmaceutically acceptable salt thereof.

4. The method of claim 1, wherein the LXRβ agonist is compound 12, or a pharmaceutically acceptable salt thereof.

5. The method of claim 1, wherein the LXRβ agonist is compound 25, or a pharmaceutically acceptable salt thereof.

6. The method of claim 1, wherein the ovarian cancer is resistant to platinum-containing chemotherapy, a PD-1 inhibitor, a PD-L1 inhibitor, a CTLA-4 inhibitor, an antimitotic agent, a topoisomerase inhibitor, an antimetabolite, an angiogenesis inhibitor, a kinase inhibitor, and/or an alkylating agent.

7. The method of claim 6, wherein the ovarian cancer progressed on or after treatment with platinum-containing chemotherapy, a PD-1 inhibitor, a PD-L1 inhibitor, an angiogenesis inhibitor, a kinase inhibitor, and/or an alkylating agent.

8. The method of claim 6, wherein the ovarian cancer has been determined to be, or is predicted to be, resistant to a PD-1 inhibitor, a PD-L1 inhibitor, a CTLA-4 inhibitor, a topoisomerase inhibitor, an antimetabolite, an angiogenesis inhibitor, a kinase inhibitor, and/or an alkylating agent.

9. The method of claim 1, wherein the method does not comprise further concurrently administering to the subject an antiproliferative agent.

10. The method of claim 1, wherein the method further comprises administration of an additional anticancer therapy.

11. The method of claim 10, wherein the additional anticancer therapy is an immunomodulator, a topoisomerase inhibitor, an antimetabolite, an angiogenesis inhibitor, a kinase inhibitor, and/or an alkylating agent.

12. The method of claim 11, wherein the immunomodulator is a PD-1 inhibitor, a CTLA4 inhibitor, and/or a PDL1 inhibitor.

13. The method of claim 11, wherein the antimitotic agent is paclitaxel or docetaxel.

14. The method of claim 11, wherein the antimetabolite is gemcitabine.

15. The method of claim 1, wherein the method comprises the suppression of the invasion of surrounding tissue by the ovarian cancer.

16. The method of claim 1, wherein the method comprises the suppression of metastatic colonization of the ovarian cancer.

17. The method of claim 16, wherein the method comprises the suppression of metastatic colonization of the ovarian cancer to the lung and/or the brain.

18. A method of treating cancer in a subject in need thereof, the method comprising administering to the subject an effective amount of an LXRβ agonist selected from:

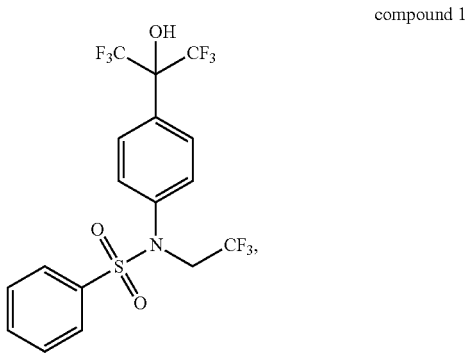

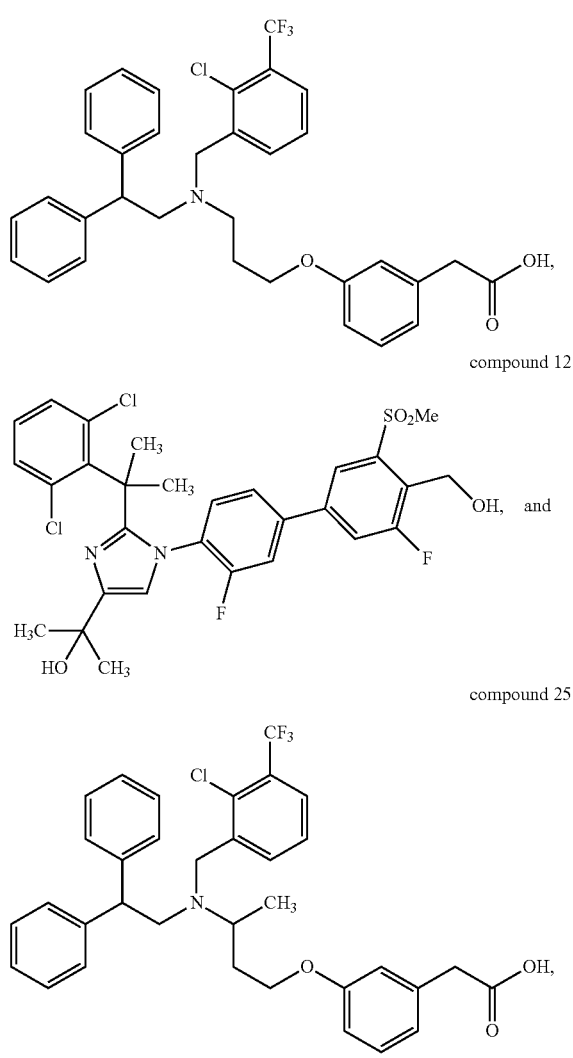

compound 2 compound 12 compound 25 or a pharmaceutically acceptable salt thereof, subsequent to at least one prior anti-cancer therapy.

19. The method of claim 18, wherein the cancer is breast cancer, colon cancer, renal cell cancer, lung cancer, hepatocellular carcinoma, gastric cancer, ovarian cancer, pancreatic cancer, esophageal cancer, prostate cancer, sarcoma, bladder cancer, or melanoma.

20. The method of claim 18, wherein the prior anti-cancer therapy is surgery, radiation therapy, and/or chemotherapy.

21. The method of claim 20, wherein the prior anti-cancer therapy is surgery.

22. The method of claim 20, wherein the prior anti-cancer therapy is radiation therapy.

23. The method of claim 18, the method further comprising administering to the subject an additional therapeutic agent.

24. The method of claim 23, wherein the additional therapeutic agent is an immunomodulator, a topoisomerase inhibitor, an antimetabolite, an angiogenesis inhibitor, a kinase inhibitor, and/or an alkylating agent.

25. The method of claim 24, wherein the immunomodulator is a PD-1 inhibitor, a CTLA4 inhibitor, and/or a PDL1 inhibitor.

26. The method of claim 18, wherein the cancer is metastatic cancer.

27. The method of claim 26, wherein the cancer has been diagnosed as metastatic.

28. The method of claim 18, wherein the method comprises the suppression of the progression or metastasis of cancer.

29. The method of claim 18, wherein the compound is compound 1.

30. The method of claim 18, wherein the compound is compound 2.

31. The method of claim 18, wherein the compound is compound 12.

32. The method of claim 18, wherein the compound is compound 25.

33. The method of claim 18, wherein the cancer is resistant to platinum-containing chemotherapy, a PD-1 inhibitor, a PD-L1 inhibitor, a CTLA-4 inhibitor, an antimitotic agent, a topoisomerase inhibitor, an antimetabolite, an angiogenesis inhibitor, a kinase inhibitor, and/or an alkylating agent.

34. The method of claim 18, wherein the cancer progressed on or after treatment with platinum-containing chemotherapy, a PD-1 inhibitor, a PD-L1 inhibitor, an angiogenesis inhibitor, a kinase inhibitor, and/or an alkylating agent.

35. The method of claim 18, wherein the cancer has been determined to be, or is predicted to be, resistant to a PD-1 inhibitor, a PD-L1 inhibitor, a CTLA-4 inhibitor, a topoisomerase inhibitor, an antimetabolite, an angiogenesis inhibitor, a kinase inhibitor, and/or an alkylating agent.

36. A method of treating small cell carcinoma in a subject in need thereof, the method comprising administering to the subject an LXRβ agonist selected from:

compound 1

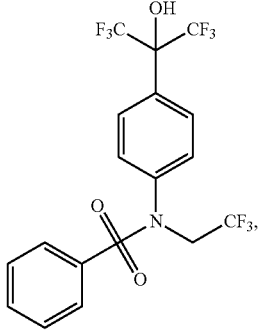

compound 2

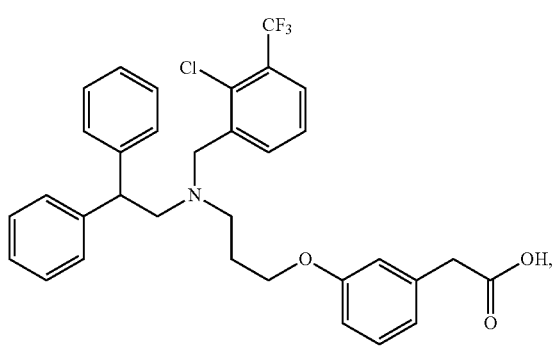

compound 12

[Chemical structure of compound 12]

compound 25

[Chemical structure of compound 25]

or a pharmaceutically acceptable salt thereof in an amount sufficient to suppress the invasion of surrounding tissue by the small cell carcinoma and/or suppress metastatic colonization of the small cell carcinoma, wherein the small cell carcinoma is lung cancer or prostate cancer.

37. The method of claim 36, wherein the LXRβ agonist is compound 1, or a pharmaceutically acceptable salt thereof.

38. The method of claim 36, wherein the LXRβ agonist is compound 2, or a pharmaceutically acceptable salt thereof.

39. The method of claim 36, wherein the LXRβ agonist is compound 12, or a pharmaceutically acceptable salt thereof.

40. The method of claim 36, wherein the LXRβ agonist is compound 25, or a pharmaceutically acceptable salt thereof.

41. The method of claim 36, wherein the small cell carcinoma is resistant to platinum-containing chemotherapy, a PD-1 inhibitor, a PD-L1 inhibitor, a CTLA-4 inhibitor, an antimitotic agent, a topoisomerase inhibitor, an antimetabolite, an angiogenesis inhibitor, a kinase inhibitor, and/or an alkylating agent.

42. The method of claim 41, wherein the small cell carcinoma progressed on or after treatment with a PD-1 inhibitor, a PD-L1 inhibitor, a CTLA-4 inhibitor, a kinase inhibitor, and/or an alkylating agent.

43. The method of claim 41, wherein the small cell carcinoma has been determined to be, or is predicted to be, resistant to a PD-1 inhibitor, a PD-L1 inhibitor, a CTLA-4 inhibitor, a topoisomerase inhibitor, an antimetabolite, an angiogenesis inhibitor, a kinase inhibitor, and/or an alkylating agent.

44. The method of claim 36, wherein the method does not comprise further concurrently administering to the subject an antiproliferative agent.

45. The method of claim 36, wherein the method further comprises administration of an additional anticancer therapy.

46. The method of claim 45, wherein the additional anticancer therapy is an immunomodulator, a topoisomerase inhibitor, an antimetabolite, an angiogenesis inhibitor, a kinase inhibitor, and/or an alkylating agent.

47. The method of claim 46, wherein the immunomodulator is a PD-1 inhibitor, a CTLA4 inhibitor, and/or a PDL1 inhibitor.

48. The method of claim 46, wherein the antimitotic agent is paclitaxel or docetaxel.

49. The method of claim 46, wherein the antimetabolite is gemcitabine.

50. The method of claim 36, wherein the method comprises the suppression of the invasion of surrounding tissue by the small cell carcinoma.

51. The method of claim 36, wherein the method comprises the suppression of metastatic colonization of the small cell carcinoma.

52. The method of claim 51, wherein the method comprises the suppression of metastatic colonization of the small cell carcinoma to the lung and/or the brain.

53. The method of claim 36, wherein the small cell carcinoma is lung cancer.

* * * * *